United States Patent
Kwon et al.

(10) Patent No.: US 10,035,765 B2
(45) Date of Patent: Jul. 31, 2018

(54) NITROGEN-CONTAINING POLYCYCLIC COMPOUND AND ORGANIC LIGHT EMITTING DEVICE USING SAME

(71) Applicant: LG CHEM, LTD., Seoul (KR)

(72) Inventors: Hyok Joon Kwon, Daejeon (KR); Minjun Kim, Daejeon (KR); Wanpyo Hong, Daejeon (KR); Kongkyeom Kim, Daejeon (KR); Seong So Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/508,438

(22) PCT Filed: Oct. 7, 2015

(86) PCT No.: PCT/KR2015/010618
§ 371 (c)(1),
(2) Date: Mar. 2, 2017

(87) PCT Pub. No.: WO2016/060404
PCT Pub. Date: Apr. 21, 2016

(65) Prior Publication Data
US 2017/0283379 A1     Oct. 5, 2017

(30) Foreign Application Priority Data

Oct. 14, 2014  (KR) .................. 10-2014-0138598
Apr. 7, 2015   (KR) .................. 10-2015-0049283

(51) Int. Cl.
*C07D 209/56* (2006.01)
*C09K 11/06* (2006.01)
*H01L 51/00* (2006.01)
*H01L 51/50* (2006.01)

(52) U.S. Cl.
CPC ............ *C07D 209/56* (2013.01); *C09K 11/06* (2013.01); *H01L 51/0072* (2013.01); *H01L 51/5056* (2013.01); *H01L 51/5072* (2013.01); *H01L 51/5092* (2013.01); *C09K 2211/1011* (2013.01); *C09K 2211/1029* (2013.01); *H01L 2251/50* (2013.01); *H01L 2933/0016* (2013.01)

(58) Field of Classification Search
CPC .................................................. C07D 209/56
See application file for complete search history.

(56) References Cited

U.S. PATENT DOCUMENTS

| 2011/0210318 | A1 | 9/2011 | Bae et al. |
| 2014/0001442 | A1 | 1/2014 | Lee et al. |
| 2014/0191208 | A1 | 7/2014 | Kim et al. |
| 2016/0005981 | A1 | 1/2016 | Kim et al. |

FOREIGN PATENT DOCUMENTS

| JP | 2008-214244 A   | 9/2008  |
| JP | 2013-539750 A   | 10/2013 |
| KR | 10-2010-0023783 A | 3/2010 |
| KR | 10-2010-0109050 A | 10/2010 |
| KR | 10-2012-0030009 A | 3/2012 |
| KR | 10-2014-0082273 A | 7/2014 |
| KR | 10-2014-01200089 A | 10/2014 |
| WO | 2010/114256 A2  | 10/2010 |
| WO | 2012/036482 A1  | 3/2012 |
| WO | 2013/015144 A1  | 1/2013 |
| WO | 2015/037965 A1  | 3/2015 |
| WO | 2015/093814 A1  | 6/2015 |
| WO | 2015/093878 A1  | 6/2015 |
| WO | 2015/167300 A1  | 11/2015 |
| WO | 2015/178731 A1  | 11/2015 |

OTHER PUBLICATIONS

Shin, et al. Document No. 156:463751, entered in STN on Mar. 22, 2012; retrieved from STN.*
Lee, et al. Document No. 153:492750, entered in STN on Oct. 7, 2010; retrieved from STN.*

* cited by examiner

*Primary Examiner* — Shawquia Jackson
(74) *Attorney, Agent, or Firm* — Dentons US LLP

(57) ABSTRACT

The present specification provides a multicyclic compound including nitrogen and an organic light emitting device using the same.

19 Claims, 4 Drawing Sheets

[Figure 1]
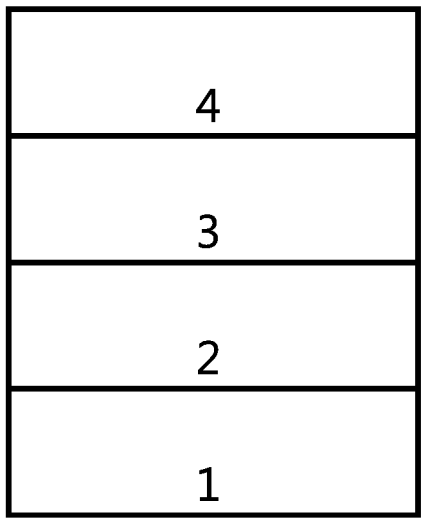
[Figure 2]
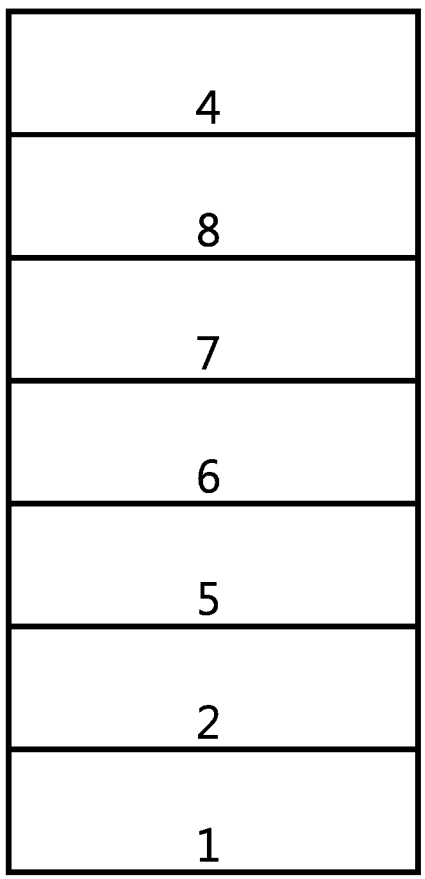

[Figure 3]
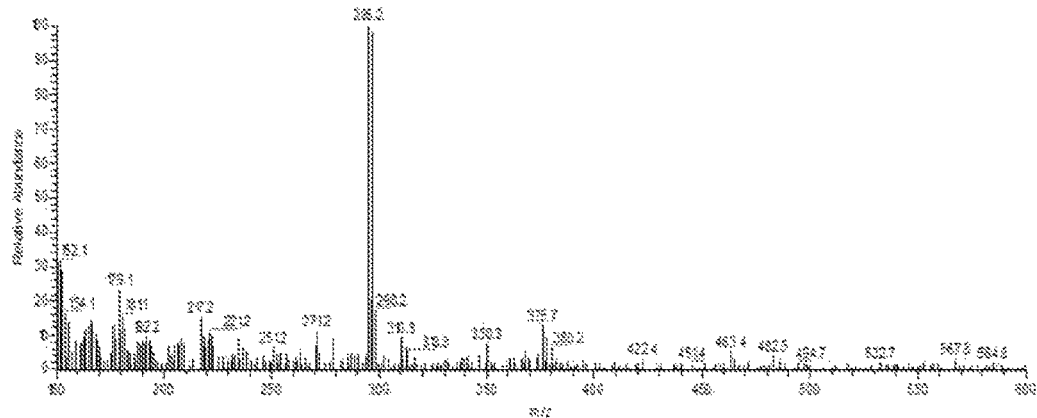
[Figure 4]
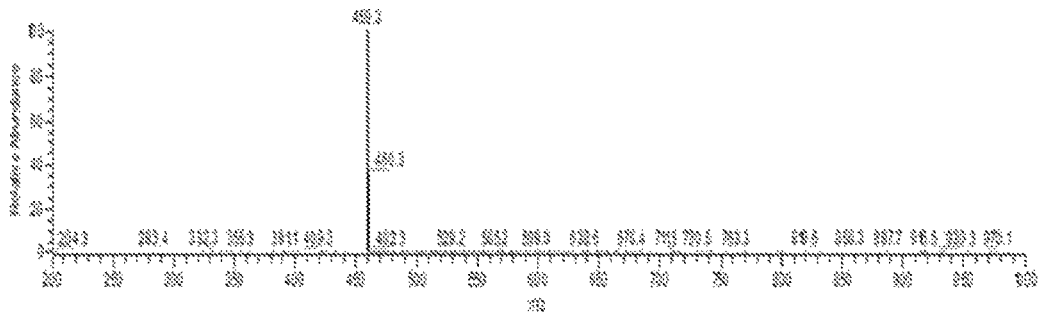
[Figure 5]
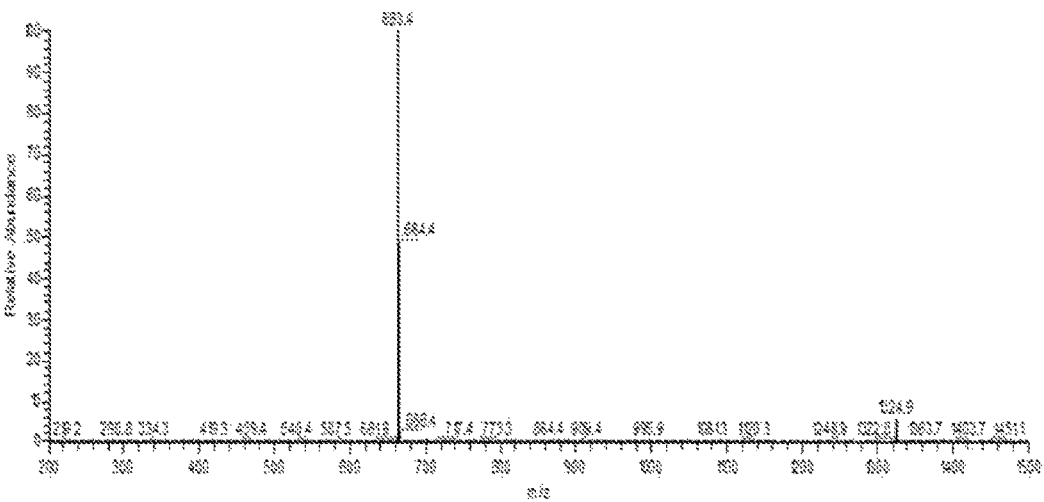

[Figure 6]
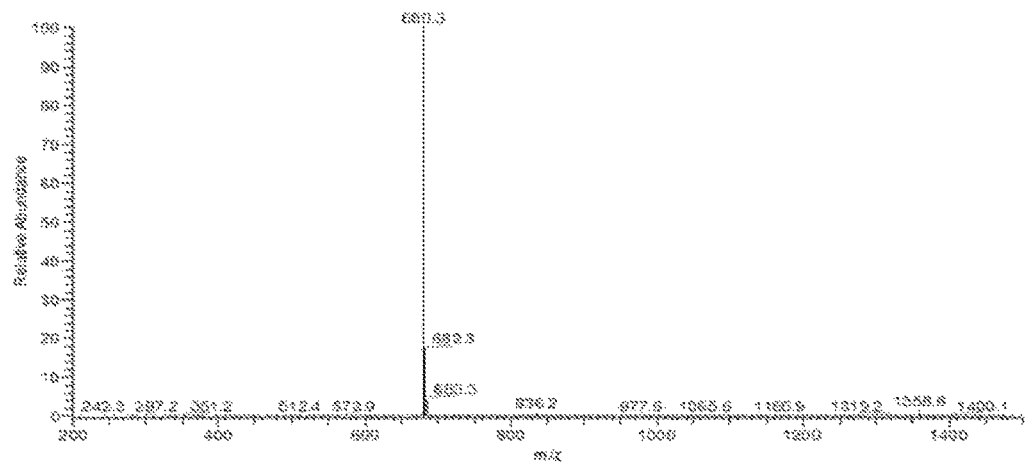
[Figure 7]
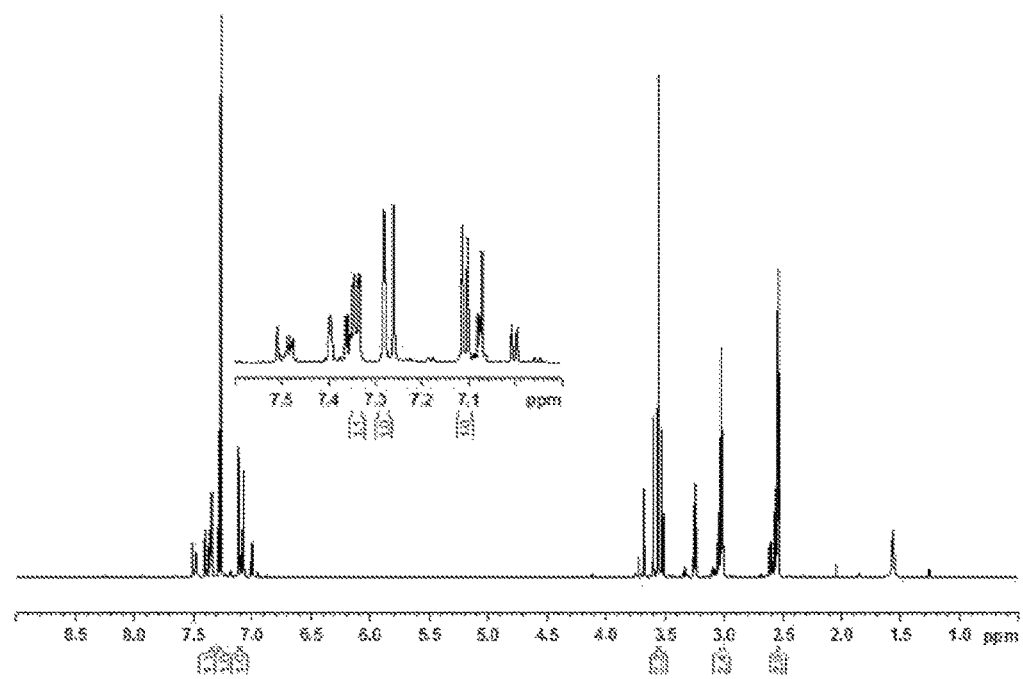

[Figure 8]
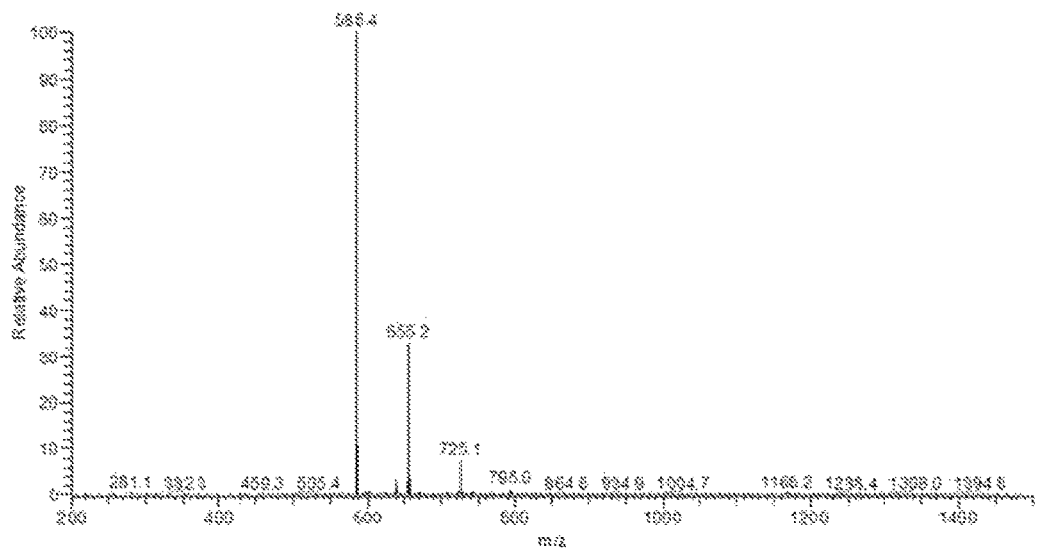
[Figure 9]
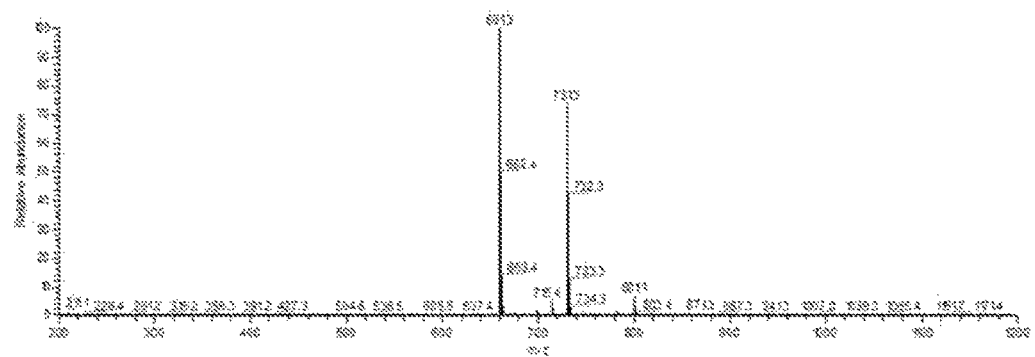

NITROGEN-CONTAINING POLYCYCLIC COMPOUND AND ORGANIC LIGHT EMITTING DEVICE USING SAME

TECHNICAL FIELD

This application is the National Stage entry of International Application No. PCT/KR2015/010618 filed Oct. 7, 2015 and claims priority to and the benefit of Korean Patent Application No. 10-2014-0138598 filed Oct. 14, 2014 and Korean Patent Application No. 10-2015-0049283 filed Apr. 7, 2015, which are contained in their entirety and incorporated herein by reference.

The present specification relates to a multicyclic compound including nitrogen and an organic light emitting device using the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multilayered structure composed of different materials in order to improve the efficiency and stability of an organic light emitting device in many cases, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

Official Gazette of Korean Patent Application Laid-Open No. 2000-0051826
Official Gazette of Korean Patent Application Laid-Open No. 2012-0030009
Official Gazette of U.S. Pat. No. 8,652,654
Official Gazette of Japanese Patent No. 5,390,728

DISCLOSURE

Technical Problem

The present specification describes a multicyclic compound including nitrogen and an organic light emitting device using the same.

Technical Solution

An exemplary embodiment of the present specification provides a compound represented by the following Formula 1:

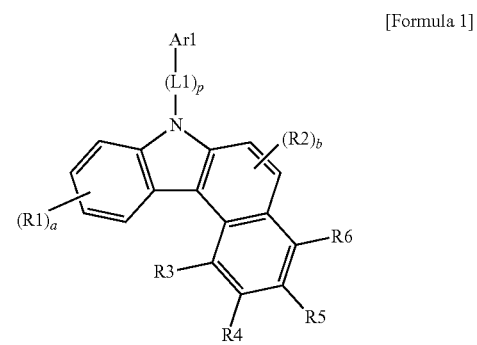

[Formula 1]

In Formula 1,
at least one of R4 and R5 is $-(L2)_q-Ar2$,
L1 and L2 are the same as or different from each other, and are each independently a direct bond; a substituted or unsubstituted alkylene; a substituted or unsubstituted arylene; or a substituted or unsubstituted heteroarylene,
Ar1 and Ar2 are the same as or different from each other, and are each independently a nitrile group; a substituted or unsubstituted aryl group; or a substituted or unsubstituted heterocyclic group,
R1 to R6 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or combine with an adjacent group to form a ring,
a is an integer of 0 to 4,
b is an integer of 0 to 2,
p and q are the same as or different from each other, and are each independently an integer of 0 to 5, and
when a, b, p, and q are each 2 or more, the structures in the parenthesis are the same as or different from each other.

Further, an exemplary embodiment of the present specification provides an organic light emitting device including: a first electrode; a second electrode provided to face the first electrode; and one or more organic material layers provided between the first electrode and the second electrode, in which one or more of the organic material layers include the compound of Formula 1.

Advantageous Effects

The compound described in the present specification may be used as a material for an organic material layer of an organic light emitting device. The compound according to at least one exemplary embodiment may improve the efficiency, achieve low driving voltage and/or improve service life characteristics in the organic light emitting device. In particular, the compound described in the present specification may be used as a material for hole injection, hole transport, hole injection and transport, light emission, electron transport, or electron injection.

DESCRIPTION OF DRAWINGS

FIG. 1 illustrates an example of an organic light emitting device composed of a substrate 1, a positive electrode 2, a light emitting layer 3, and a negative electrode 4.

FIG. 2 illustrates an example of an organic light emitting device composed of a substrate 1, a positive electrode 2, a hole injection layer 5, a hole transporting layer 6, a light emitting layer 7, an electron transporting layer 8, and a negative electrode 4.

FIG. 3 is a view illustrating MS data which are data confirming the synthesis of Intermediate 1-A-3.

FIG. 4 is a view illustrating MS data which are data confirming the synthesis of Intermediate 2-A-1.

FIG. 5 is a view illustrating MS data which are data confirming the synthesis of Compound 327.

FIG. 6 is a view illustrating MS data which are data confirming the synthesis of Compound 436.

FIG. 7 is a view illustrating NMR data which are data confirming the synthesis of Intermediate 1-A-1.

FIG. 8 is a view illustrating MS data which are data confirming the synthesis of Compound 559.

FIG. 9 is a view illustrating MS data which are data confirming the synthesis of Compound 571.

MODE FOR INVENTION

Hereinafter, the present specification will be described in more detail.

An exemplary embodiment of the present specification provides the compound represented by Formula 1.

In the present specification, ⌇ means a bond which is linked to another substituent.

Examples of the substituents will be described below, but are not limited thereto.

In the present specification, the term "substituted or unsubstituted" means that a group is unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group, or is unsubstituted or substituted with two or more substituents linked among the substituents exemplified above. For example, "the substituent to which two or more substituents are linked" may be a biphenyl group. That is, the biphenyl group may also be an aryl group, and may be interpreted as a substituent to which two phenyl groups are linked.

According to an exemplary embodiment of the present specification, the expression "substituted or unsubstituted" may preferably mean that a group is unsubstituted or substituted with one or more substituents selected from the group consisting of deuterium, a halogen group, an alkyl group, an aryl group, and a heterocyclic group.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the number of carbon atoms of a carbonyl group is not particularly limited, but is preferably 1 to 40. Specifically, the carbonyl group may be a compound having the following structures, but is not limited thereto.

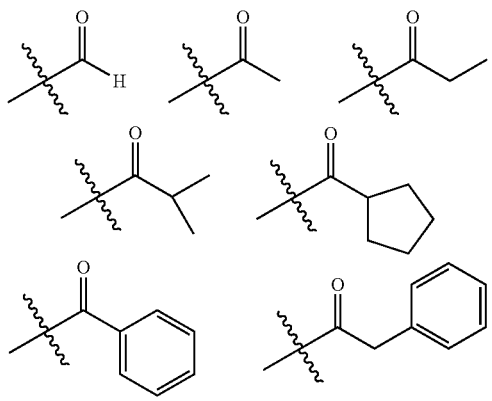

In the present specification, in an ester group, the oxygen of the ester group may be substituted with a straight-chained, branched, or cyclic alkyl group having 1 to 25 carbon atoms, or an aryl group having 6 to 25 carbon atoms. Specifically, the ester group may be a compound having the following structural formulae, but is not limited thereto.

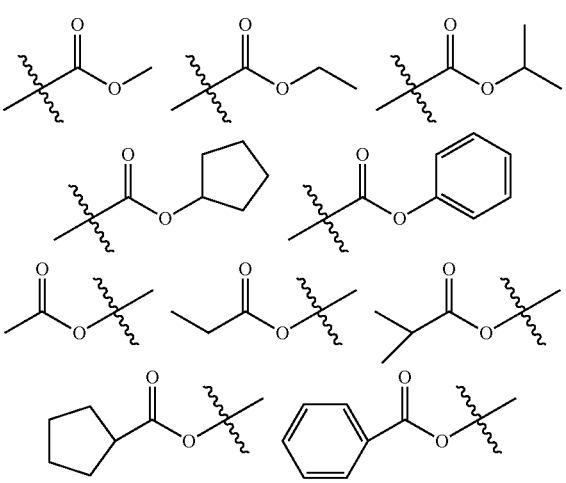

In the present specification, the number of carbon atoms of an imide group is not particularly limited, but is preferably 1 to 25. Specifically, the imide group may be a compound having the following structures, but is not limited thereto.

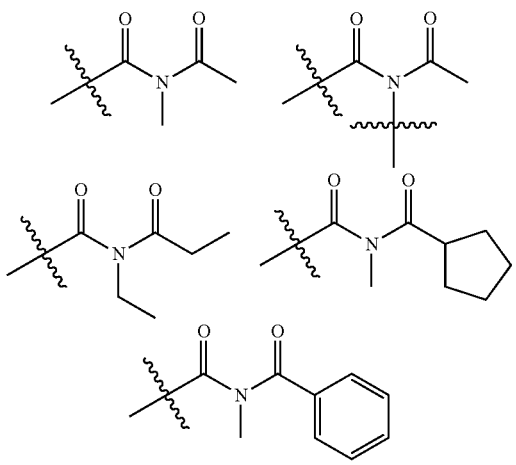

In the present specification, a silyl group may be represented by a formula of —SiRR'R", and R, R', and R" may be each hydrogen; a substituted or unsubstituted alkyl group; or a substituted or unsubstituted aryl group. Specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be represented by a formula of —BRR', and R and R' may be each hydrogen; a substituted or unsubstituted alkyl group; or a substituted or unsubstituted aryl group. Specific examples of the boron group include a trimethylboron group, a triethylboron group, a t-butyldimethylboron group, a triphenylboron group, a phenylboron group, and the like, but are not limited thereto.

In the present specification, examples of a halogen group include fluorine, chlorine, bromine or iodine.

In the present specification, the alkyl group may be straight-chained or branched, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group may be straight-chained or branched, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but has preferably 3 to 60 carbon atoms, and according to an exemplary embodiment, the number of carbon atoms of the cycloalkyl group is 3 to 30. According to still another exemplary embodiment, the number of carbon atoms of the cycloalkyl group is 3 to 20. According to yet another exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including the two or more aryl groups may include a monocyclic aryl group, a multicyclic aryl group, or both a monocyclic aryl group and a multicyclic aryl group.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group, and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic heterocyclic group or a multicyclic heterocyclic group. The heteroarylamine group including the two or more heterocyclic groups may include a monocyclic heterocyclic group, a multicyclic heterocyclic group, or both a monocyclic heterocyclic group and a multicyclic heterocyclic group.

In the present specification, the arylheteroarylamine group means an amine group substituted with an aryl group and a heterocyclic group.

In the present specification, examples of the arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group or a multicyclic aryl group. The arylphosphine group including the two or more aryl groups may include a monocyclic aryl group, a polycyclic aryl group, or both a monocyclic aryl group and a multicyclic aryl group.

In the present specification, examples of the arylamine group mean a substituted or unsubstituted monocyclic diarylamine group, a substituted or unsubstituted multicyclic diarylamine group, or a substituted or unsubstituted monocyclic and multicyclic diarylamine group.

In the present specification, the aryl group is not particularly limited, but has preferably 6 to 60 carbon atoms, and may be a monocyclic aryl group or a multicyclic aryl group. According to an exemplary embodiment, the number of carbon atoms of the aryl group is 6 to 30. According to an exemplary embodiment, the number of carbon atoms of the aryl group is 6 to 20. When the aryl group is a monocyclic aryl group, examples of the monocyclic aryl group include a phenyl group, a biphenyl group, a terphenyl group, and the like, but are not limited thereto. Examples of the multicyclic aryl group include a naphthyl group, an anthracenyl group, a phenanthryl group, a pyrenyl group, a perylenyl group, a chrysenyl group, a fluorenyl group, a triphenylene group, and the like, but are not limited thereto.

When the fluorenyl group is substituted, the fluorenyl group may be

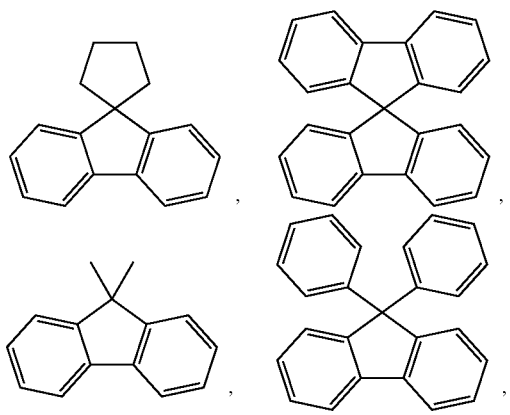

and the like. However, the group is not limited thereto.

In the present specification, the heterocyclic group is a heterocyclic group including one or more of O, N, S, P, Se, and Si as a hetero element, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazole group, a benzocarbazole group, a benzothiophene group, a dibenzothiophene group, a benzofuranyl group, a phenanthroline group, a thiazolyl group, an isooxazolyl group, an oxadiazolyl group, a thiadiazolyl group, a benzothiazolyl group, a phenothiazinyl group, a dibenzofuranyl group, and the like, but are not limited thereto.

In the present specification, the description on the above-described aryl group may be applied to an aryl group of an aryloxy group, an arylthioxy group, an arylsulfoxy group, an arylphosphine group, an aralkyl group, an aralkylamine group, an aralkenyl group, an alkylaryl group, and an arylamine group.

In the present specification, the description on the above-described alkyl group may be applied to an alkyl group of an alkylthioxy group, an alkylsulfoxy group, an aralkyl group, an aralkylamine group, an alkylaryl group, and an alkylamine group.

In the present specification, the description on the above-described heterocyclic group may be applied to a heteroaryl group and a heteroaryl in a heteroarylamine. In the present specification, the description on the above-described alkenyl group may be applied to an alkenyl group of an aralkenyl group.

In the present specification, the meaning of combining with an adjacent group to form a ring means combining with an adjacent group to form a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; and a condensed ring thereof.

In the present specification, the aliphatic hydrocarbon ring means a ring composed only of carbon and hydrogen atoms as a ring which is not an aromatic group. In the present specification, examples of the aromatic hydrocarbon ring include a phenyl group, a naphthyl group, an anthracenyl group, and the like, but are not limited thereto.

In the present specification, the aliphatic hetero ring means an aliphatic ring including one or more of hetero atoms.

In the present specification, the aromatic hetero ring means an aromatic ring including one or more of hetero atoms.

In the present specification, the aliphatic hydrocarbon ring, the aromatic hydrocarbon ring, the aliphatic hetero ring, and the aromatic hetero ring may be monocyclic or multicyclic.

According to an exemplary embodiment of the present specification, Ar2 is a substituted or unsubstituted aryl group; or a substituted or unsubstituted heterocyclic group.

According to an exemplary embodiment of the present specification, Ar2 is a substituted or unsubstituted aryl group having 6 to 50 carbon atoms; or a substituted or unsubstituted heterocyclic group having 2 to 30 carbon atoms.

According to an exemplary embodiment of the present specification, Ar2 is a substituted or unsubstituted aryl group; or a substituted or unsubstituted heterocyclic group including one or more of N, O, and S.

According to an exemplary embodiment of the present specification, Ar2 is a substituted or unsubstituted aryl group; or a substituted or unsubstituted heterocyclic group including one or more N's.

According to an exemplary embodiment of the present specification, Ar2 is a substituted or unsubstituted monocyclic to tricyclic aryl group; or a substituted or unsubstituted monocyclic to tricyclic heterocyclic group including one or more of N, O, and S.

According to an exemplary embodiment of the present specification, Ar2 is a substituted or unsubstituted monocyclic to tricyclic aryl group; or a substituted or unsubstituted monocyclic to tricyclic heterocyclic group including one or more N's.

According to an exemplary embodiment of the present specification, Ar2 is a substituted or unsubstituted monocyclic or bicyclic aryl group; or a substituted or unsubstituted heterocyclic group.

According to an exemplary embodiment of the present specification, Ar2 is a substituted or unsubstituted phenyl group; a substituted or unsubstituted biphenyl group; a substituted or unsubstituted terphenyl group; a substituted or unsubstituted naphthyl group; a substituted or unsubstituted phenanthryl group; a substituted or unsubstituted pyrenyl group; a substituted or unsubstituted perylenyl group; a substituted or unsubstituted chrysenyl group; a substituted or unsubstituted fluorenyl group; or a substituted or unsubstituted heterocyclic group.

According to an exemplary embodiment of the present specification, Ar2 is a phenyl group; a biphenyl group; a terphenyl group; a naphthyl group; a phenanthryl group; a pyrenyl group; a perylenyl group; a chrysenyl group; a fluorenyl group substituted with an alkyl group; or a substituted or unsubstituted heterocyclic group.

According to an exemplary embodiment of the present specification, Ar2 is a phenyl group which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group; a biphenyl group which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group; a naphthyl group which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group; a phenanthryl group which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group; a fluorenyl group which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group; a carbazole group which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group; a benzocarbazole group which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group; a dibenzothiophene group which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group; a dibenzofuranyl group which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group; or a triazine group which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group.

According to an exemplary embodiment of the present specification, Ar2 is a phenyl group; a biphenyl group; a naphthyl group; a phenanthryl group; a fluorenyl group substituted with an alkyl group or an aryl group; a carbazole group substituted with an aryl group; a carbazole group; a benzocarbazole group; a benzocarbazole group substituted with an aryl group; a dibenzothiophene group; a dibenzofuranyl group; or a triazine group substituted with an aryl group.

According to an exemplary embodiment of the present specification, Ar2 is a phenyl group; a biphenyl group; a naphthyl group; a phenanthryl group; a fluorenyl group substituted with an alkyl group; a carbazole group substituted with an aryl group; a carbazole group; a benzocarbazole group; a benzocarbazole group substituted with an aryl group; a dibenzothiophene group; a dibenzofuranyl group; or a triazine group substituted with an aryl group.

According to an exemplary embodiment of the present specification, Ar2 is a substituted or unsubstituted aryl group; a substituted or unsubstituted carbazole group; a substituted or unsubstituted benzocarbazole group; a substituted or unsubstituted dibenzothiophene group; a substituted or unsubstituted dibenzofuranyl group; or a substituted or unsubstituted triazine group.

According to an exemplary embodiment of the present specification, Ar2 is a substituted or unsubstituted phenyl group; a substituted or unsubstituted biphenyl group; a substituted or unsubstituted terphenyl group; a substituted or unsubstituted naphthyl group; a substituted or unsubstituted phenanthryl group; a substituted or unsubstituted pyrenyl group; a substituted or unsubstituted perylenyl group; a substituted or unsubstituted chrysenyl group; a substituted or unsubstituted fluorenyl group; a substituted or unsubstituted carbazole group; a substituted or unsubstituted benzocarbazole group; a substituted or unsubstituted dibenzothiophene group; a substituted or unsubstituted dibenzofuranyl group; or a substituted or unsubstituted triazine group.

According to an exemplary embodiment of the present specification, Ar2 is a phenyl group; a biphenyl group; a terphenyl group; a naphthyl group; a phenanthryl group; a pyrenyl group; a perylenyl group; a chrysenyl group; a fluorenyl group substituted with an alkyl group or an aryl group; a substituted or unsubstituted carbazole group; a substituted or unsubstituted benzocarbazole group; a substituted or unsubstituted dibenzothiophene group; a substituted or unsubstituted dibenzofuranyl group; or a substituted or unsubstituted triazine group.

According to an exemplary embodiment of the present specification, Ar2 is a substituted or unsubstituted heterocyclic group.

According to an exemplary embodiment of the present specification, Ar2 is a substituted or unsubstituted heterocyclic group having 2 to 30 carbon atoms.

According to an exemplary embodiment of the present specification, Ar2 is a substituted or unsubstituted monocyclic to pentacyclic heterocyclic group.

According to an exemplary embodiment of the present specification, Ar2 is a substituted or unsubstituted monocyclic to tricyclic heterocyclic group.

According to an exemplary embodiment of the present specification, Ar2 is a substituted or unsubstituted monocyclic heterocyclic group.

According to an exemplary embodiment of the present specification, Ar2 is a substituted or unsubstituted heterocyclic group including one or more of N, O, and S atoms.

According to an exemplary embodiment of the present specification, Ar2 is a substituted or unsubstituted heterocyclic group including one or more of O and S atoms.

According to an exemplary embodiment of the present specification, Ar2 is a substituted or unsubstituted heterocyclic group including one or more N atoms.

According to an exemplary embodiment of the present specification, Ar2 is a substituted or unsubstituted monocyclic to pentacyclic heterocyclic group including one or more N atoms.

According to an exemplary embodiment of the present specification, Ar2 is a substituted or unsubstituted monocyclic to tricyclic heterocyclic group including one or more N atoms.

According to an exemplary embodiment of the present specification, Ar2 is a substituted or unsubstituted pyridyl group, a substituted or unsubstituted pyrimidyl group, a substituted or unsubstituted pyrazinyl group, a substituted or unsubstituted triazine group, a substituted or unsubstituted aziridine group, a substituted or unsubstituted azaindolidine group, a substituted or unsubstituted imidazole group, a substituted or unsubstituted indole group, a substituted or unsubstituted isoindole group, a substituted or unsubstituted indazole group, a substituted or unsubstituted purine group, a substituted or unsubstituted pteridine group, a substituted or unsubstituted β-carboline group, a substituted or unsubstituted naphthyridine group, a substituted or unsubstituted quinazoline group, a substituted or unsubstituted phenothiazine group, a substituted or unsubstituted acridyl group, a substituted or unsubstituted phenanthroline group, a substituted or unsubstituted phenazine group, a substituted or unsubstituted dibenzofuranyl group, a substituted or unsubstituted dibenzothiophene group, a substituted or unsubstituted carbazole group, or a substituted or unsubstituted benzocarbazole group.

According to an exemplary embodiment of the present specification, Ar2 is a pyridyl group, a pyrimidyl group, a pyrazinyl group, a triazine group which is unsubstituted or substituted with an aryl group, an aziridine group, an azaindolidine group, an imidazole group, an indole group, an isoindole group, an indazole group, a purine group, a pteridine group, a β-carboline group, a naphthyridine group, a quinazoline group, a phenothiazine group, an acridyl group, a phenanthroline group, a phenazine group, a dibenzofuranyl group, a dibenzothiophene group, a carbazole group which is unsubstituted or substituted with an aryl group, or a benzocarbazole group which is unsubstituted or substituted with an aryl group.

According to an exemplary embodiment of the present specification, Ar2 is a substituted or unsubstituted thiophene group, a substituted or unsubstituted furan group, a substituted or unsubstituted pyrrole group, a substituted or unsubstituted imidazole group, a substituted or unsubstituted thiazole group, a substituted or unsubstituted oxazole group, a substituted or unsubstituted oxadiazole group, a substituted or unsubstituted triazole group, a substituted or unsubstituted pyridyl group, a substituted or unsubstituted bipyridyl group, a substituted or unsubstituted pyrimidyl group, a substituted or unsubstituted triazine group, a substituted or unsubstituted triazole group, a substituted or unsubstituted acridyl group, a substituted or unsubstituted pyridazine group, a substituted or unsubstituted pyrazinyl group, a substituted or unsubstituted quinolinyl group, a substituted or unsubstituted quinazoline group, a substituted or unsubstituted quinoxalinyl group, a substituted or unsubstituted phthalazinyl group, a substituted or unsubstituted pyridopyrimidinyl group, a substituted or unsubstituted pyridopyrazinyl group, a substituted or unsubstituted pyrazinopyrazinyl group, a substituted or unsubstituted isoquinoline group, a substituted or unsubstituted indole group, a substituted or unsubstituted carbazole group, a substituted or unsubstituted benzoxazole group, a substituted or unsubstituted benzoimidazole group, a substituted or unsubstituted benzothiazole group, a substituted or unsubstituted benzocarbazole group, a substituted or unsubstituted benzothiophene group, a substituted or unsubstituted dibenzothiophene group, a substituted or unsubstituted benzofuranyl group, a substituted or unsubstituted phenanthroline group, a substituted or unsubstituted thiazolyl group, a substituted or unsubstituted isooxazolyl group, a substituted or unsubstituted oxadiazolyl group, a substituted or unsubstituted thiadiazolyl group, a substituted or unsubstituted benzothiazolyl group, a substituted or unsubstituted phenothiazinyl group, or a substituted or unsubstituted dibenzofuranyl group.

According to an exemplary embodiment of the present specification, Ar2 is a thiophene group, a furan group, a pyrrole group, an imidazole group, a thiazole group, an oxazole group, an oxadiazole group, a triazole group, a pyridyl group, a bipyridyl group, a pyrimidyl group, a triazine group which is unsubstituted or substituted with an aryl group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group which is unsubstituted or substituted with an aryl group, a benzoxazole group, a benzoimidazole group, a benzothiazole group, a benzocarbazole group which is unsubstituted or substituted with an aryl group, a benzothiophene group, a dibenzothiophene group, a benzofuranyl group, a phenanthroline group, a thiazolyl group, an isooxazolyl group, an oxadiazolyl group, a thiadiazolyl group, a benzothiazolyl group, a phenothiazinyl group, or a dibenzofuranyl group.

According to an exemplary embodiment of the present specification, Ar2 in Formula 1 may be any one selected from the following structures.

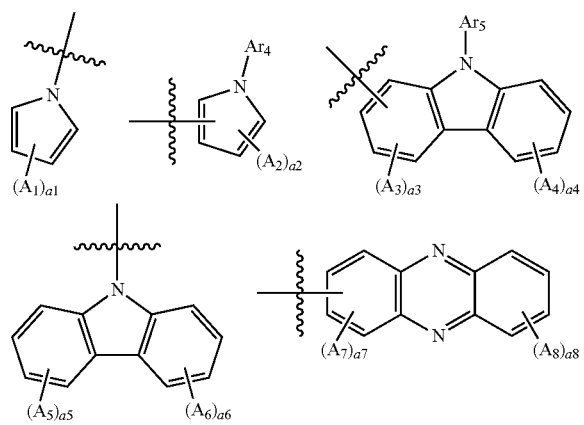

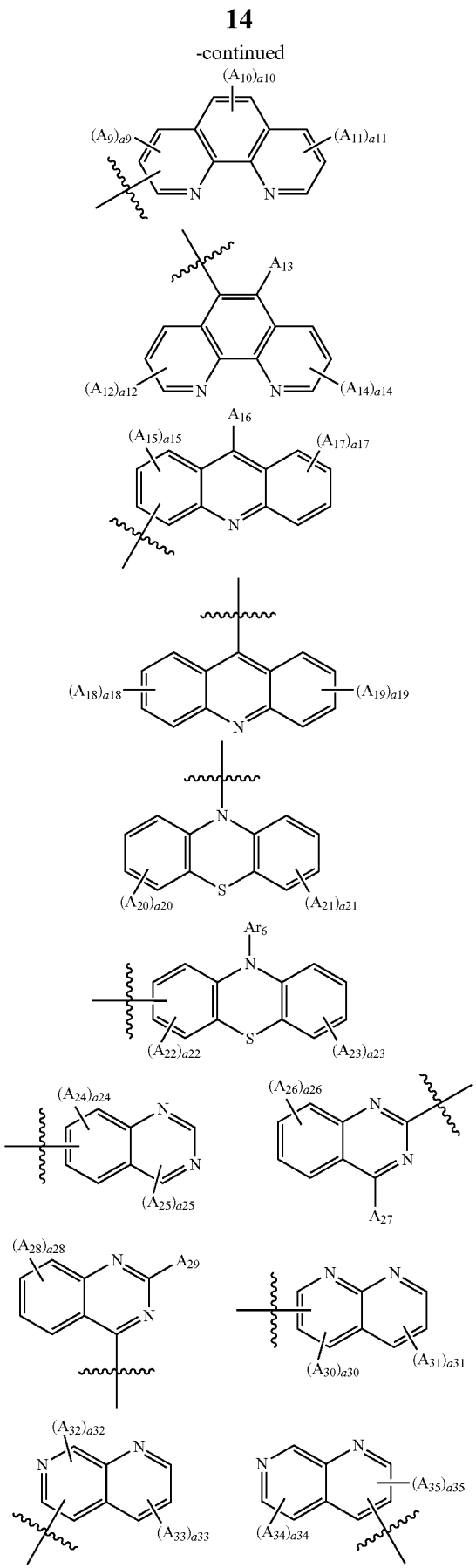

-continued

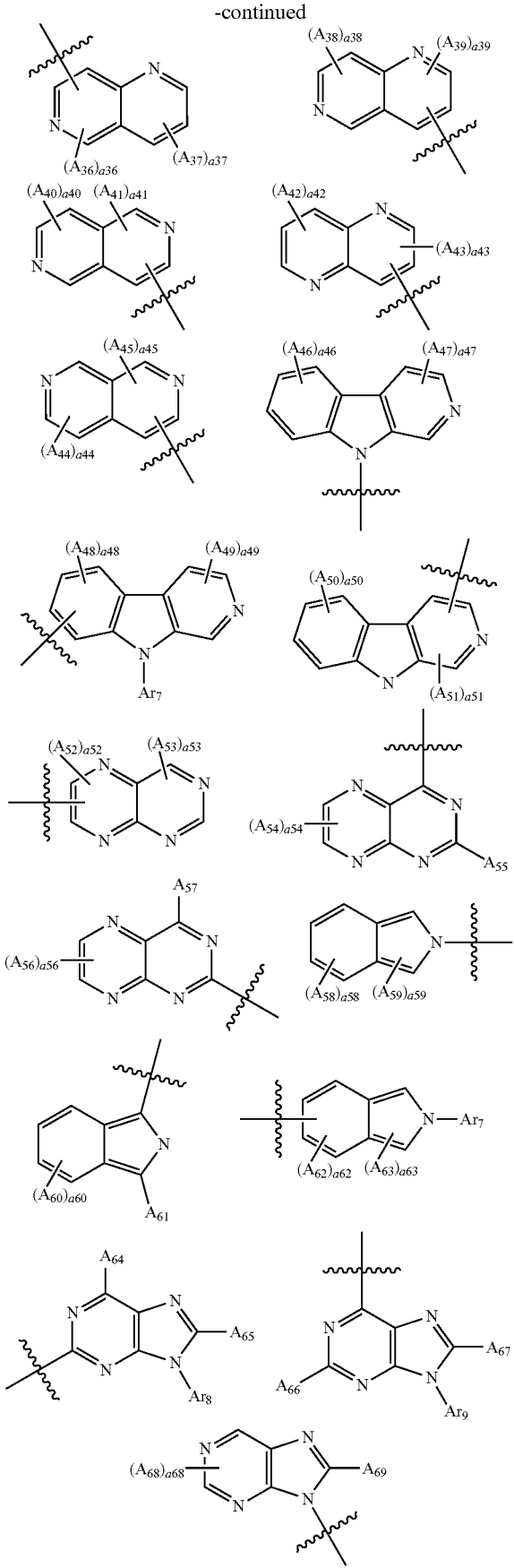

In the structural formulae, $A_1$ to $A_{89}$ are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or may combine with an adjacent group to form a ring, a1, a4, a5, a6, a8, a17, a18, a19, a20, a21, a23, a26, a28, a46, a50, a58, a60, and a71 are the same as or different from each other, and are each independently an integer of 0 to 4, a2, a3, a7, a11, a12, a14, a15, a22, a24, a31, a33, a34, a37, a38, a40, a42, a44, a47, a48, a49, a62, a73, a76, a85, a86, and a88 are the same as or different from each other, and are each independently an integer of 0 to 3, a9, a10, a25, a30, a32, a35, a36, a39, a41, a43, a45, a51, a53, a54, a56, a59, a63, a68, a70, a72, a74, a75, a84, a87, and a89 are the same as or different from each other, and are each independently an integer of 0 to 2, a52 is an integer of 0 to 1, and when a1 to a15, a17 to a26, a28, a30 to a54, a56, a58 to a60, a62, a63, a68, a70 to a72, and a84 to a89 are 2 or more, the structures in the parenthesis are the same as or different from each other.

According to an exemplary embodiment of the present specification, Ar2 is a substituted or unsubstituted carbazole group, a substituted or unsubstituted benzocarbazole group, or a substituted or unsubstituted dibenzocarbazole group.

According to an exemplary embodiment of the present specification, Ar2 is a carbazole group, a benzocarbazole group, or a dibenzocarbazole group.

According to an exemplary embodiment of the present specification, Ar2 in Formula 1 may be any one selected from the following structures.

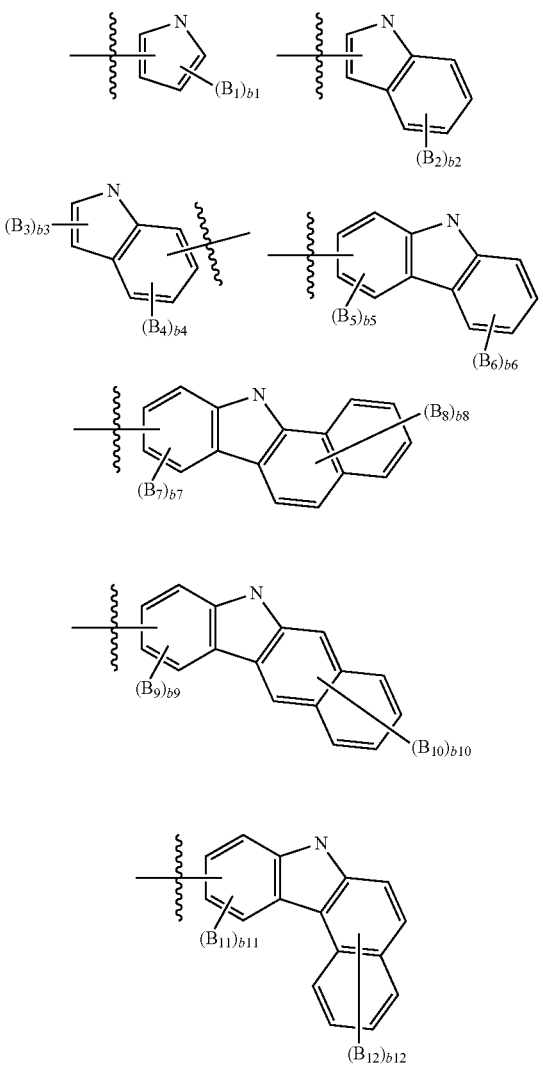

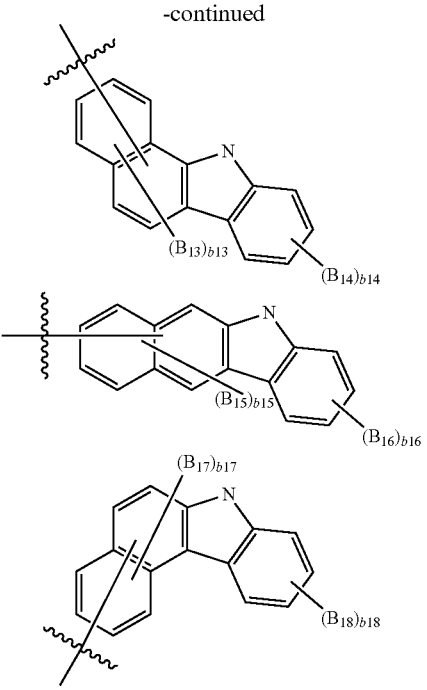

In the structural formulae, $B_1$ to $B_{18}$ are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or may combine with an adjacent group to form a ring, b1, b4, b5, b7, b9, and b11 are the same as or different from each other, and are each independently an integer of 0 to 3, b2, b6, b14, b16, and b18 are the same as or different from each other, and are each independently an integer of 0 to 4, b3 is an integer of 0 to 2, b8, b10, and b12 are the same as or different from each other, and are each independently an integer of 0 to 6, b13, b15, and b17 are the same as or different from each other, and are each independently an integer of 0 to 5, and when b1 to b18 are 2 or more, the structures in the parenthesis are the same as or different from each other.

According to an exemplary embodiment of the present specification, Ar2 in Formula 1 may be any one selected from the following structures.

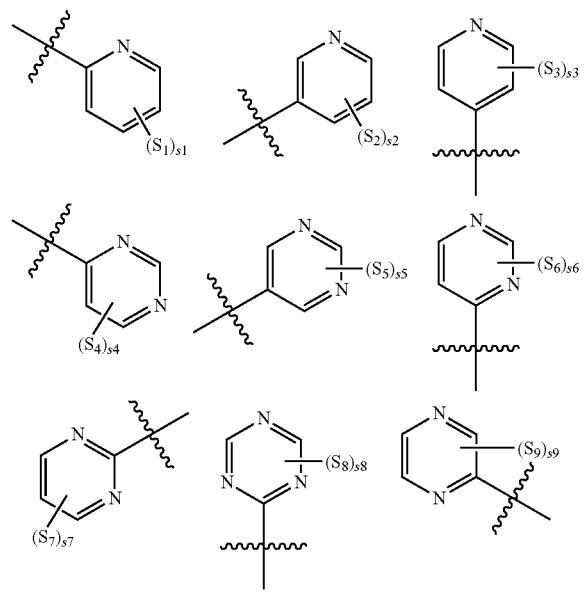

In the structural formulae, $S_1$ to $S_9$ are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or may combine with an adjacent group to form a ring, s1, s2, and s3 are the same as or different from each other, and are each independently an integer of 0 to 4, and s4, s5, s6, s7, and s9 are the same as or different from each other, and are each independently an integer of 0 to 3, s8 is an integer of 0 to 2, and when s1 is 2 or more, $S_1$'s are the same as or different from each other, when s2 is 2 or more, $S_2$'s are the same as or different from each other, when s3 is 2 or more, $S_3$'s are the same as or different from each other, when s4 is 2 or more, $S_4$'s are the same as or different from each other, when s5 is 2 or more, $S_5$'s are the same as or different from each other, when s6 is 2 or more, $S_6$'s are the same as or different from each other, when s7 is 2 or more, $S_7$'s are the same as or different from each other, when s8 is 2 or more, $S_8$'s are the same as or different from each other, and when s9 is 2 or more, $S_9$'s are the same as or different from each other.

According to an exemplary embodiment of the present specification, Ar2 is a substituted or unsubstituted monocyclic heterocyclic group including one or more N atoms.

According to an exemplary embodiment of the present specification, Ar2 is a substituted or unsubstituted pyridine group; a substituted or unsubstituted pyrimidyl group; a substituted or unsubstituted pyrazinyl group; or a substituted or unsubstituted triazine group.

According to an exemplary embodiment of the present specification, Ar2 is a pyridine group; a pyrimidyl group; a pyrazinyl group; or a triazine group.

According to an exemplary embodiment of the present specification, Ar2 is a substituted or unsubstituted heterocyclic group including one or more S atoms.

According to an exemplary embodiment of the present specification, Ar2 is a substituted or unsubstituted monocyclic to pentacyclic heterocyclic group including one or more S atoms.

According to an exemplary embodiment of the present specification, Ar2 is a substituted or unsubstituted monocyclic to tricyclic heterocyclic group including one or more S atoms.

According to an exemplary embodiment of the present specification, Ar2 is a substituted or unsubstituted thiophene group, a substituted or unsubstituted benzothiophene group, or a substituted or unsubstituted dibenzothiophene group.

According to an exemplary embodiment of the present specification, Ar2 is a thiophene group, a benzothiophene group, or a dibenzothiophene group.

According to an exemplary embodiment of the present specification, Ar2 in Formula 1 may be any one selected from the following structures.

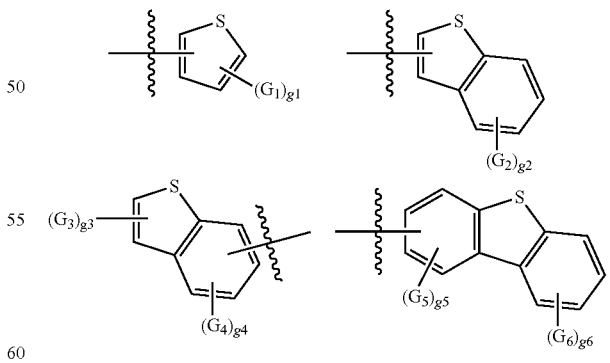

In the structural formulae, $G_1$ to $G_6$ are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or may combine with an adjacent group to form a ring, g1, g4, and g5 are the same as or different from each other, and are each independently an integer of 0 to 3, g2 and g6 are the same as or different from each other, and are each independently an integer of 0 to 4, g3 is an integer of 0 to 2, and when g1 to g6 are each 2 or more, the structures in the parenthesis are the same as or different from each other.

According to an exemplary embodiment of the present specification, Ar2 is a substituted or unsubstituted heterocyclic group including one or more O atoms.

According to an exemplary embodiment of the present specification, Ar2 is a substituted or unsubstituted furan group, a substituted or unsubstituted benzofuranyl group, or a substituted or unsubstituted dibenzofuranyl group.

According to an exemplary embodiment of the present specification, Ar2 is a furan group, a benzofuranyl group, or a dibenzofuranyl group.

According to an exemplary embodiment of the present specification, Ar2 in Formula 1 may be any one selected from the following structures.

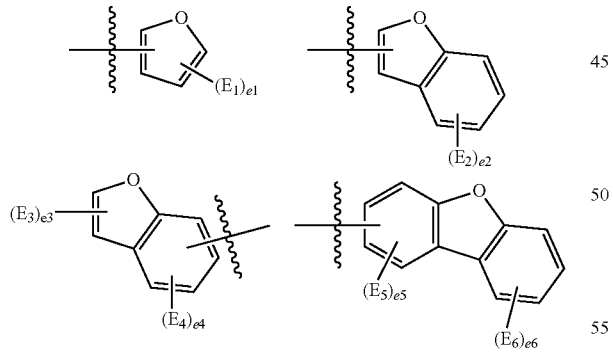

In the structural formulae, $E_1$ to $E_6$ are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or may combine with an adjacent group to form a ring, e1, e4, and e5 are the same as or different from each other, and are each independently an integer of 0 to 3, e2 and e6 are the same as or different from each other, and are each independently an integer of 0 to 4, e3 is an integer of 0 to 2, and when e1 to e6 are 2 or more, the structures in the parenthesis are the same as or different from each other.

According to an exemplary embodiment of the present specification, Formula 1 may be represented by the following Formula 2 or 3.

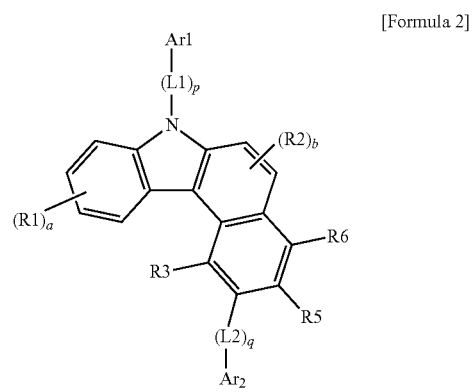

[Formula 2]

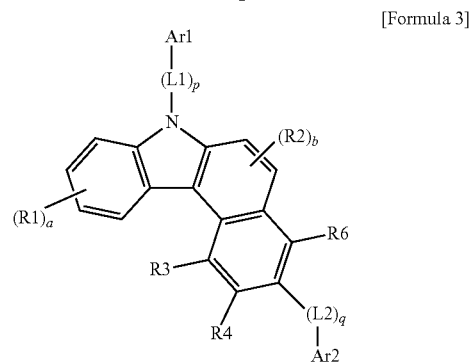

[Formula 3]

In Formulae 2 and 3, the definitions of Ar1, Ar2, R1 to R6, L1, L2, a, b, p, and q are the same as those in Formula 1.

According to an exemplary embodiment of the present specification, Formula 1 may be represented by the following Formula 4 or 5.

[Formula 4]

[Structure showing carbazole with Ar1, (L1)p, (R1)a, (R2)b, R3, R5, R6, and second carbazole with Ar3, (L2)q, (Y1)m, (Y2)n]

[Formula 5]

[Structure showing carbazole with Ar1, (L1)p, (R1)a, (R2)b, R3, R4, R6, (L2)q, and second carbazole with Ar3, (Y1)m, (Y2)n]

In Formulae 4 and 5, the definitions of Ar1, R1 to R6, L1, L2, a, b, p, and q are the same as those in Formula 1, the definition of Ar3 is the same as that of Ar1, Y1 and Y2 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or combine with an adjacent group to form a ring, m is an integer of 0 to 3 and n is an integer of 0 to 4, and when m and n are each 2 or more, the structures in the parenthesis are the same as or different from each other.

According to an exemplary embodiment of the present specification, Formula 1 may be represented by the following Formula 6 or 7.

[Formula 6]

[Structure showing carbazole with Ar1, (L1)p, (R1)a, (R2)b, R3, R5, R6, and second carbazole Ar3, (Y1)m, (Y2)n]

[Formula 7]

[Structure showing carbazole with Ar1, (L1)p, (R1)a, (R2)b, R3, R4, R6, and second carbazole Ar3, (Y1)m, (Y2)n]

In Formulae 6 and 7, the definitions of Ar1, R1 to R6, L1, a, b, and p are the same as those in Formula 1, the definition of Ar3 is the same as that of Ar1, Y1 and Y2 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or combine with an adjacent group to form a ring, m is an integer or 0 to 3 and n is an integer of 0 to 4, and when m and n are each 2 or more, the structures in the parenthesis are the same as or different from each other.

According to an exemplary embodiment of the present specification, Formula 1 may be represented by the following Formula 8 or 9.

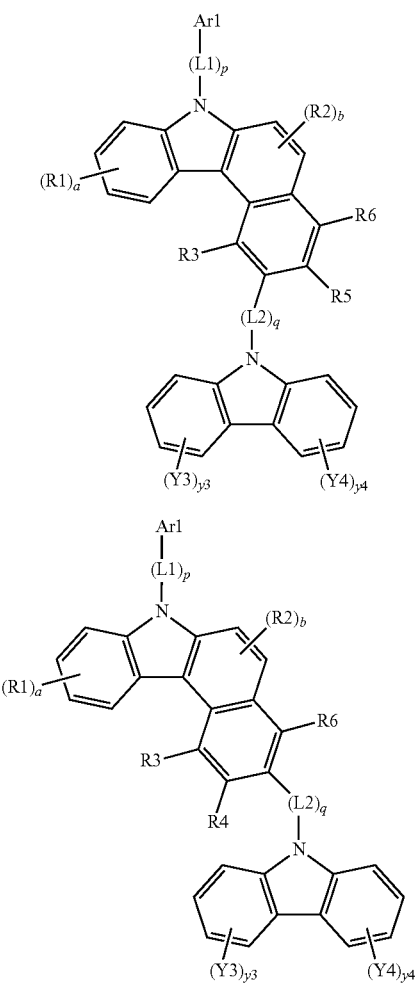

[Formula 8]

[Formula 9]

In Formulae 8 and 9, the definitions of Ar1, R1 to R6, L1, L2, a, b, p, and q are the same as those in Formula 1, Y3 and Y4 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or combine with an adjacent group to form a ring, y3 and y4 are the same as or different from each other, and are each independently an integer of 0 to 4, and when y3 and y4 are each 2 or more, the structures in the parenthesis are the same as or different from each other.

According to an exemplary embodiment of the present specification, Formula 1 may be represented by the following Formula 10 or 11.

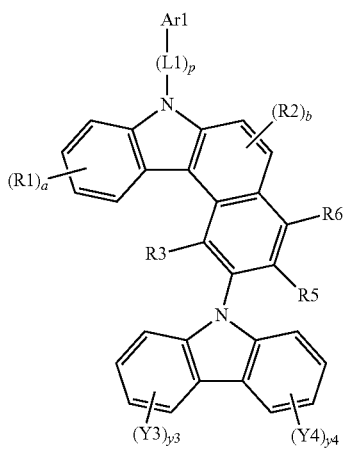

[Formula 10]

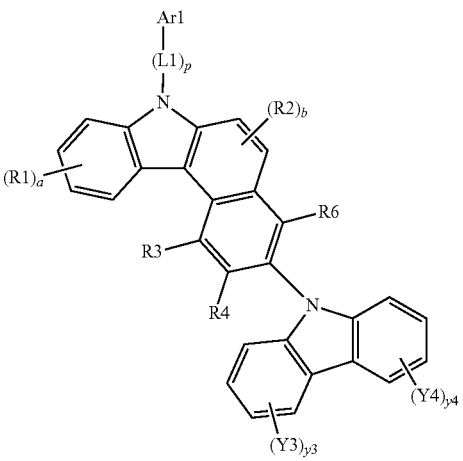

[Formula 11]

In Formulae 10 and 11, the definitions of Ar1, R1 to R6, L1, a, b, and p are the same as those in Formula 1, Y3 and Y4 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or combine with an adjacent group to form a ring, y3 and y4 are the same as or different from each other, and are each independently an integer of 0 to 4, and when y3 and y4 are each 2 or more, the structures in the parenthesis are the same as or different from each other.

According to an exemplary embodiment of the present specification, Formula 1 may be represented by the following Formula 12 or 13.

[Formula 12]

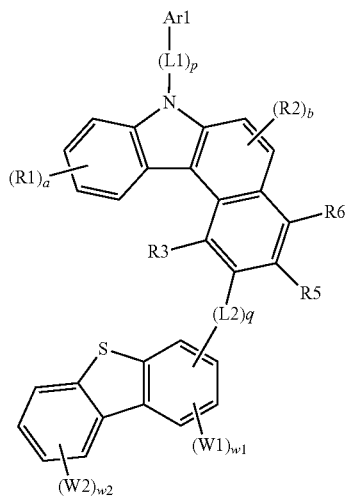

[Formula 13]

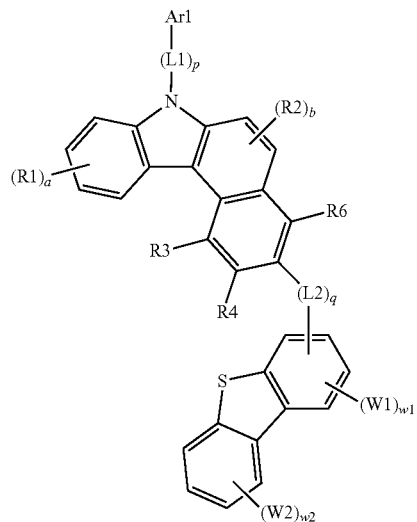

In Formulae 12 and 13, the definitions of Ar1, R1 to R6, L1, L2, a, b, p, and q are the same as those in Formula 1, W1 and W2 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or combine with an adjacent group to form a ring, w1 is an integer of 0 to 3, w2 is an integer of 0 to 4, and when w1 and w2 are each 2 or more, the structures in the parenthesis are the same as or different from each other.

According to an exemplary embodiment of the present specification, Formula 1 may be represented by the following Formula 14 or 15.

[Formula 14]

[Formula 15]

In Formulae 14 and 15, the definitions of Ar1, R1 to R6, L1, a, b, and p are the same as those in Formula 1, W1 and W2 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or combine with an adjacent group to form a ring, w1 is an integer of 0 to 3, w2 is an integer of 0 to 4, and when w1 and w2 are each 2 or more, the structures in the parenthesis are the same as or different from each other.

According to an exemplary embodiment of the present specification, Formula 1 may be represented by the following Formula 16 or 17.

[Formula 16]

[Formula 17]

In Formulae 16 and 17, the definitions of Ar1, R1 to R6, L1, L2, a, b, p, and q are the same as those in Formula 1, T1 and T2 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or combine with an adjacent group to form a ring, t1 is an integer of 0 to 3, t2 is an integer of 0 to 4, and when t1 and t2 are each 2 or more, the structures in the parenthesis are the same as or different from each other.

According to an exemplary embodiment of the present specification, Formula 1 may be represented by the following Formula 18 or 19.

[Formula 18]

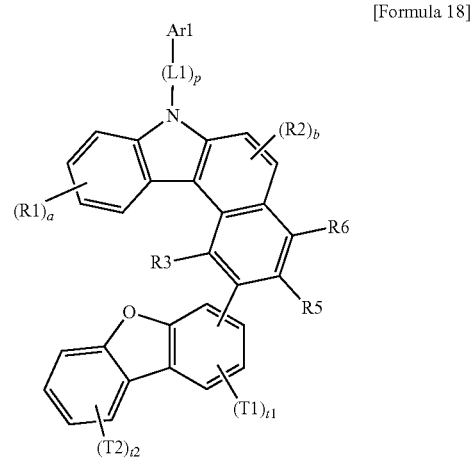

[Formula 19]

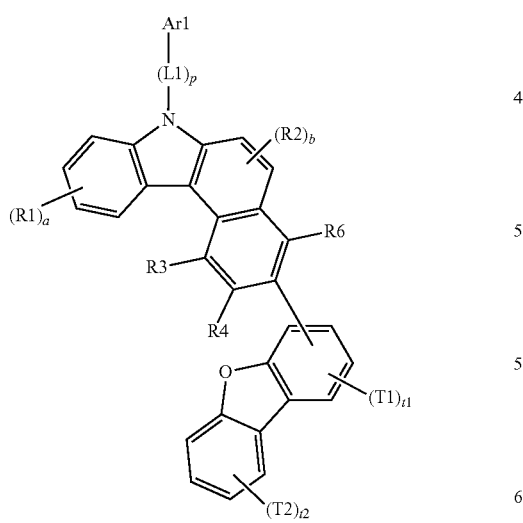

In Formulae 18 and 19, the definitions of Ar1, R1 to R6, L1, a, b, and p are the same as those in Formula 1, T1 and T2 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or combine with an adjacent group to form a ring, t1 is an integer of 0 to 3, t2 is an integer of 0 to 4, and when t1 and t2 are each 2 or more, the structures in the parenthesis are the same as or different from each other.

According to an exemplary embodiment of the present specification, Formula 1 may be represented by the following Formula 20 or 21.

[Formula 20]

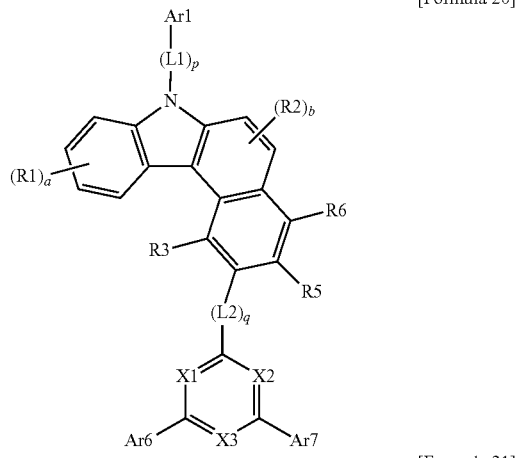

[Formula 21]

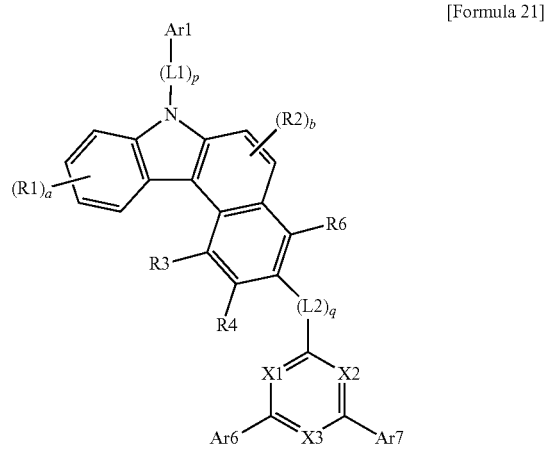

In Formulae 20 and 21, the definitions of Ar1, R1 to R6, L1, L2, a, b, p, and q are the same as those in Formula 1, Ar6 and Ar7 are the same as or different from each other, and are each independently a nitrile group; a substituted or unsubstituted aryl group; or a substituted or unsubstituted heterocyclic group, X1 to X3 are the same as or different from each other, and are each independently CR or N, and R is hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or combines with an adjacent group to form a ring.

According to an exemplary embodiment of the present specification, Formula 1 may be represented by the following Formula 22 or 23.

[Formula 22]

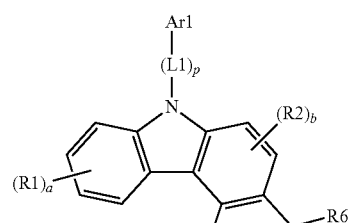

[Formula 23]

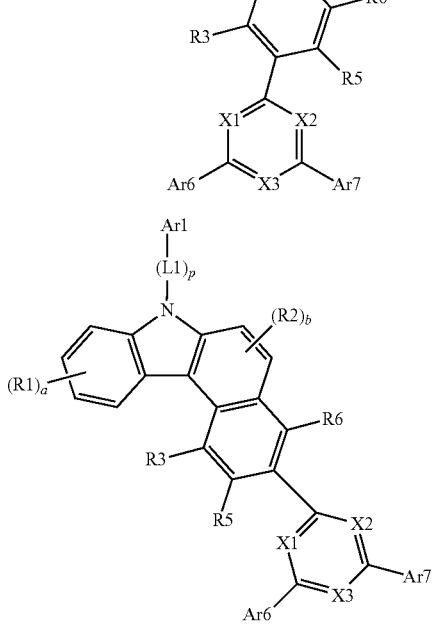

In Formulae 22 and 23, the definitions of Ar1, R1 to R6, L1, a, b, and p are the same as those in Formula 1, Ar6 and Ar7 are the same as or different from each other, and are each independently a nitrile group; a substituted or unsubstituted aryl group; or a substituted or unsubstituted heterocyclic group, X1 to X3 are the same as or different from each other, and are each independently CR or N, and R is hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or combines with an adjacent group to form a ring.

According to an exemplary embodiment of the present specification, Ar1 is a substituted or unsubstituted aryl group; or a substituted or unsubstituted heterocyclic group.

According to an exemplary embodiment of the present specification, Ar1 is an aryl group which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group; or a heterocyclic group which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group.

According to an exemplary embodiment of the present specification, Ar1 is a substituted or unsubstituted aryl group; or a substituted or unsubstituted heterocyclic group including one or more of N, O, and S.

According to an exemplary embodiment of the present specification, Ar1 is a substituted or unsubstituted aryl group; or a substituted or unsubstituted heterocyclic group including one or more N's.

According to an exemplary embodiment of the present specification, Ar1 is a substituted or unsubstituted monocyclic to tricyclic aryl group; or a substituted or unsubstituted monocyclic to tricyclic heterocyclic group.

According to an exemplary embodiment of the present specification, Ar1 is a substituted or unsubstituted monocyclic to tricyclic aryl group; or a substituted or unsubstituted heterocyclic group including one or more N's.

According to an exemplary embodiment of the present specification, Ar1 is a substituted or unsubstituted monocyclic to tricyclic aryl group; or a substituted or unsubstituted monocyclic to tricyclic heterocyclic group including one or more N's.

According to an exemplary embodiment of the present specification, Ar1 is a substituted or unsubstituted phenyl group; a substituted or unsubstituted naphthyl group; a substituted or unsubstituted biphenyl group; a substituted or unsubstituted terphenyl group; a substituted or unsubstituted phenanthryl group; a substituted or unsubstituted fluorenyl group; a substituted or unsubstituted pyridyl group; a substituted or unsubstituted pyrimidyl group; a substituted or unsubstituted pyrazinyl group; a substituted or unsubstituted triazine group; a substituted or unsubstituted quinazoline group; or a substituted or unsubstituted imidazole group.

According to an exemplary embodiment of the present specification, Ar1 is a phenyl group; a naphthyl group; a biphenyl group; a terphenyl group; a phenanthryl group; a fluorenyl group; a pyridyl group; a pyrimidyl group which is substituted with an aryl group; a pyrazinyl group; a triazine group substituted with an aryl group; a quinazoline group which is unsubstituted or substituted with an aryl group; or an imidazole group.

According to an exemplary embodiment of the present specification, L1 and L2 are the same as or different from each other, and are each independently a direct bond; a substituted or unsubstituted alkylene; a substituted or unsubstituted arylene; or a substituted or unsubstituted heteroarylene.

According to an exemplary embodiment of the present specification, L1 is a direct bond; a substituted or unsubstituted alkylene; a substituted or unsubstituted arylene; or a substituted or unsubstituted heteroarylene.

According to an exemplary embodiment of the present specification, L1 is a direct bond; a substituted or unsubstituted alkylene; a substituted or unsubstituted phenylene; a substituted or unsubstituted biphenylylene; a substituted or unsubstituted terphenylene; a substituted or unsubstituted naphthylene; a substituted or unsubstituted anthracenylene; a substituted or unsubstituted phenanthrylene; a substituted or unsubstituted pyrenylene; a substituted or unsubstituted perylenylene; a substituted or unsubstituted chrysenylene; a substituted or unsubstituted fluorenylene; or a substituted or unsubstituted heteroarylene.

According to an exemplary embodiment of the present specification, L1 is a direct bond; a substituted or unsubstituted arylene; or a substituted or unsubstituted heteroarylene including one or more of N, O, and S.

According to an exemplary embodiment of the present specification, L1 is a direct bond; a substituted or unsubstituted arylene; or a substituted or unsubstituted heteroarylene including one or more N's.

According to an exemplary embodiment of the present specification, L1 is a substituted or unsubstituted arylene; or a substituted or unsubstituted heteroarylene.

According to an exemplary embodiment of the present specification, L1 is a substituted or unsubstituted monocyclic to tricyclic arylene; or a substituted or unsubstituted monocyclic to tricyclic heteroarylene.

According to an exemplary embodiment of the present specification, L1 is a substituted or unsubstituted monocyclic to tricyclic arylene; or a substituted or unsubstituted monocyclic to tricyclic heteroarylene including one or more of N, O, and S.

According to an exemplary embodiment of the present specification, L1 is a substituted or unsubstituted monocyclic to tricyclic arylene; or a substituted or unsubstituted monocyclic to tricyclic heteroarylene including one or more N's.

According to an exemplary embodiment of the present specification, L1 is a substituted or unsubstituted phenylene; a substituted or unsubstituted divalent pyridyl group; a substituted or unsubstituted divalent pyrimidyl group; a substituted or unsubstituted divalent pyrazinyl group; a substituted or unsubstituted divalent triazine group; or a substituted or unsubstituted divalent imidazole group.

According to an exemplary embodiment of the present specification, L1 is phenylene; a divalent pyridyl group; a divalent pyrimidyl group; a divalent pyrazinyl group; a divalent triazine group; or a divalent imidazole group.

According to an exemplary embodiment of the present specification, L1 is a direct bond; a substituted or unsubstituted alkylene; or a substituted or unsubstituted arylene.

According to an exemplary embodiment of the present specification, L1 is a direct bond; a substituted or unsubstituted alkylene; a substituted or unsubstituted phenylene; a substituted or unsubstituted biphenylylene; a substituted or unsubstituted terphenylene; a substituted or unsubstituted naphthylene; a substituted or unsubstituted anthracenylene; a substituted or unsubstituted phenanthrylene; a substituted or unsubstituted pyrenylene; a substituted or unsubstituted perylenylene; a substituted or unsubstituted chrysenylene; or a substituted or unsubstituted fluorenylene.

According to an exemplary embodiment of the present specification, L1 is a direct bond.

According to an exemplary embodiment of the present specification, L2 is a direct bond; a substituted or unsubstituted alkylene; a substituted or unsubstituted arylene; or a substituted or unsubstituted heteroarylene.

According to an exemplary embodiment of the present specification, L2 is a direct bond; a substituted or unsubstituted alkylene; a substituted or unsubstituted monocyclic or bicyclic arylene; or a substituted or unsubstituted heteroarylene.

According to an exemplary embodiment of the present specification, L2 is a direct bond; a substituted or unsubstituted arylene; or a substituted or unsubstituted heteroarylene.

According to an exemplary embodiment of the present specification, L2 is a direct bond; a substituted or unsubstituted alkylene; a substituted or unsubstituted phenylene; a substituted or unsubstituted biphenylylene; a substituted or unsubstituted terphenylene; a substituted or unsubstituted naphthylene; a substituted or unsubstituted phenanthrylene; a substituted or unsubstituted pyrenylene; a substituted or unsubstituted perylenylene; a substituted or unsubstituted chrysenylene; a substituted or unsubstituted fluorenylene; or a substituted or unsubstituted heteroarylene.

According to an exemplary embodiment of the present specification, L2 is a direct bond; a substituted or unsubstituted alkylene; phenylene; biphenylylene; terphenylene; naphthylene; phenanthrylene; pyrenylene; perylenylene; chrysenylene; fluorenylene; or a substituted or unsubstituted heteroarylene.

According to an exemplary embodiment of the present specification, L2 is a direct bond; a substituted or unsubstituted arylene; or a substituted or unsubstituted heteroarylene including one or more of N, O, and S.

According to an exemplary embodiment of the present specification, L2 is a direct bond; a substituted or unsubstituted arylene; or a substituted or unsubstituted heteroarylene including one or more N's.

According to an exemplary embodiment of the present specification, L2 is a a substituted or unsubstituted arylene; or a substituted or unsubstituted heteroarylene.

According to an exemplary embodiment of the present specification, L2 is a substituted or unsubstituted monocyclic to tricyclic arylene; or a substituted or unsubstituted monocyclic to tricyclic heteroarylene.

According to an exemplary embodiment of the present specification, L2 is a substituted or unsubstituted monocyclic to tricyclic arylene; or a substituted or unsubstituted monocyclic to tricyclic heteroarylene including one or more of N, O, and S.

According to an exemplary embodiment of the present specification, L2 is a substituted or unsubstituted monocyclic to tricyclic arylene; or a substituted or unsubstituted monocyclic to tricyclic heteroarylene including one or more N's.

According to an exemplary embodiment of the present specification, L2 is a direct bond; a substituted or unsubstituted alkylene; a substituted or unsubstituted phenylene; a substituted or unsubstituted biphenylylene; a substituted or unsubstituted terphenylene; a substituted or unsubstituted naphthylene; a substituted or unsubstituted phenanthrylene; a substituted or unsubstituted pyrenylene; a substituted or unsubstituted perylenylene; a substituted or unsubstituted chrysenylene; a substituted or unsubstituted fluorenylene; a substituted or unsubstituted divalent carbazole group; a substituted or unsubstituted divalent benzocarbazole group; a substituted or unsubstituted divalent dibenzofuranyl group; a substituted or unsubstituted dibenzothiophene group; or a substituted or unsubstituted divalent triazine group.

According to an exemplary embodiment of the present specification, L2 is a direct bond; a substituted or unsubstituted phenylene; a substituted or unsubstituted divalent carbazole group; a substituted or unsubstituted divalent benzocarbazole group; a substituted or unsubstituted divalent dibenzofuranyl group; a substituted or unsubstituted dibenzothiophene group; or a substituted or unsubstituted divalent triazine group.

According to an exemplary embodiment of the present specification, L2 is a direct bond; a substituted or unsubstituted alkylene; or a substituted or unsubstituted arylene.

According to an exemplary embodiment of the present specification, L2 is a direct bond; or an arylene which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group.

According to an exemplary embodiment of the present specification, L2 is a direct bond; or an arylene which is unsubstituted or substituted with one or more substituents selected from the group consisting of deuterium, a halogen group, an alkyl group, an aryl group, and a heterocyclic group.

According to an exemplary embodiment of the present specification, L2 is a direct bond; a phenylene which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group; or a naphthalene which is unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group.

According to an exemplary embodiment of the present specification, L2 may be any one selected from the following structures.

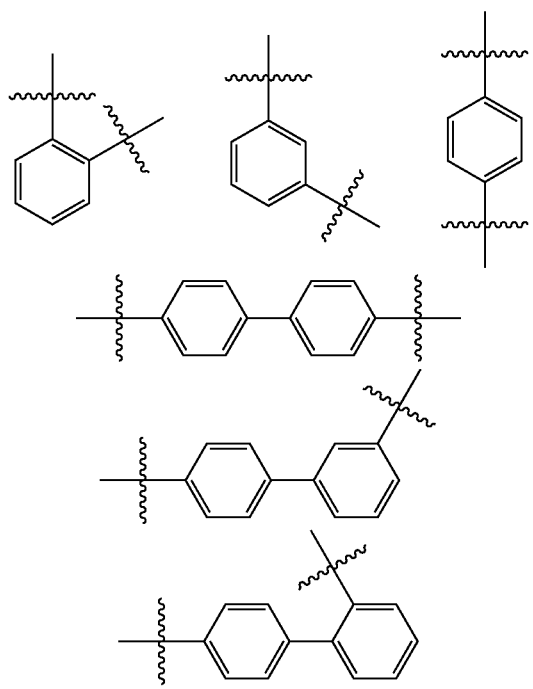

-continued

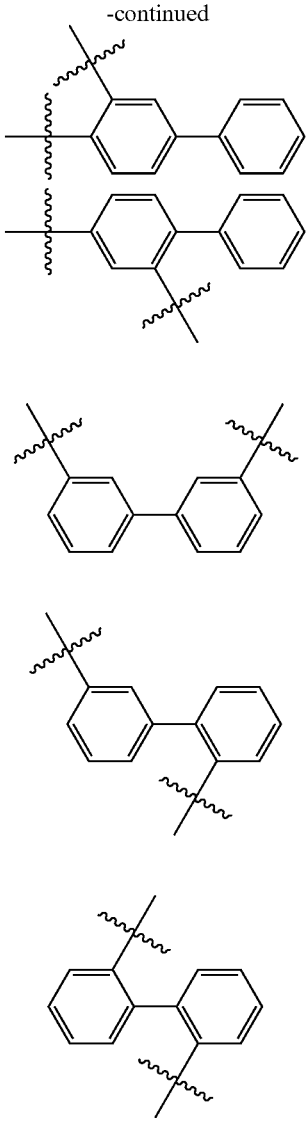

The structures may be unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group.

According to an exemplary embodiment of the present specification, L2 is a direct bond; a phenylene which is unsubstituted or substituted with one or more substituents selected from the group consisting of deuterium, a halogen group, an alkyl group, an aryl group, and a heterocyclic group; or a naphthalene which is unsubstituted or substituted with one or more substituents selected from the group consisting of deuterium, a halogen group, an alkyl group, an aryl group, and a heterocyclic group.

According to an exemplary embodiment of the present specification, L2 is a direct bond; phenylene; or naphthalene.

According to an exemplary embodiment of the present specification, L2 is a direct bond.

According to an exemplary embodiment of the present specification, p is an integer of 0 to 2.

According to an exemplary embodiment of the present specification, q is an integer of 0 to 2.

According to an exemplary embodiment of the present specification, groups which are not -(L2)$_q$-Ar2 in R1, R2, and R3 to R6 are the same as or different from each other, and are each independently hydrogen; deuterium; a halogen group; a nitrile group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or two or more adjacent substituents combine with each other to form a substituted or unsubstituted hydrocarbon ring or heterocyclic ring.

According to an exemplary embodiment of the present specification, groups which are not -(L2)$_q$-Ar2 in R1, R2, and R3 to R6 are a substituted or unsubstituted alkyl group; a substituted or unsubstituted aryl group; or a substituted or unsubstituted heterocyclic group, or two or more adjacent substituents combine with each other to form a substituted or unsubstituted hydrocarbon ring or heterocyclic ring.

According to an exemplary embodiment of the present specification, groups which are not -(L2)$_q$-Ar2 in R1, R2, and R3 to R6 are a substituted or unsubstituted alkyl group; a substituted or unsubstituted aryl group; or a substituted or unsubstituted heterocyclic group.

According to an exemplary embodiment of the present specification, groups which are not -(L2)$_q$-Ar2 in R1, R2, and R3 to R6 are a substituted or unsubstituted alkyl group having 1 to 6 carbon atoms; a substituted or unsubstituted aryl group having 6 to 50 carbon atoms; or a substituted or unsubstituted heterocyclic group having 3 to 30 carbon atoms.

According to an exemplary embodiment of the present specification, groups which are not -(L2)$_q$-Ar2 in R1, R2, and R3 to R6 are a substituted or unsubstituted alkyl group having 1 to 6 carbon atoms; a substituted or unsubstituted aryl group having 6 to 20 carbon atoms; or a substituted or unsubstituted heterocyclic group having 3 to 20 carbon atoms.

According to an exemplary embodiment of the present specification, groups which are not -(L2)$_q$-Ar2 in R1, R2, and R3 to R6 are a substituted or unsubstituted alkyl group having 1 to 6 carbon atoms; a substituted or unsubstituted monocyclic or bicyclic aryl group; or a substituted or unsubstituted monocyclic or bicyclic heterocyclic group.

According to an exemplary embodiment of the present specification, groups which are not -(L2)$_q$-Ar2 in R1, R2, and R3 to R6 are hydrogen.

According to an exemplary embodiment of the present specification, R1 and R2 are hydrogen.

According to an exemplary embodiment of the present invention, the compound of Formula 1 may be selected from the following compounds.

1
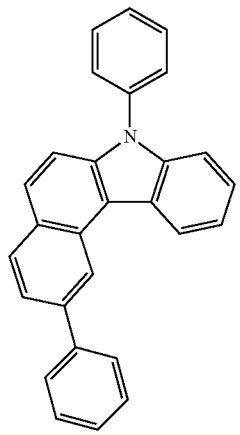
2
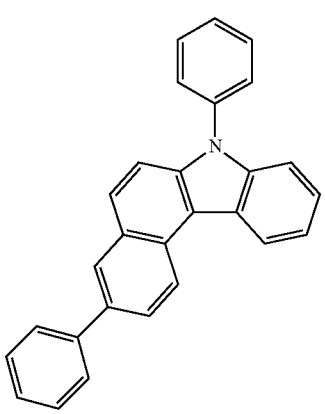
3
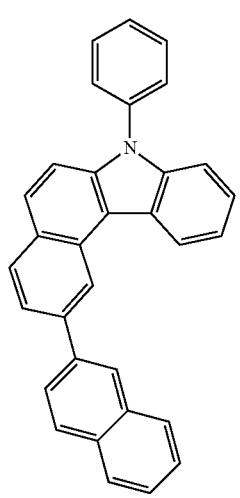
4
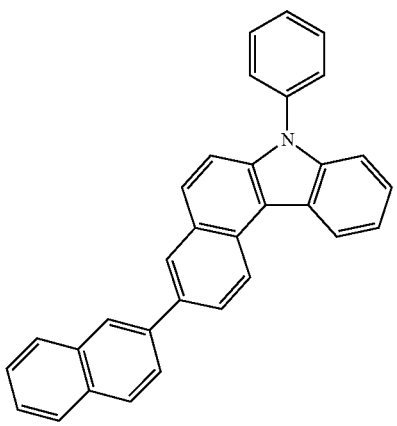
5
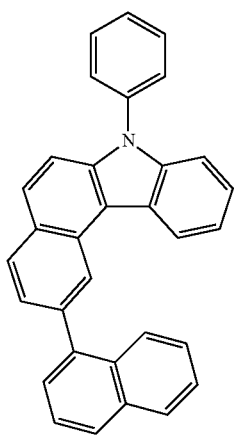
6
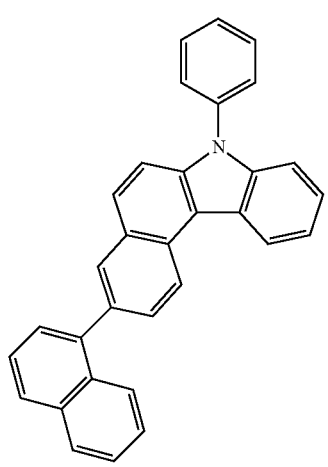

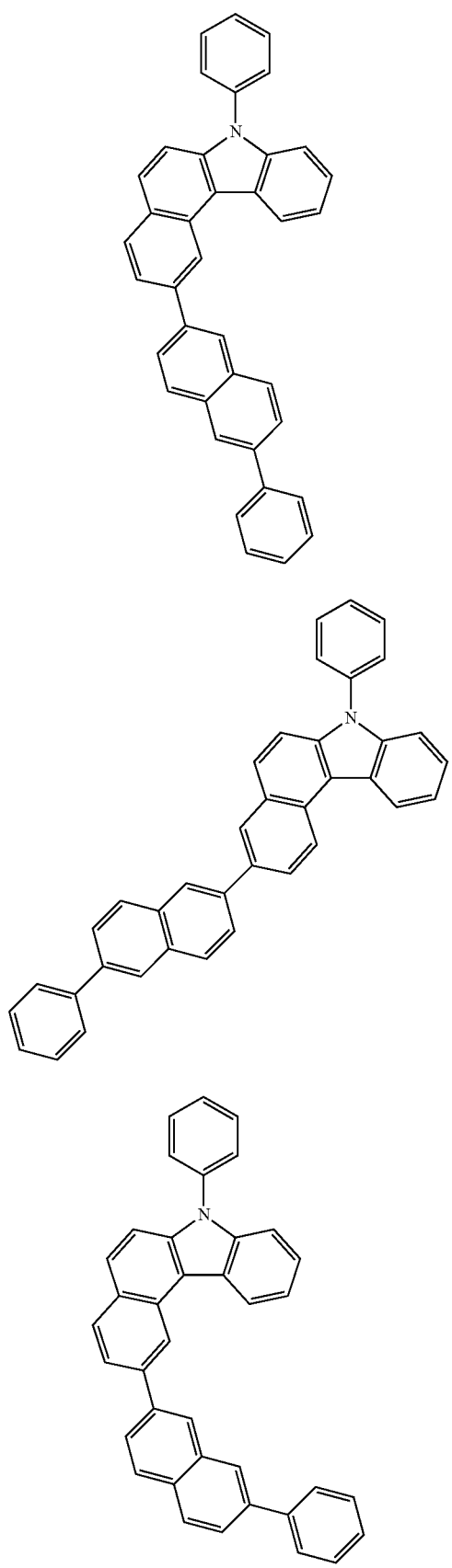
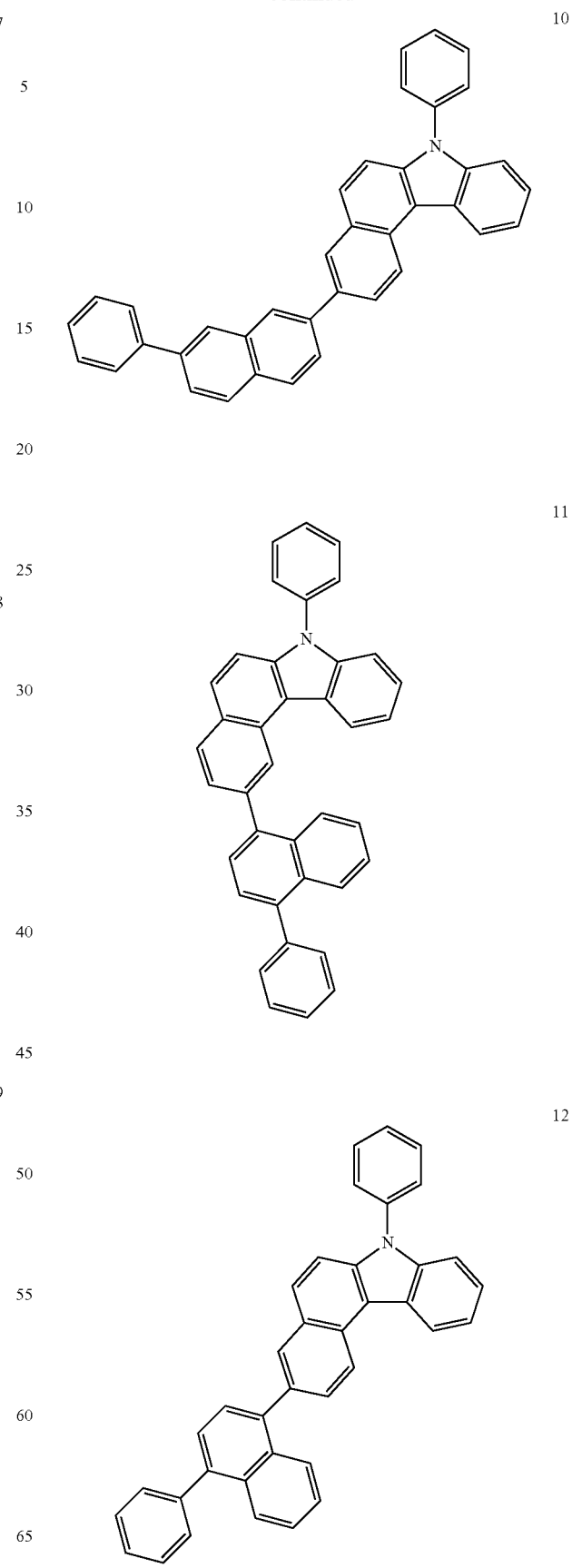

13
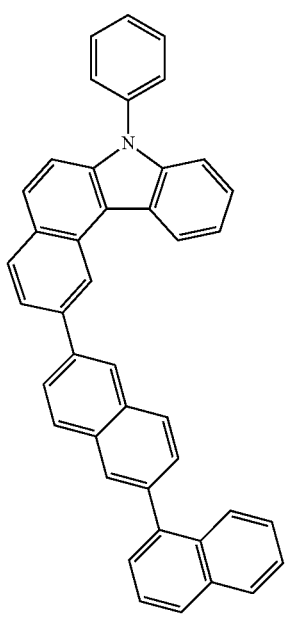
14
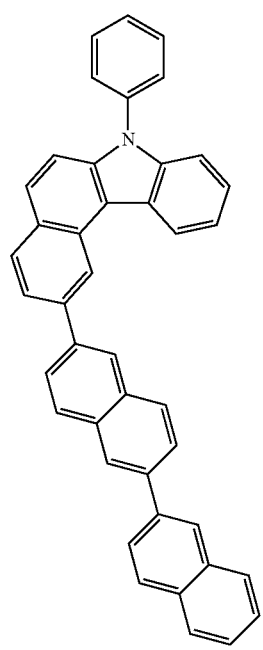
15
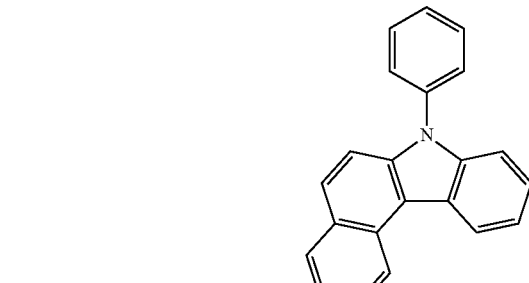
16
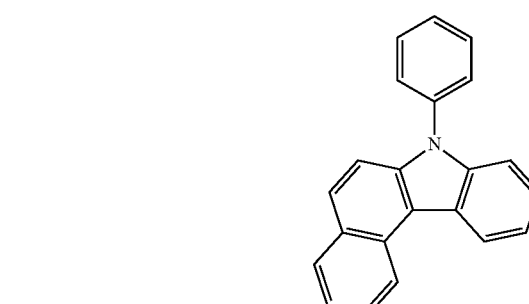
17
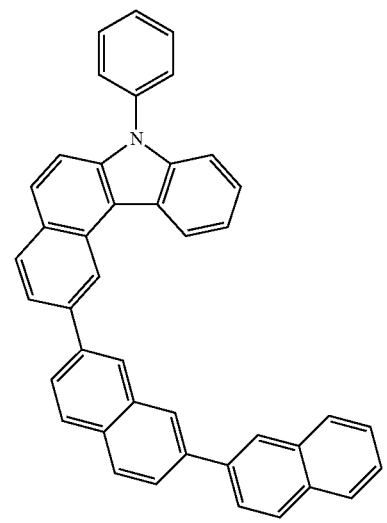

18
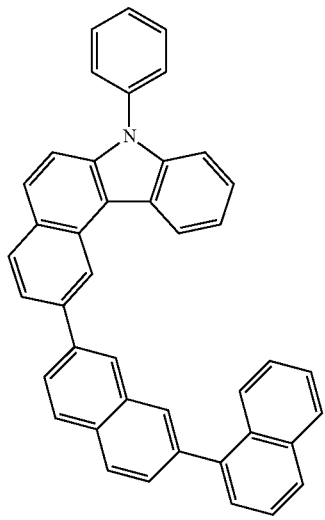
19
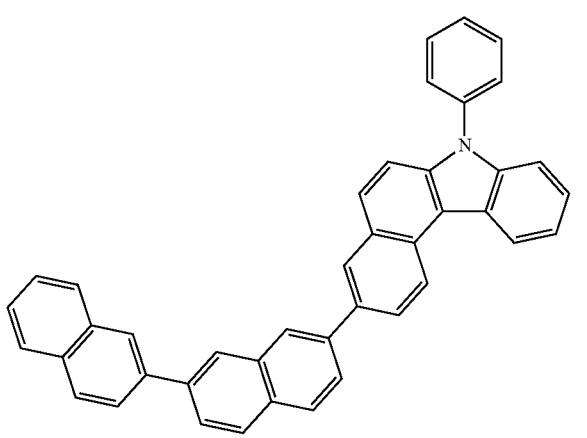
20
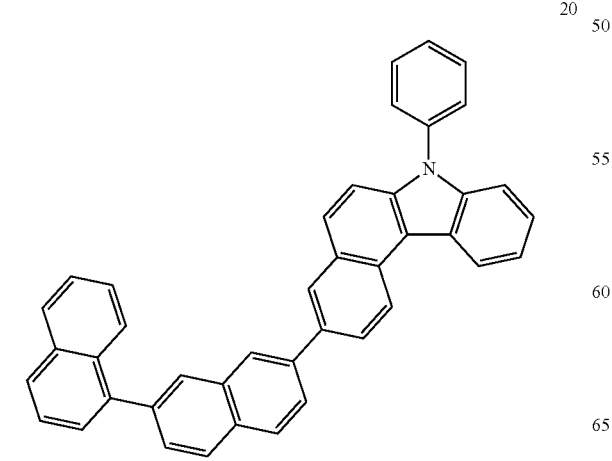
21
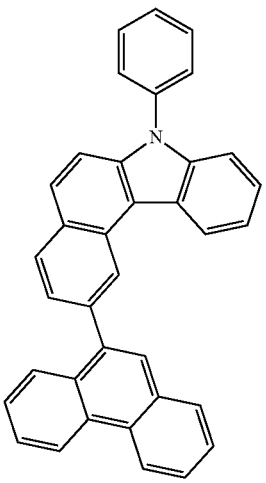
22
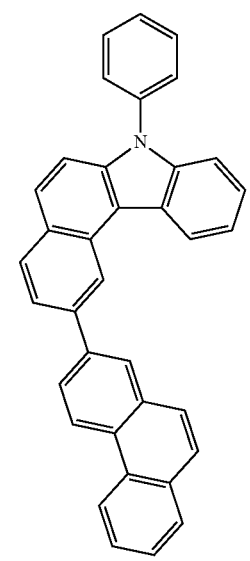
23
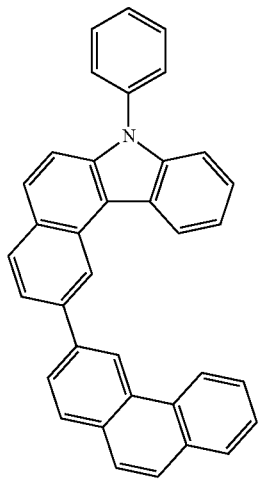

24
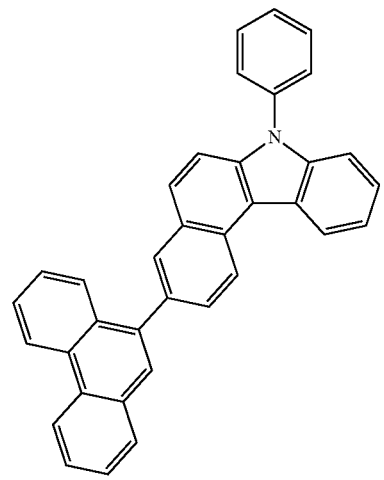
25
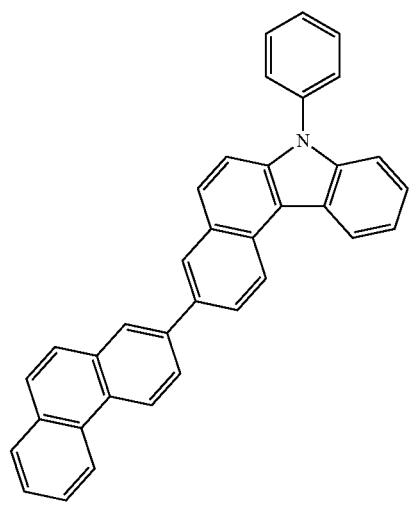
26
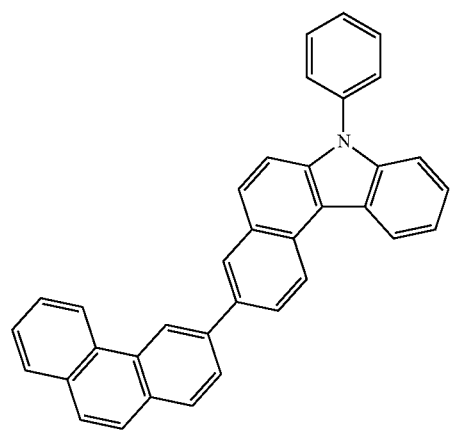
27
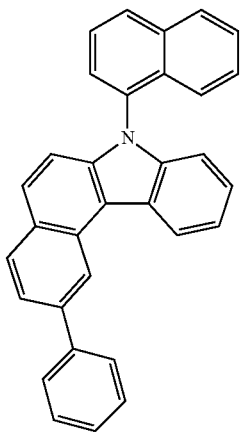
28
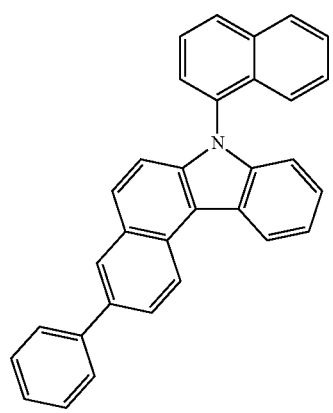
29
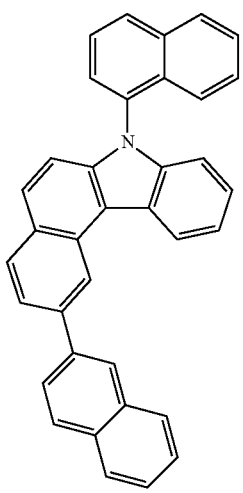

30
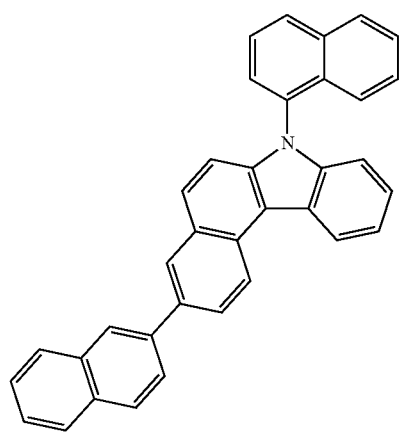
31
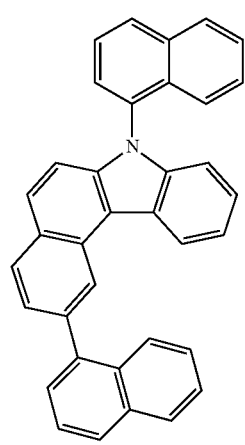
32
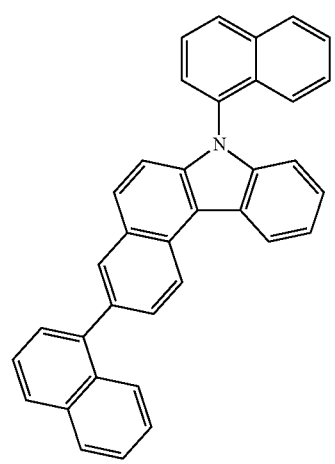
33
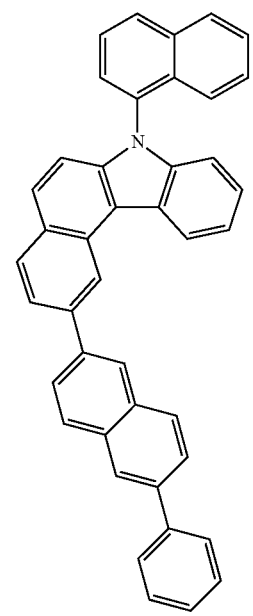
34
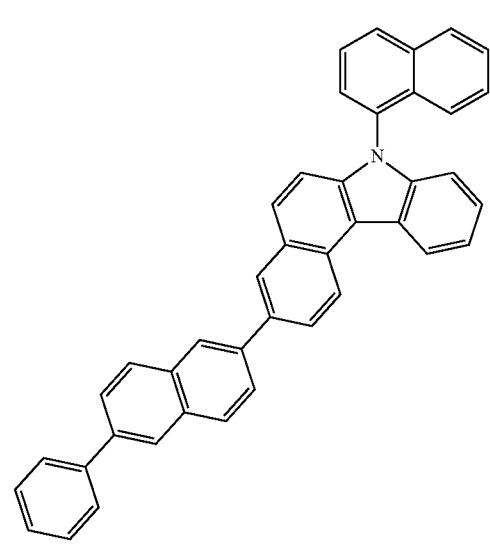
35
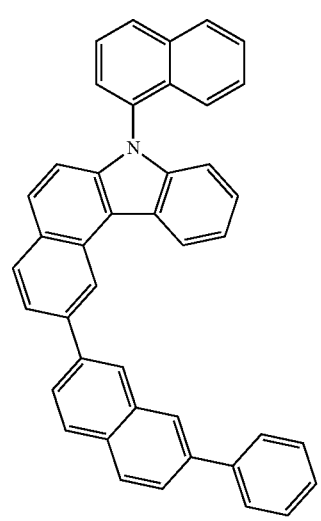

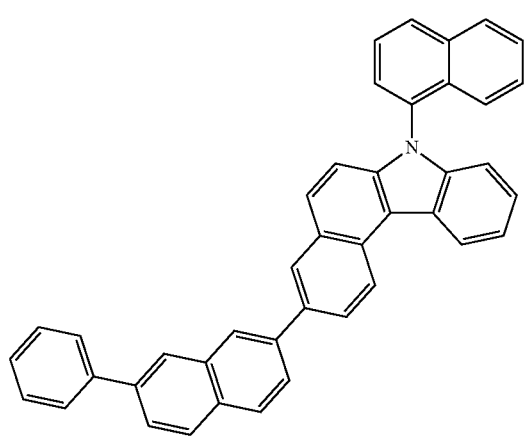
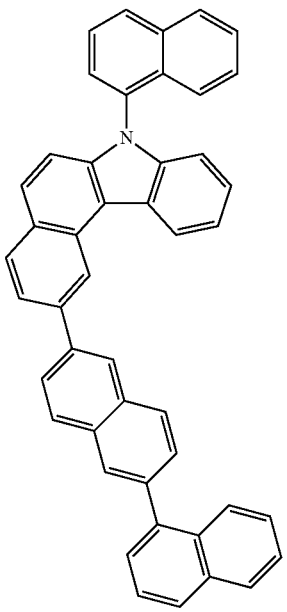

-continued
41
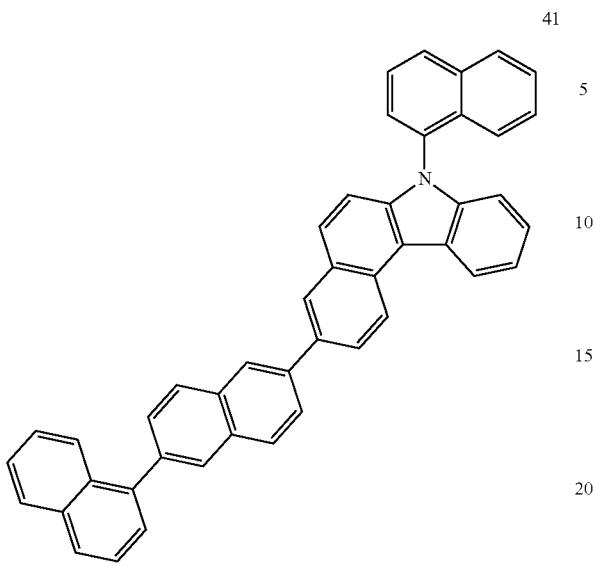
42
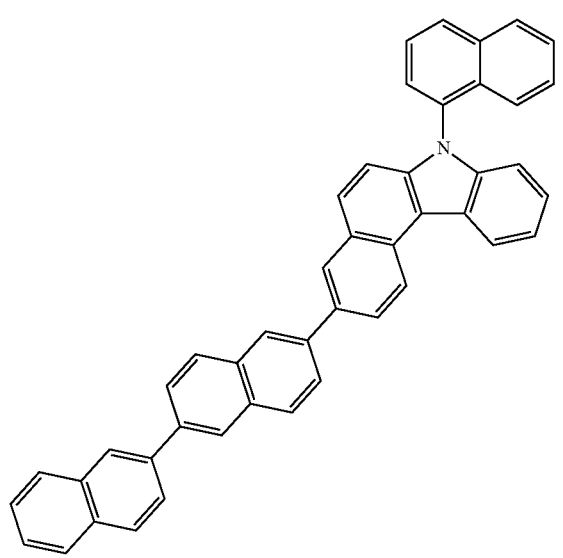
43
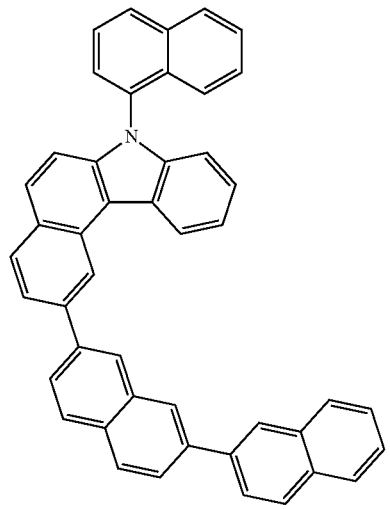
44
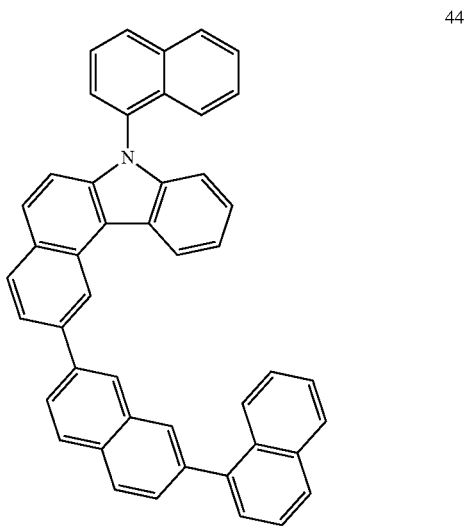
45
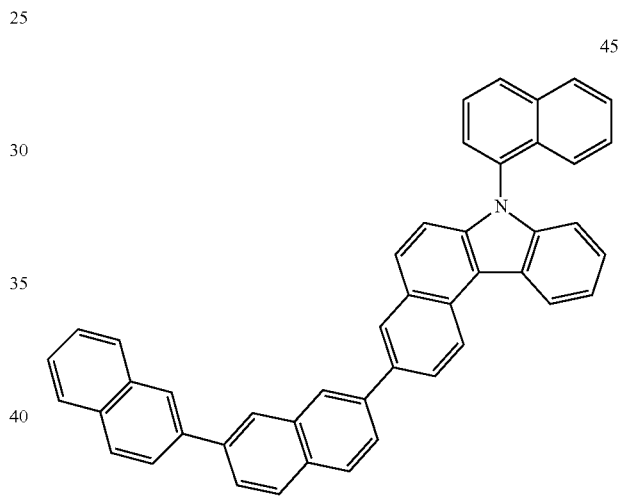
46
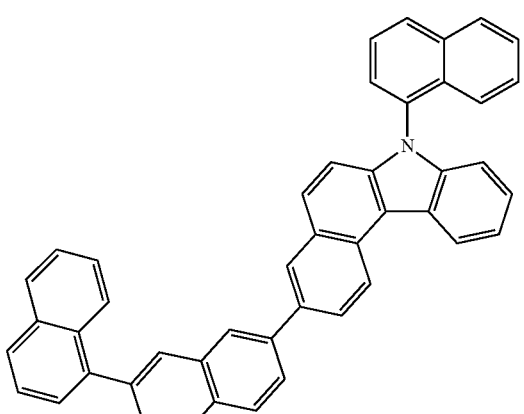

47
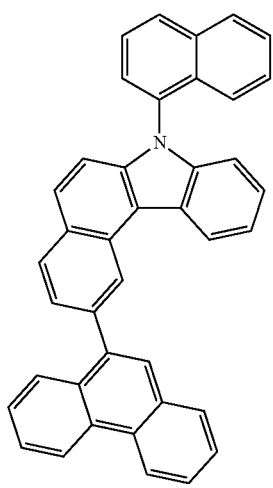
48
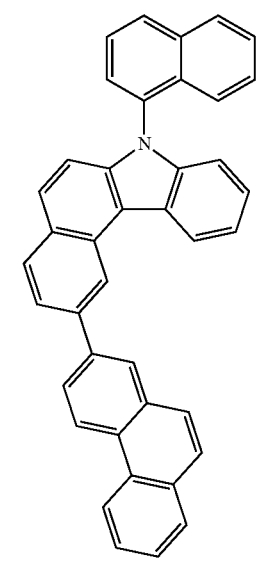
49
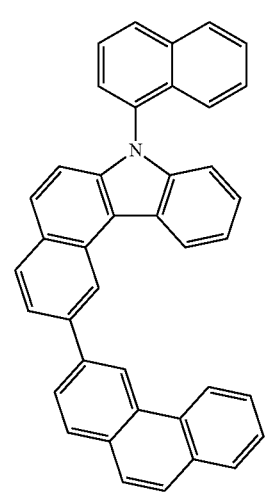
50
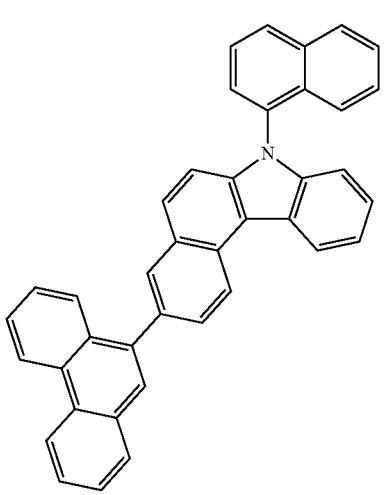
51
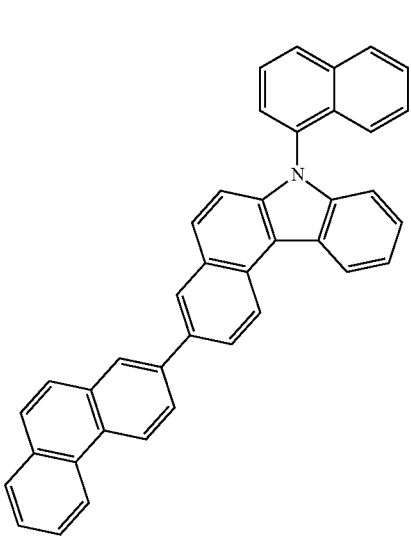
52
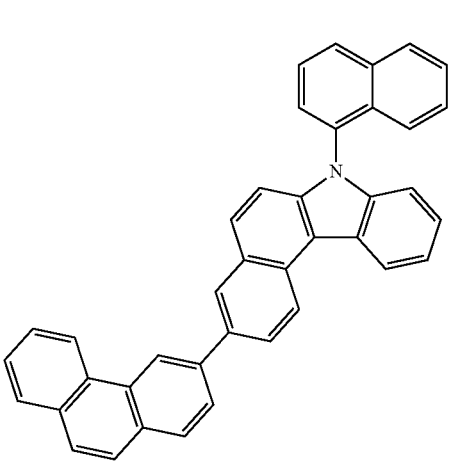

53
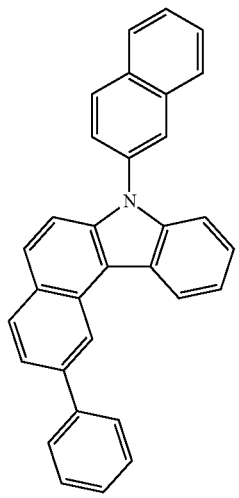
54
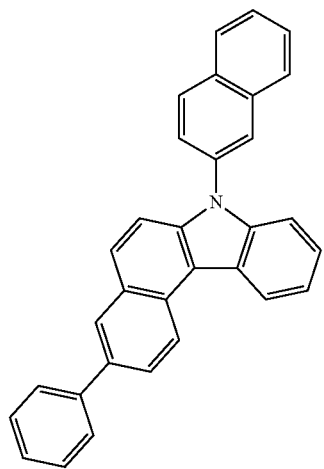
55
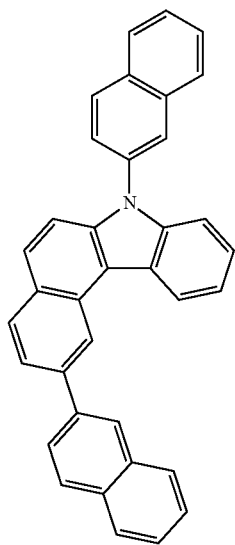
56
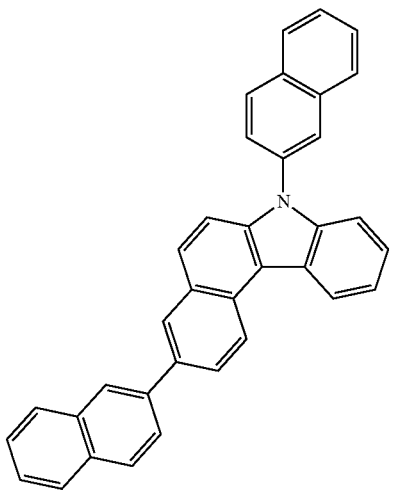
57
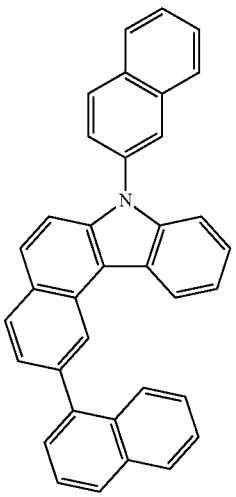
58
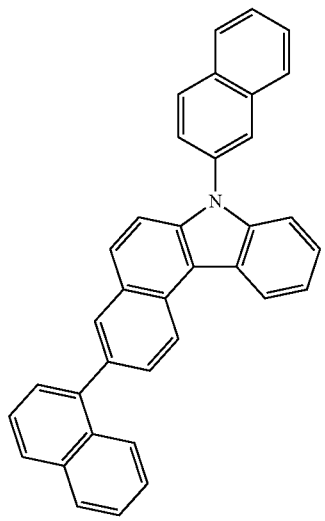

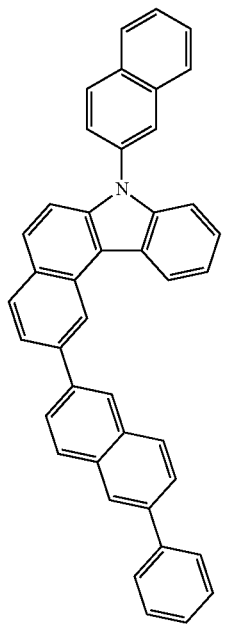
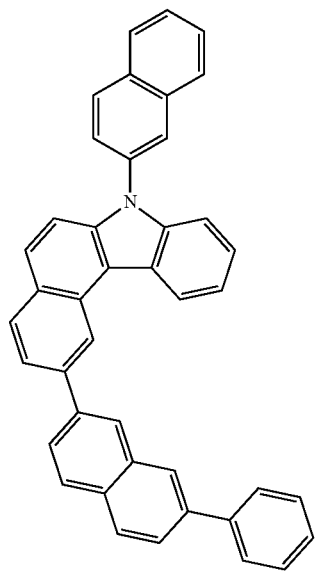
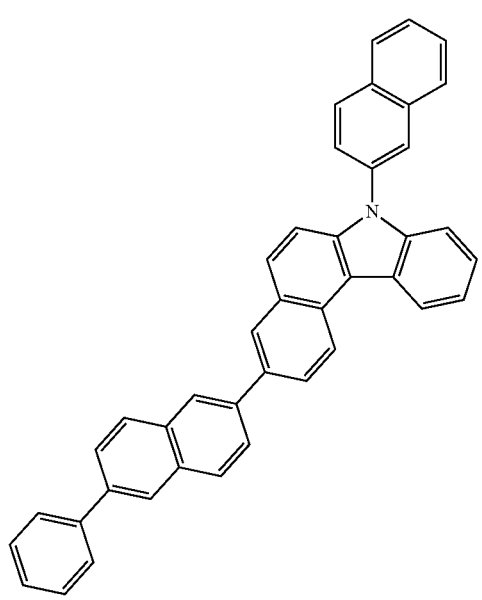

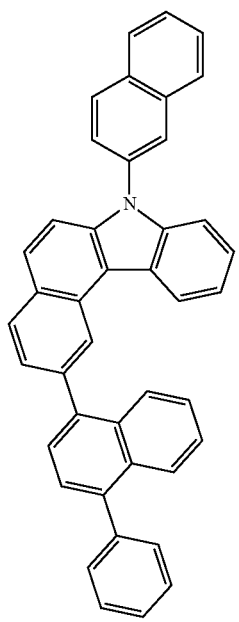
63
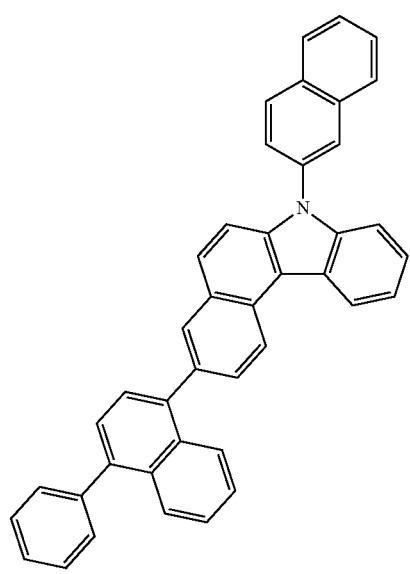
64
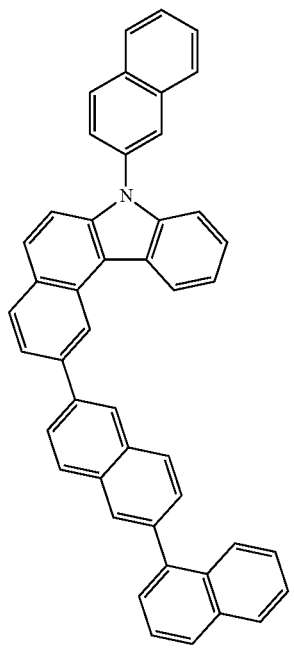
65
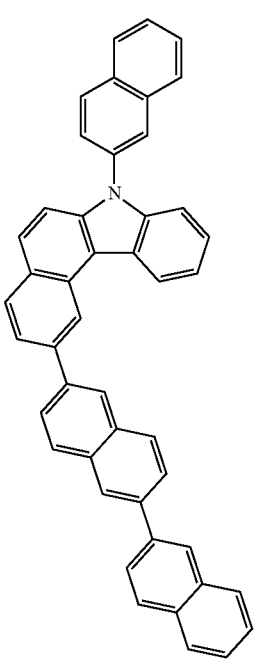
66

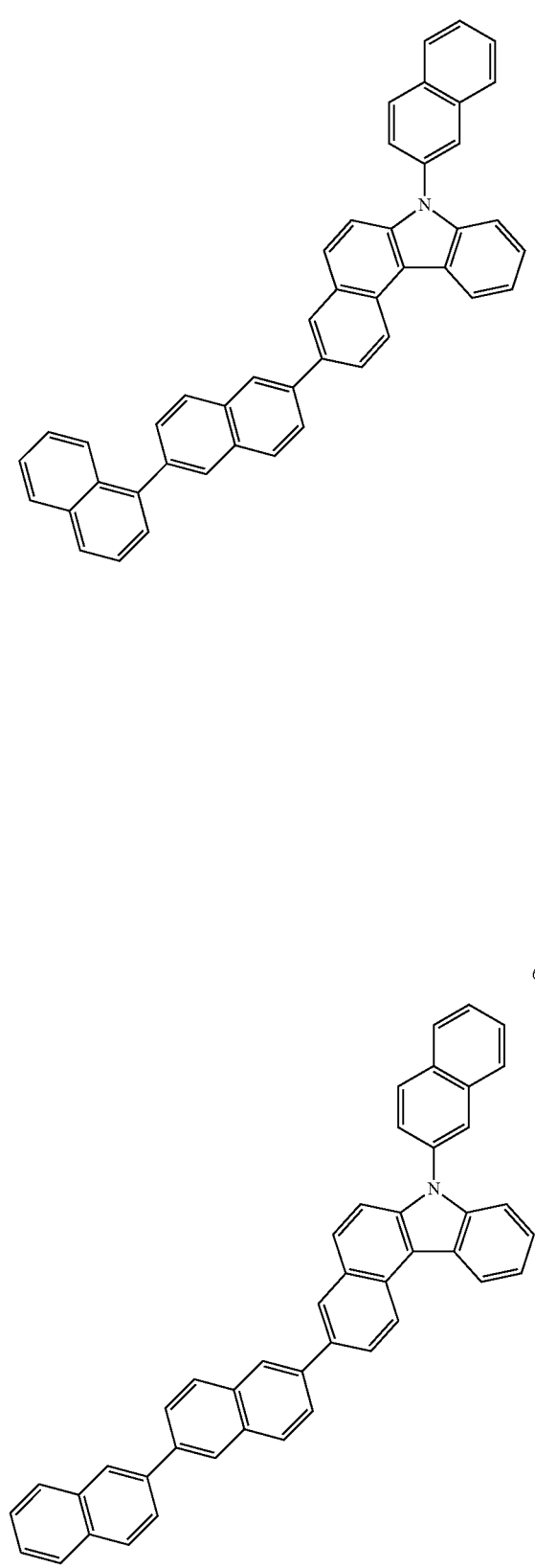
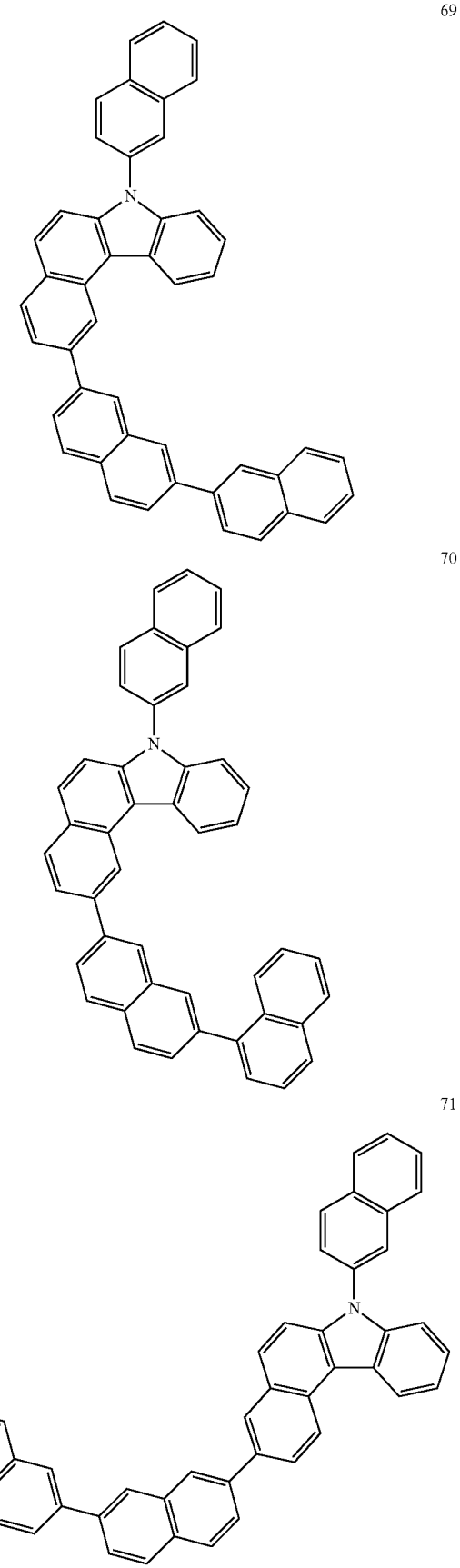

-continued
72
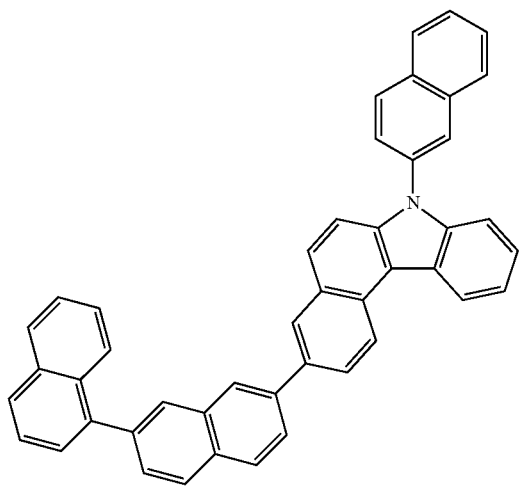
73
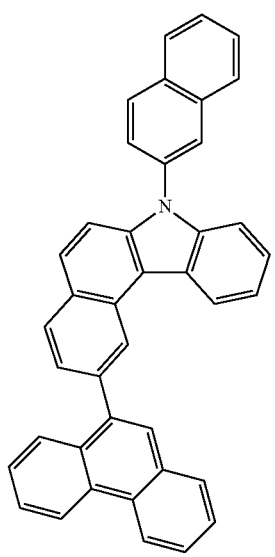
74
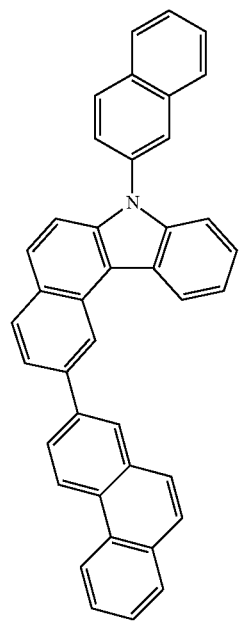
-continued
75
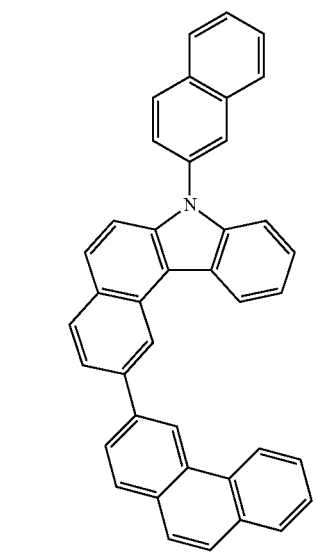
76
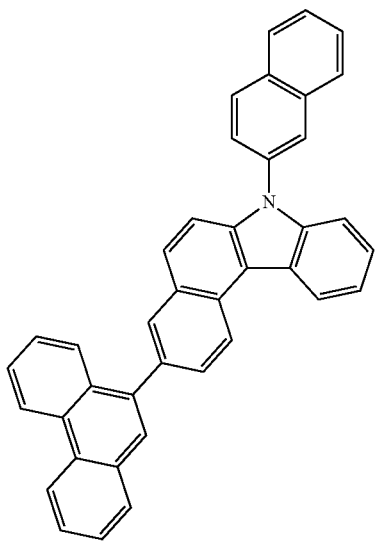
77

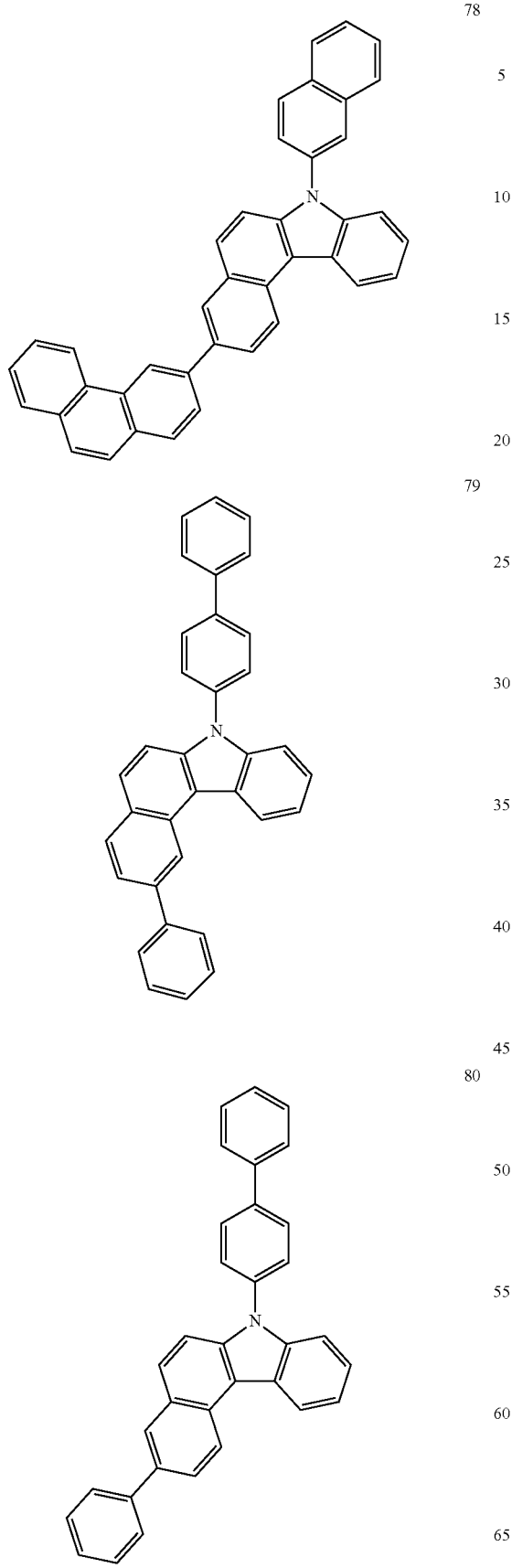
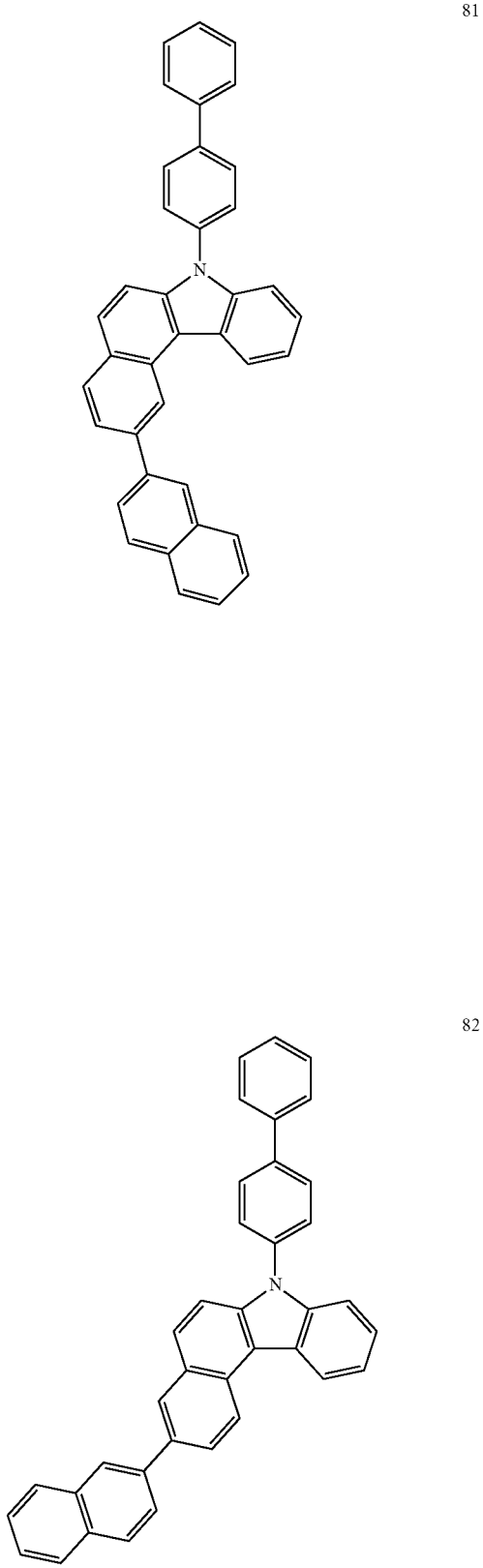

83
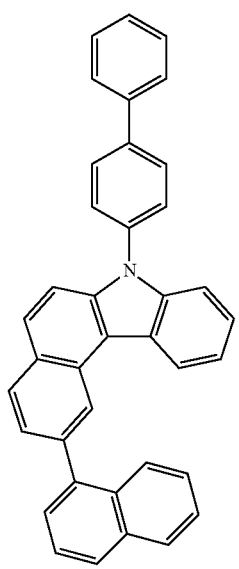
84
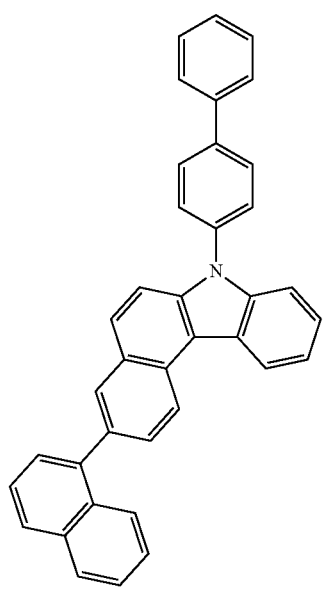
85
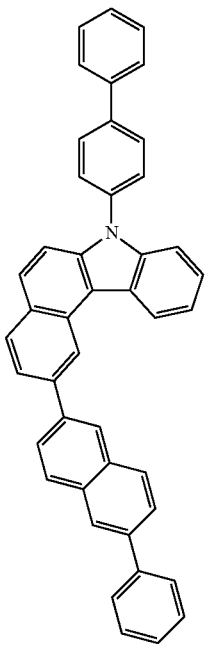
86
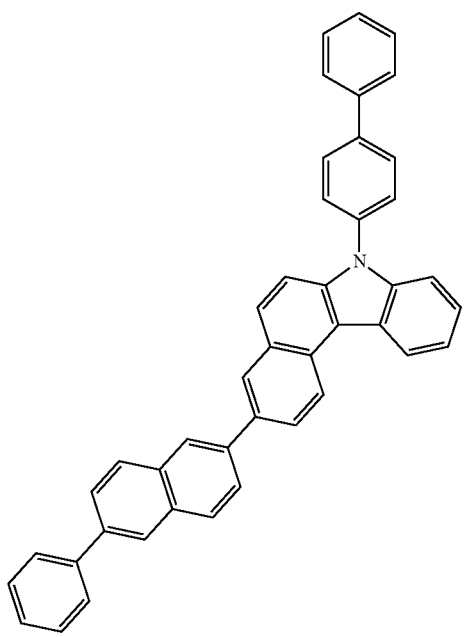

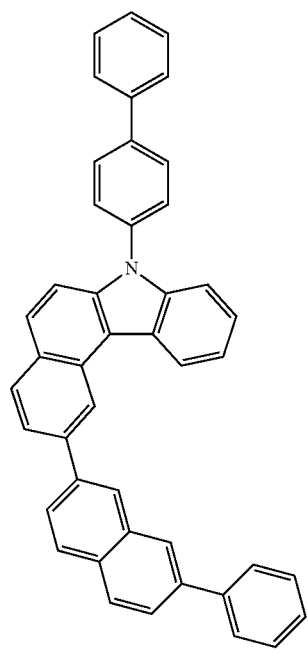
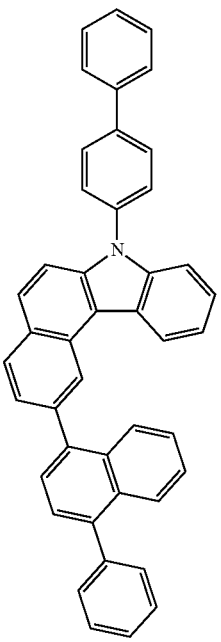

91
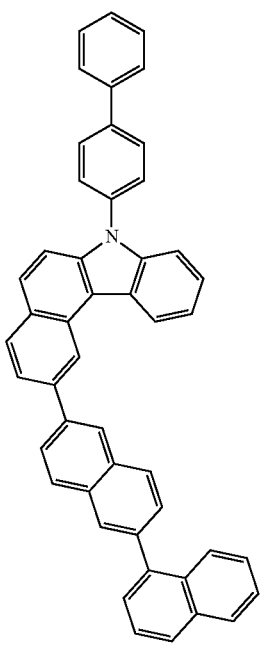
92
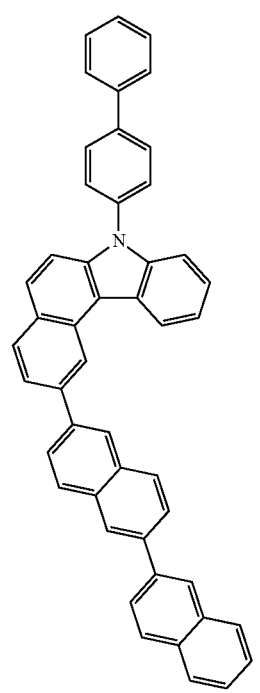
93
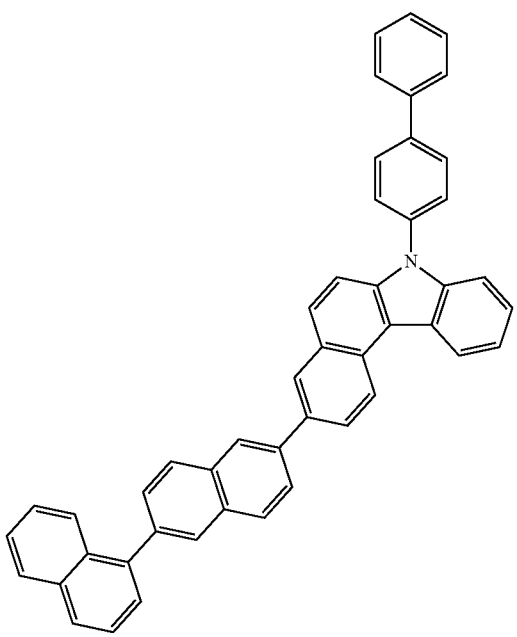
94
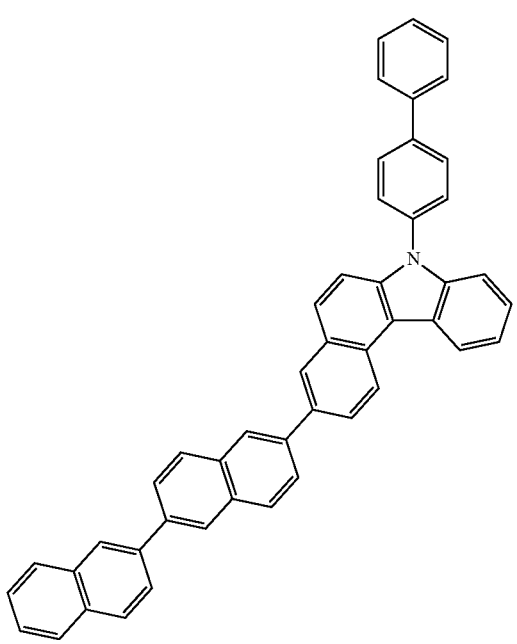

77
-continued
95
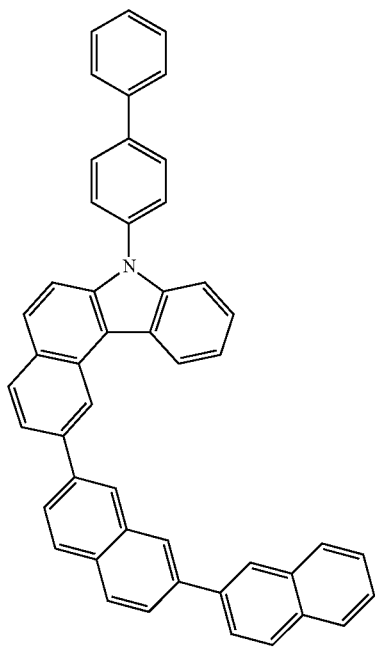
96
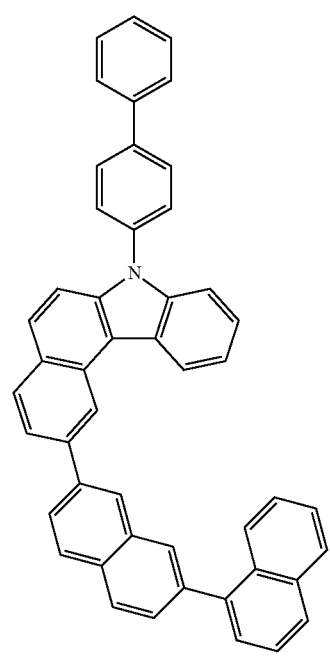
78
-continued
97
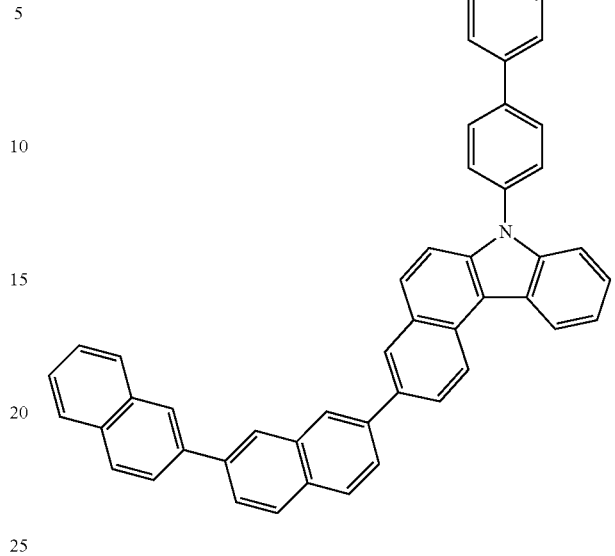
98
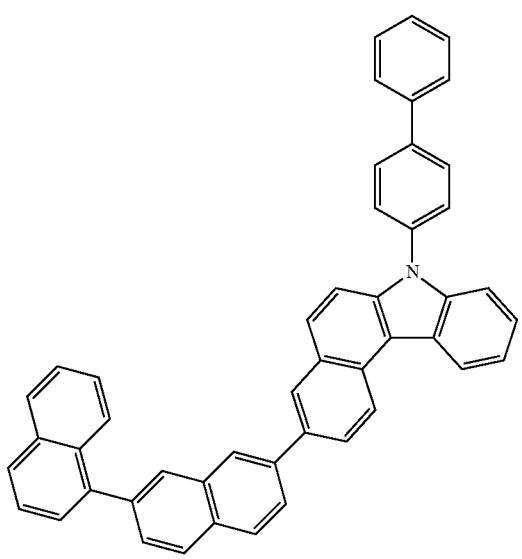

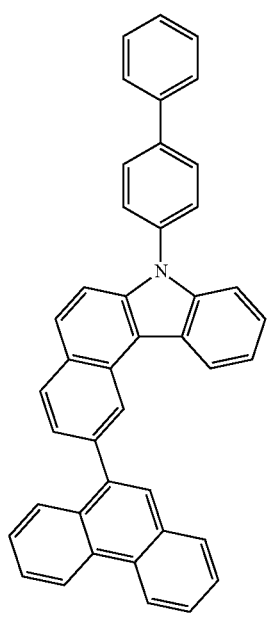
99
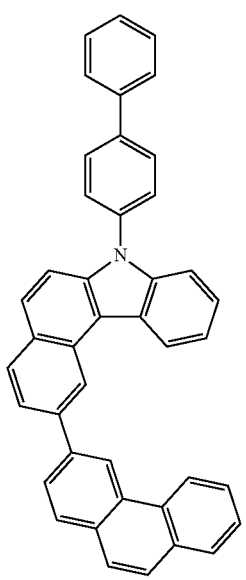
101
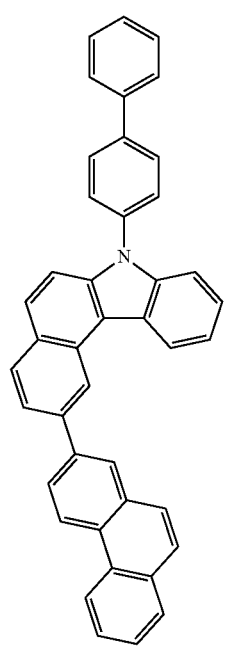
100

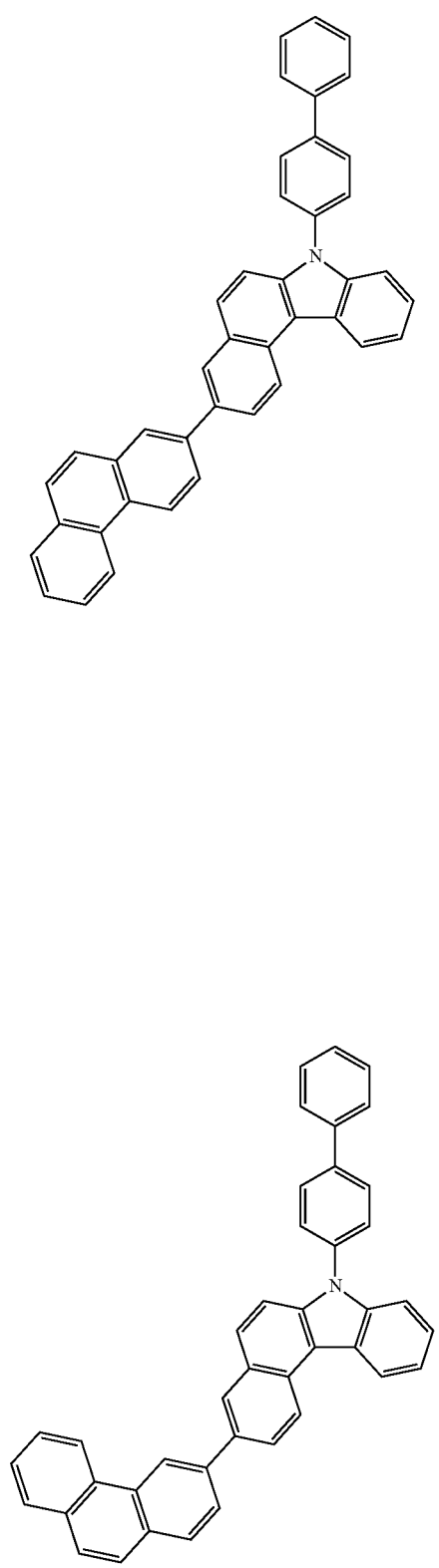
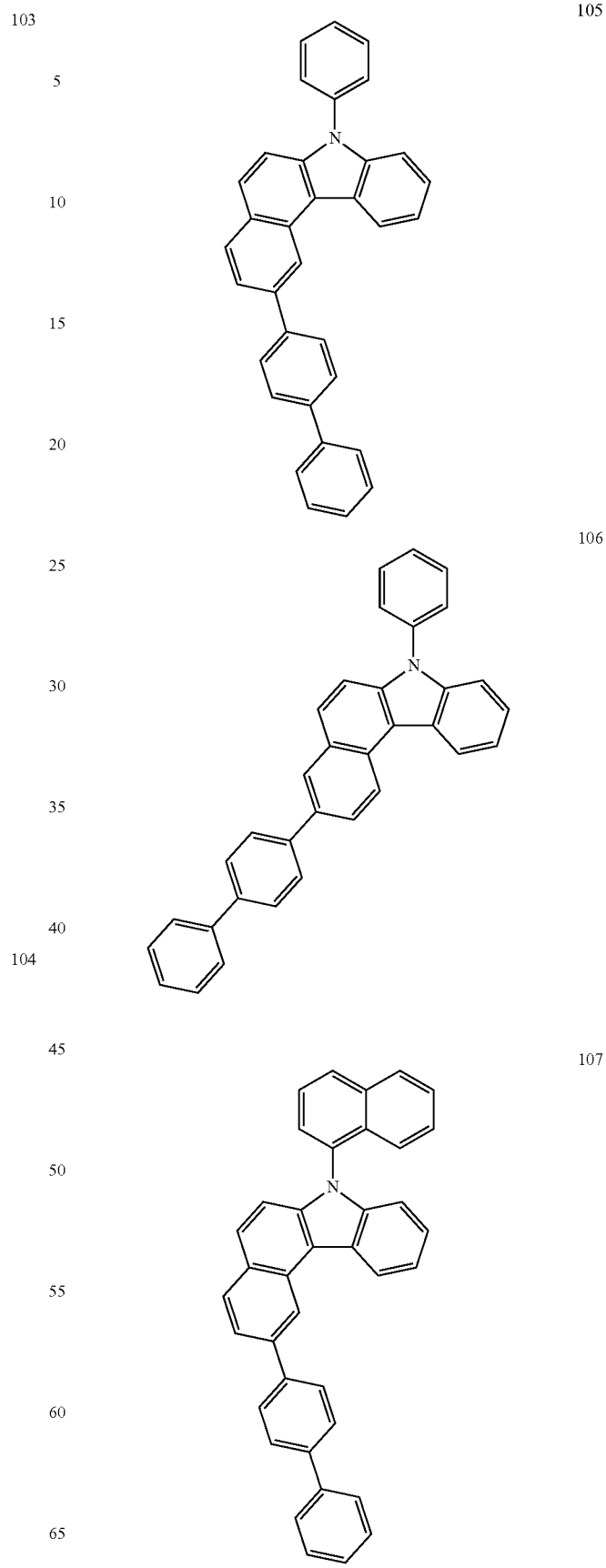

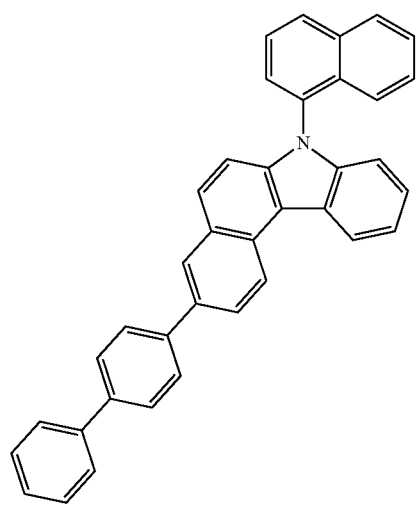
108
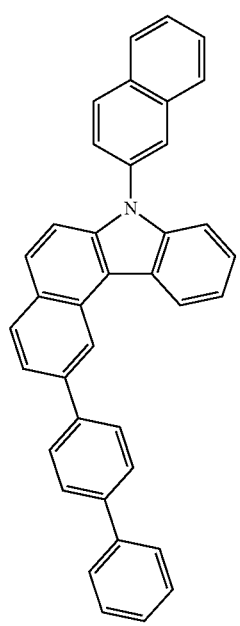
109
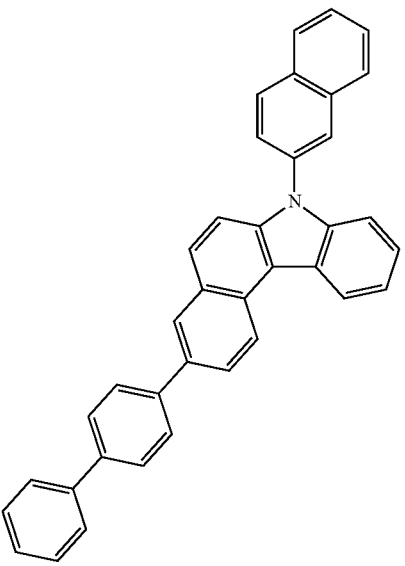
110
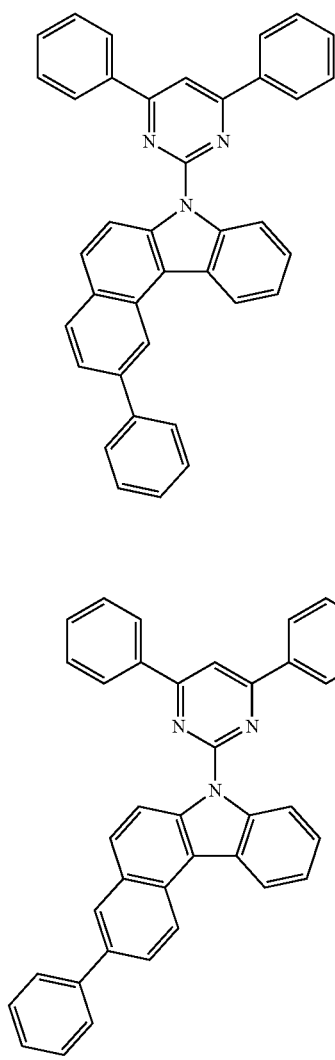
111
112

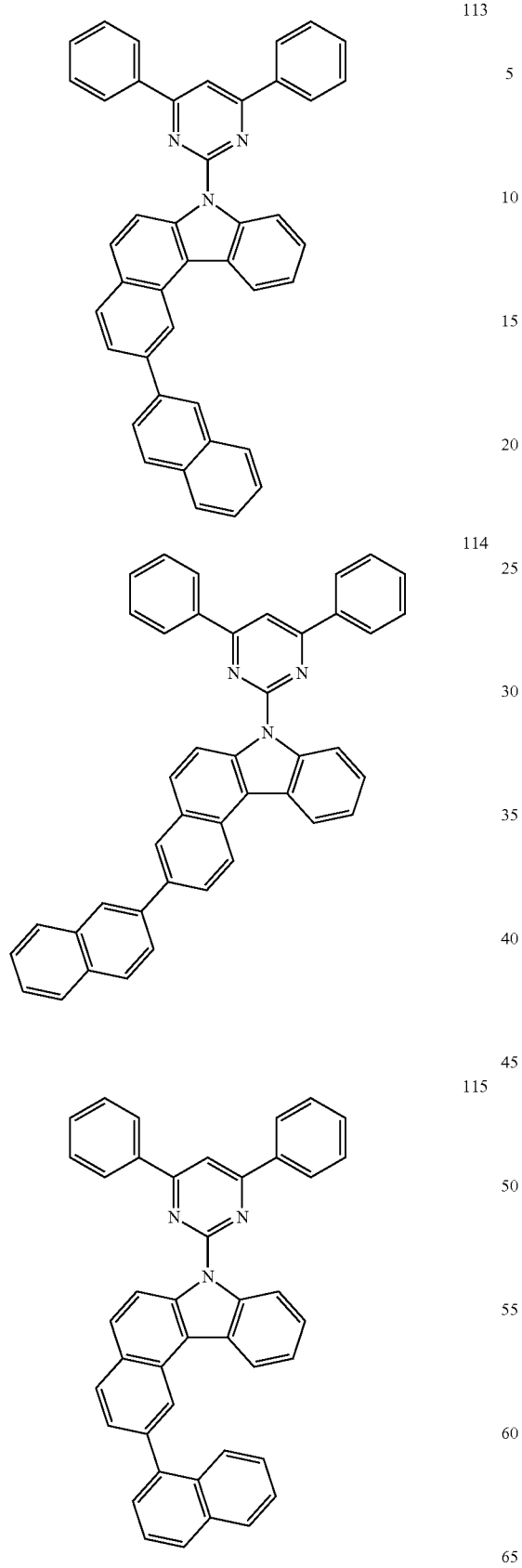
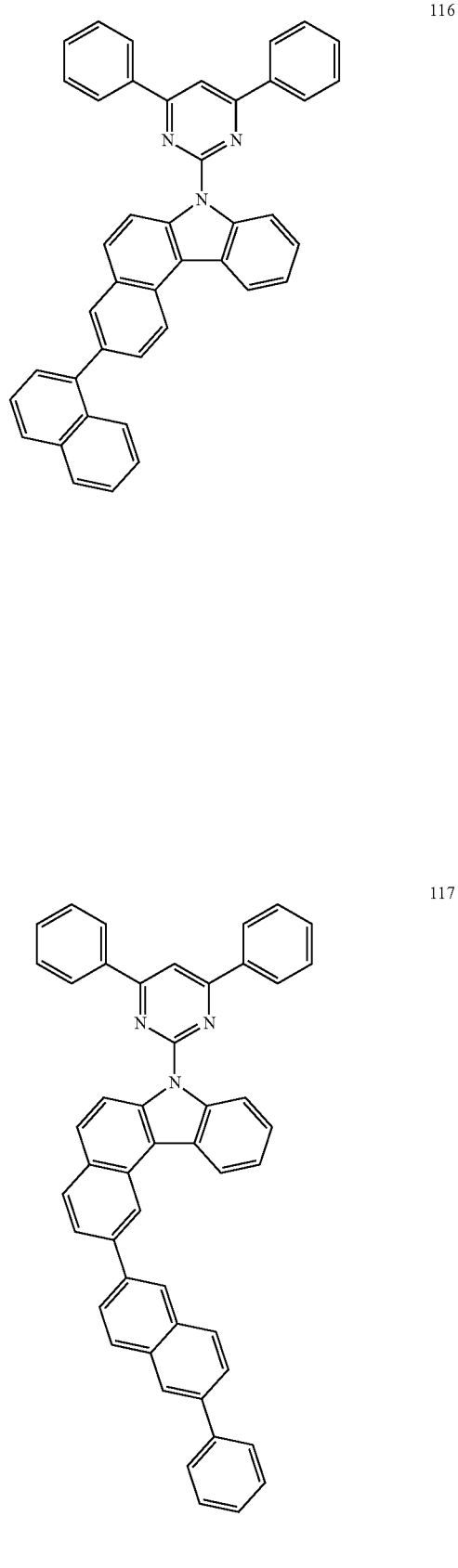

118
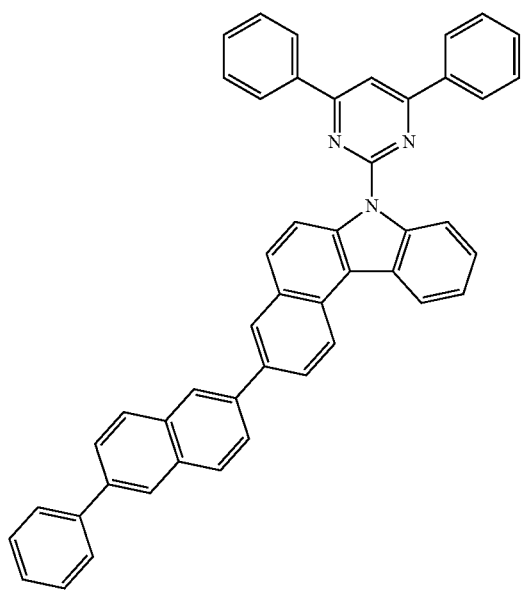
120
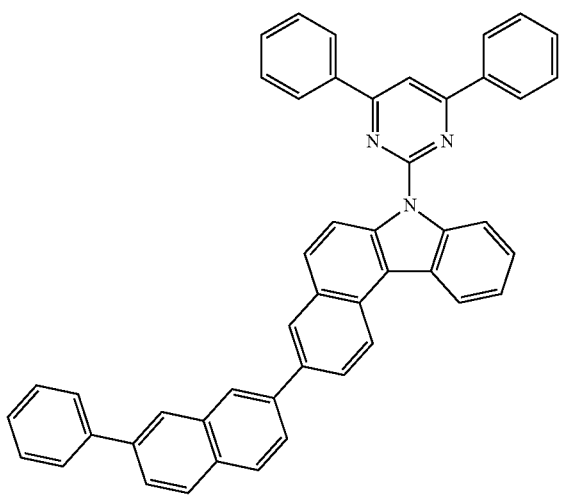
119
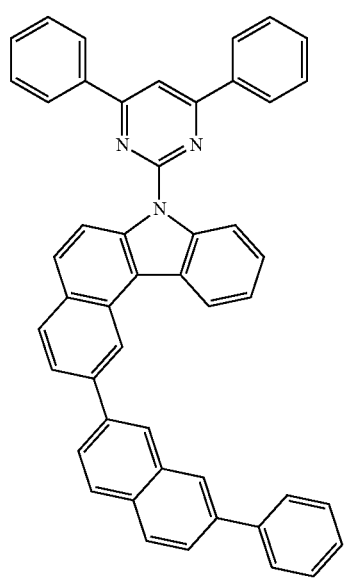
121
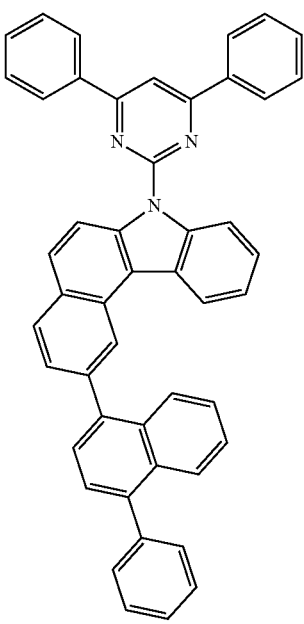

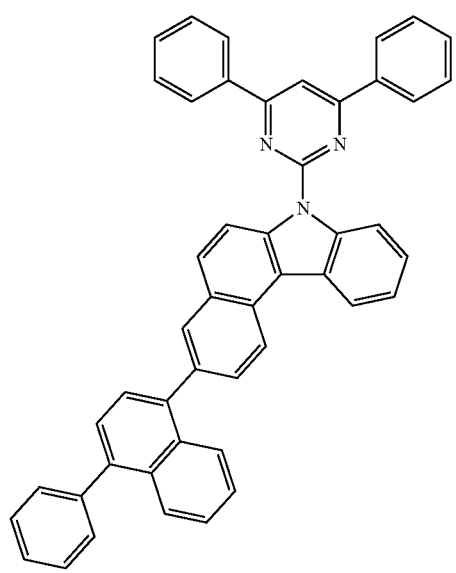
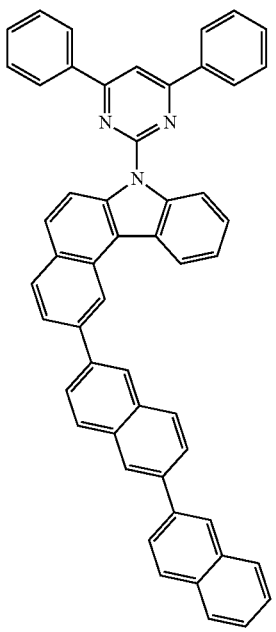
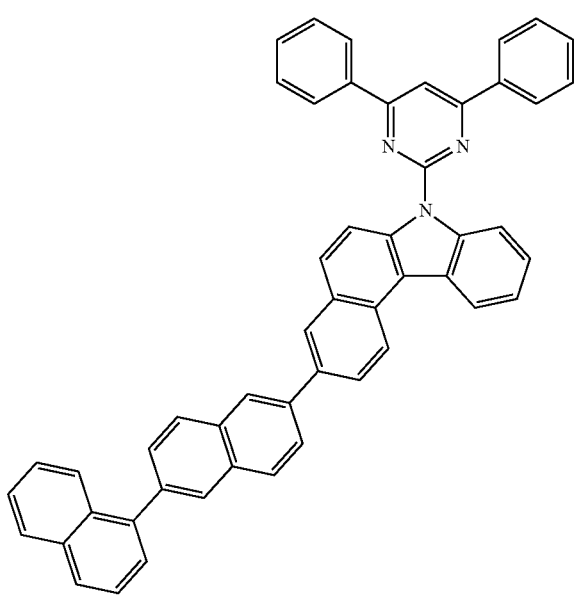

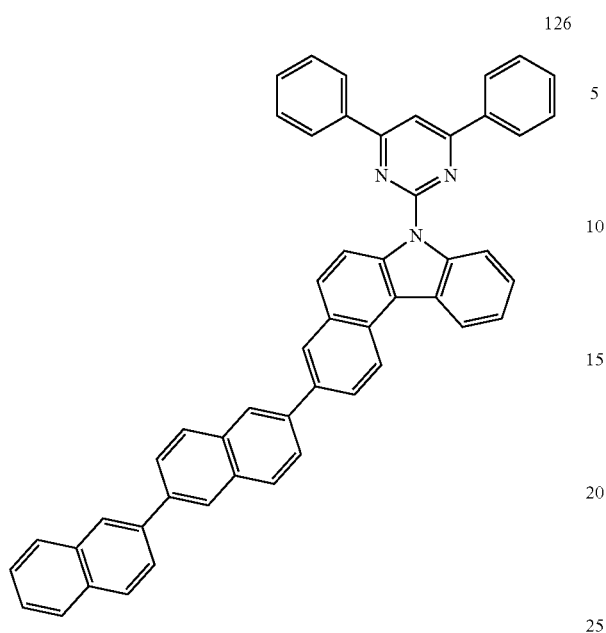
126
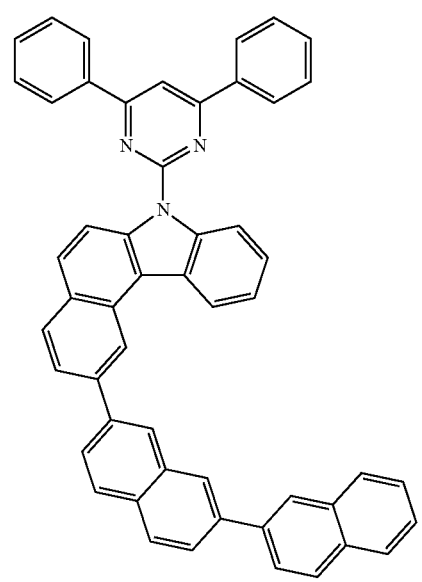
127
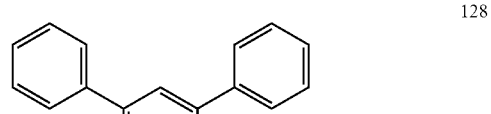
128
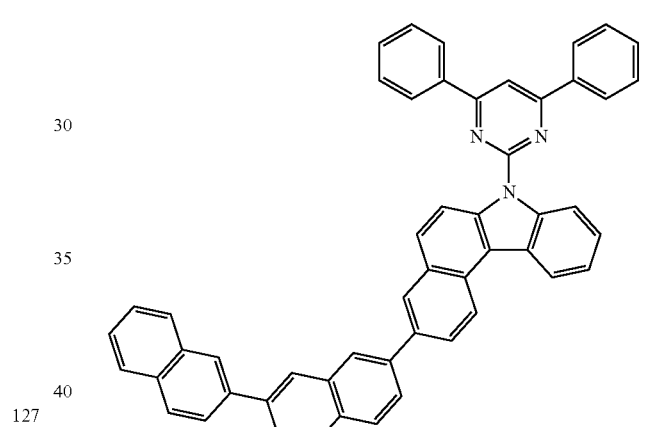
129
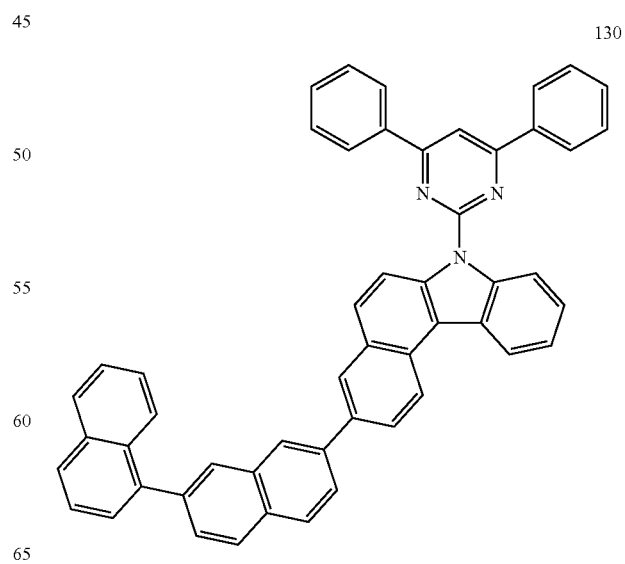
130

131
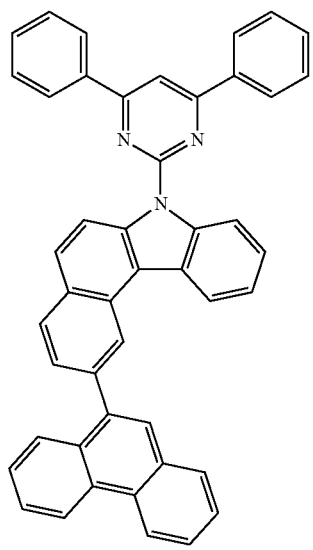
132
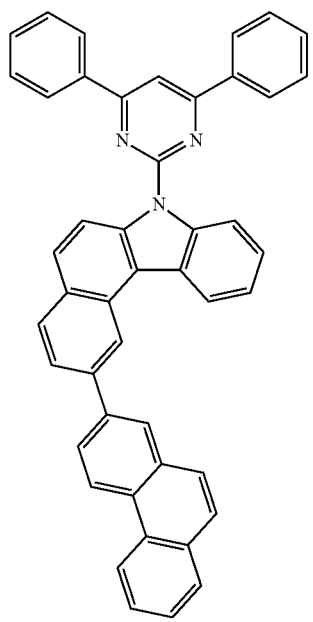
133
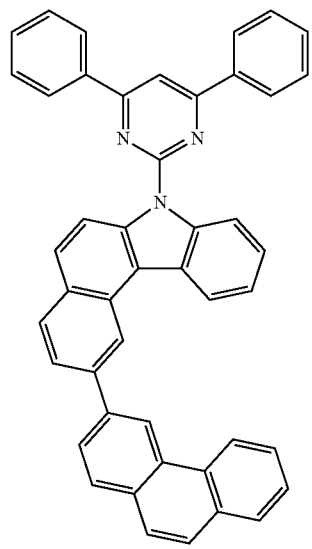
134
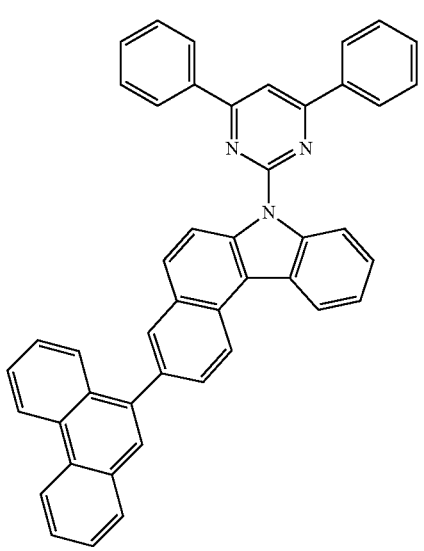
135
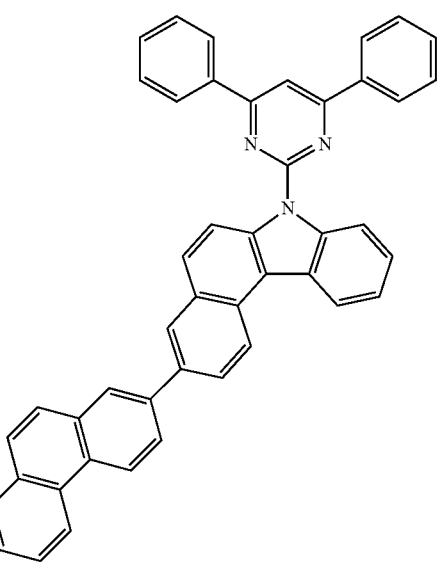

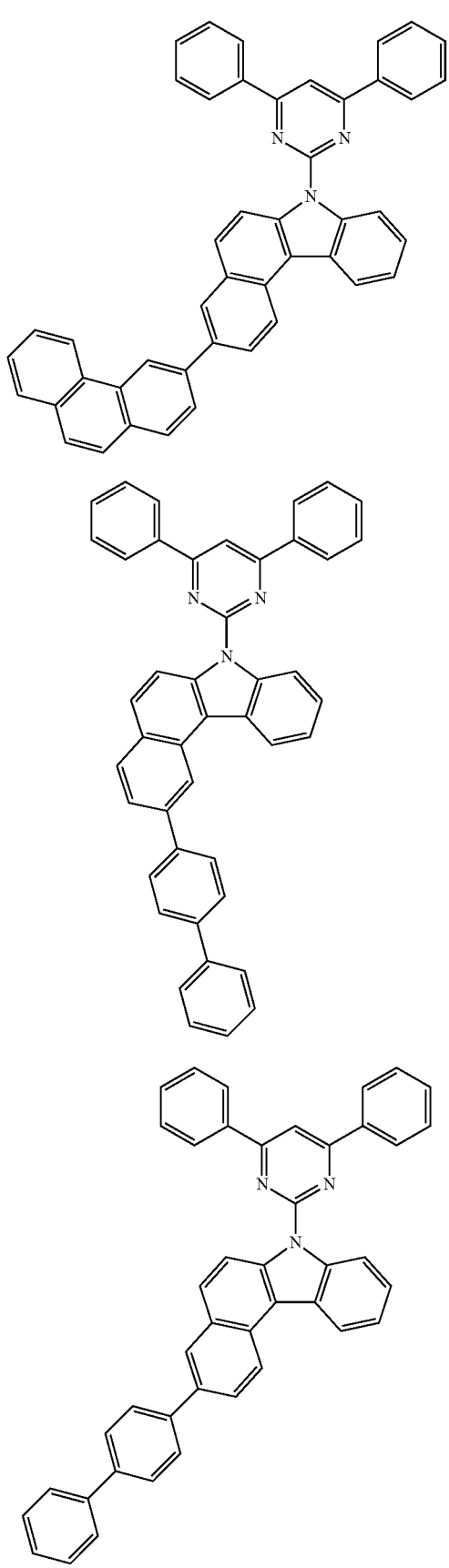
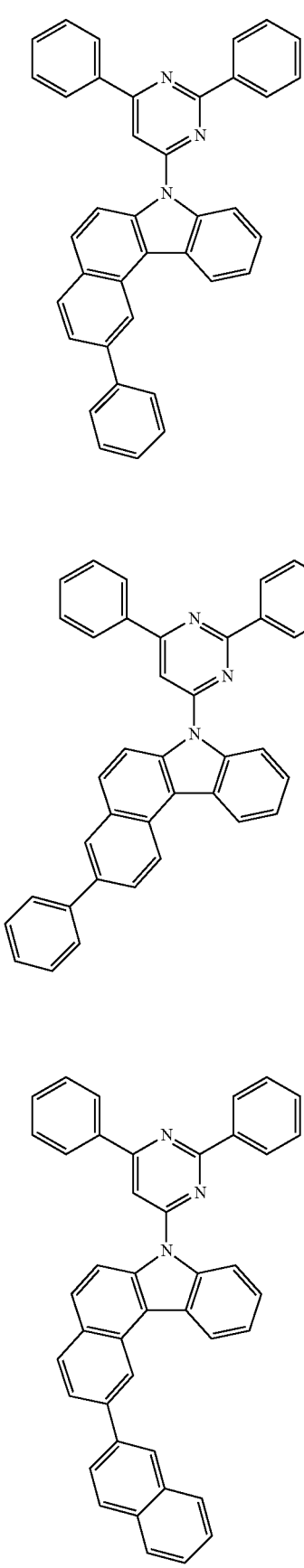

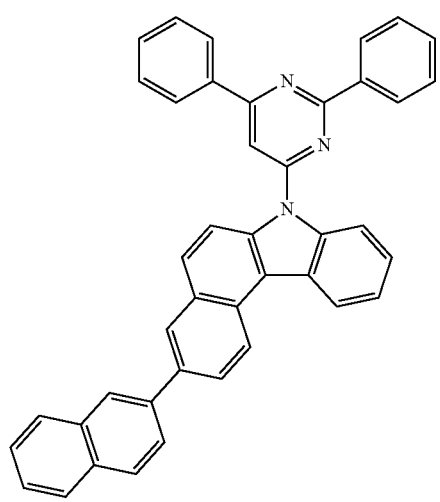
142
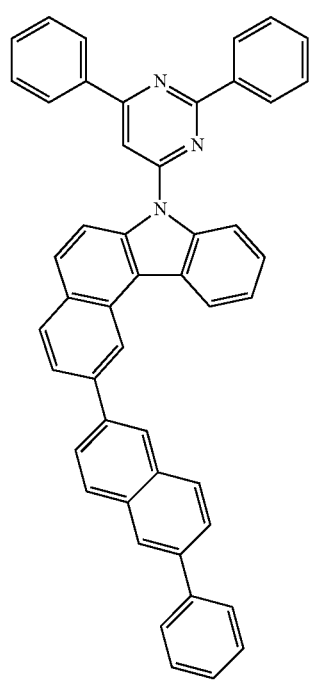
145
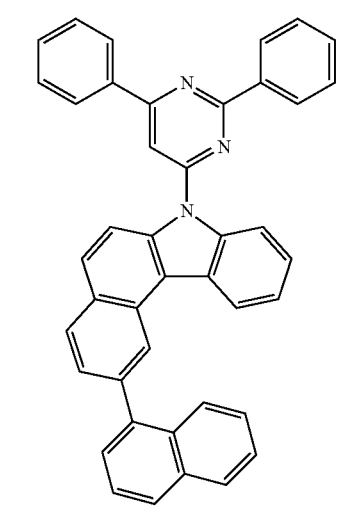
143
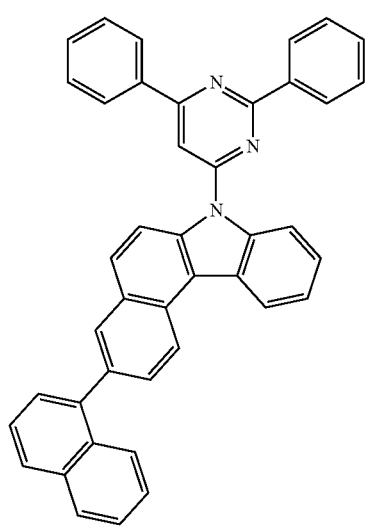
144
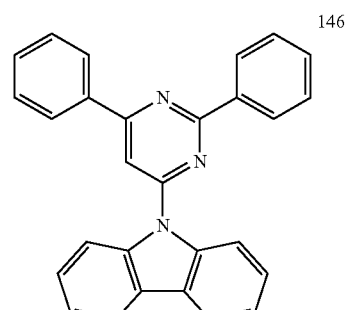
146

147
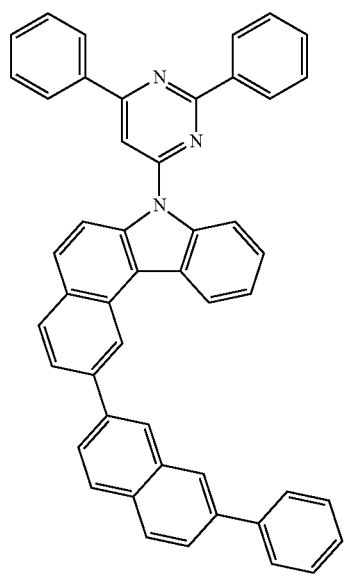
149
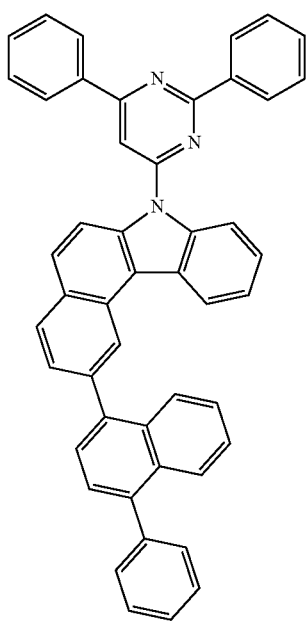
148
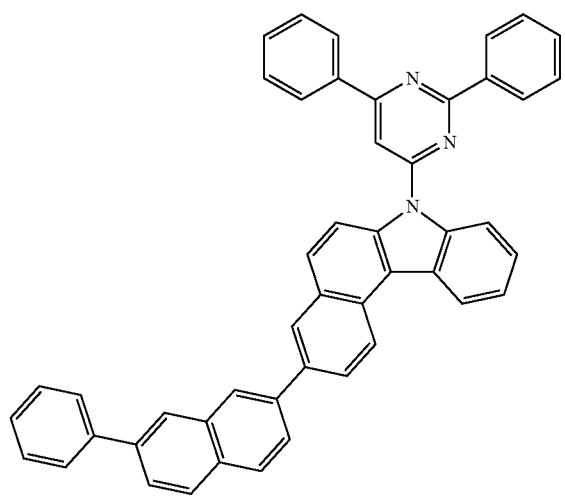
150
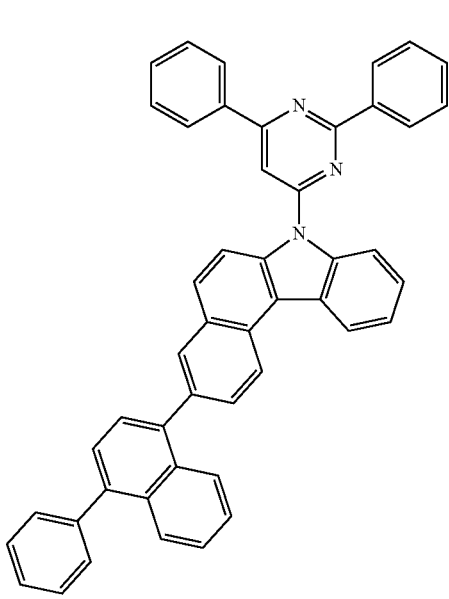

101 102
-continued -continued
151 153
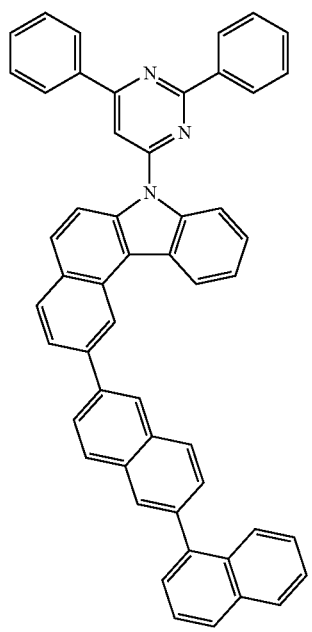
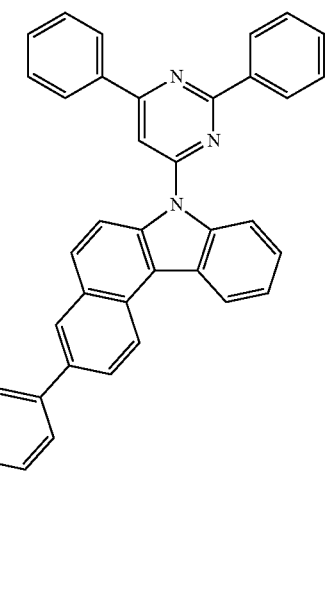
152 154

-continued
155
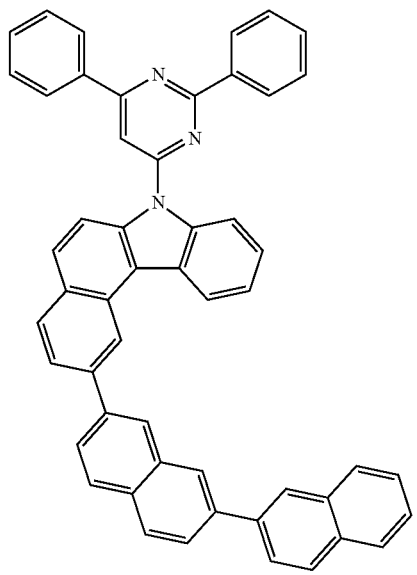
156
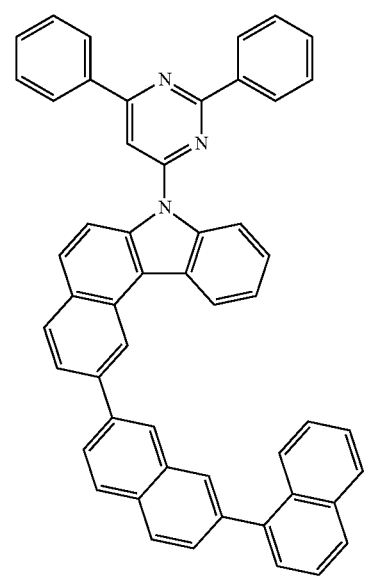
157
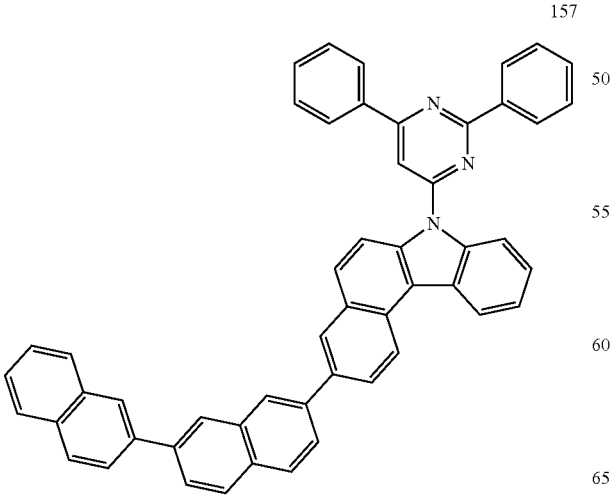
-continued
158
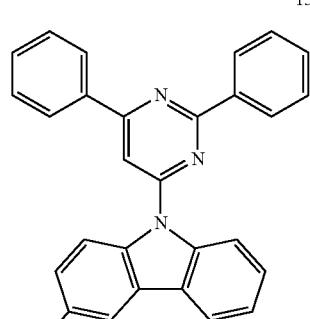
159
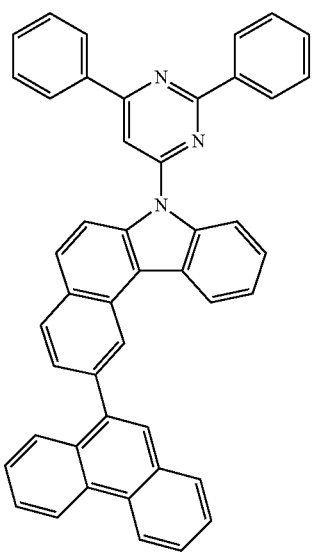

105
-continued
160
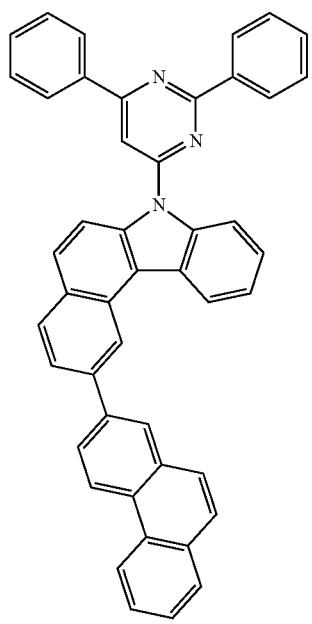
161
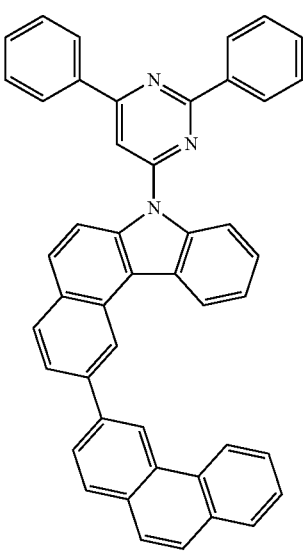
106
-continued
162
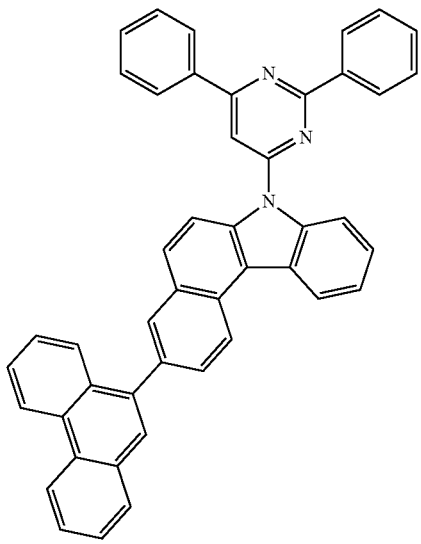
163
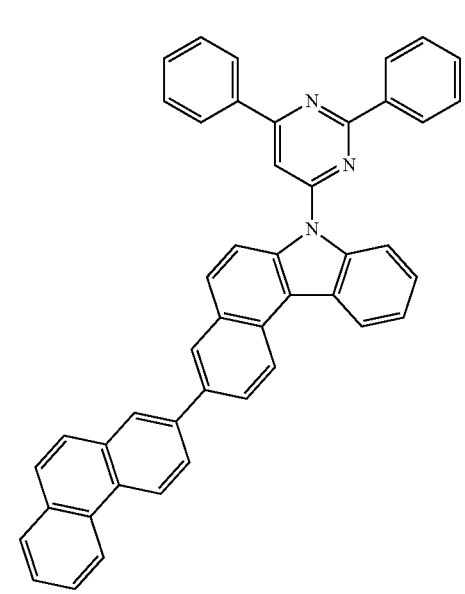
164
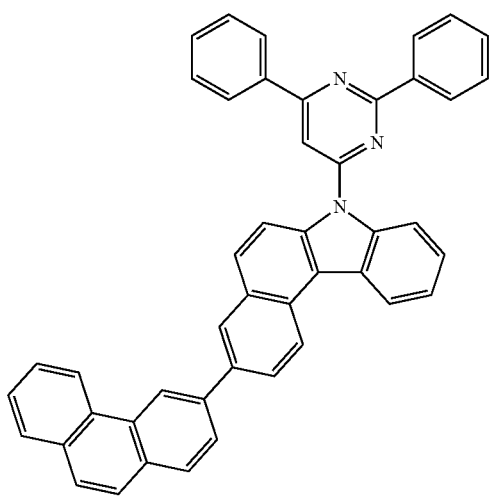

107
-continued
108
-continued
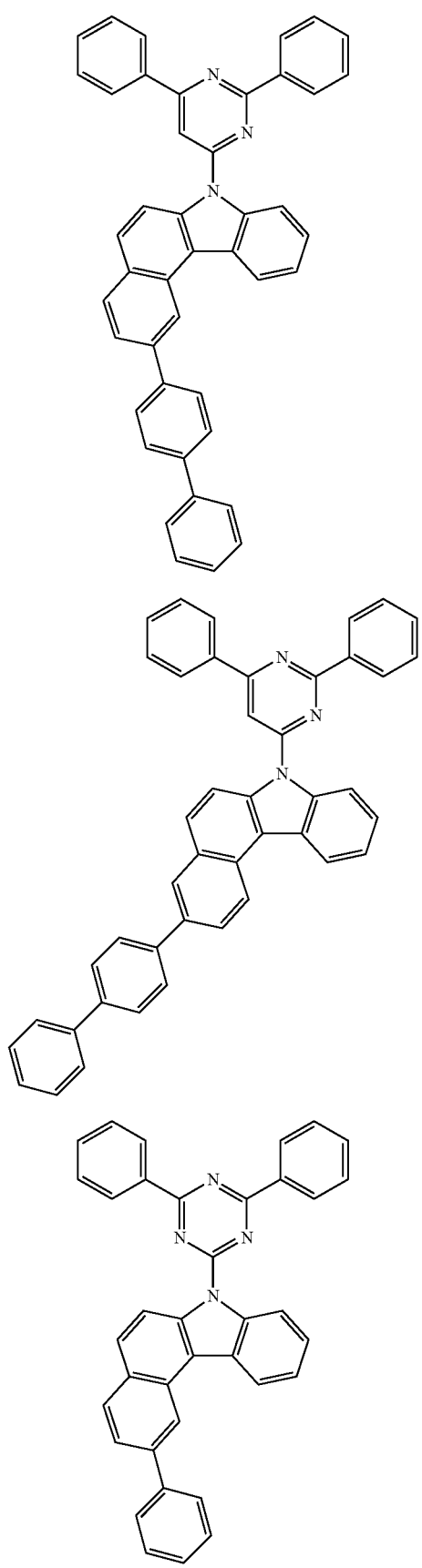
165
166
167
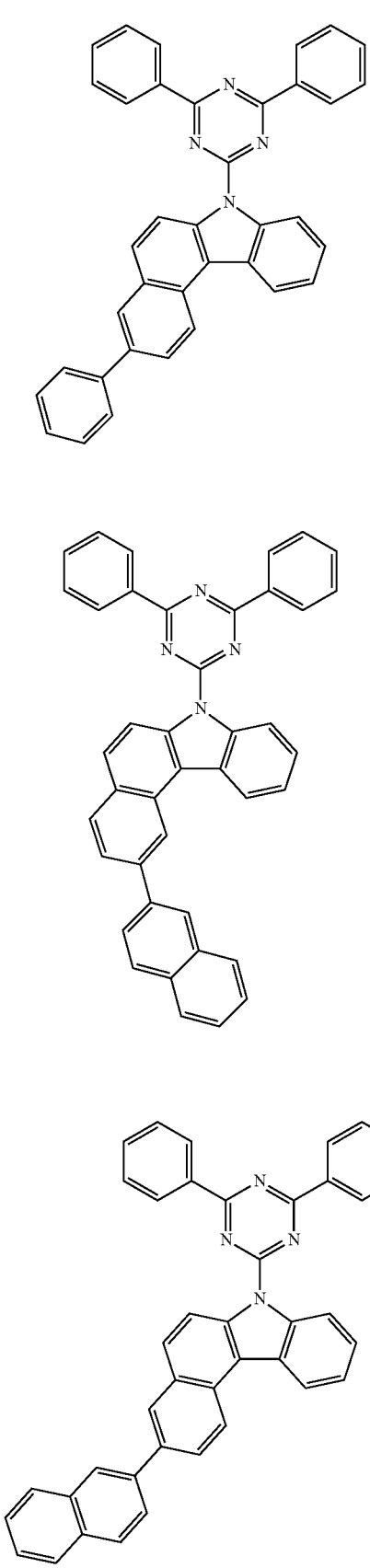
168
169
170

171
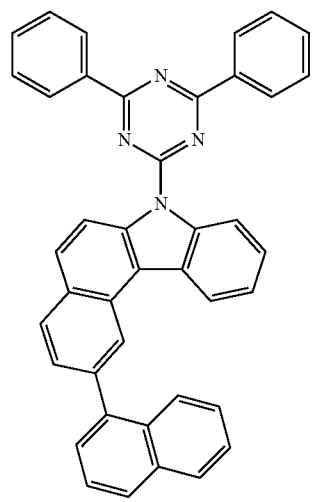
172
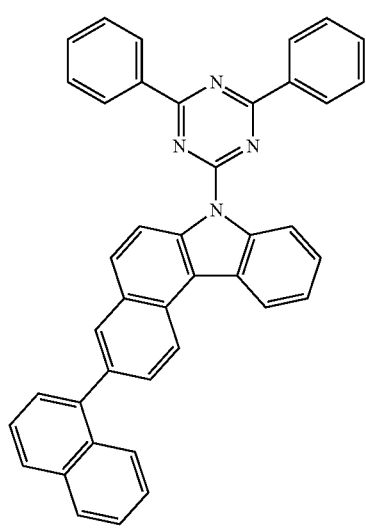
173
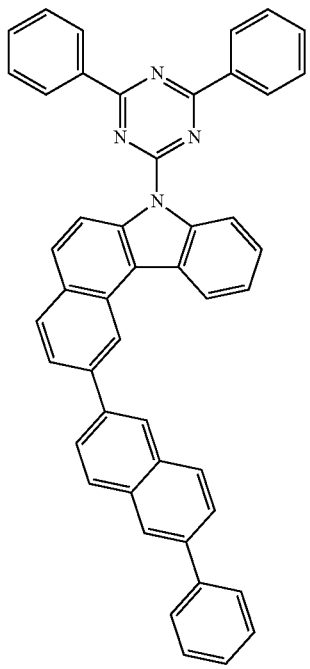
174
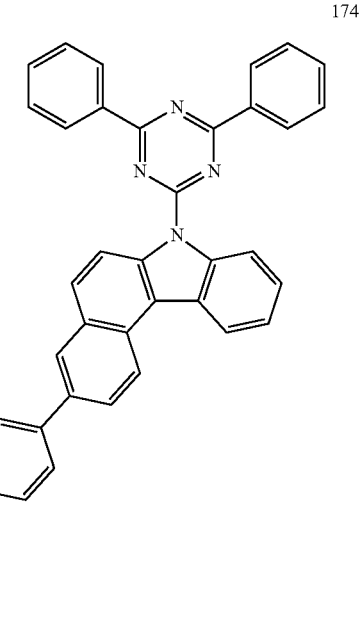

111
-continued
175
112
-continued
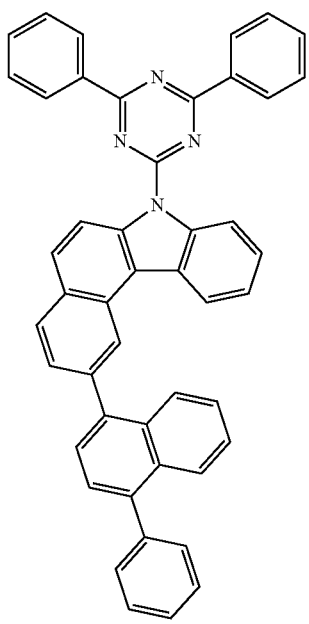
177
176
112
-continued
178
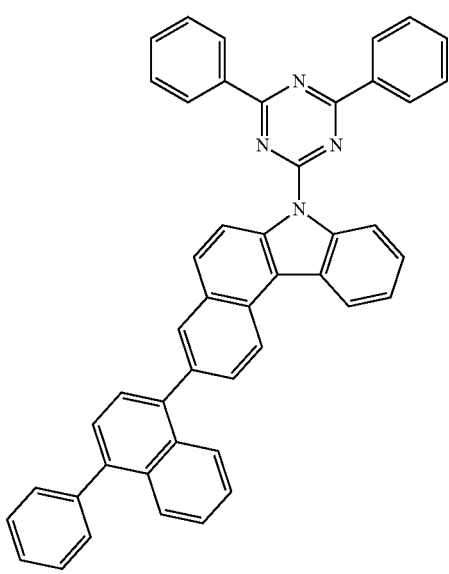

179
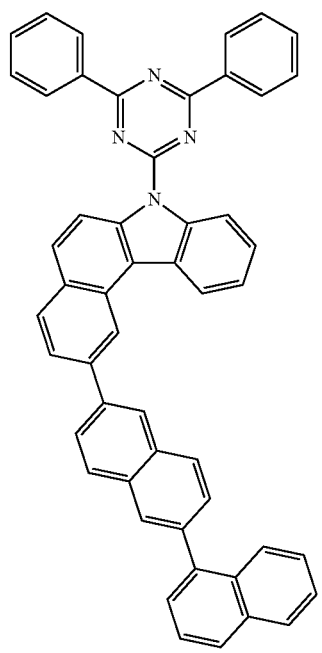
181
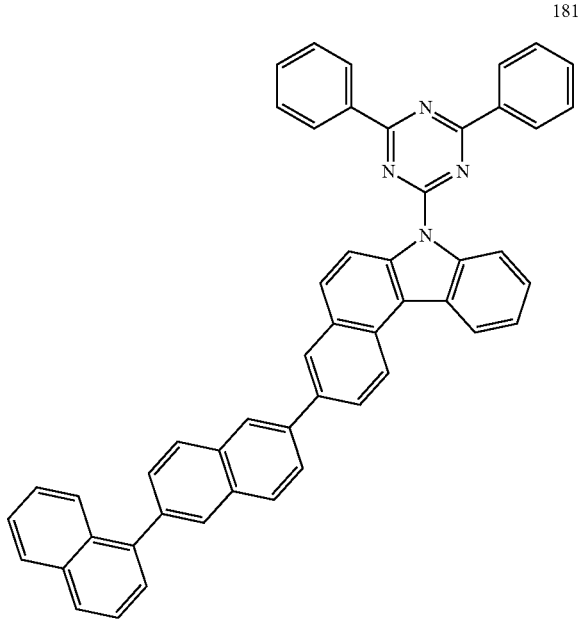
180
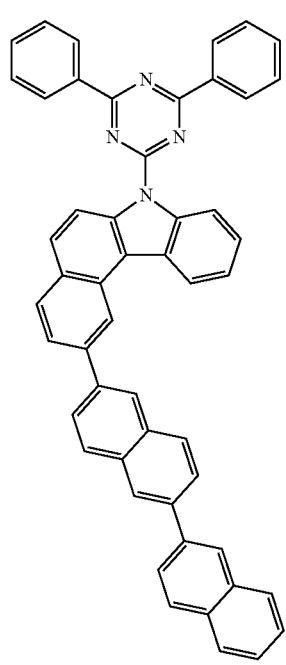
182
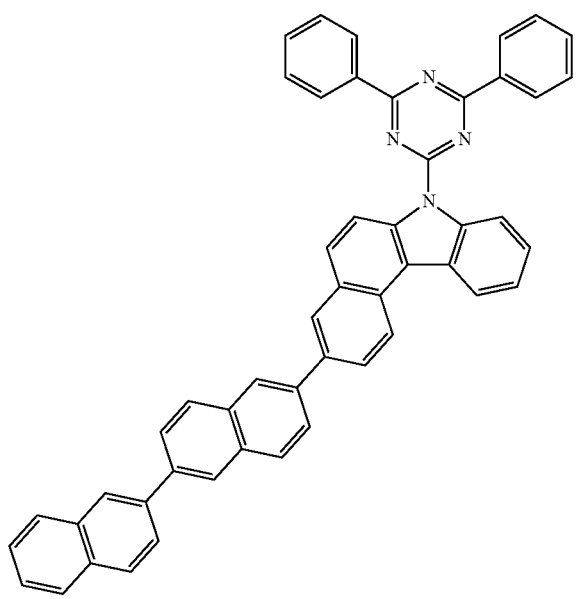

183
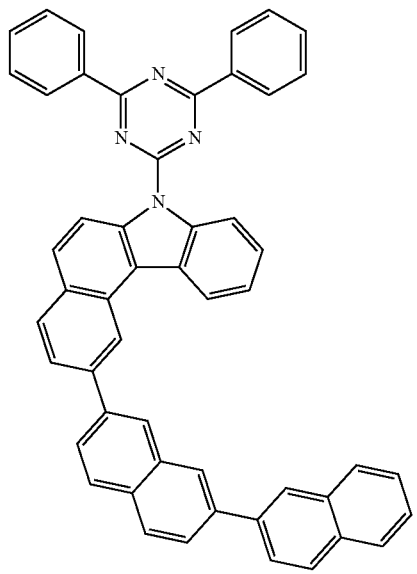
184
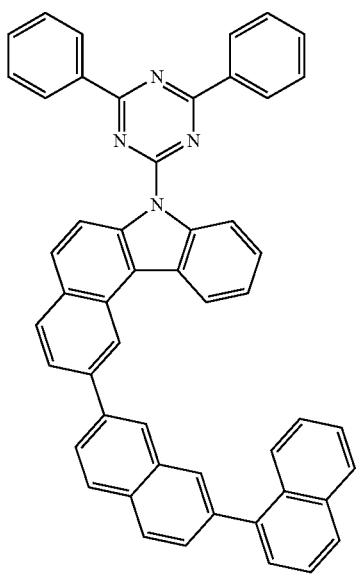
185
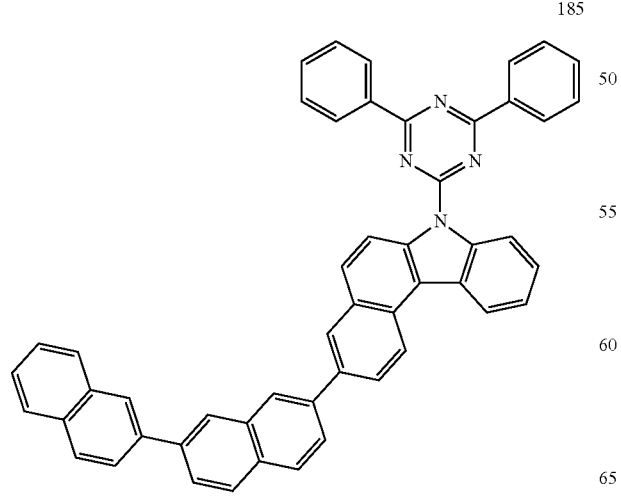
186
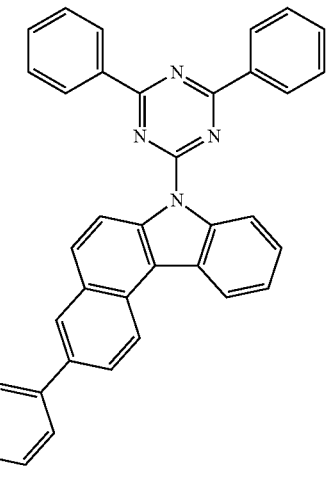
187
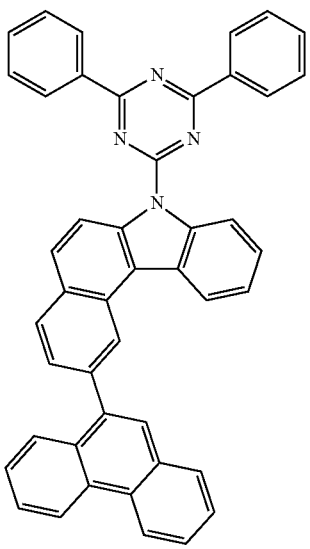
188
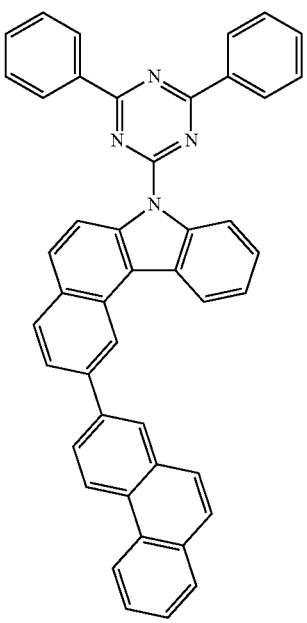

117
-continued
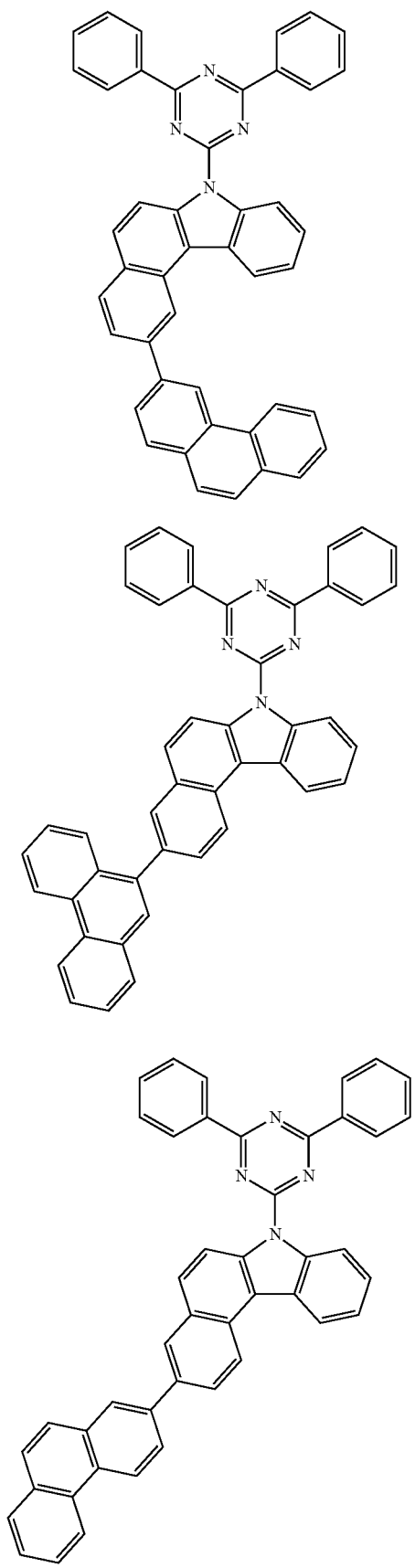
118
-continued
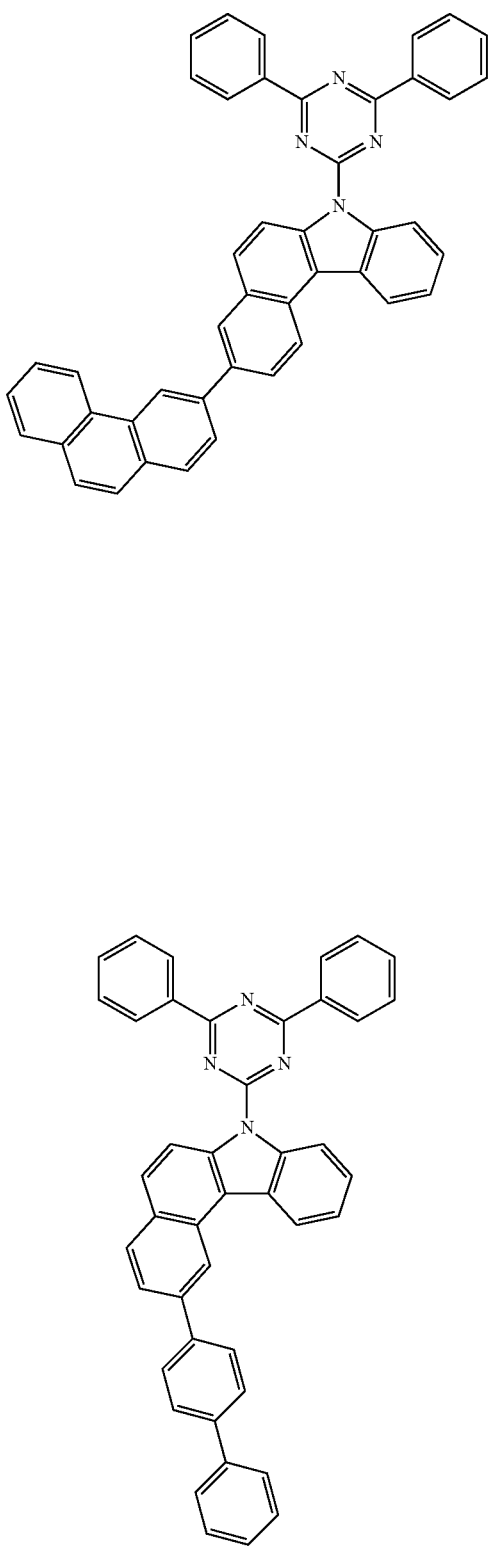

194
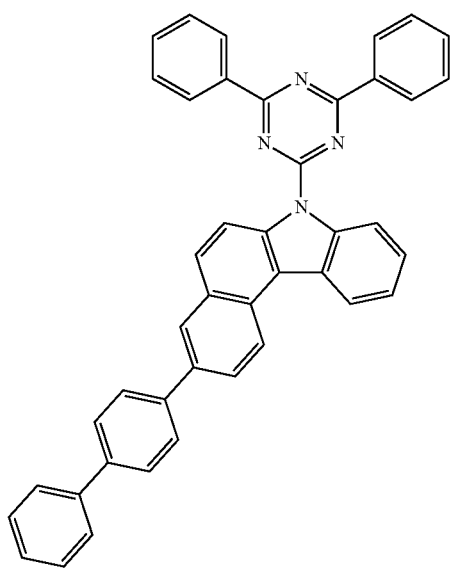
195
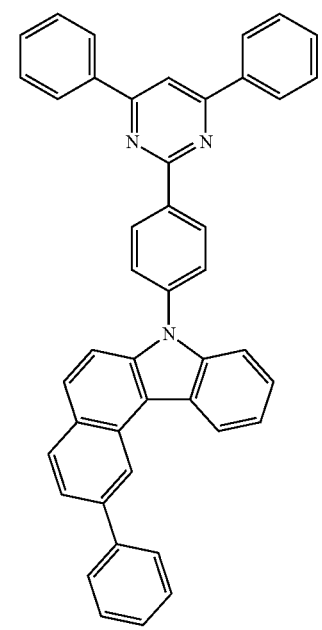
196
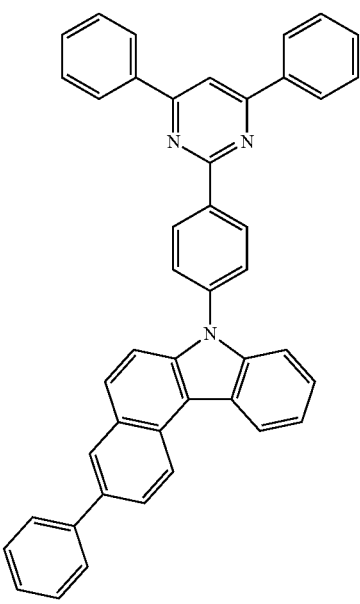
197
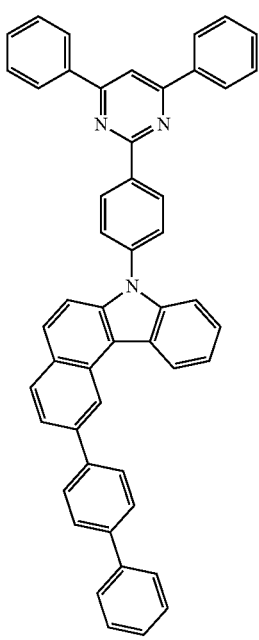

121
-continued
198
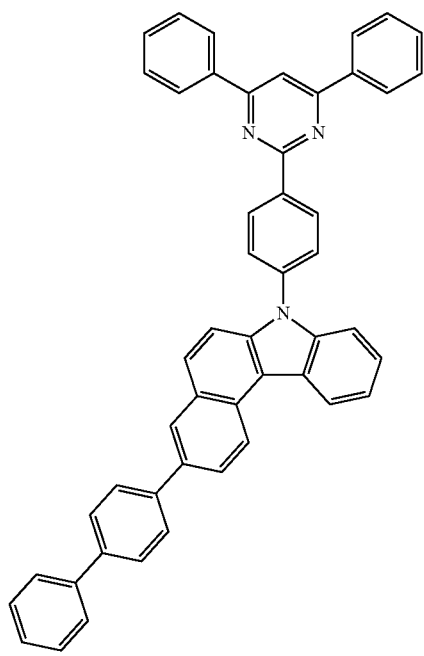
199
122
-continued
200
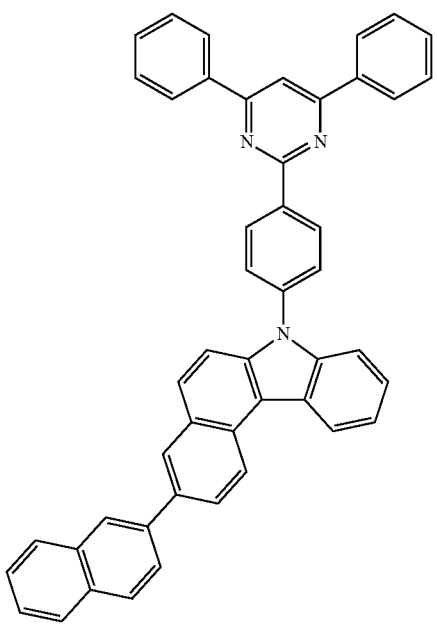
201

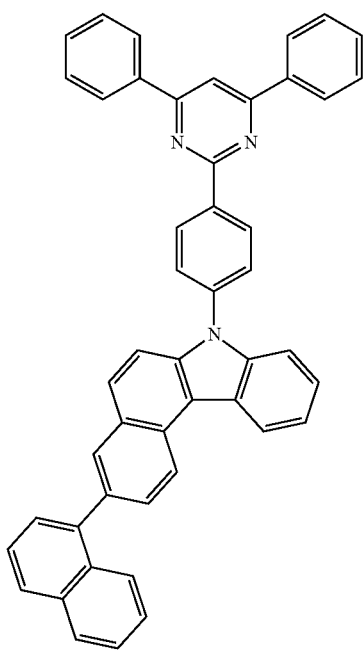
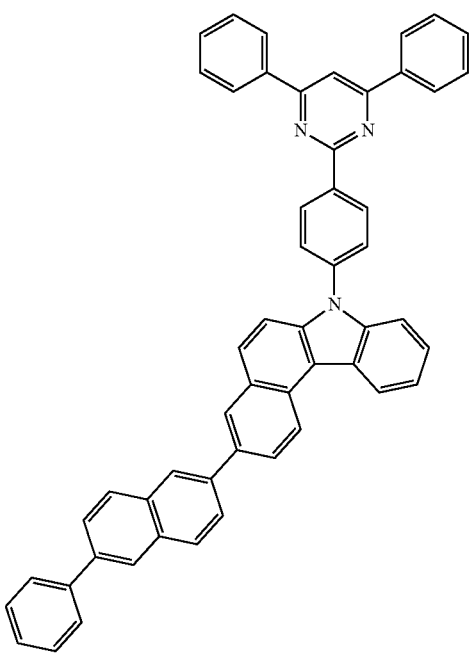

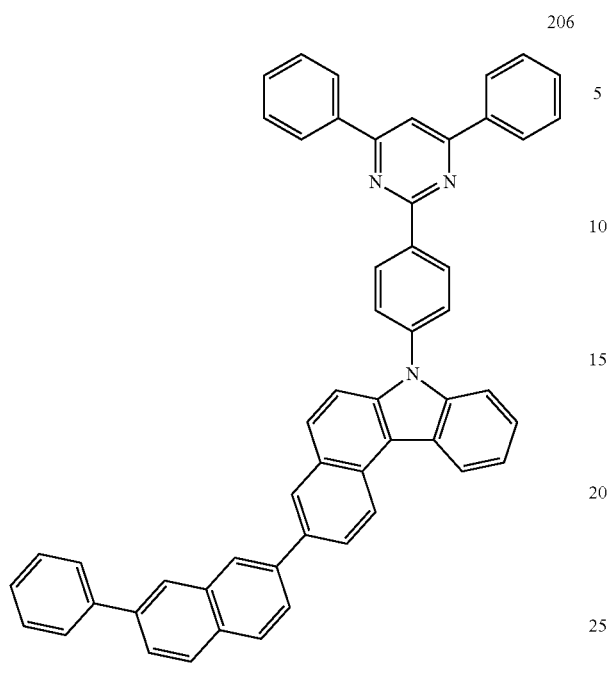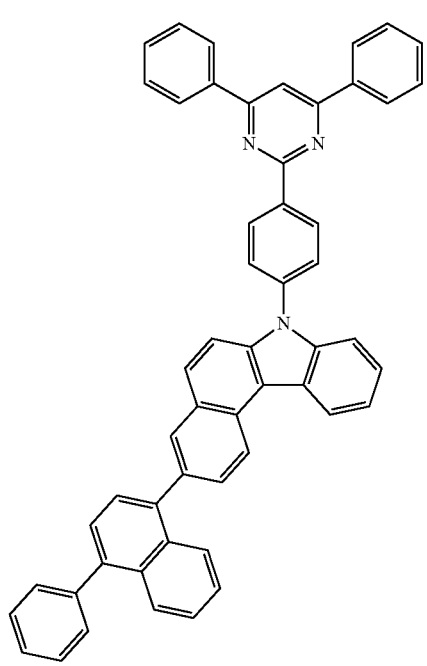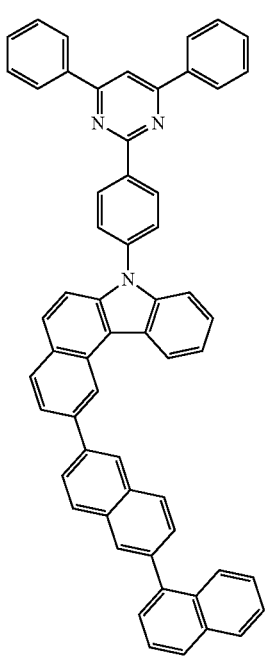

127
-continued
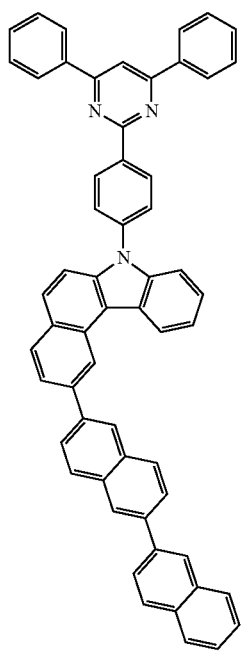
210
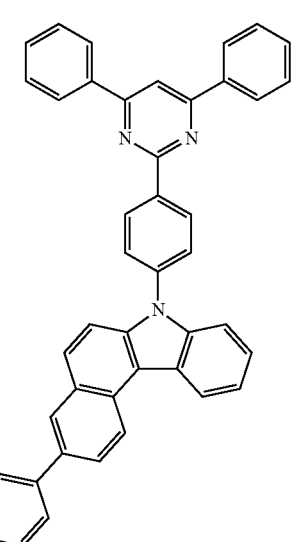
211
128
-continued
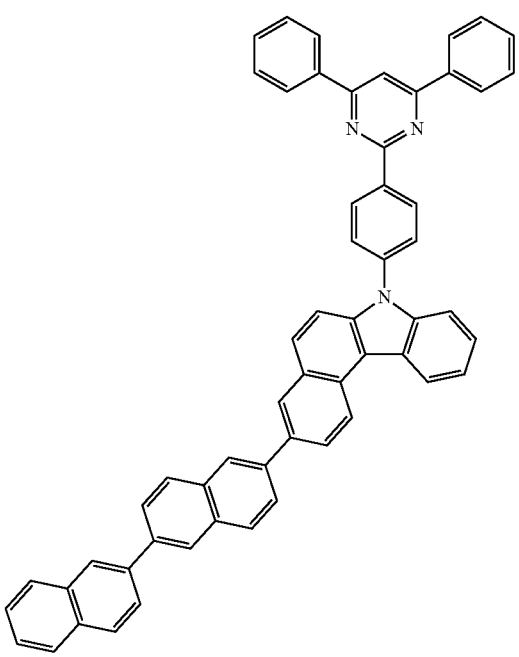
212 213

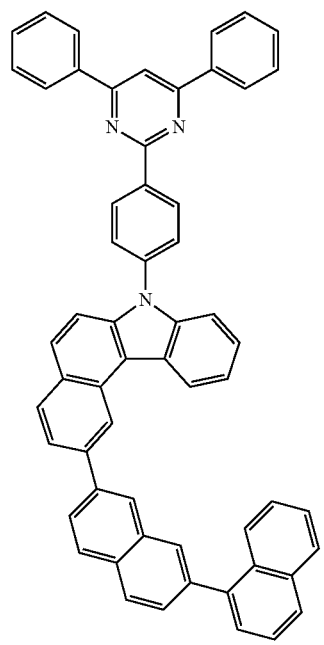
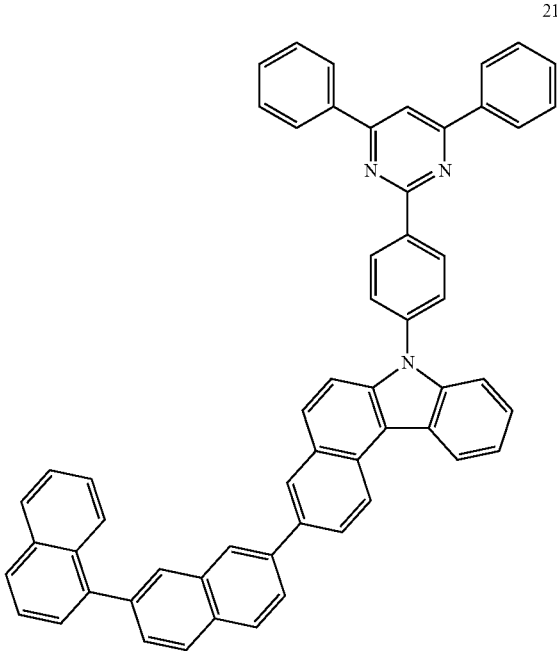
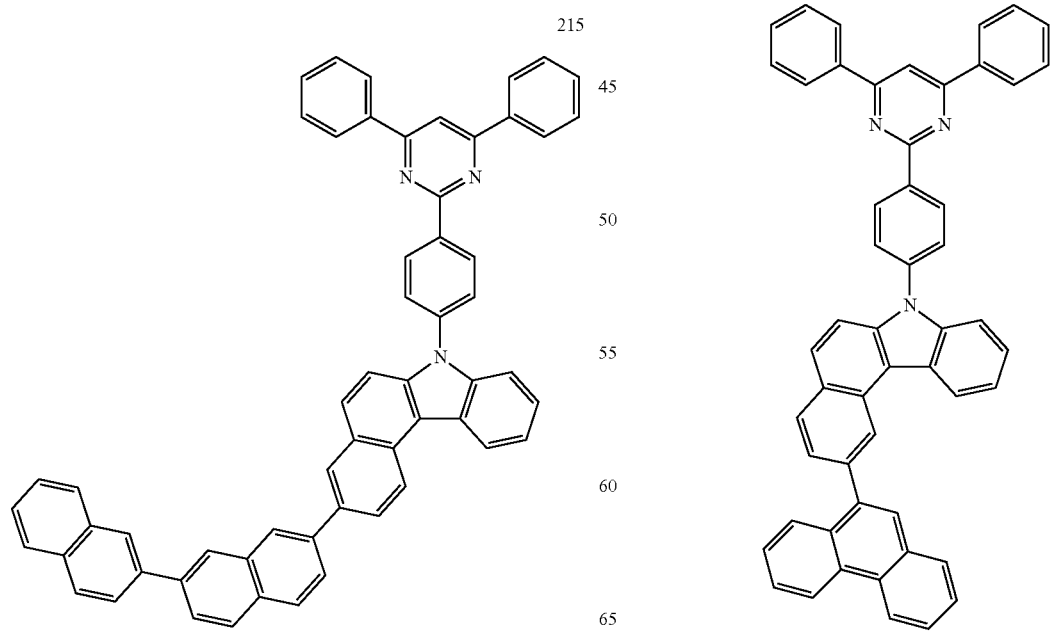

131
-continued
218
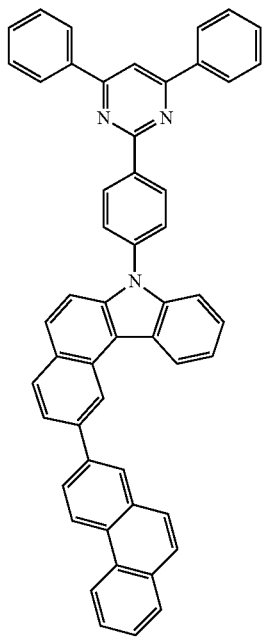
132
-continued
220
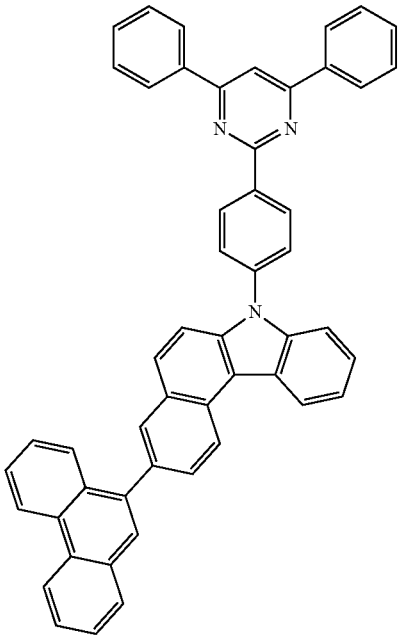
219
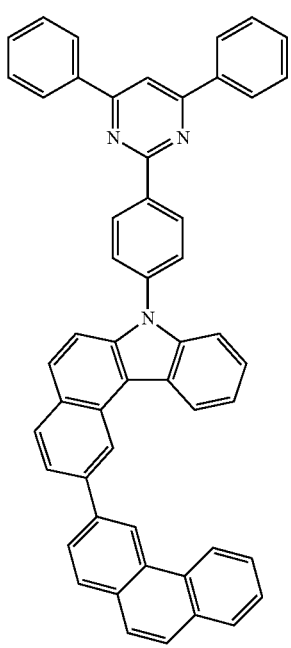
221
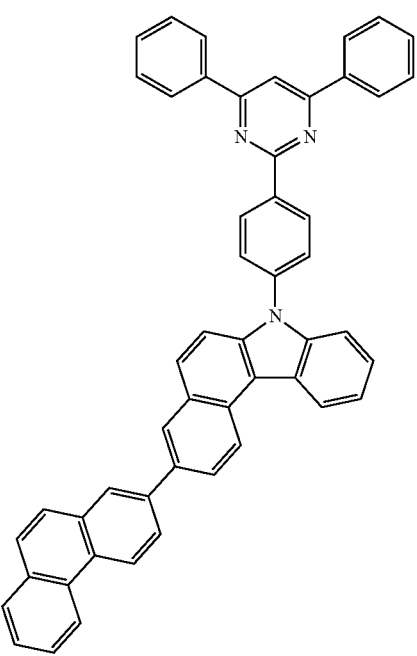

133
-continued
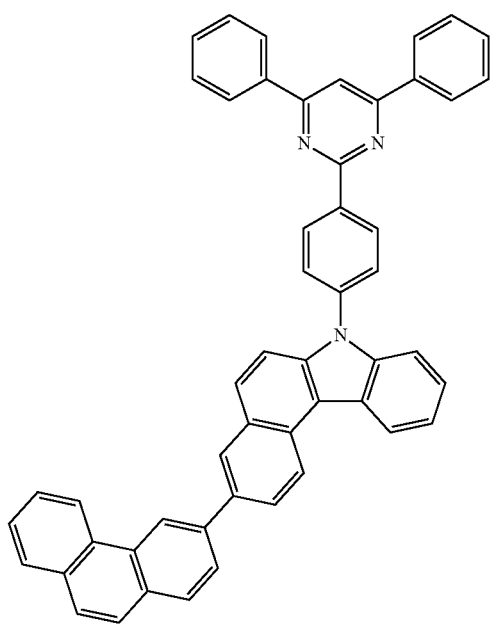
222
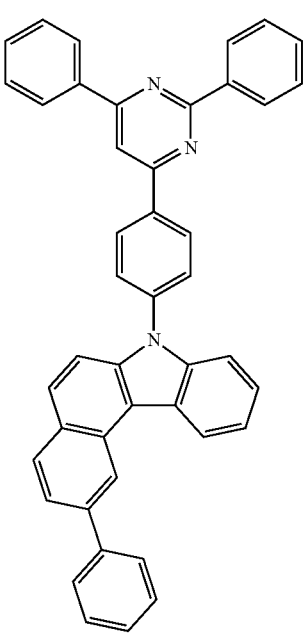
223
134
-continued
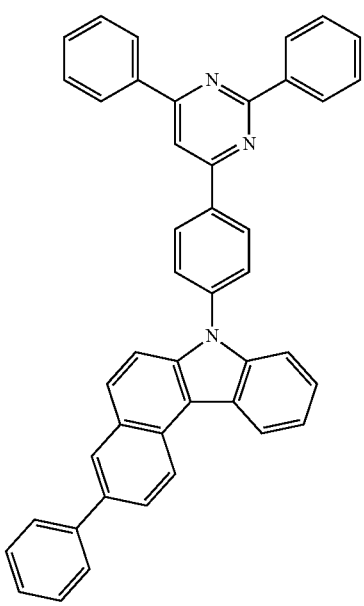
224
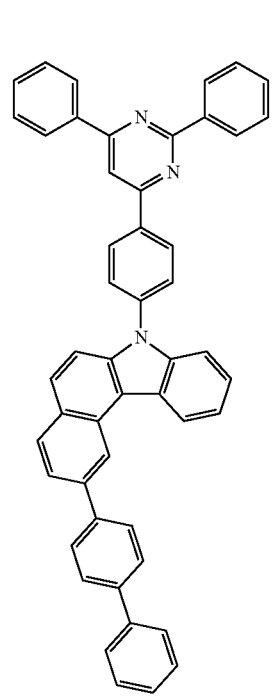
225

135
-continued
226
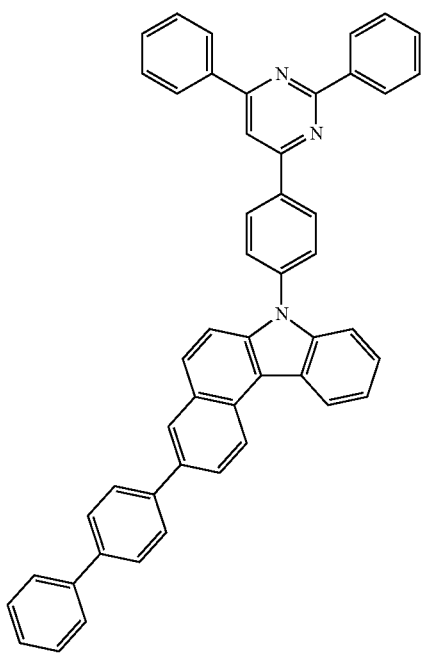
227
136
-continued
228
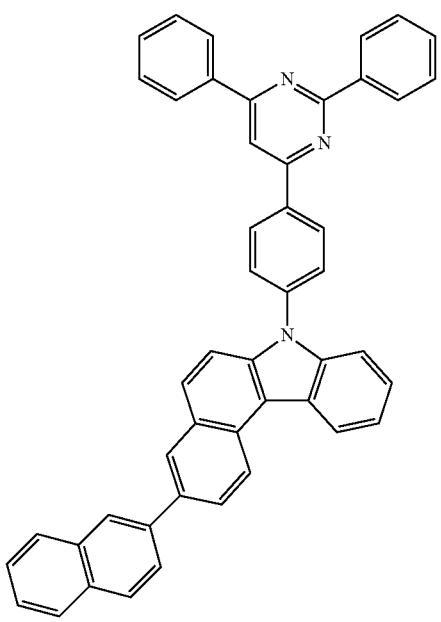
229

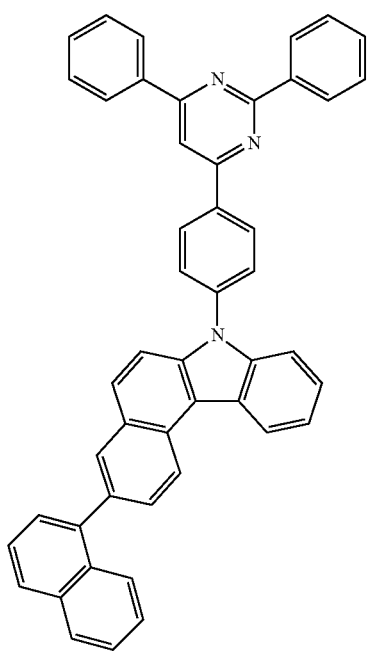
230
231
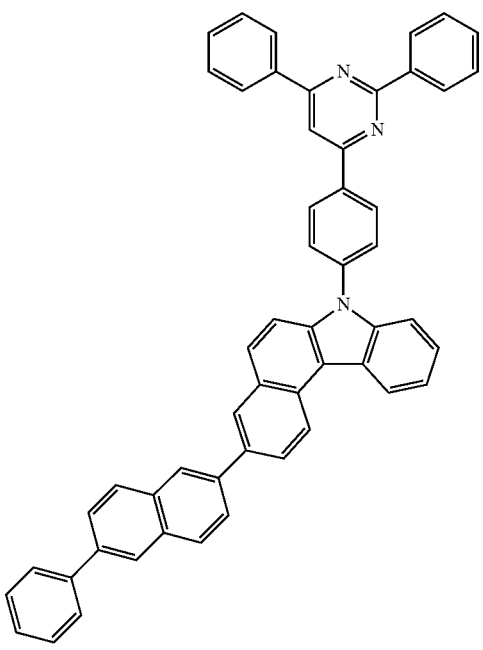
232
233

-continued
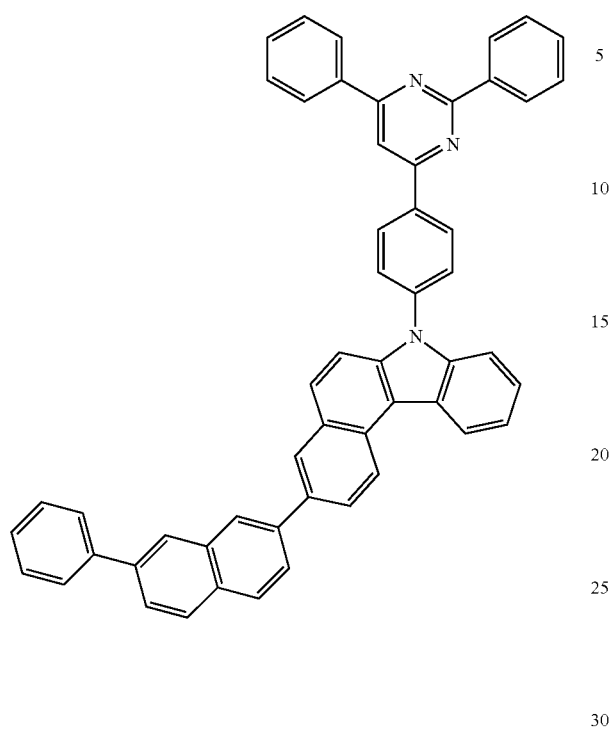
234
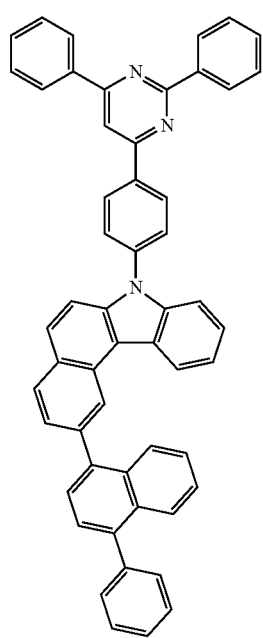
235
-continued
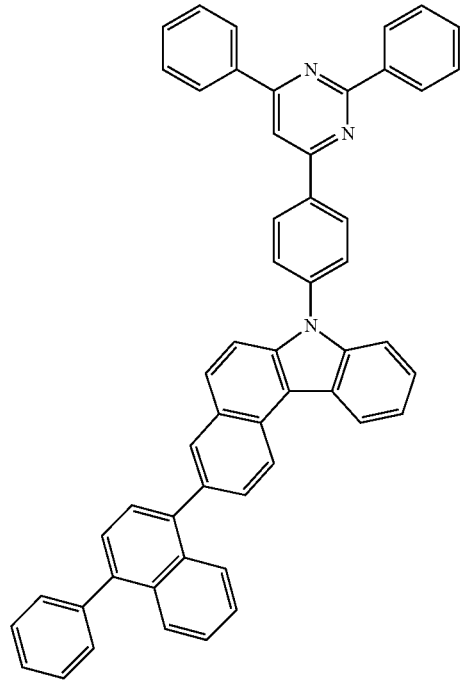
236
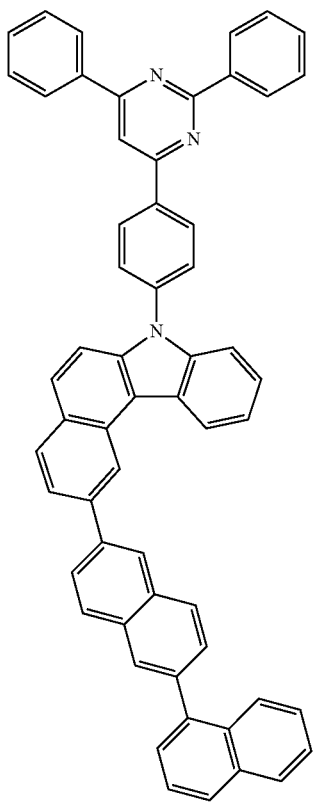
237

-continued
238
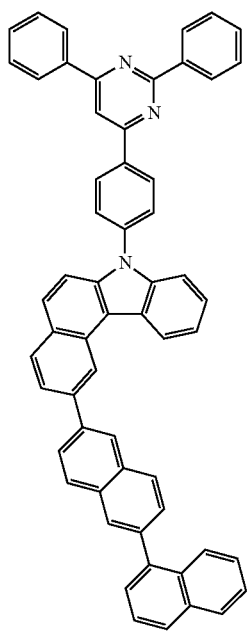
239
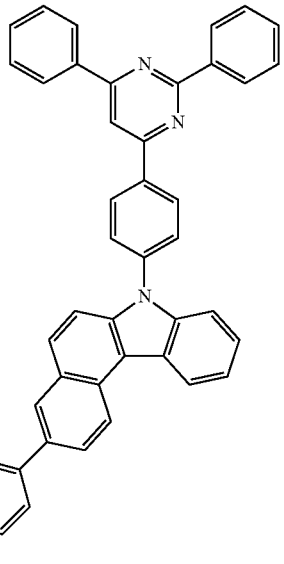
-continued
240
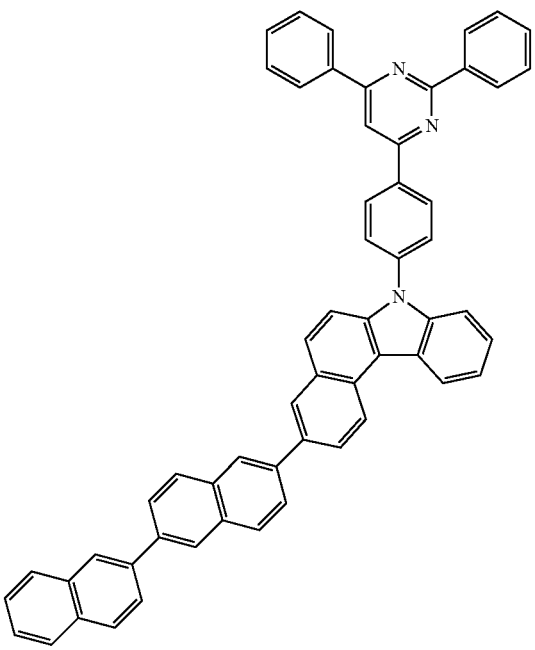
241
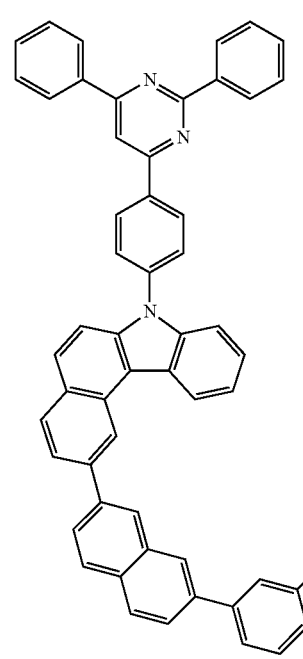

143
-continued
242
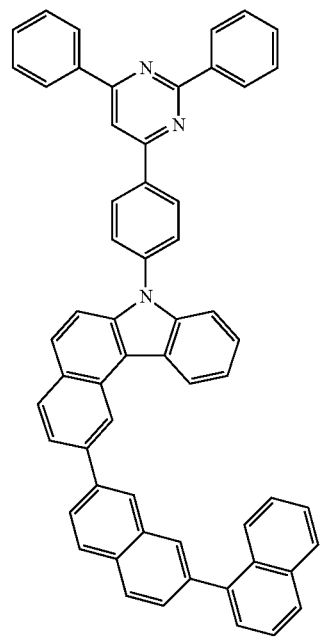
243
244
-continued
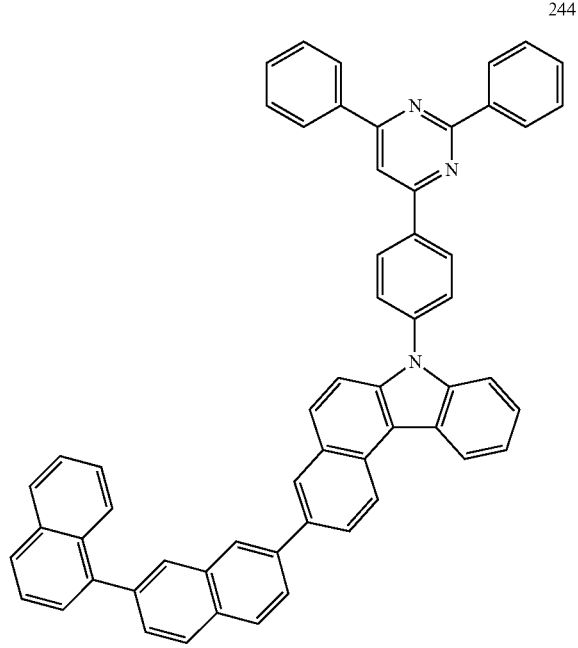
245
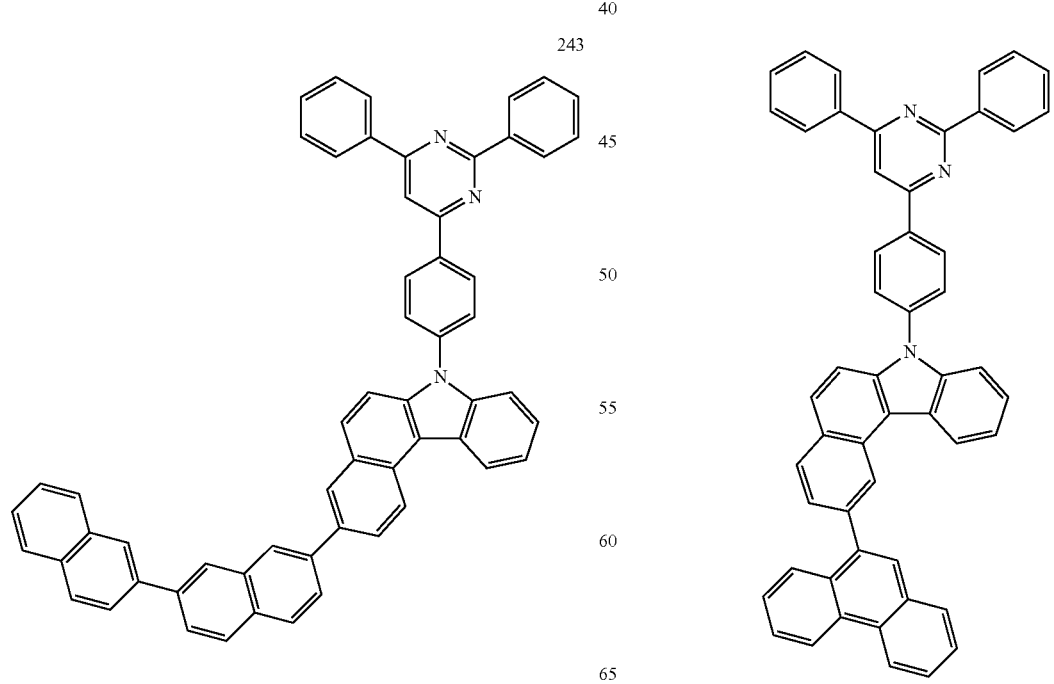

246
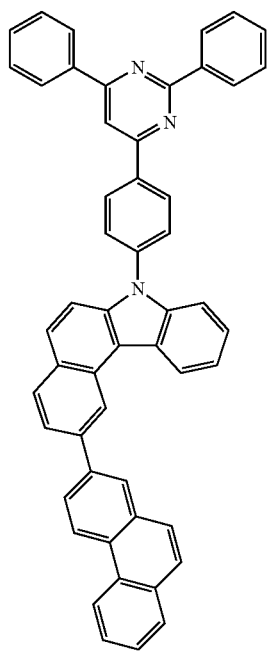
248
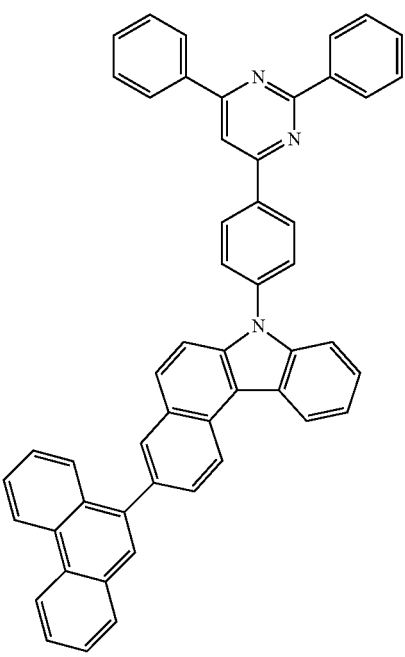
247
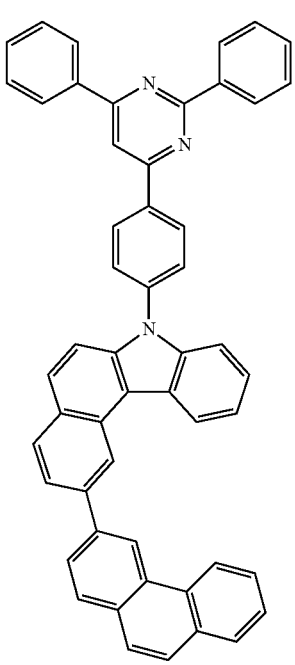
249
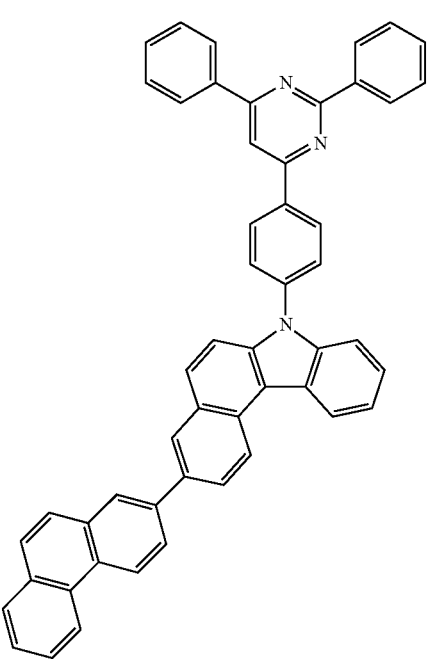

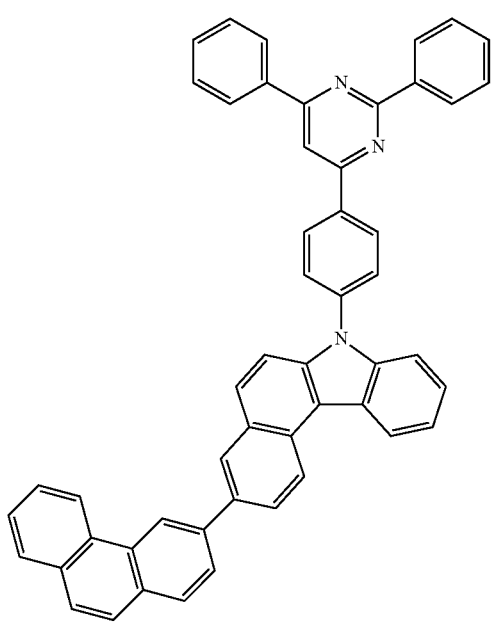
250
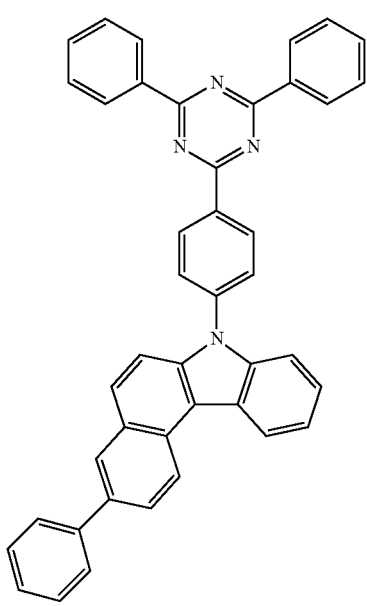
252
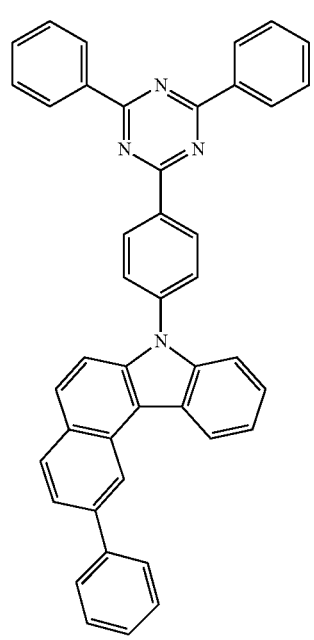
251
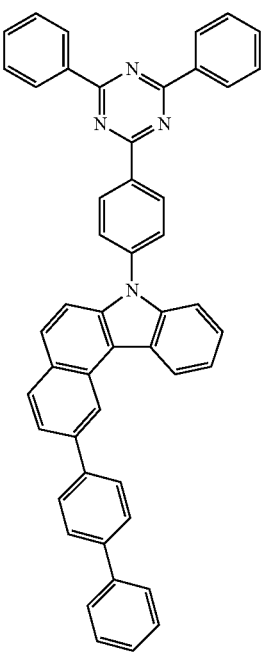
253

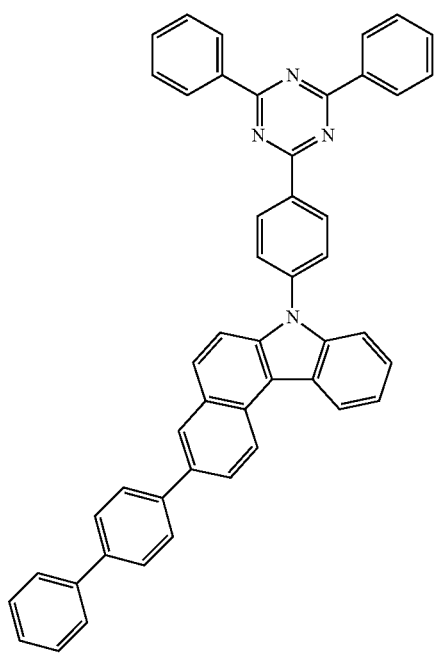
254
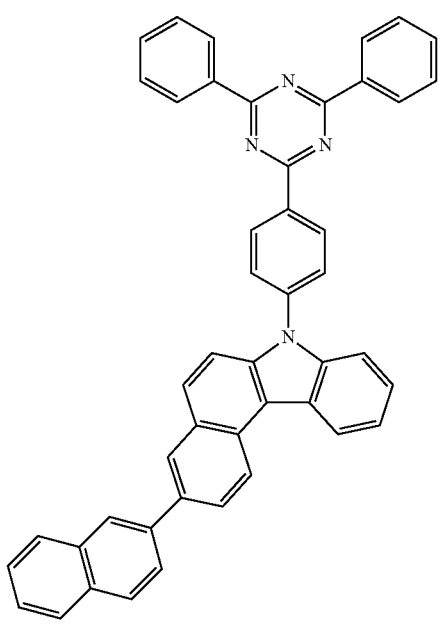
256
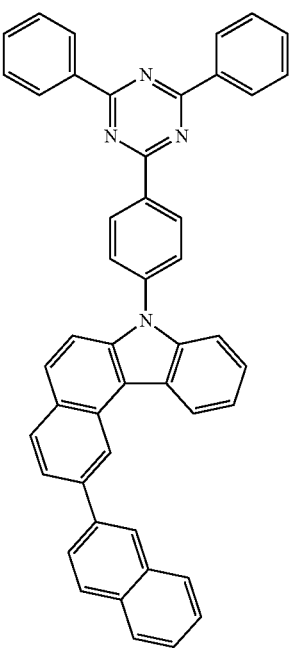
255
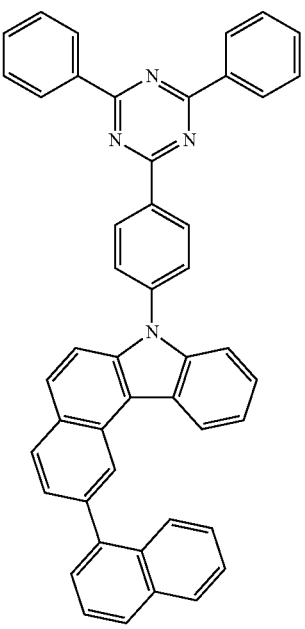
257

151
-continued
258
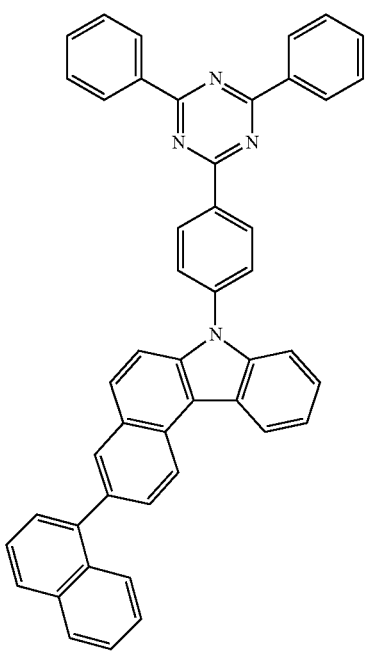
259
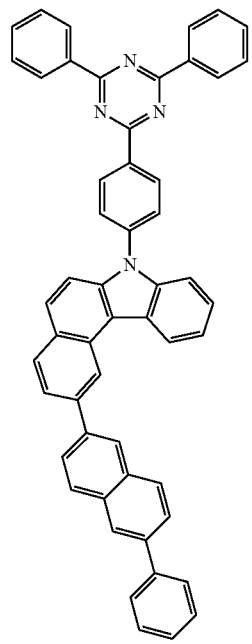
152
-continued
260
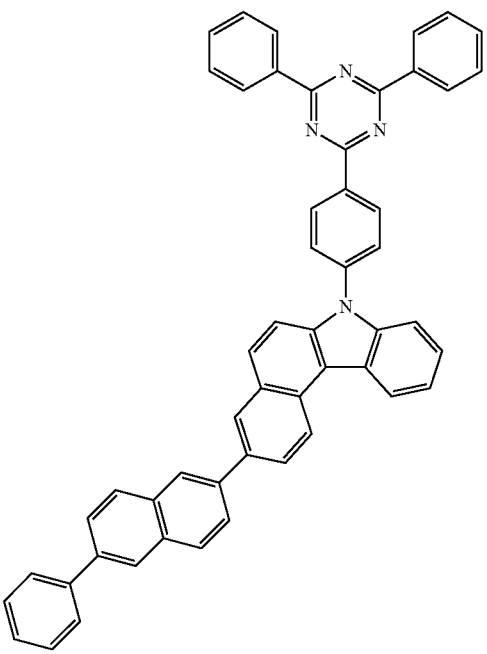
261
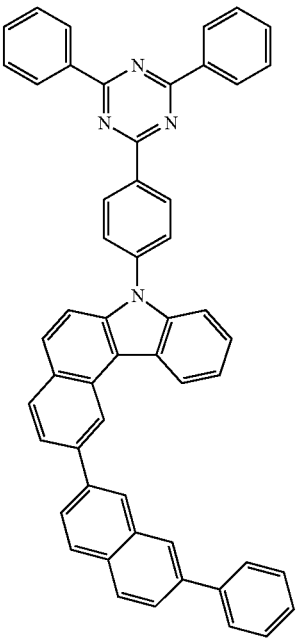

262
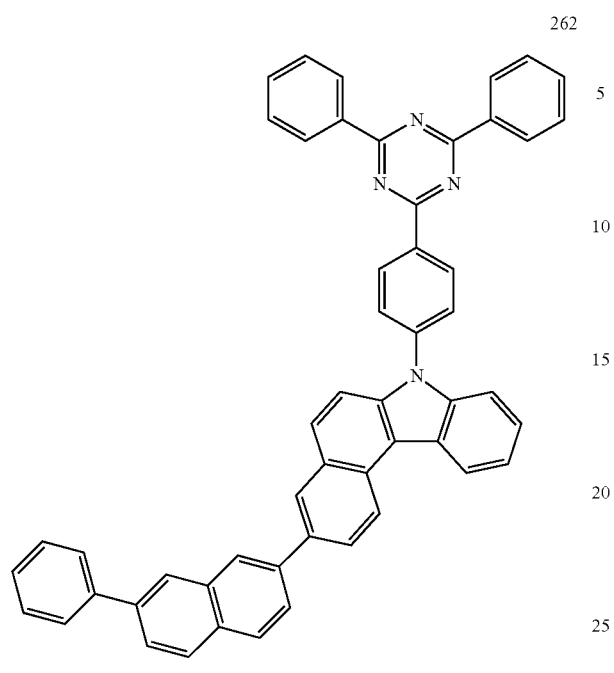
263
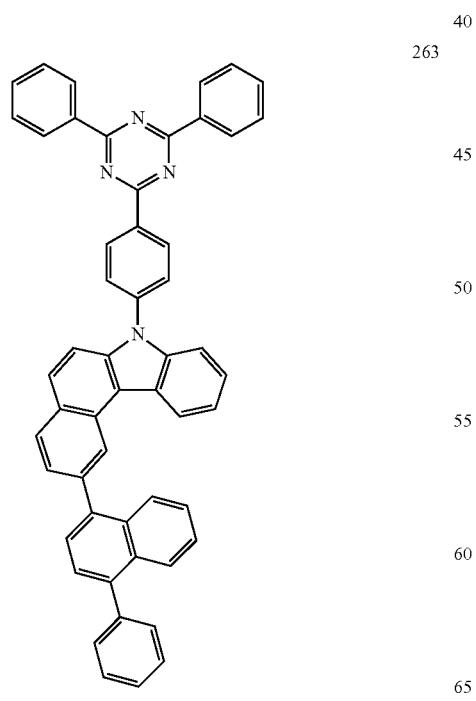
264
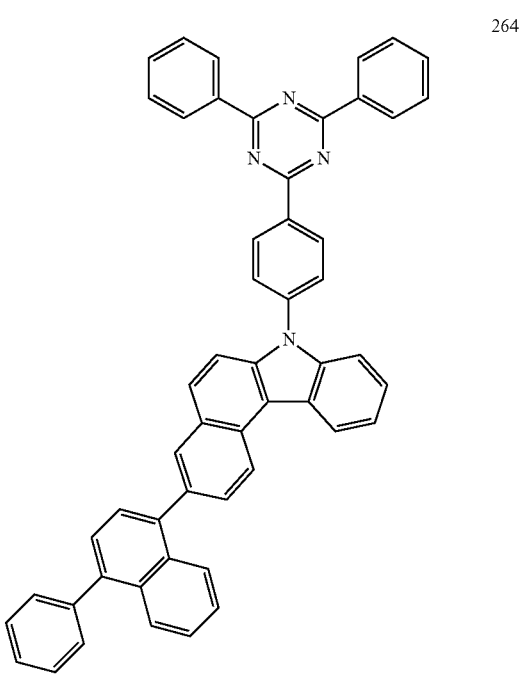
265
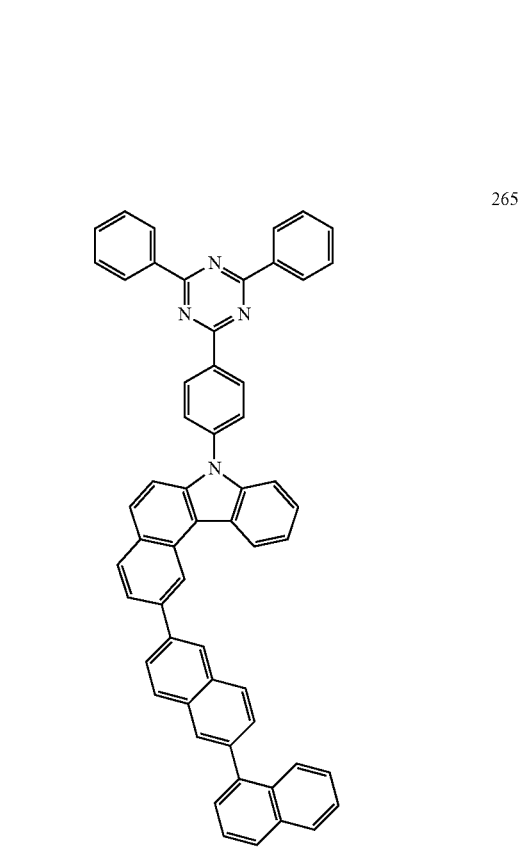

266
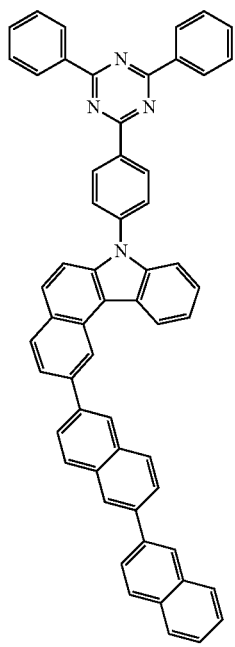
267
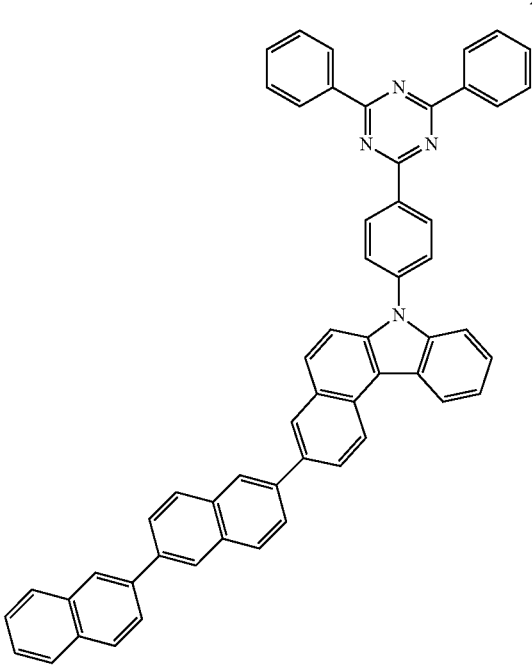
268
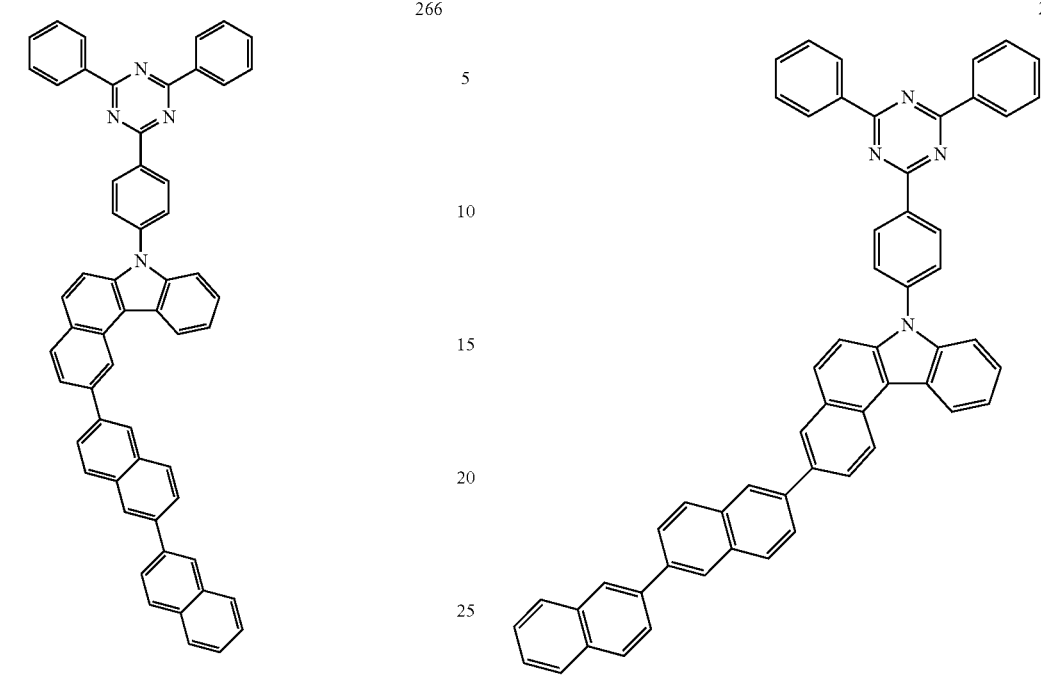
269
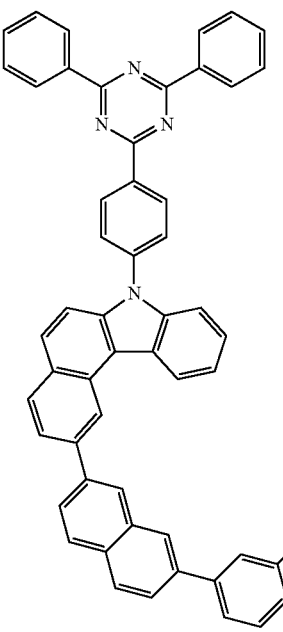

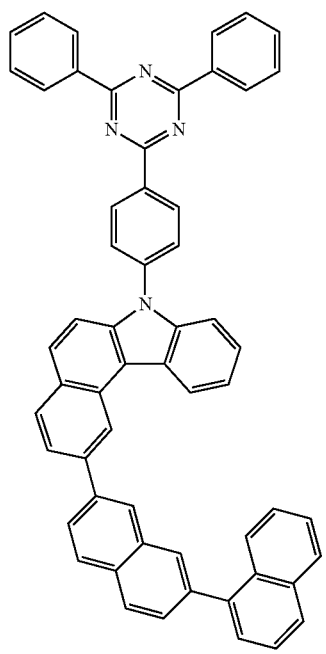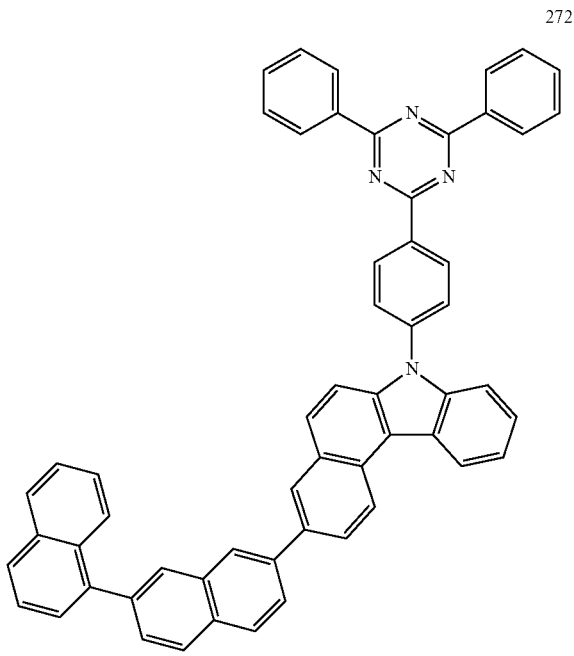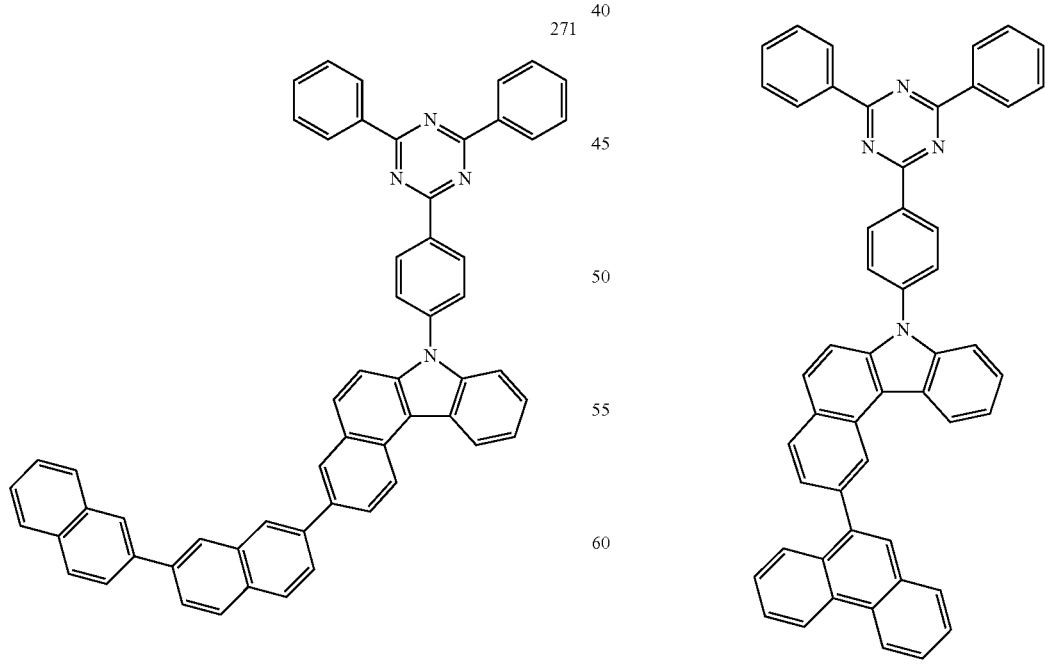

274
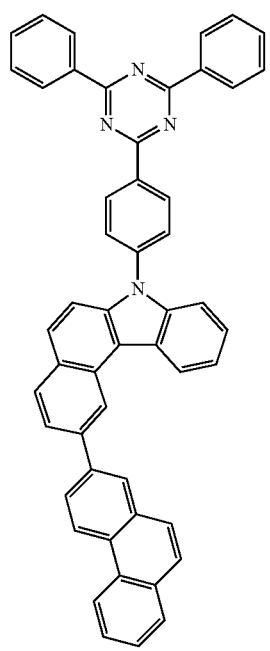
276
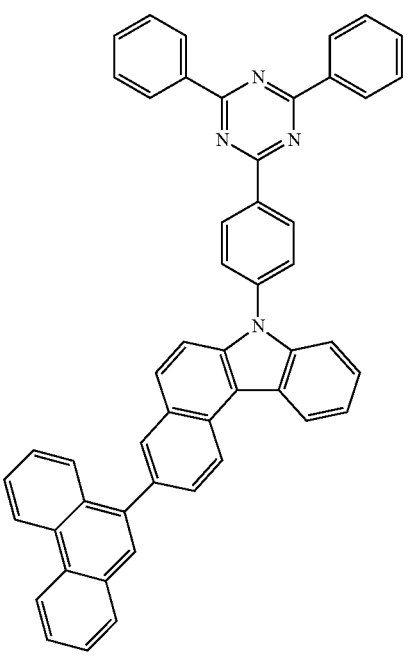
275
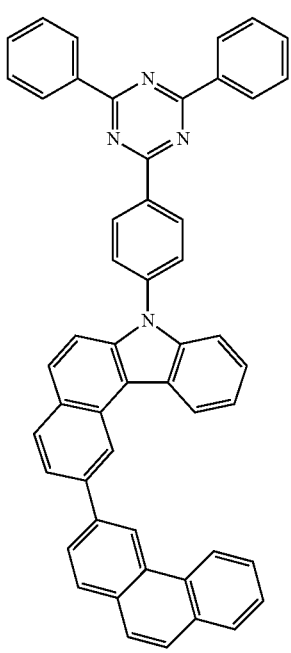
277
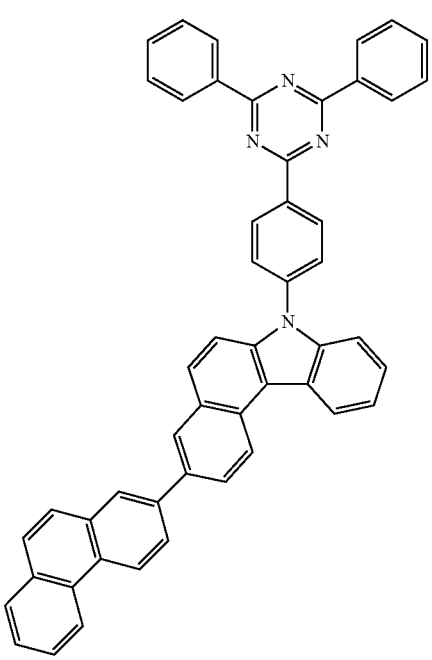

278
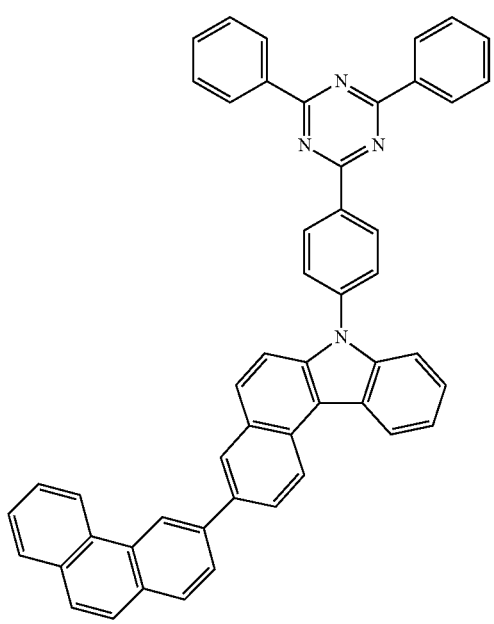
279
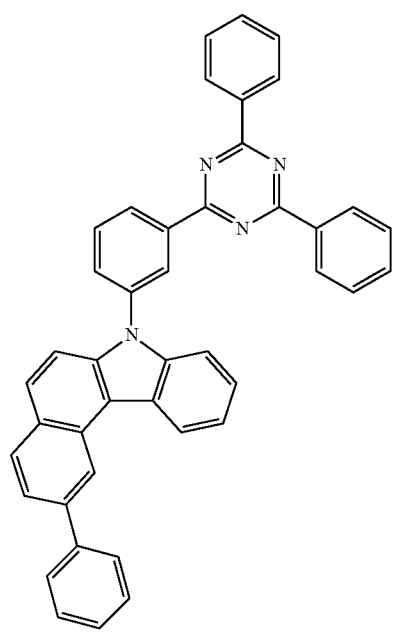
280
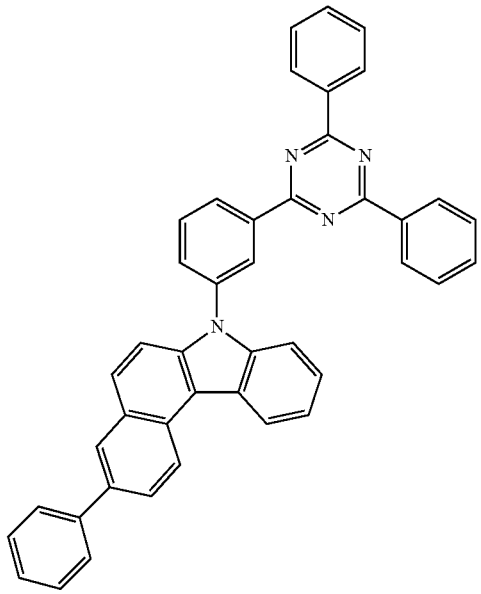
281
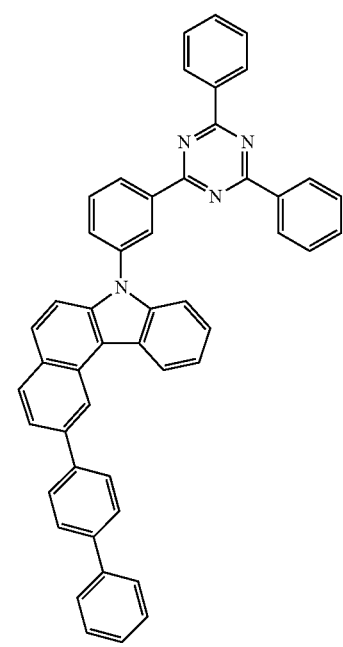

282
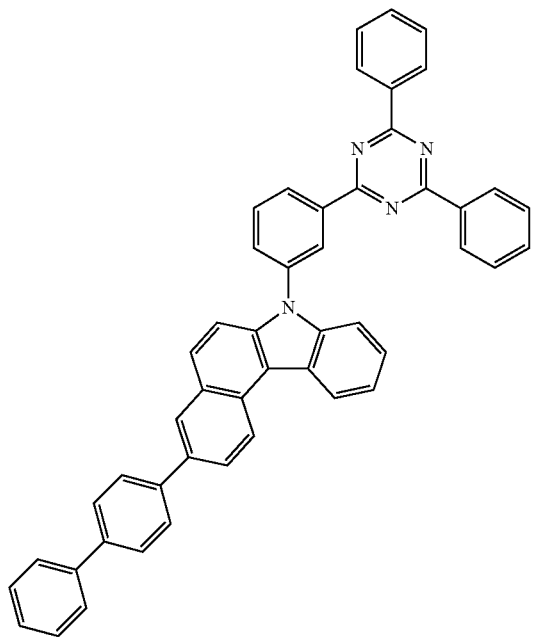
283
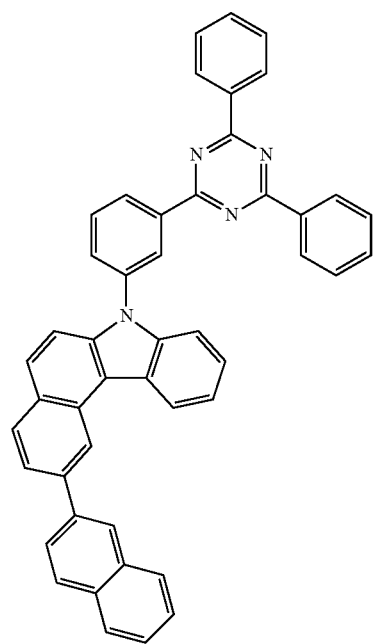
284
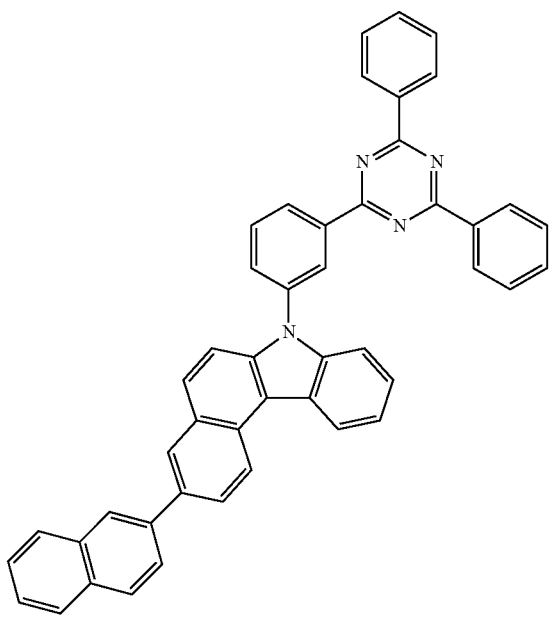
285
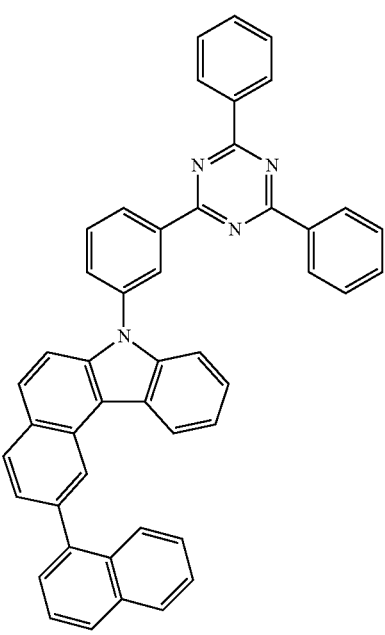

286
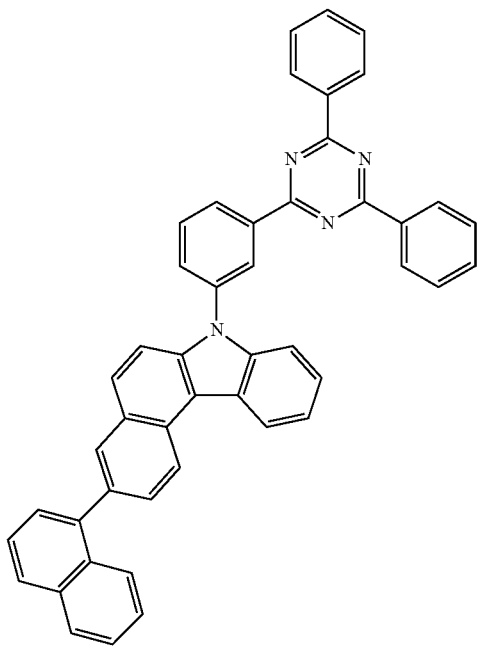
287
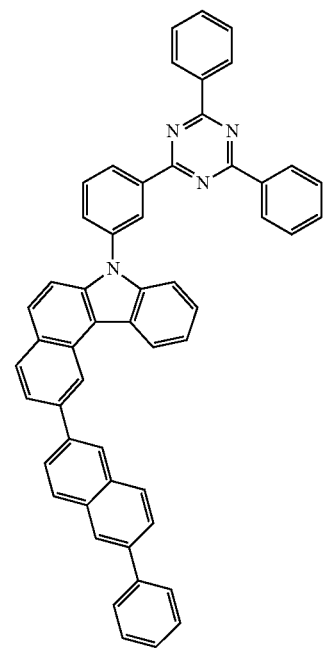
288
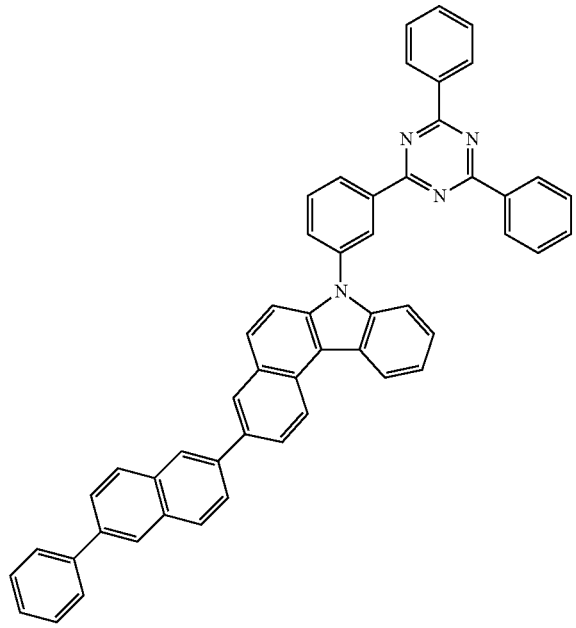
289
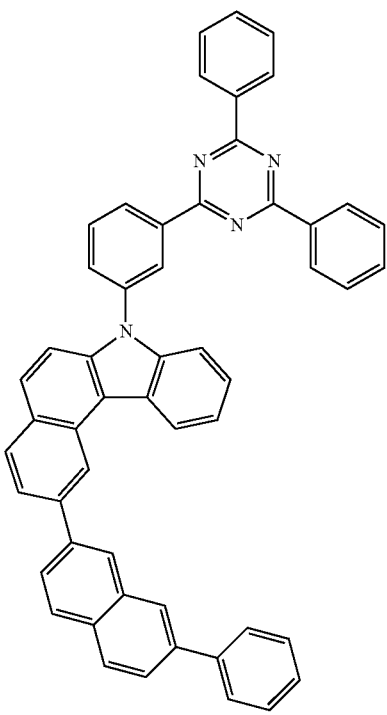

167
-continued
290
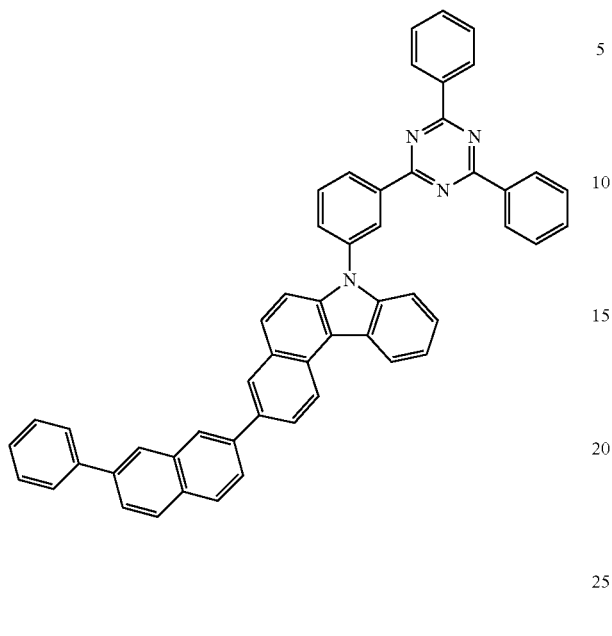
291
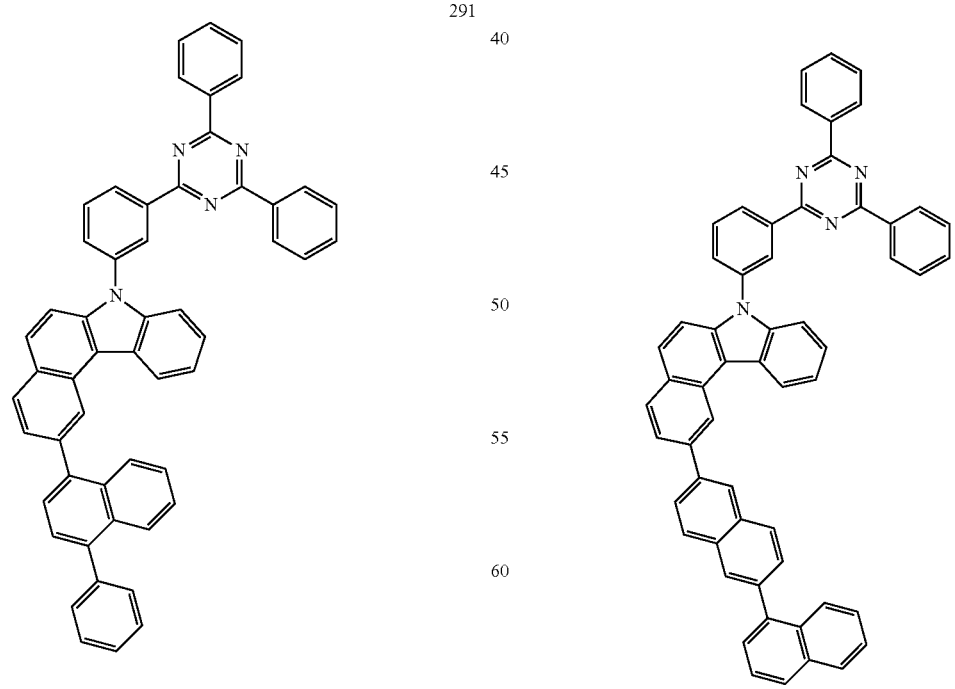
168
-continued
292
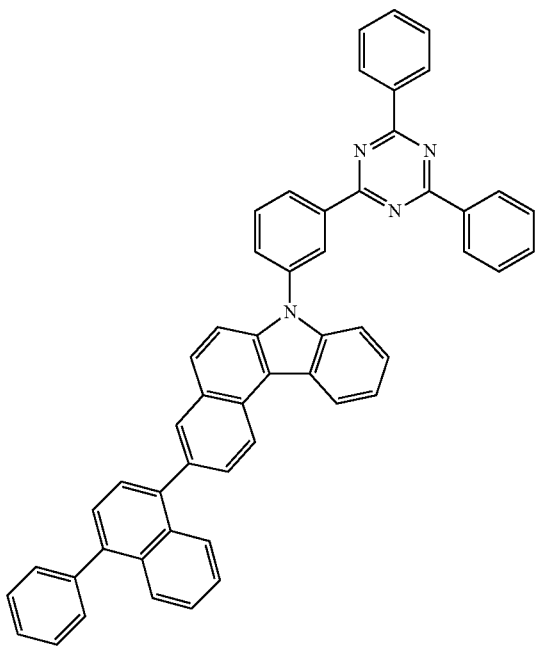
293

-continued
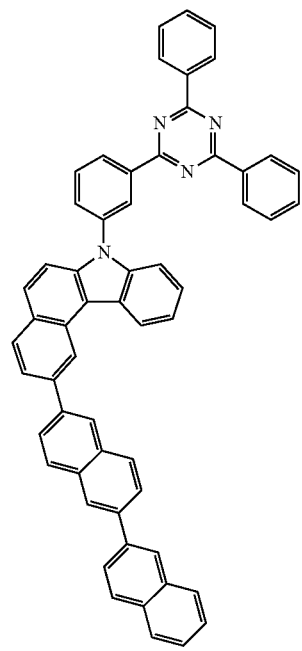
294
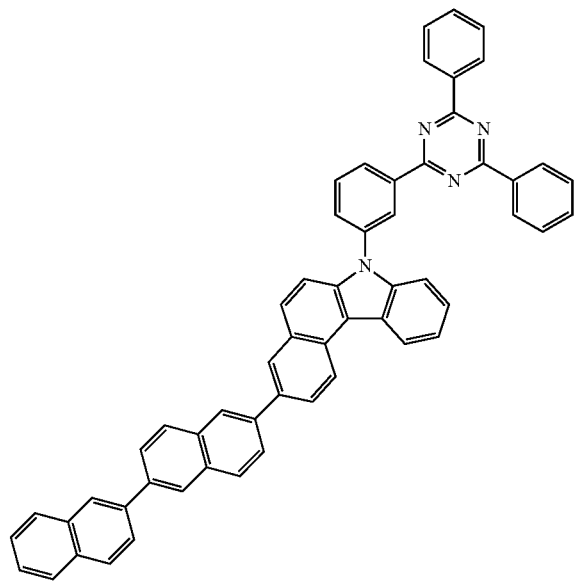
296
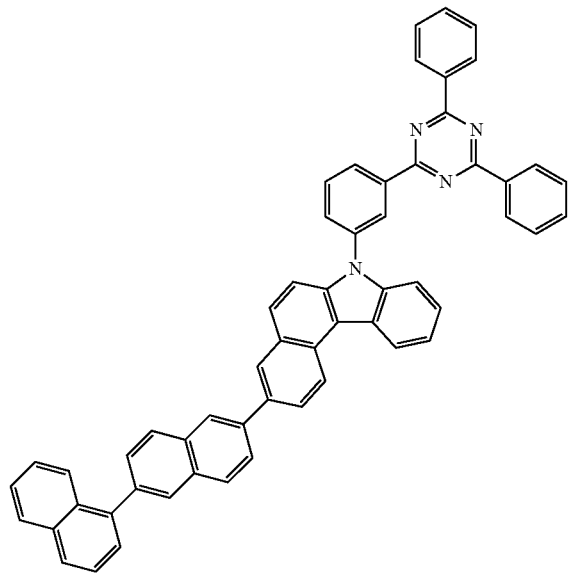
295
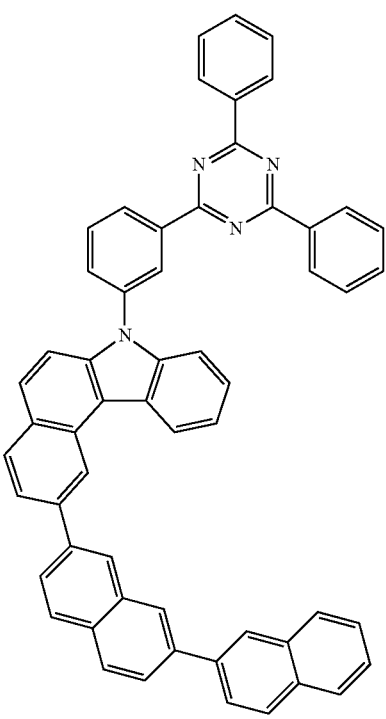
297

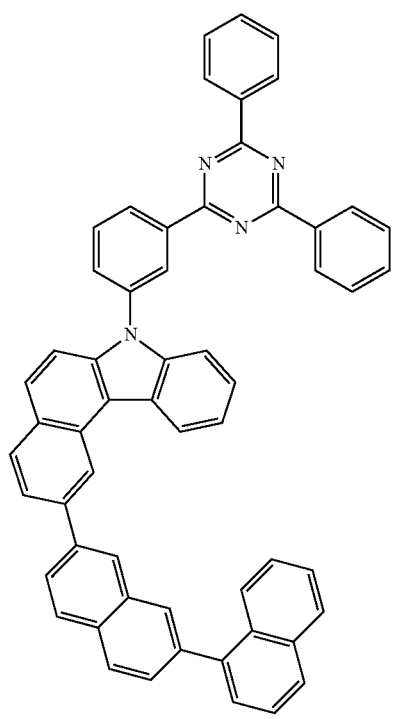
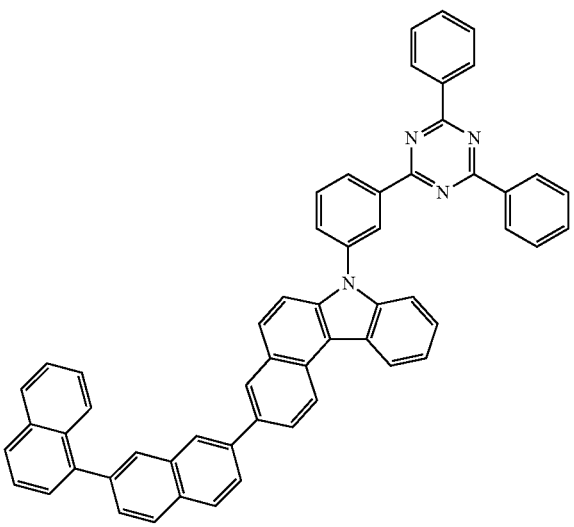
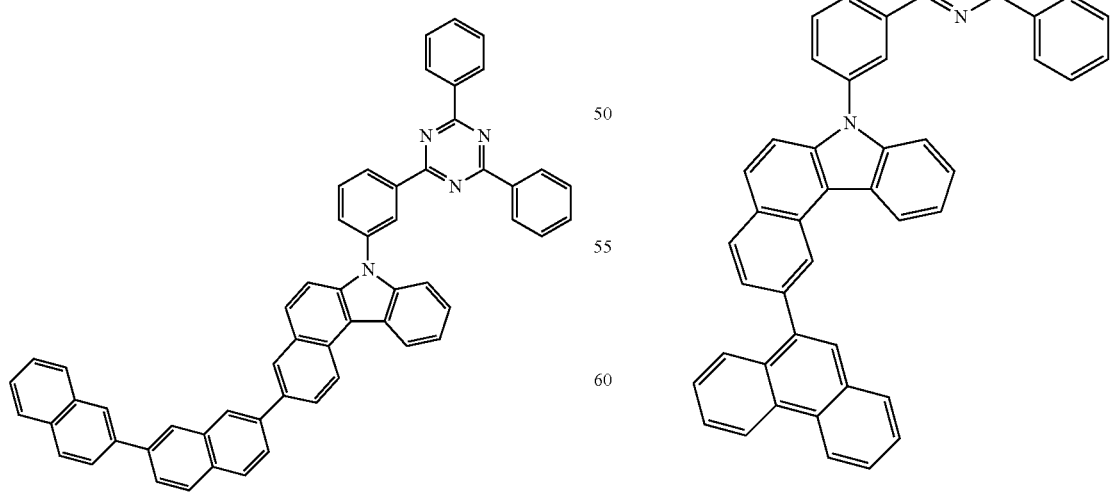

-continued
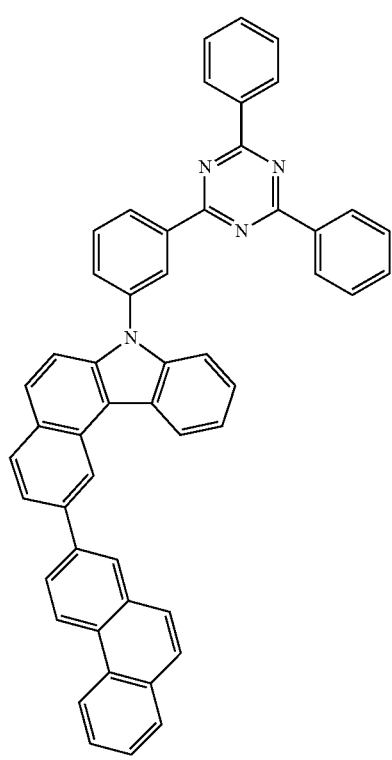
302
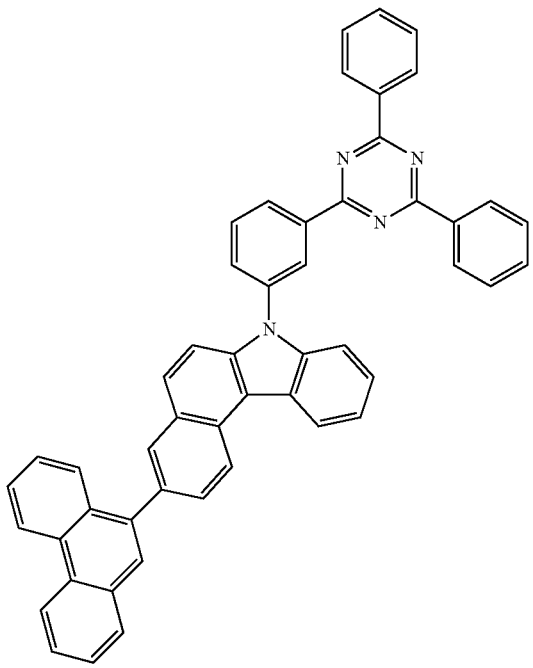
304
-continued
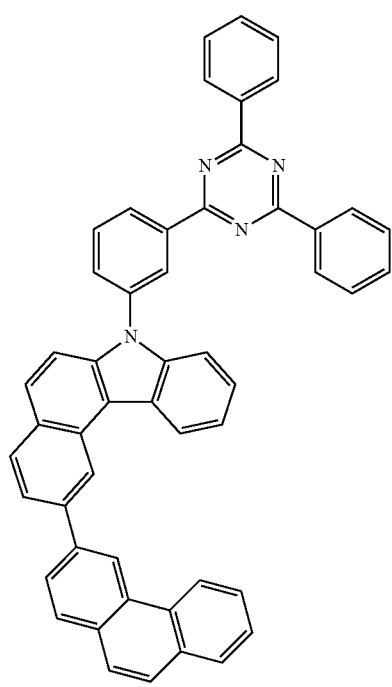
303
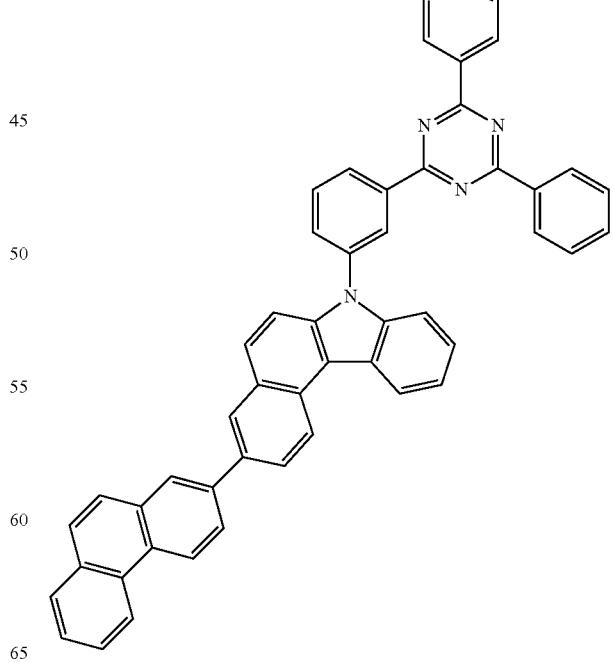
305

306
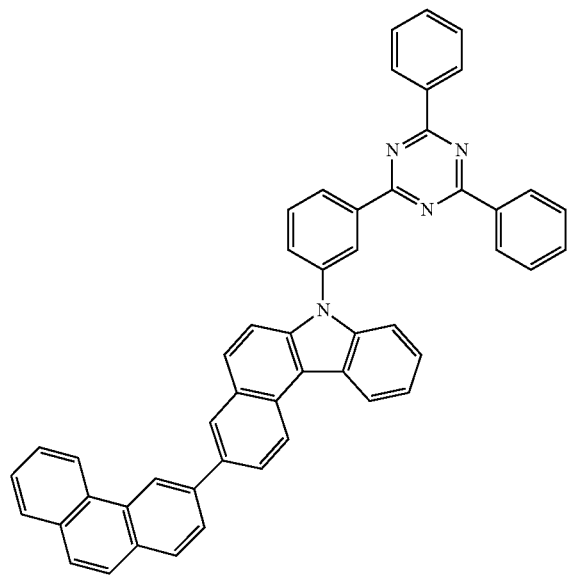
308
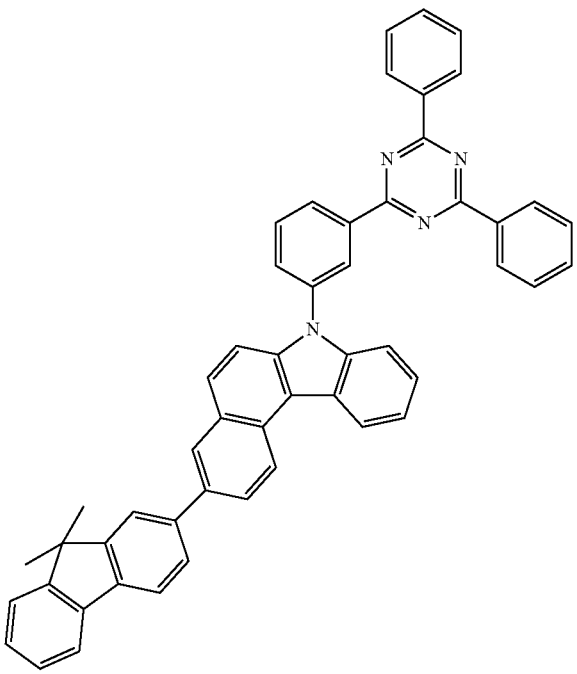
307
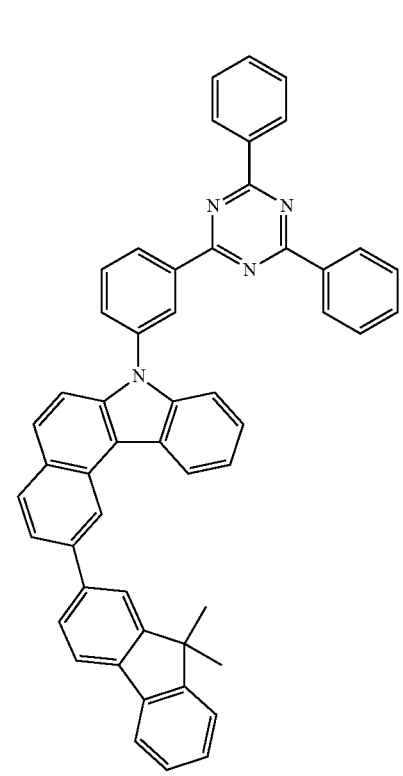
309
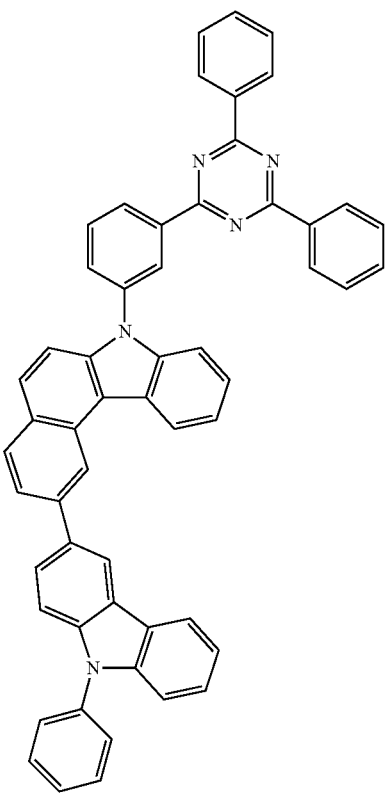

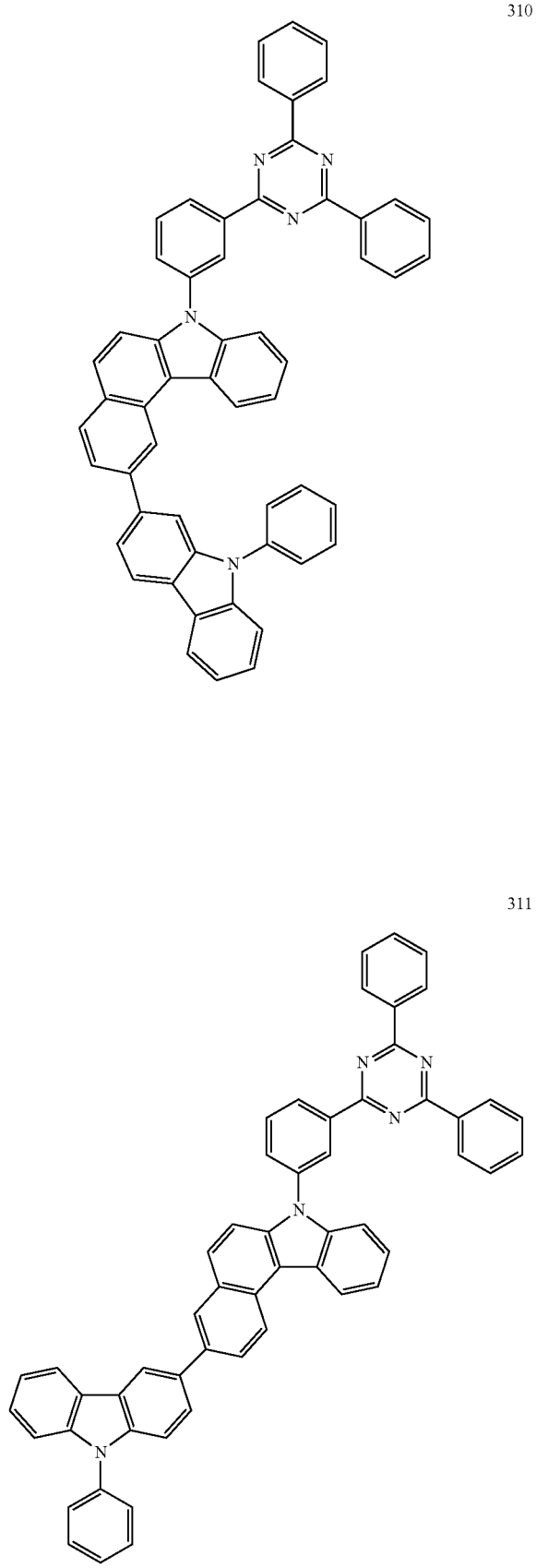
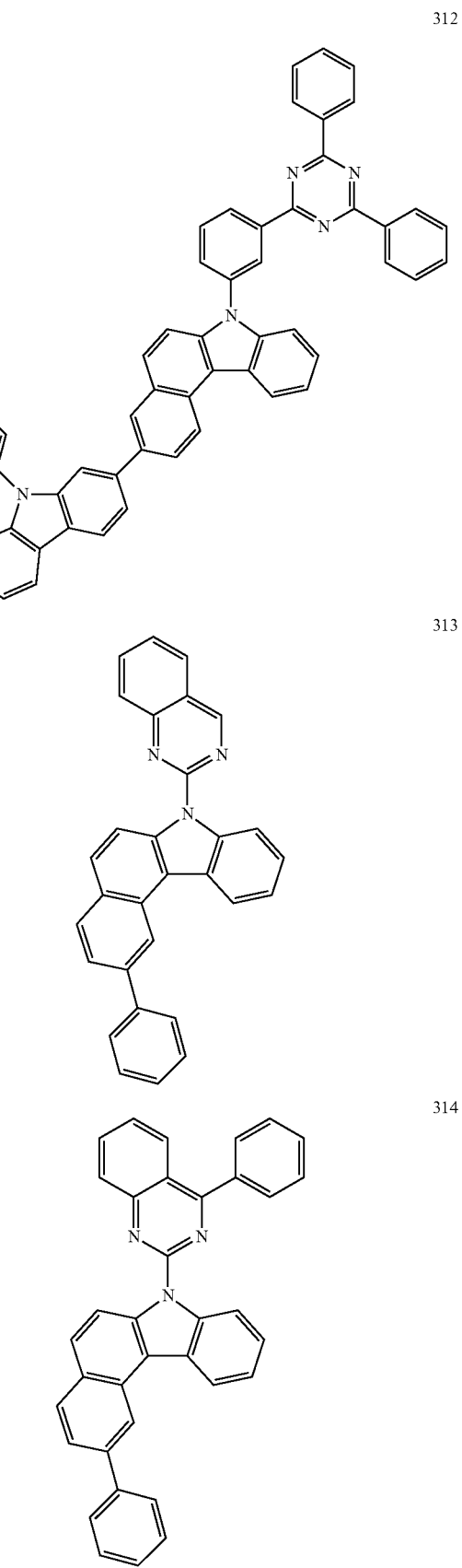

-continued
315
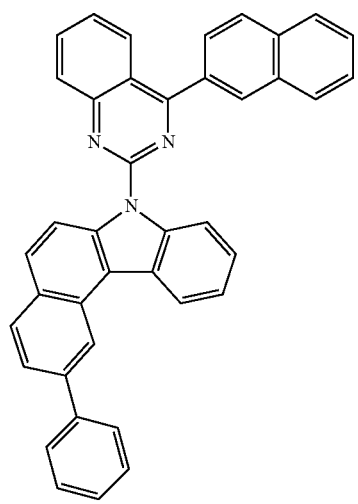
316
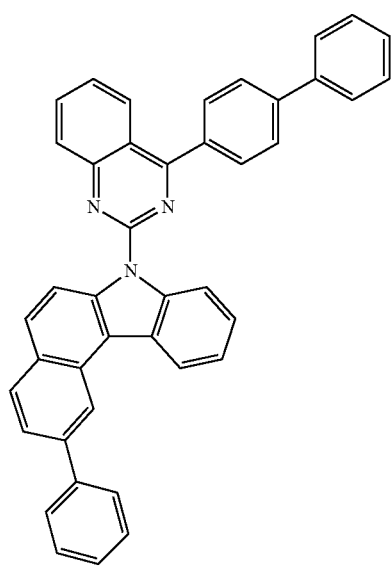
317
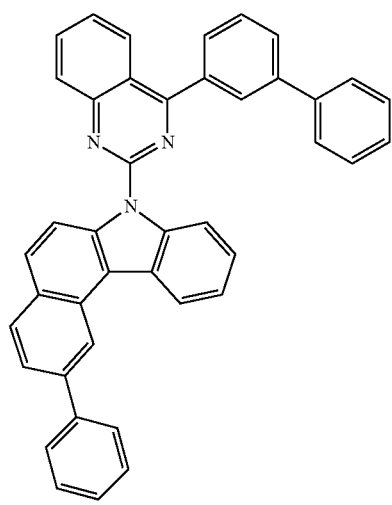
-continued
318
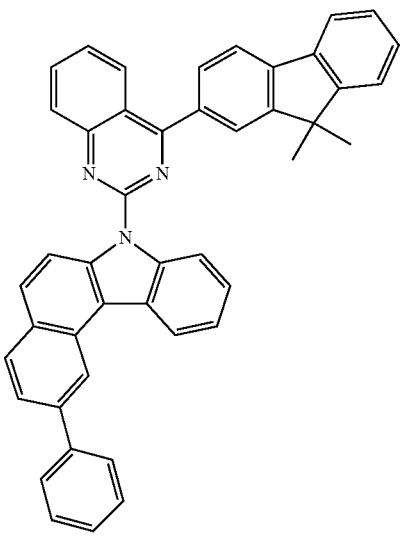
319
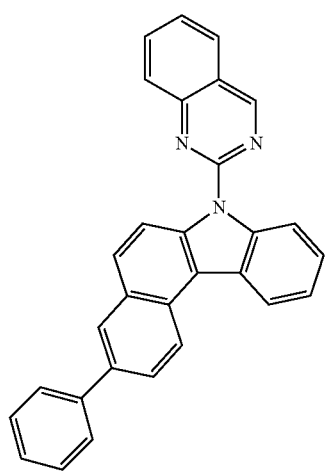
320
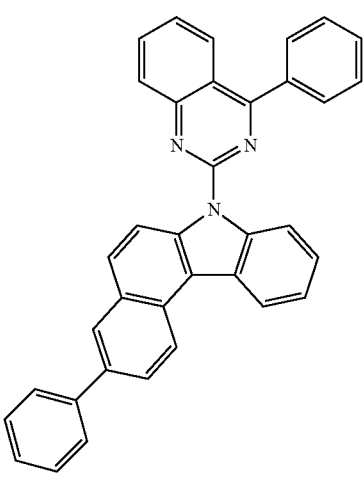

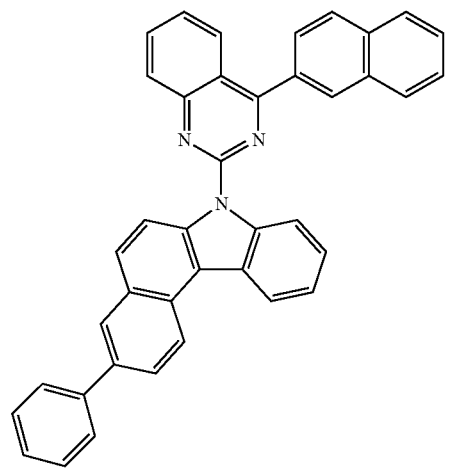
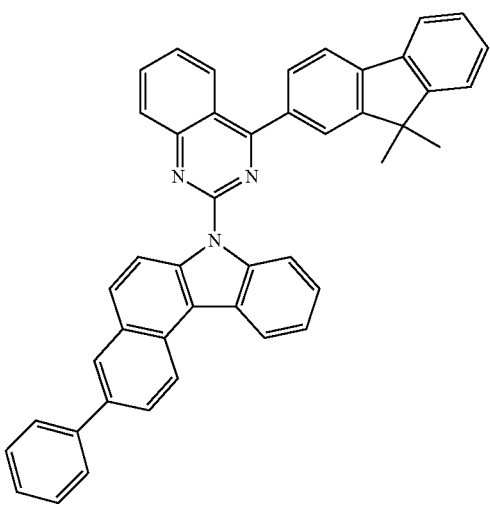
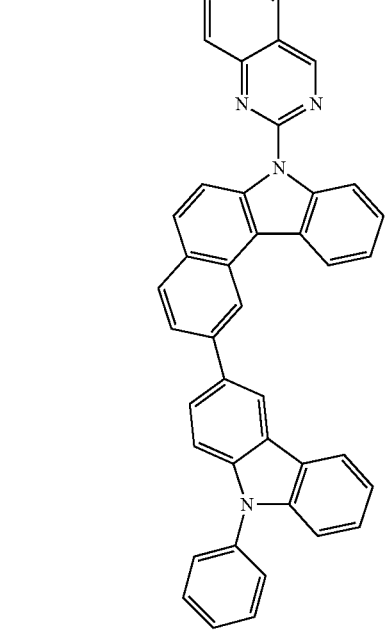

327
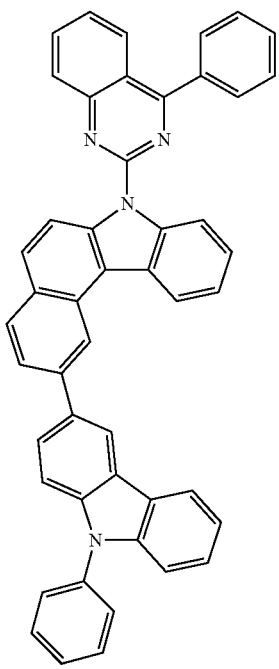
328
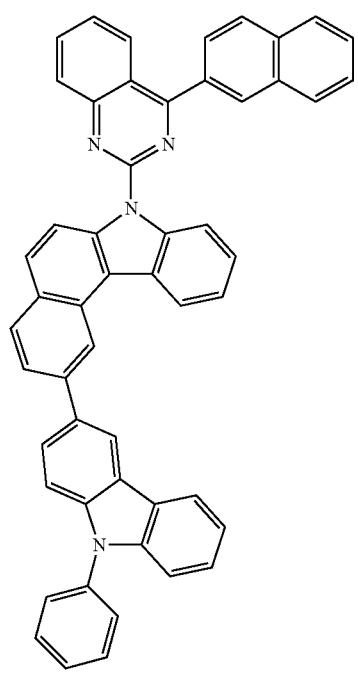
329
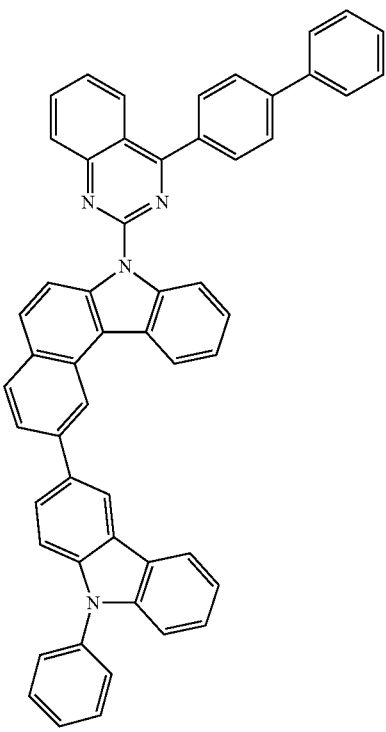
330
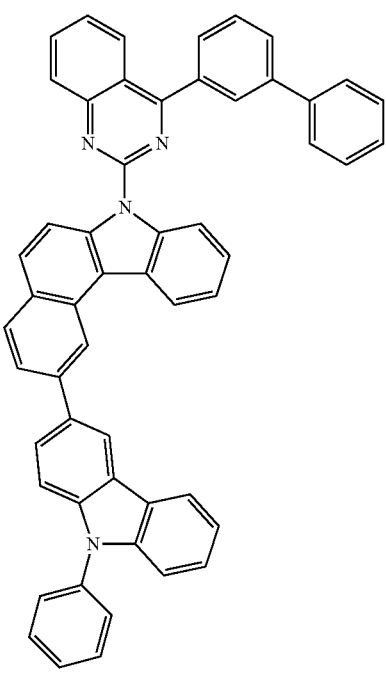

331
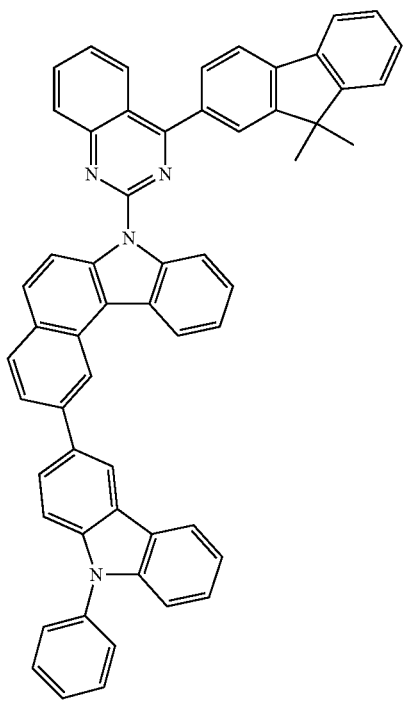
332
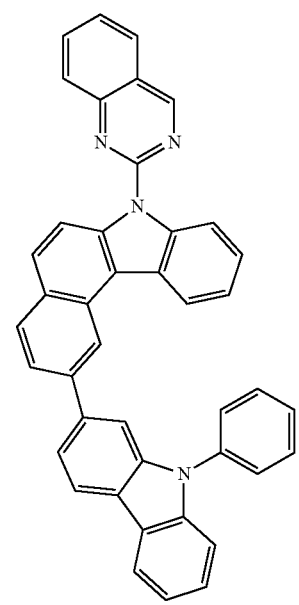
333
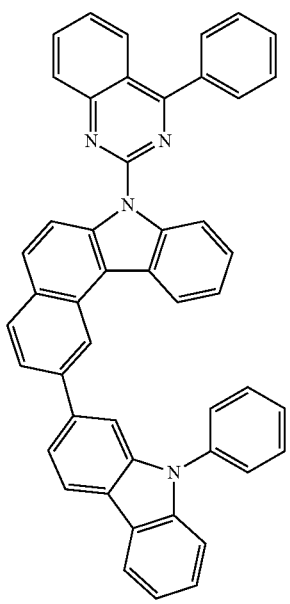
334
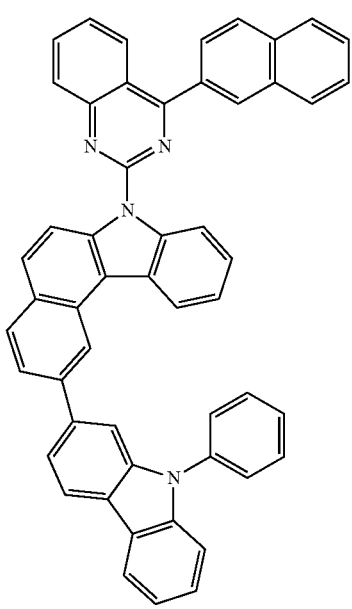

187
-continued
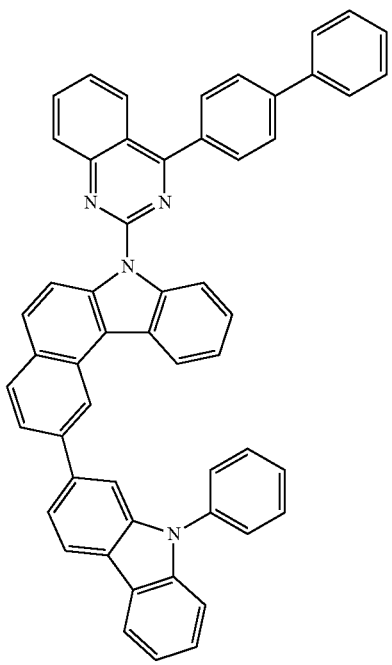
335
188
-continued
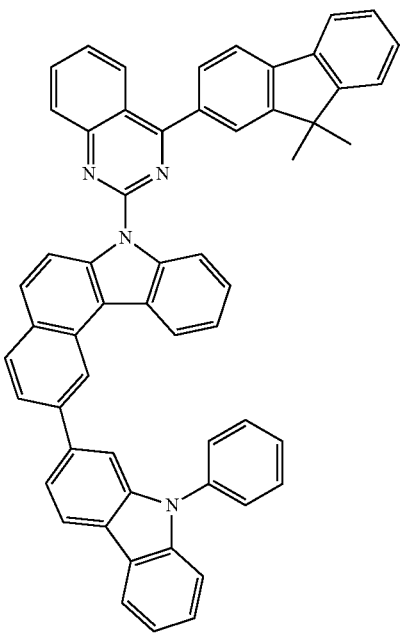
337
336
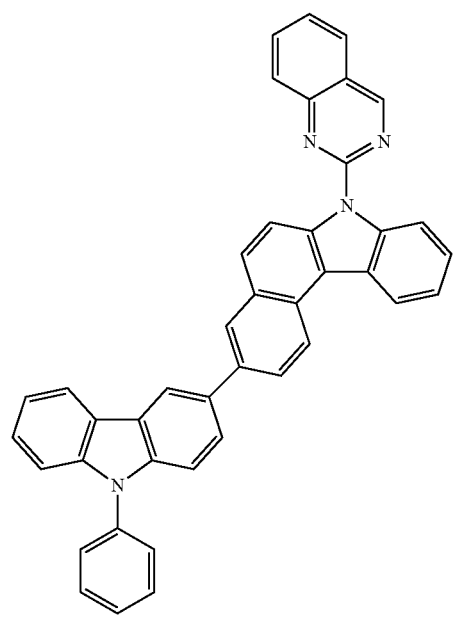
338

189
-continued
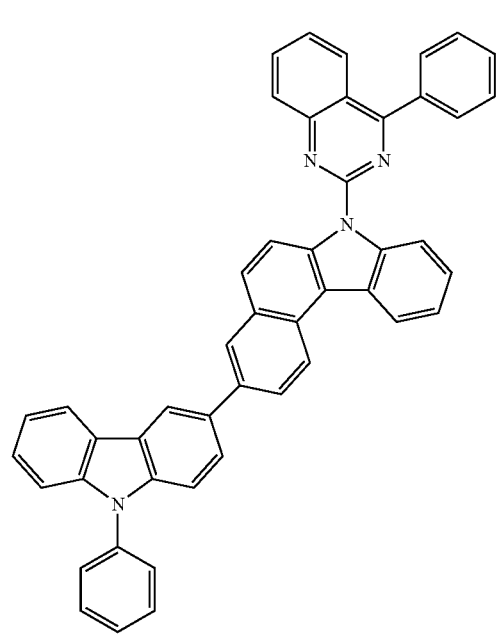
190
-continued
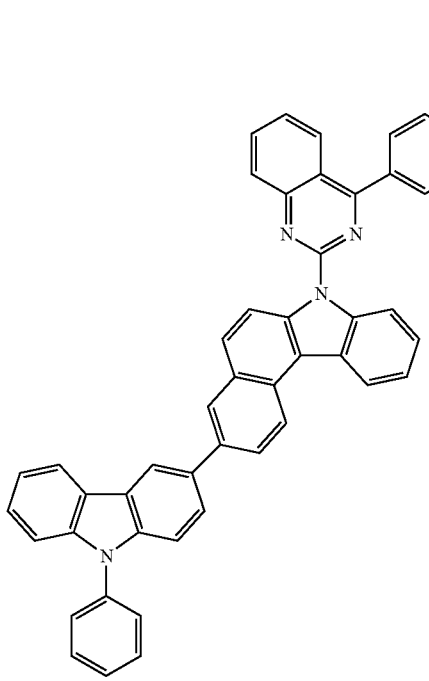
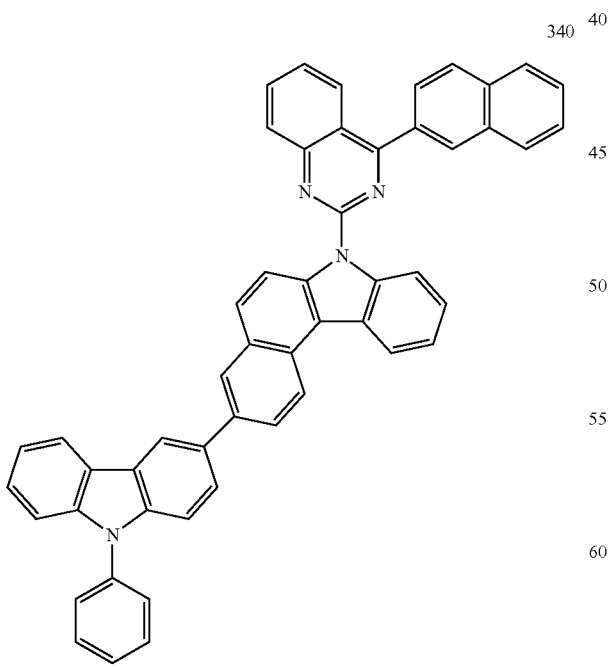
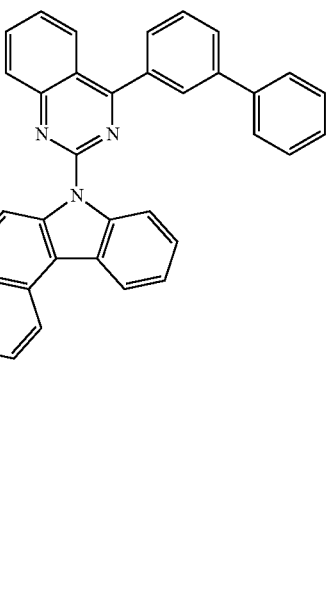

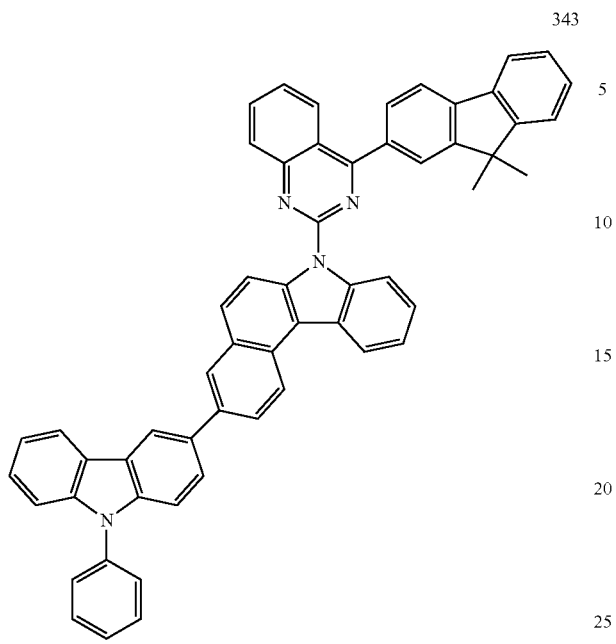
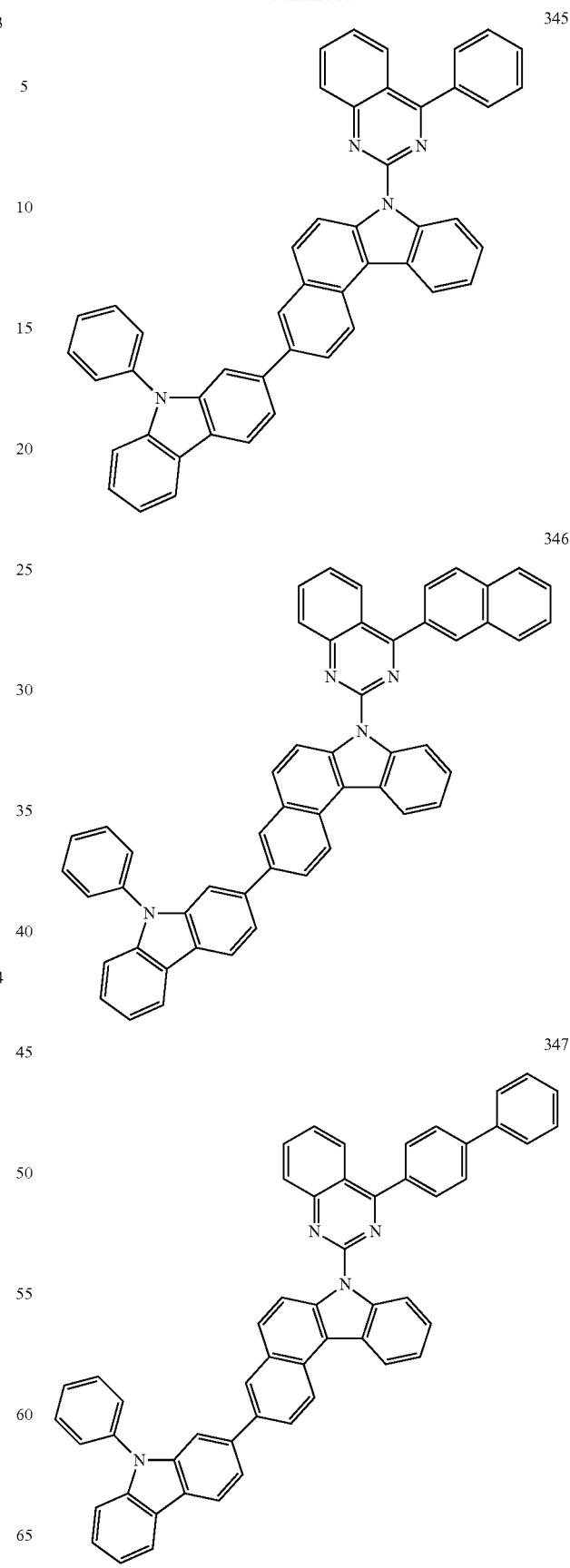

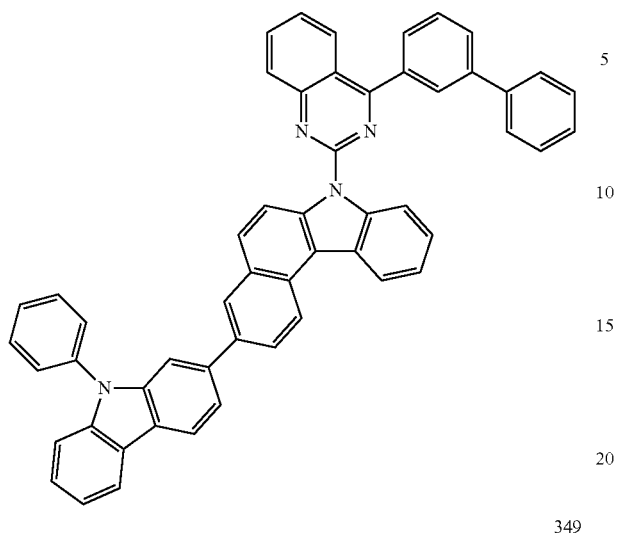
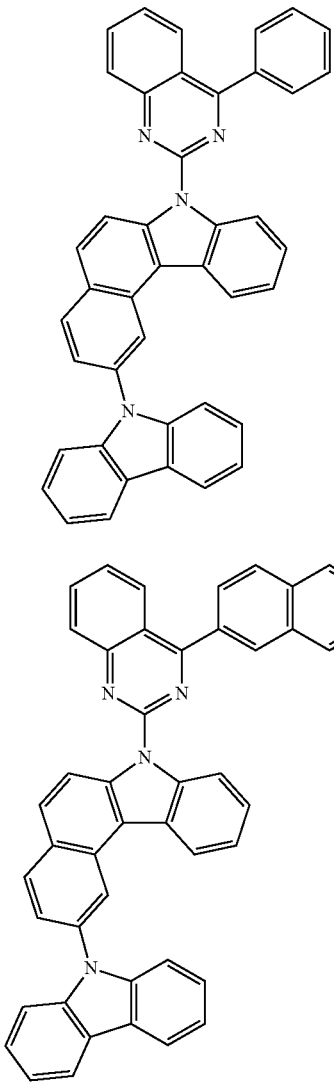
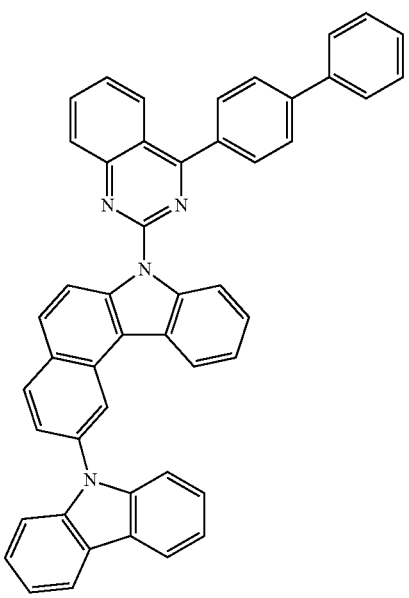

-continued

354

355

-continued

356

357

358
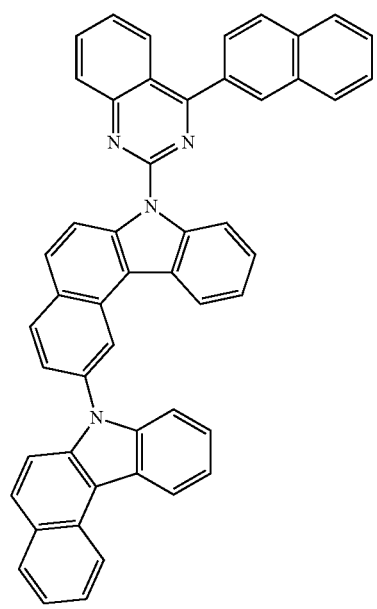
360
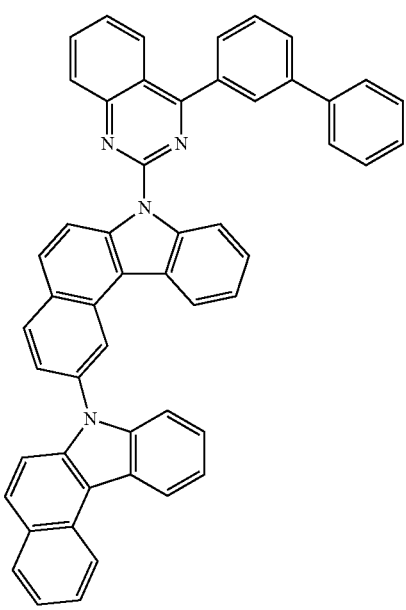
359
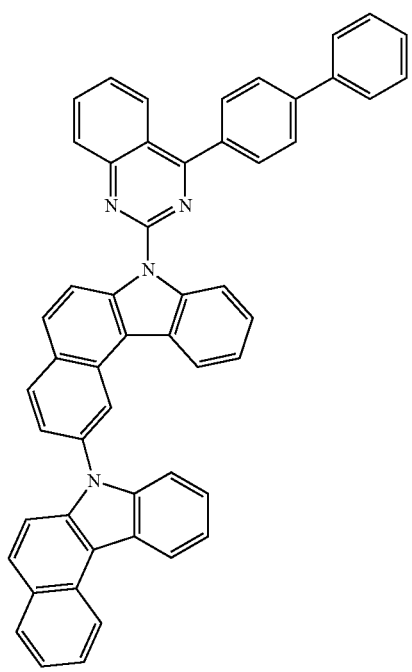
361
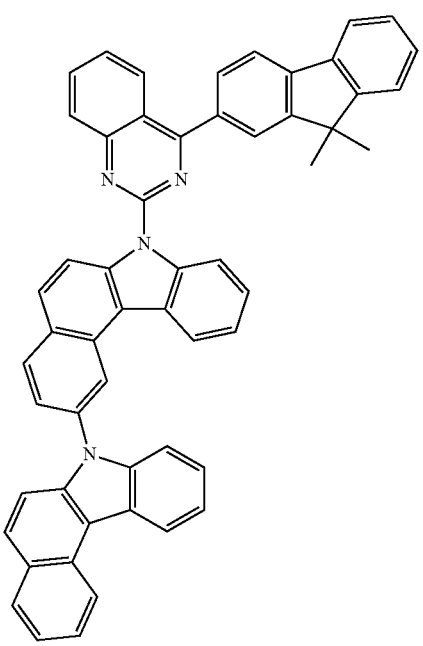

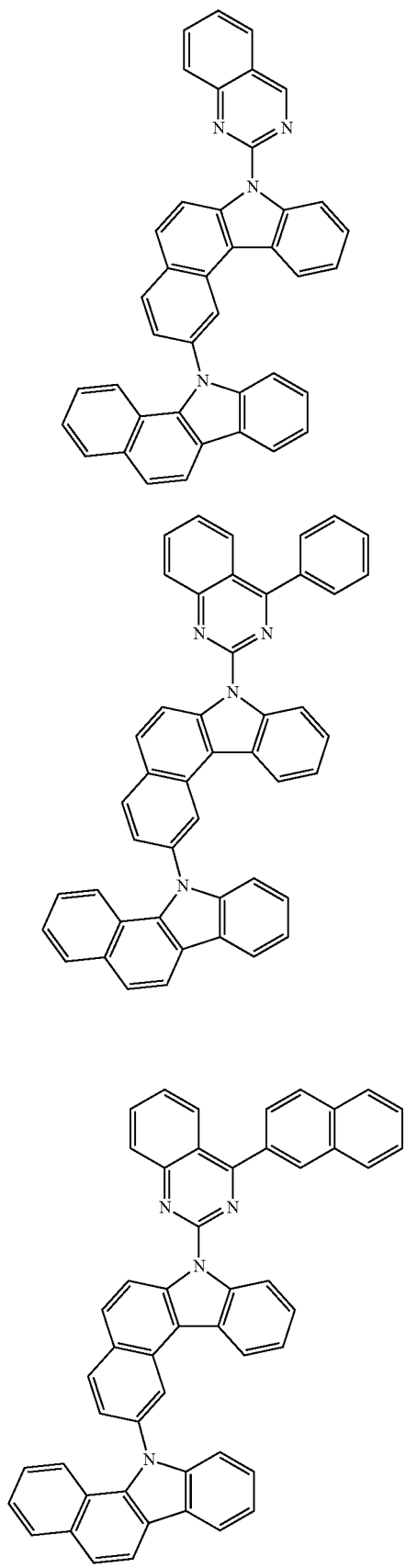
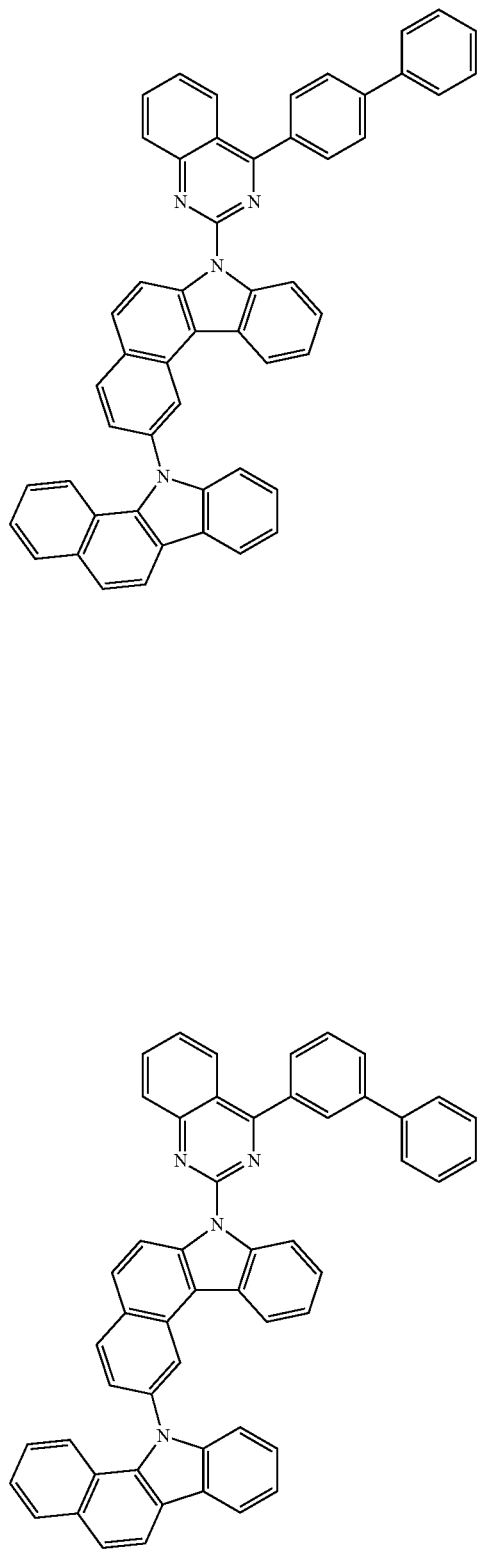

201
-continued
202
-continued
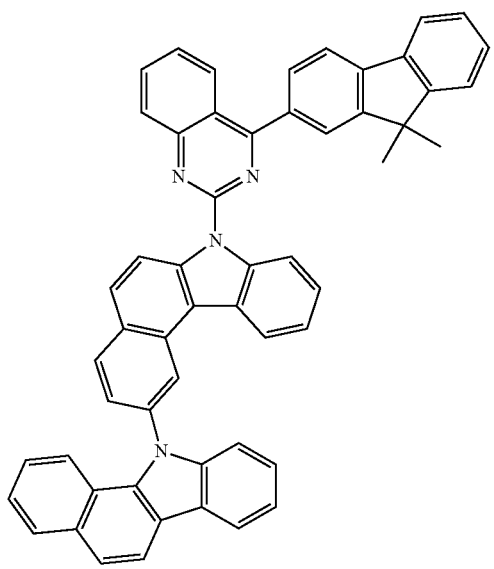
367
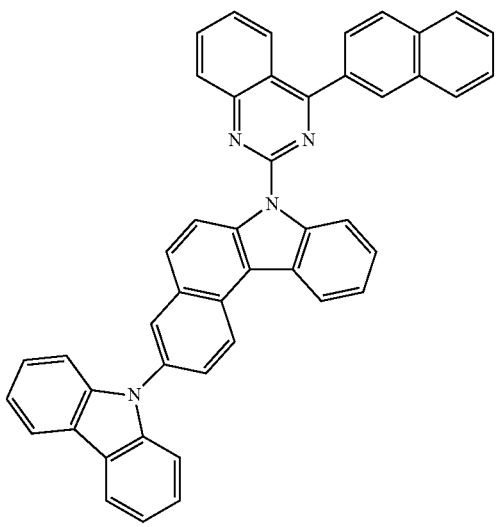
370
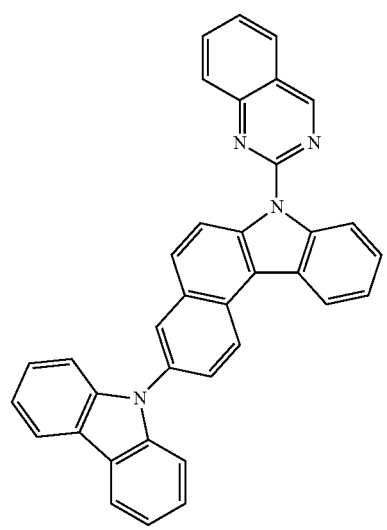
368
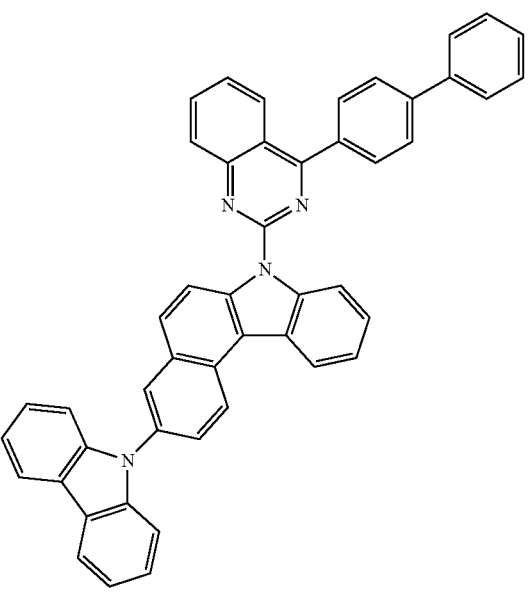
371

-continued
372
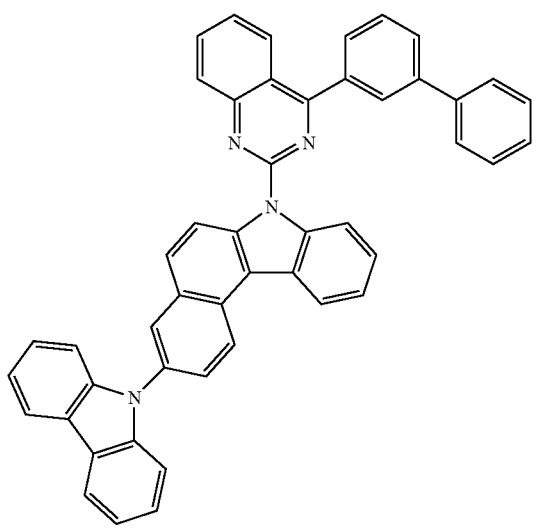
373
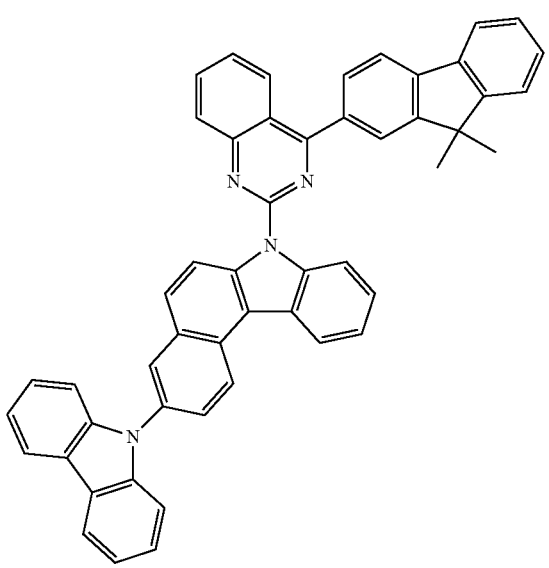
-continued
374
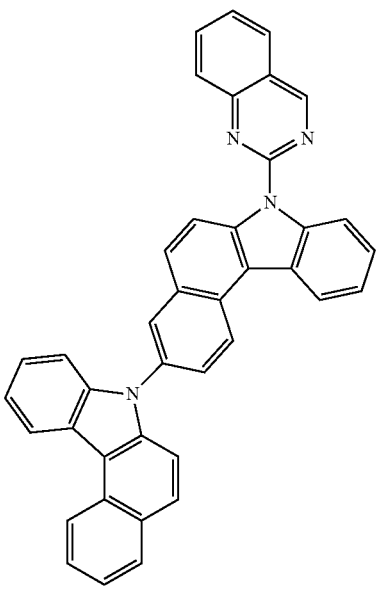
375
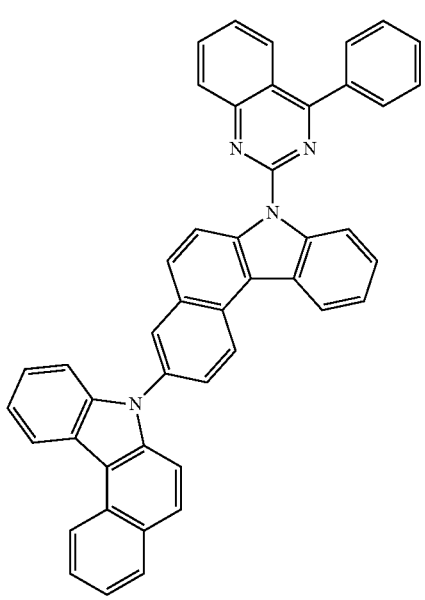

-continued
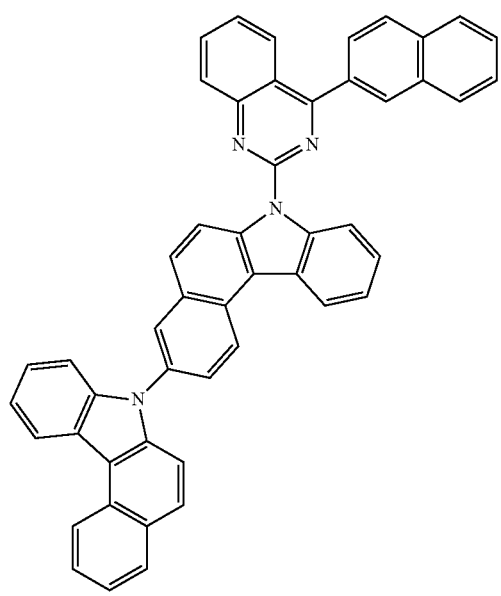
376
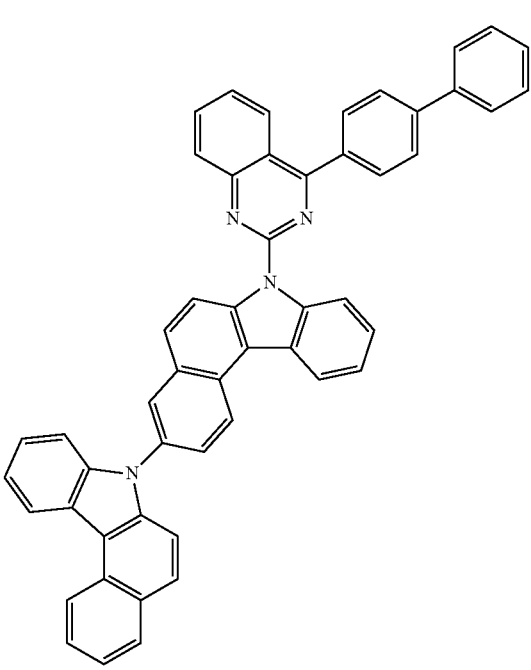
377
-continued
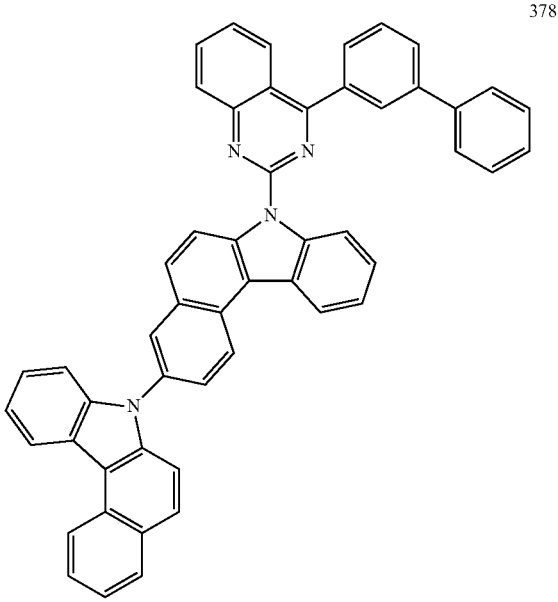
378
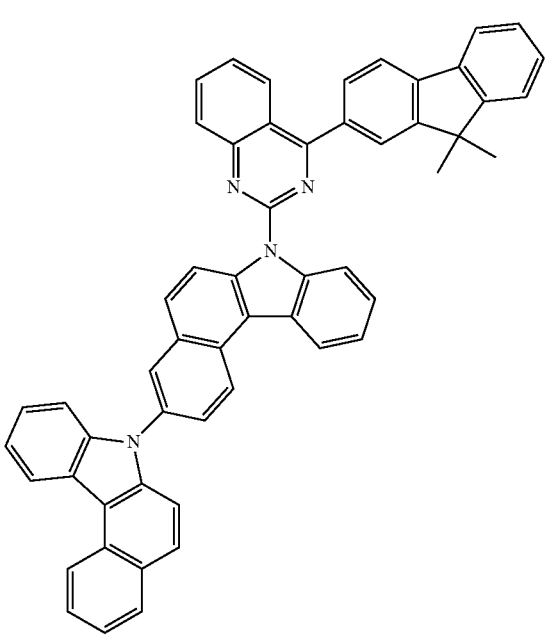
379

207
-continued
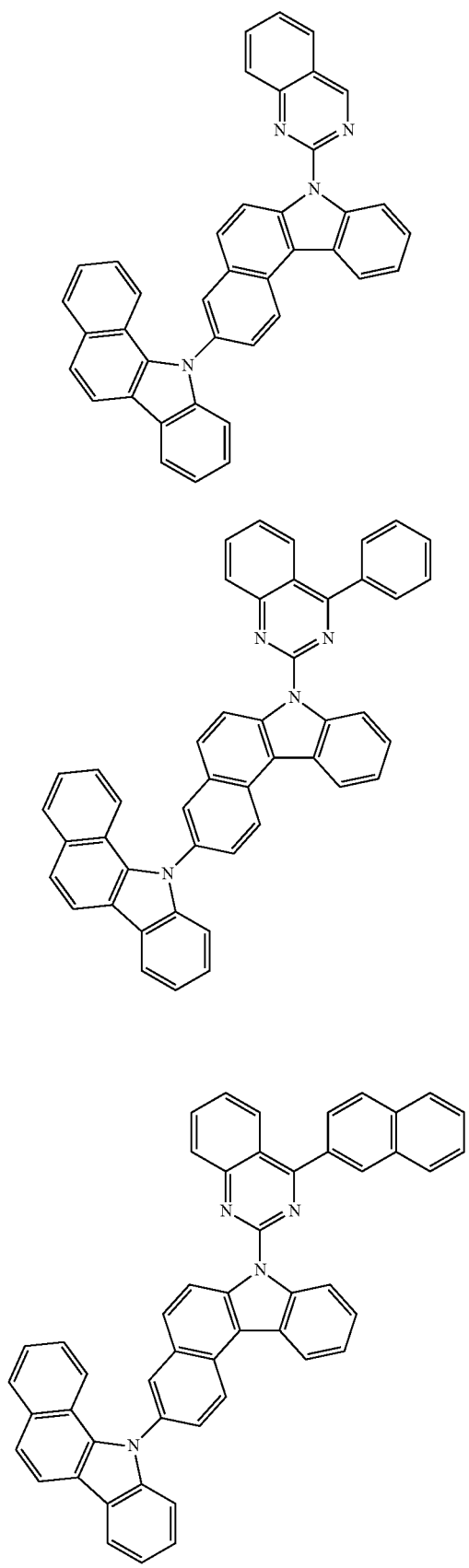
380
381
382
208
-continued
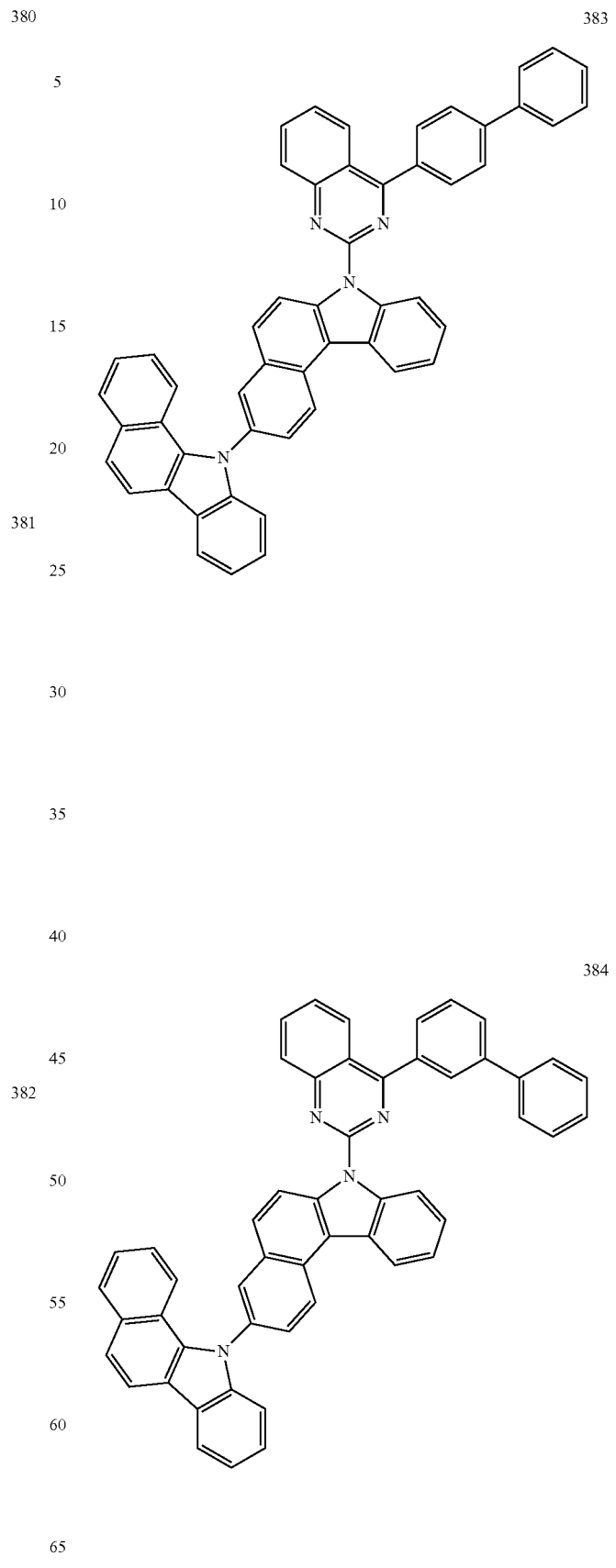
383
384

-continued
385
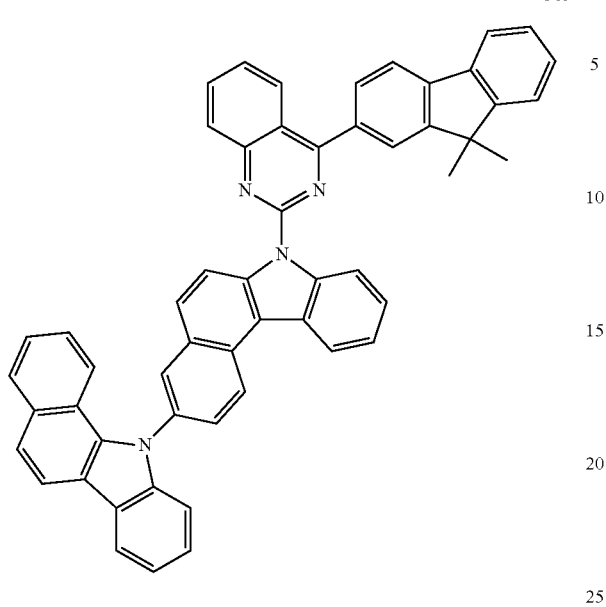
386
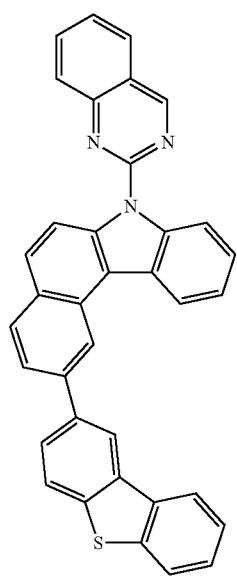
-continued
387
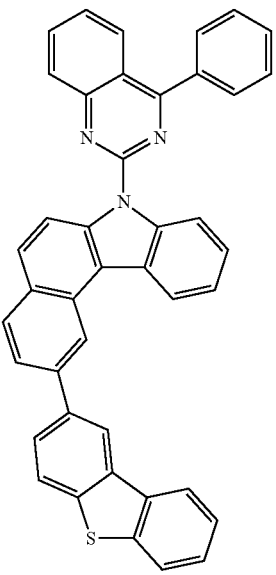
388
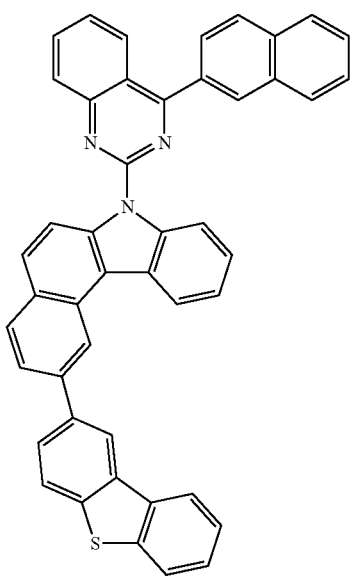

389
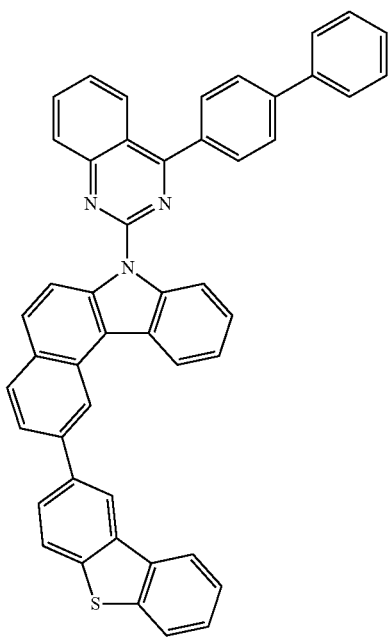
391
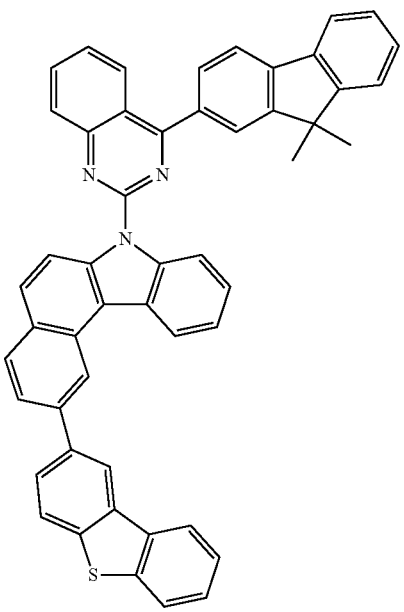
390
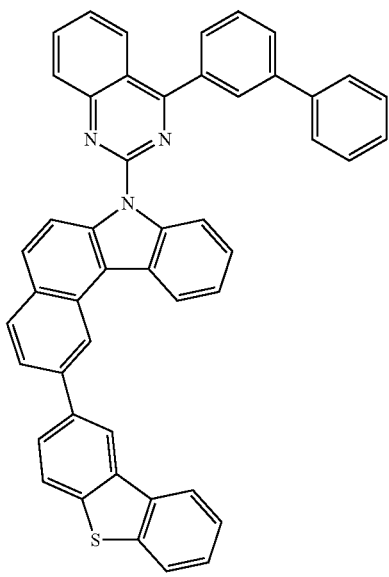
392
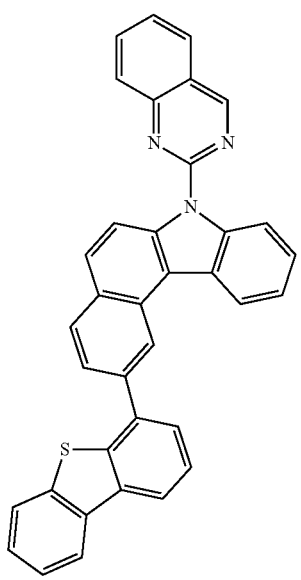

393
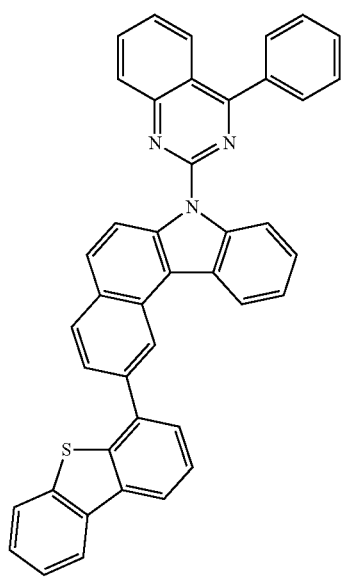
395
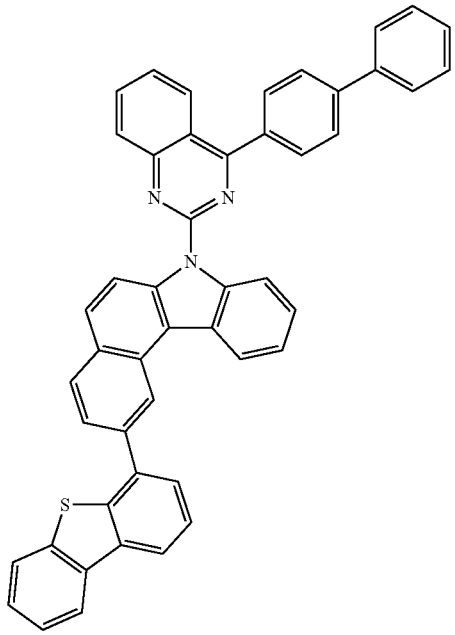
394
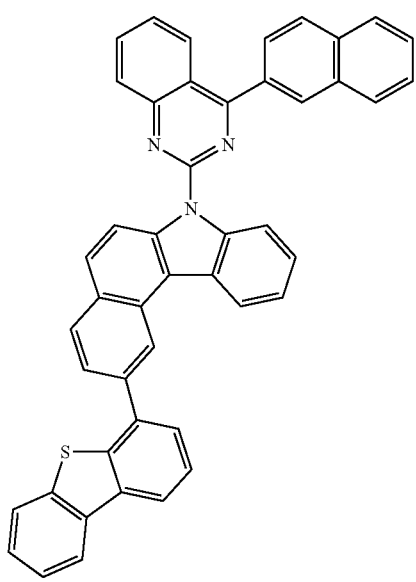
396
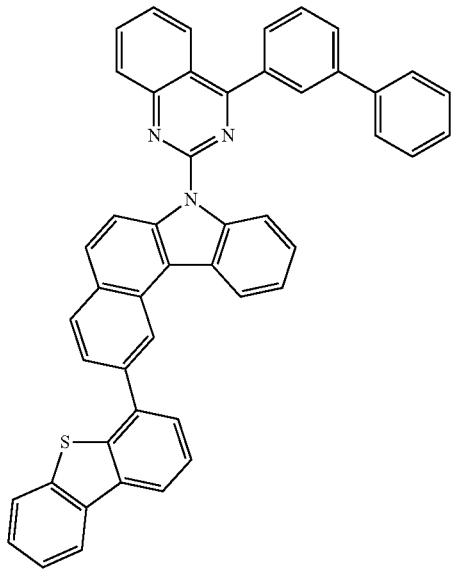

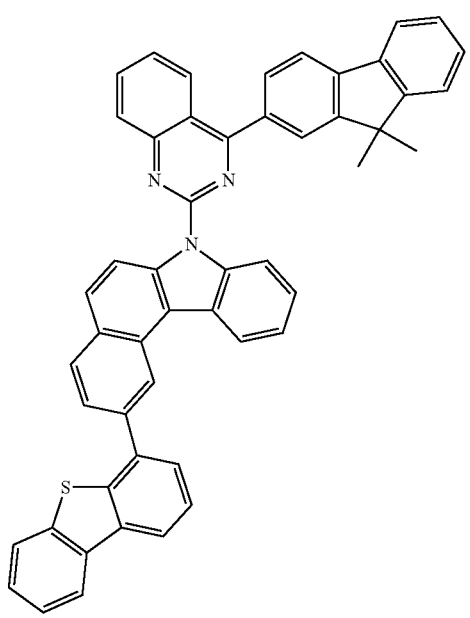
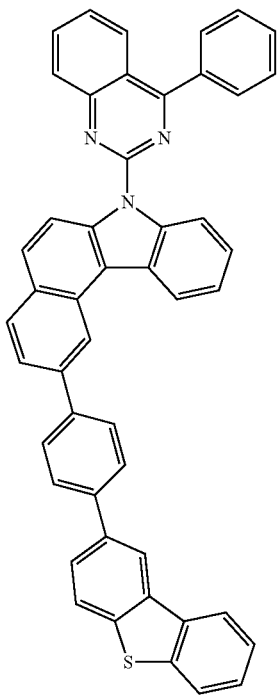

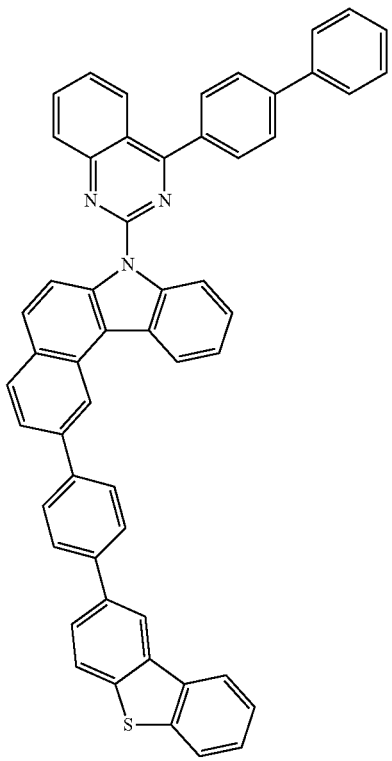
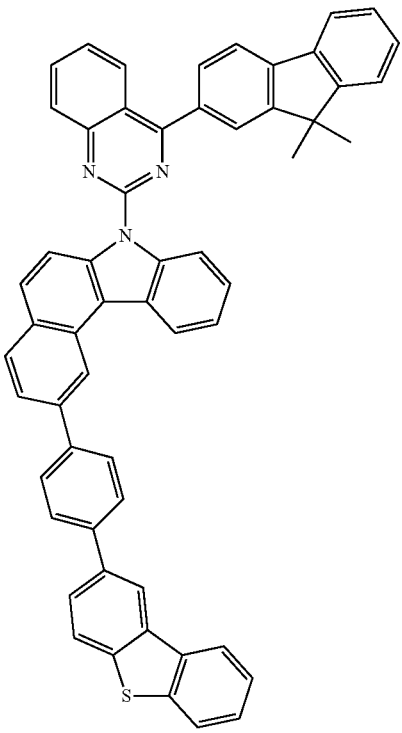

219
-continued
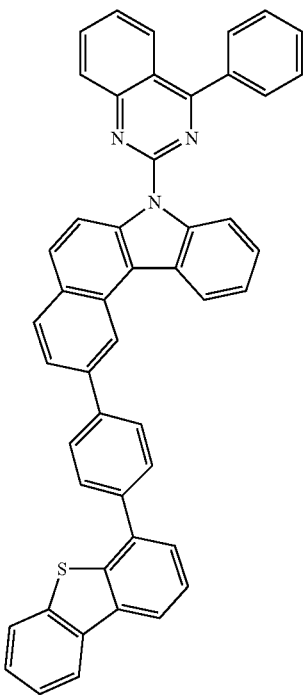
405
220
-continued
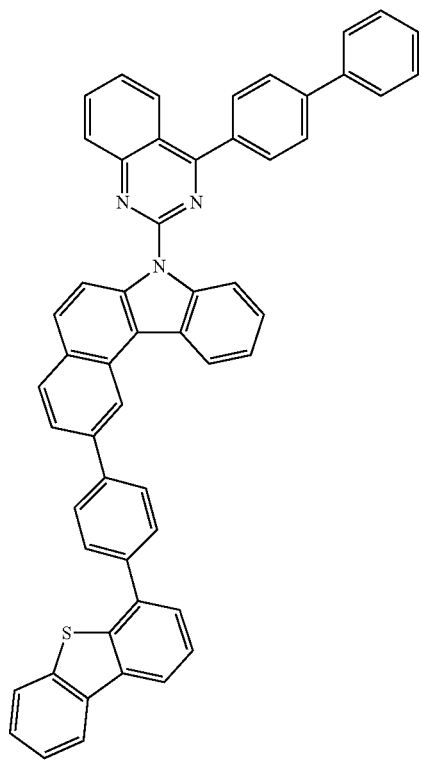
407
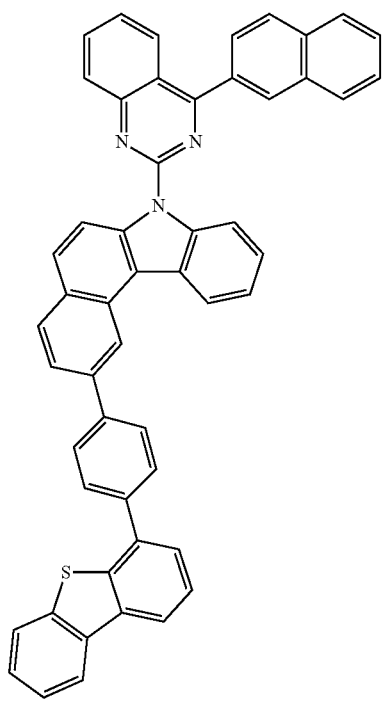
406
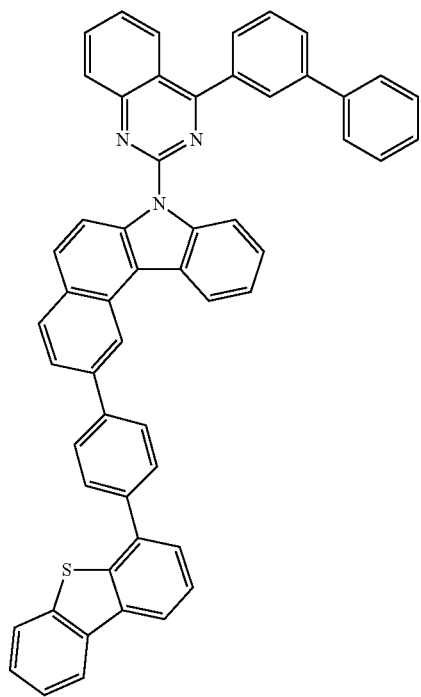
408

409
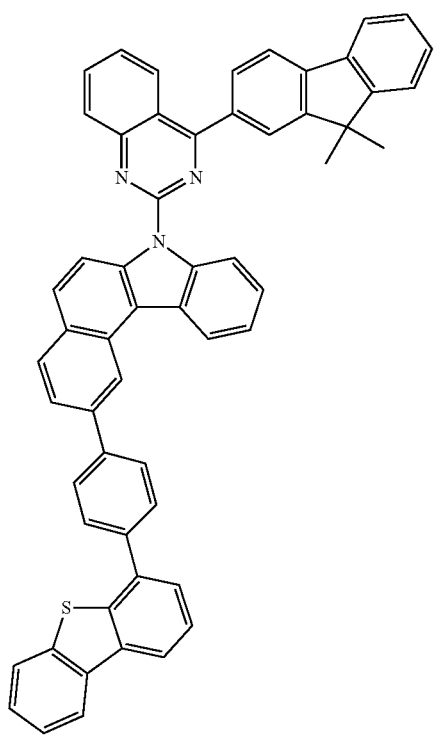
411
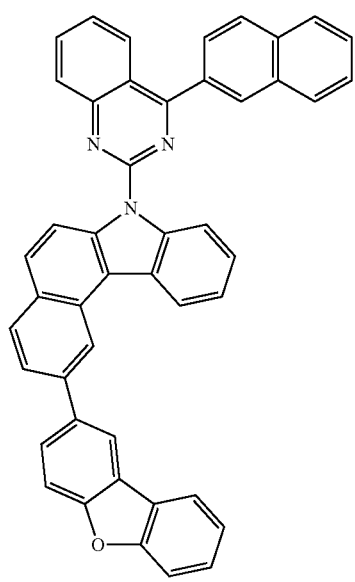
410
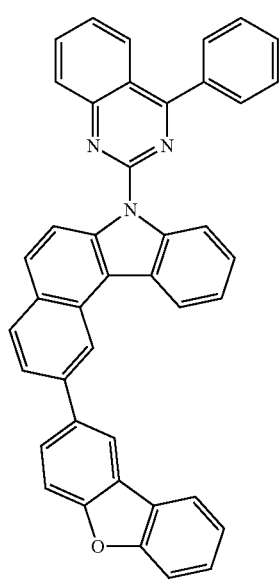
412
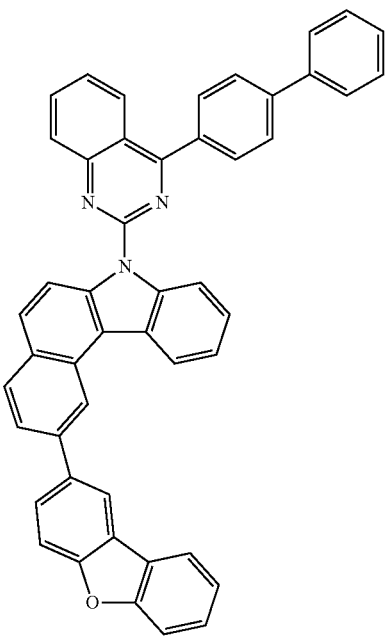

413
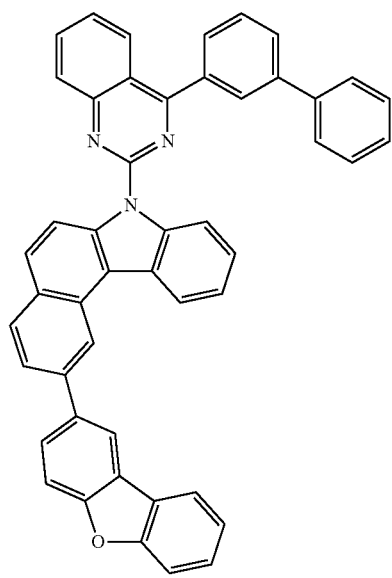
415
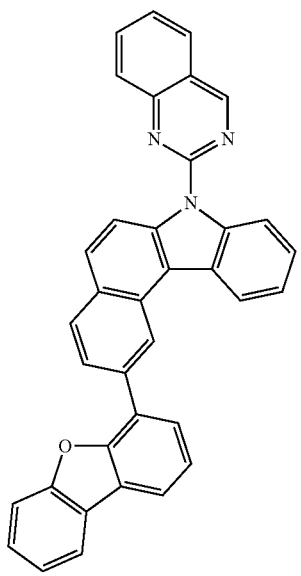
414
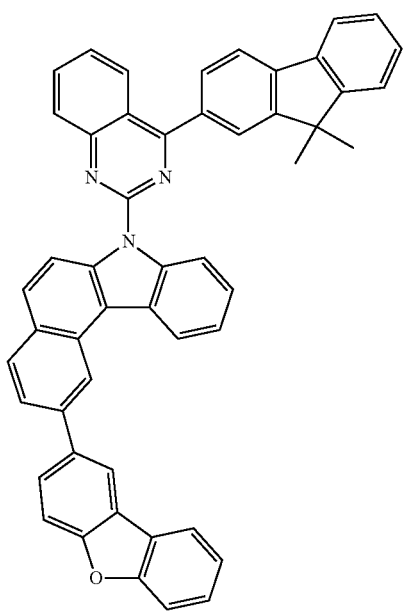
416
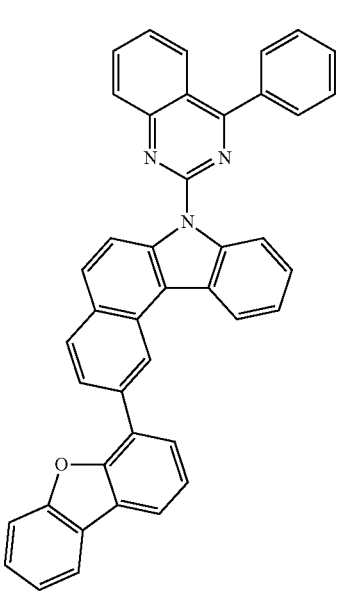

225
-continued
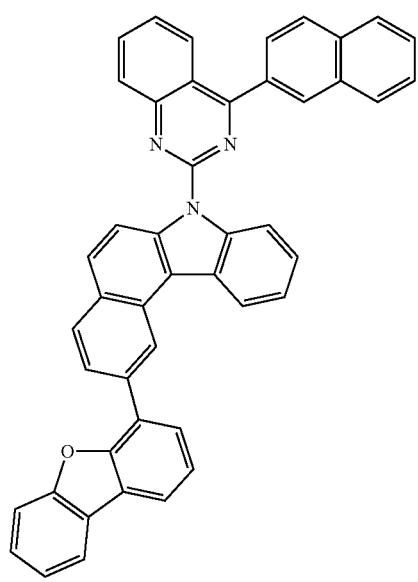
417
226
-continued
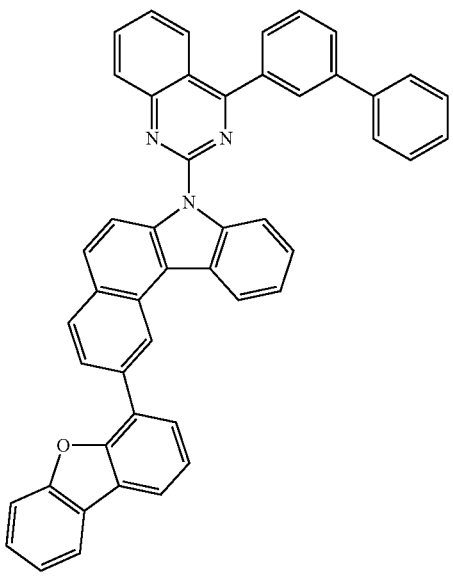
419
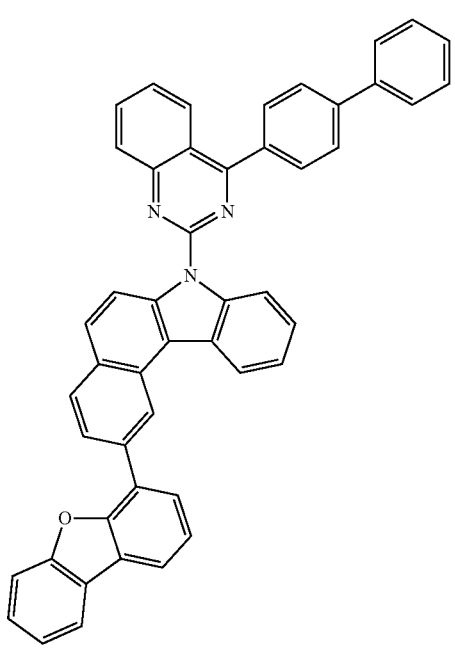
418
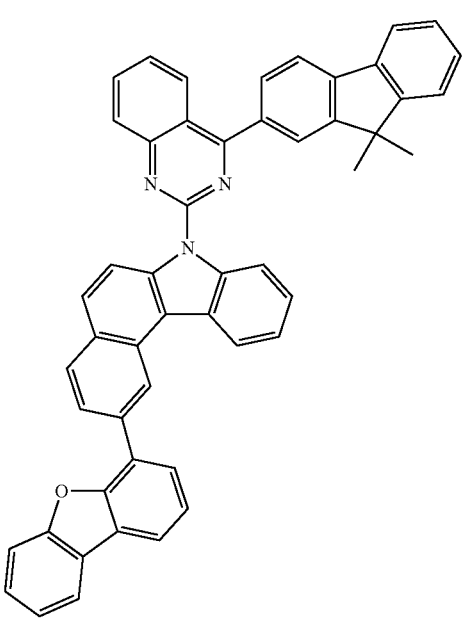
420

227
-continued
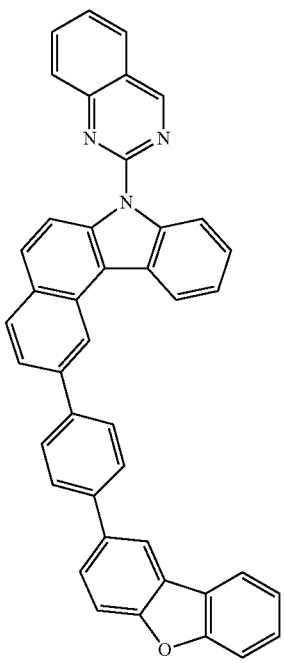
421
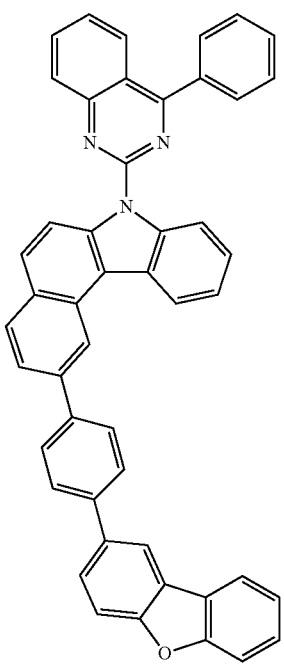
422
228
-continued
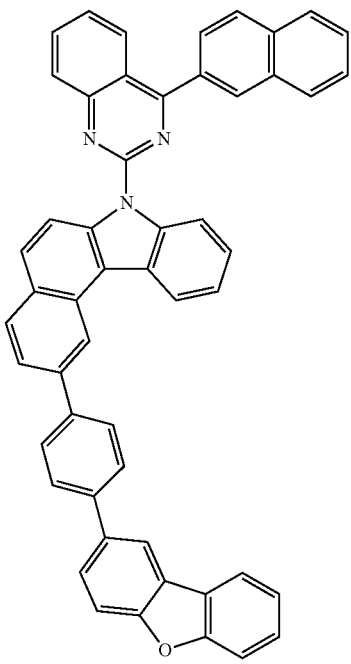
423
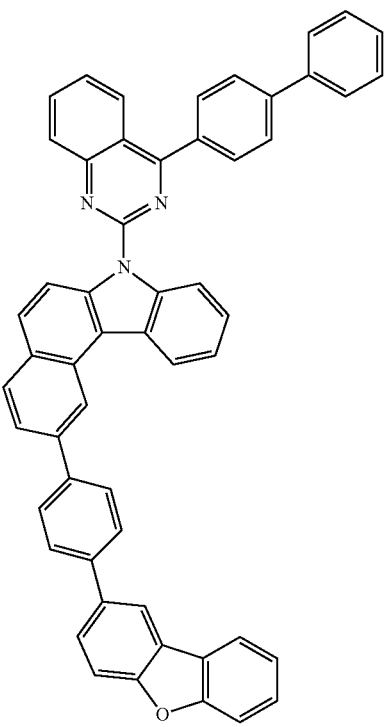
424

229
-continued
425
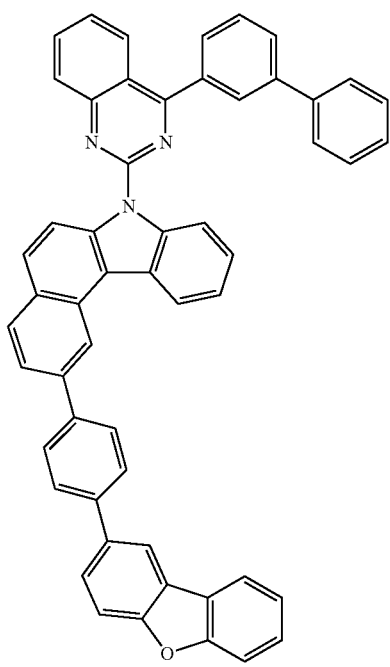
427
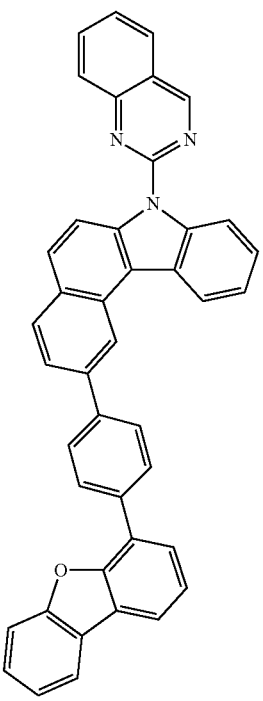
426
230
-continued
428
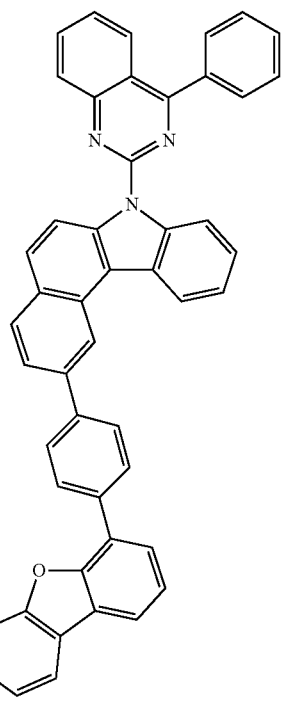

231
-continued
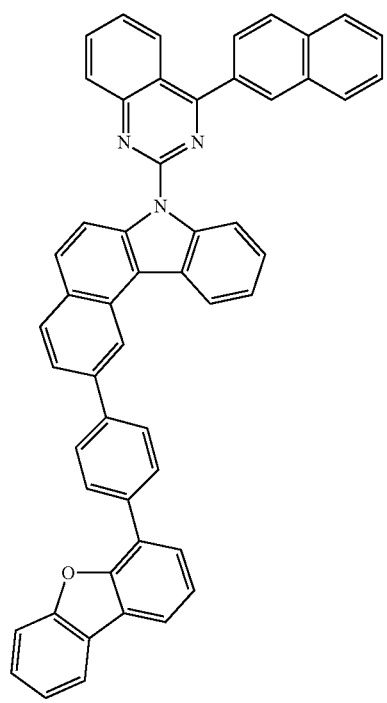
429
232
-continued
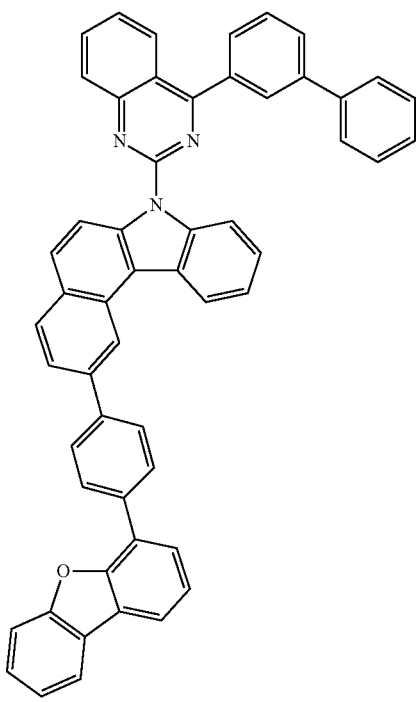
431
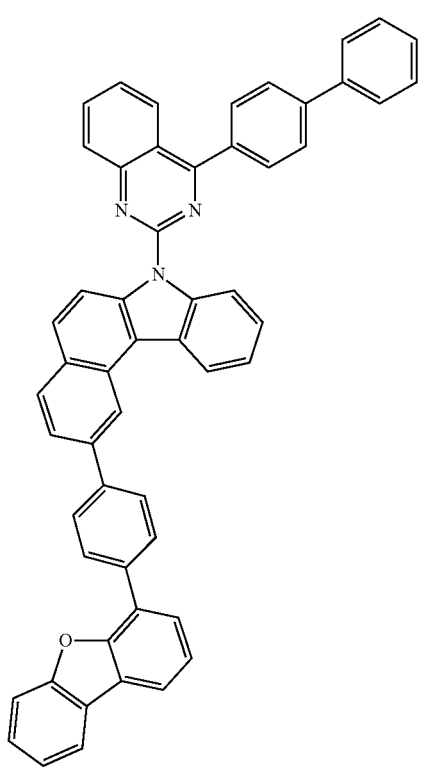
430
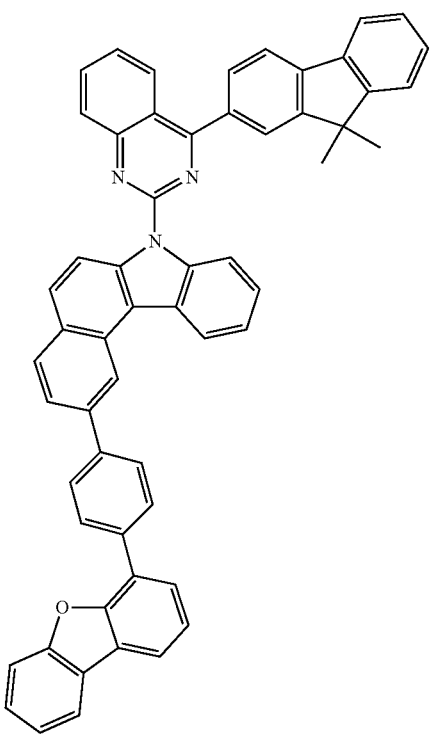
432

433
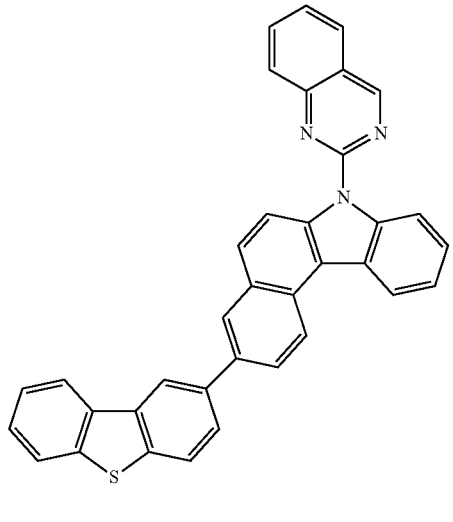
434
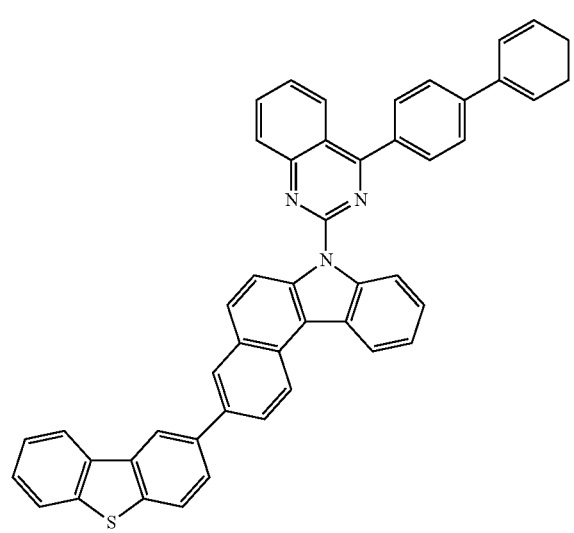
435
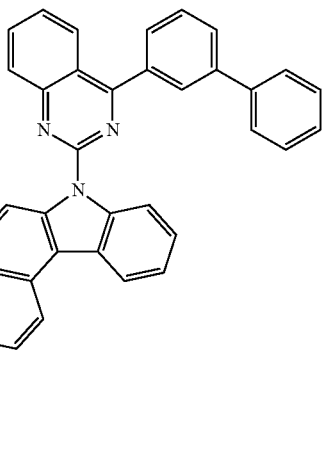
436
437
438
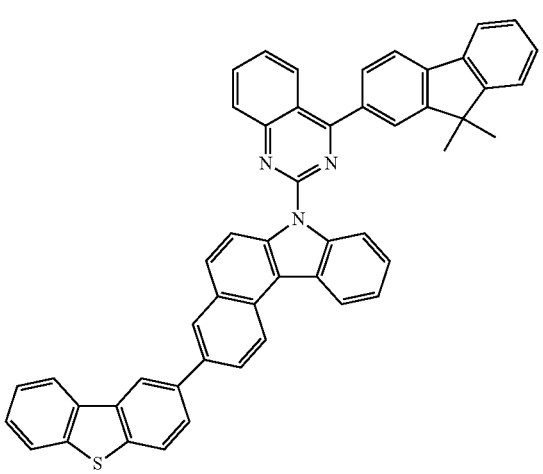

-continued
439
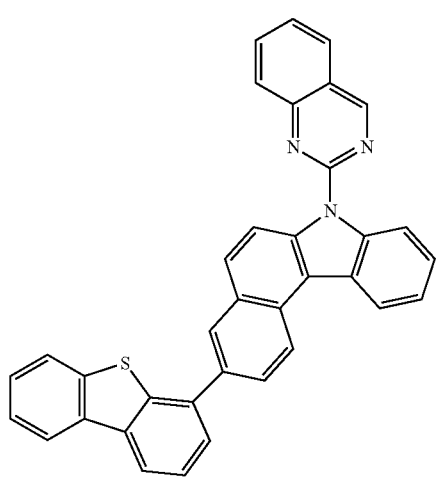
440
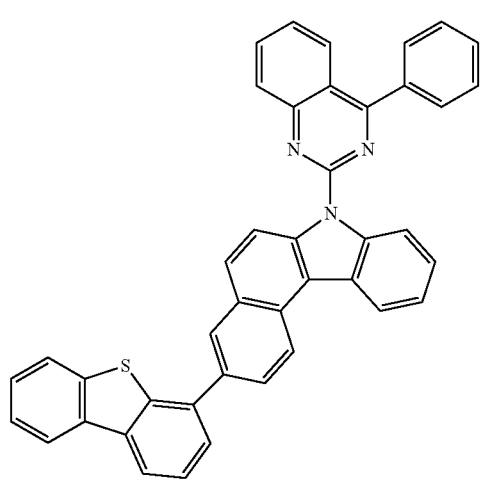
441
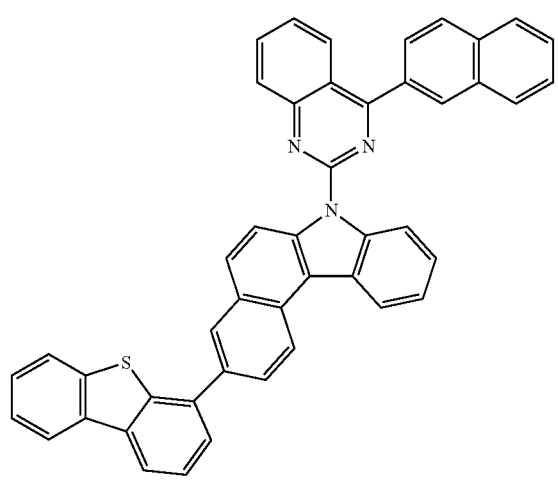
-continued
442
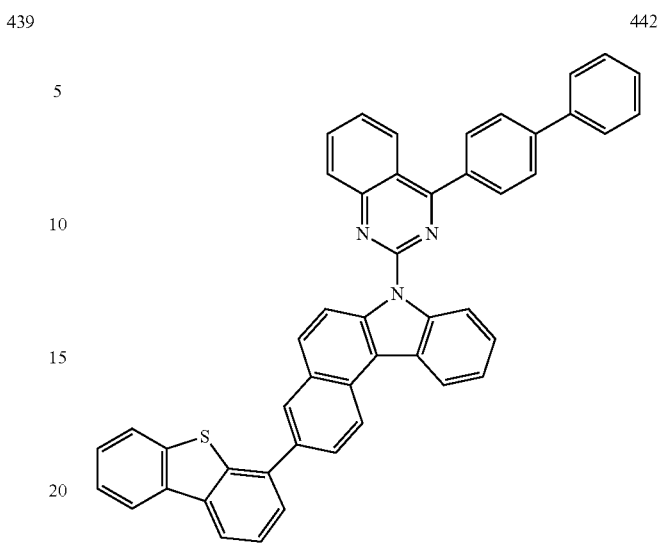
443
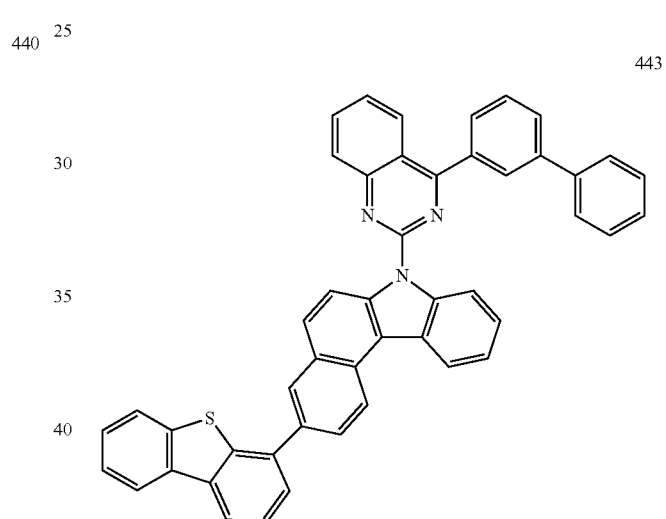
444
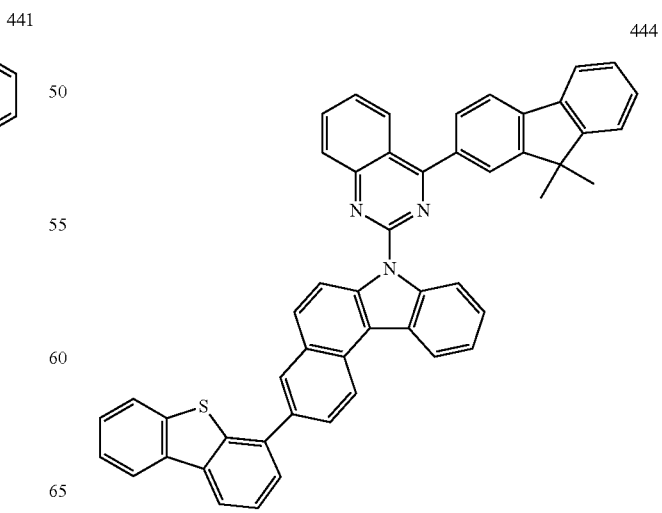

445
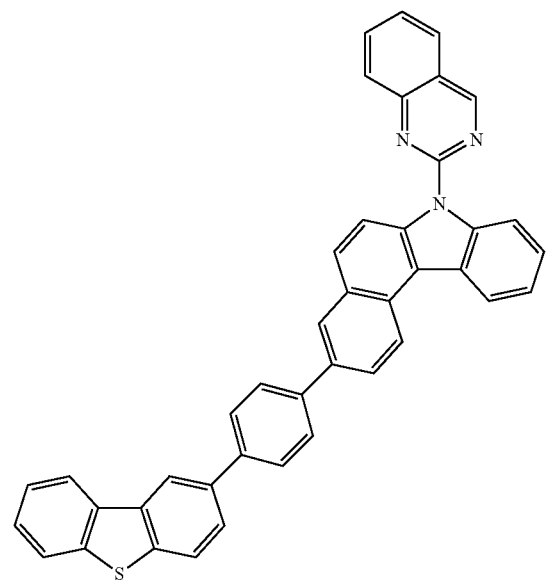
446
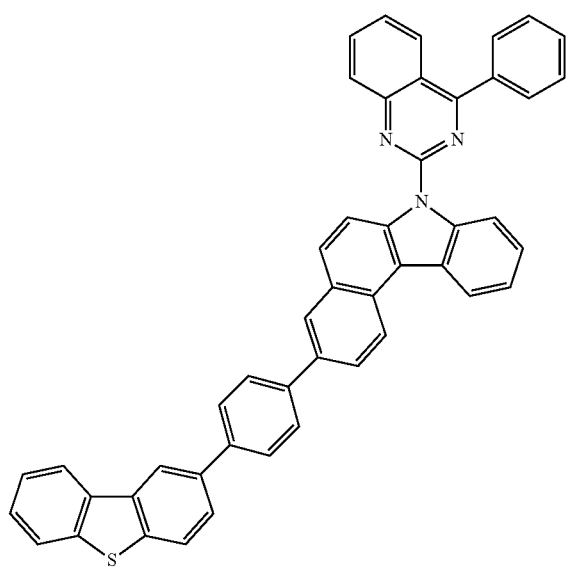
447
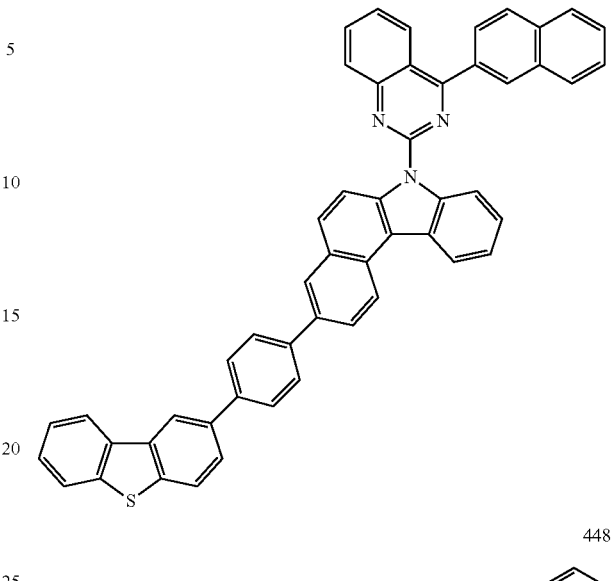
448

449
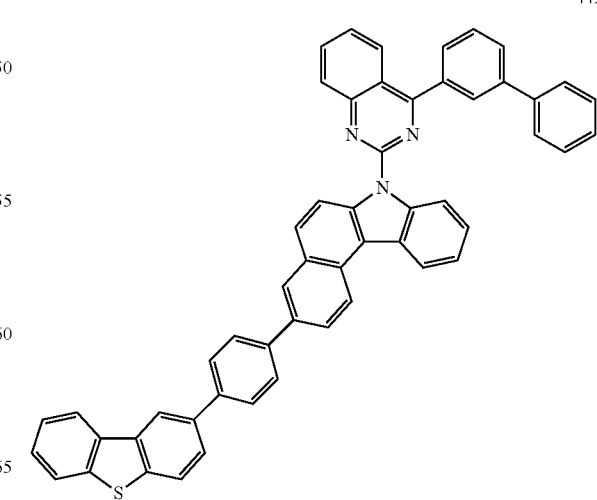

450
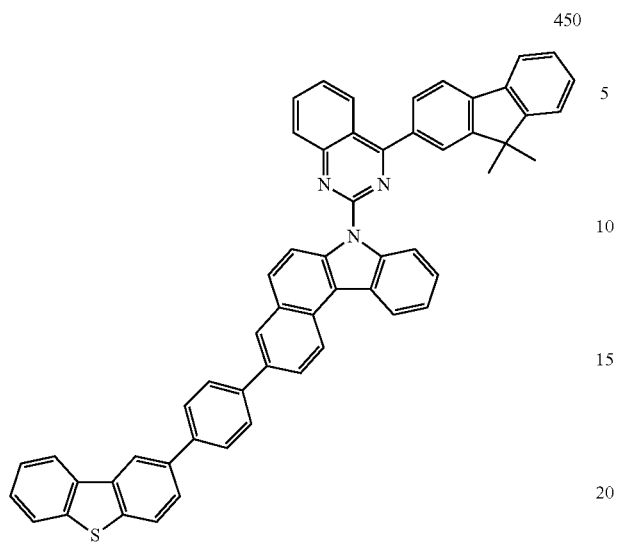
451
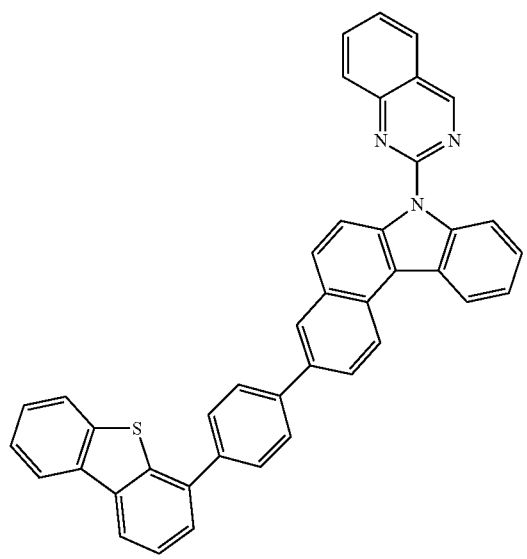
452
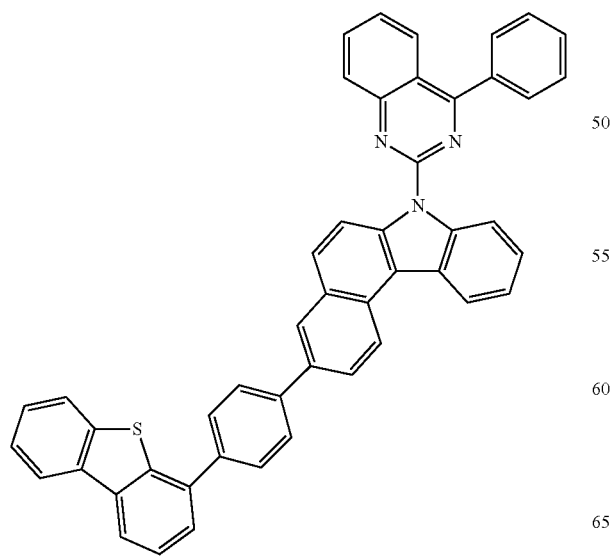
453
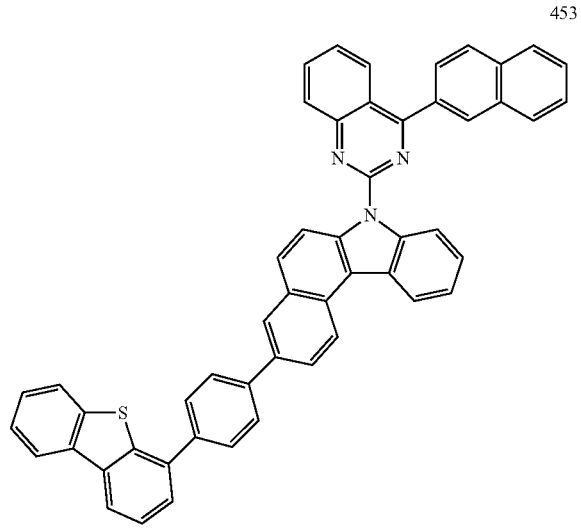
454
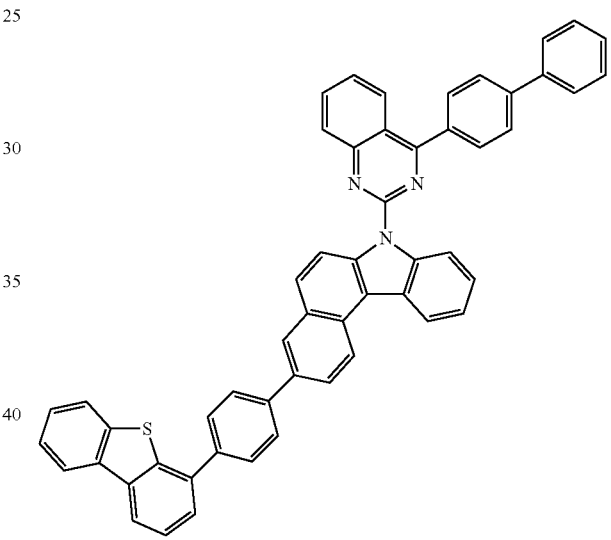
455

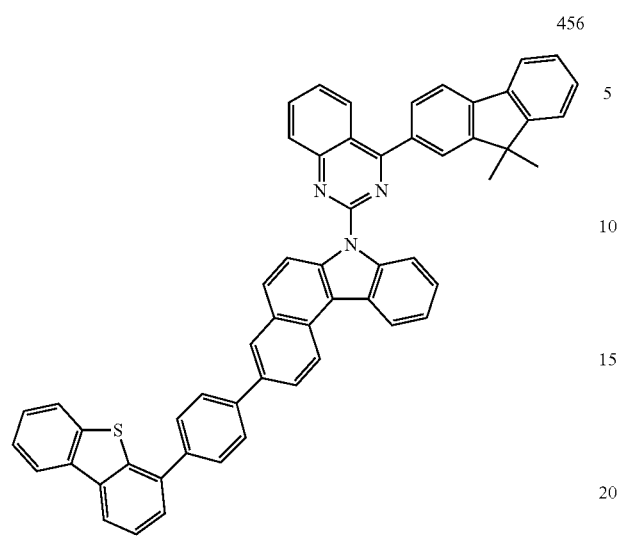
456
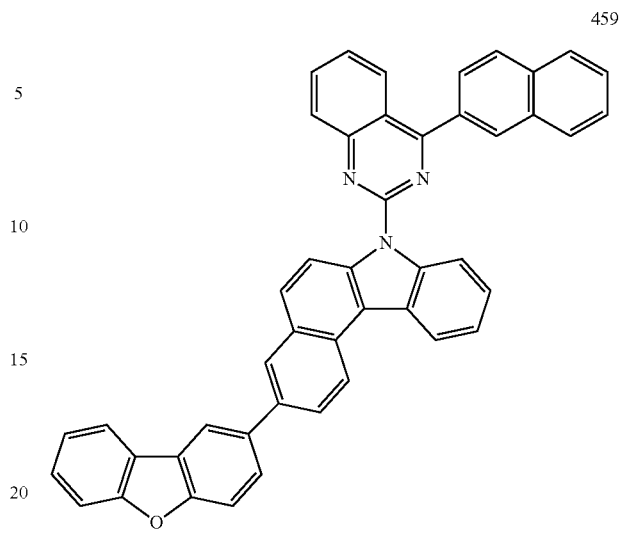
459
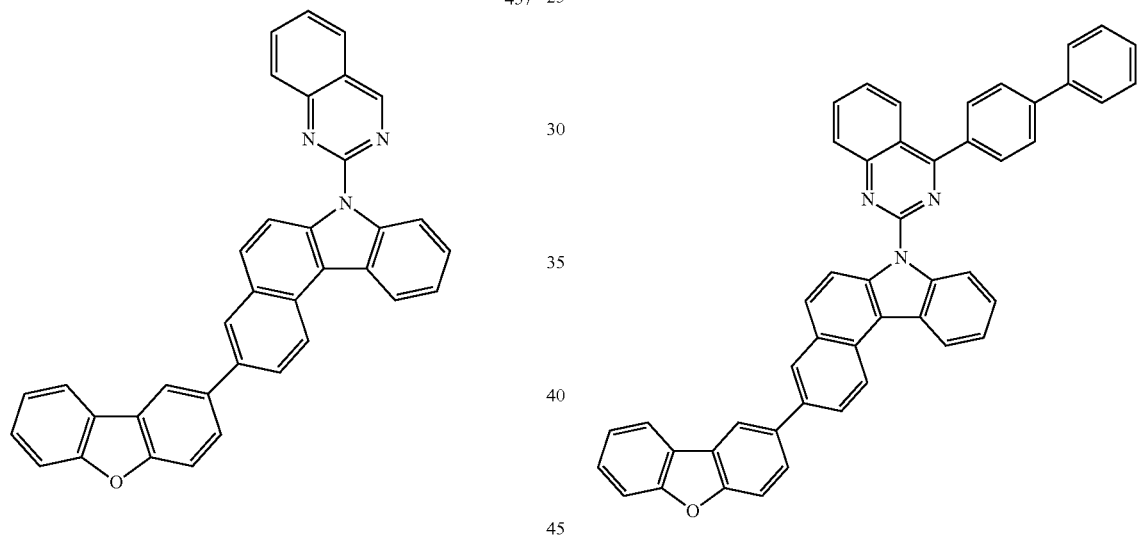
457
458
460
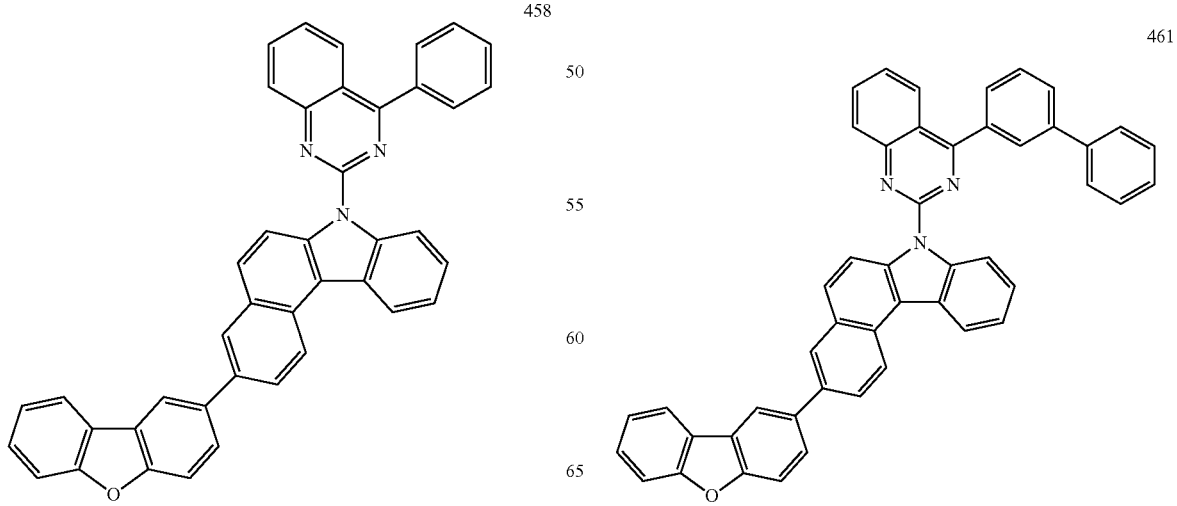
461

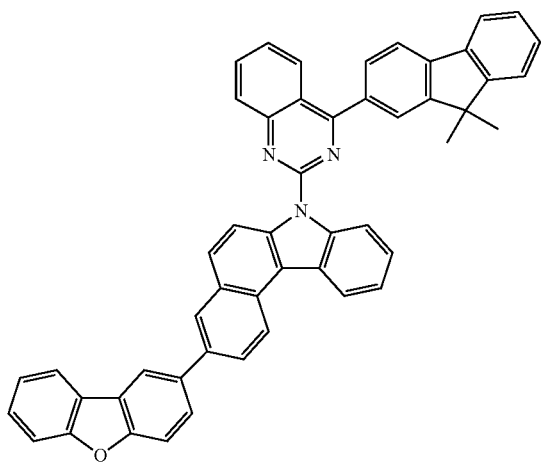
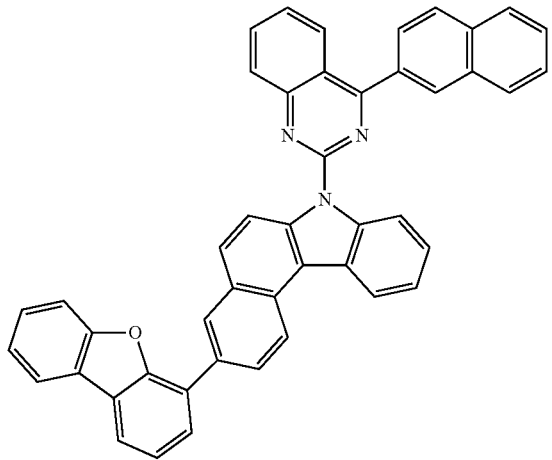

245
-continued
468
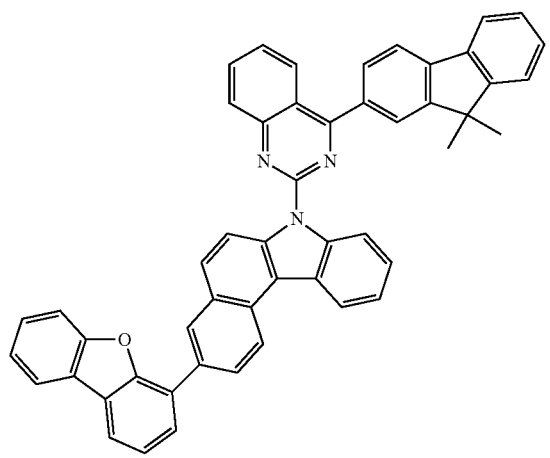
469
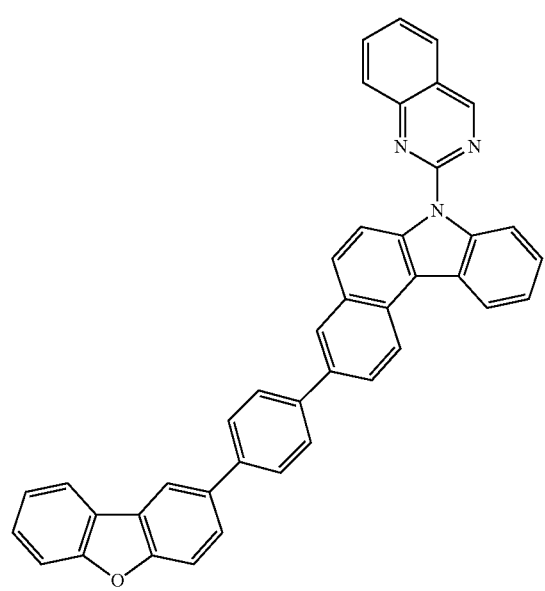
470
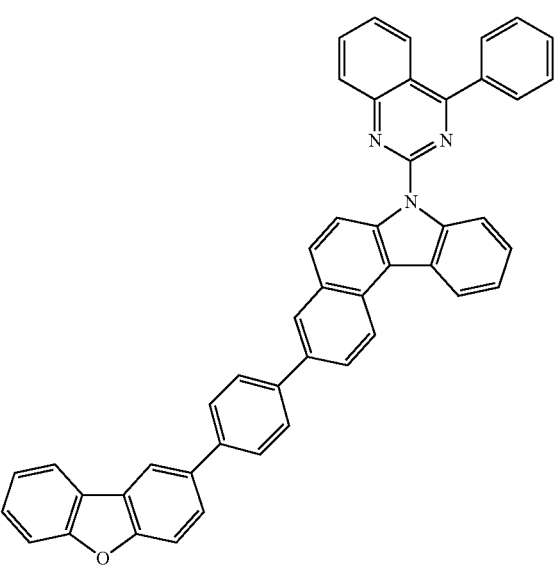
246
-continued
471
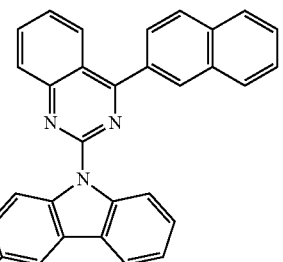
472
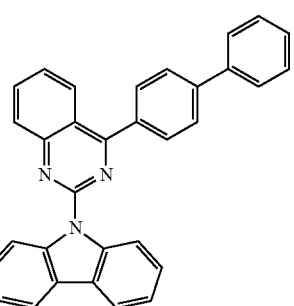
473
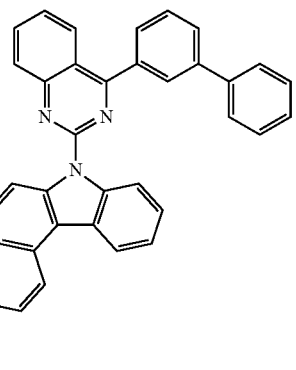

US 10,035,765 B2
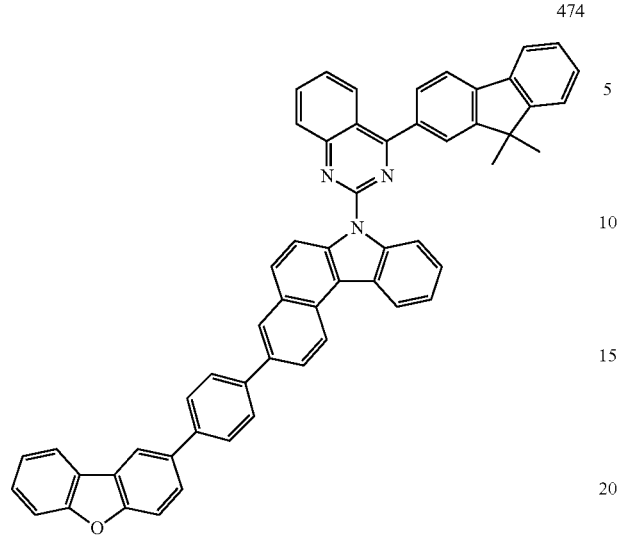
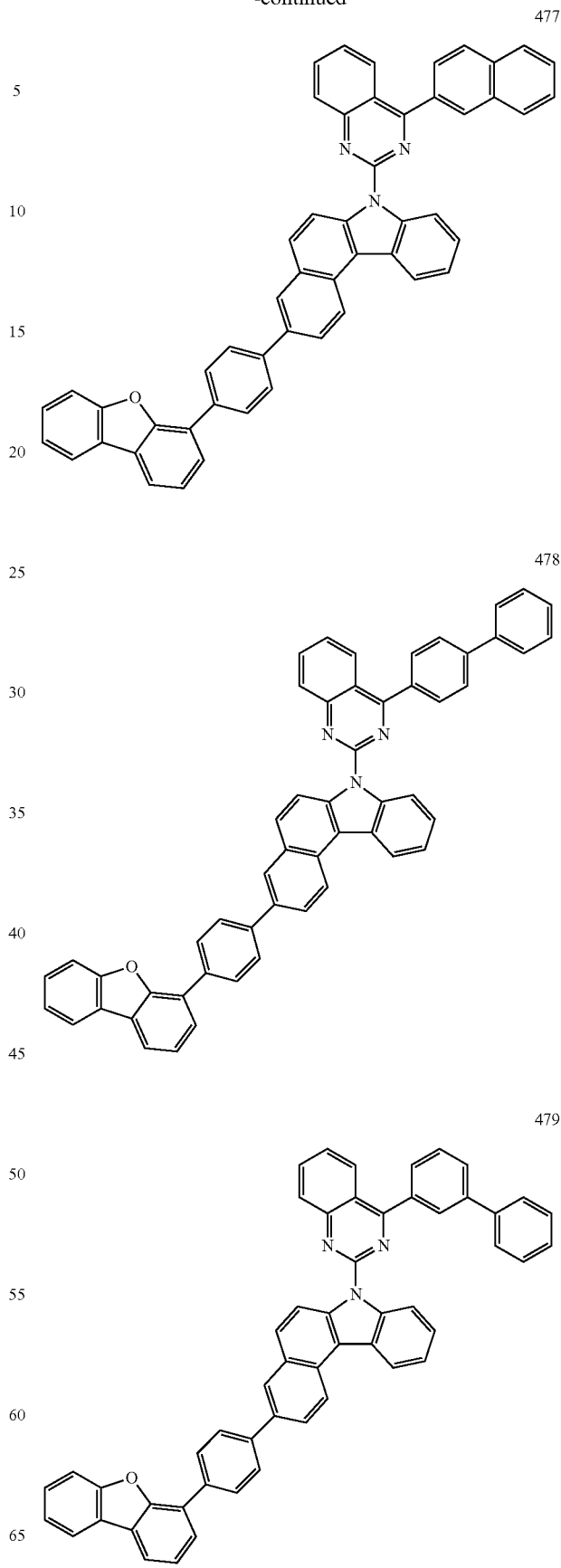

-continued
480
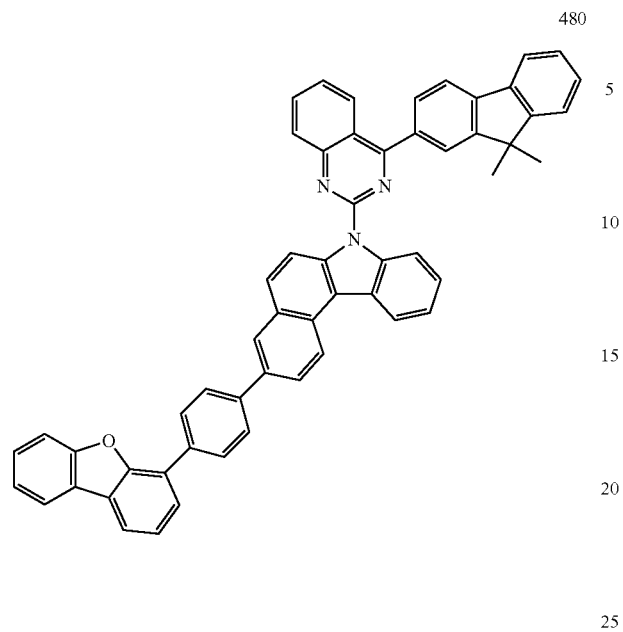
481
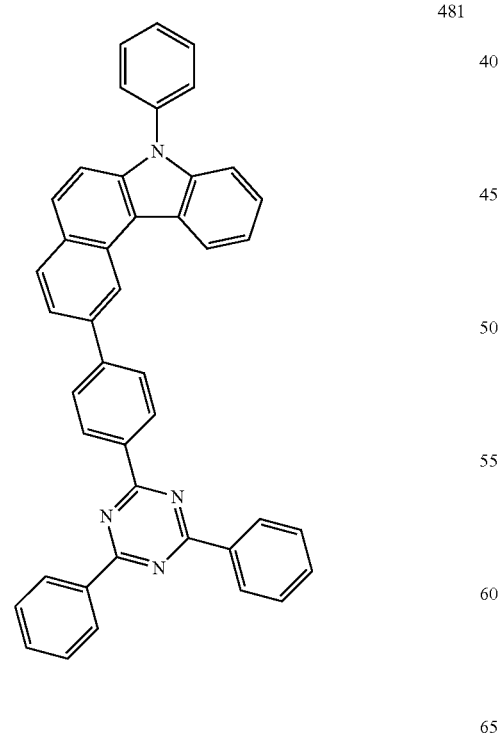
-continued
482
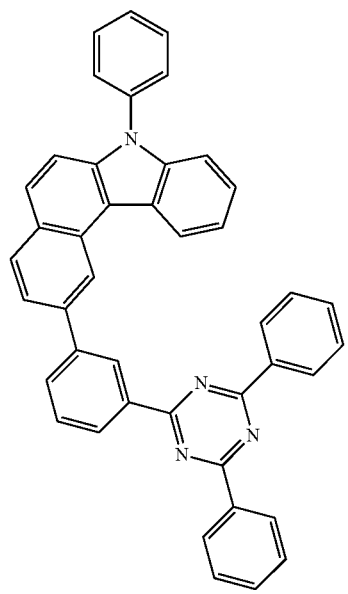
483
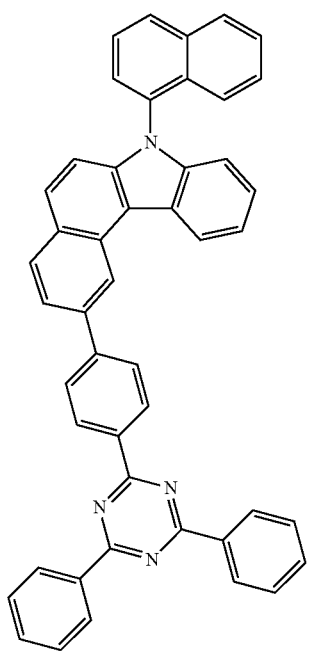

251
-continued
484
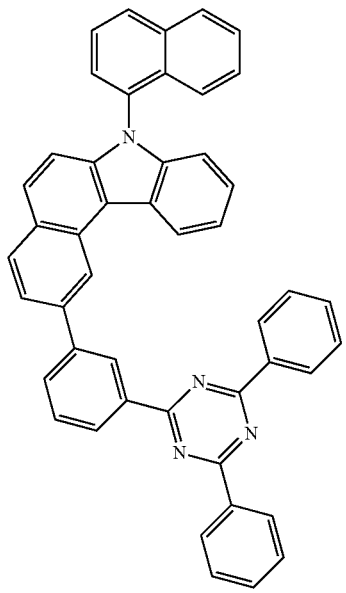
485
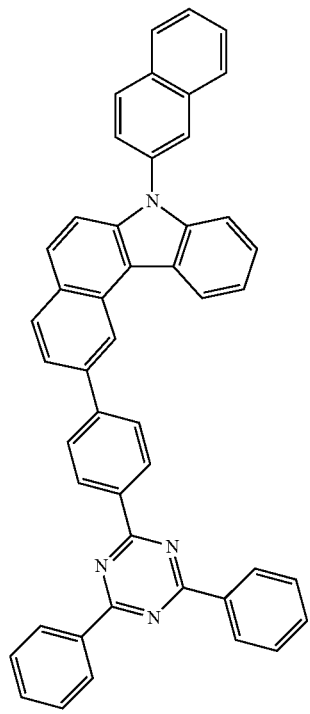
252
-continued
486
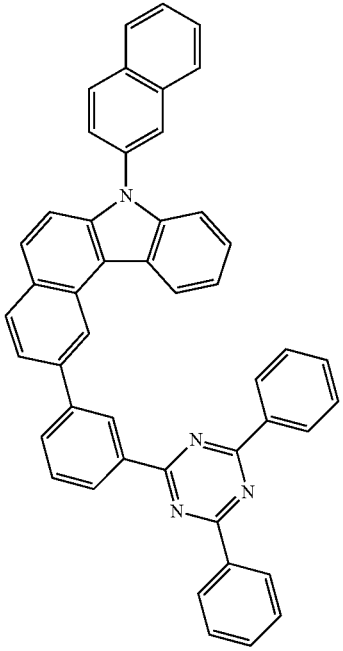
487
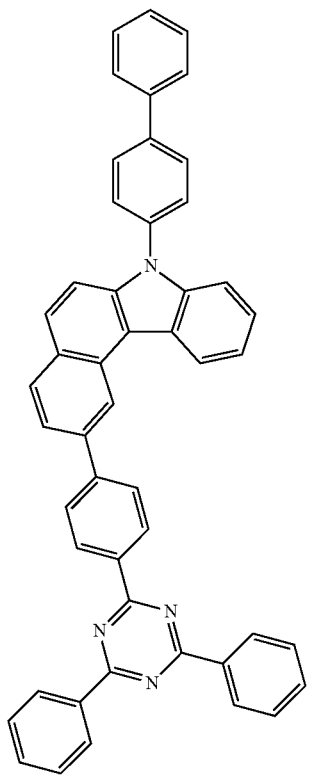

253
-continued
489
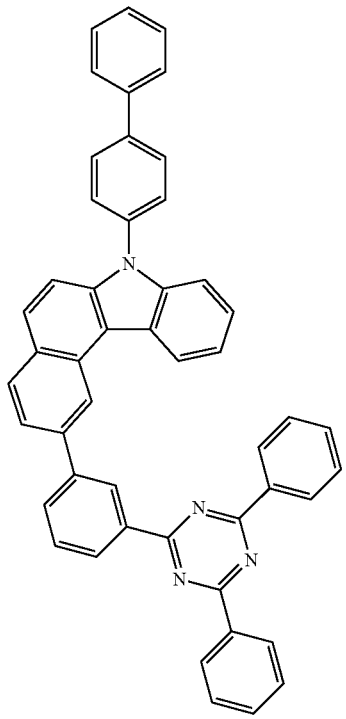
490
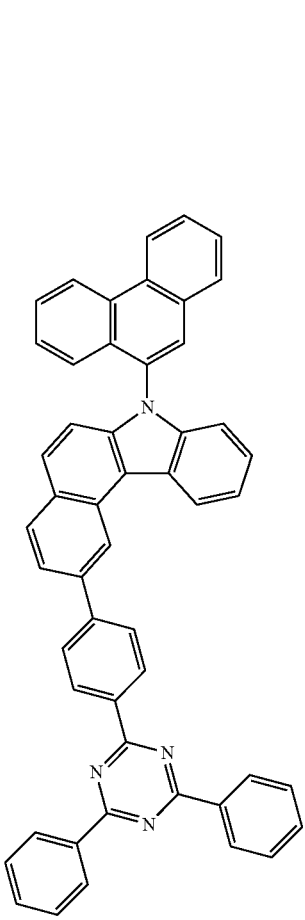
254
-continued
491
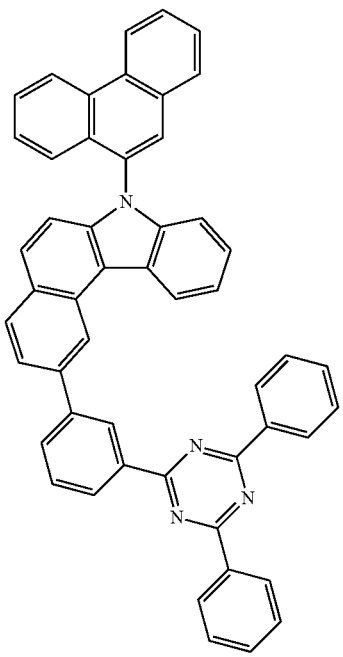
492
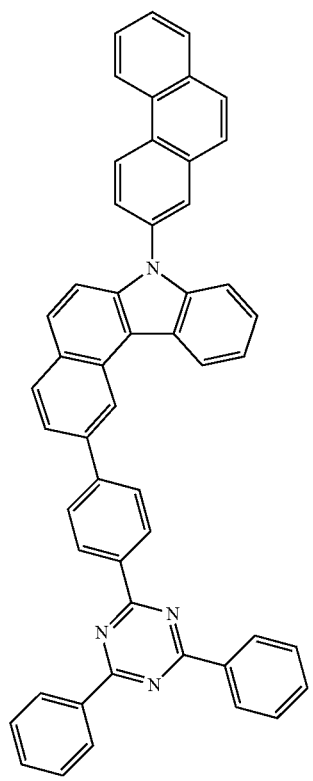

255
-continued
493
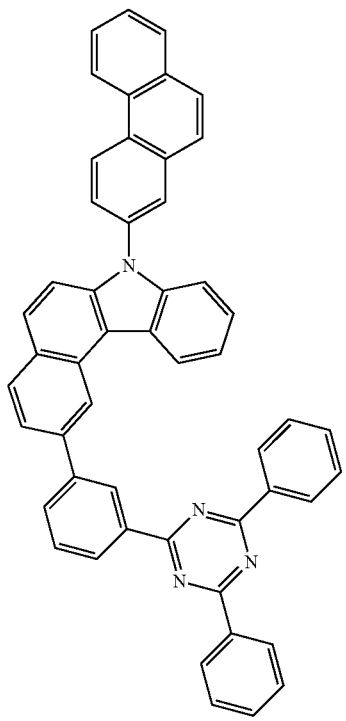
494
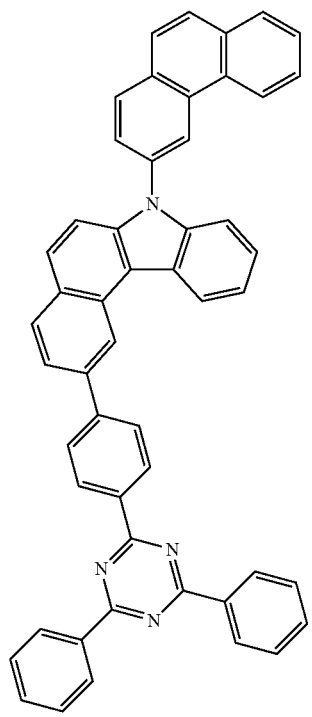
256
-continued
495
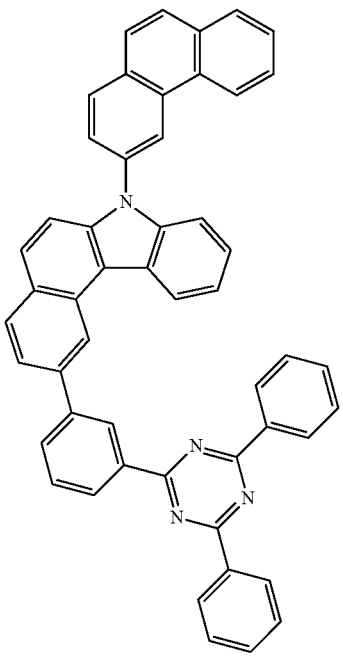
496
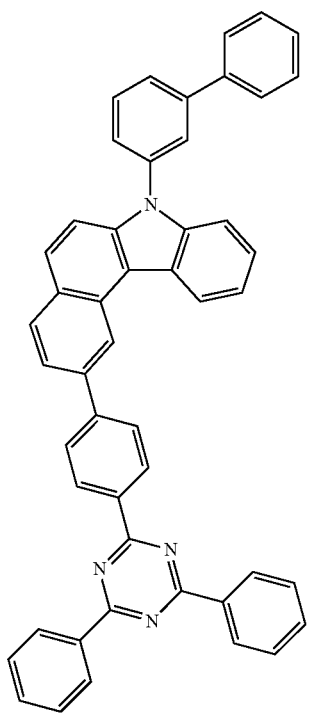

257
-continued
258
-continued
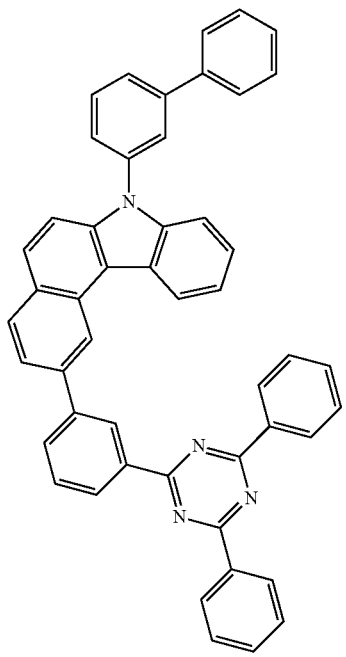
497
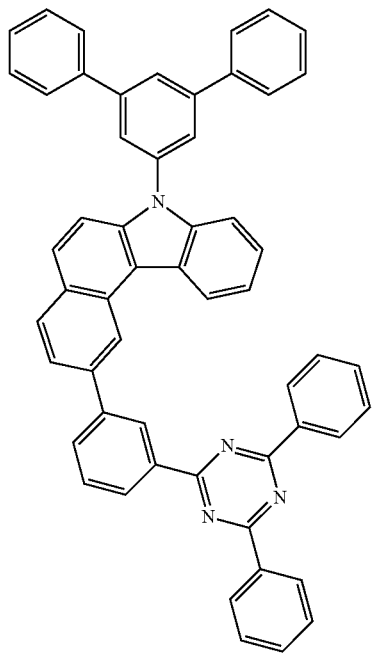
499
498
500
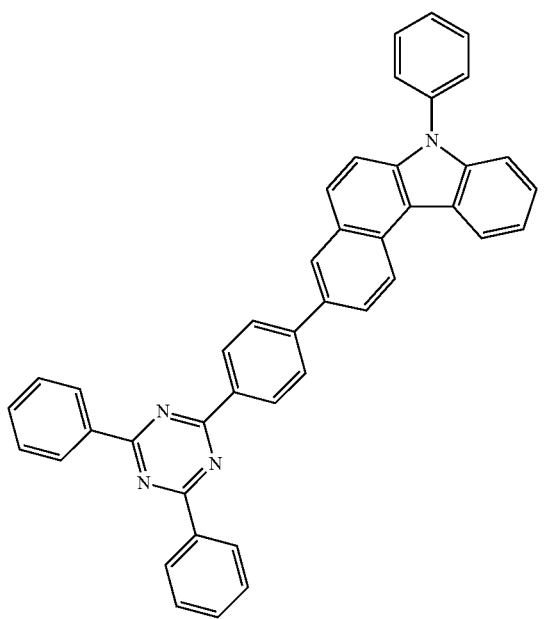

259 -continued
260 -continued
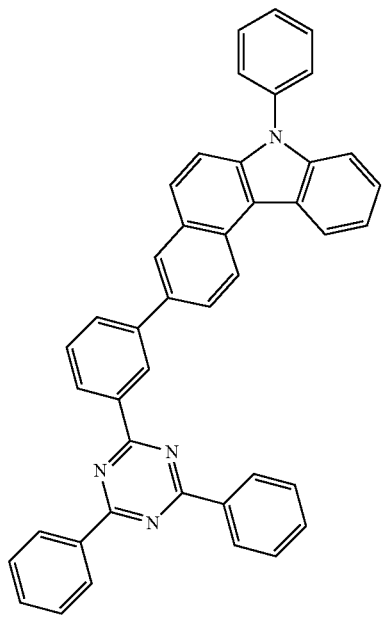
501
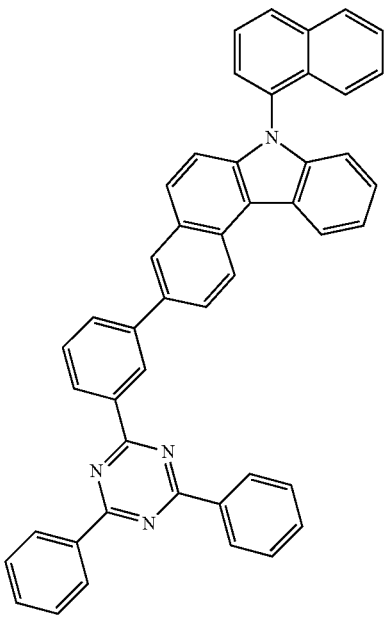
503
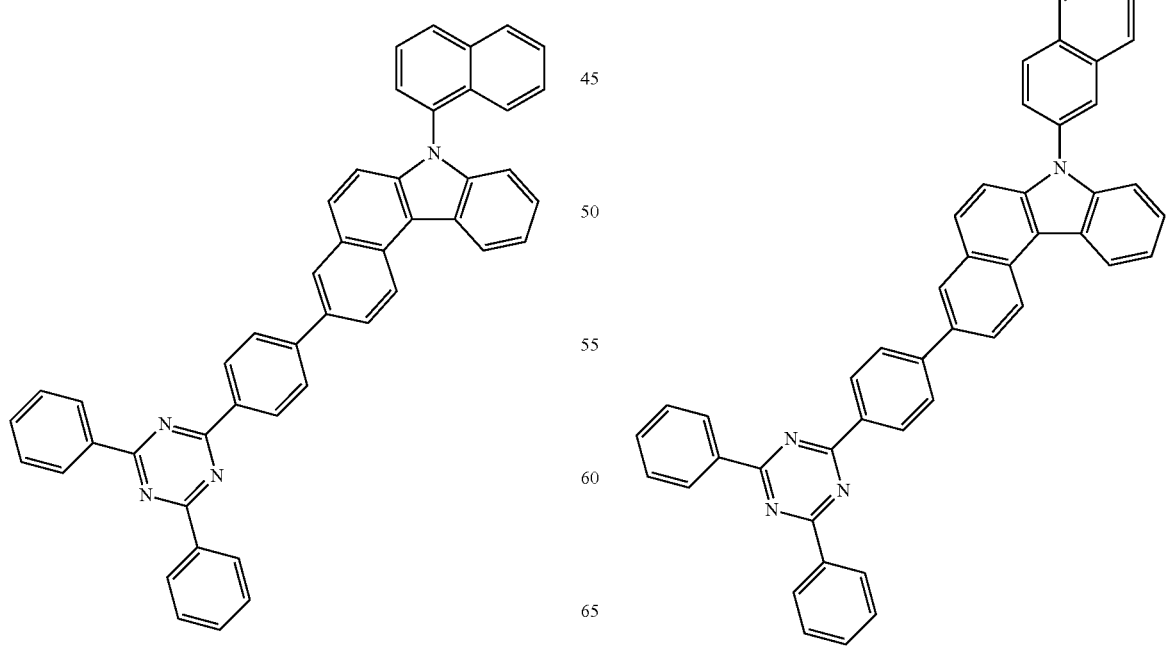

261
-continued
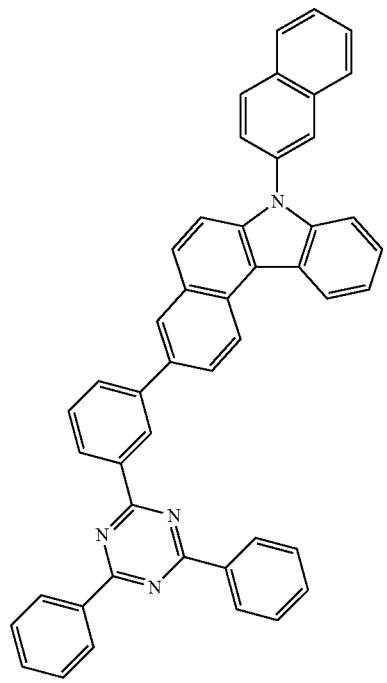
505
262
-continued
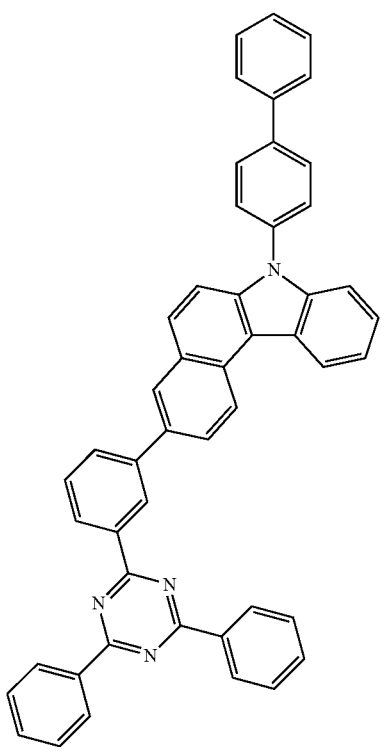
507
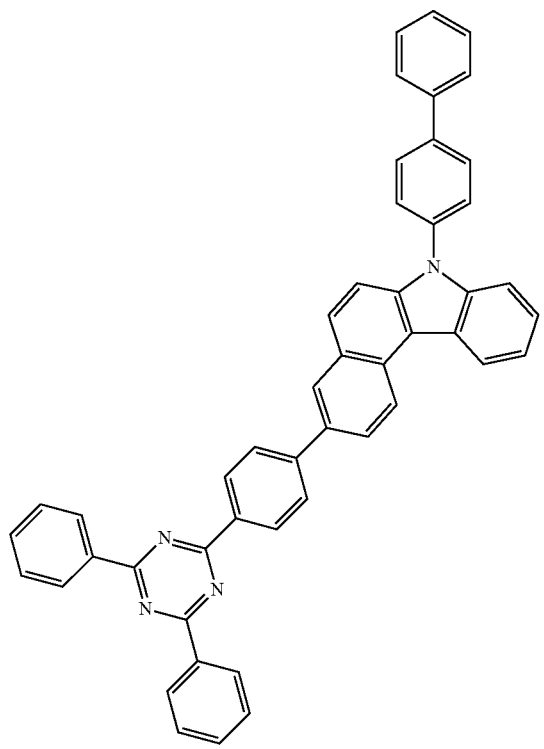
506
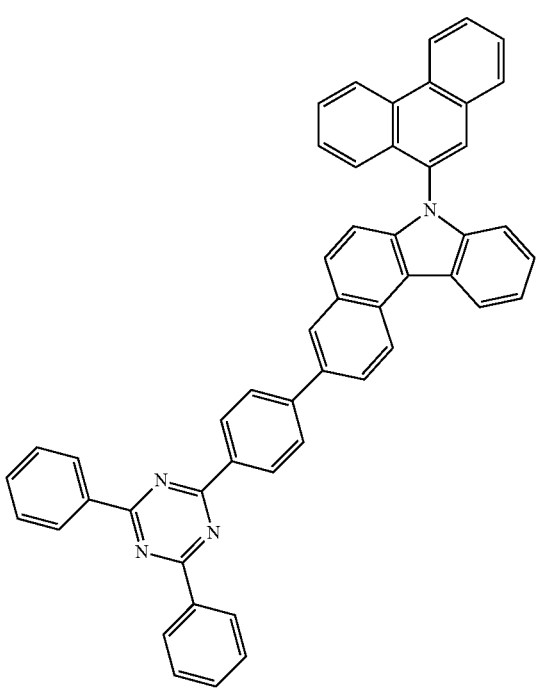
508

263
-continued
509
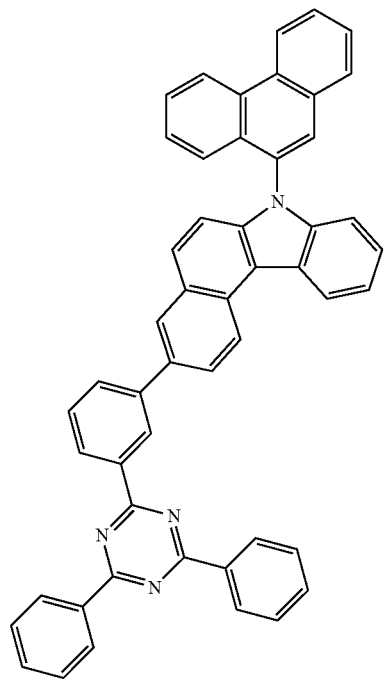
510
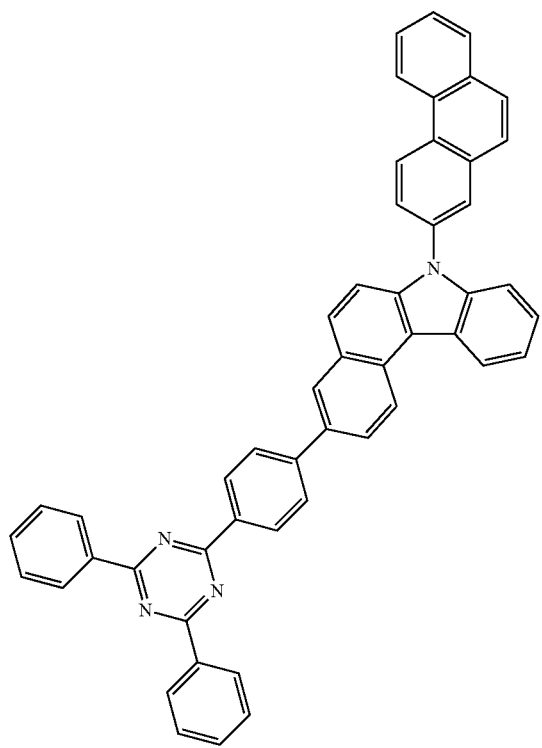
264
-continued
511
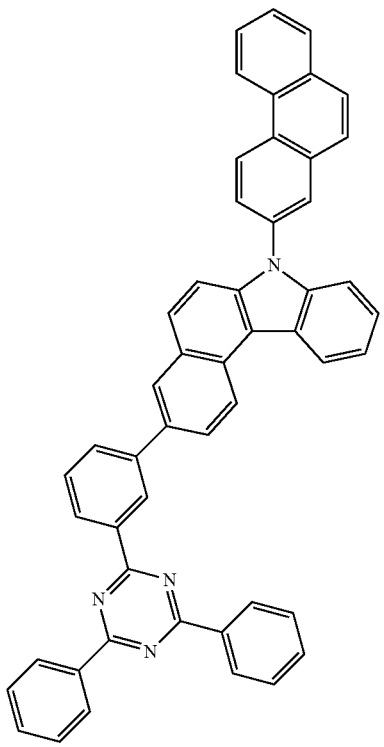
512
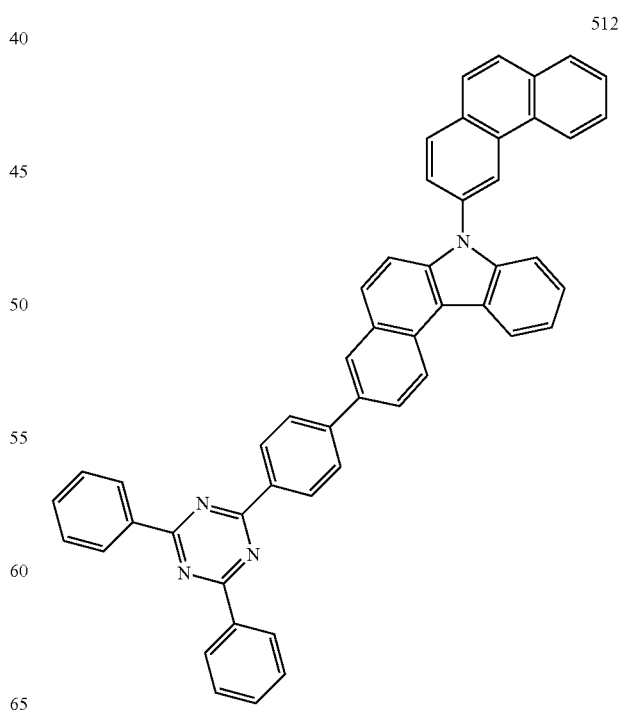

513
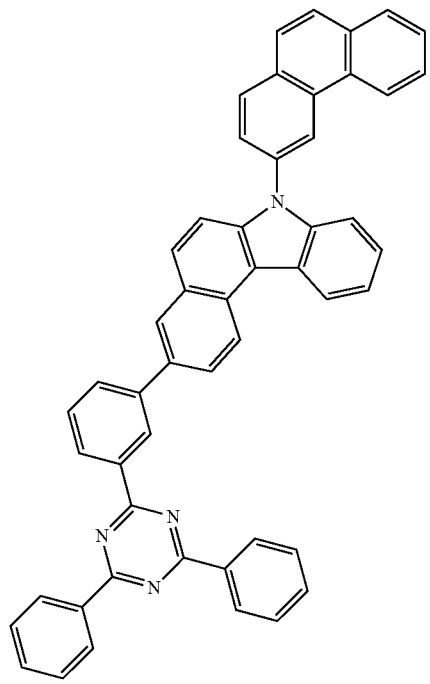
514
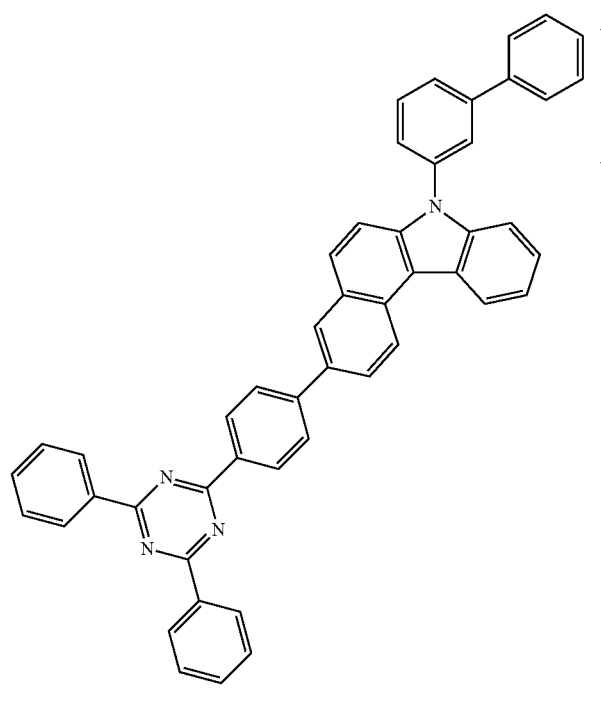
515
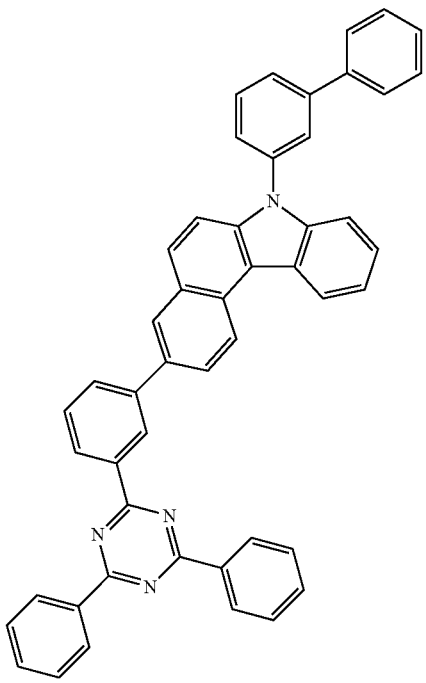
516
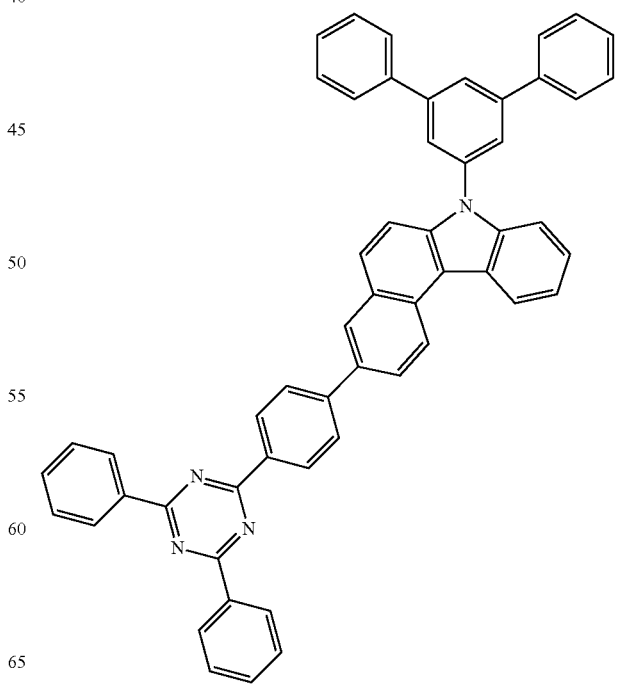

267
-continued
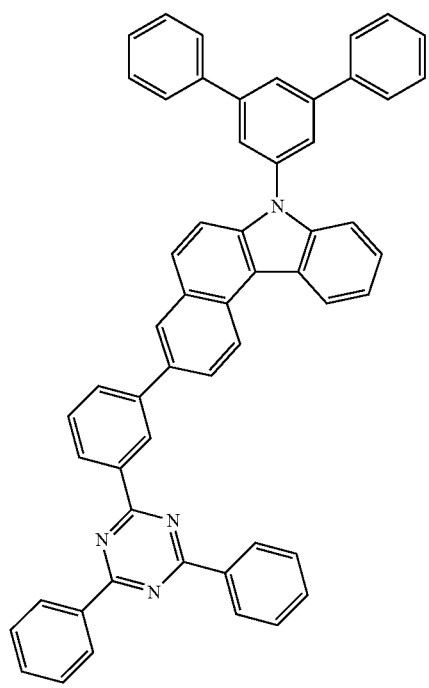
517
268
-continued
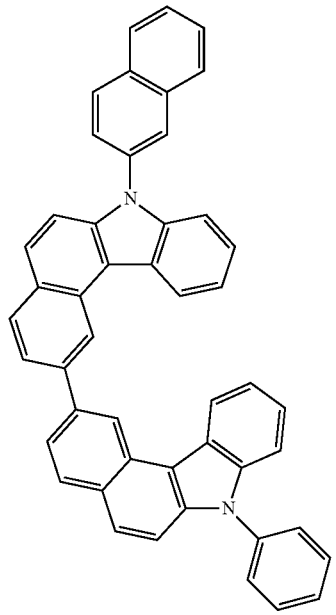
519
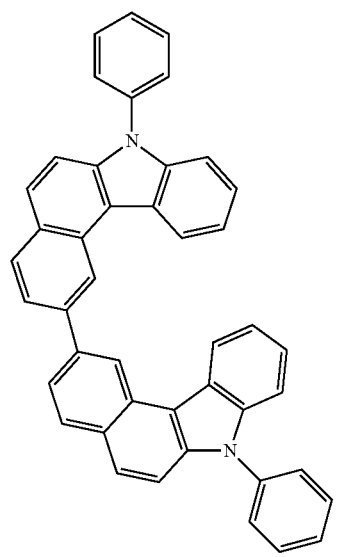
518
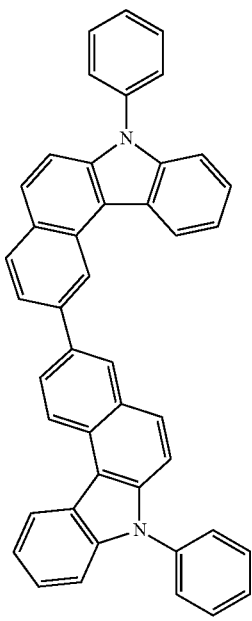
520

269
-continued
521
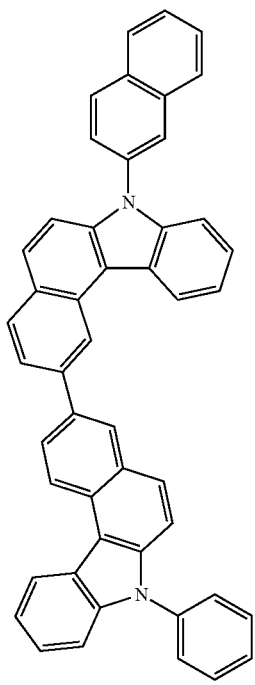
523
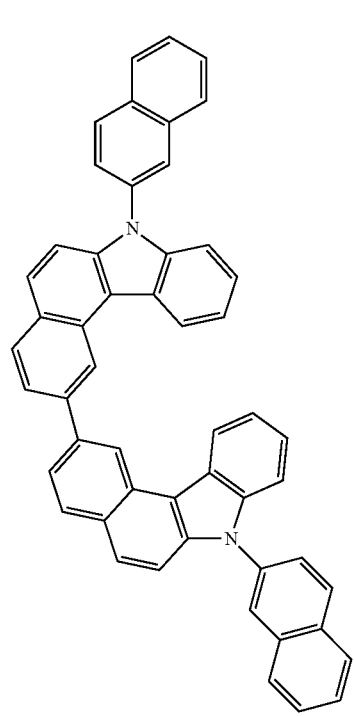
270
-continued
524
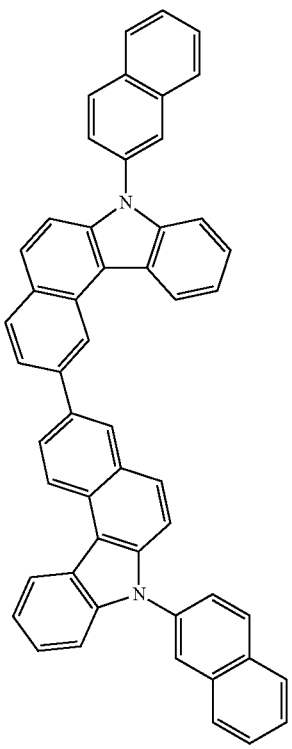
525
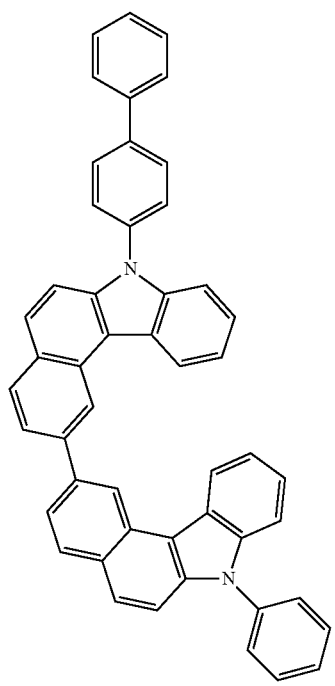

271
-continued
526
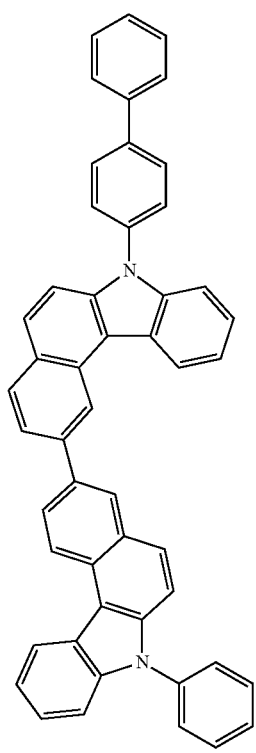
527
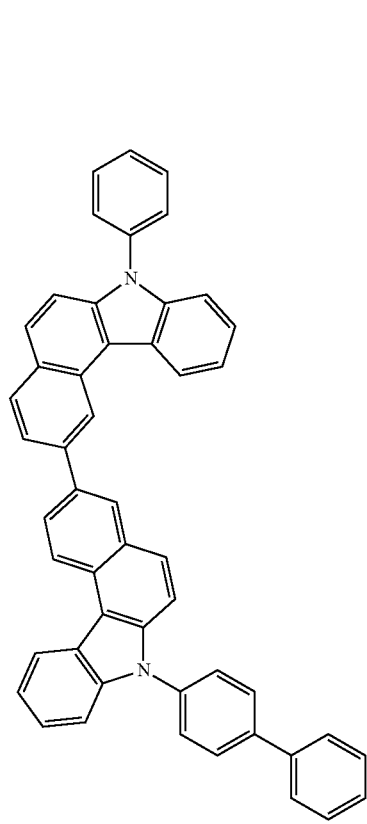
272
-continued
528
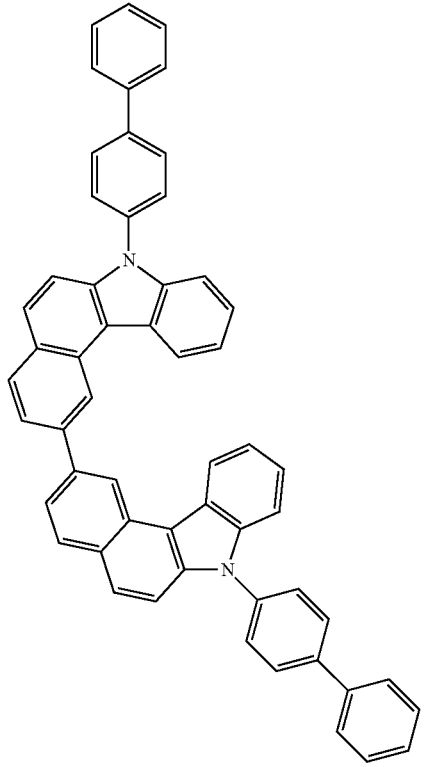
529
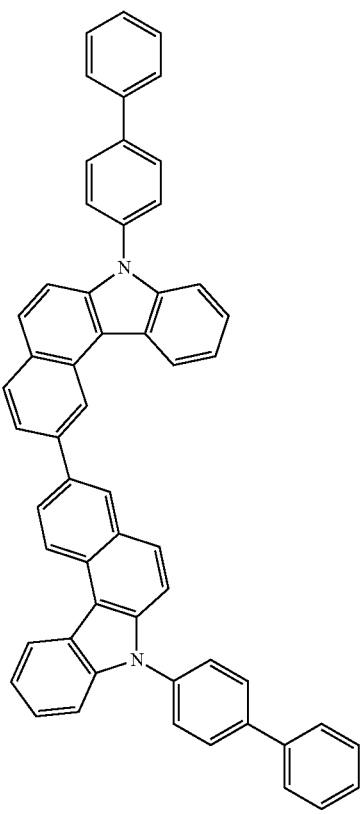

273
-continued
530
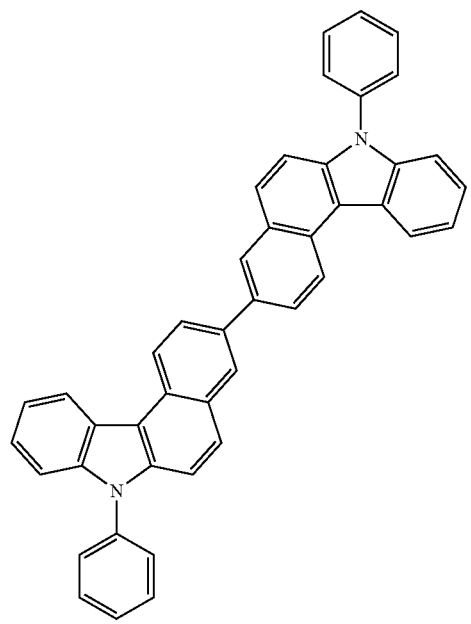
531
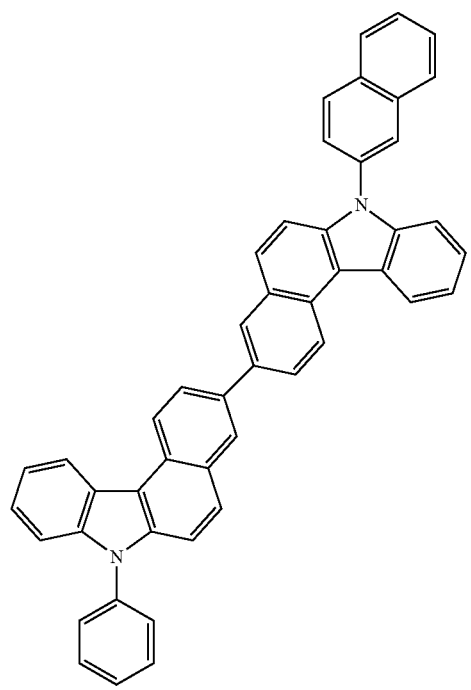
274
-continued
532
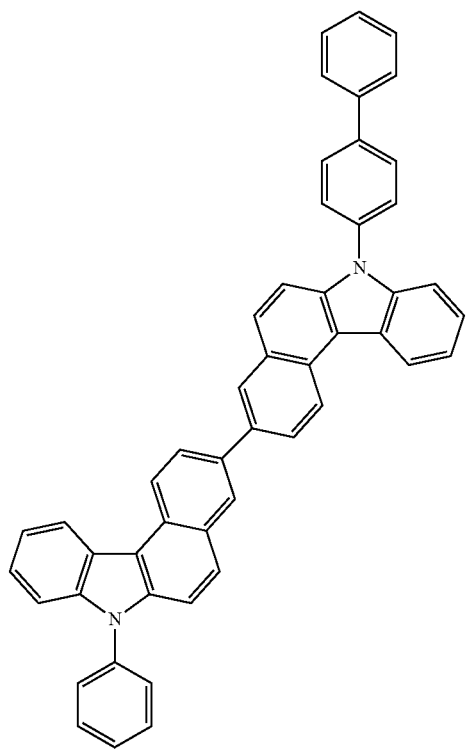
533
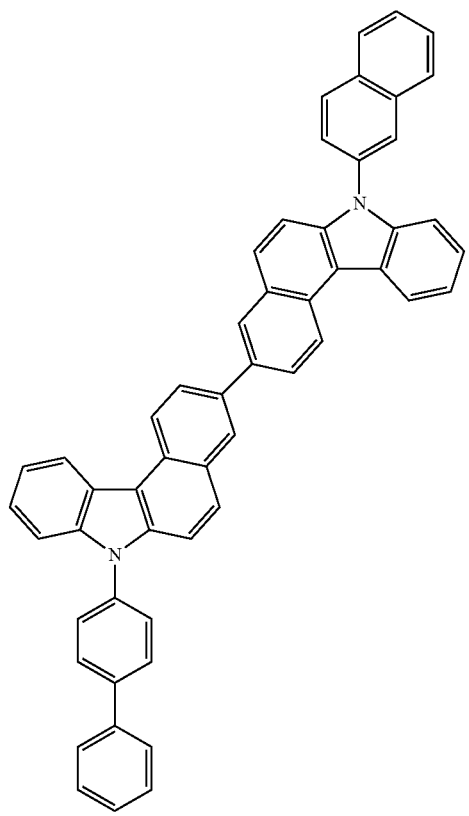

275
-continued
534
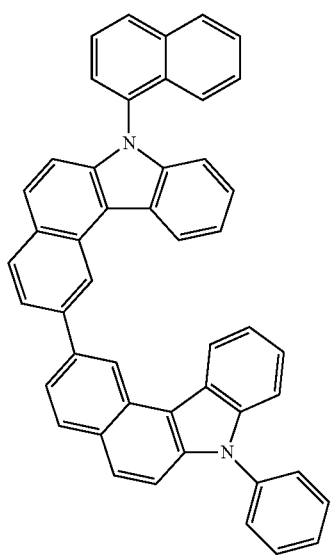
276
-continued
536
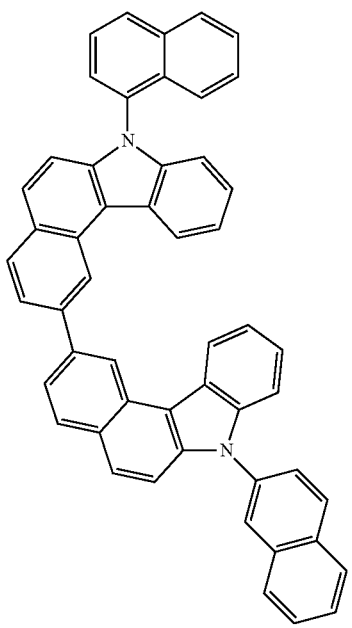
535
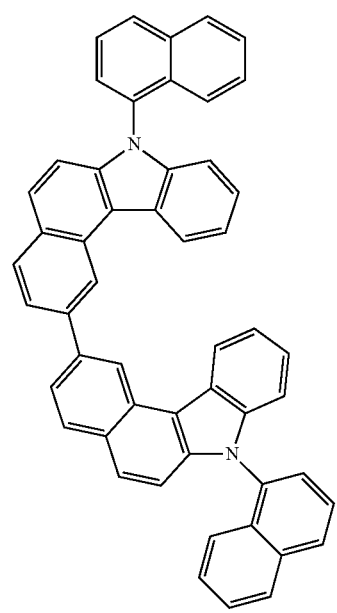
537
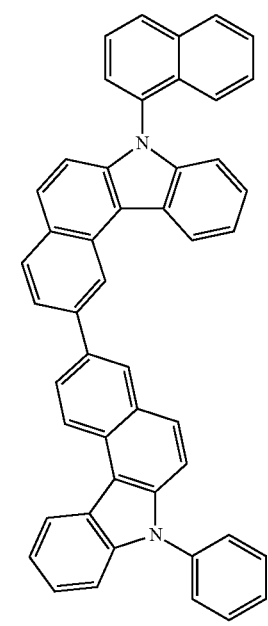

277
-continued
538
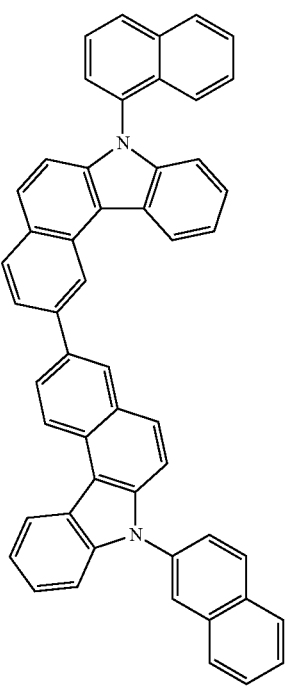
539
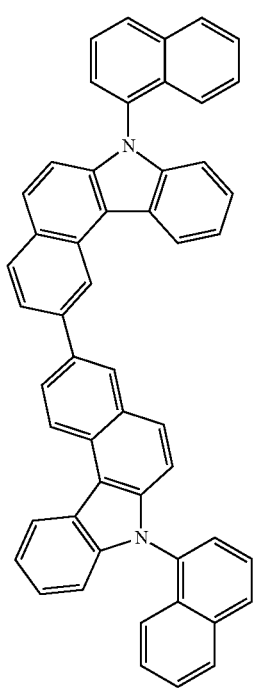
278
-continued
540
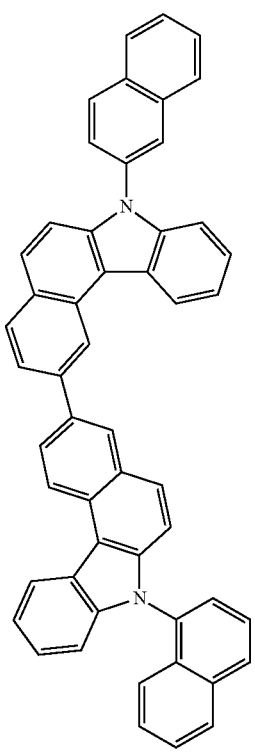
541
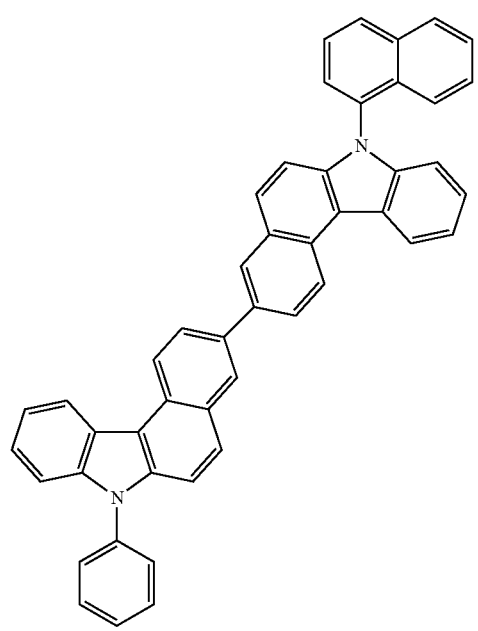

279
-continued
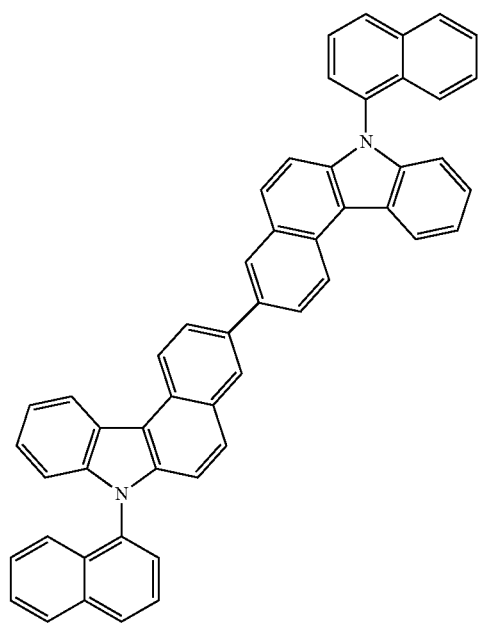
542
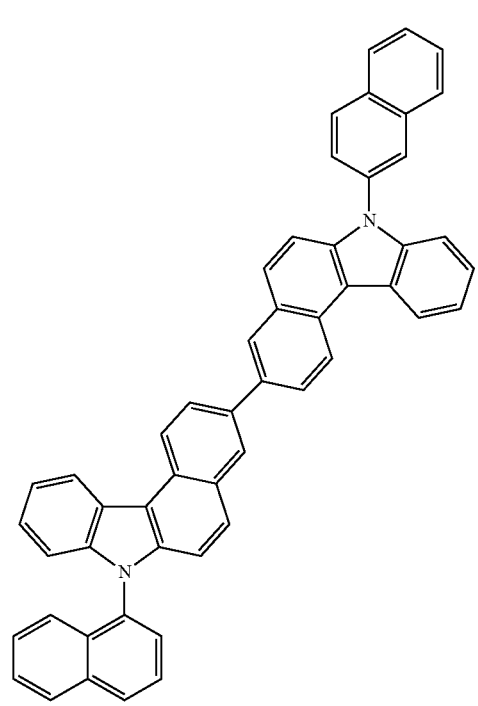
543
280
-continued
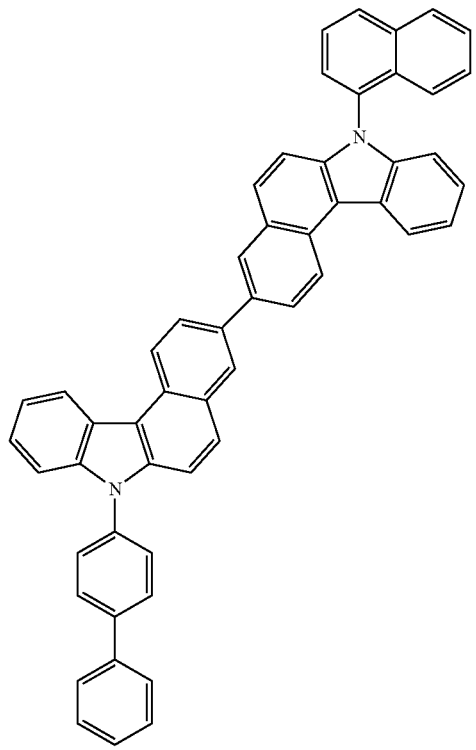
544
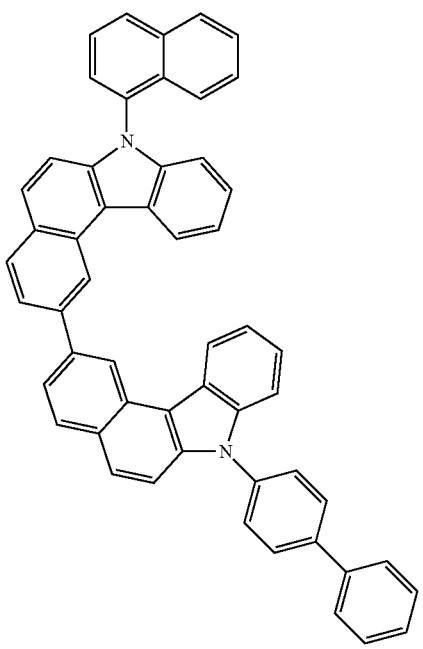
545

281
-continued
546
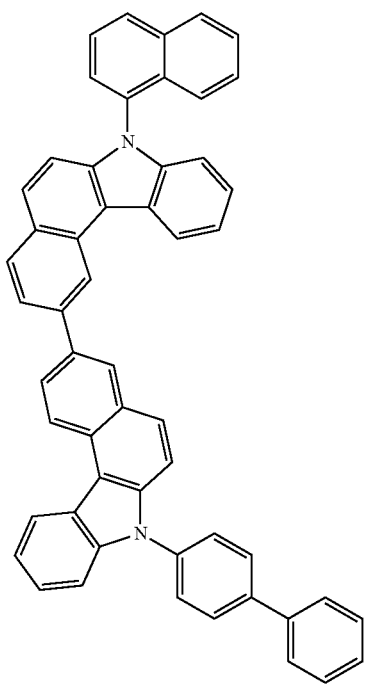
547
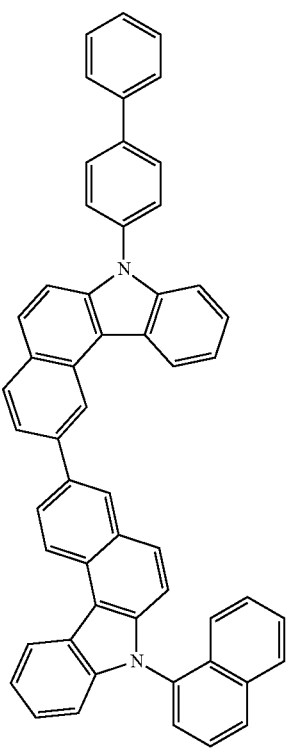
282
-continued
548
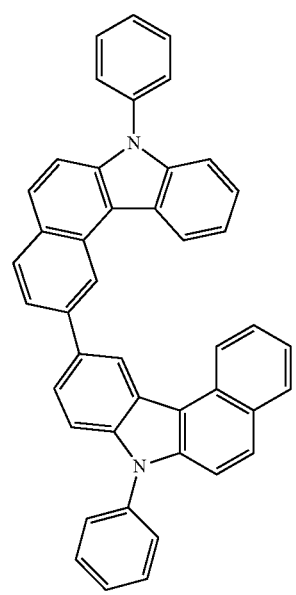
549
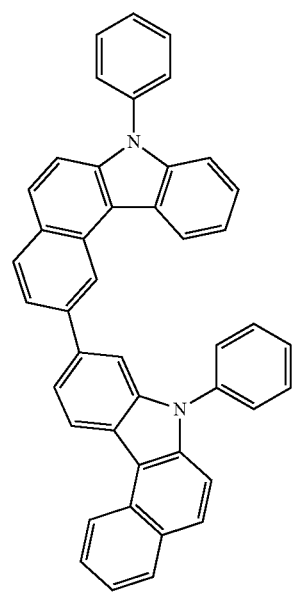

283
-continued
550
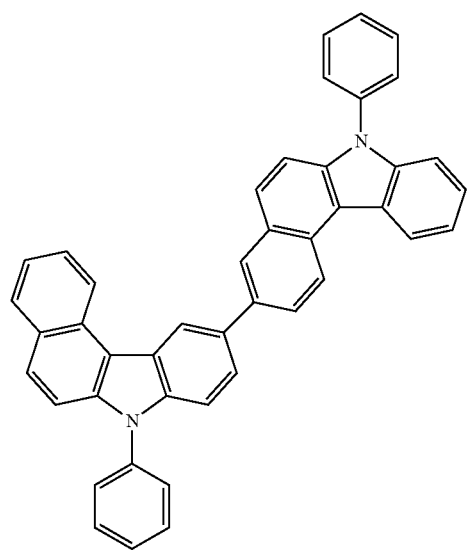
551
552
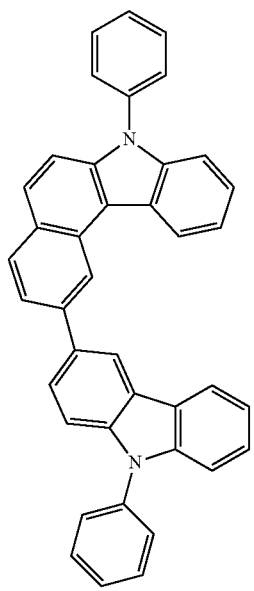
553
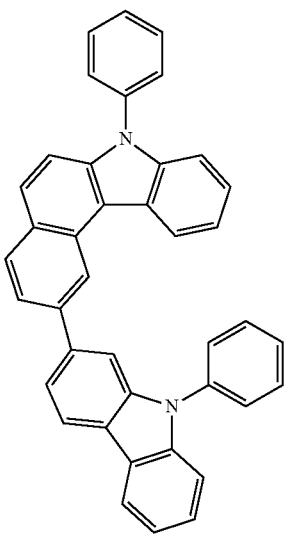

554
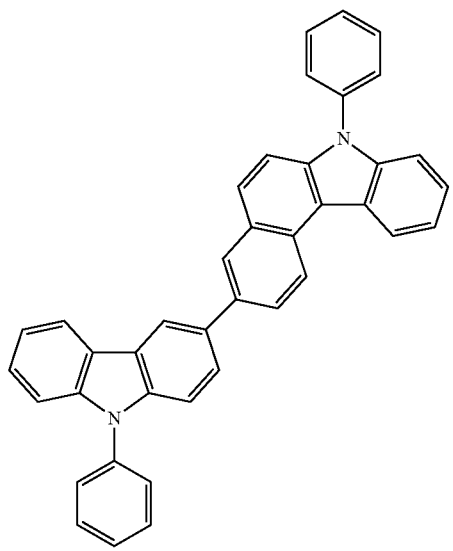
555
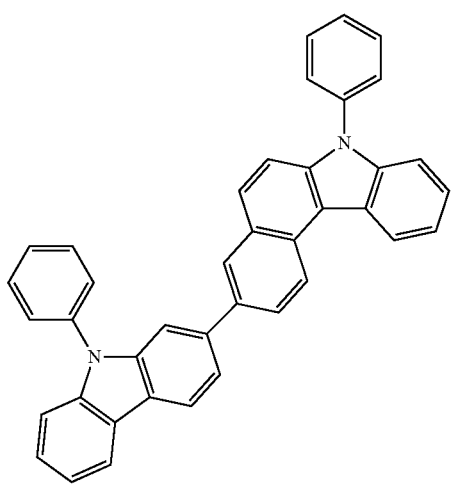
556
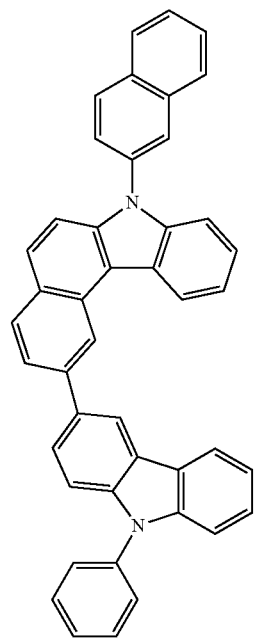
557
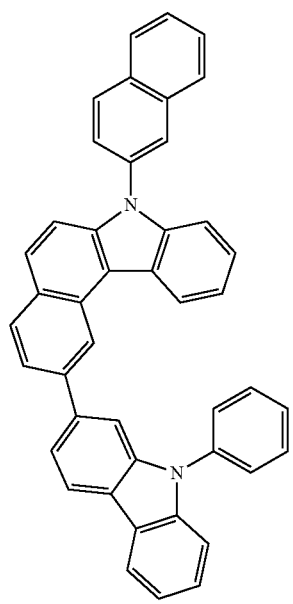

558
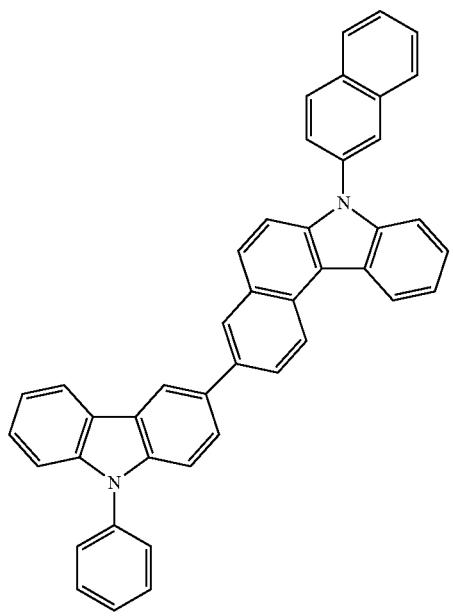
559
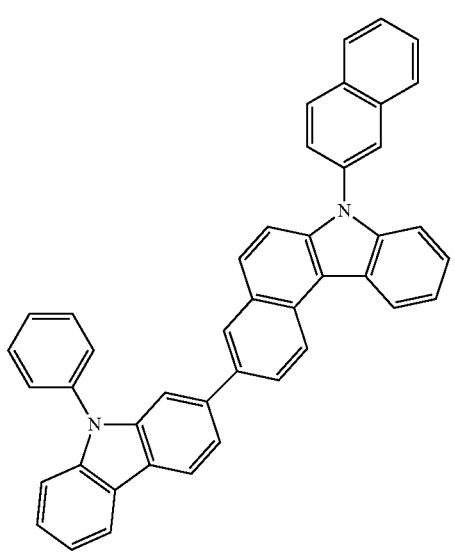
560
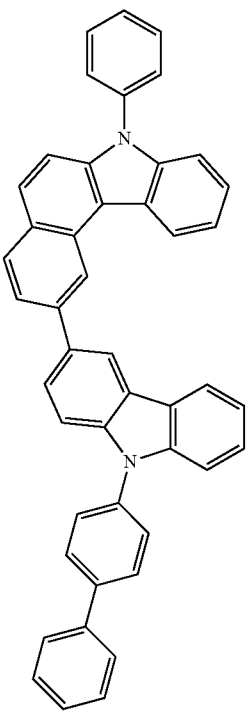
561
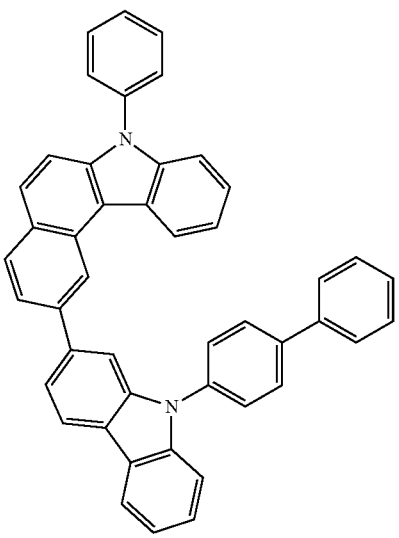

562
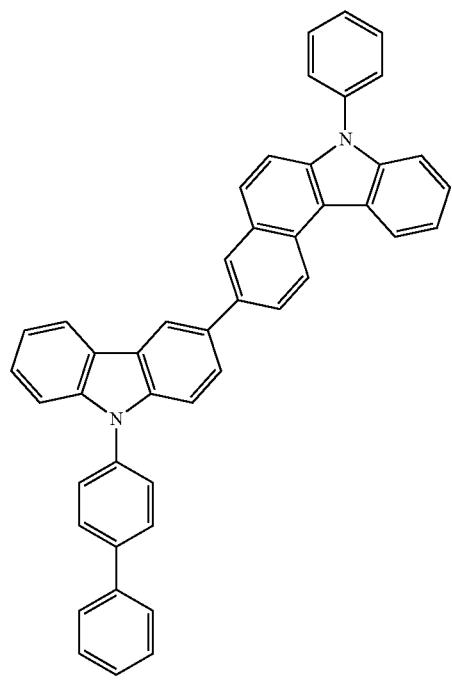
563
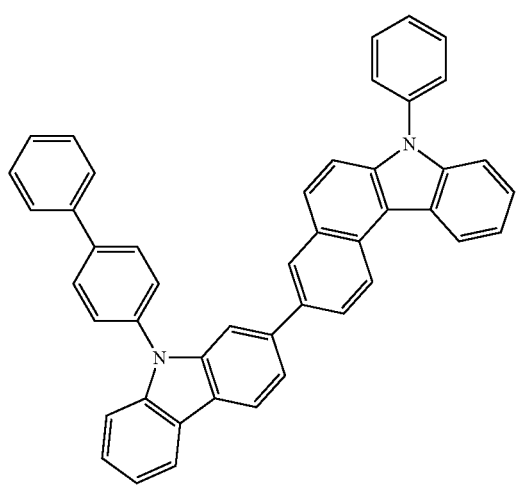
564
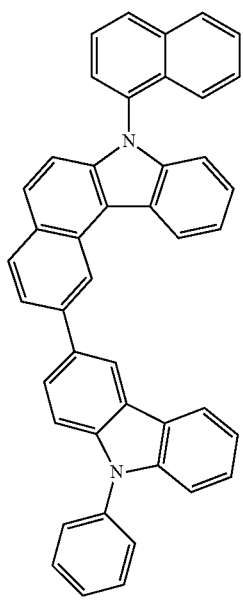
565
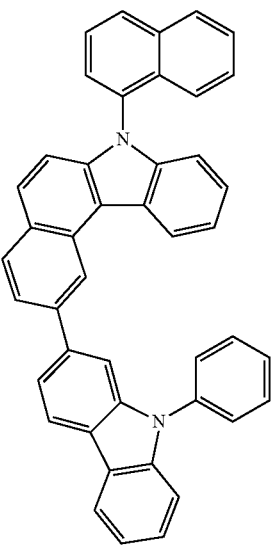

291
-continued
567
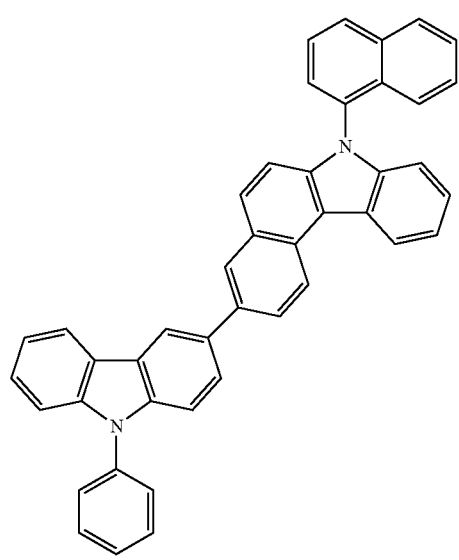
568
569
292
-continued
570
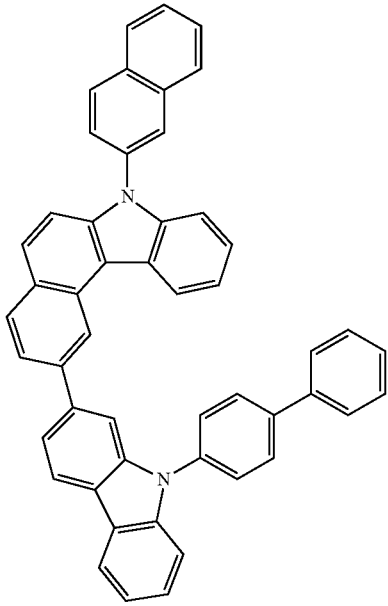
571

572
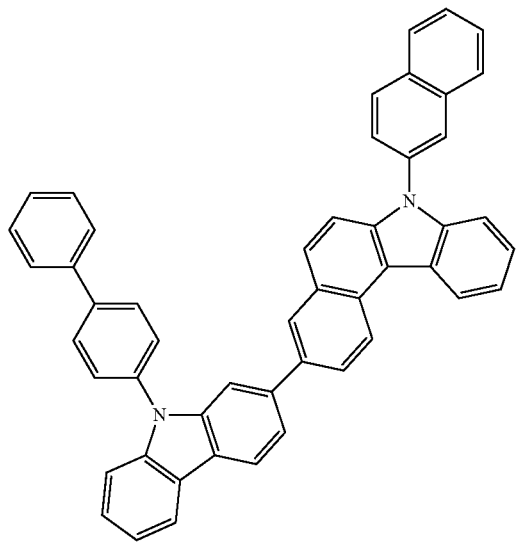
573
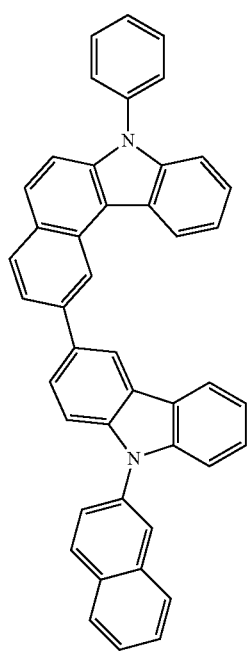
574
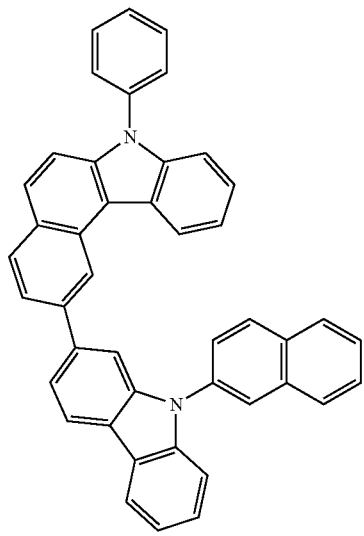
575
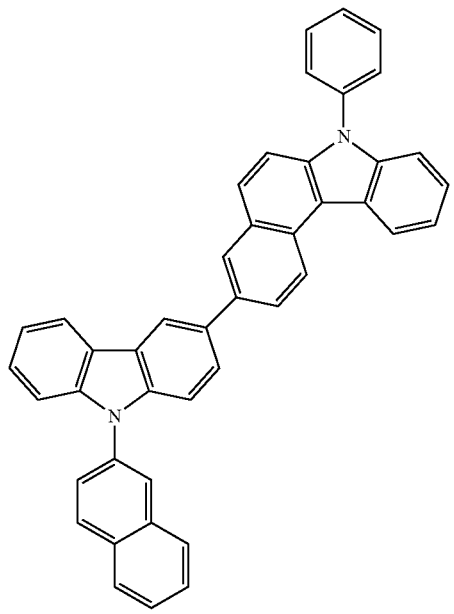
576
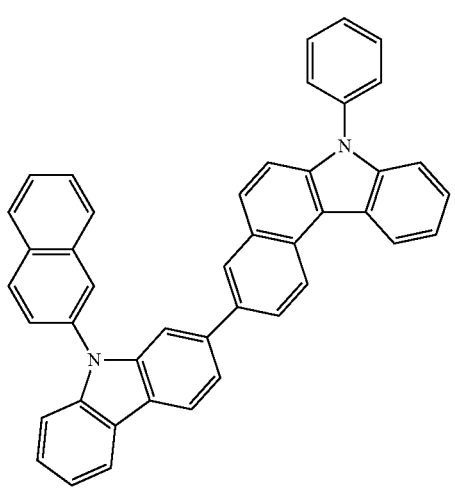

The compound represented by Formula 1 may be prepared based on the Preparation Examples to be described below. According to an exemplary embodiment, the compound may be prepared by the method such as the following Reaction Formula 1.

[Reaction Formula 1]

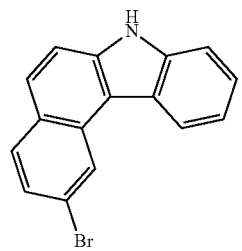

Intermediate 1-A-3

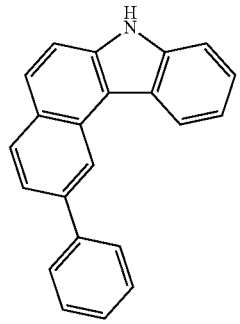

Intermediate 3-A-1

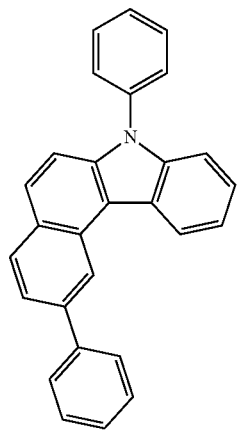

Compound 1

For the compound represented by Formula 1, Intermediate 3-A-1 is synthesized by a Suzuki reaction using phenyl boronic acid in Intermediate 1-A-3 as in Reaction Formula 1. Next, the compound represented by Formula 1 may be synthesized by an Ullmann reaction of Intermediate 3-A-1 with iodobenzene.

Further, the present specification provides an organic light emitting device including the compound represented by Formula 1.

An exemplary embodiment of the present specification provides an organic light emitting device including: a first electrode; a second electrode provided to face the first electrode; and one or more organic material layers provided between the first electrode and the second electrode, in which one or more layers of the organic material layers include the compound of Formula 1.

The organic material layer of the organic light emitting device of the present specification may also be composed of a single-layered structure, but may be composed of a multi-layered structure in which two or more organic material layers are stacked. For example, the organic light emitting device of the present invention may have a structure including a hole injection layer, a hole transporting layer, a light emitting layer, an electron transporting layer, an electron injection layer, and the like as organic material layers. However, the structure of the organic light emitting device is not limited thereto, and may include a fewer number of organic layers.

In an exemplary embodiment of the present specification, the organic material layer includes a hole injection layer, a hole transporting layer, or a layer which simultaneously injects and transports holes, and the hole injection layer, the hole transporting layer, or the layer which simultaneously injects and transports holes includes the compound of Formula 1.

In another exemplary embodiment, the organic material layer includes a light emitting layer, and the light emitting layer includes the compound of Formula 1. In an exemplary embodiment of the present specification, the light emitting layer includes the compound of Formula 1 as a host, and includes a phosphorescent dopant compound as a dopant.

In an exemplary embodiment of the present specification, the phosphorescent dopant compound is any one of the following compounds.

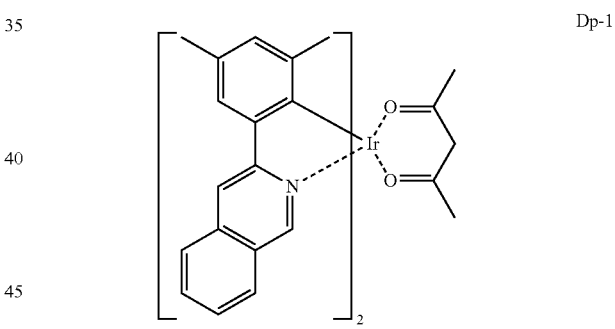

Dp-1

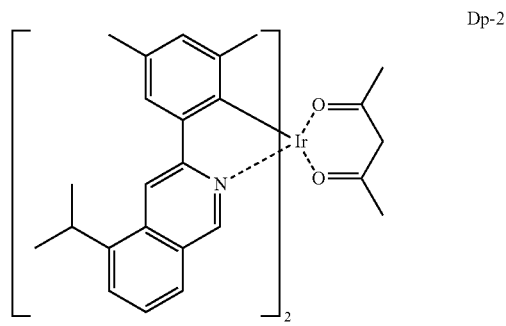

Dp-2

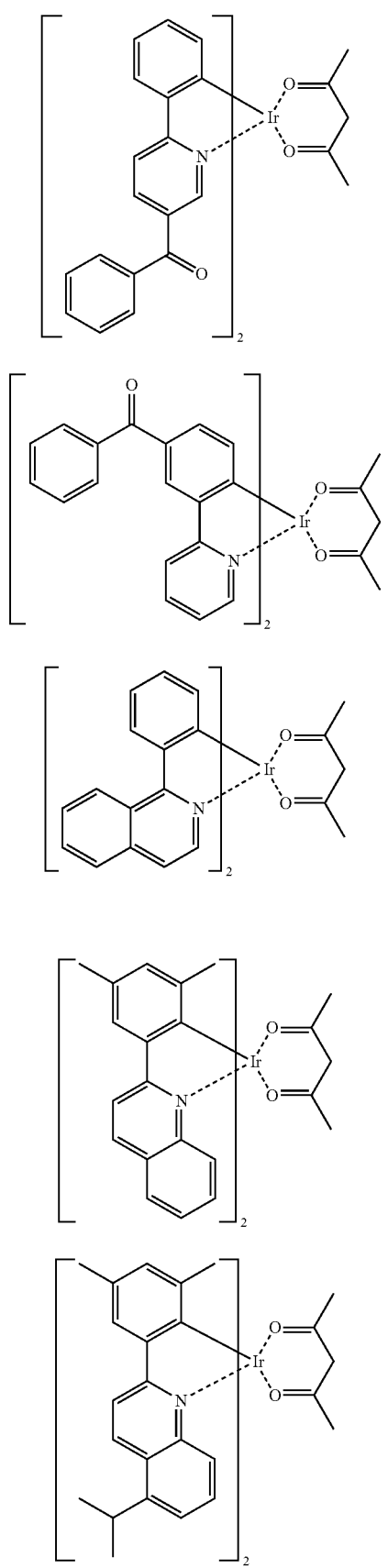
Dp-3
Dp-4
Dp-5
Dp-6
Dp-7
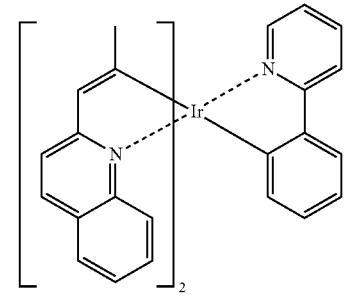
Dp-8
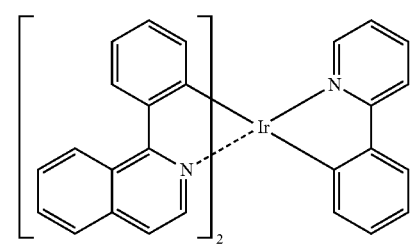
Dp-9
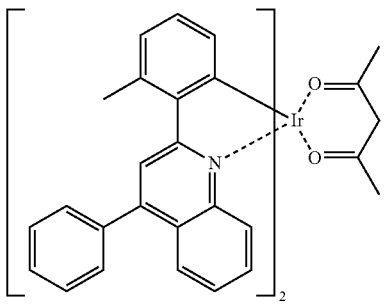
Dp-10
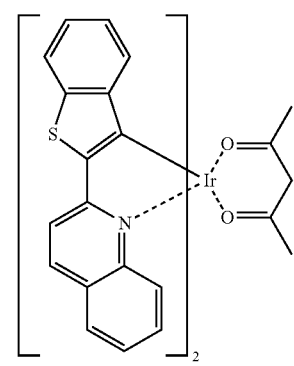
Dp-11
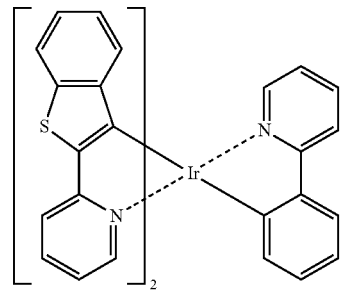
Dp-12

DP-13 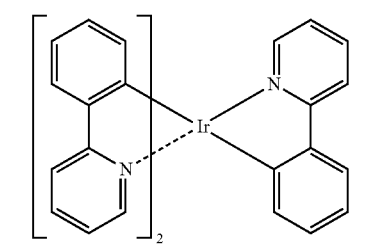
Dp-14 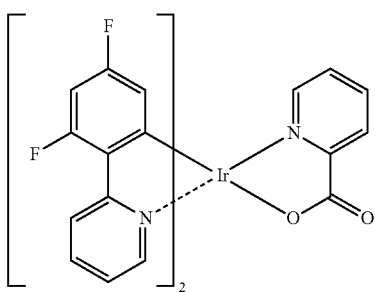
Dp-15 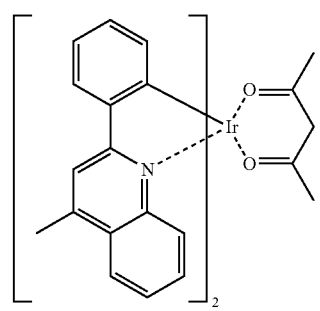
Dp-16 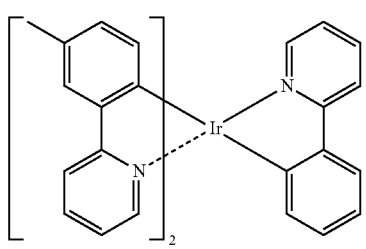
Dp-17 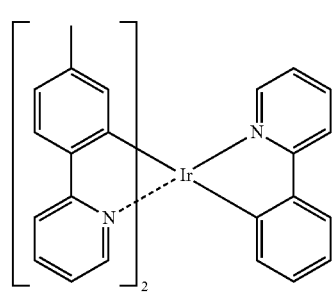
Dp-18 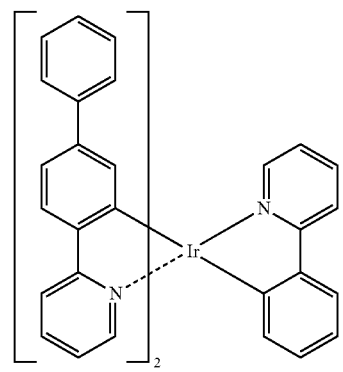
Dp-19 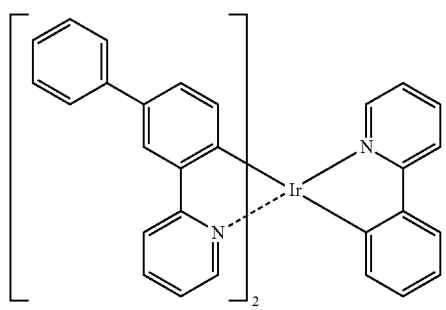
Dp-20 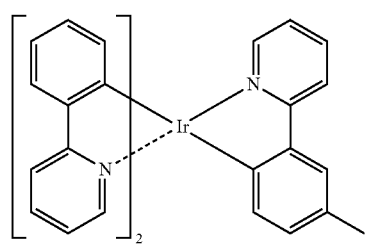
Dp-21 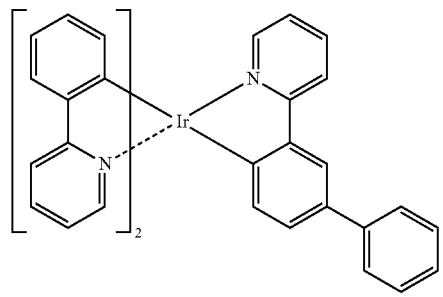
Dp-22 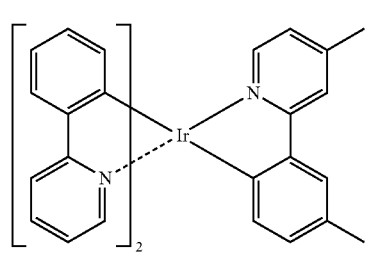

-continued

Dp-23

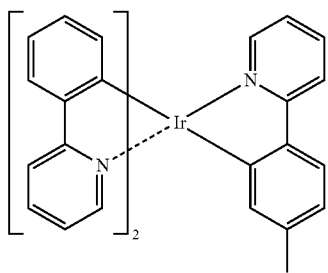

Dp-24

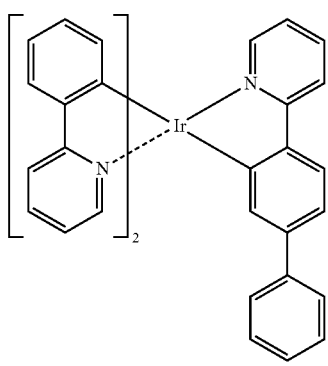

Dp-25

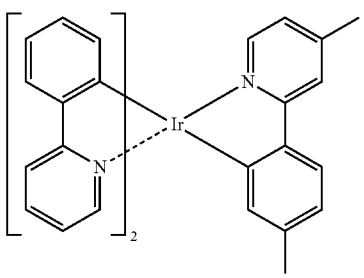

Dp-26

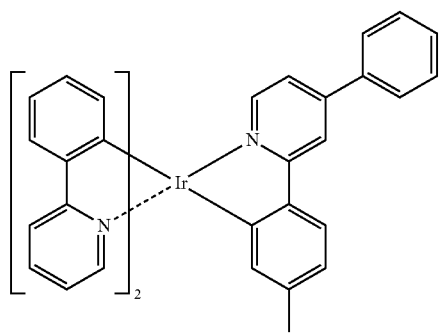

-continued

Dp-27

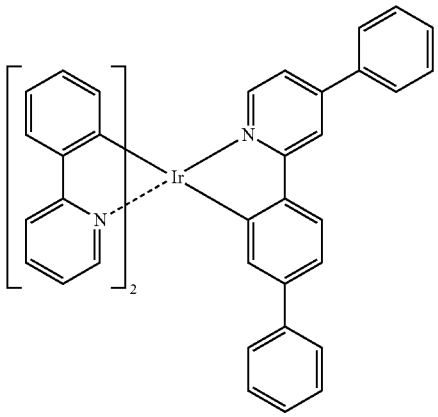

In an exemplary embodiment of the present specification, the organic material layer includes an electron transporting layer or an electron injection layer, and the electron transporting layer or the electron injection layer includes the compound of Formula 1. In an exemplary embodiment of the present specification, the electron transporting layer, the electron injection layer, or the layer which simultaneously transports and injects electrons includes the compound of Formula 1.

In another exemplary embodiment, the organic material layer includes a light emitting layer and an electron transporting layer, and the electron transporting layer includes the compound of Formula 1.

In still another exemplary embodiment, the organic light emitting device may be an organic light emitting device having a structure (normal type) in which a positive electrode, one or more organic material layers, and a negative electrode are sequentially stacked on a substrate.

In yet another exemplary embodiment, the organic light emitting device may be an organic light emitting device having a reverse-direction structure (inverted type) in which a negative electrode, one or more organic material layers, and a positive electrode are sequentially stacked on a substrate.

For example, the structure of the organic light emitting device according to an exemplary embodiment of the present specification is illustrated in FIGS. 1 and 2.

FIG. 1 illustrates an example of an organic light emitting device composed of a substrate 1, a positive electrode 2, a light emitting layer 3, and a negative electrode 4. In the structure, the compound may be included in the light emitting layer.

FIG. 2 illustrates an example of an organic light emitting device composed of a substrate 1, a positive electrode 2, a hole injection layer 5, a hole transporting layer 6, a light emitting layer 7, an electron transporting layer 8, and a negative electrode 4. In the structure, the compound may be included in one or more layers of the hole injection layer, the hole transporting layer, the light emitting layer, and the electron transporting layer.

The organic light emitting device of the present specification may be manufactured by the materials and methods known in the art, except that one or more layers of the organic material layers include the compound of the present specification, that is, the compound of Formula 1.

When the organic light emitting device includes a plurality of organic material layers, the organic material layers may be formed of the same material or different materials.

The organic light emitting device of the present specification may be manufactured by the materials and methods known in the art, except that one or more layers of the organic material layers include the compound of Formula 1, that is, the compound represented by Formula 1.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transporting layer, a light emitting layer, and an electron transporting layer thereon, and then depositing a material, which may be used as a negative electrode, thereon, by using a physical vapor deposition (PVD) method such as sputtering or e-beam evaporation. In addition to the method as described above, an organic light emitting device may be made by subsequently depositing a negative electrode material, an organic material layer, and a positive electrode material on a substrate.

Further, the compound of Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto.

In an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or SnO$_2$:Sb; an electrically conductive polymer, such as poly(3-methylthiophene), poly[3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structure material, such as LiF/Al or LiO$_2$/Al, and the like, but are not limited thereto.

The hole injection material is preferably a compound which has a capability of transporting holes to a layer which injects holes from an electrode, and thus has an effect of injecting holes at a positive electrode and an excellent effect of injecting holes into a light emitting layer or a light emitting material, prevents excitons, which are produced from the light emitting layer, from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transporting layer is a layer which receives holes from a hole injection layer and transports holes to a light emitting layer, and a hole transporting material is suitably a material which may receive holes from a positive electrode or a hole injection layer to transfer the holes to a light emitting layer, and has high mobility for the holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons from a hole transporting layer and an electron transporting layer, respectively, and combine the holes and the electrons to emit light in a visible ray region, and is preferably a material having good quantum efficiency to fluorescence or phosphorescence. Specific examples thereof include: an 8-hydroxy-quinoline aluminum complex (Alq$_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a condensed aromatic ring derivative, or a hetero ring-containing compound, and the like. Specific examples of the condensed aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a condensed aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto.

Further, examples of the metal complex include an iridium complex, a platinum complex, and the like, but are not limited thereto.

The electron transporting material is a material which receives electrons from an electron injection layer and transports the electrons to a light emitting layer, and an electron transporting material is a material which may inject electrons well from a negative electrode and may transfer the electrons to the light emitting layer, and is suitably a material which has high mobility for the electrons. Specific examples thereof include: an Al complex of 8-hydroxyquinoline; a complex including Alq$_3$; an organic radical compound; a hydroxyflavone-metal complex, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons, which are produced from the light emitting layer, from moving to the hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The organic light emitting device according to the present specification may be a top emission type, a bottom emission type, or a dual emission type according to the material to be used.

In an exemplary embodiment of the present specification, the compound of Formula 1 may be included in an organic solar cell or an organic transistor in addition to the organic light emitting device.

The preparation of the compound represented by Formula 1 and the organic light emitting device including the same will be specifically described in the following Examples. However, the following Examples are provided for exemplifying the present specification, and the scope of the present specification is not limited thereby.

SYNTHESIS OF INTERMEDIATE

Synthesis of Intermediate 1-A-3

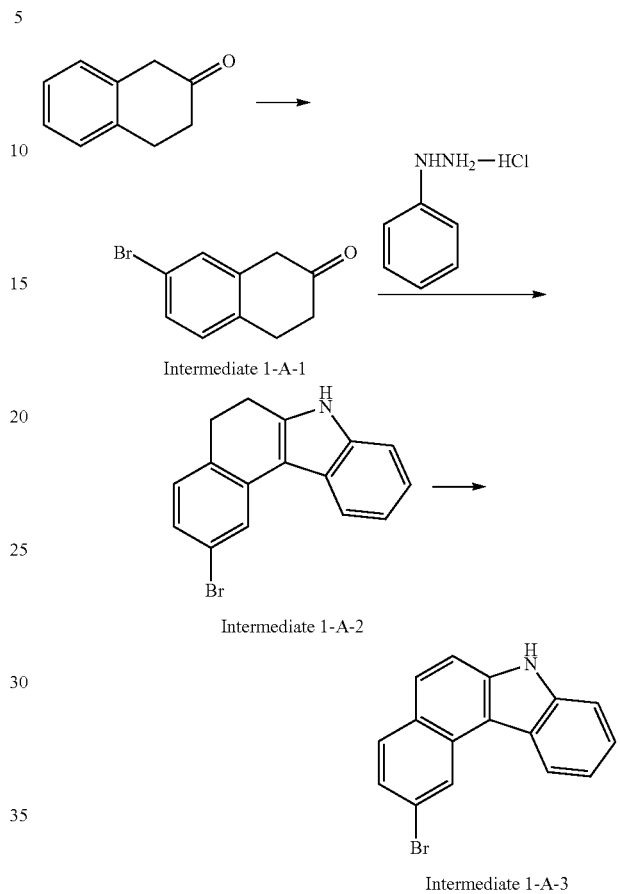

Synthesis of Intermediate 1-A-1

Trichloroaluminium (aluminium chloride, hereinafter, referred to as AlCl$_3$, CAS#7446-70-0) (31.9 g, 239 mmol) was put into 30 ml of CH$_2$Cl$_2$ under nitrogen flow by the same method mentioned in US Patent Publication No. 2009-0076076, the resulting mixture was stirred at 0° C. for 10 minutes, and then b-tetralone (17.5 g, 120 mmol) was added thereto. The resulting mixture was stirred for 20 minutes, and Br$_2$ (6.74 ml, 131 mmol) was slowly added thereto at the same temperature. After the addition of bromine was completed, the reaction solution was stirred at normal temperature for another 1 hour. After the reaction was terminated, the reaction solution was poured into an ice bath, and extraction was performed with ethyl acetate (EA). The extracted organic material is dried over MgSO$_4$ and concentrated by a rotary evaporator, and then the concentrated solution was column purified to obtain 19 g (yield 71.1%) of Intermediate 1-A-1 (7-bromo-3,4-dihydronaphthalen-2(1H)-one). FIG. 7 is a view illustrating NMR data which are data confirming the synthesis of Intermediate 1-A-1.

[M]=225

Synthesis of Intermediate 1-A-2

Intermediate 1-A-1 (20 g, 89 mmol) obtained by the method and phenylhydrazine hydrochloride (CAS#59-88-1)

(12.9 g, 89 mmol) were put into 300 ml of ethanol (EtOH), a small amount of hydrochloric acid was added thereto, and then the resulting mixture was heated and refluxed under nitrogen flow for 1 hour. After the reaction was terminated, the product was cooled to normal temperature, filtered, and dried in a vacuum oven overnight to obtain 23 g (yield 88.7%) of Intermediate 1-A-2 (2-bromo-6,7-dihydro-5H-benzo[c]carbazole). FIG. 3 is a view illustrating MS data which are data confirming the synthesis of Intermediate 1-A-3.

[M+H]=299

Synthesis of Intermediate 1-A-3

25 g of Intermediate 1-A-2 (20 g, 67 mmol) obtained by the above method was put into 400 ml of CH₃CN, tetrachloro-1,4-benzoquinone (chloranil, hereinafter, referred to as DDQ, CAS#118-75-2) (21 g, 84.7 mmol) at a solid state was slowly added dropwise thereto in the same equivalent as Intermediate 1-A-2 under the cold bath conditions of 0° C. After the reaction was terminated, NaOH (10%) and water were put into the reaction solution, and the organic layer was extracted. The reaction solution was concentrated and recrystallized with hexane to obtain 13 g (yield 64.7%) of Intermediate 1-A-3 (2-bromo-7H-benzo[c]carbazole).

Synthesis of Intermediate 1-B-2

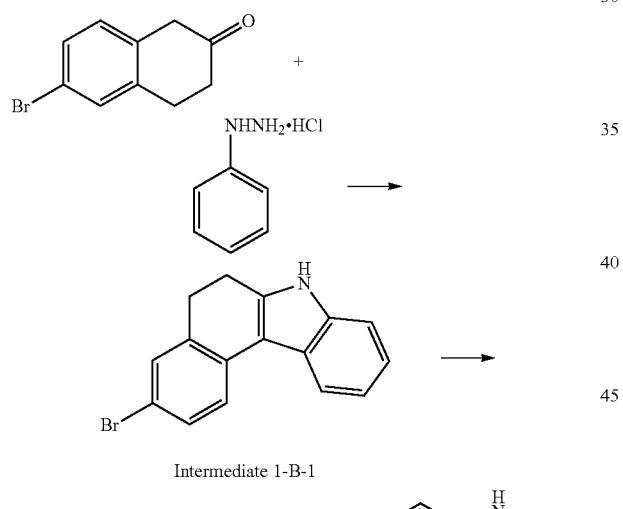

Intermediate 1-B-1

Intermediate 1-B-2

Synthesis of Intermediate 1-B-1

6-bromo-2-tetralone (CAS#4133-35-1) (30 g, 33 mmol) and phenylhydrazine hydrochloride (19 g, 133 mmol) were used in the same manner as in the synthesis method of Intermediate 1-A-2 to obtain Intermediate 1-B-1 (3-bromo-6,7-dihydro-5H-benzo[c]carbazole).

[M+H]=298

Synthesis of Intermediate 1-B-2

Intermediate 1-B-1 previously obtained was completely used and the same method as in the synthesis method of Intermediate 1-A-3 using DDq (30 g, 133 mmol) was performed to obtain 25.5 g (1-B-1 and 1-B-2, total yield 64.6%) of Intermediate 1-B-2 (3-bromo-7H-benzo[c]carbazole).

Synthesis of Intermediate 1-C-1

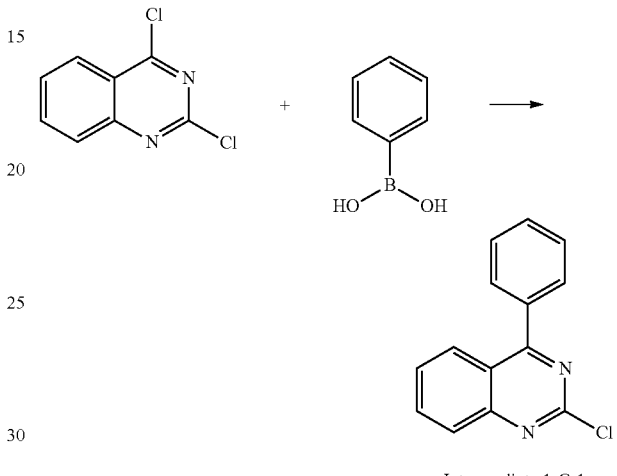

Intermediate 1-C-1

After 2,4-dichloroginazoline (CAS#607-68-1) (10 g, 50 mmol) and phenylboronic acid (PBA, CAS#98-80-6) (6.10 g, 50 mmol) were dissolved in 200 ml of toluene and 100 ml of ethanol, potassium carbonate (CAS#584-08-7) (41 g, 300 mmol) was dissolved in water, the resulting solution was put into the reaction solution, and the resulting mixture was stirred under heating for 30 minutes. After 30 minutes, tetrakis(triphenylphosphine) palladium (0) (CAS#14221-01-3) (1.7 g, 1.5 mmol) was added thereto, and the resulting mixture was additionally reacted for 2 hours. After the reaction was terminated, water in excess was added thereto, extraction was performed with ethyl acetate (hereinafter, referred to as EA) to obtain an organic layer, and then the organic layer was column purified to obtain 8.3 g (yield 68.7%) of Intermediate 1-C-1.

[M]=240

Synthesis of Intermediate 1-C-2

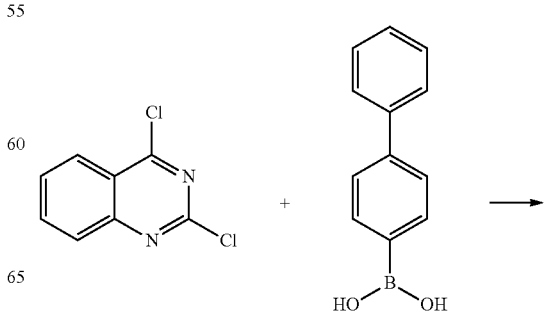

Synthesis of Intermediate 1-C-4

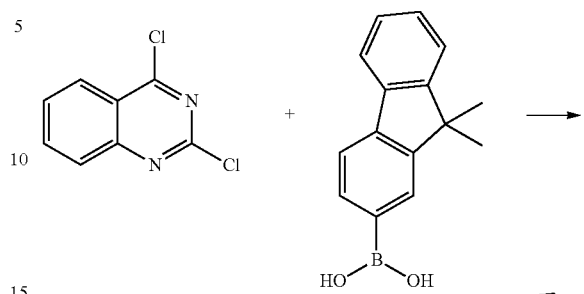

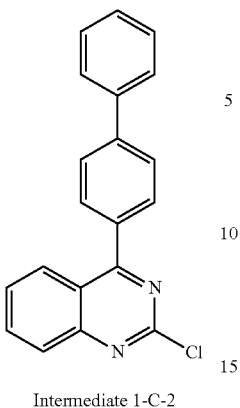

Intermediate 1-C-2

The same method as in the synthesis method of Intermediate 1-C-1 using 2,4-dichloroginazoline (CAS#607-68-1) (20 g, 100 mmol) and 4-biphenylboronic acid (PBA) (CAS#5122-94-1) (20 g, 100 mmol) was performed to obtain 23.3 g (yield 73.2%) of Intermediate 1-C-2.

[M]=317

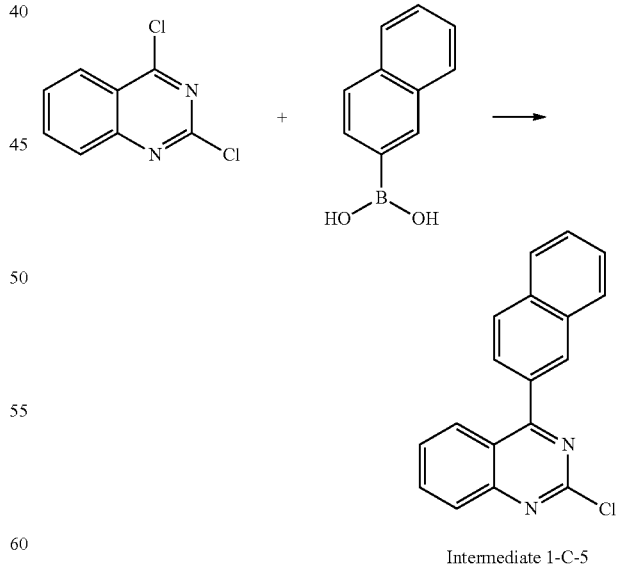

Intermediate 1-C-4

The same method as in the synthesis method of Intermediate 1-C-1 using 2,4-dichloroginazoline (CAS#607-68-1) (20 g, 100 mmol) and 9,9-dimethyl-9H-fluoren-2-yl boronic acid (CAS#333432-28-3) (23.8 g, 100 mmol) was performed to obtain 18.6 g (yield 52.1%) of Intermediate 1-C-4.

[M]=356

Synthesis of Intermediate 1-C-3

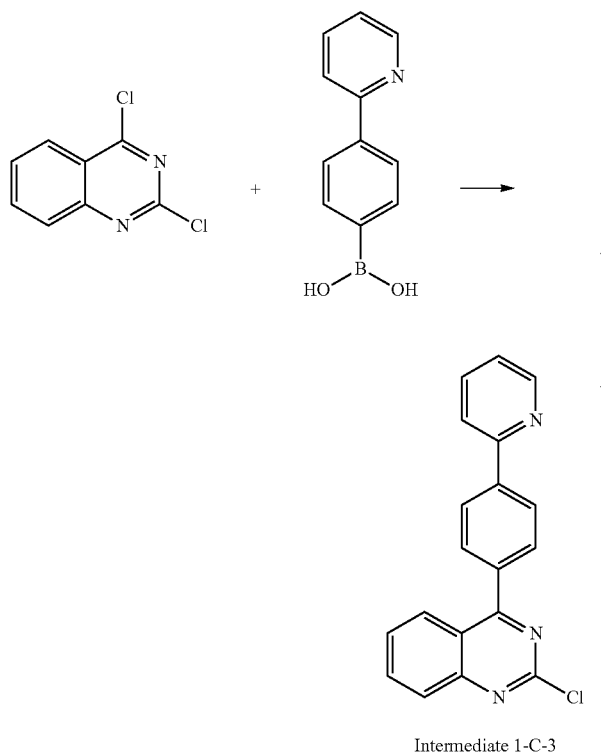

Intermediate 1-C-3

The same method as in the synthesis method of Intermediate 1-C-1 using 2,4-dichloroginazoline (CAS#607-68-1) (20 g, 100 mmol) and 4-(2-pyridyl)-phenylboronic acid (CAS#170230-27-0) (20 g, 100 mmol) was performed to obtain 23.8 g (yield 74.9%) of Intermediate 1-C-3.

[M]=317

Synthesis of Intermediate 1-C-5

Intermediate 1-C-5

The same method as in the synthesis method of Intermediate 1-C-1 using 2,4-dichloroginazoline (CAS#607-68-1) (20 g, 100 mmol) and 2-naphthyl boronic acid (CAS#32316-92-0) (18.1 g, 100 mmol) was performed to obtain 26.7 g (yield 91.3%) of Intermediate 1-C-5.

[M]=290

Synthesis of Intermediate 2-A-1

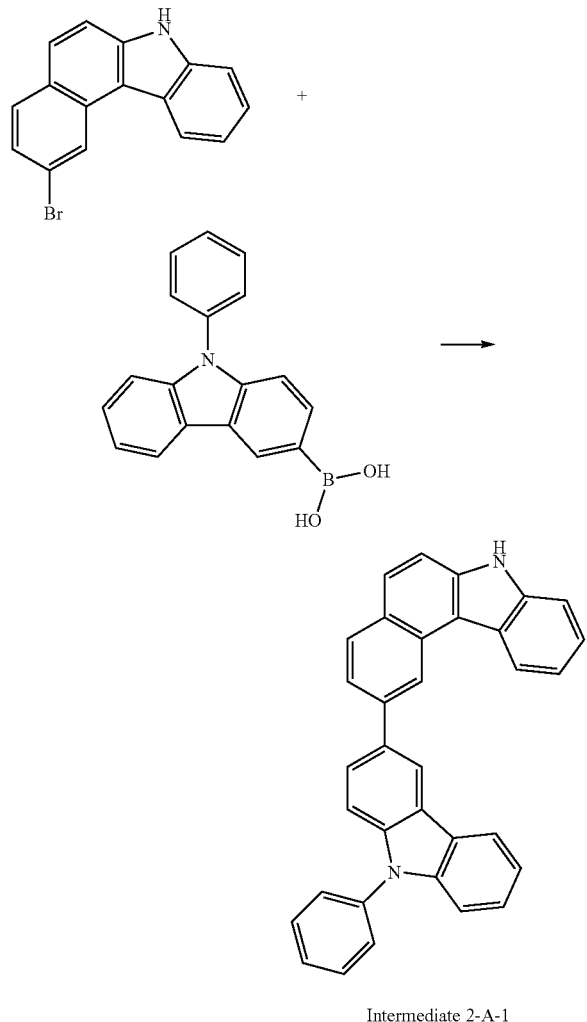

Intermediate 2-A-1

10 g (34 mmol) of Intermediate 1-A-3 and N-phenylcarbazole-3-boronic acid (10.7 g, 37 mmol) were used under the same conditions as in the synthesis method of Intermediate 1-C-1 to obtain 10.8 g (yield 69.8%) of Intermediate 2-A-1. FIG. 4 is a view illustrating MS data which are data confirming the synthesis of Intermediate 2-A-1.

[M+H]=458

Synthesis of Intermediate 2-A-2

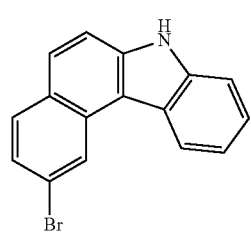

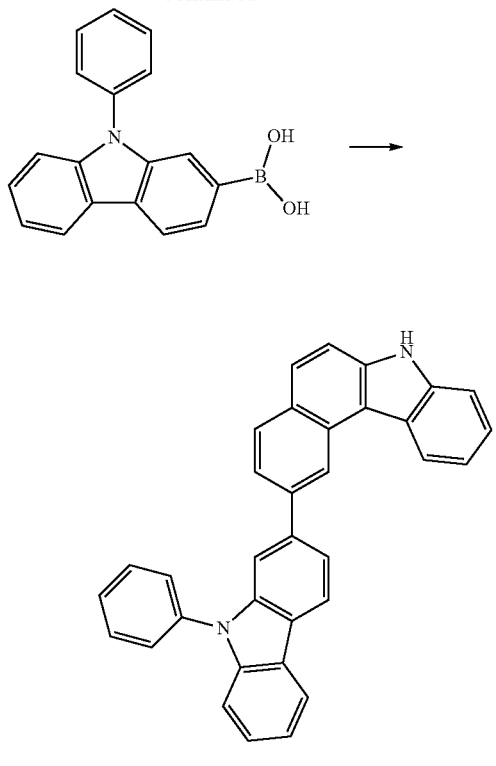

Intermediate 2-A-2

8 g (27 mmol) of Intermediate 1-A-3 and N-phenylcarbazole-2-boronic acid (8.1 g, 28.3 mmol) were used under the same conditions as in the synthesis method of Intermediate 1-C-1 to obtain 8.7 g (yield 70.1%) of Intermediate 2-A-2.

[M+H]=458

Synthesis of Intermediate 2-B-1

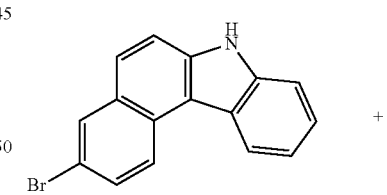

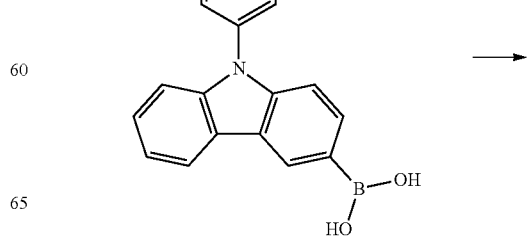

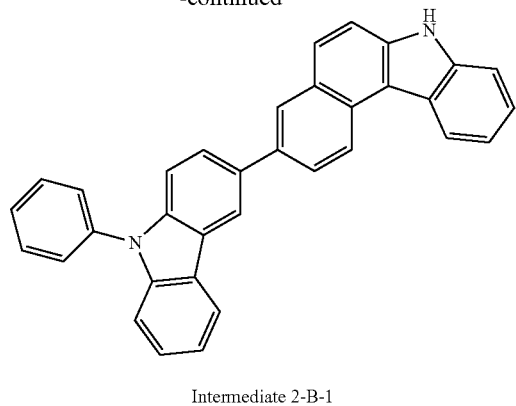

Intermediate 2-B-1

10 g (34 mmol) of Intermediate 1-B-2 and N-phenylcarbazole-3-boronic acid (10.2 g, 37 mmol) were used under the same conditions as in the synthesis method of Intermediate 1-C-1 to obtain 10.7 g (yield 69.0%) of Intermediate 2-B-1.

[M+H]=458

Synthesis of Intermediate 2-B-2

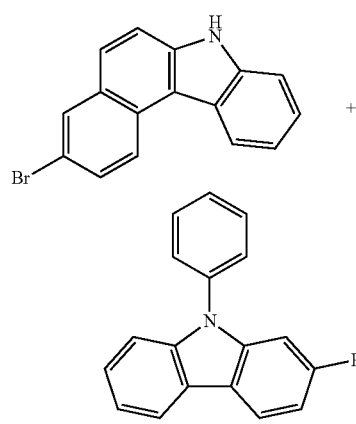

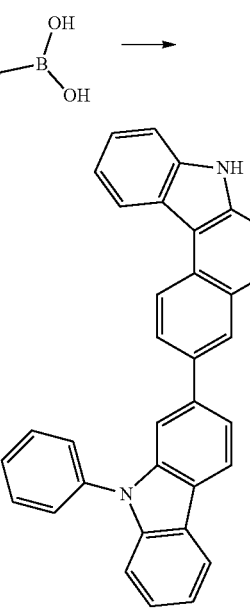

Intermediate 2-B-2

11 g (37 mmol) of Intermediate 1-B-2 and N-phenylcarbazole-2-boronic acid (11.2 g, 39 mmol) were used under the same conditions as in the synthesis method of Intermediate 1-C-1 to obtain 11.2 g (yield 65.7%) of Intermediate 2-B-2.

[M+H]=458

Synthesis of Intermediate 3-A-1

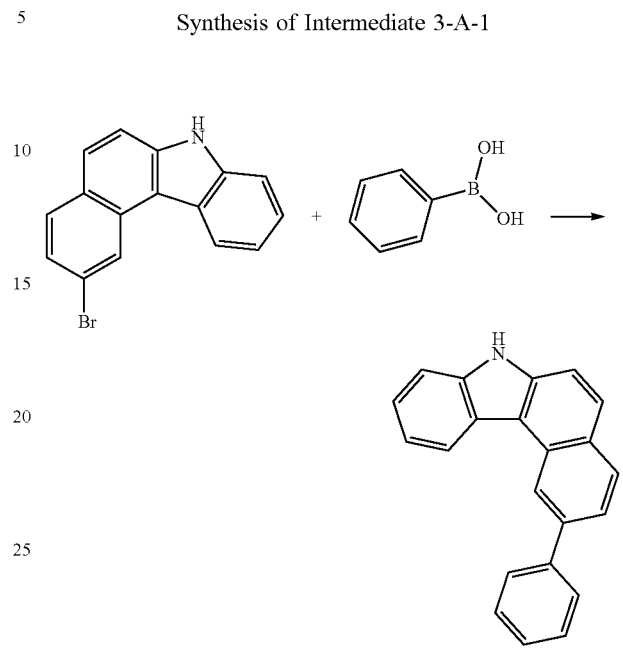

Intermediate 3-A-1

8 g (27 mmol) of Intermediate 1-A-3 and 3.5 g (28 mmol) of phenyl boronic acid were used in the same manner as in the synthesis method of Intermediate 1-C-1 to synthesize 7.3 g (yield 92.7%) of Intermediate 3-A-1.

[M+H]=293

Synthesis of Intermediate 3-B-1

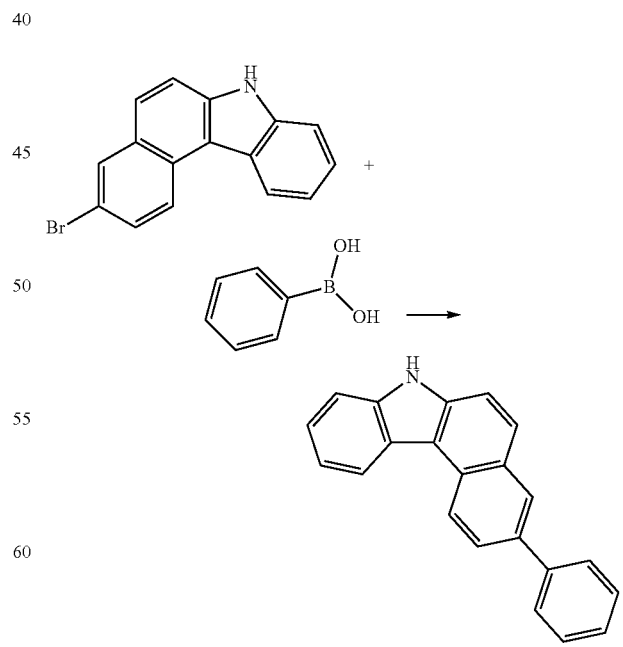

Intermediate 3-B-1

9 g (30 mmol) of Intermediate 1-B-2 and 3.9 g (32 mmol) of phenyl boronic acid were used in the same manner as in the synthesis method of Intermediate 1-C-1 to synthesize 8.3 g (yield 93.2%) of Intermediate 3-B-1.

[M+H]=293

Synthesis of Intermediate 3-A-2

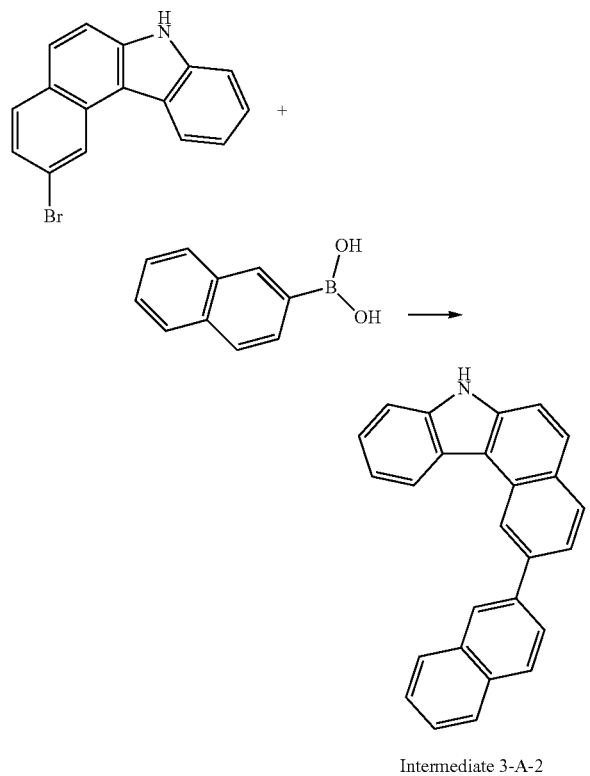

Intermediate 3-A-2

10 g (33 mmol) of Intermediate 1-A-3 and 6.1 g (35 mmol) of 2-naphthyl boronic acid were used in the same manner as in the synthesis method of Intermediate 1-C-1 to synthesize 10.68 g (yield 92.1%) of Intermediate 3-A-2.

[M+H]=343

Synthesis of Intermediate 3-B-2

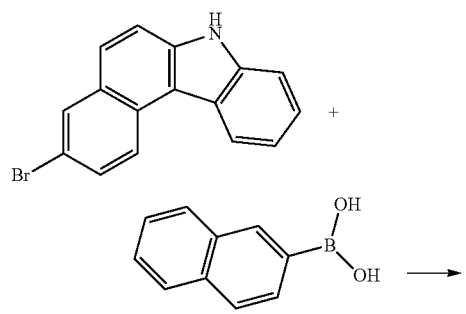

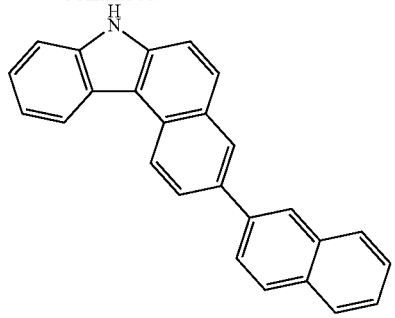

Intermediate 3-B-2

10 g (33 mmol) of Intermediate 1-B-2 and 6.1 g (35 mmol) of 2-naphthyl boronic acid were used in the same manner as in the synthesis method of Intermediate 1-C-1 to synthesize 10.68 g (yield 92.1%) of Intermediate 3-B-2.

[M+H]=343

PREPARATION EXAMPLES

Preparation Example 1

Synthesis of Compound 3

11 g (32 mmol) of Intermediate 3-A-2 synthesized above was added together with copper (Cu, CAS#7440-50-8 (4.15 g, 64 mmol) and potassium phosphate (hereinafter, referred to as K₃PO₄) (20.4 g, 96 mmol) to the solvent of iodobenzene (CAS#591-50-4), and the resulting mixture was stirred under heating (hereinafter, referred to as Ullmann conditions) overnight. After the reaction was terminated, the reaction solution was cooled to normal temperature, and then ethanol (EtOH) in excess was added thereto to precipitate a compound, extraction with CHCl₃ was performed, and then moisture was removed and recrystallization was performed using ethyl acetate (EA) to obtain 10.0 g (yield 74.5%) of Compound 3.

[M]=419

Preparation Example 2

Synthesis of Compound 19

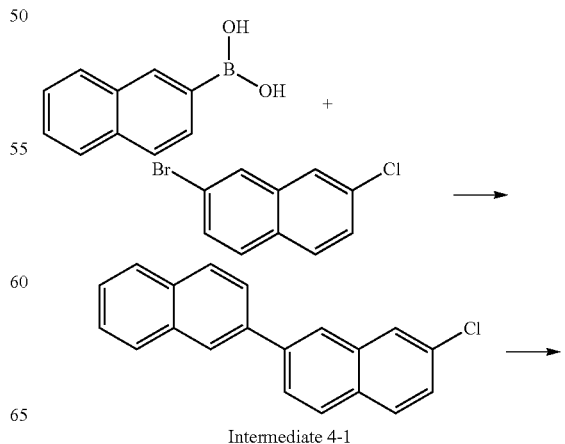

Intermediate 4-1

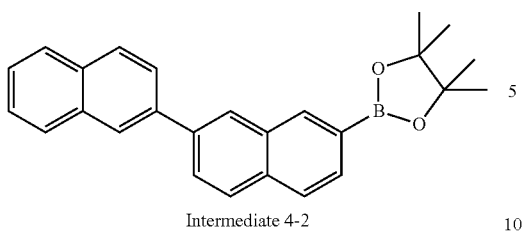

Intermediate 4-2

Synthesis of Intermediate 4-1

7.5 g (43.4 mmol) of 2-naphthylboronic acid and 2-bromo-7-chloronaphthalene (CAS#321939-67-7) (10 g, 41 mmol) were used in the same manner as in the synthesis method of Intermediate 1-C-1 to synthesize 10.6 g (yield 88.7%) of Intermediate 4-1.

[M]=288

Synthesis of Intermediate 4-2

Compound 4-1 (8.0 g, 27.7 mmol) obtained by the aforementioned method, bis(pinacolato)diboron (CAS#73183-34-3) (10.5 g, 41.6 mmol), and potassium acetate (CAS#127-08-2) (8.2 g, 83.1 mmol) were added to 100 ml of dioxane, and the resulting mixture was stirred under heating for 30 minutes. After 30 minutes, Pd(dppf)$_2$Cl$_2$ (dichloro[1,1'-bis(diphenylphosphino)ferrocene]palladium (II)-dichloromethane adduct, CAS#95464-05-4) (0.67 g, 0.83 mmol) was added to the reaction solution. After the resulting mixture was stirred under heating for 12 hours, the reaction solvent was concentrated by a pressure reducer, and then moisture was removed from an organic layer obtained by performing extraction with 160 ml of chloroform, the organic layer was allowed to pass through a silica pad, and then the solution was concentrated and hexane was used to obtain Intermediate 4-2 (9.4 g, 89%).

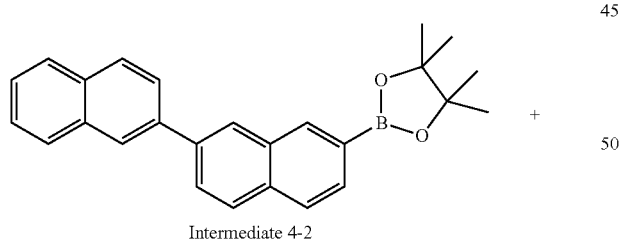

Intermediate 4-2

+

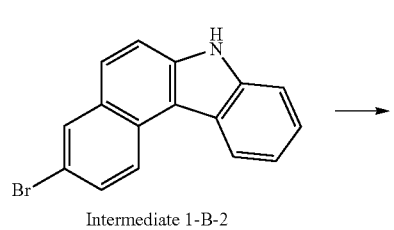

Intermediate 1-B-2

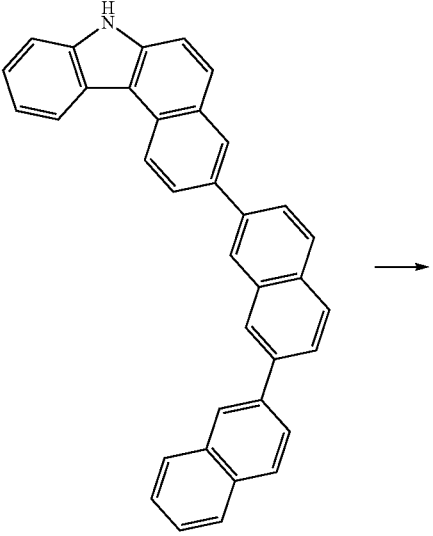

Intermediate 4-B-3

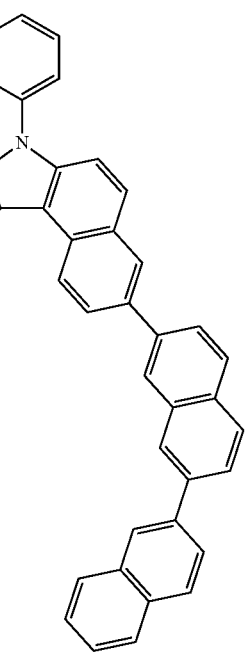

Intermediate 19

Synthesis of Intermediate 4-B-3

Intermediate 4-2 (35 mmol) and 10 g (34 mmol) of Intermediate 1-B-2 were used in the same manner as in the synthesis method of Intermediate 1-C-1 to synthesize 13.8 g (yield 87.4%) of Intermediate 4-B-3.

[M+H]=470

Synthesis of Compound 19

12 g (26 mmol) of Intermediate 4-B-3 synthesized and iodobenzene as a solvent were used to synthesize 11 g (yield 78.4%) of Compound 19 under the Ullmann conditions.

[M]=545

Preparation Example 3

Synthesis of Compound 82

7 g (20 mmol) of Intermediate 3-B-2 already synthesized and 4-iodobiphenyl (CAS#1591-31-7) (6.0 g, 21 mmol) were put into xylene, sodium t-butoxide (hereinafter, referred to as NaOtBu, CAS#865-48-5) (2.9 g, 30.5 mmol) were added thereto, and the resulting mixture was stirred under heating. After stirring for 30 minutes, bis(tri-tert-butylphosphine)palladium (0) (hereinafter, referred to as BTP) (0.02 g, 3.05 mmol) was added thereto, and the resulting mixture was additionally stirred under heating overnight. After the reaction was terminated (hereinafter, referred to as Buchwald conditions), the reaction product was cooled to normal temperature, EtOH in excess was added thereto, the precipitate was precipitated, and then put into N-methyl-2-pyrollidone (hereinafter, referred to as NMP, CAS#872-50-4), the resulting mixture was heated and refluxed for 2 hours, and the precipitate was produced again while being cooled to normal temperature. The precipitate produced was washed with ethanol (EtOH) to obtain 7.7 g (yield 75.8%) of Compound 82.

[M]=495

Preparation Example 4

Synthesis of Compound 114

8 g (23 mmol) of Intermediate 3-B-2 already synthesized was slowly added together with sodium hydride (hereinafter, referred to as NaH, CAS#7646-69-7) (1.2 g, 30 mmol) to anhydrous dimethylacetamide (hereinafter, referred to as DMF, CAS#68-12-2) under nitrogen flow. The resulting mixture was stirred at normal temperature for 1 hour, and then 2-chloro-4,6-diphenyl-1,3-pyrimidine (CAS#2915-16-4, 6.5 g, 24 mmol) was added thereto, and the resulting mixture was stirred at normal temperature overnight. After the reaction was terminated, the precipitate produced was filtered, and then washed with EtOH, and then extraction with EA was performed to obtain 11.0 g (yield 82.6%) of Compound 114.

[M]=573

Preparation Example 5

Synthesis of Compound 167

7 g (24 mmol) of Intermediate 3-A-1 already synthesized and 2-chloro-4,6-diphenyl-1,3,6-triazine (CAS#3842-55-5) (6.7 g, 25 mmol) were used in the same manner as in the synthesis method of Compound 114 to obtain 11.6 g (yield 92.6%) of Compound 167.

[M]=524

Preparation Example 6

Synthesis of Compound 200

10 g (29 mmol) of 3-B-2 already synthesized and 2-(4-chlorophenyl)-4,6-diphenyl-pyrimidine (CAS#152529-17-4) (10.5 g, 31 mmol) were used in the same manner as in the synthesis method of Compound 82 to obtain 17 g (yield 91.1%) of Compound 200.

[M]=649

Preparation Example 7

Synthesis of Compound 280

9.5 g (32 mmol) of 3-B-1 already synthesized and 2-(3-bromophenyl)-4,6-diphenyl-1,3,5-triazine (CAS#864377-31-1) (13.2 g, 34 mmol) were used in the same manner as in the synthesis method of Compound 82 to obtain 17 g (yield 88.4%) of Compound 280.

[M]=600

Preparation Example 8

Synthesis of Compound 315

8 g (27 mmol) of 3-A-1 already synthesized and 6.9 g (29 mmol) of Intermediate 1-C-1 were used in the same manner as in the synthesis method of Compound 114 to obtain 12.5 g (yield 91.8%) of Compound 315.

[M]=497

Preparation Example 9

Synthesis of Compound 327

15.4 g (3.5 mmol) of Intermediate 2-A-1 already synthesized and 8.5 g (33.8 mmol) of Intermediate 1-C-1 already synthesized were used in the same manner as in Compound 114 to obtain 14 g (yield 62.9%) of Compound 327. FIG. 5 is a view illustrating MS data which are data confirming the synthesis of Compound 327.

[M+H]=663

Preparation Example 10

Synthesis of Compound 328

13 g (28 mmol) of Intermediate 2-A-2 already synthesized and 8.7 g (30 mmol) of Intermediate 1-C-5 already synthesized were used in the same manner as in Compound 114 to obtain 17.7 g (yield 87.5%) of Compound 328.

[M+H]=713

Preparation Example 11

Synthesis of Compound 339

11 g (23 mmol) of Intermediate 2-B-1 already synthesized and 5.9 g (24 mmol) of Intermediate 1-C-1 already synthesized were used in the same manner as in Compound 114 to obtain 12 g (yield 78.3%) of Compound 339.

[M+H]=663

Preparation Example 12

Synthesis of Compound 346

7 g (15 mmol) of Intermediate 2-B-2 already synthesized and 4.7 g (16 mmol) of Intermediate 1-C-5 already synthesized were used in the same manner as in Compound 114 to obtain 8.7 g (yield 79.8%) of Compound 346.

[M+H]=713

Preparation Example 13

Synthesis of Compound 370

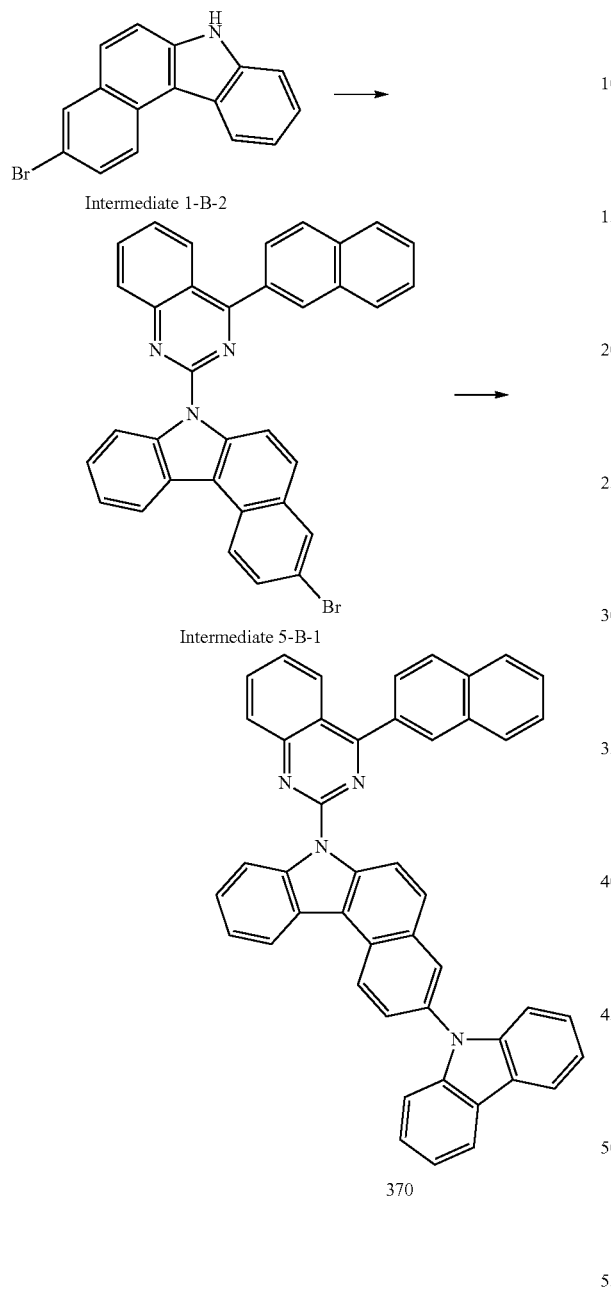

Synthesis of Intermediate 5-B-1

7 g (17 mmol) of Intermediate 1-B-2 already synthesized and 5.1 g (18 mmol) of Intermediate 1-C-5 already synthesized were used in the same manner as in Compound 114 to obtain 12.2 g (yield 93.5%) of Intermediate 5-B-1.

[M]=550

Synthesis of Compound 370

10 g (19 mmol) of Intermediate 5-B-1 already synthesized, 9H-carbazole (CAS#86-74-8) (3.3 g, 20 mmol), and 11.6 g (55 mmol) of $K_3PO_4$ were put into 70 ml of xylene, and the resulting mixture was heated and refluxed under nitrogen flow for 1 hour. After 1 hour, bis(dibenzylideneacetone)palladium(o) (hereinafter, referred to as d(ba)2, CAS#32005-36-0) (0.31 g, 0.5 mmol) and 4,5-bis(diphenylphosphino)-9,9-dimethylxanthene (hereinafter, referred to as Xanphos, CAS#161265-03-8) (0.31 g, 0.5 mmol) were simultaneously put into the reaction solution, and the resulting mixture was heated and refluxed overnight. After the reaction was terminated, the product was cooled to normal temperature, ethanol (EtOH) in excess was added thereto, and the precipitate was produced and filtered. The filtered precipitate was stirred with water in excess and tetrahydrofuran (THF), and then recrystallized with ethyl acetate (EA) to obtain 7.9 g (yield 68.4%) of Compound 370.

[M]=636

Preparation Example 14

Synthesis of Compound 376

8 g (15 mmol) of Intermediate 5-B-1 already synthesized and 7H-benzo[c]carbazole (CAS#205-25-4) (3.8 g, 17 mmol) were used in the same manner as in the synthesis method of Compound 370 to obtain 6.2 g (yield 62.4%) of Compound 376.

[M]=686

Preparation Example 15

Synthesis of Compound 393

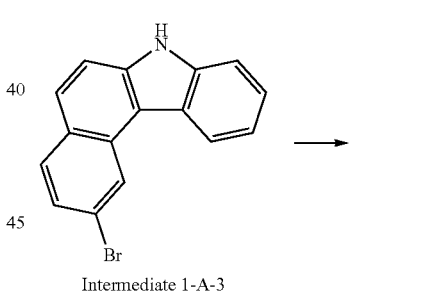

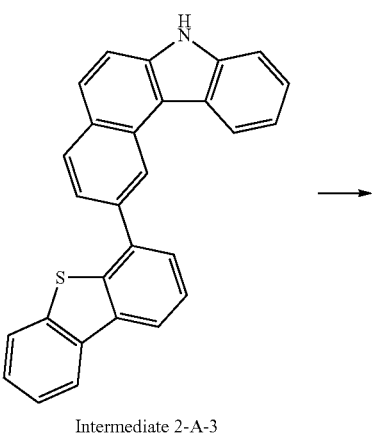

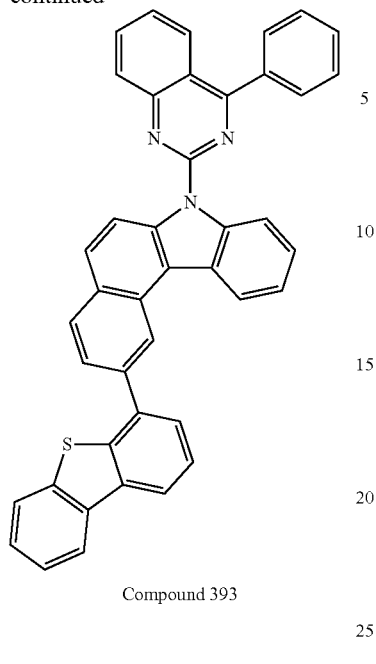

Compound 393

Synthesis of Intermediate 2-A-3

10 g (33 mmol) of Intermediate 1-A-3 already synthesized and 4-dibenzothiophenylboronic acid (CAS#108847-20-7) (8.5 g, 37 mmol) were used in the same manner as in the synthesis method of Intermediate 1-C-1 to obtain 11.9 g (yield 88.4%) of Intermediate 2-A-3.

[M+H]=400

Synthesis of Compound 393

10 g (25 mmol) of Intermediate 2-A-3 already synthesized and 6.6 g (28 mmol) of Intermediate 1-C-1 already synthesized were used in the same manner as in Compound 114 to obtain 11.2 g (yield 74.4%) of Compound 393.

[M]=603

Preparation Example 16

Synthesis of Compound 411

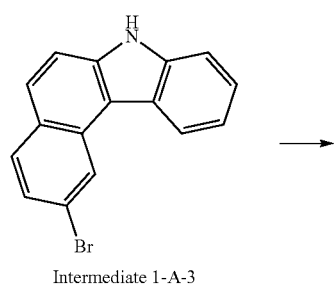

Intermediate 1-A-3

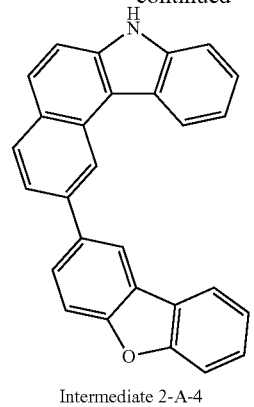

Intermediate 2-A-4

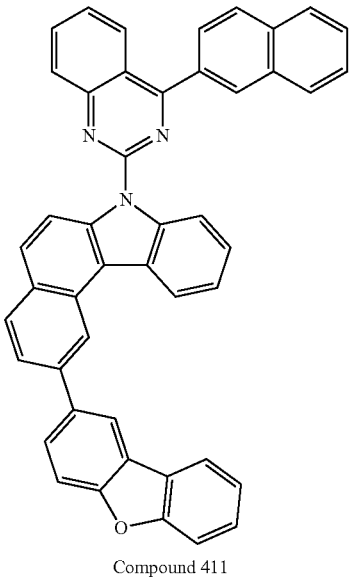

Compound 411

Synthesis of Intermediate 2-A-4

15 g (51 mmol) of Intermediate 1-A-3 already synthesized and dibenzofuran-2-ylboronic acid (CAS#402936-15-6) (11.8 g, 56 mmol) were used in the same manner as in the synthesis method of Intermediate 1-C-1 to obtain 15.4 g (yield 81.1%) of Intermediate 2-A-4.

[M+H]=384

Synthesis of Compound 411

10 g (26 mmol) of Intermediate 2-A-4 already synthesized and 8.3 g (29 mmol) of Intermediate 1-C-5 already synthesized were used in the same manner as in Compound 114 to obtain 12 g (yield 72.4%) of Compound 411.

[M]=637

Preparation Example 17

Synthesis of Compound 436

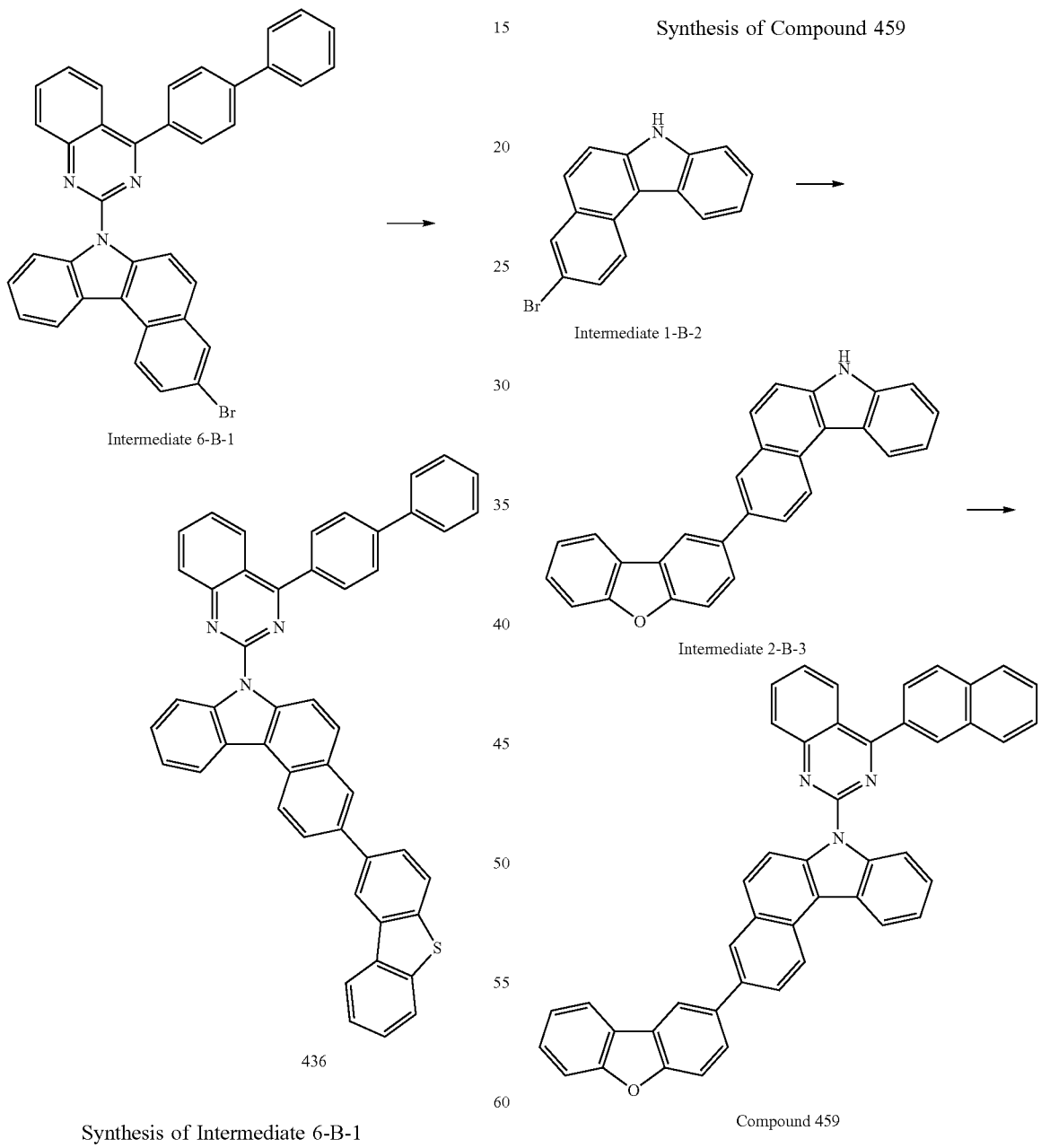

Intermediate 1-B-2

Intermediate 6-B-1

436

Synthesis of Intermediate 6-B-1

10 g (34 mmol) of Intermediate 1-B-2 already synthesized and 11.2 g (35 mmol) of Intermediate 1-C-2 already synthesized were used in the same manner as in Compound 114 to obtain 15.8 g (yield 81.2%) of Intermediate 6-B-1.
[M]=576

Synthesis of Compound 436

7.0 g (12 mmol) of Intermediate 6-B-1 already synthesized and 2-dibenzothiophenylboronic acid (CAS#668983-97-9) (2.9 g, 13 mmol) were used in the same mannera as in the synthesis method of Intermediate 1-C-1 to obtain 5.0 g (yield 60.6%) of compound 436. FIG. 6 is a view illustrating MS data which are data confirming the synthesis of Compound 436.

[M]=679

Preparation Example 18

Synthesis of Compound 459

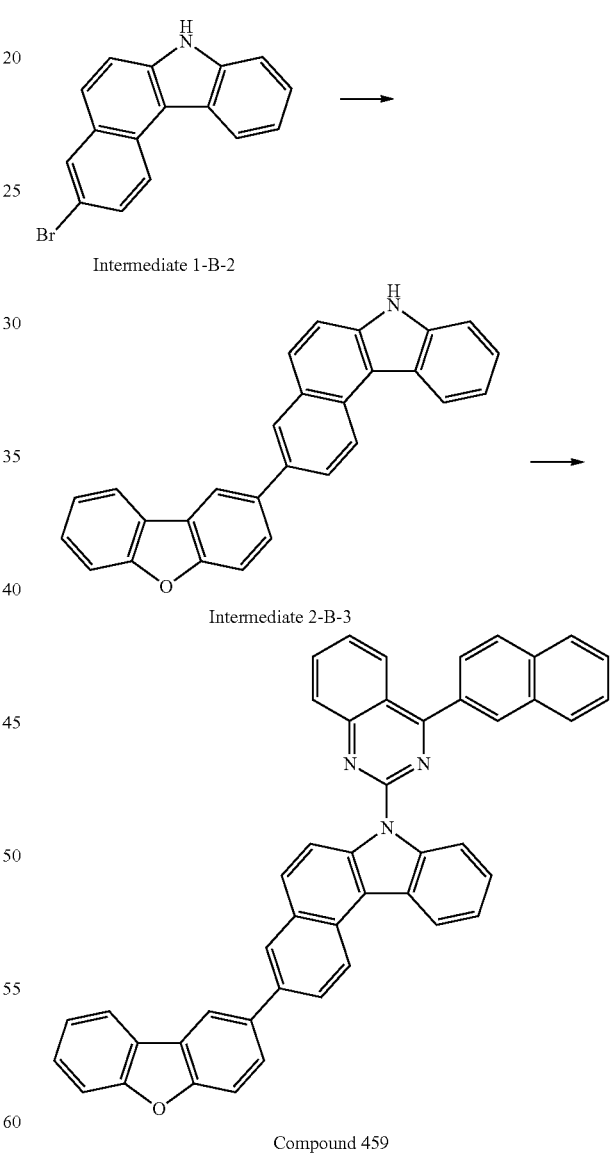

Intermediate 1-B-2

Intermediate 2-B-3

Compound 459

Compound 459 was synthesized by using Intermediate 1-B-2 instead of Intermediate 1-A-3 in Compound 411 already synthesized.

[M]=637

Preparation Example 19

Synthesis of Compound 466

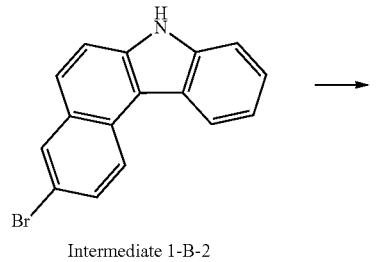

Intermediate 1-B-2

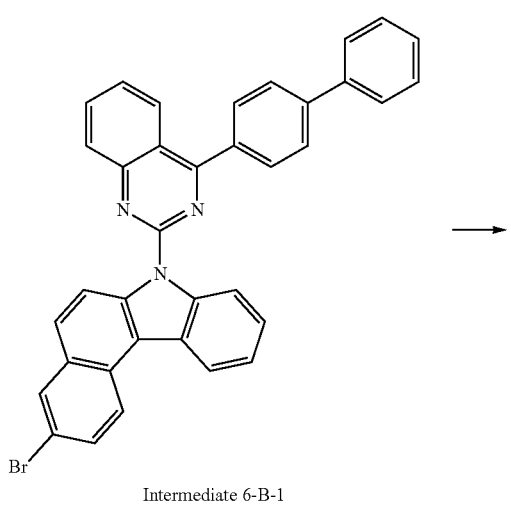

Intermediate 6-B-1

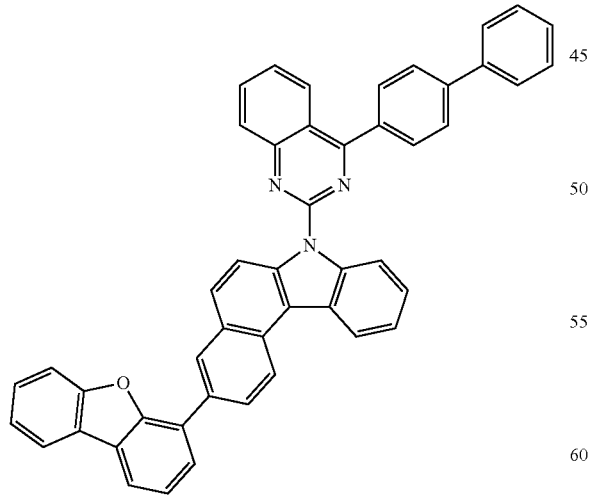

Compound 466

Compound 466 was synthesized by using dibenzofuran-4-ylboronic acid instead of 2-dibenzothiophenylboronic acid in Compound 436 already synthesized.

Preparation Example 20

Synthesis of Compound 505

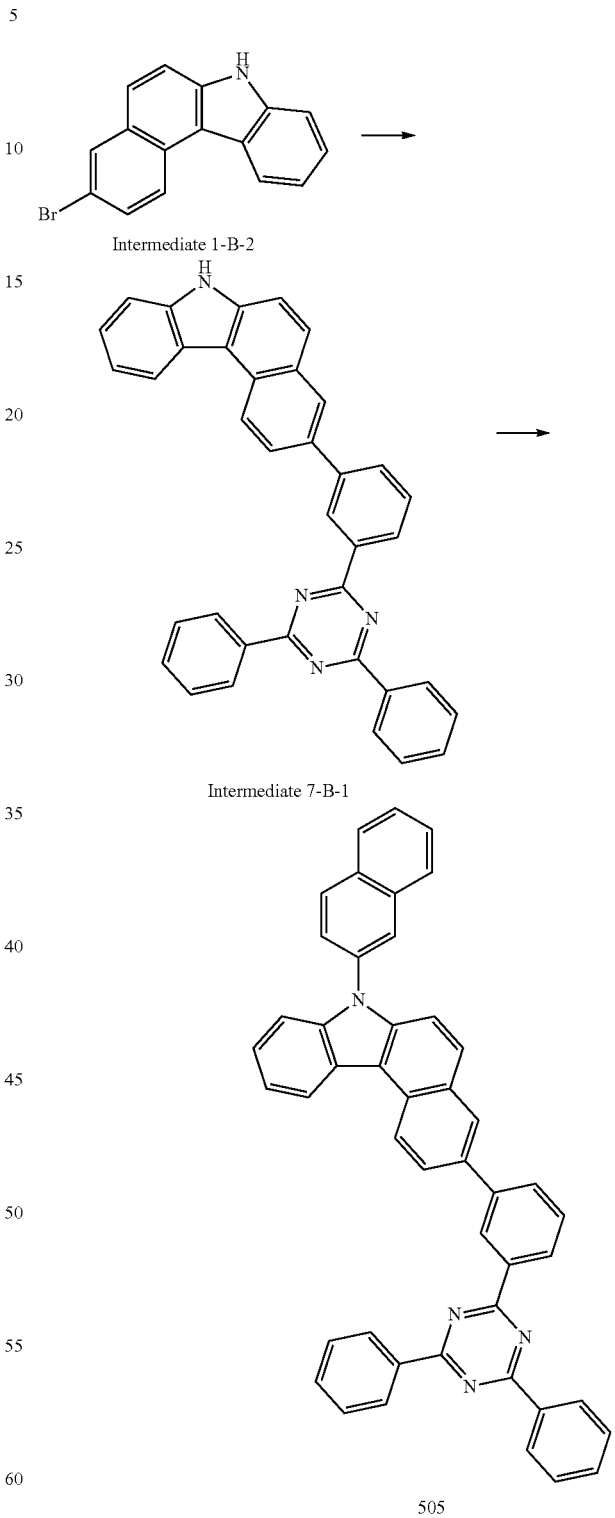

Synthesis of Intermediate 7-B-1

8 g (27 mmol) of Intermediate 1-B-2 already synthesized and 2,4-diphenyl-6-[3-(4,4,5,5-tetramethyl-1,3,2-dioxaborolan-2-yl)phenyl]-1,3,5-triazine (CAS#1269508-31-7) (12.3 g, 28 mmol) were used in the same manner as in the synthesis method of Compound 1-C-1 to obtain 10 g (yield 71.4%) of Intermediate 7-B-1.

[M+H]=525

Synthesis of Compound 505

8 g (15 mmol) of Intermediate 7-B-1 synthesized and 2-bromonaphthalene (CAS#580-13-2) (3.8 g, 18 mmol) were used in the same manner as in the synthesis method of Compound 82 to obtain 7.7 g (yield 77.9%) of Compound 505.

[M]=650

Preparation Example 21

Synthesis of Compound 518

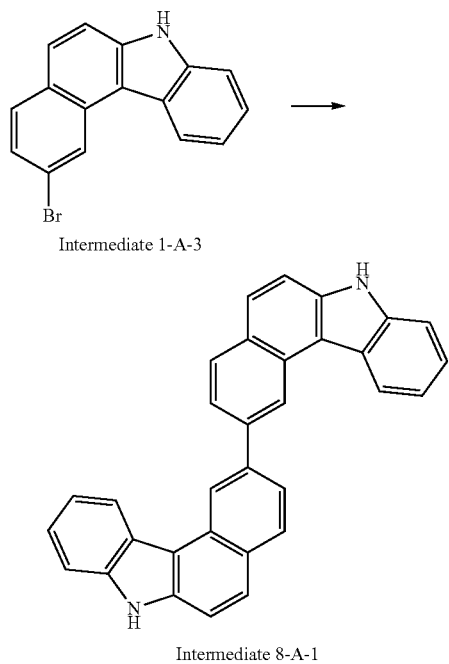

Intermediate 1-A-3

Intermediate 8-A-1

Compound 518

Synthesis of Intermediate 8-A-1

20 g (67 mmol) of Intermediate 1-A-3 was put into 300 ml of dioxane, 42 g (202 mmol) of $K_3PO_4$ was changed from KOAc as the base in the synthesis method of Intermediate 4-2, and the same procedure was performed to obtain 9.6 g (yield 65.9%) of Intermediate 8-A-1.

[M]=432

Synthesis of Compound 518

7 g (16 mmol) of Intermediate 8-A-1 synthesized was used in the same manner as in the synthesis method of Intermediate 3-A-2 to obtain 5.6 g (yield 58.9%) of Compound 518.

[M]=584

Preparation Example 22

Synthesis of Compound 554

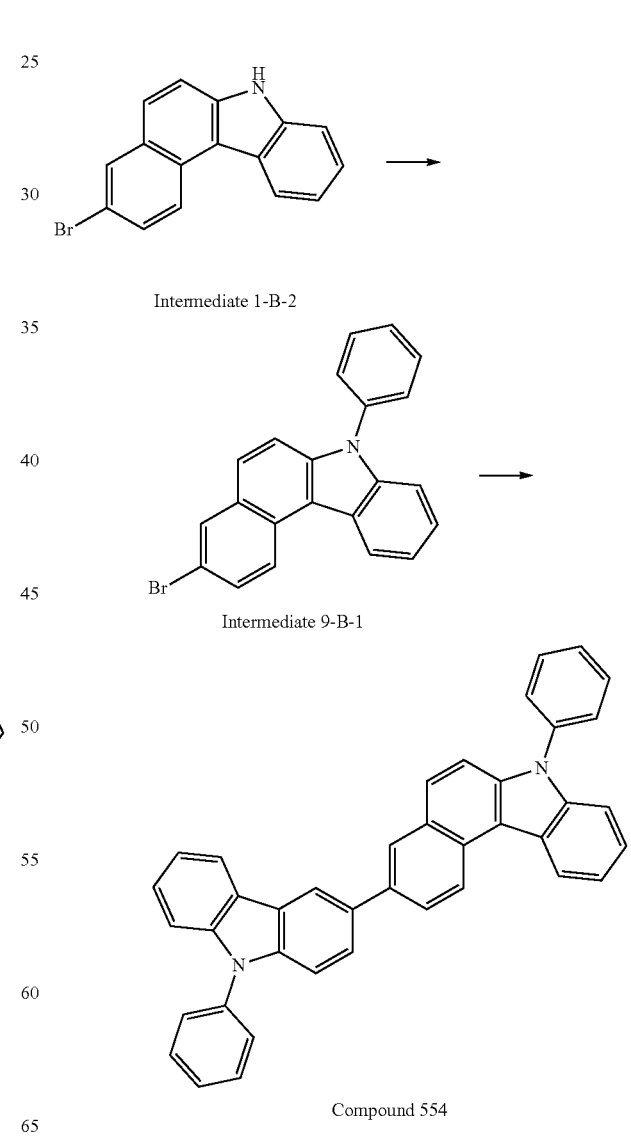

Intermediate 1-B-2

Intermediate 9-B-1

Compound 554

Synthesis of Intermediate 9-B-1

11 g (37 mmol) of Intermediate 1-B-2 was used in the same manner as in the synthesis method of Intermediate 3-A-2 to obtain 10.1 g (yield 73.4%) of Intermediate 9-B-1.

[M+H]=372

Synthesis of Compound 554

9 g (24 mmol) of Intermediate 9-B-1 and (N-phenyl-9H-carbazol-3-yl) boronic acid (CAS#854952-58-2)(8.4 g, 29 mmol) were used in the same manner as in the synthesis method of Intermediate 1-C-2 to obtain 11 g (yield 85.2%) of Compound 554.

[M]=533

Comparative Example 1

A glass substrate (Corning 7059 glass) thinly coated with indium tin oxide (ITO) to have a thickness of 1,000 Å was put into distilled water in which a dispersant was dissolved, and ultrasonically washed. A product manufactured by Fischer Co., was used as the detergent, and distilled water twice filtered using a filter manufactured by Millipore Co., was used as the distilled water. After the ITO was washed for 30 minutes, ultrasonic washing was conducted repeatedly twice using distilled water for 10 minutes. After the washing using distilled water was completed, ultrasonic washing was conducted using isopropyl alcohol, acetone, and methanol solvents in this order, and drying was then conducted. Hexanitrile hexaazatriphenylene (HAT-CN) was vacuum deposited to have a thickness of 500 Å by heating on a transparent ITO electrode, which was thus prepared, thereby forming a hole injection layer. HT1 (400 Å) which transports holes was vacuum deposited thereon, and then the host H1 and the dopant Dp-6 compound were vacuum deposited as a light emitting layer to have a thickness of 300 Å. And then, the E1 compound (300 Å) was vacuum deposited by heating sequentially as an electron injection layer and an electron transporting layer. A negative electrode was formed by sequentially depositing lithium fluoride (LiF) and aluminum to have a thickness of 12 Å and 2,000 Å, respectively, on the electron transporting layer, thereby manufacturing an organic light emitting device. In the aforementioned procedure, the deposition rates of the organic material, LiF, and aluminum were maintained at 1 Å/sec, 0.2 Å/sec, and 3 to 7 Å/sec, respectively.

[HAT-CN]

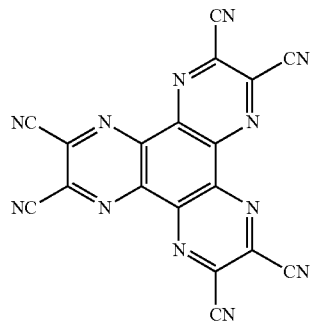

[HT1]

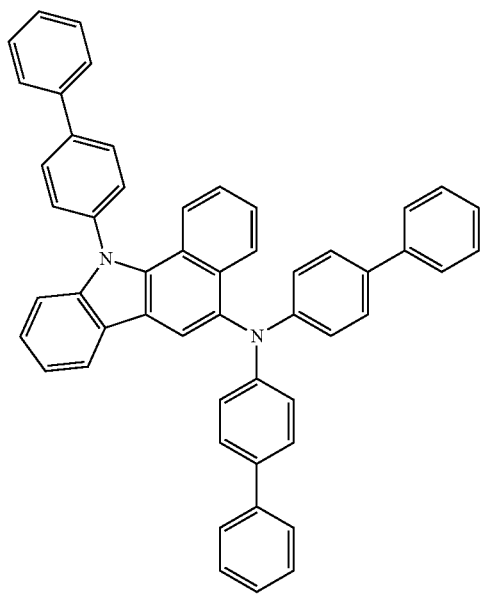

[NPB]

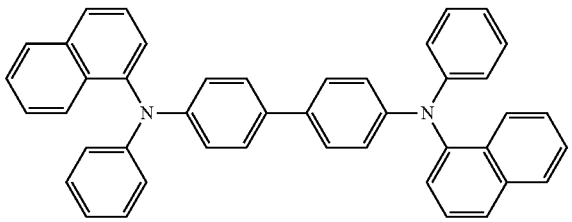

[H1]

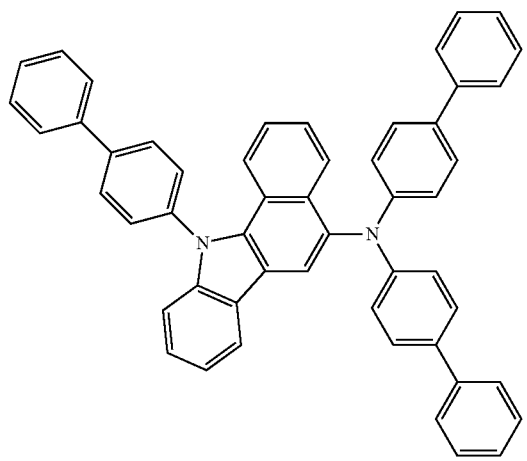

[H2]

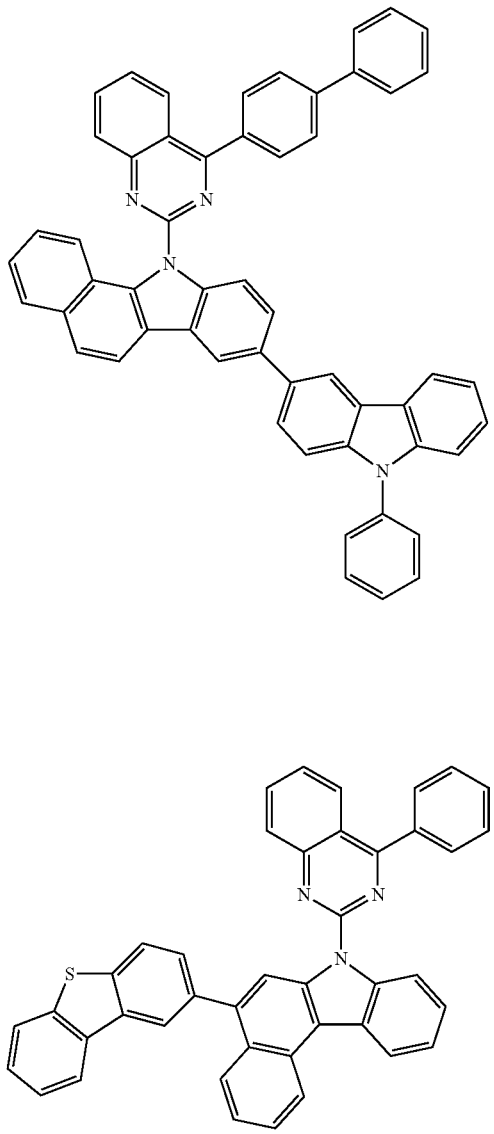

[H3]

[H4]

[H5]

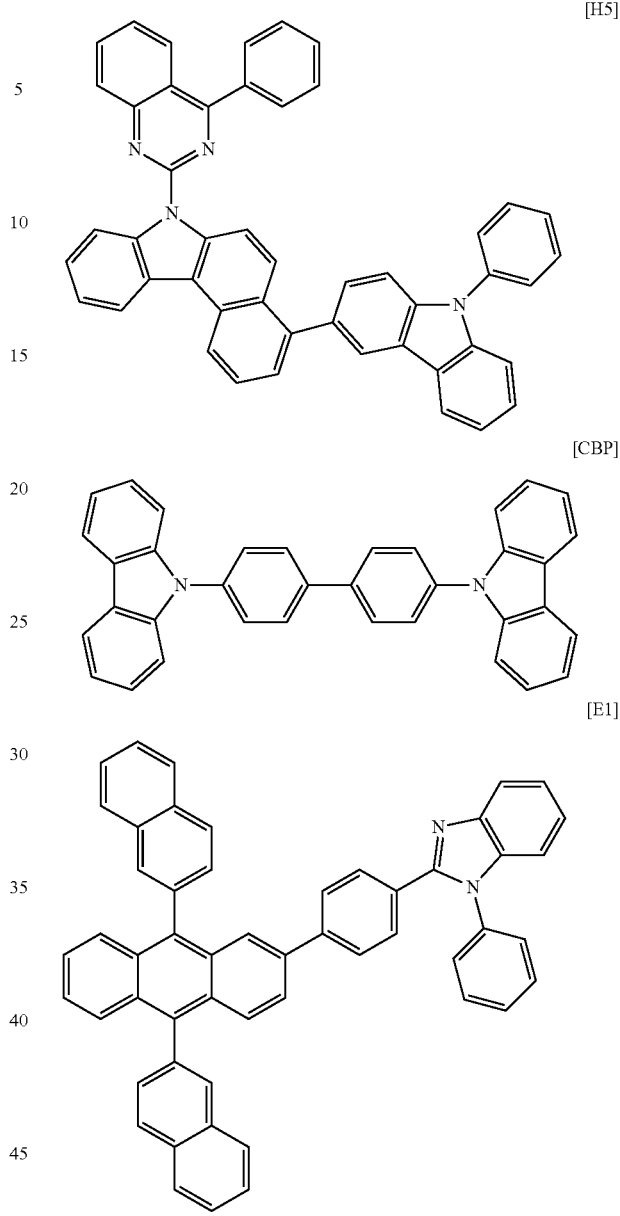

[CBP]

[E1]

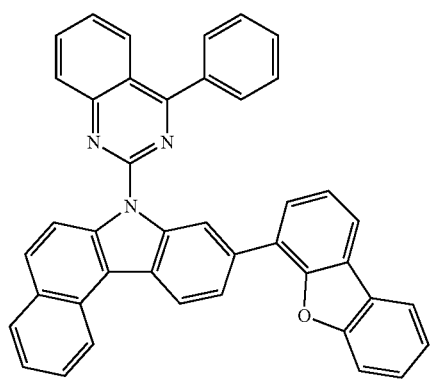

Comparative Example 2

An organic light emitting device was manufactured in the same manner as in Comparative Example 1, except that [H2] was used instead of [H1] in Comparative Example 1.

Comparative Example 3

An organic light emitting device was manufactured in the same manner as in Comparative Example 1, except that [H3] was used instead of [H1] in Comparative Example 1.

Comparative Example 4

An organic light emitting device was manufactured in the same manner as in Comparative Example 1, except that [H4] was used instead of [H1] in Comparative Example 1.

Comparative Example 5

An organic light emitting device was manufactured in the same manner as in Comparative Example 1, except that [H5] was used instead of [H1] in Comparative Example 1.

Example 1

An organic light emitting device was manufactured in the same manner as in Comparative Example 1, except that [Compound 315] was used instead of [H1] in Comparative Example 1.

Example 2

An organic light emitting device was manufactured in the same manner as in Comparative Example 1, except that [Compound 327] was used instead of [H1] in Comparative Example 1.

Example 3

An organic light emitting device was manufactured in the same manner as in Comparative Example 1, except that [Compound 339] was used instead of [H1] in Comparative Example 1.

Example 4

An organic light emitting device was manufactured in the same manner as in Comparative Example 1, except that [Compound 346] was used instead of [H1] in Comparative Example 1.

Example 5

An organic light emitting device was manufactured in the same manner as in Comparative Example 1, except that [Compound 370] was used instead of [H1] in Comparative Example 1.

Example 6

An organic light emitting device was manufactured in the same manner as in Comparative Example 1, except that [Compound 376] was used instead of [H1] in Comparative Example 1.

Example 7

An organic light emitting device was manufactured in the same manner as in Comparative Example 1, except that [Compound 393] was used instead of [H1] in Comparative Example 1.

Example 8

An organic light emitting device was manufactured in the same manner as in Comparative Example 1, except that [Compound 411] was used instead of [H1] in Comparative Example 1.

Example 9

An organic light emitting device was manufactured in the same manner as in Comparative Example 1, except that [Compound 436] was used instead of [H1] in Comparative Example 1.

Example 10

An organic light emitting device was manufactured in the same manner as in Comparative Example 1, except that [Compound 459] was used instead of [H1] in Comparative Example 1.

Example 11

An organic light emitting device was manufactured in the same manner as in Comparative Example 1, except that [Compound 466] was used instead of [H1] in Comparative Example 1.

When current was applied to the organic light emitting devices manufactured in Comparative Examples 1 to 4 and Examples 1 to 11, the results of Table 1 were obtained.

TABLE 1

|  | Compound | Driving voltage (V) | Current efficiency (cd/A) | Power efficiency (lm/w) | Service life (T95@ 10 mA) | x-coordinate | y-coordinate |
|---|---|---|---|---|---|---|---|
| Comparative Example | H1 | 4.71 | 23.76 | 16.32 | 73 | 0.666 | 0.332 |
|  | H2 | 5.32 | 22.21 | 13.50 | 93 | 0.661 | 0.331 |
|  | H3 | 4.88 | 21.23 | 11.32 | 97 | 0.660 | 0.331 |
|  | H4 | 5.01 | 23.02 | 12.45 | 100 | 0.661 | 0.330 |
|  | H5 | 4.85 | 20.04 | 10.88 | 88 | 0.661 | 0.332 |
| Example | 315 | 5.10 | 23.10 | 13.21 | 102 | 0.658 | 0.337 |
|  | 327 | 5.18 | 23.37 | 13.24 | 183 | 0.660 | 0.338 |
|  | 339 | 4.83 | 22.95 | 12.99 | 179 | 0.655 | 0.344 |
|  | 346 | 4.81 | 23.04 | 13.77 | 225 | 0.663 | 0.335 |
|  | 370 | 4.78 | 23.65 | 13.90 | 145 | 0.661 | 0.333 |
|  | 376 | 4.82 | 23.59 | 13.85 | 164 | 0.662 | 0.334 |
|  | 393 | 4.85 | 22.87 | 12.87 | 165 | 0.662 | 0.331 |
|  | 411 | 4.83 | 23.24 | 13.47 | 172 | 0.661 | 0.334 |
|  | 436 | 4.77 | 22.91 | 12.75 | 168 | 0.662 | 0.332 |
|  | 459 | 4.88 | 23.47 | 13.79 | 173 | 0.661 | 0.331 |
|  | 466 | 4.86 | 23.13 | 13.22 | 180 | 0.662 | 0.332 |

EXPLANATION OF REFERENCE NUMERALS AND SYMBOLS

1: Substrate
2: Positive electrode
3: Light emitting layer
4: Negative electrode
5: Hole injection layer
6: Hole transporting layer
7: Light emitting layer
8: Electron transporting layer

The invention claimed is:

1. A multicyclic compound including nitrogen represented by following Formula 1:

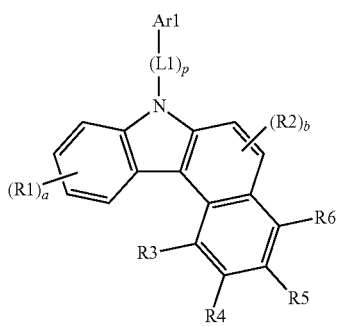

[Formula 1]

wherein in Formula 1:
at least one of R4 and R5 is -(L2)$_q$-Ar2,
L1 and L2 are the same as or different from each other, and are each independently a direct bond; a substituted or unsubstituted alkylene; a substituted or unsubstituted arylene; or a substituted or unsubstituted heteroarylene,
Ar1 and Ar2 are the same as or different from each other, and are each independently a nitrile group; a substituted or unsubstituted aryl group; or a substituted or unsubstituted heterocyclic group,
R1 to R6 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or combine with an adjacent group to form a ring, with the proviso that none of R3 to R6 is anthracene,
a is an integer of 0,
b is an integer of 0,
p and q are the same as or different from each other, and are each independently an integer of 0 to 5, and
when p, and q are each 2 or more, the structures in the parenthesis are the same as or different from each other.

2. The compound of claim 1, wherein Formula 1 is represented by following Formula 2 or 3:

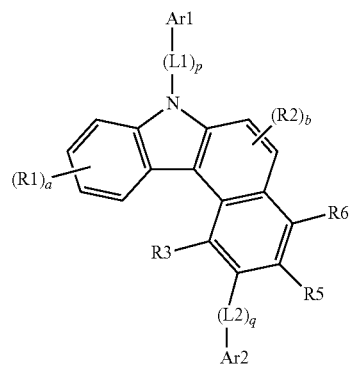

[Formula 2]

[Formula 3]

wherein in Formulae 2 and 3:
the definitions of Ar1, Ar2, R1 to R6, L1, L2, a, b, p, and q are the same as those in Formula 1.

3. The compound of claim 1, wherein Ar2 is any one selected from the following structural formulae:

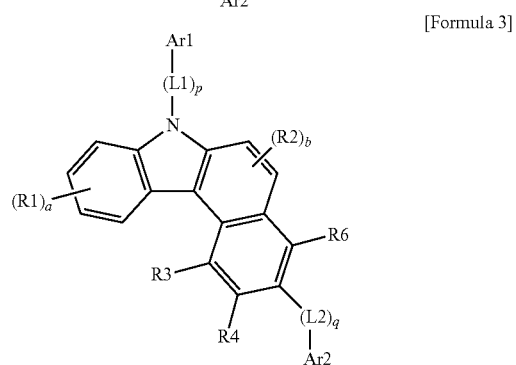

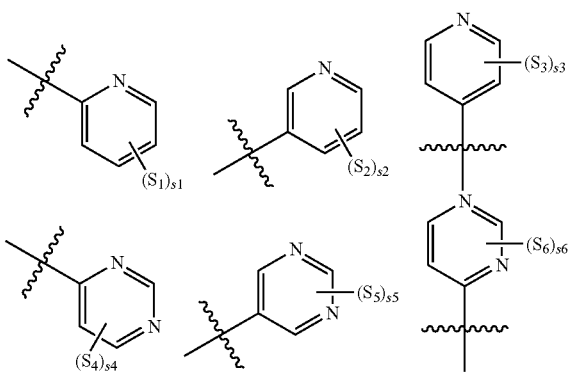

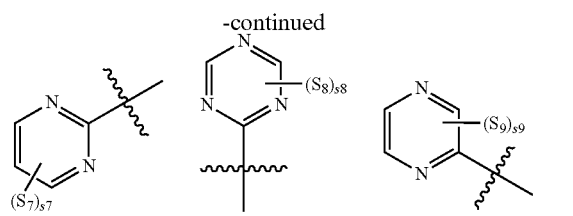

wherein in the structural formulae:

$S_1$ to $S_9$ are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group, or optionally combine with an adjacent group to form a ring, s1, s2, and s3 are the same as or different from each other, and are each independently an integer of 0 to 4, s4, s5, s6, s7, and s9 are the same as or different from each other, and are each independently an integer of 0 to 3, s8 is an integer of 0 to 2, and when s1 is 2 or more, $S_1$'s are the same as or different from each other, when s2 is 2 or more, $S_2$'s are the same as or different from each other, when s3 is 2 or more, $S_3$'s are the same as or different from each other, when s4 is 2 or more, $S_4$'s are the same as or different from each other, when s5 is 2 or more, $S_5$'s are the same as or different from each other, when s6 is 2 or more, $S_6$'s are the same as or different from each other, when s7 is 2 or more, $S_7$'s are the same as or different from each other, when s8 is 2, $S_8$'s are the same as or different from each other, and when s9 is 2 or more, $S_9$'s are the same as or different from each other.

4. The compound of claim 1, wherein Ar2 is any one selected from the following structural formulae:

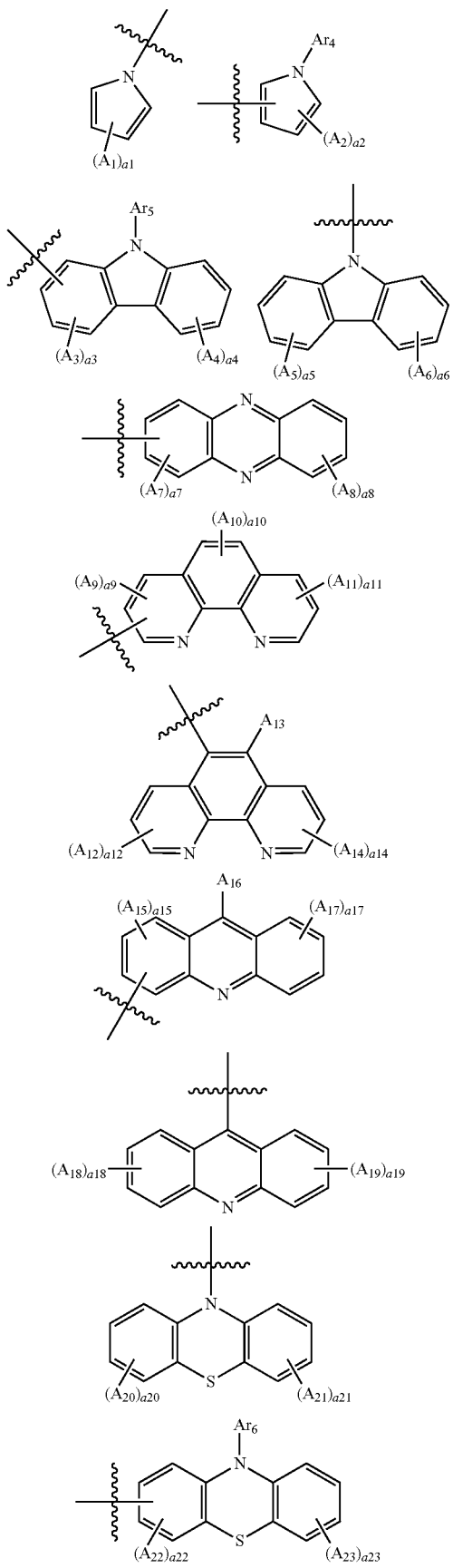

-continued

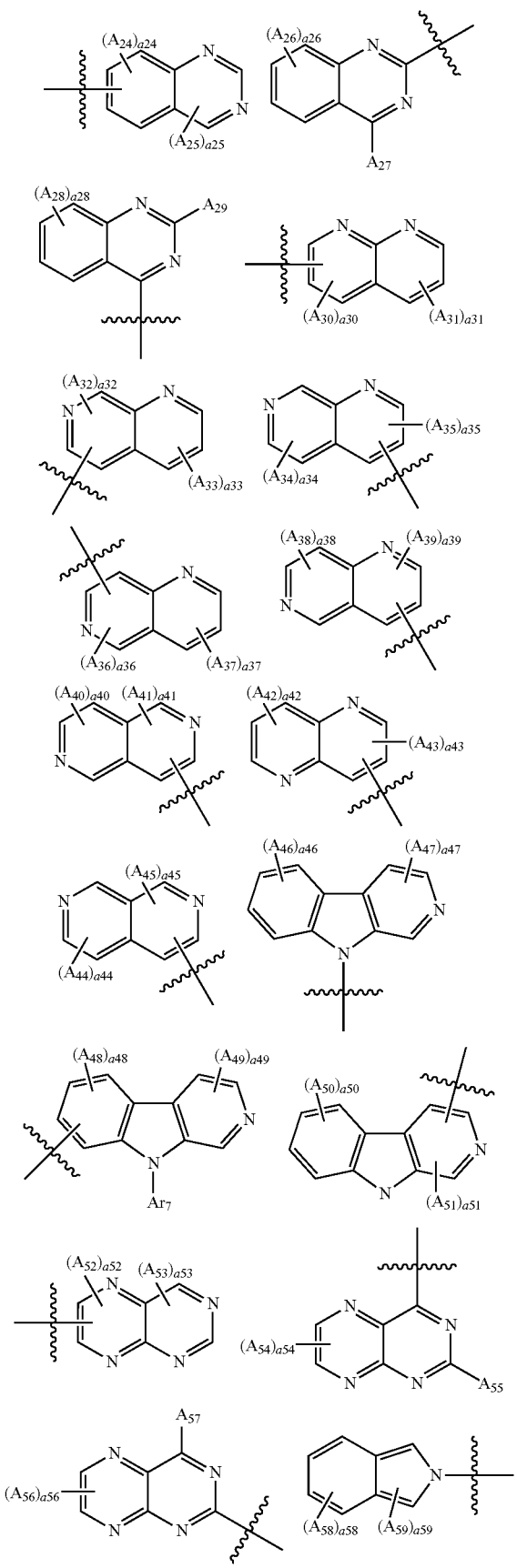
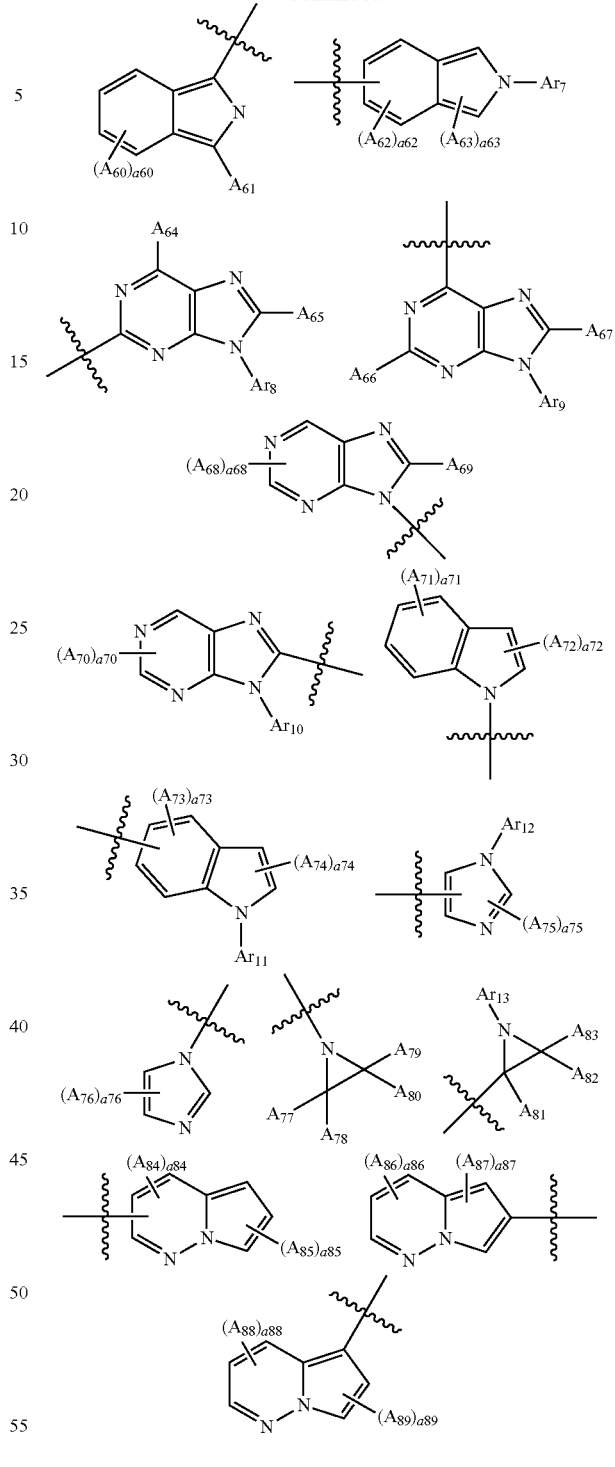

wherein in the structural formulae:
$A_1$ to $A_{89}$ are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group, or optionally combine with an adjacent group to form a ring, a1, a4, a5, a6, a8, a17, a18, a19, a20, a21, a23, a26, a28, a46, a50, a58, a60, and a71 are the same as or different from each other, and are each independently an integer of 0 to 4, a2, a3, a7, a11, a12, a14, a15, a22, a24, a31, a33, a34, a37, a38, a40, a42, a44, a47, a48, a49, a62, a73, a76, a85, a86, and a88 are the same as or different from each other, and are each independently an integer of 0 to 3, a9, a10, a25, a30, a32, a35, a36, a39, a41, a43, a45, a51, a53, a54, a56, a59, a63, a68, a70, a72, a74, a75, a84, a87, and a89 are the same as or different from each other, and are each independently an integer of 0 to 2, a52 is an integer of 0 to 1, and when a1 to a15, a17 to a26, a28, a30 to a51, a53, a54, a56, a58 to a60, a62, a63, a68, a70 to a72, and a84 to a89 are 2 or more, the structures in the parenthesis are the same as or different from each other.

5. The compound of claim 1, wherein Ar2 is any one selected from the following structural formulae:

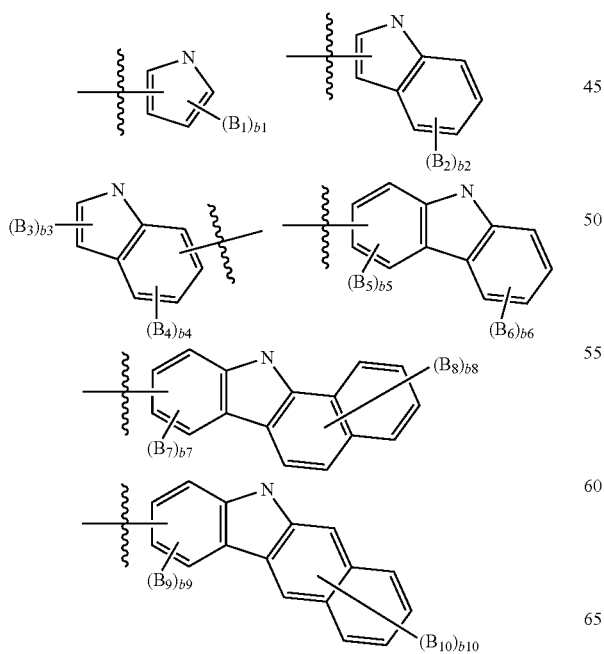

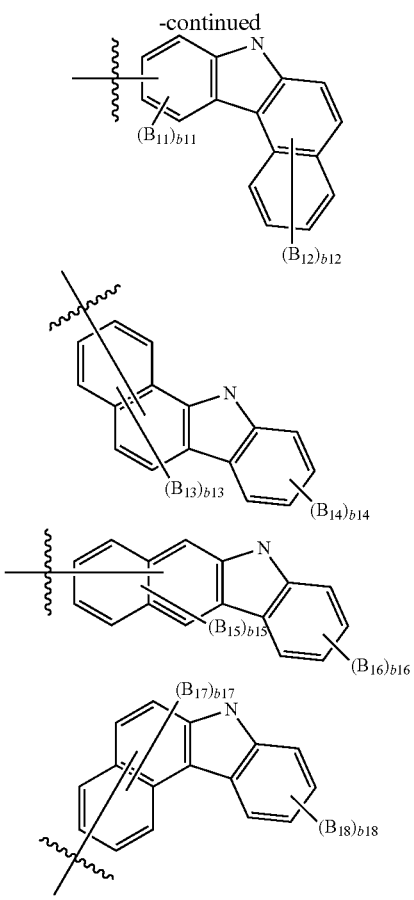

wherein in the structural formulae:

$B_1$ to $B_{18}$ are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group, or optionally combine with an adjacent group to form a ring, b1, b4, b5, b7, b9, and b11 are the same as or different from each other, and are each independently an integer of 0 to 3, b2, b6, b14, b16, and b18 are the same as or different from each other, and are each independently an integer of 0 to 4, b3 is an integer of 0 to 2, b8, b10, and b12 are the same as or different from each other, and are each independently an integer of 0 to 6, b13, b15, and b17 are the same as or different from each other, and are each independently an integer of 0 to 5, and when b1 to b18 are 2 or more, the structures in the parenthesis are the same as or different from each other.

6. The compound of claim 1, wherein Ar2 is any one selected from the following structural formulae:

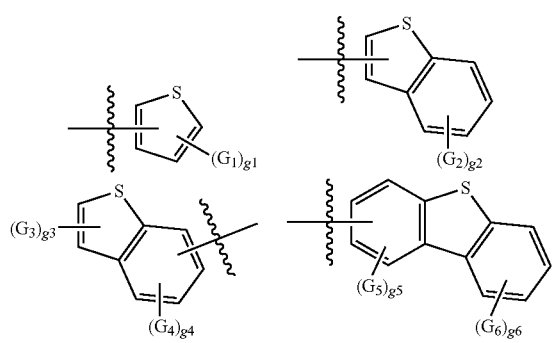

wherein in the structural formulae:

G₁ to G₆ are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group, or optionally combine with an adjacent group to form a ring, g1, g4, and g5 are the same as or different from each other, and each independently an integer of 0 to 3, g2 and g6 are the same as or different from each other, and are each independently an integer of 0 to 4, g3 is an integer of 0 to 2, and when g1 to g6 are each 2 or more, the structures in the parenthesis are the same as or different from each other.

7. The compound of claim 1, wherein Ar2 is any one selected from the following structural formulae:

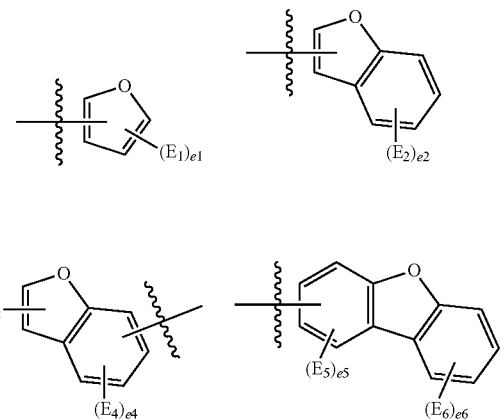

wherein in the structural formulae:

E₁ to E₆ are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group, or optionally combine with an adjacent group to form a ring, e1, e4, and e5 are the same as or different from each other, and are each independently an integer of 0 to 3, e2 and e6 are the same as or different from each other, and are each independently an integer of 0 to 4, e3 is an integer of 0 to 2, and when e1 to e6 are 2 or more, the structures in the parenthesis are the same as or different from each other.

8. The compound of claim 1, wherein Ar2 is a phenyl group; a biphenyl group; a naphthyl group; a phenanthryl group; a fluorenyl group substituted with an alkyl group; a carbazole group substituted with an aryl group; a carbazole group; a benzocarbazole group; a benzocarbazole group substituted with an aryl group; a dibenzothiophene group; a dibenzofuranyl group; or a triazine group substituted with an aryl group.

9. The compound of claim 1, wherein Formula 1 is represented by following Formula 4 or 5:

[Formula 4]

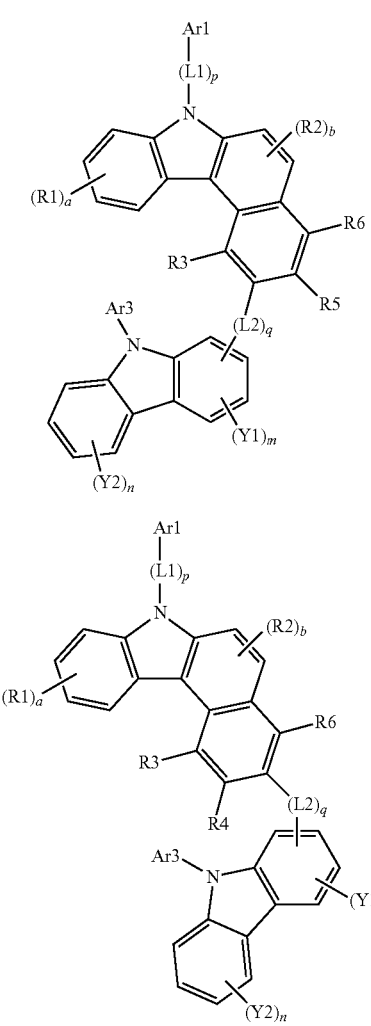

[Formula 5]

[Formula 8]

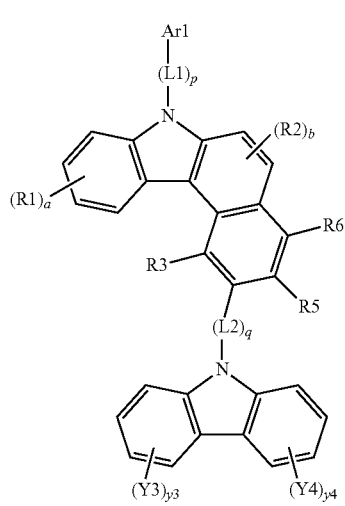

[Formula 9]

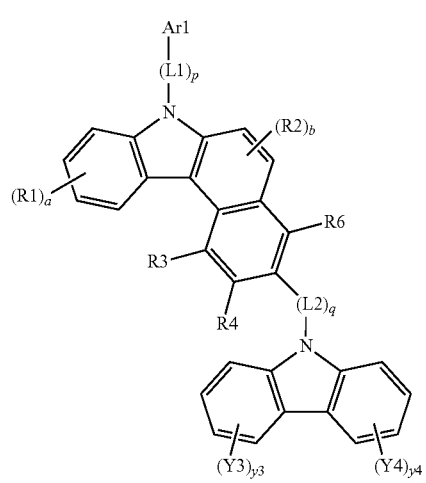

wherein in Formulae 4 and 5:
the definitions of Ar1, R1 to R6, L1, L2, a, b, p, and q are the same as those in Formula 1,
the definition of Ar3 is the same as that of Ar1,
Y1 and Y2 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted aryl- heteroarylamine group; a substituted or unsubstituted arylphosphine group; a substituted or unsubstituted phosphine oxide group; a substituted or unsubstituted aryl group; or a substituted or unsubstituted heterocyclic group, or combine with an adjacent group to form a ring,
m is an integer or 0 to 3 and n is an integer of 0 to 4, and when m and n are each 2 or more, the structures in the parenthesis are the same as or different from each other.

10. The compound of claim 1, wherein Formula 1 is represented by following Formula 8 or 9:

wherein in Formulae 8 and 9:
the definitions of Ar1, R1 to R6, L1, L2, a, b, p, and q are the same as those in Formula 1,
Y3 and Y4 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or combine with an adjacent group to form a ring, y3 and y4 are the same as or different from each other, and are each independently an integer of 0 to 4, and when y3 and y4 are each 2 or more, the structures in the parenthesis are the same as or different from each other.

11. The compound of claim 1, wherein Formula 1 is represented by following Formula 12 or 13:

[Formula 12]

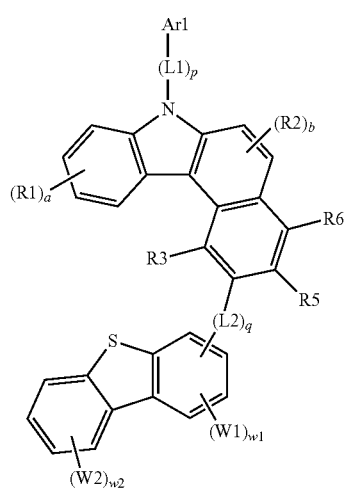

[Formula 13]

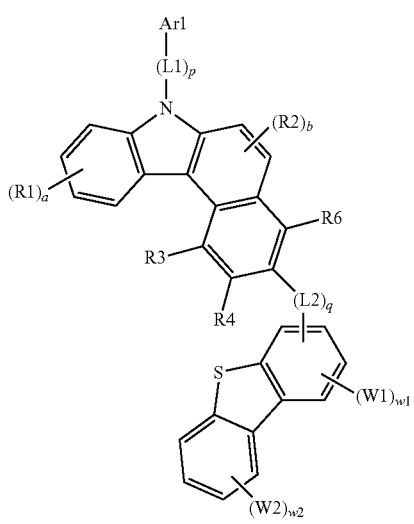

in Formulae 12 and 13:

the definitions of Ar1, R1 to R6, L1, L2, a, b, p, and q are the same as those in Formula 1, W1 and W2 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or combine with an adjacent group to form a ring, w1 is an integer of 0 to 3, w2 is an integer of 0 to 4, and when w1 and w2 are each 2 or more, the structures in the parenthesis are the same as or different from each other.

12. The compound of claim 1, wherein Formula 1 is represented by following Formula 16 or 17:

[Formula 16]

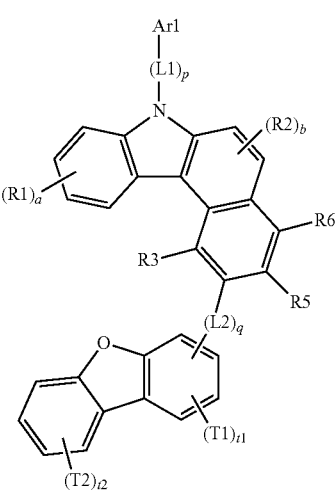

[Formula 17]

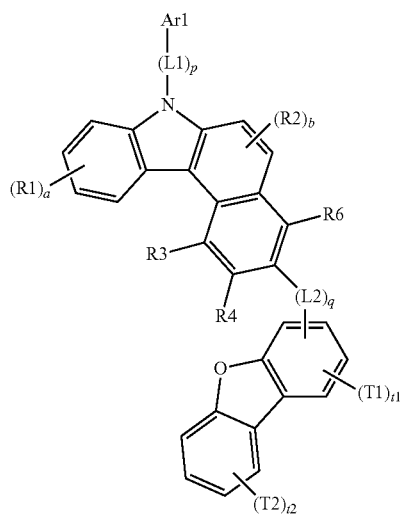

wherein in Formulae 16 and 17:

the definitions of Ar1, R1 to R6, L1, L2, a, b, p, and q are the same as those in Formula 1, T1 and T2 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or combine with an adjacent group to form a ring, t1 is an integer of 0 to 3, t2 is an integer of 0 to 4, and when t1 and t2 are each 2 or more, the structures in the parenthesis are the same as or different from each other.

13. The compound of claim 1, wherein Formula 1 is represented by following Formula 20 or 21:

[Formula 20]

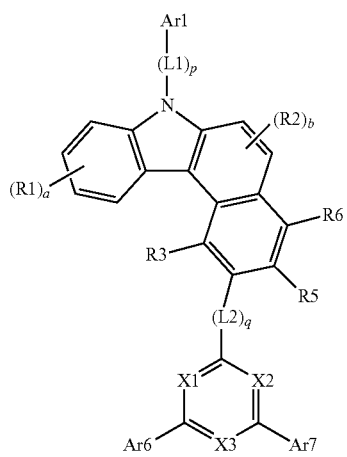

[Formula 21]

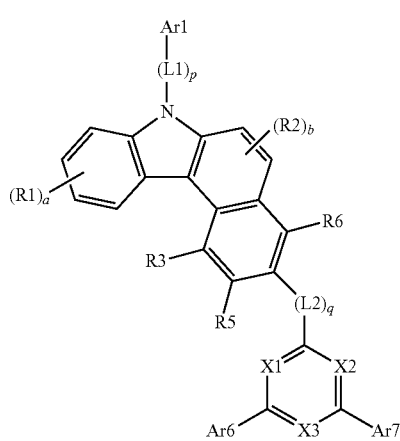

wherein in Formulae 20 and 21:

the definitions of Ar1, R1 to R6, L1, L2, a, b, p, and q are the same as those in Formula 1, Ar6 and Ar7 are the same as or different from each other, and are each independently a nitrile group; a substituted or unsubstituted aryl group; or a substituted or unsubstituted heterocyclic group, X1 to X3 are the same as or different from each other, and are each independently CR or N, and R is hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or combines with an adjacent group to form a ring.

14. The compound of claim 1, wherein L2 is any one selected from the following structures:

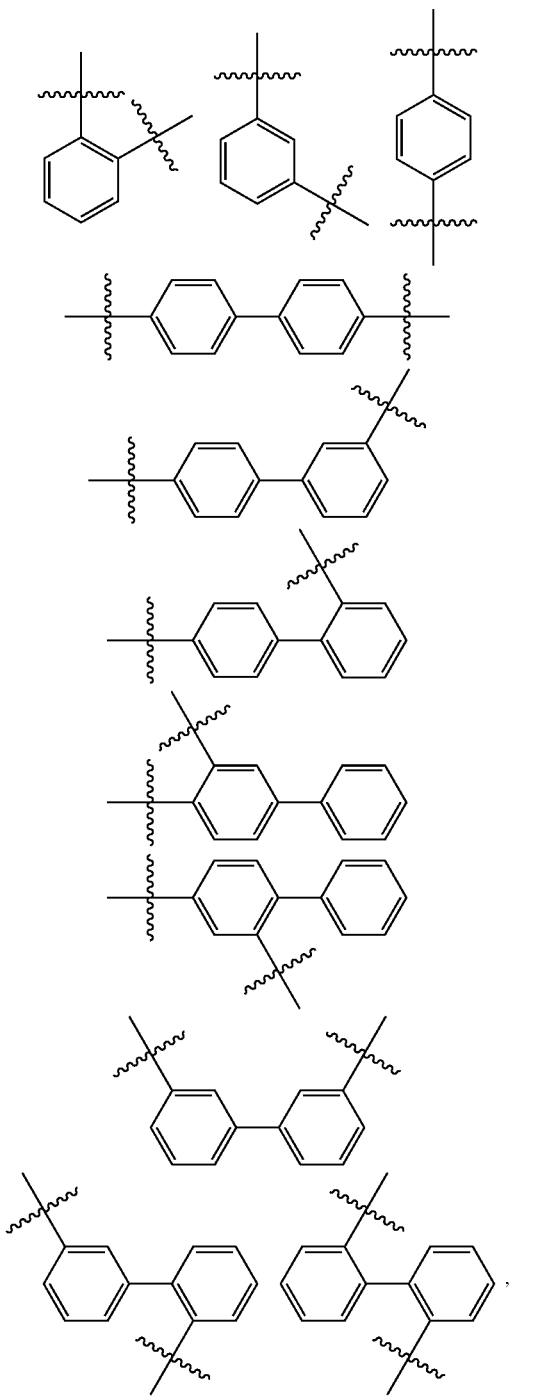

wherein the structures are optionally unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group.

15. The compound of claim 1, wherein the compound of Formula 1 is any one selected from the following structural formulae:

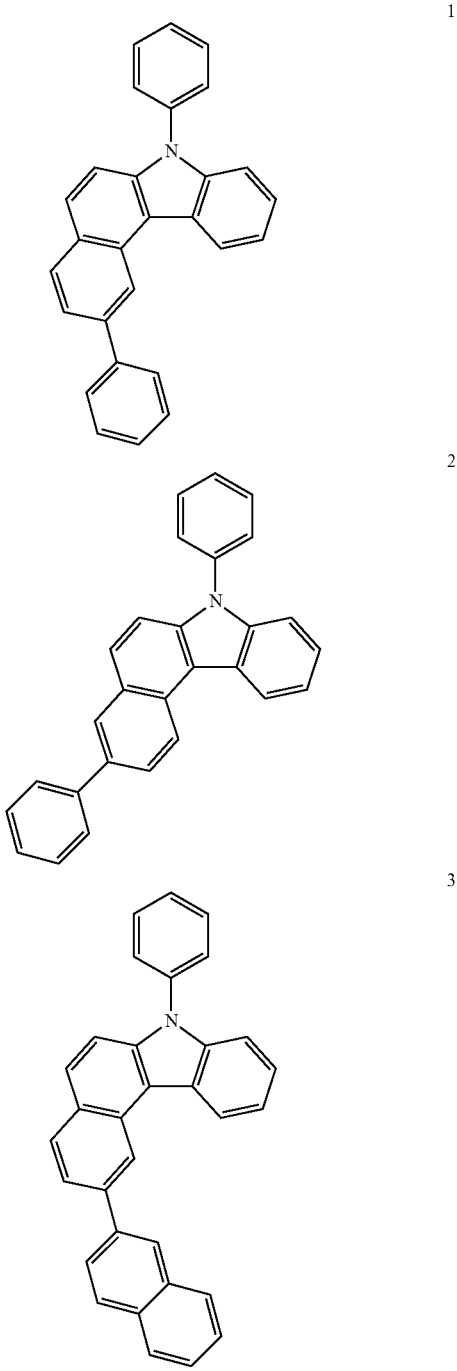 [SMILES: c1ccc(-c2ccc3ccc4c(c3c2)c2ccccc2n4-c2ccccc2)cc1 ; c1ccc(-c2ccc3c(ccc4c3c3ccccc3n4-c3ccccc3)c2)cc1 ; c1ccc(-n2c3ccccc3c3c4cc(-c5ccc6ccccc6c5)ccc4ccc32)cc1]

| 4 | 7 |
|---|---|
| 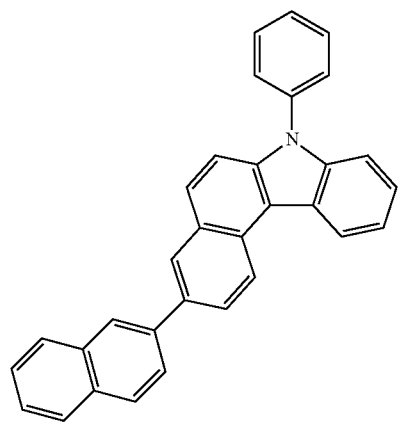 | 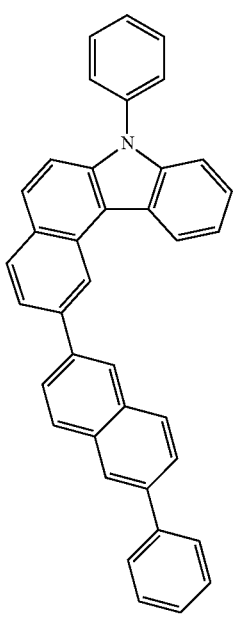 |
| 5 | 8 |
| 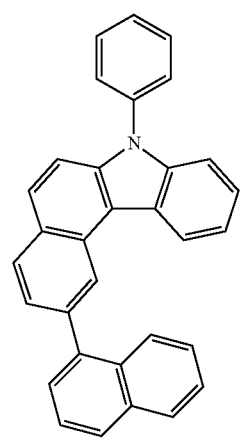 | 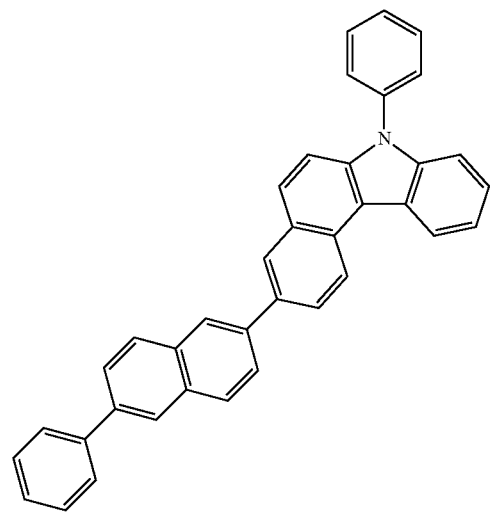 |
| 6 | 9 |
| 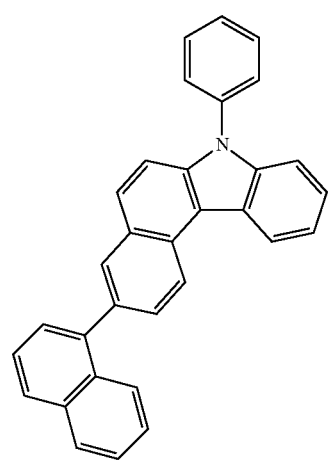 | 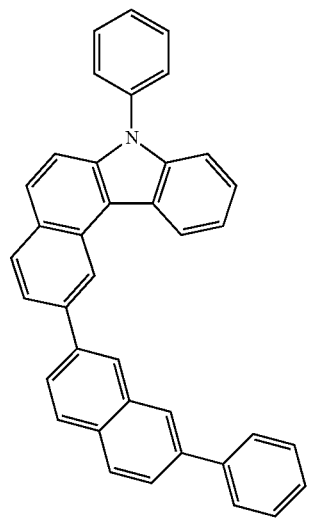 |

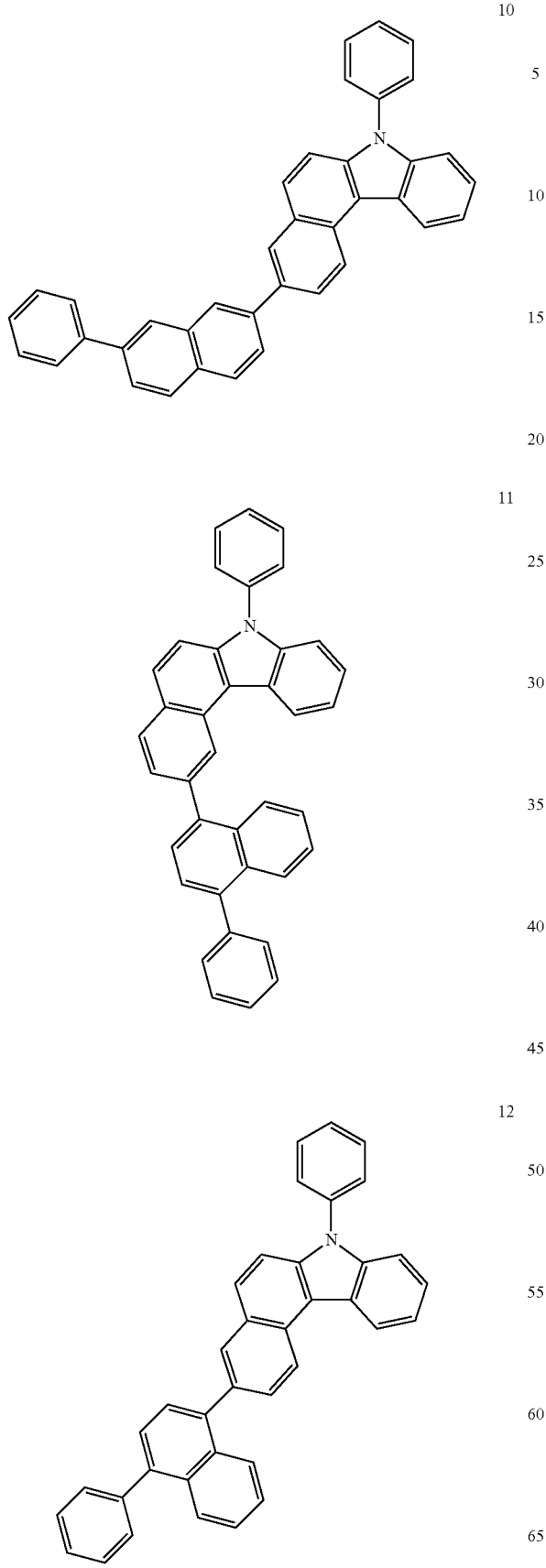
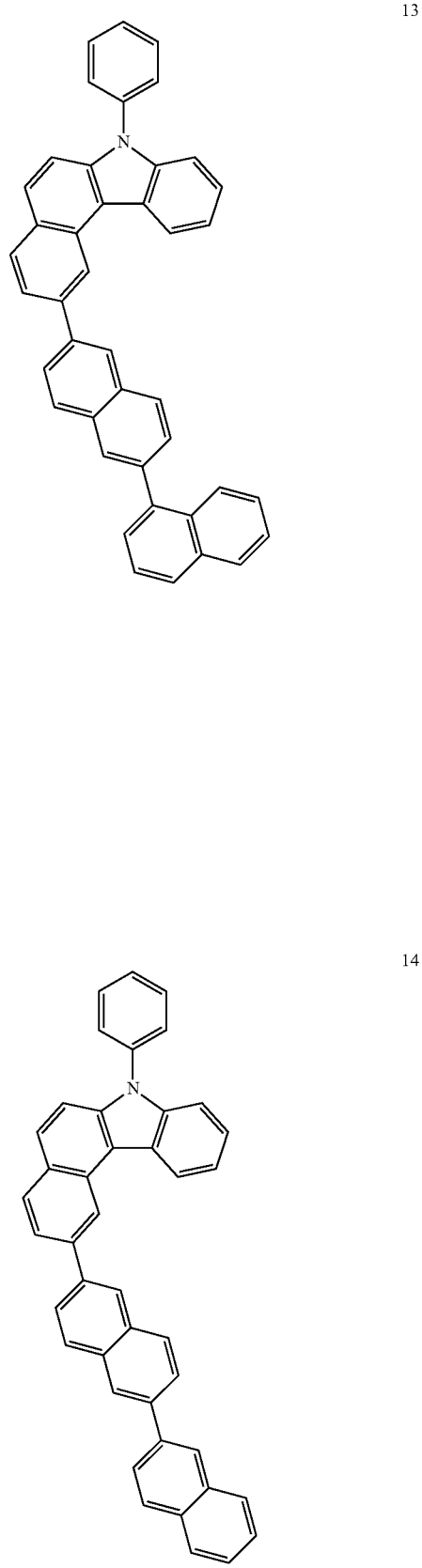

15
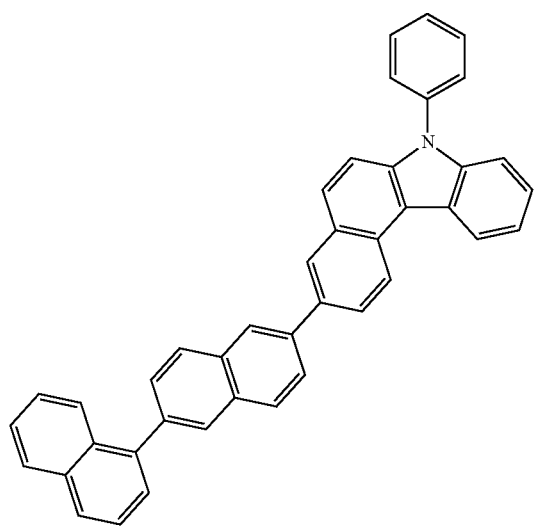
16
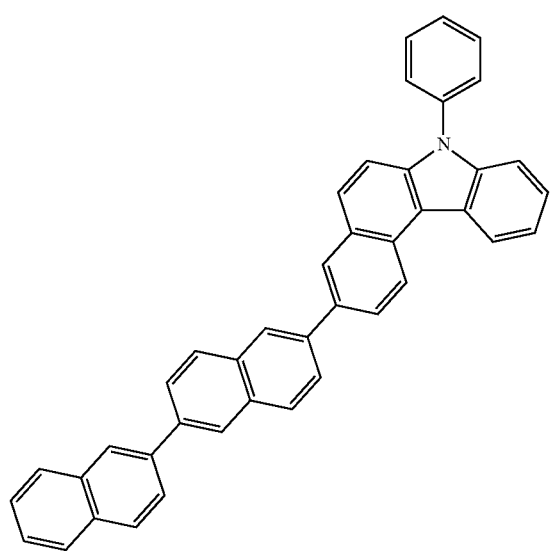
17
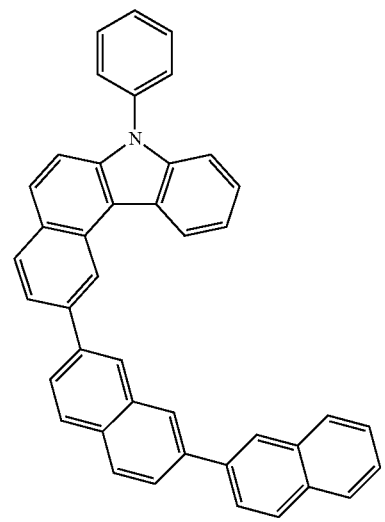
18
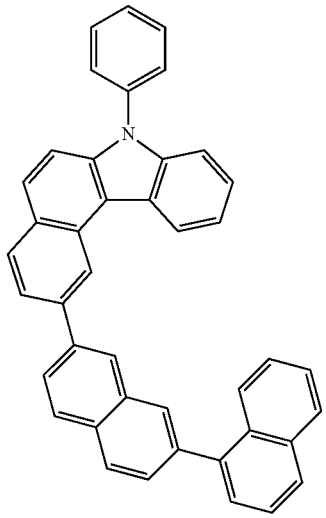
19
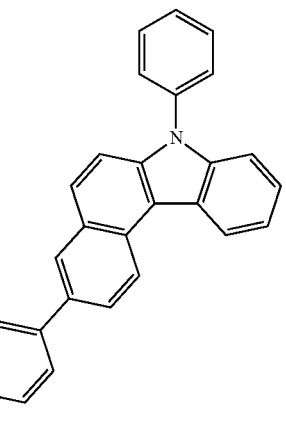
20

| 361-continued | 362-continued |
|---|---|
| 21<br />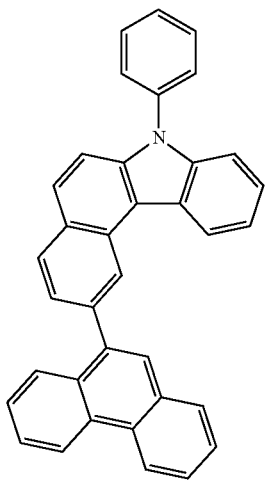 | 24<br />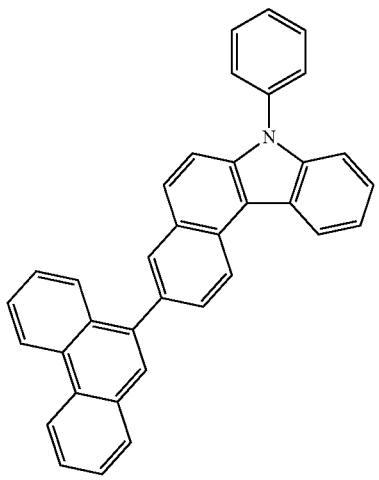 |
| 22<br />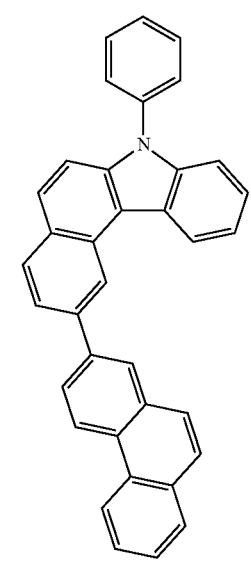 | 25<br />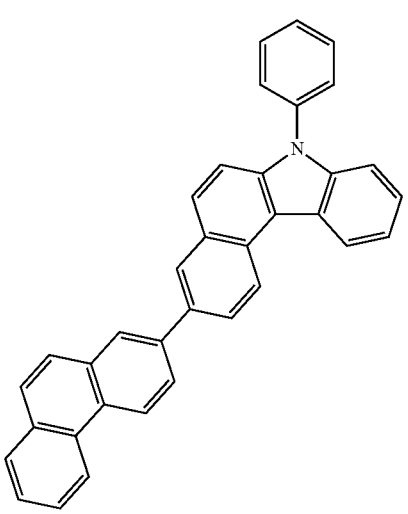 |
| 23<br />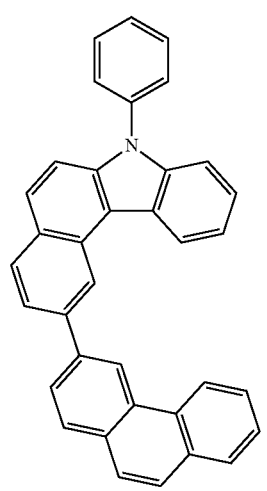 | 26<br />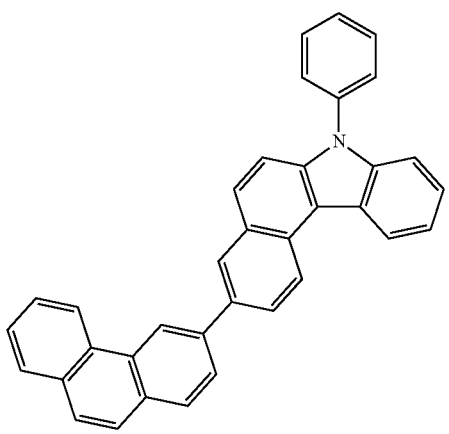 |

27
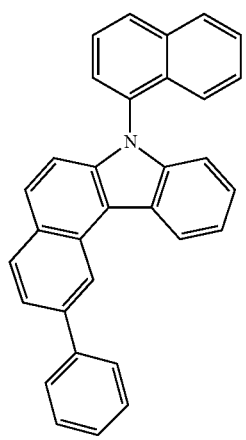
28
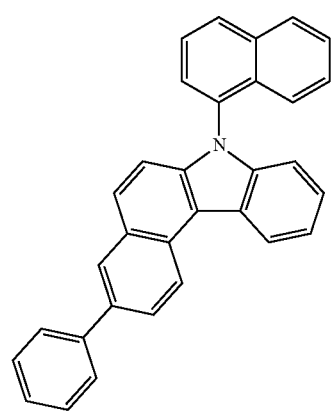
29
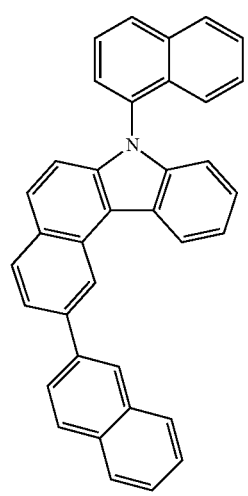
30
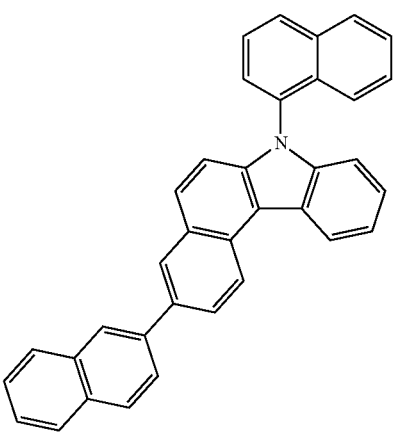
31
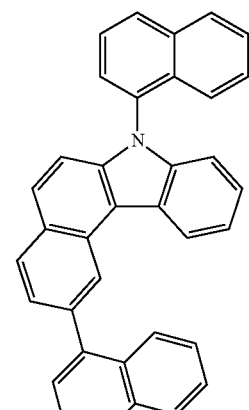
32
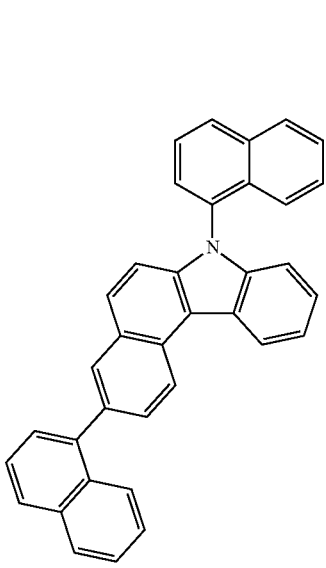

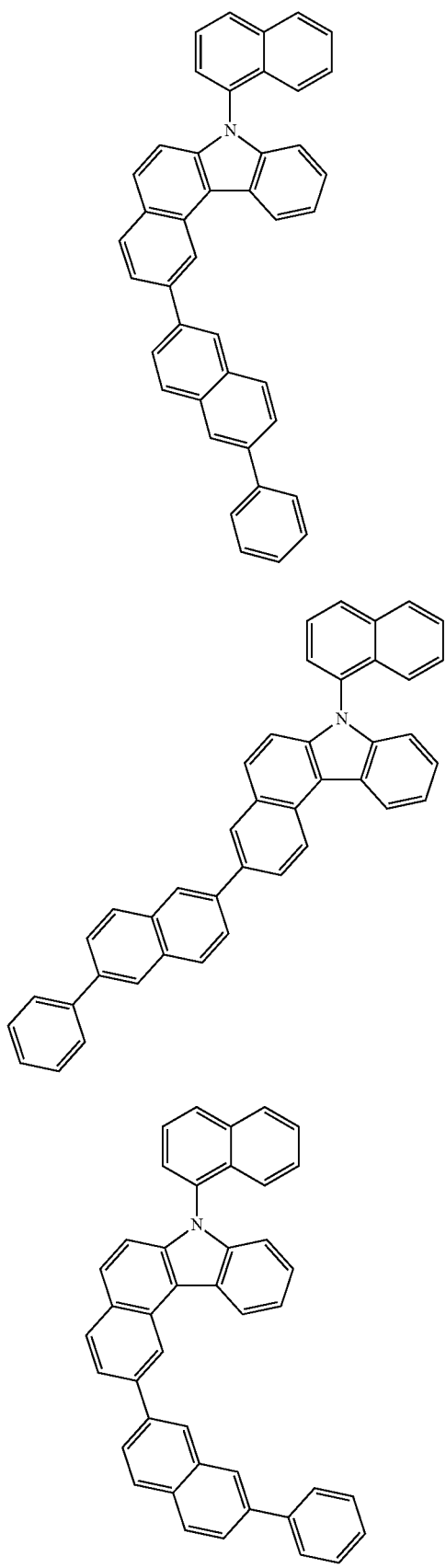
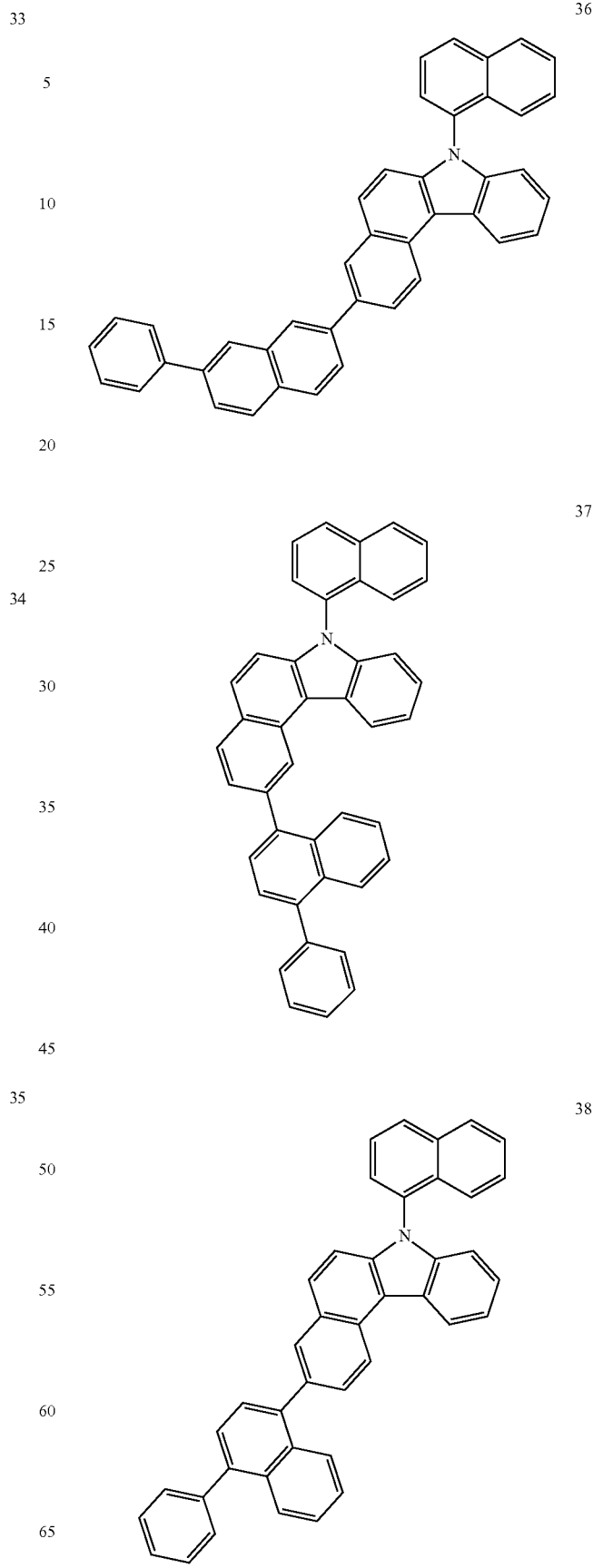

39
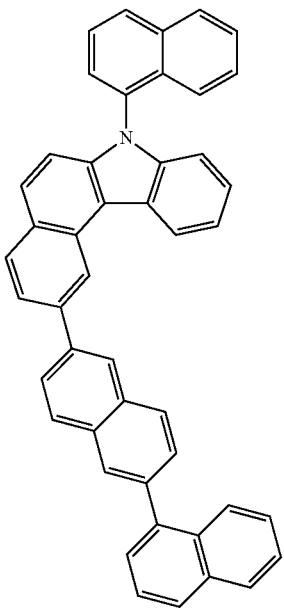
40
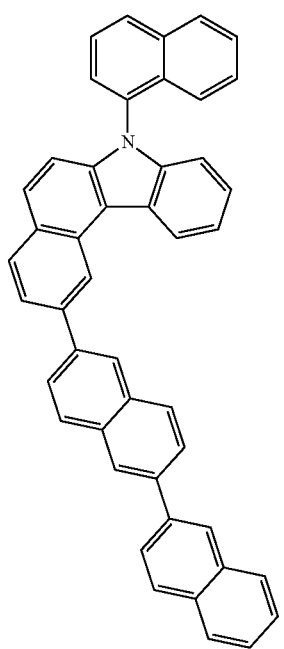
41
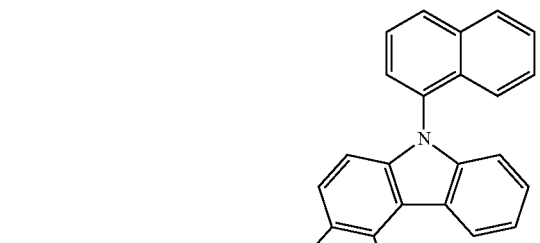
42

43
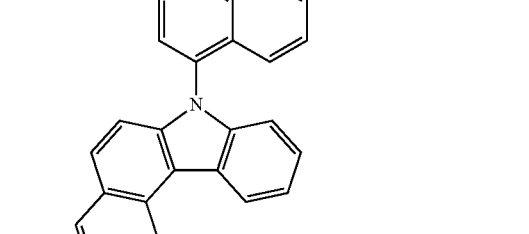

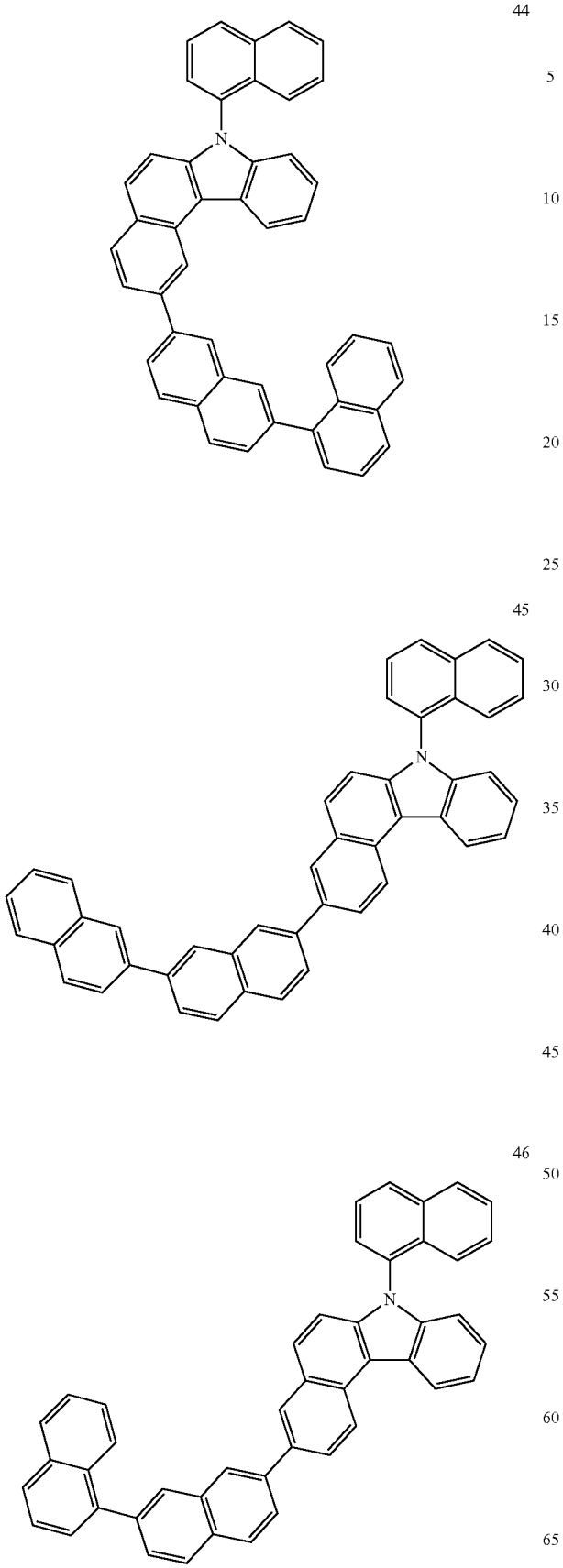
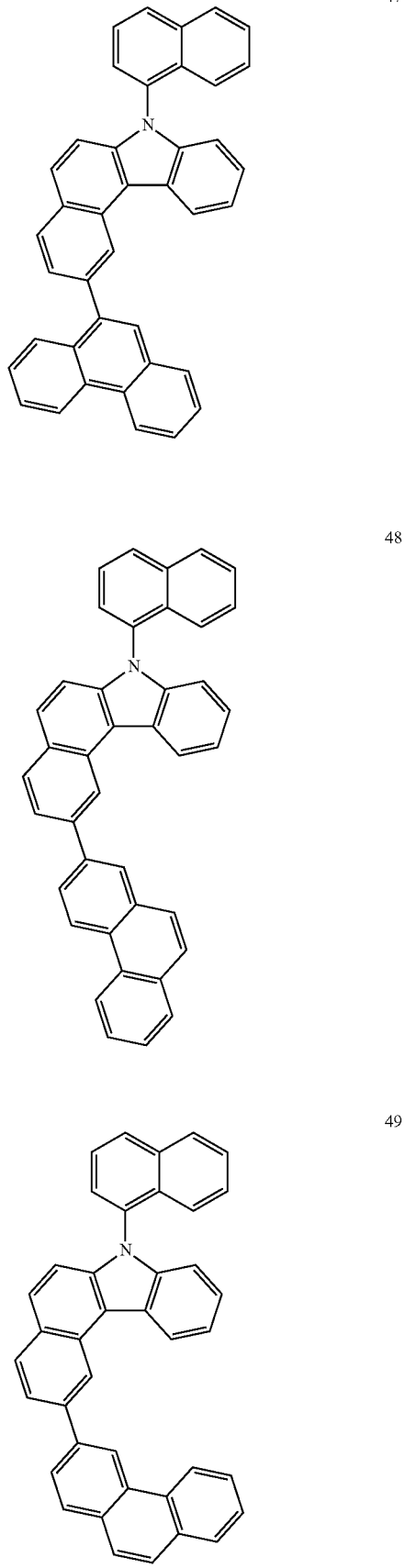

50
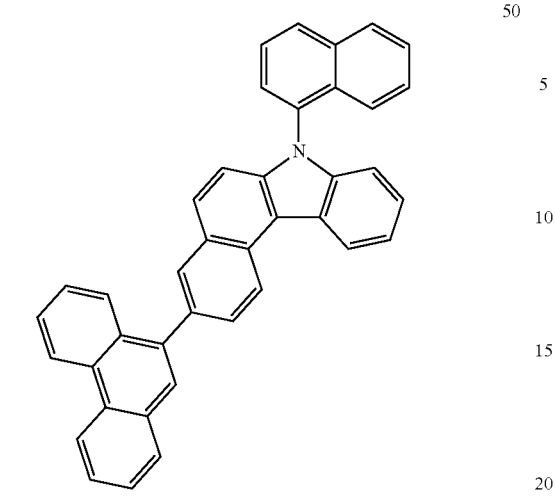
51
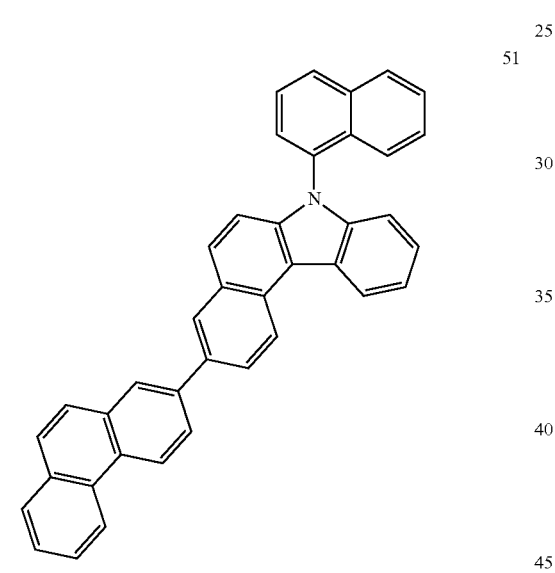
52
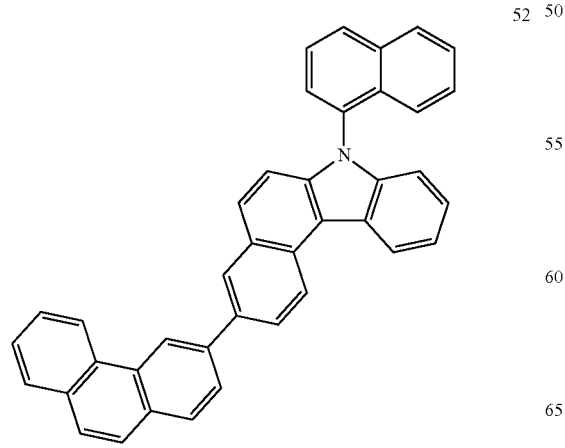
53
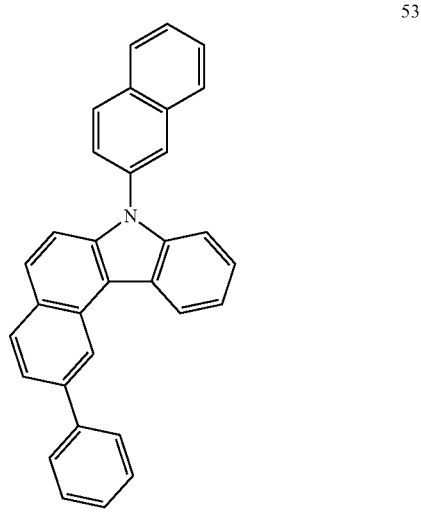
54
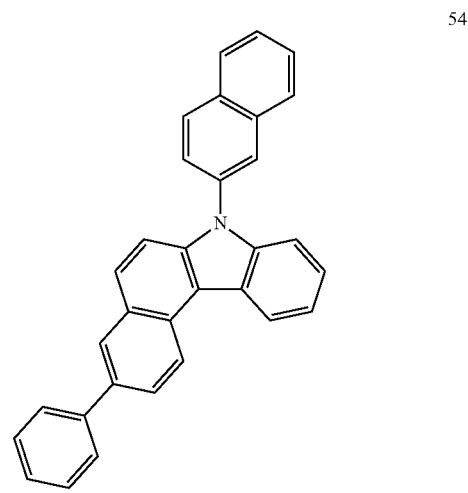
55
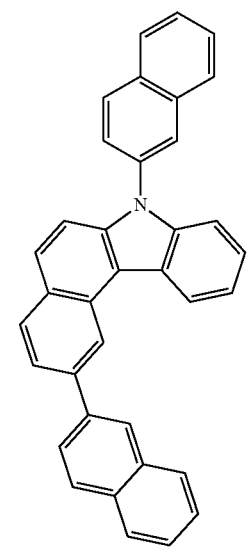

56
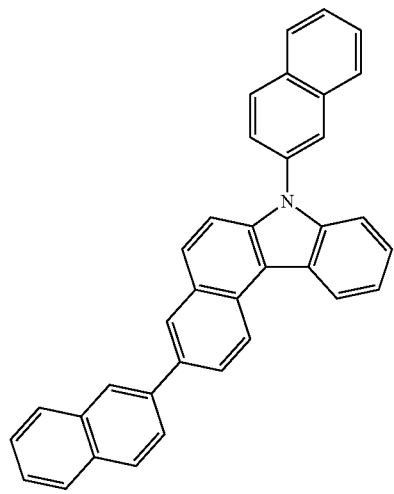
57
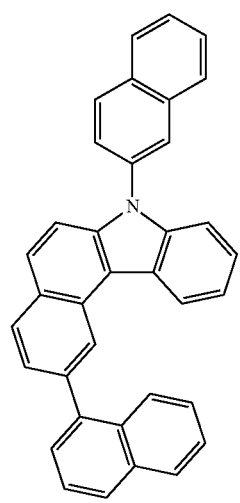
58
59
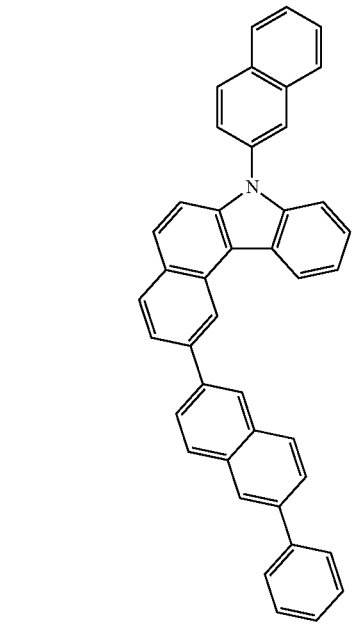
60
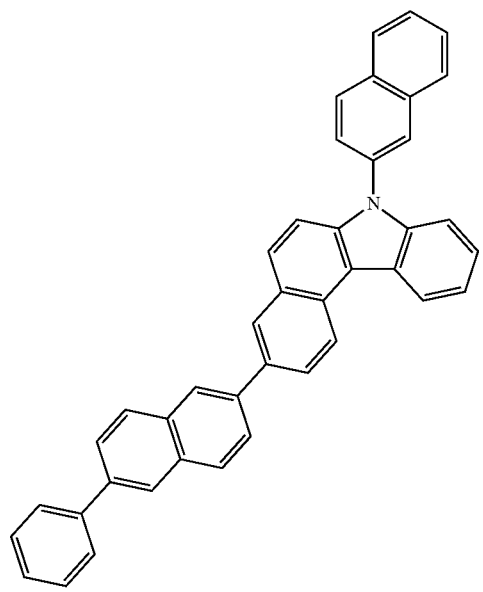

-continued
61
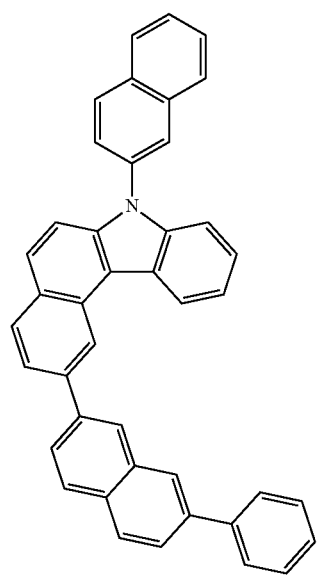
62
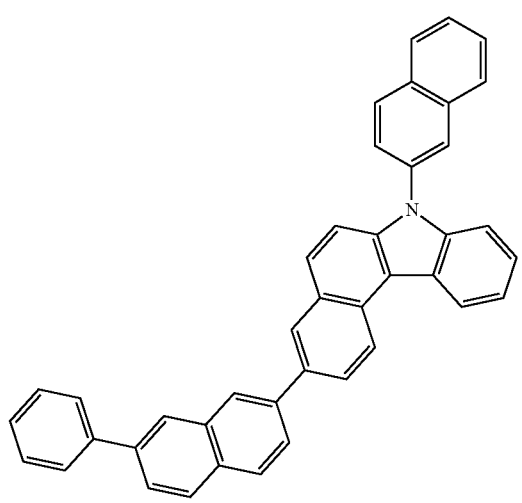
-continued
63
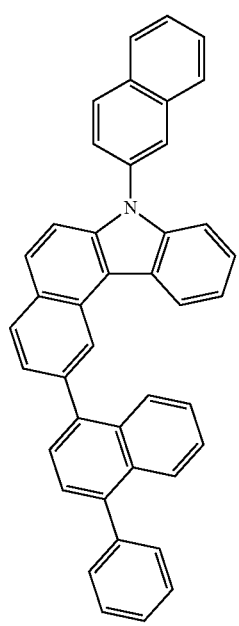
64
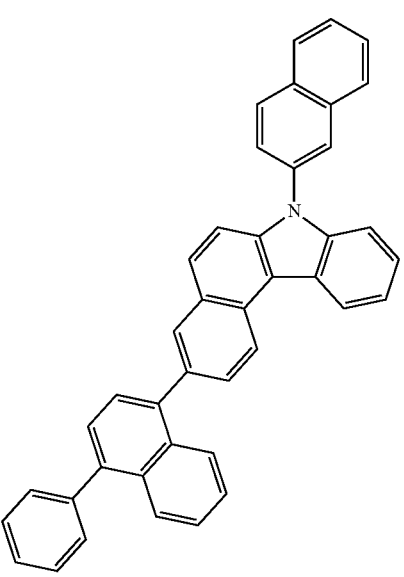

65
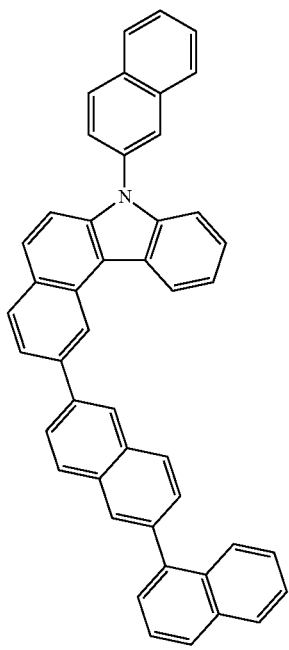
67
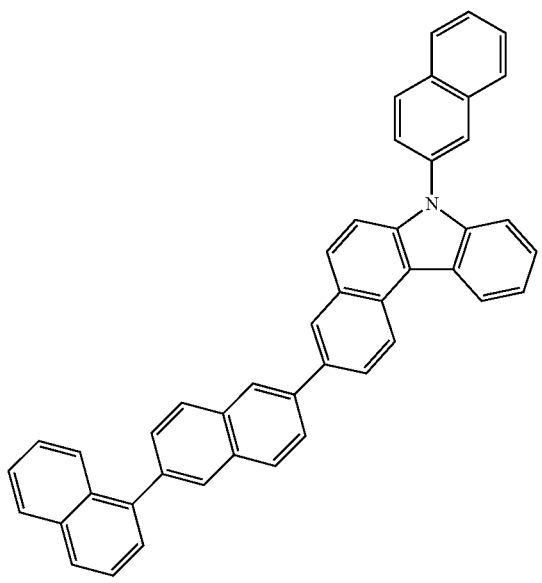
66
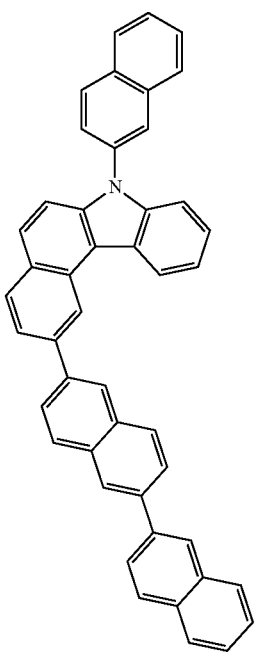
68
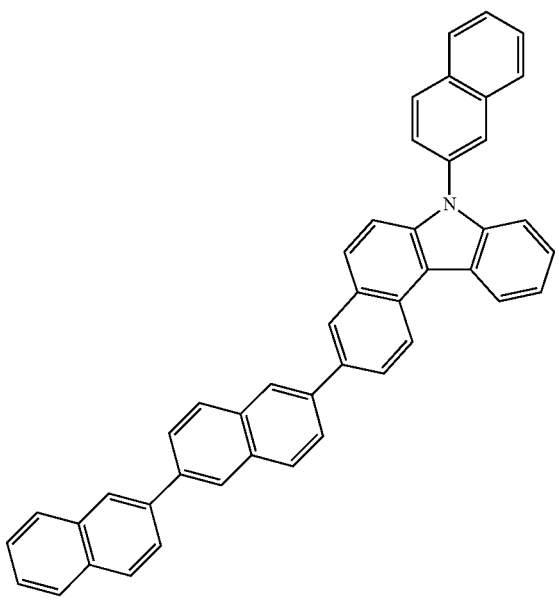

379
-continued
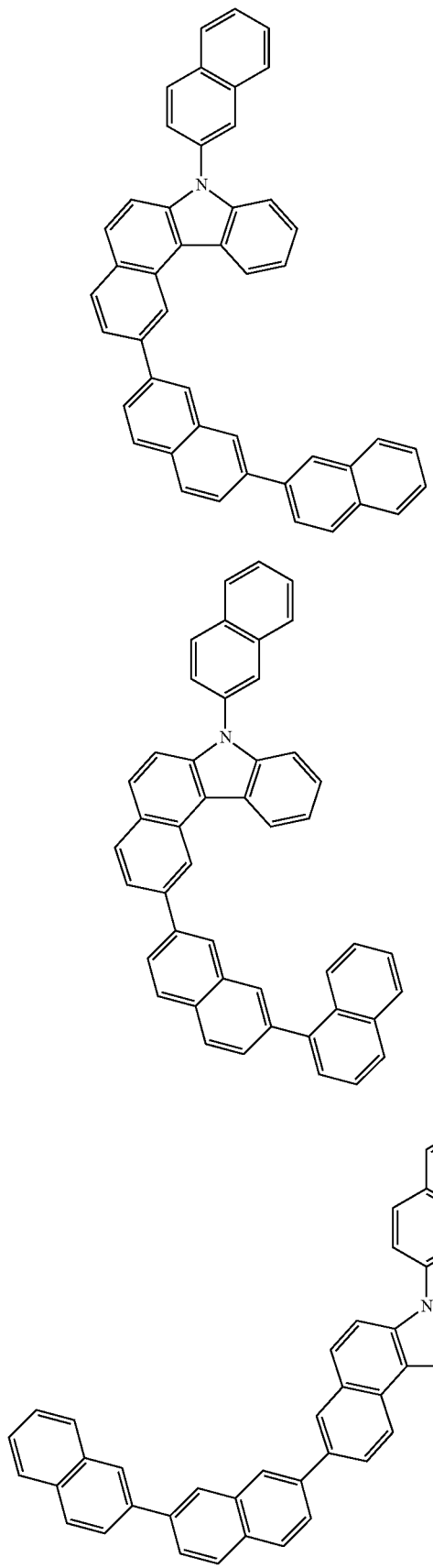
380
-continued
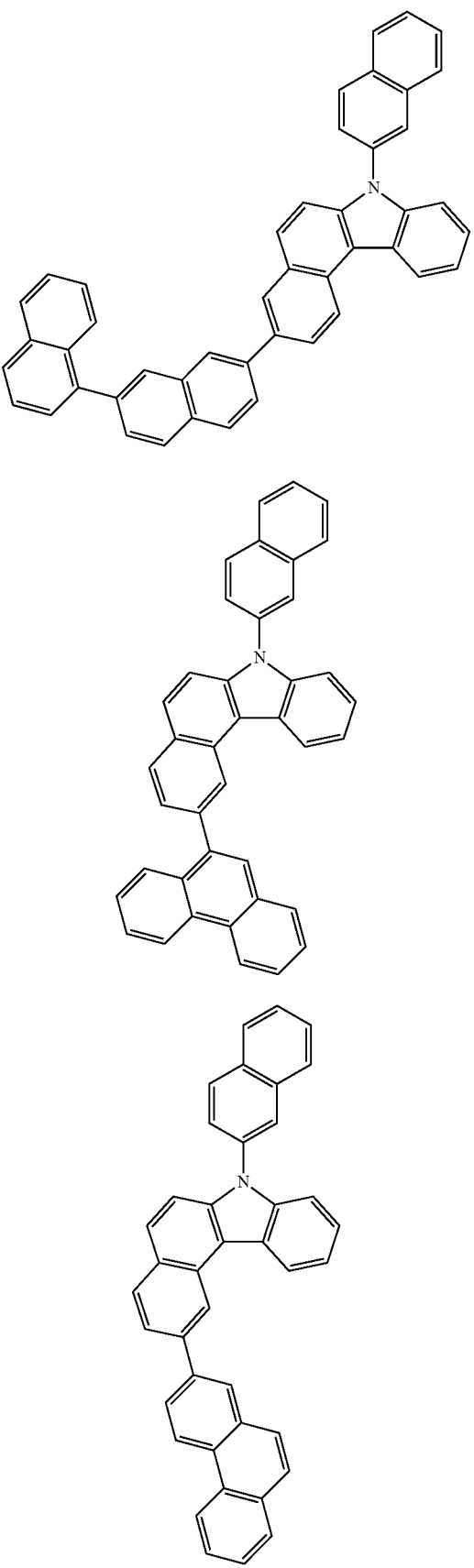

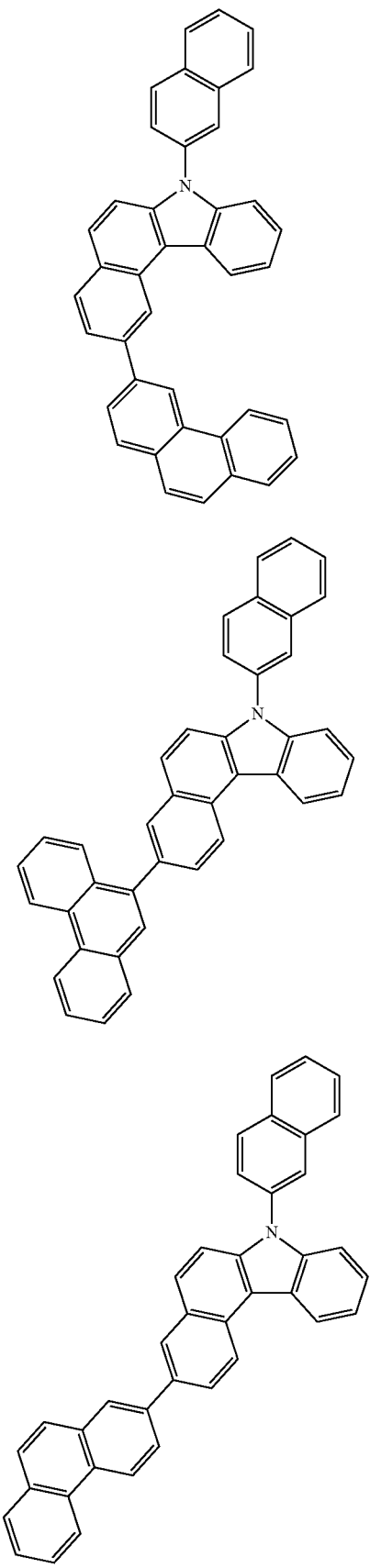
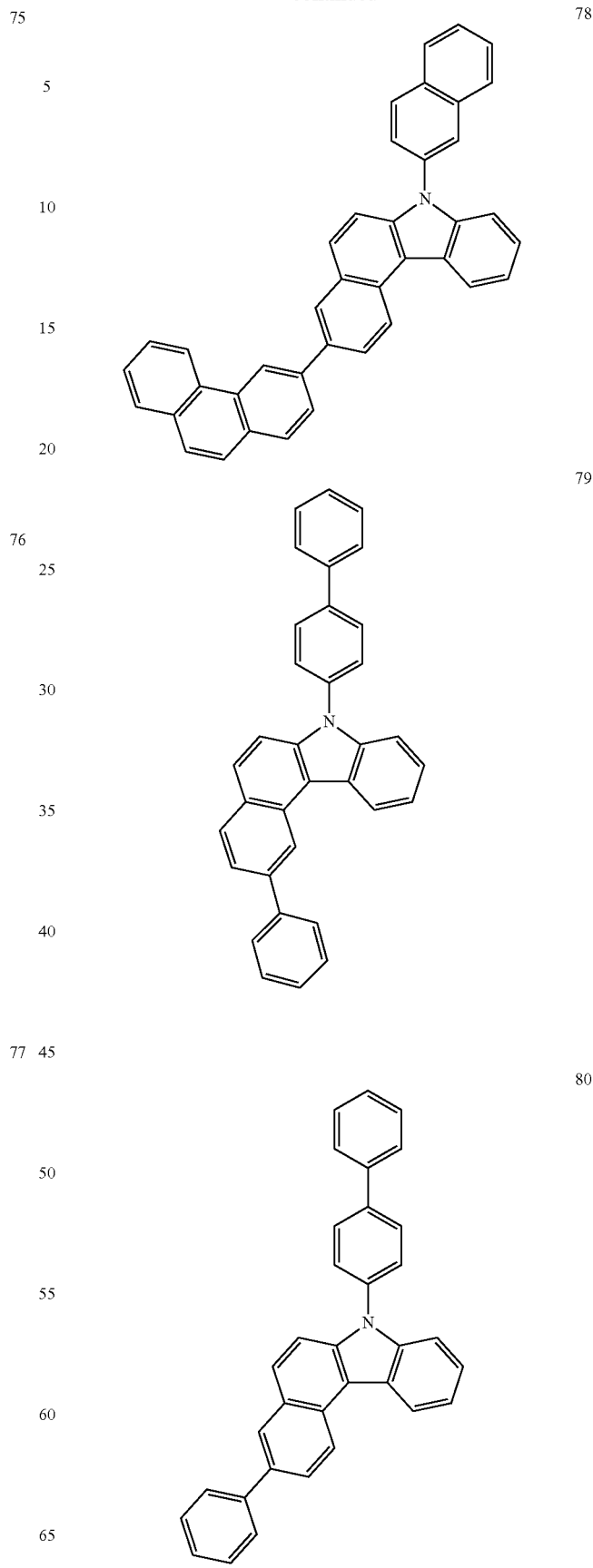

81
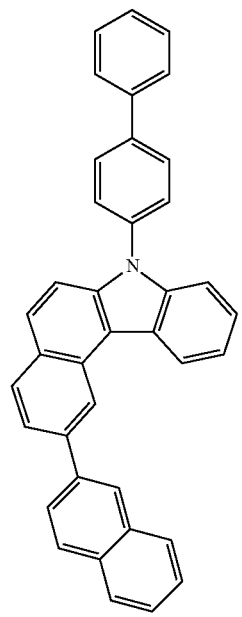
82
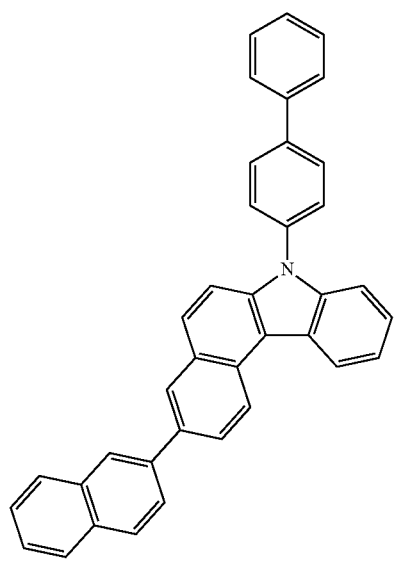
83
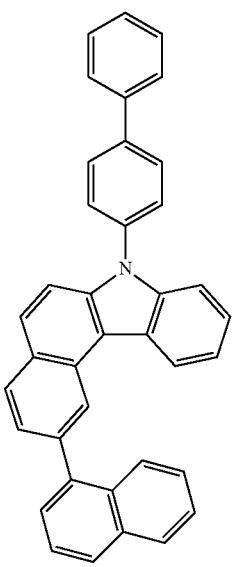
84
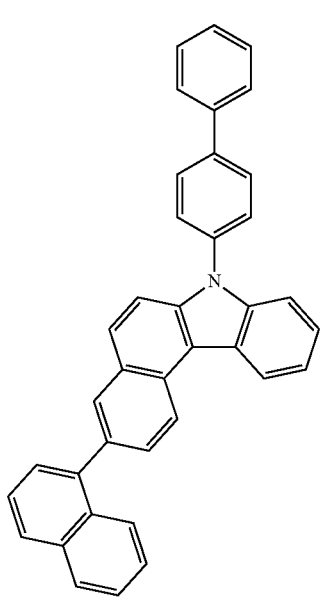

385 386
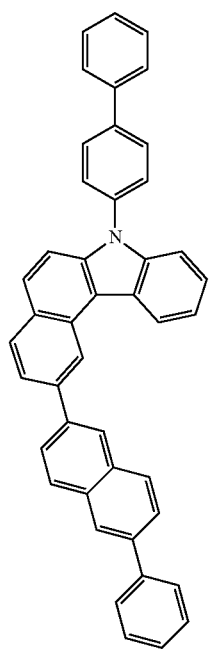  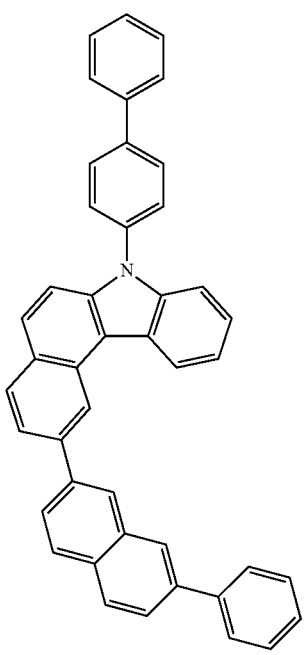
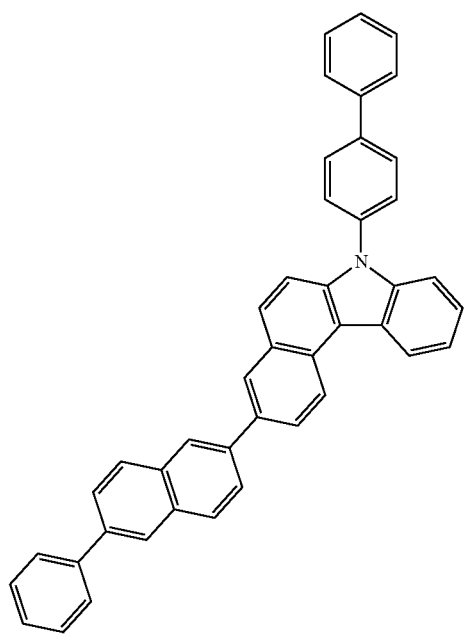

387
-continued
388
-continued
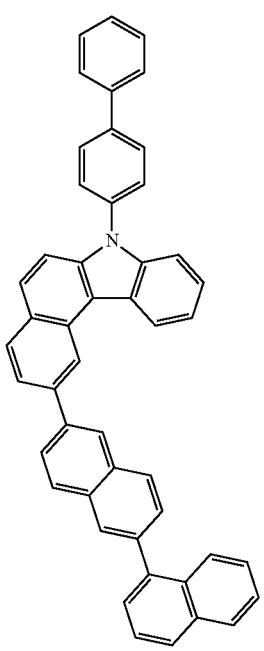
89
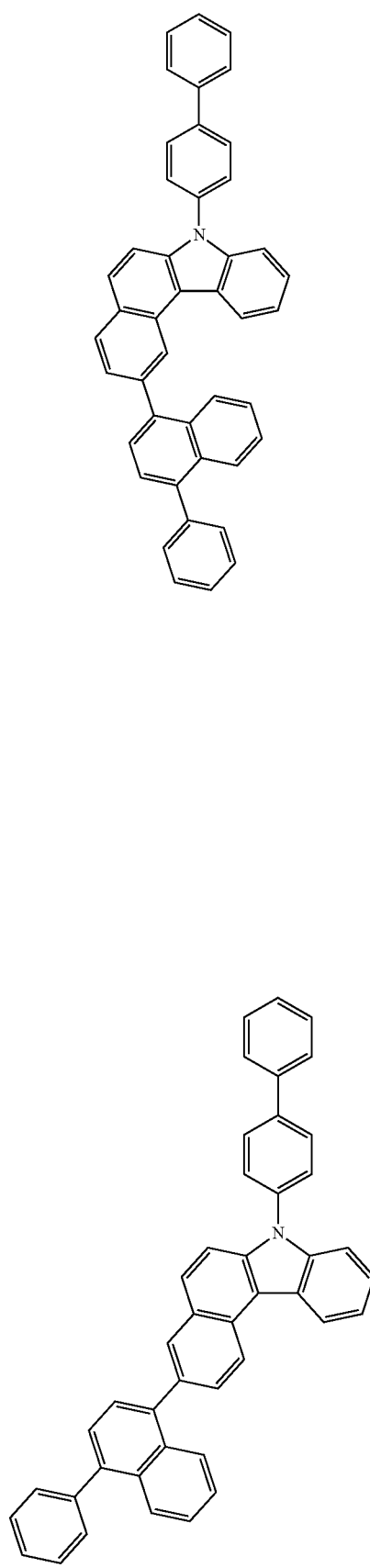
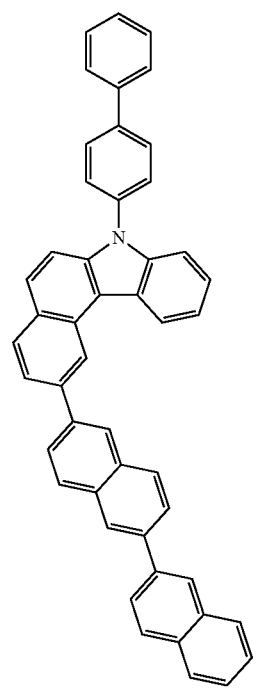
91
92

93
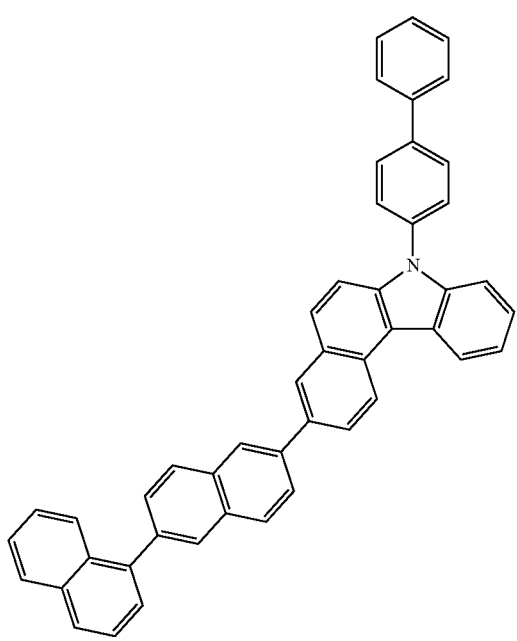
95
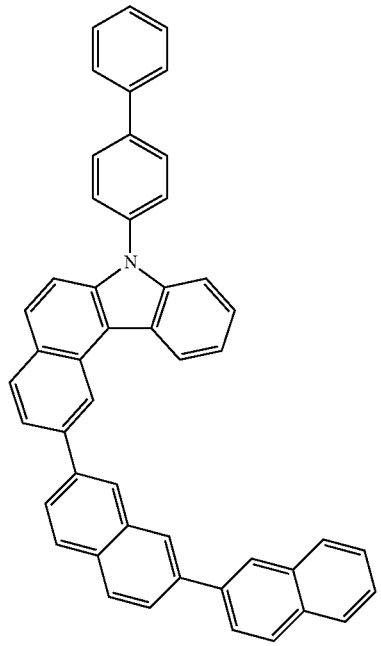
94
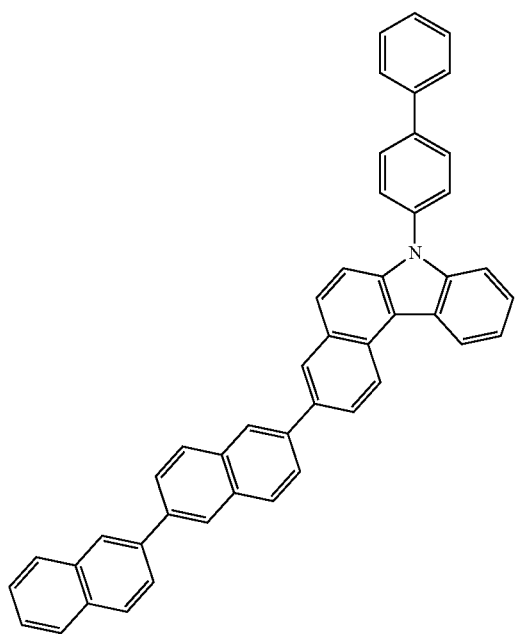
96
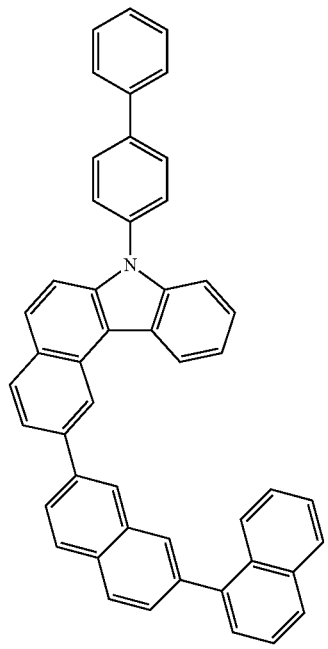

391
-continued
392
-continued
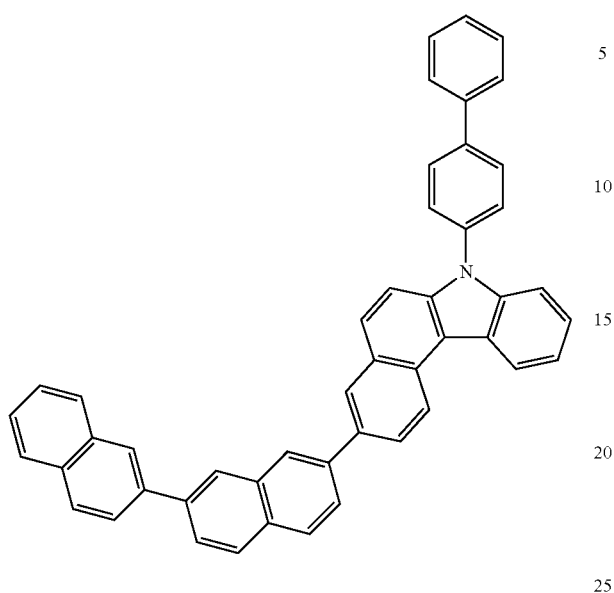
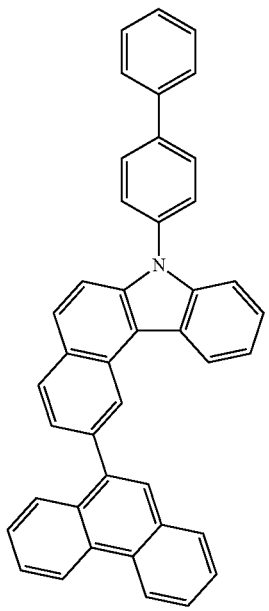
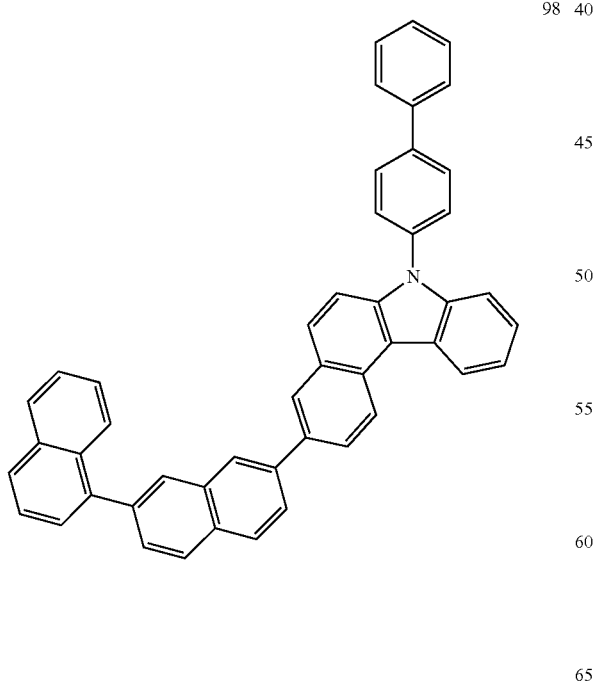

101
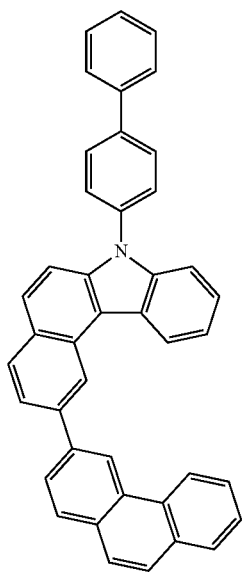
102
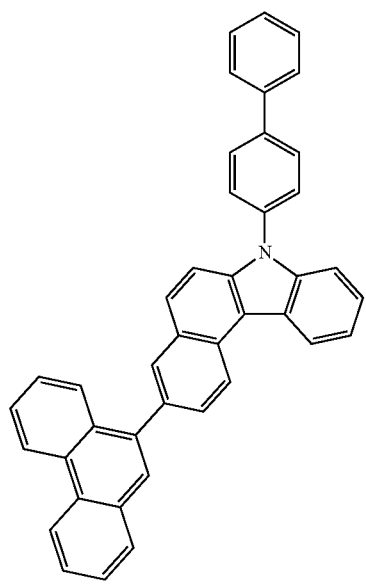
103
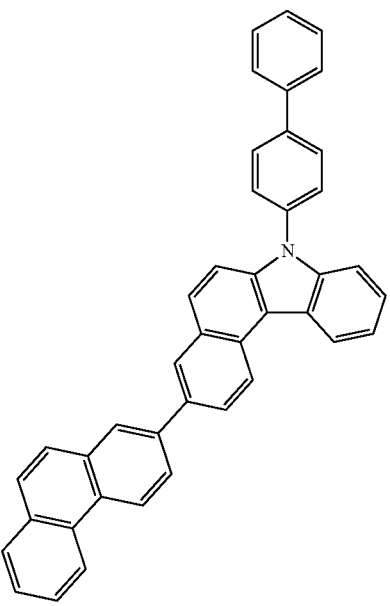
104
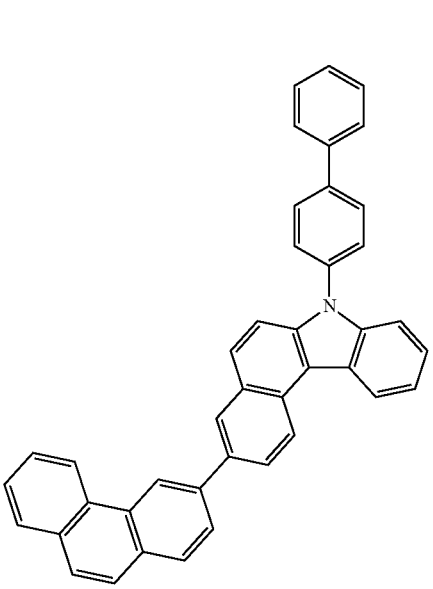

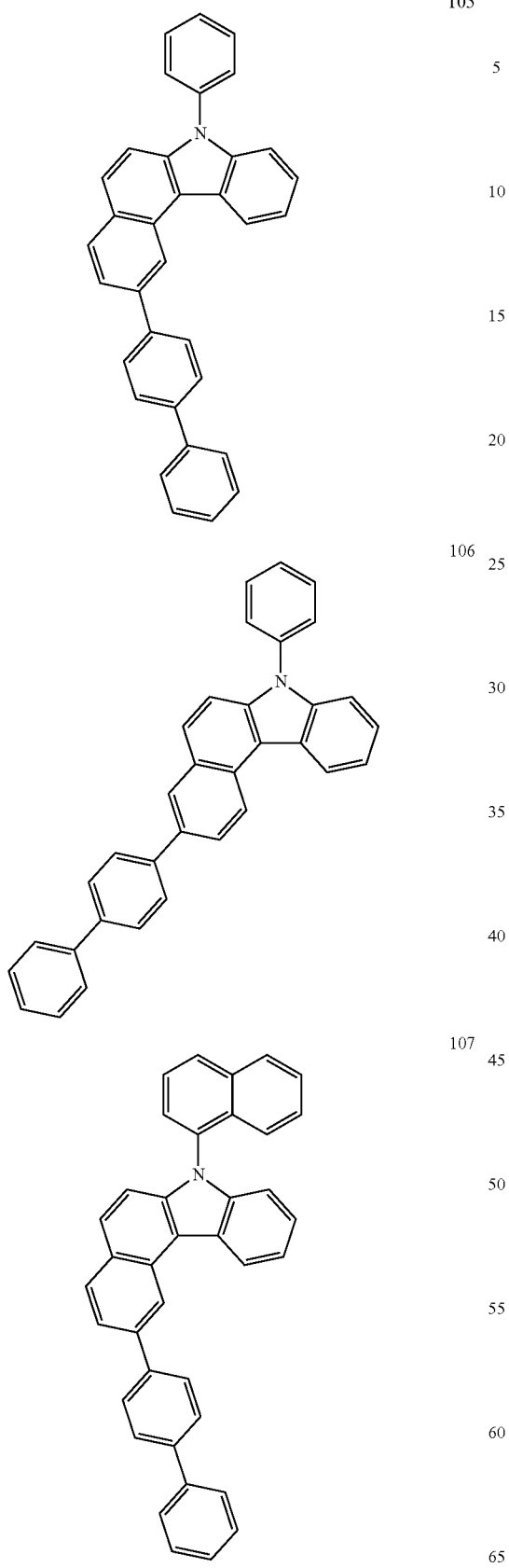
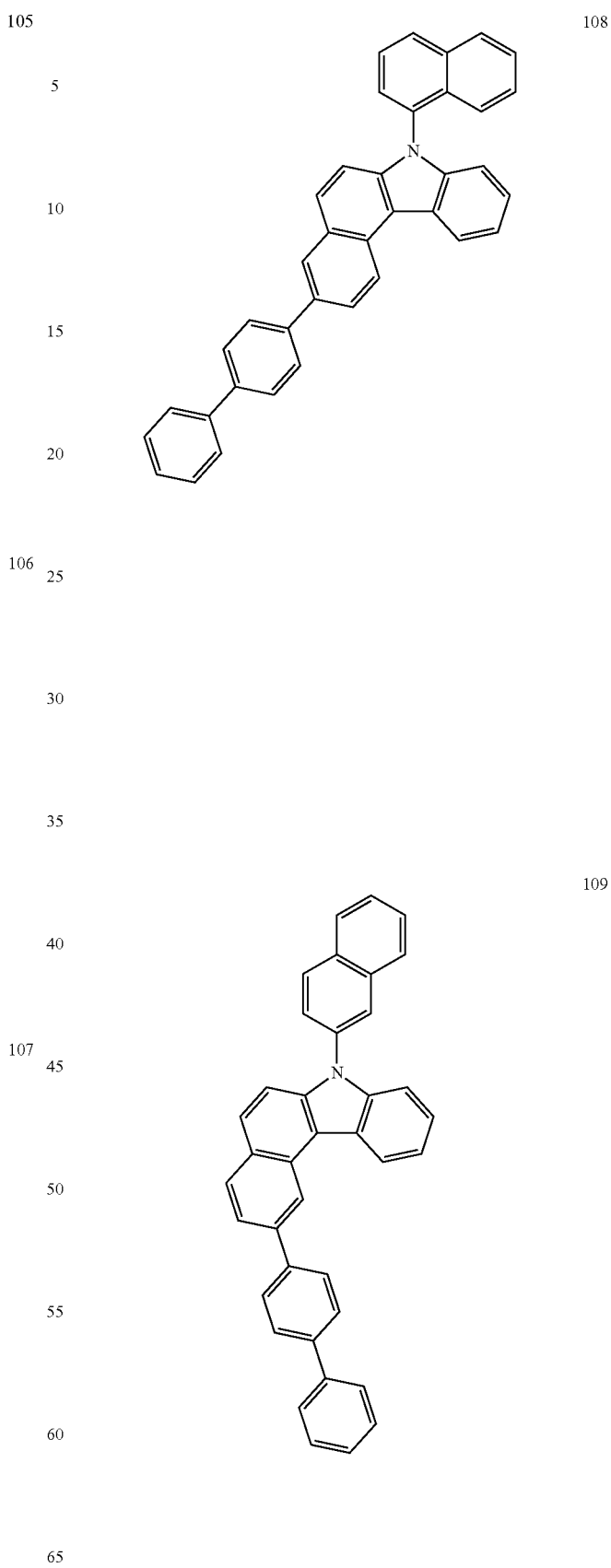

-continued
110
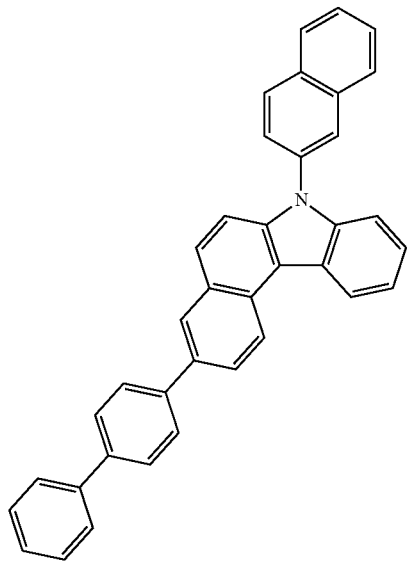
111
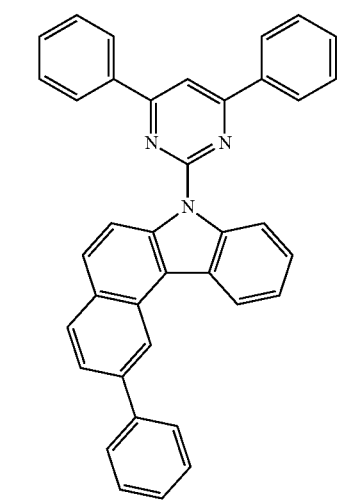
112
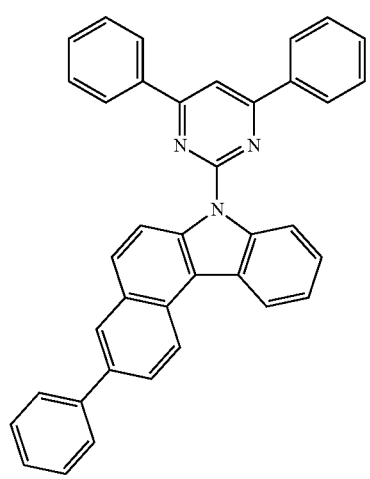
-continued
113
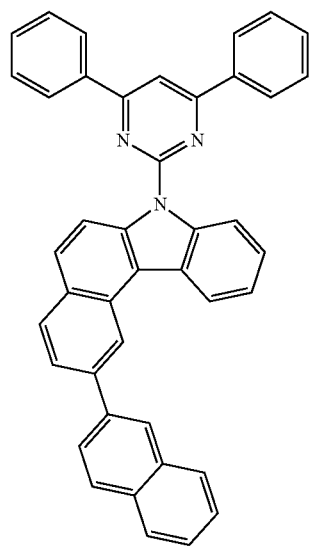
114
115

399
-continued
116
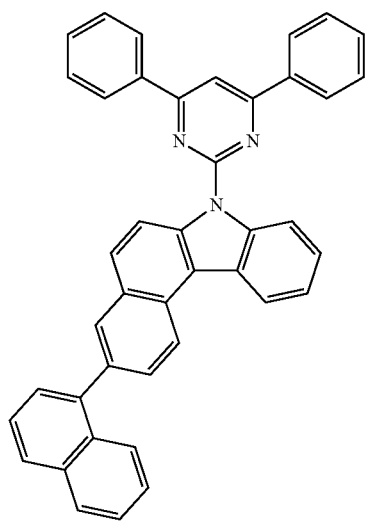
117
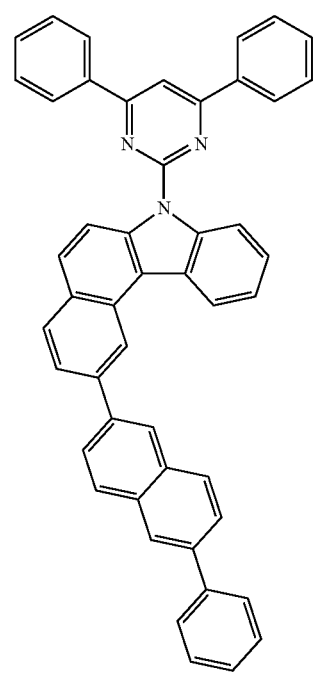
400
-continued
118
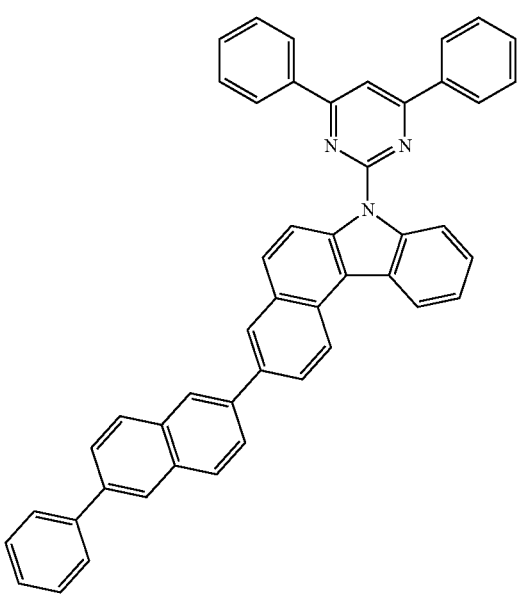
119
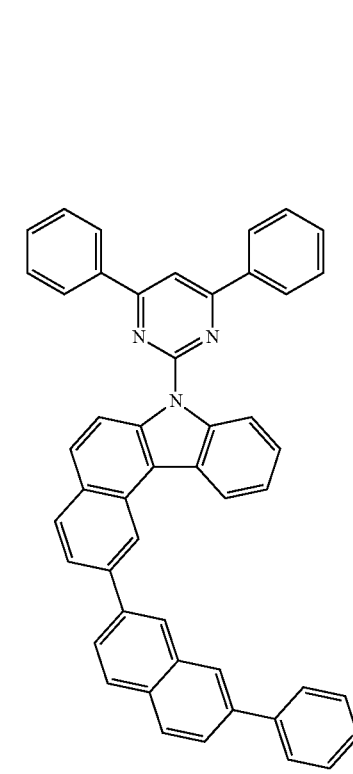

401
-continued
120
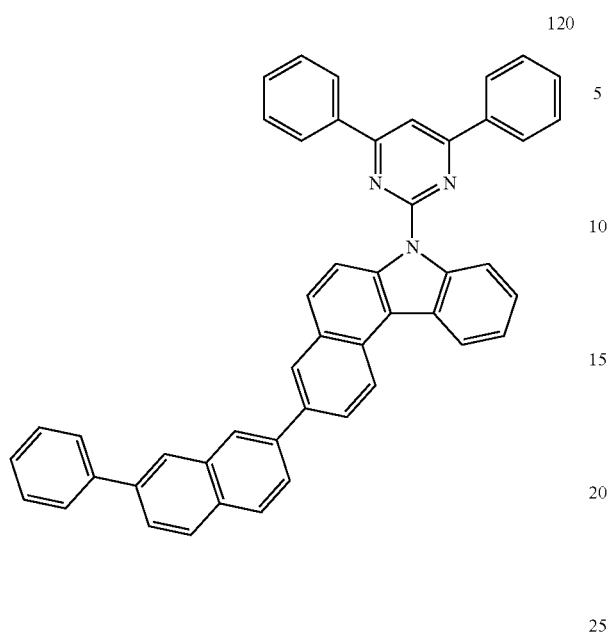
402
-continued
122
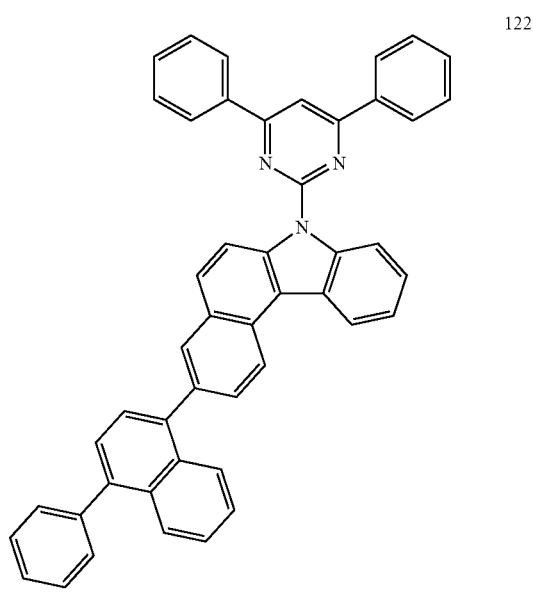
121
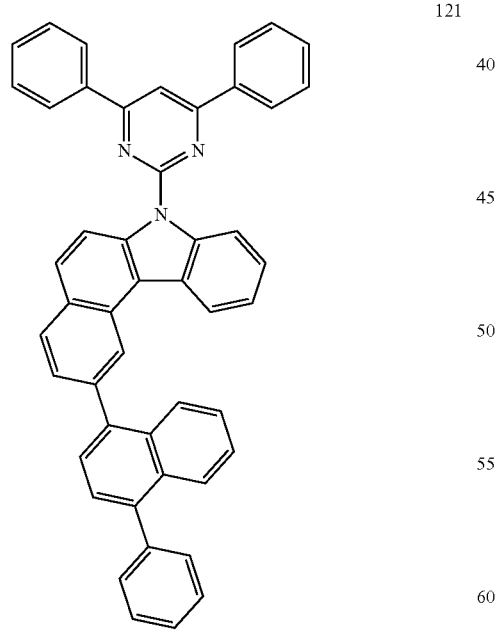
123
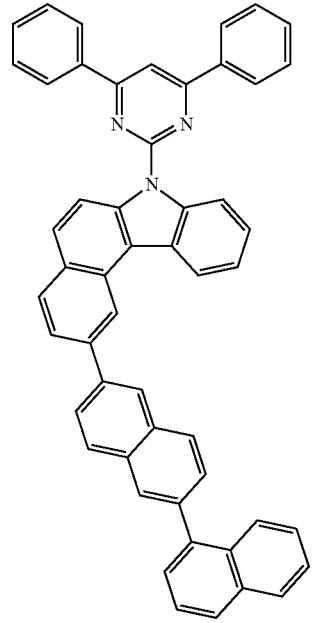

403
-continued
124
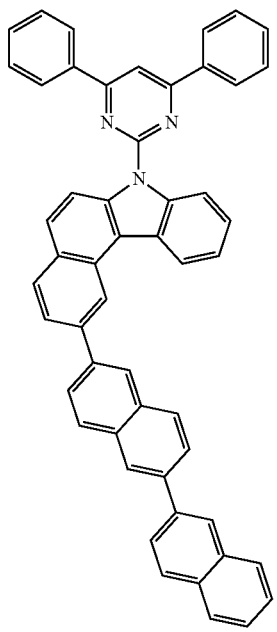
404
-continued
126
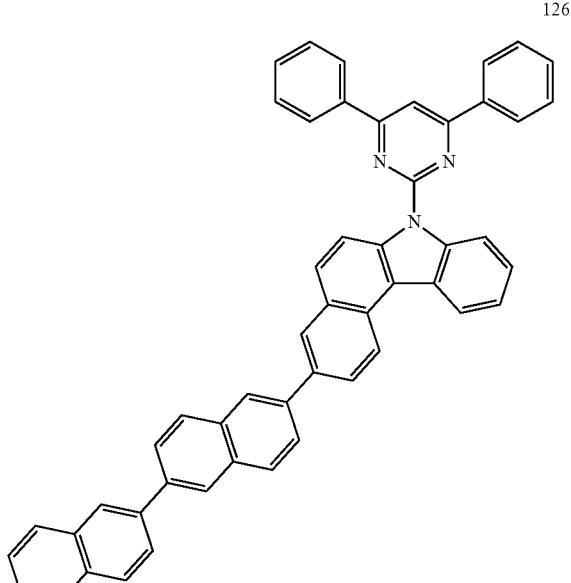
125
127
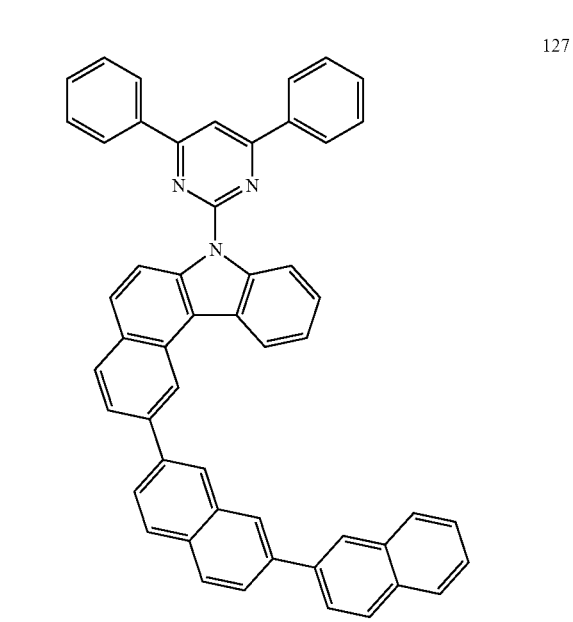

405
-continued
406
-continued
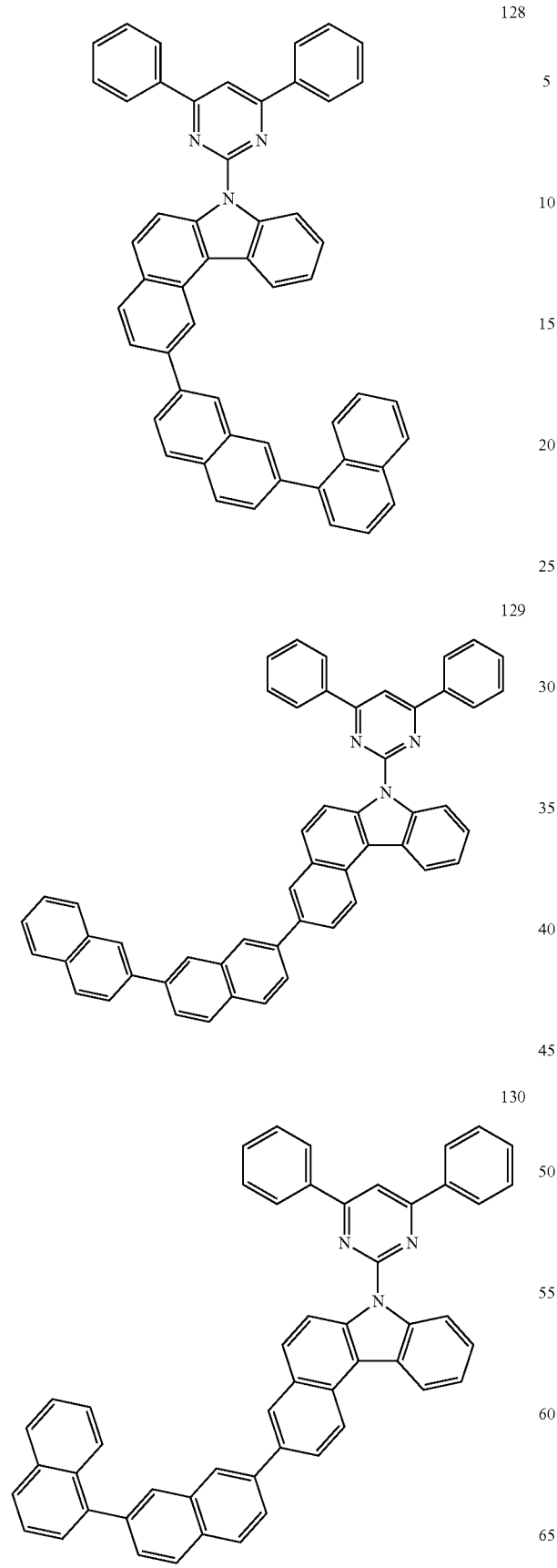
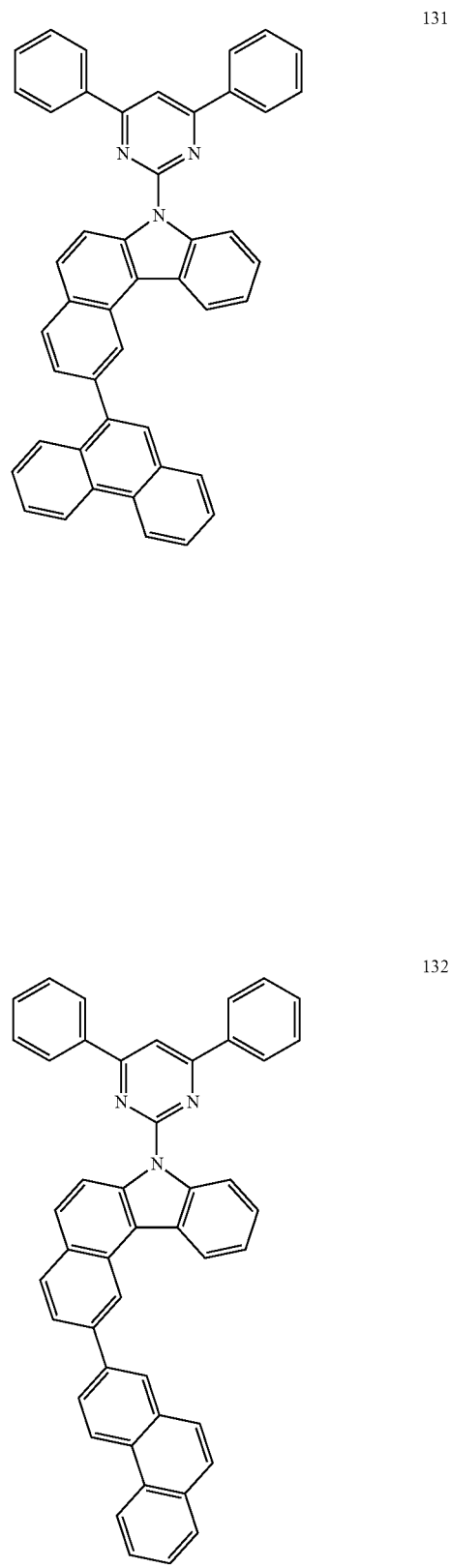

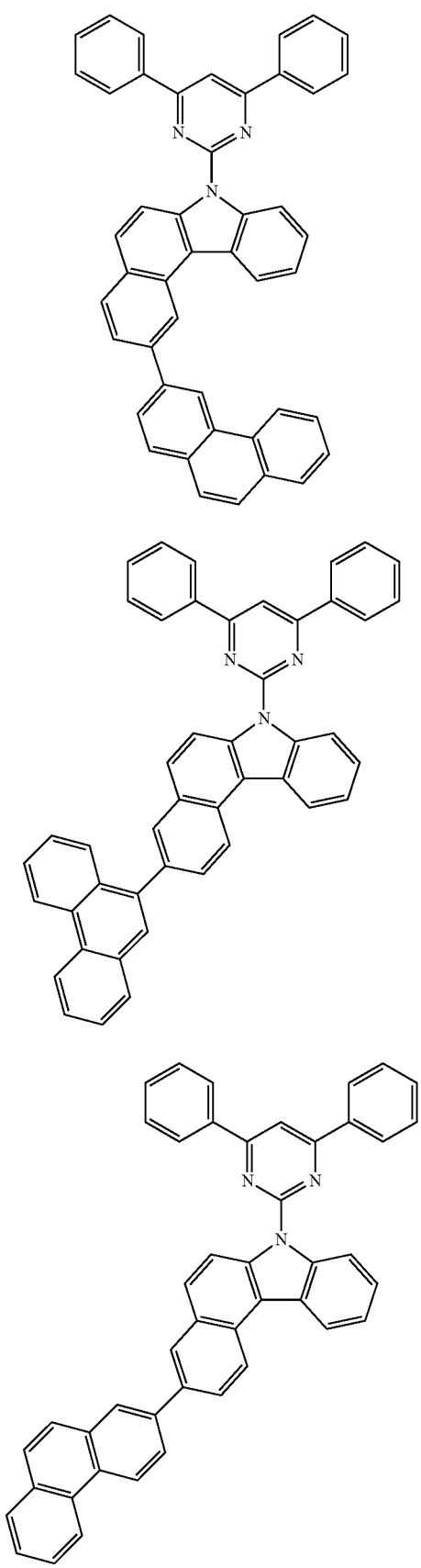
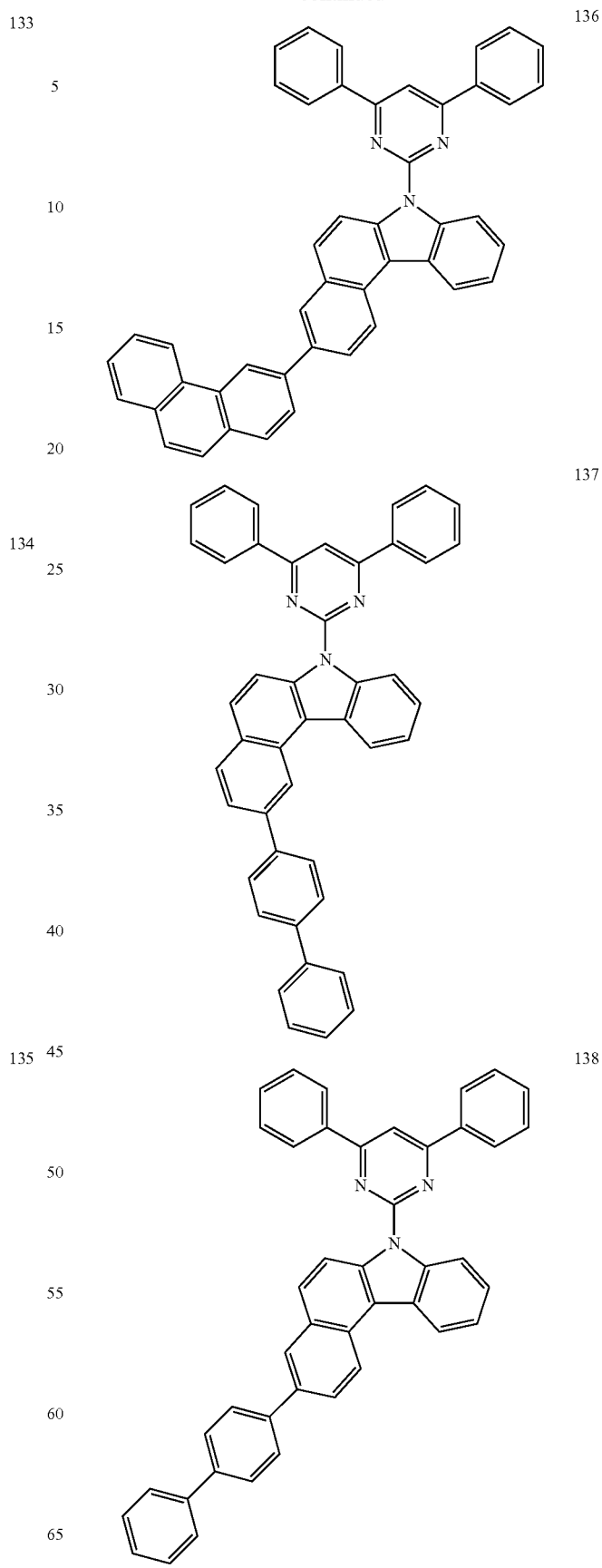

-continued
139
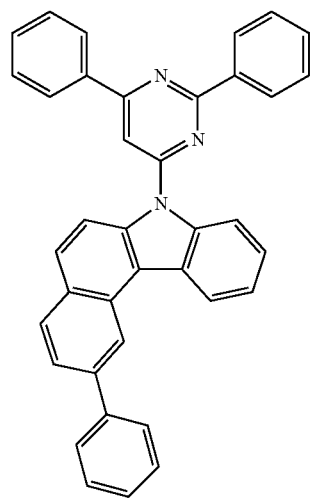
140
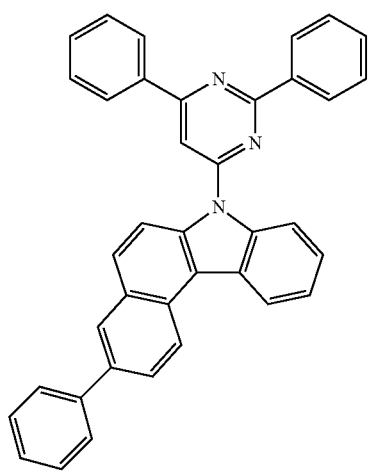
141
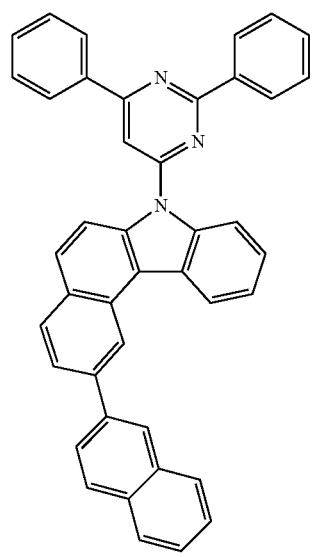
-continued
142
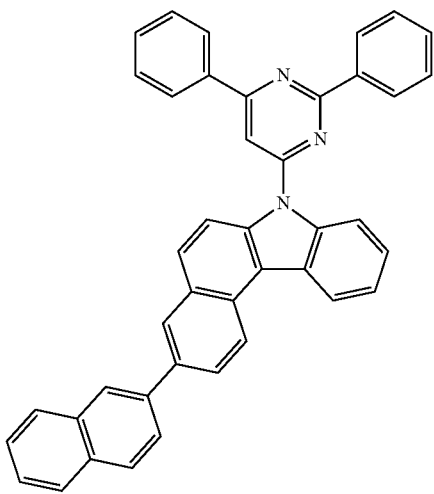
143
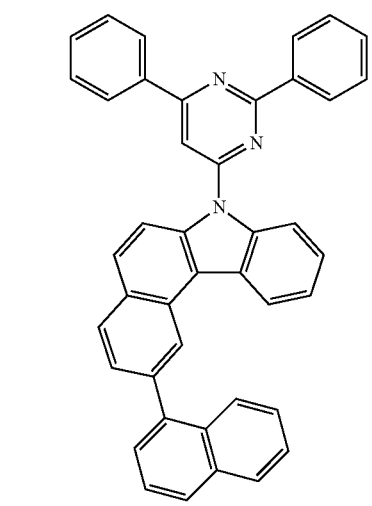
144
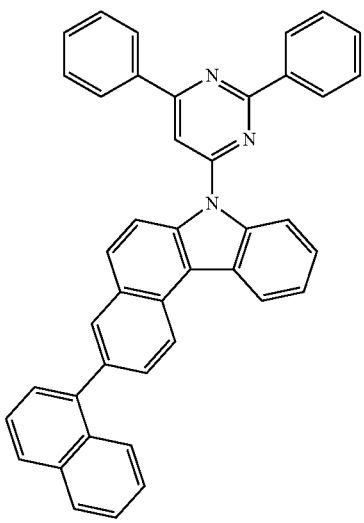

411
-continued
145
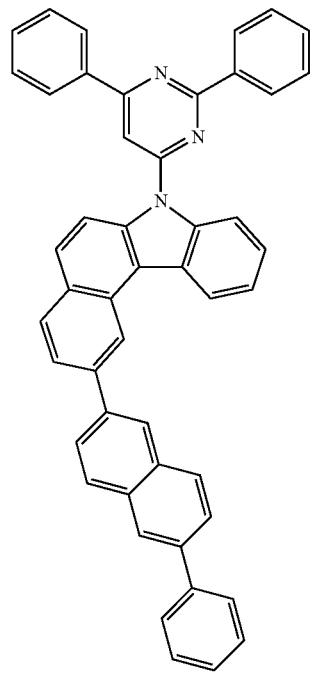
146
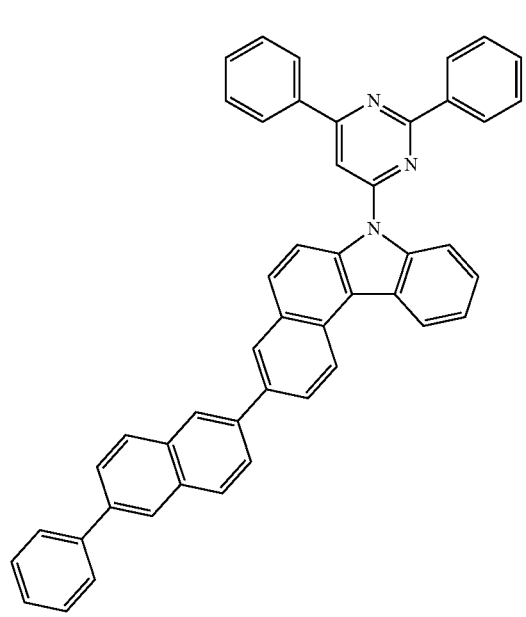
412
-continued
147
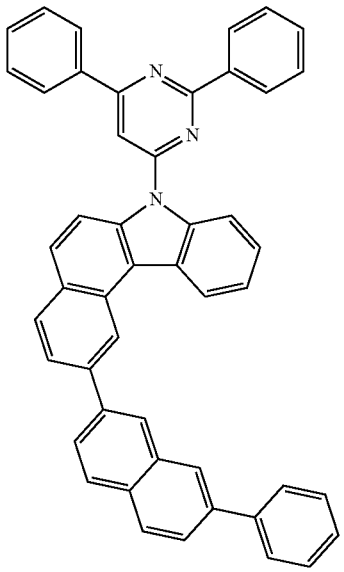
148
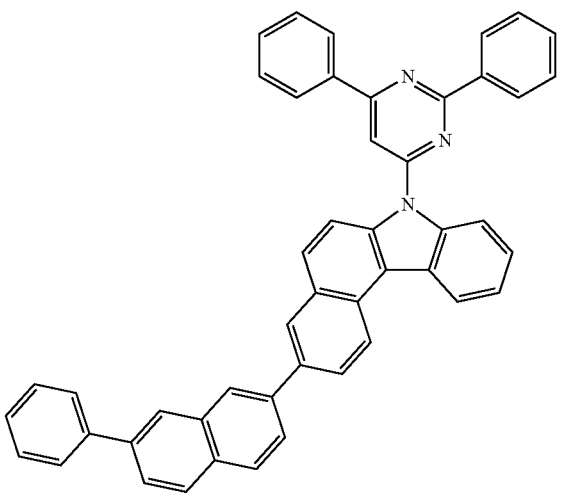

413
-continued
149
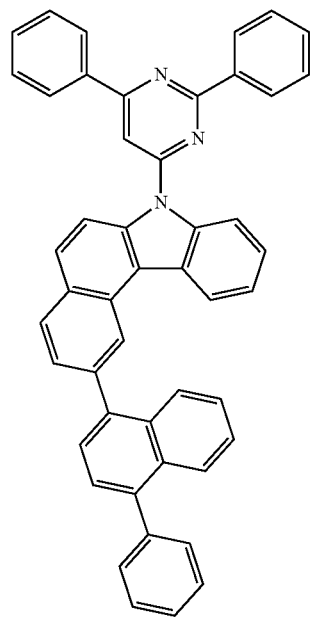
150
414
-continued
151
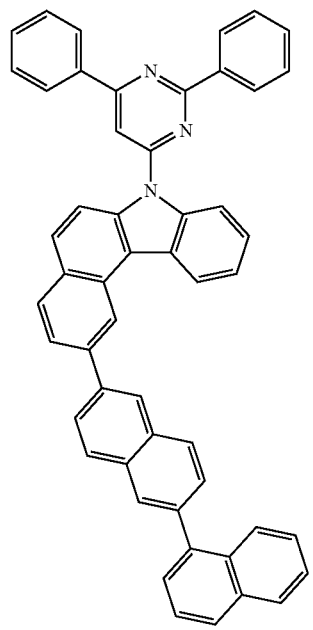
152
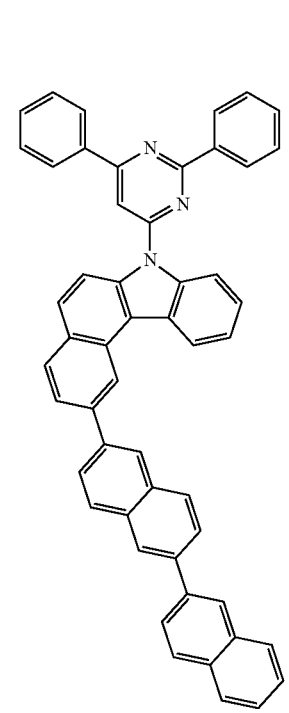

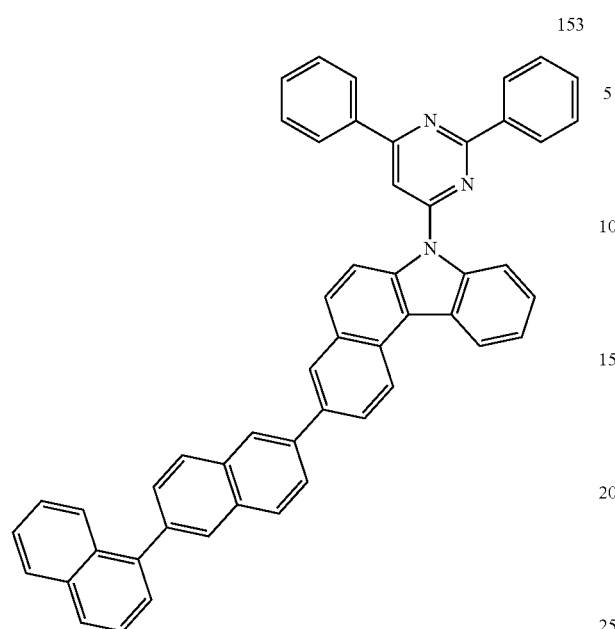
153
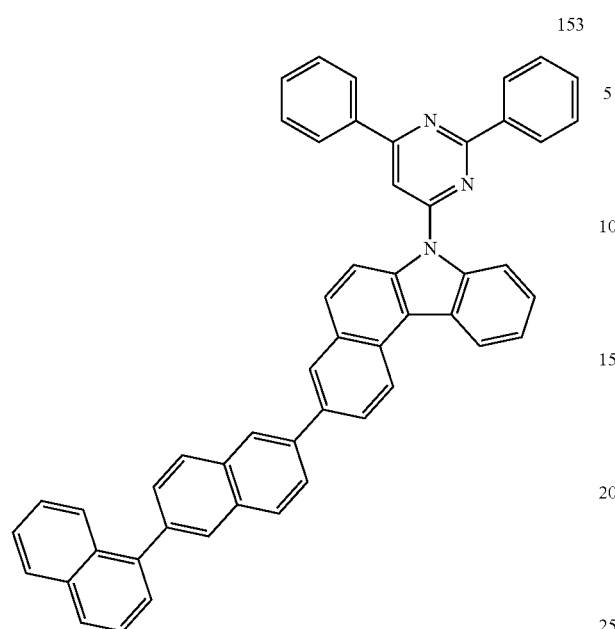
154
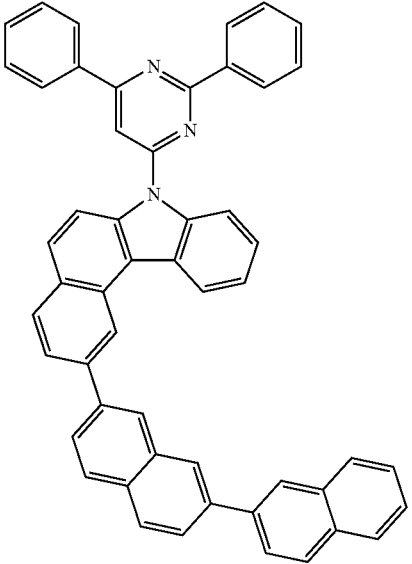
155
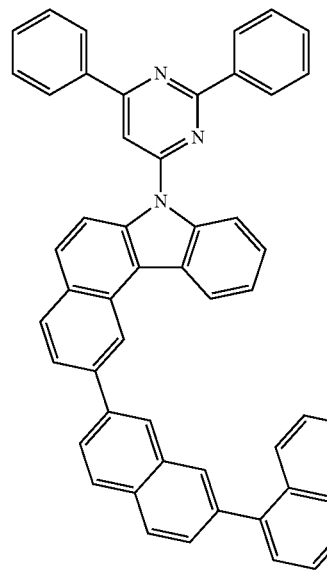
156
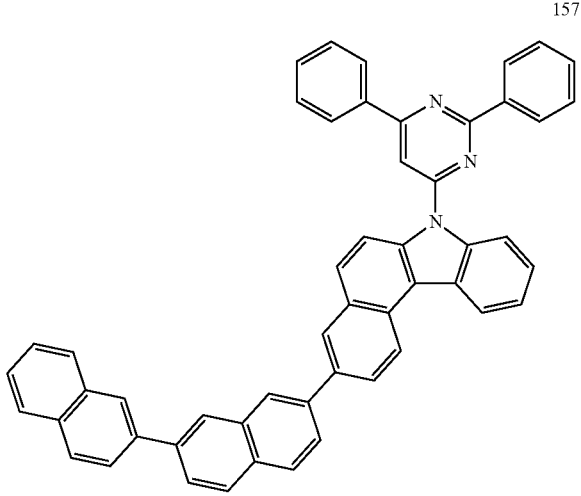
157

-continued
158
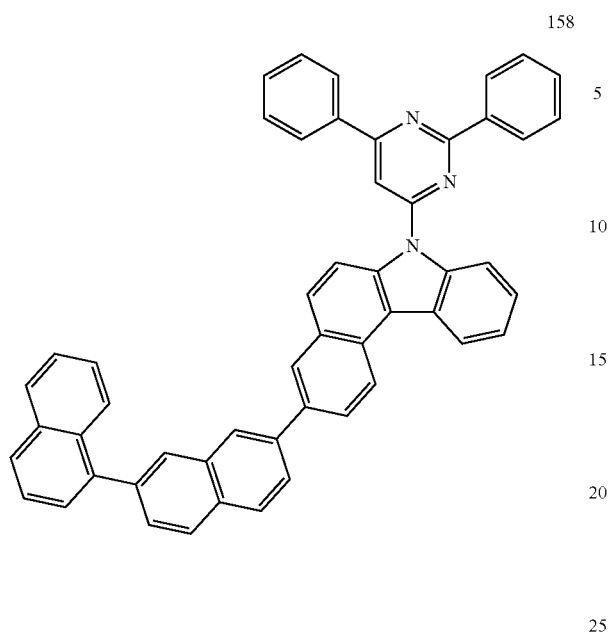
159
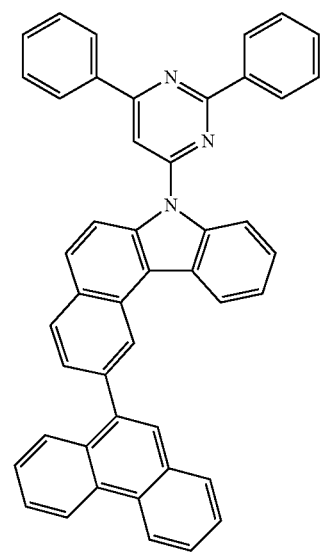
-continued
160
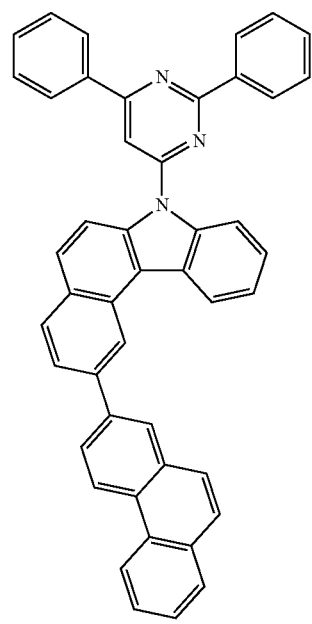
161
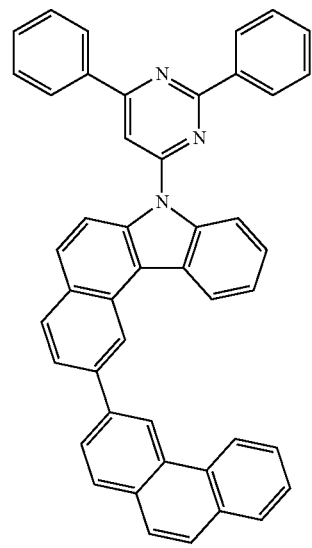

419
-continued
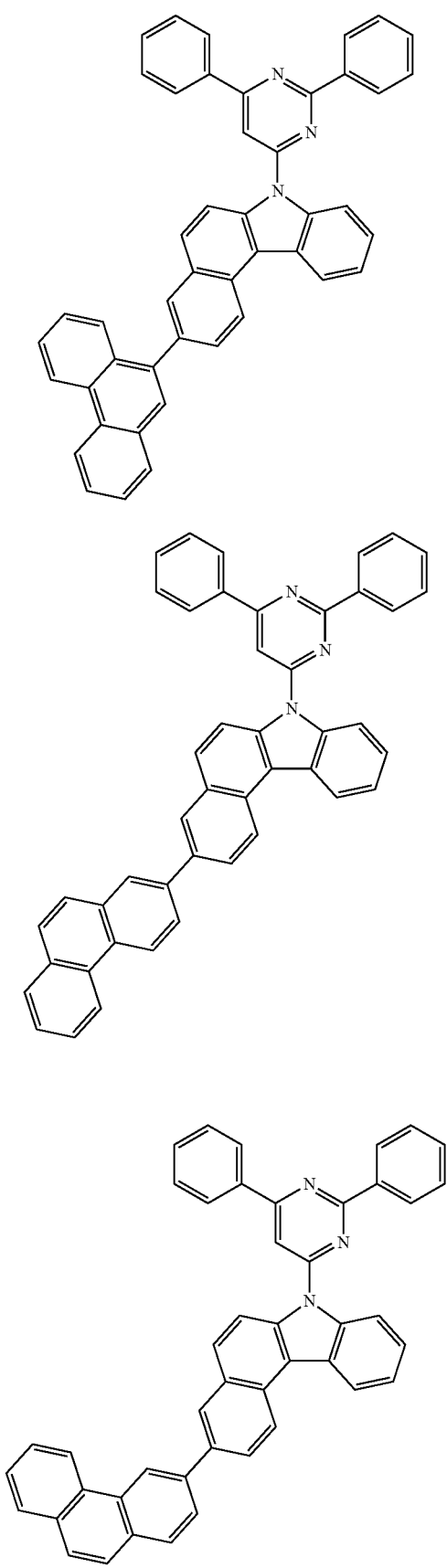
420
-continued
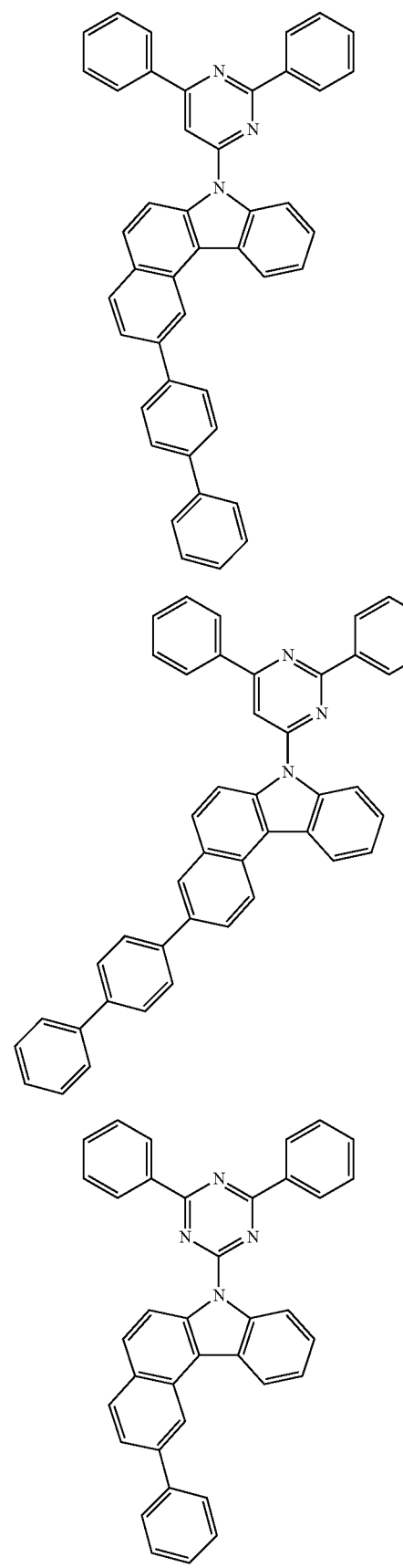

421
-continued
422
-continued
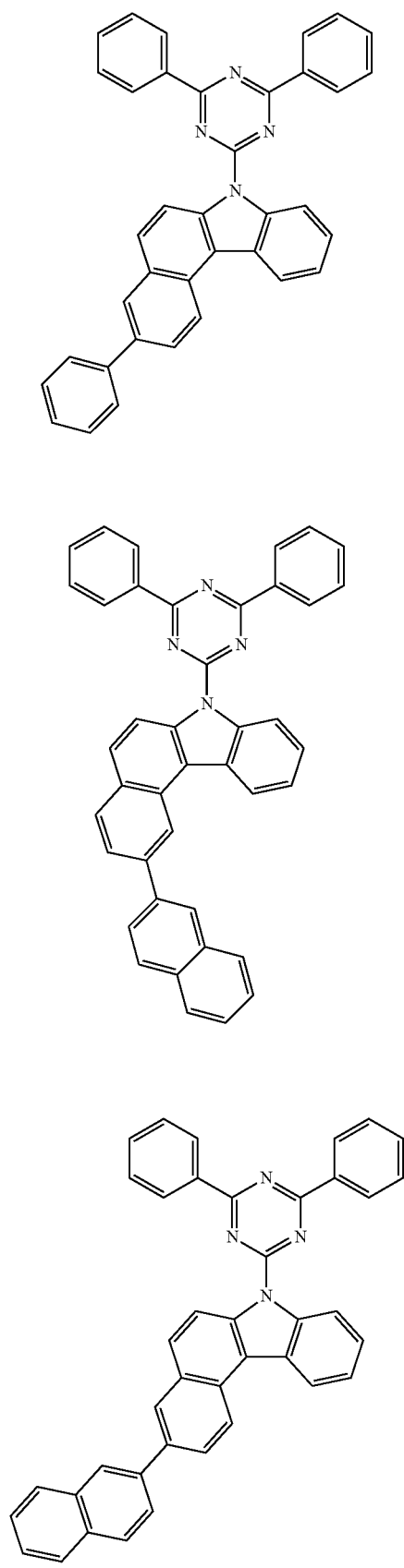
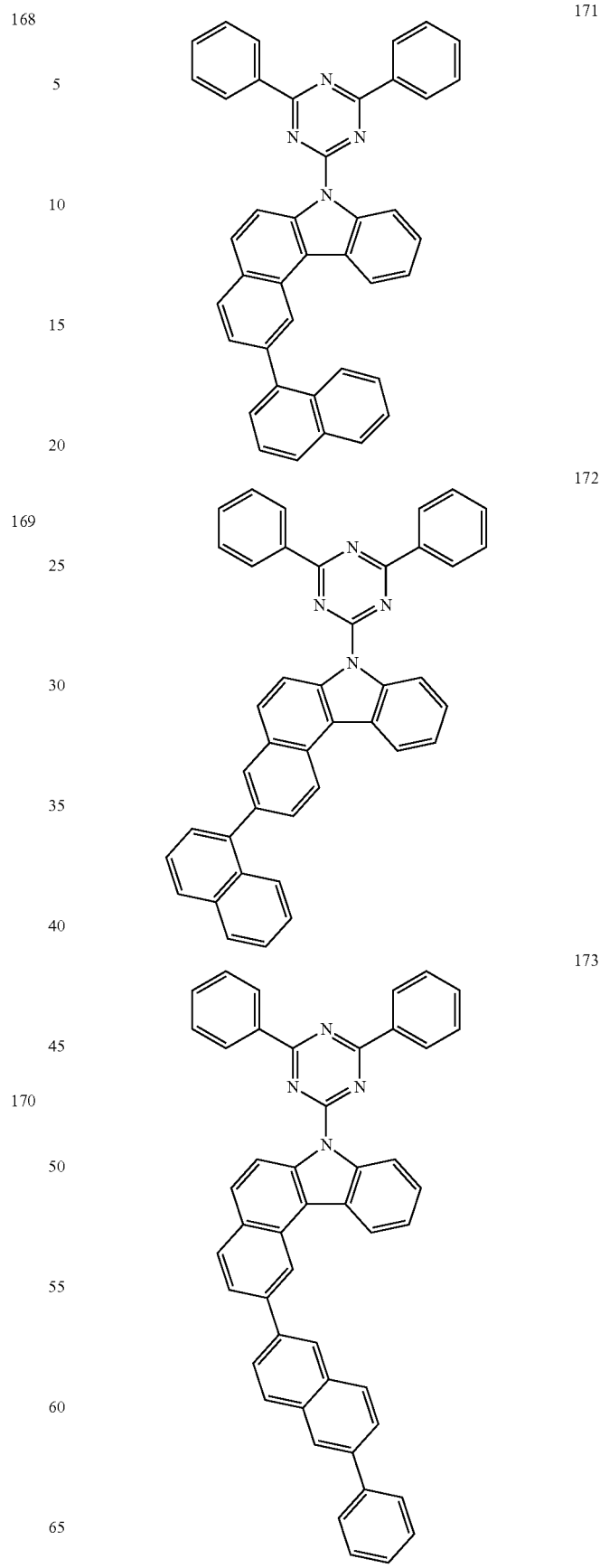

423
-continued
174
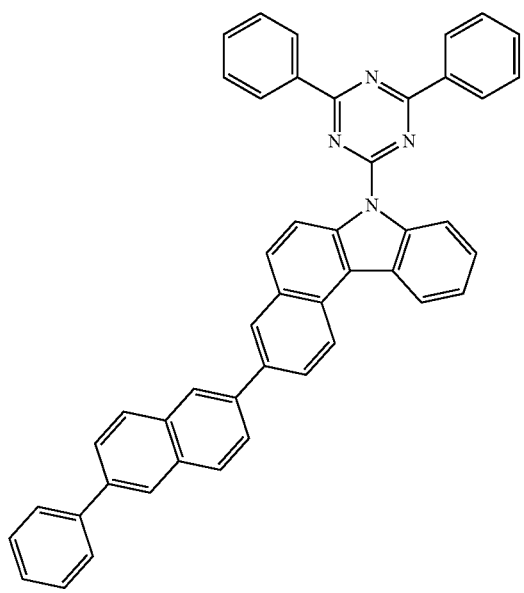
424
-continued
176
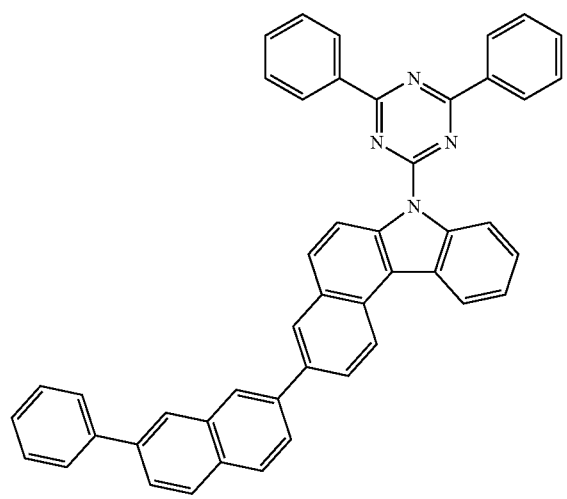
175
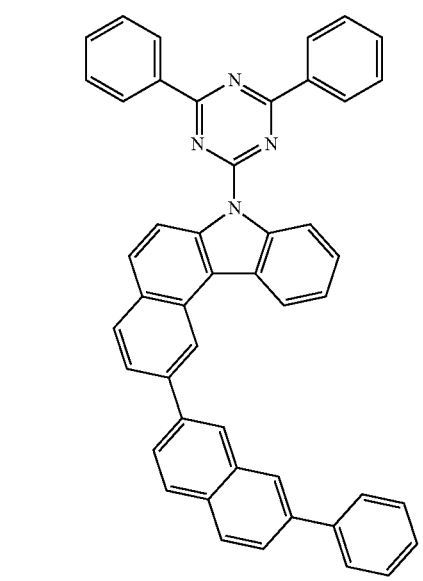
177
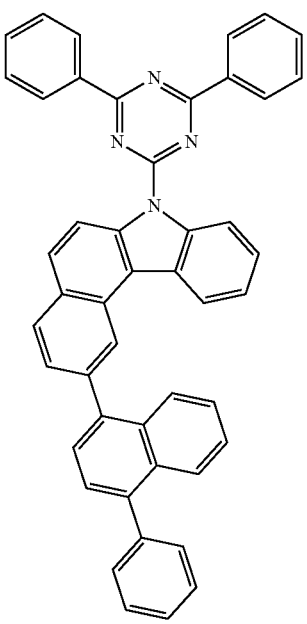

425
-continued
426
-continued
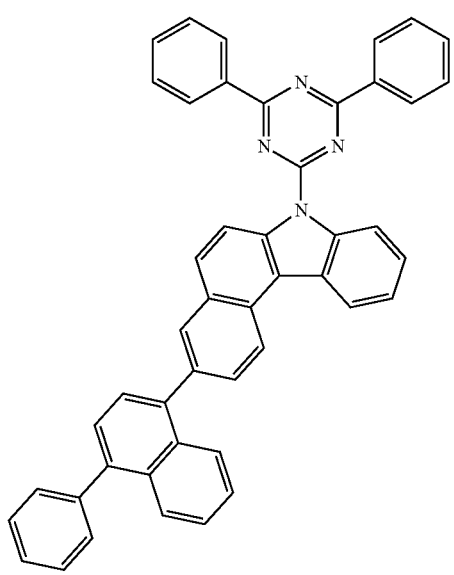
178
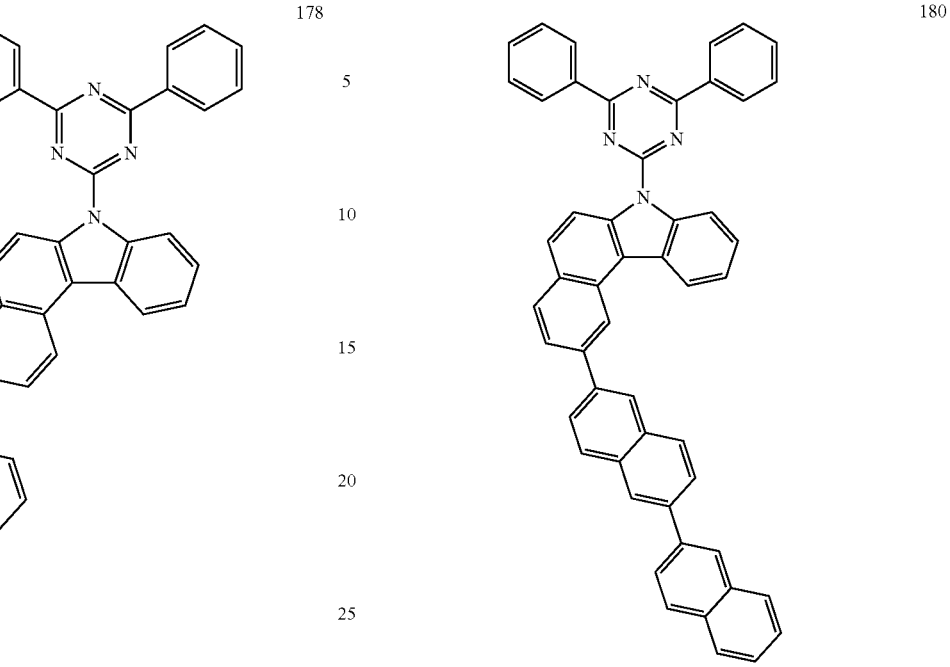
180
179
181
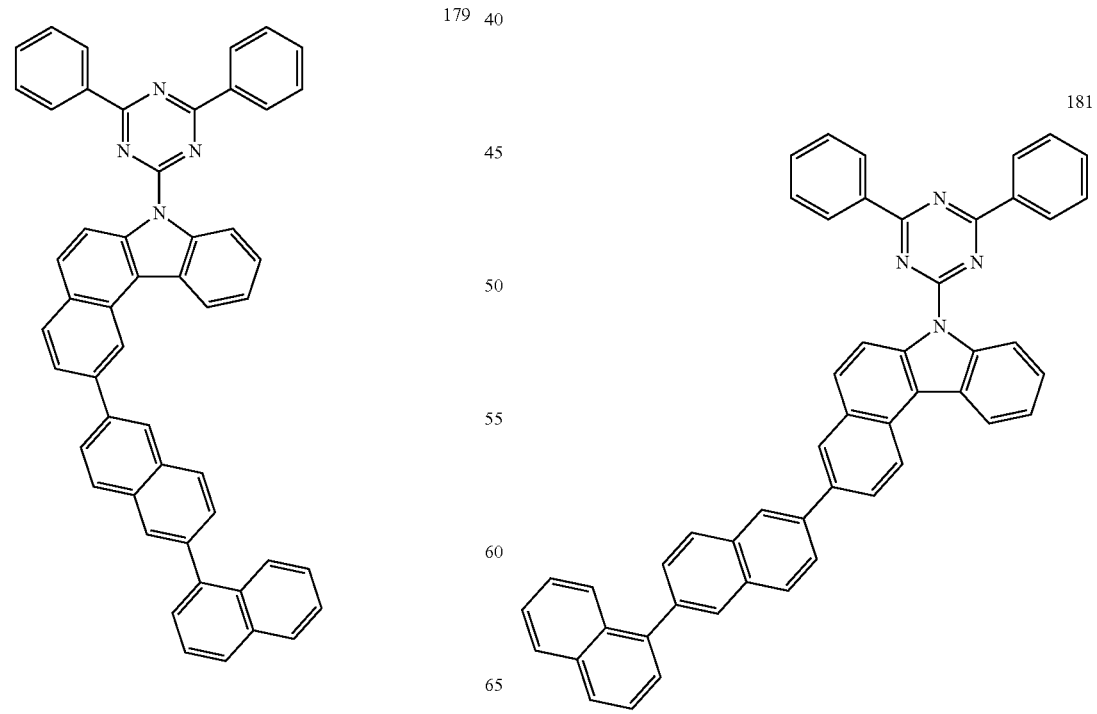

-continued
182
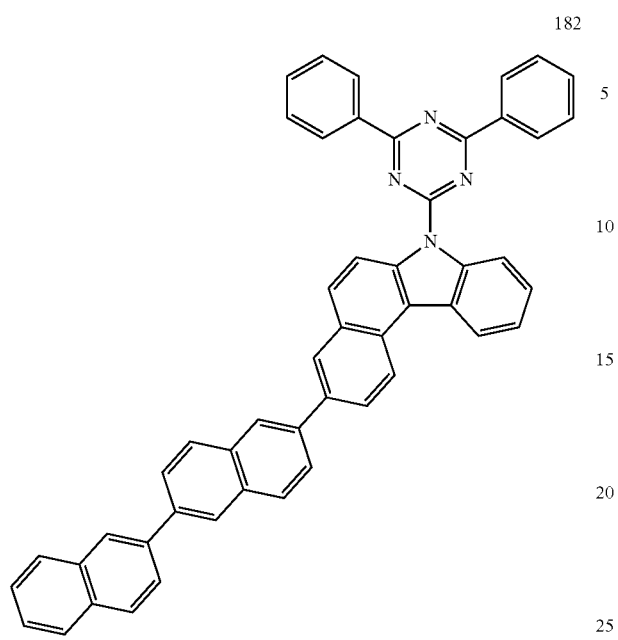
183
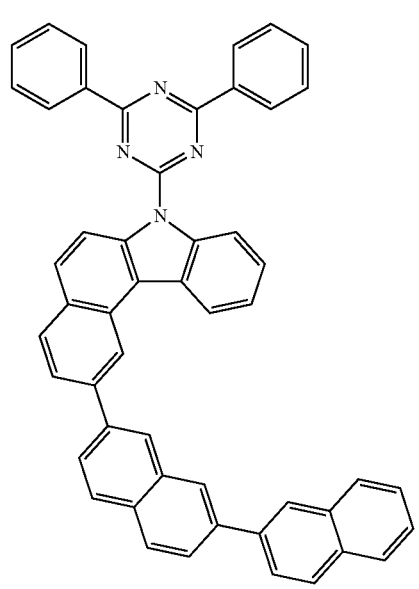
184
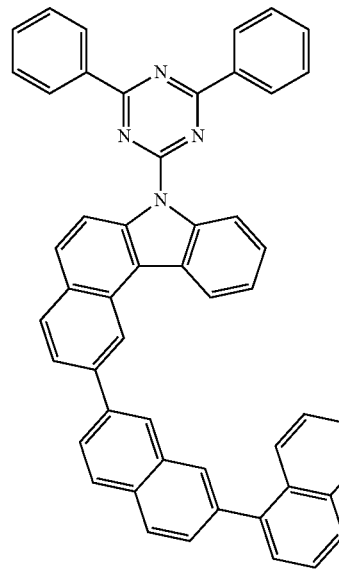
185
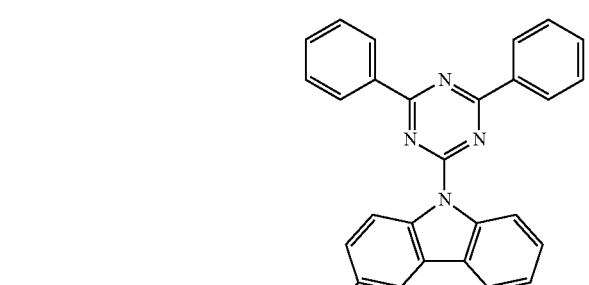
186
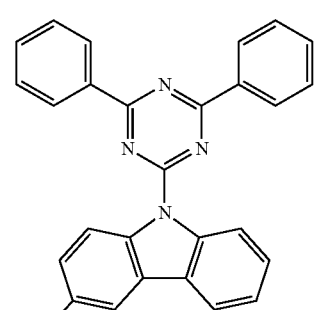

429
-continued
187
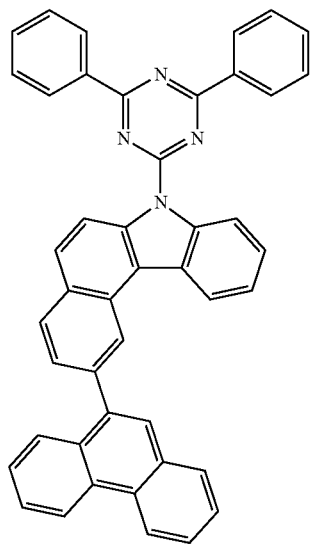
188
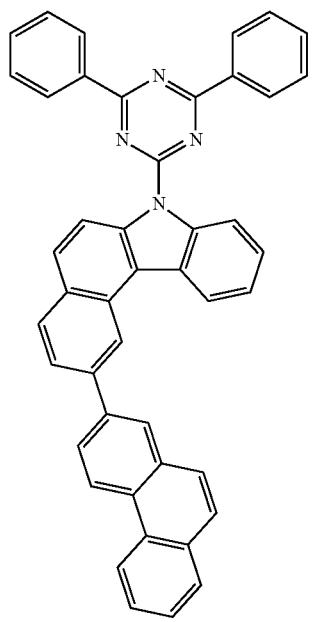
430
-continued
189
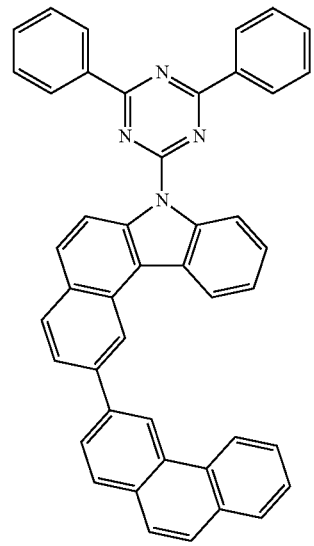
190
191
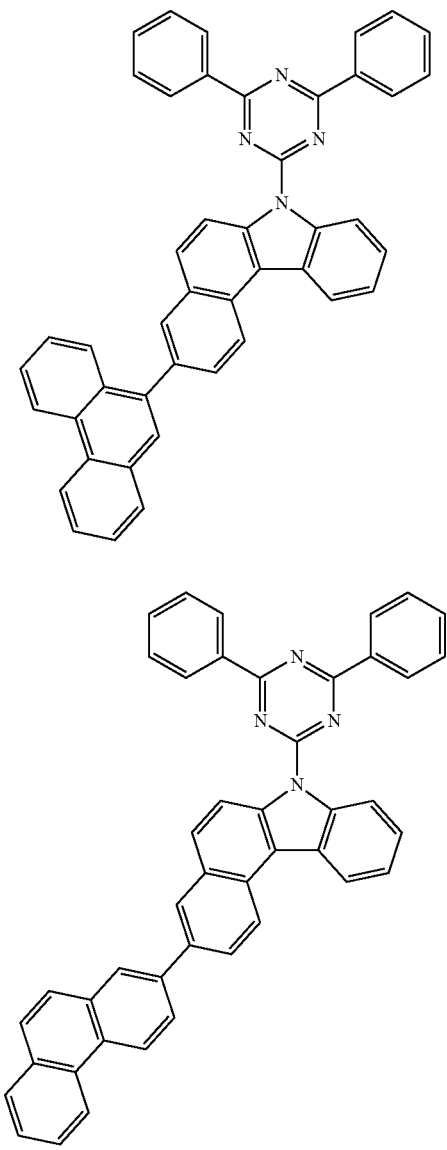

192
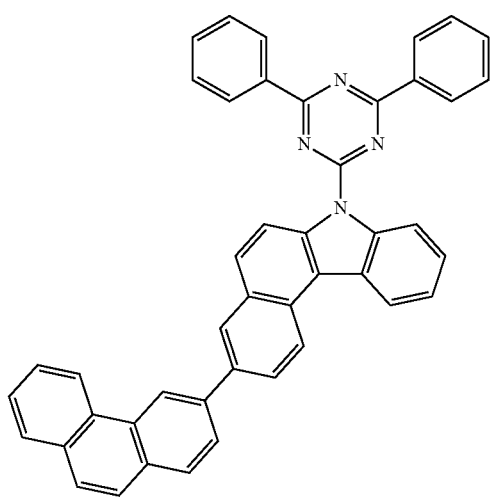
194
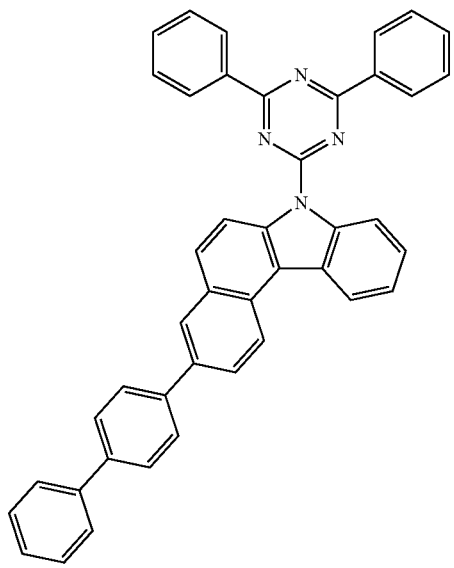
193
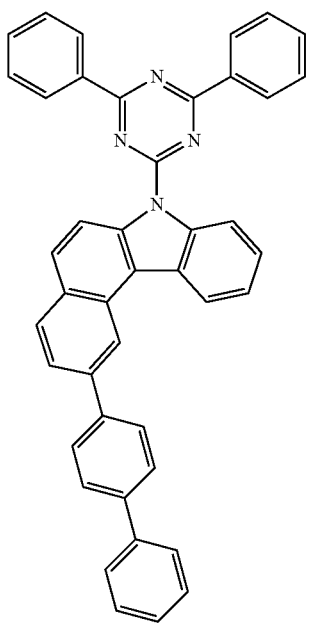
195
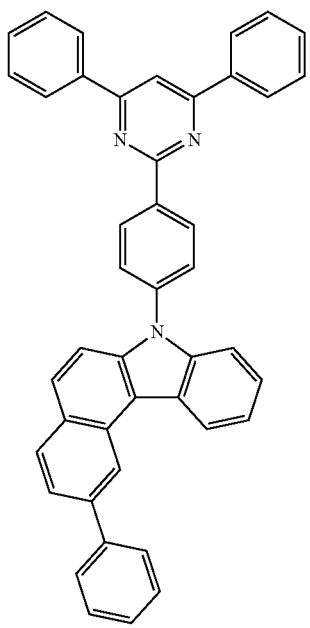

433
-continued
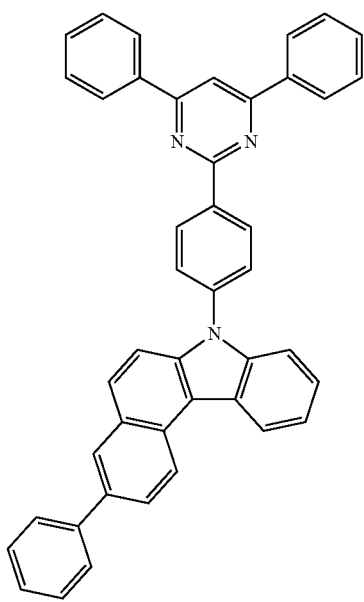
196
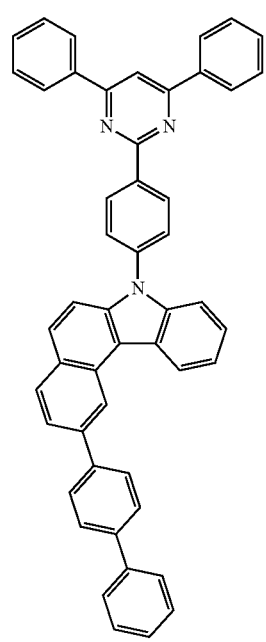
197
434
-continued
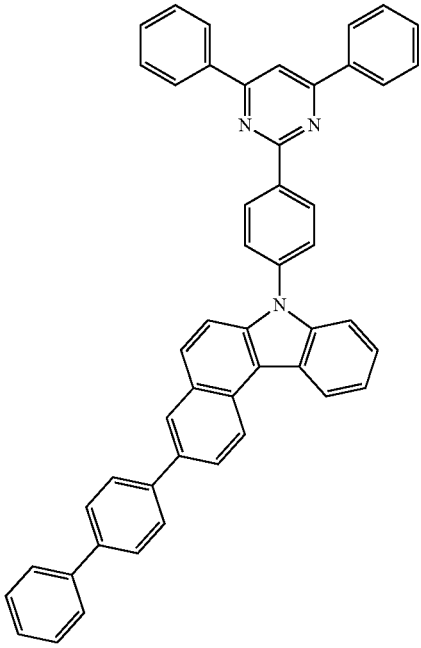
198
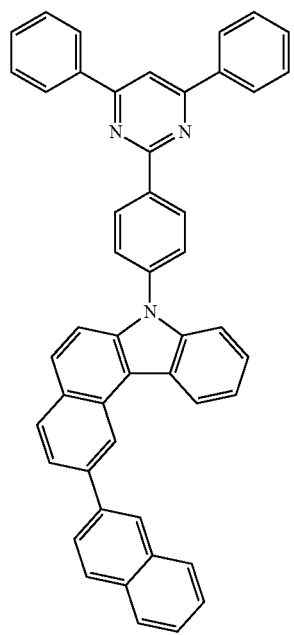
199

435
-continued
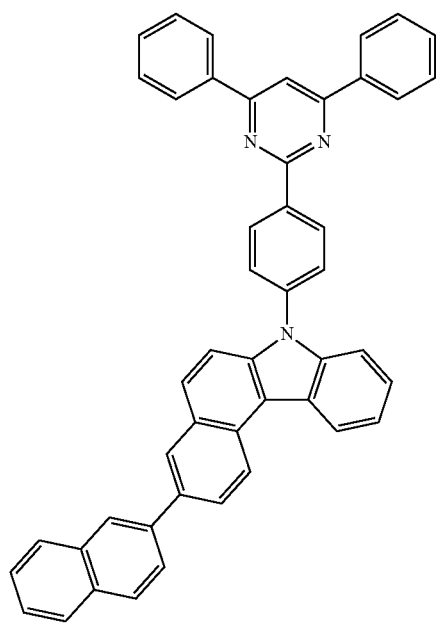
200
201
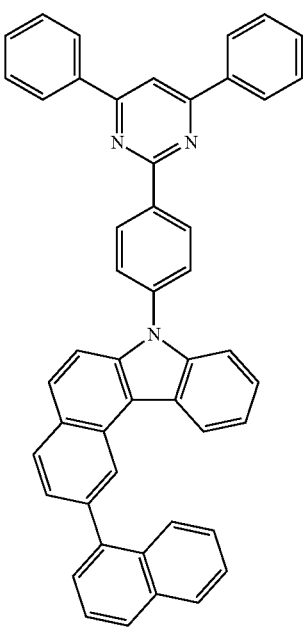
436
-continued
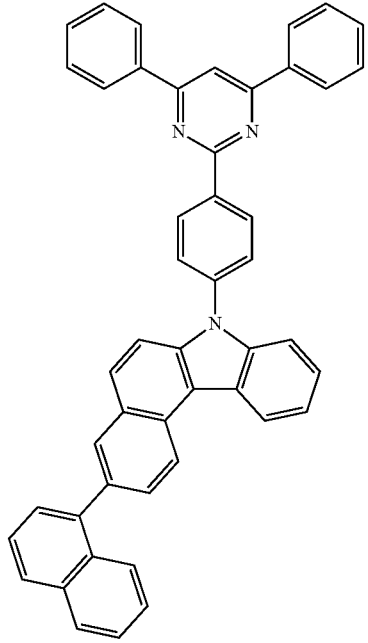
202
203
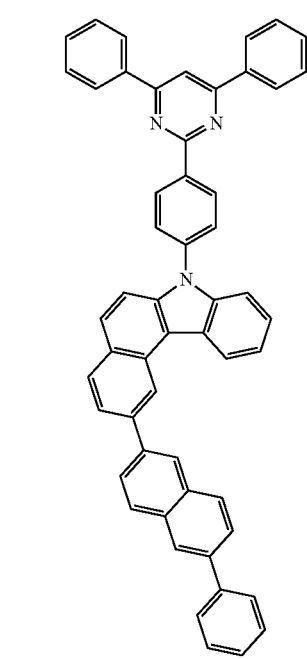

437
-continued
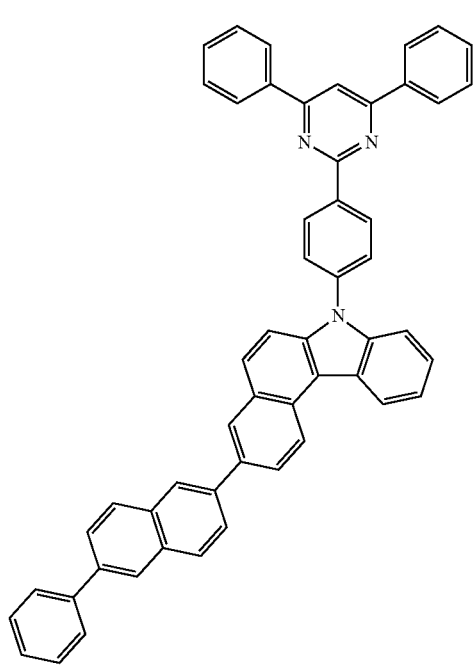
204
438
-continued
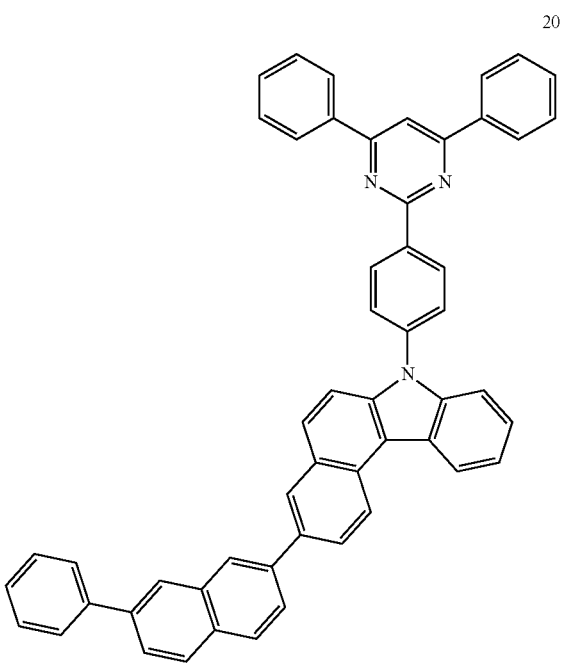
206
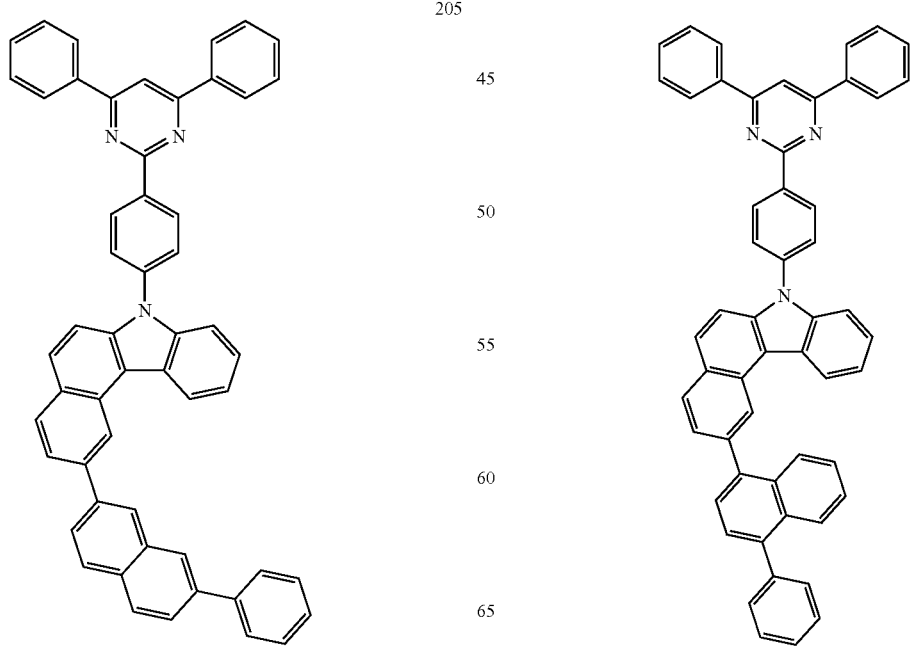
205
207

439
-continued
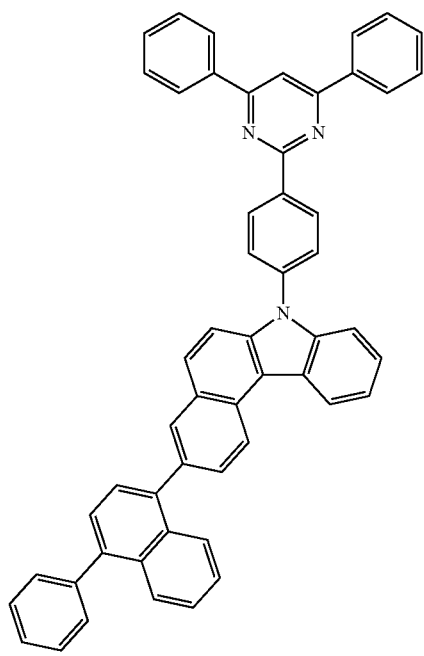
208
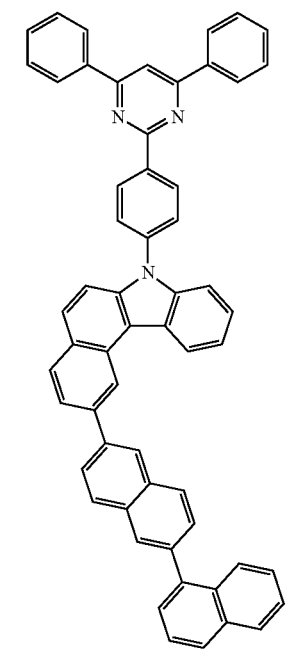
209
440
-continued
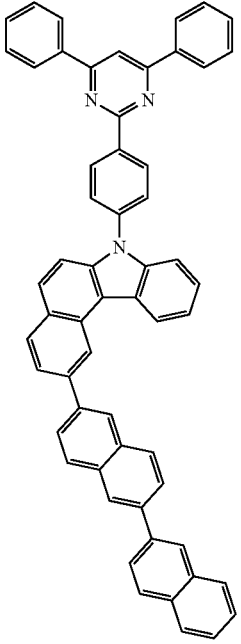
210
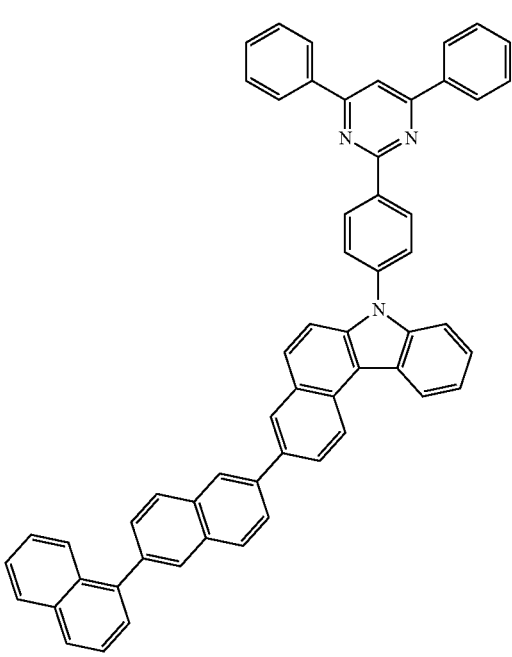
211

441
-continued
212
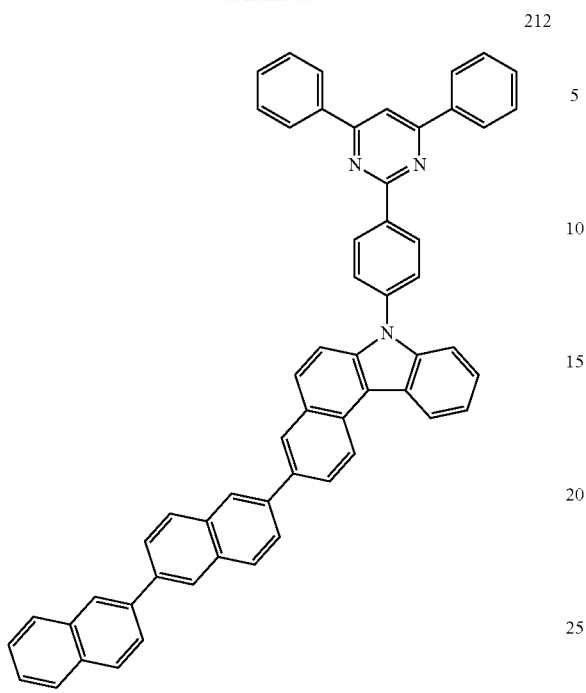
213
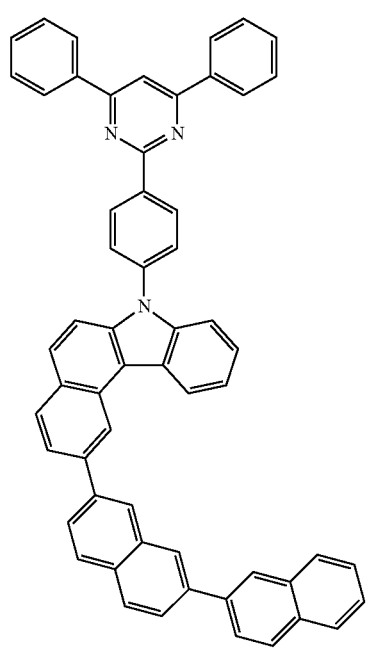
442
-continued
214
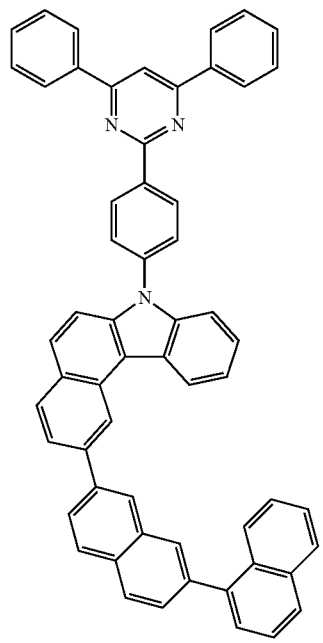
215
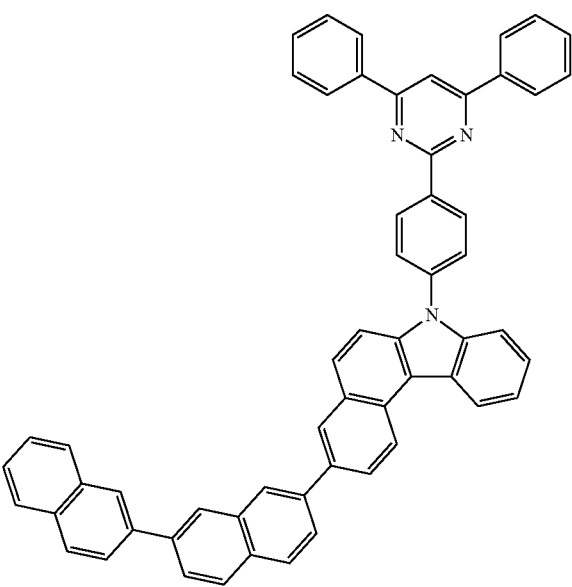

443
-continued
216
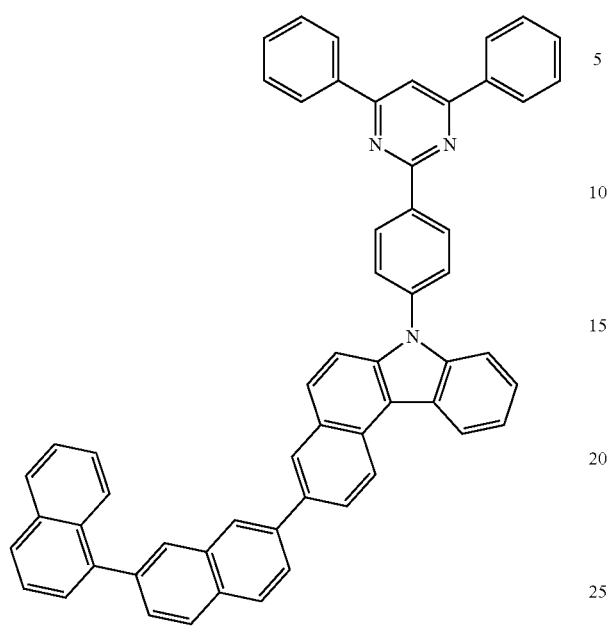
444
-continued
218
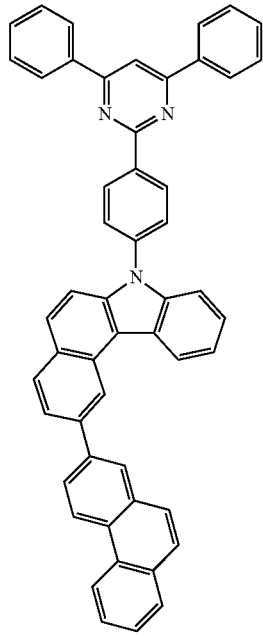
217
219
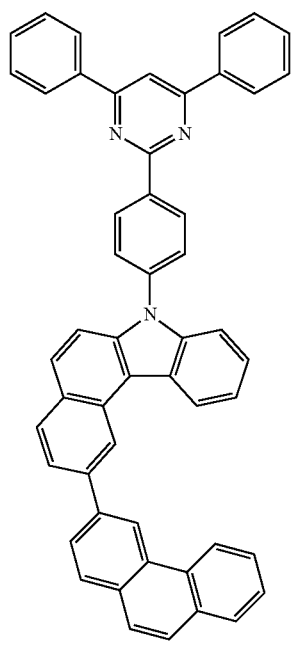

445
-continued
220
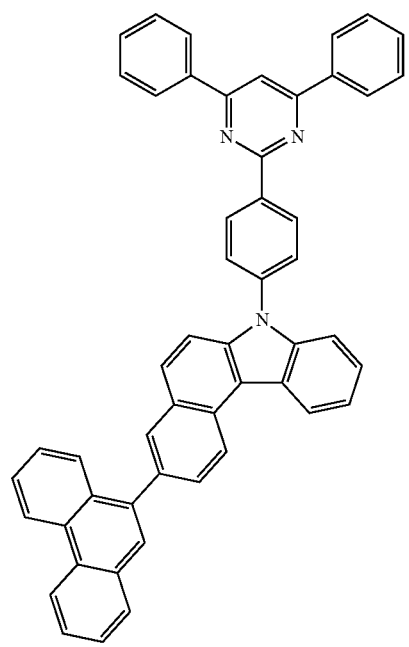
221
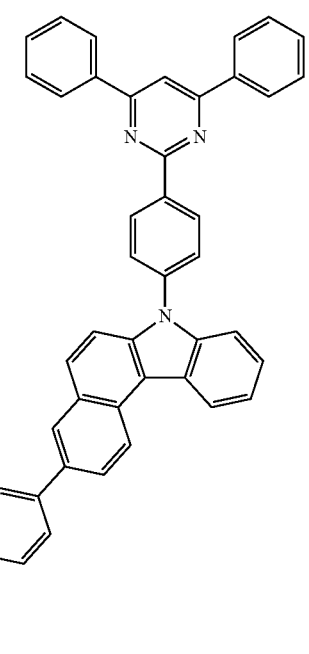
446
-continued
222
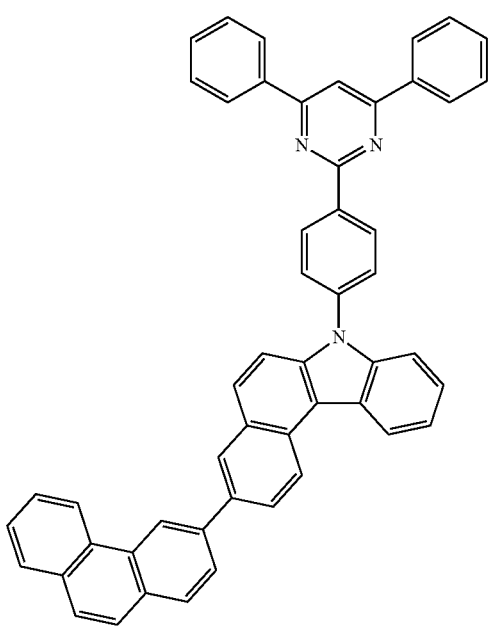
223
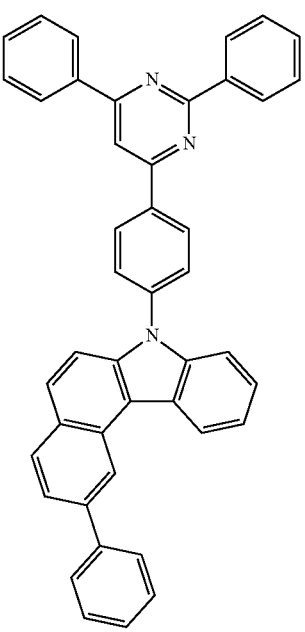

447
-continued
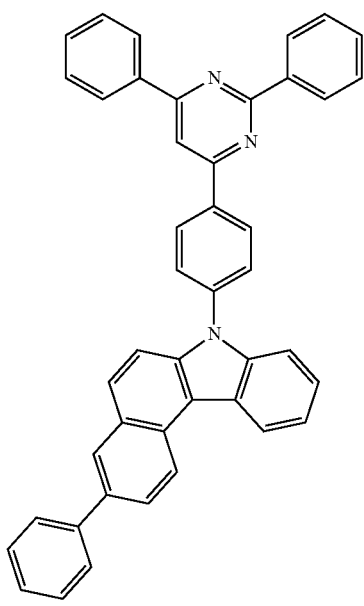
224
448
-continued
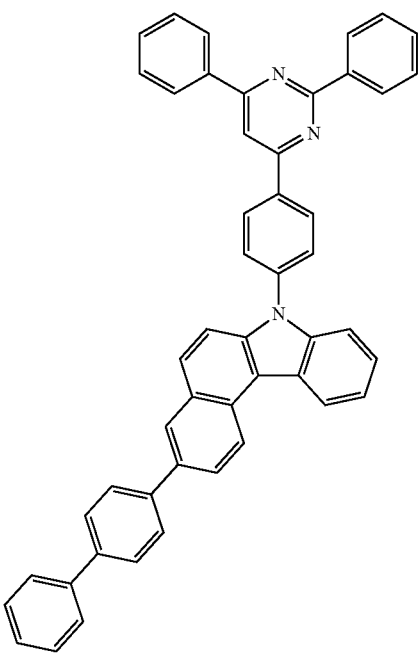
226
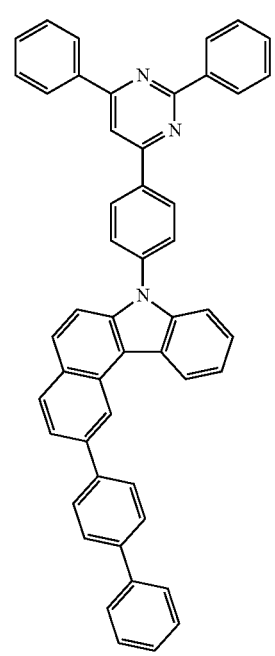
225
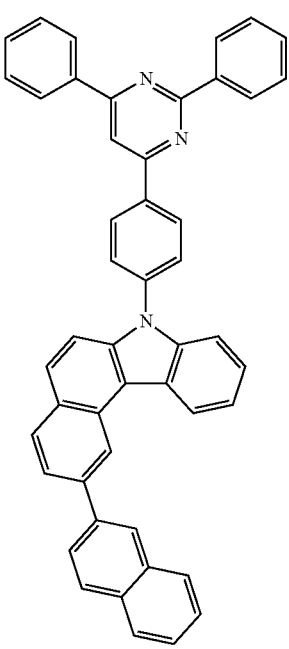
227

449
-continued
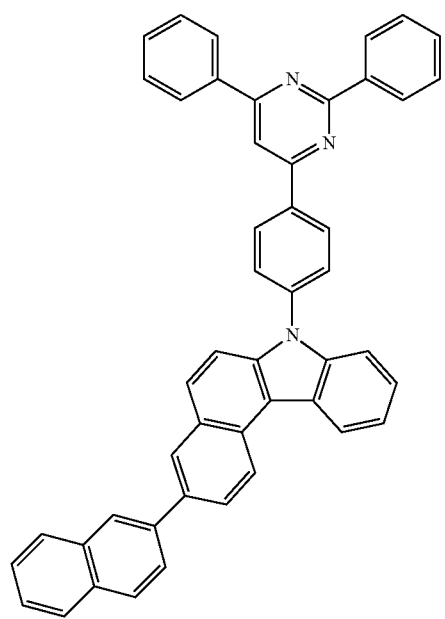
228
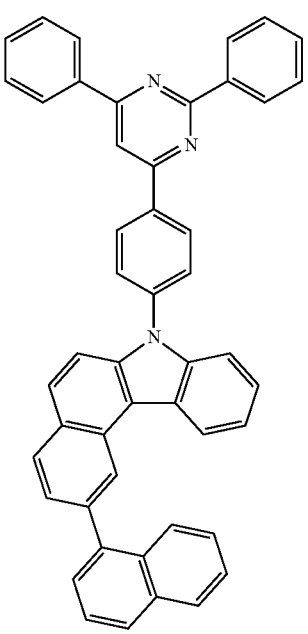
229
450
-continued
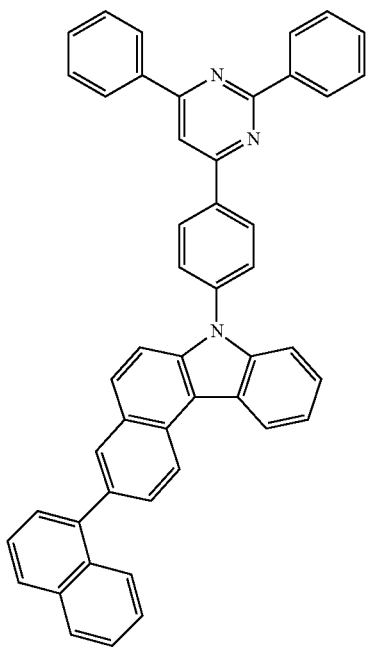
230
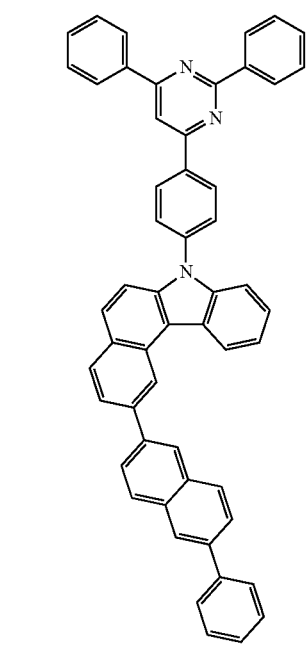
231

451
-continued
232
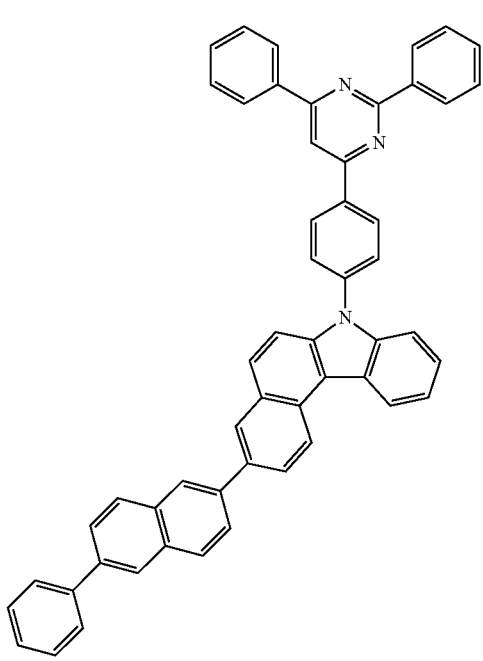
452
-continued
234
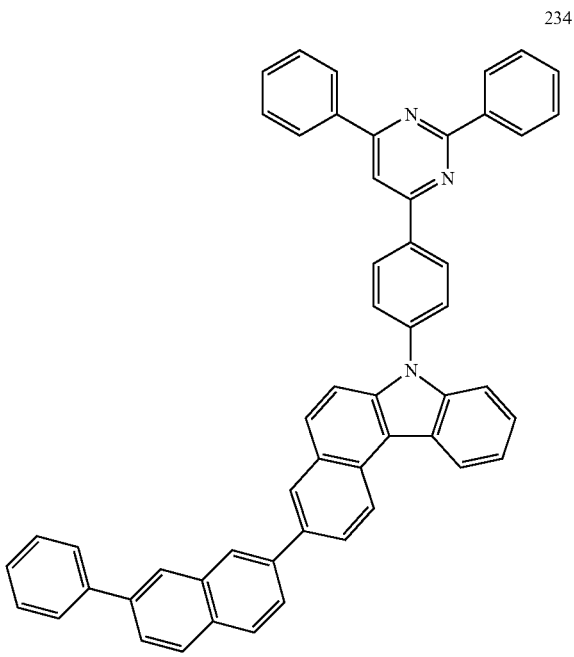
233
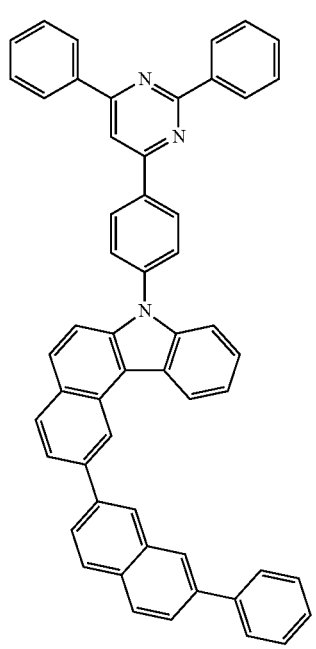
235

453
-continued
236
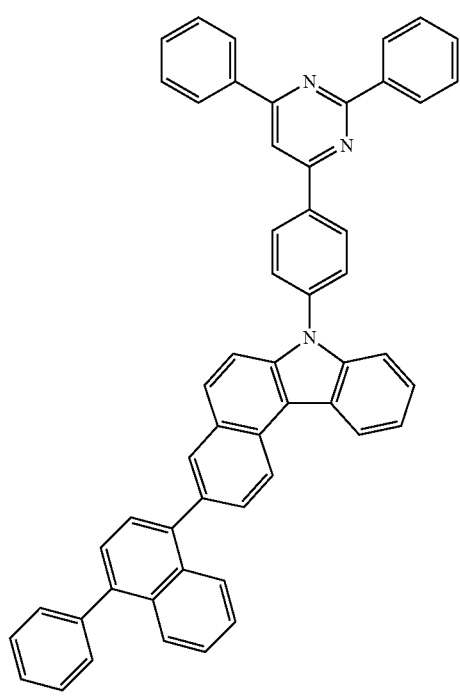
237
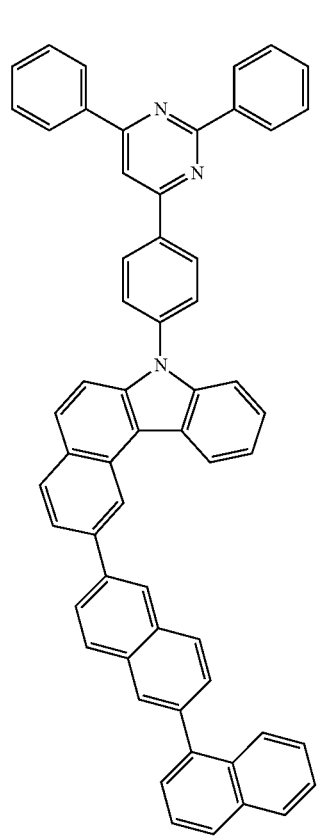
454
-continued
238
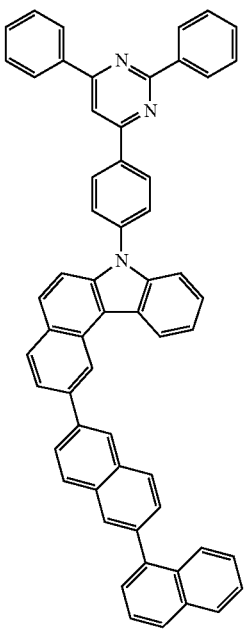
239
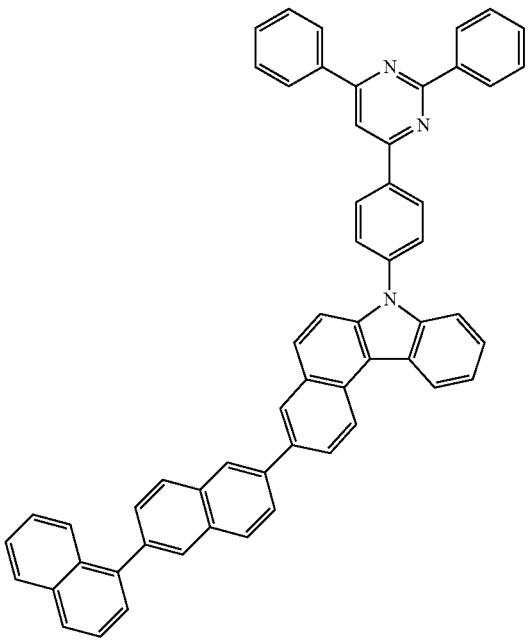

455
-continued
456
-continued
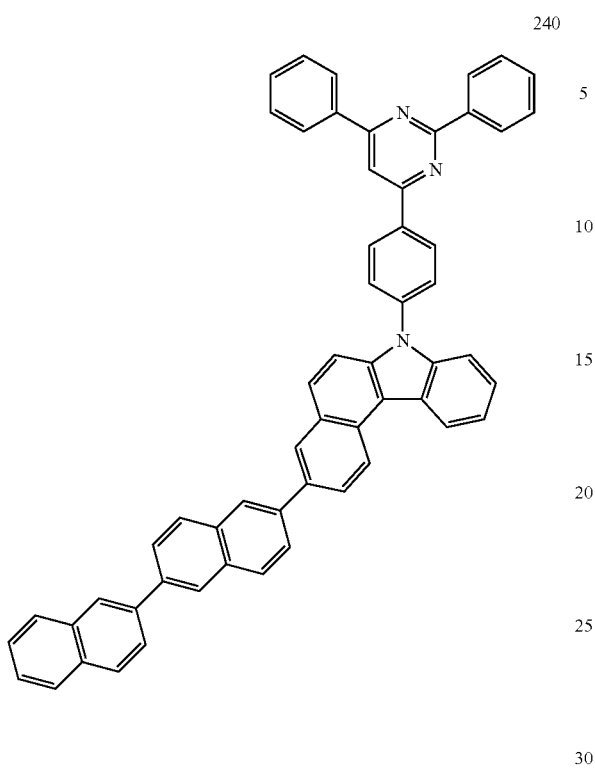
240
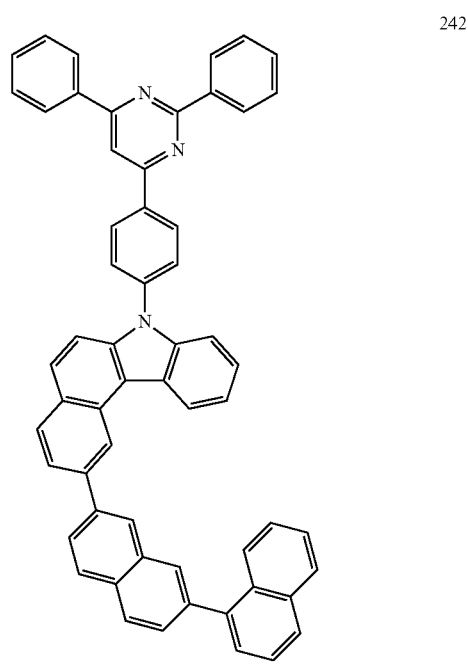
242
241
243
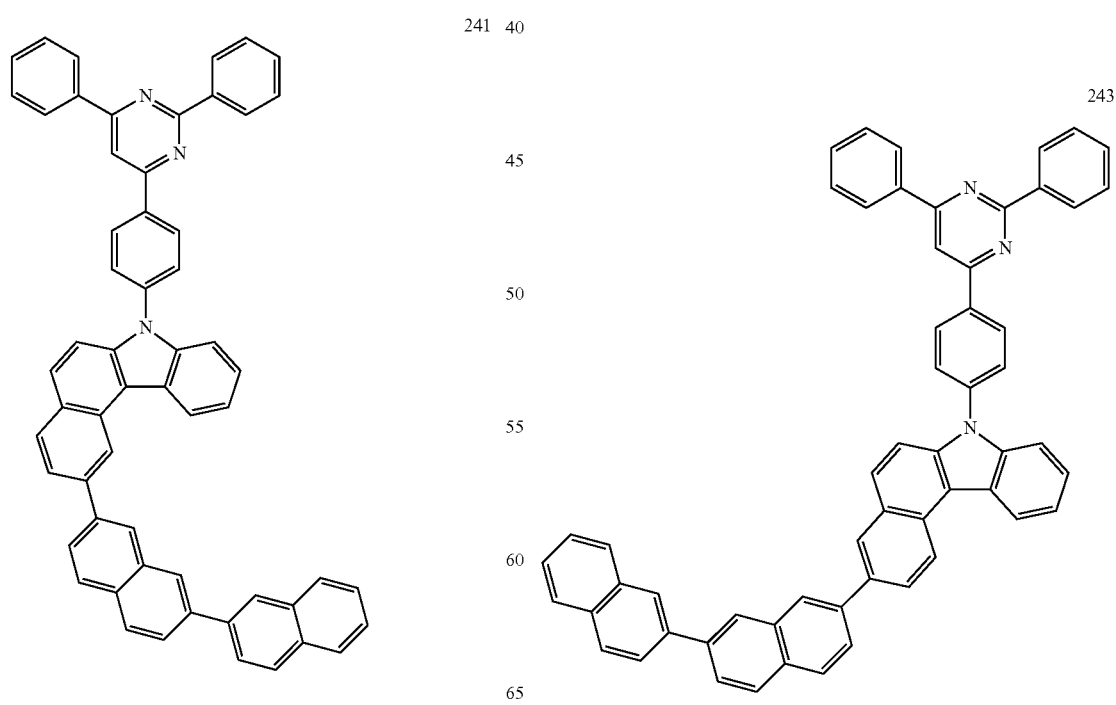

-continued
244
245
246
247
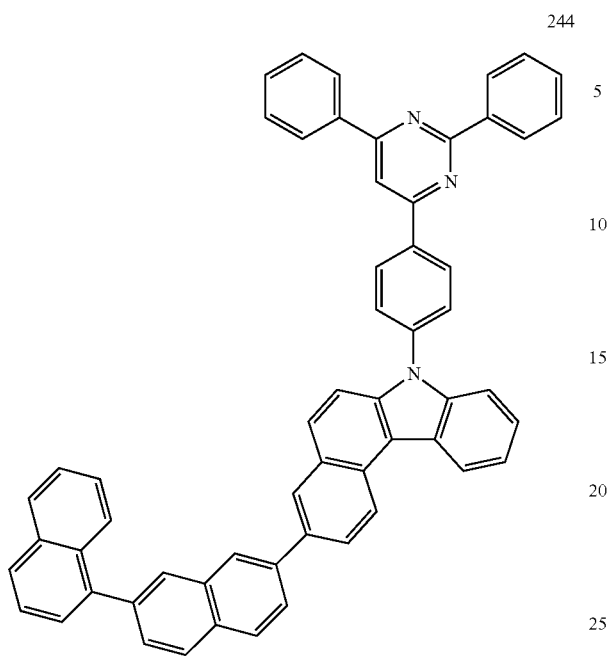
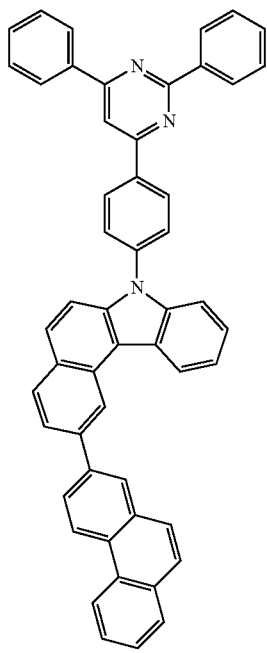

459
-continued
248
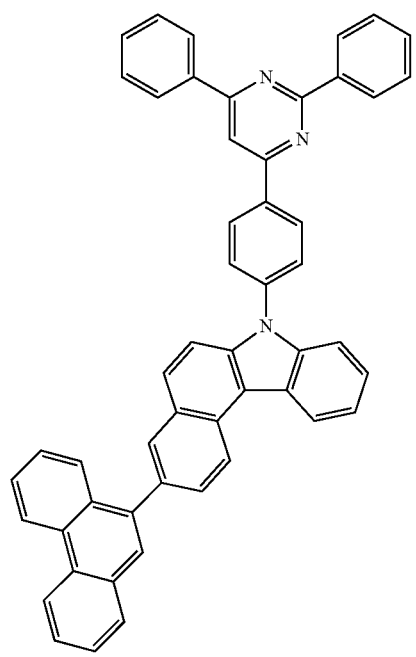
249
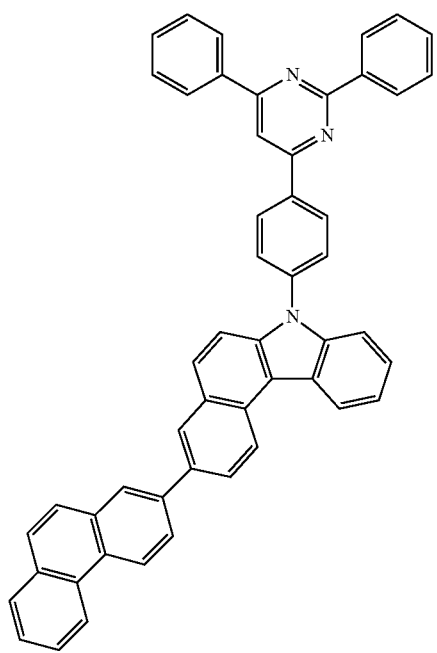
460
-continued
250
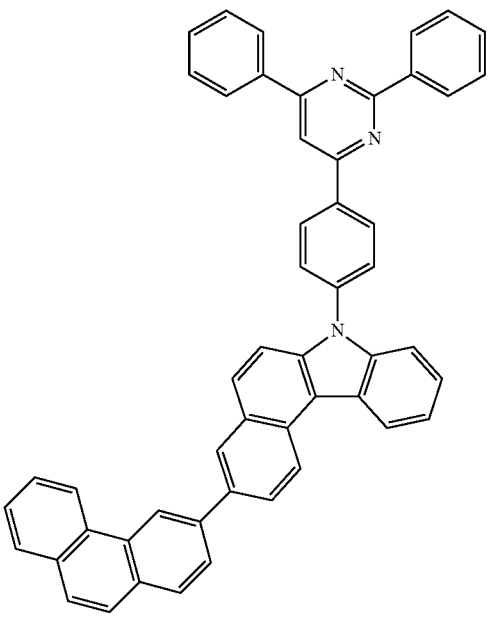
251
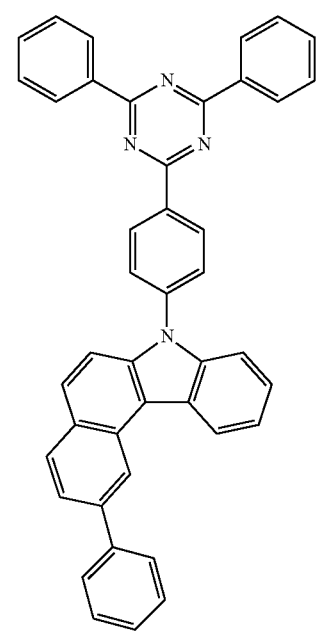

461
-continued
462
-continued
252
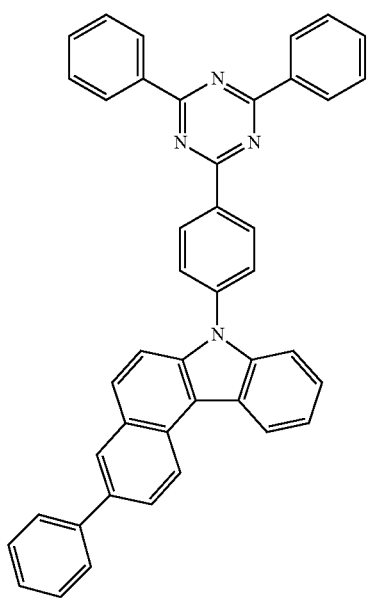
254
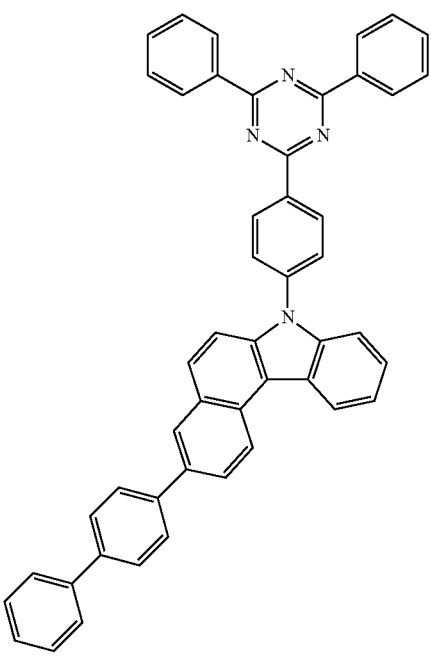
253
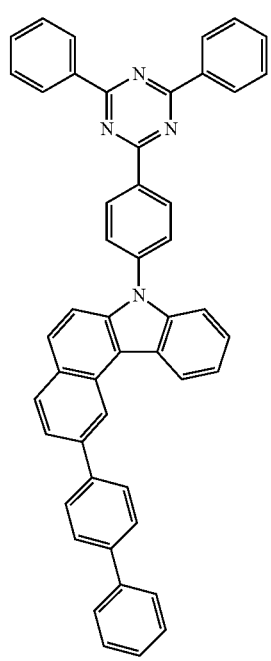
255
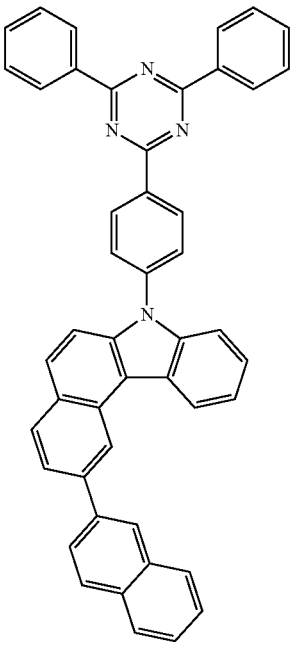

463
-continued
256
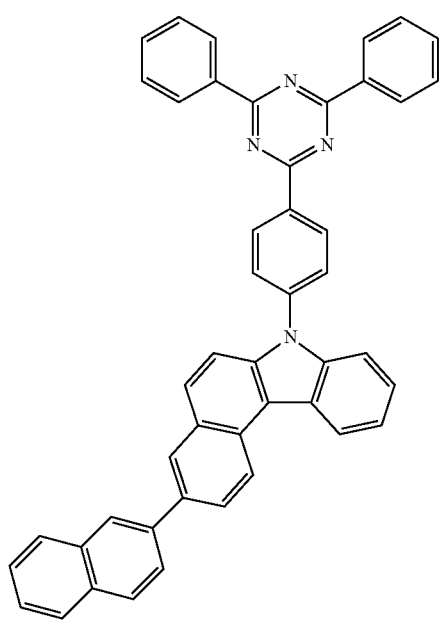
257
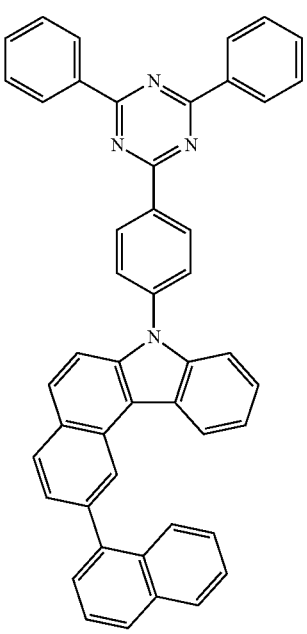
464
-continued
258
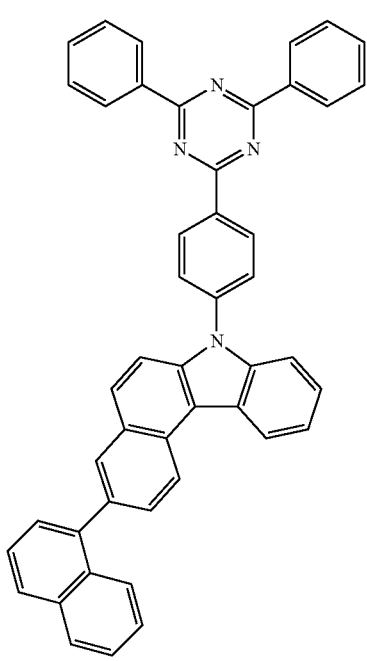
259

465
-continued
260
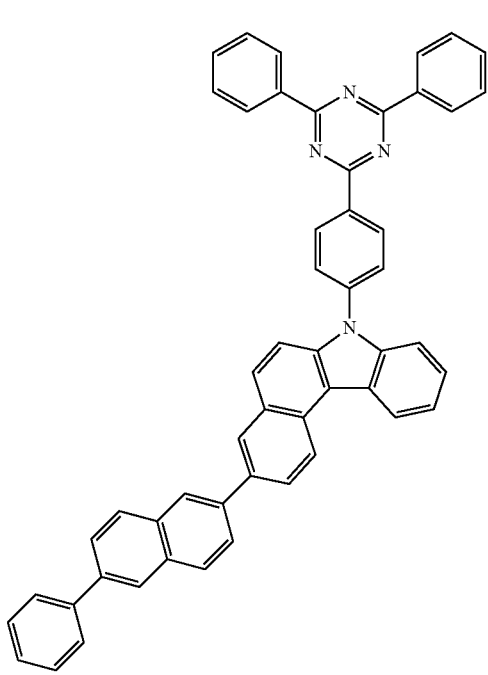
261
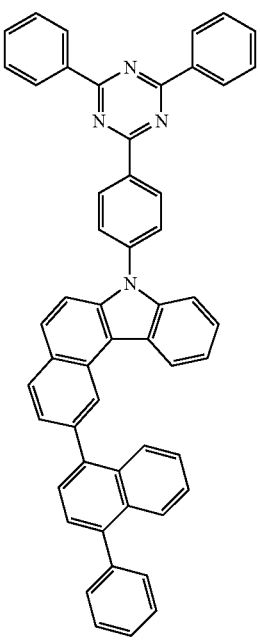
466
-continued
262
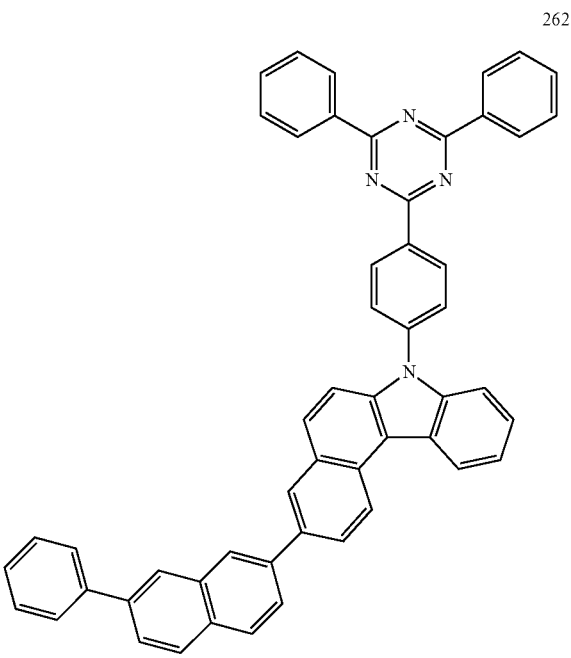
263

467
-continued
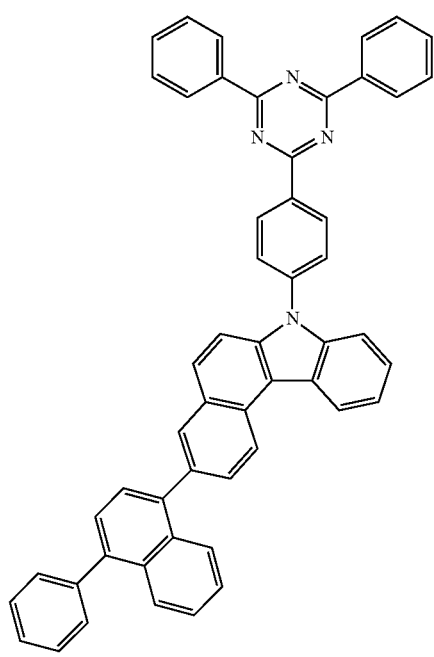
264
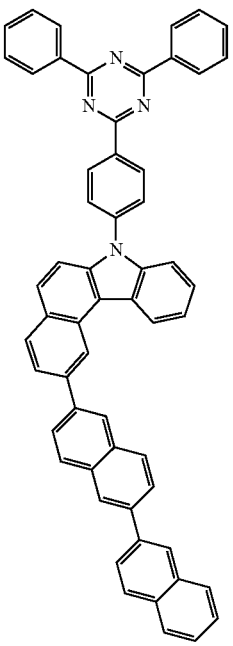
266
265
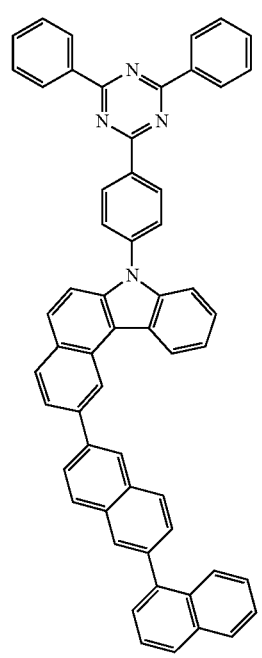
468
-continued
267
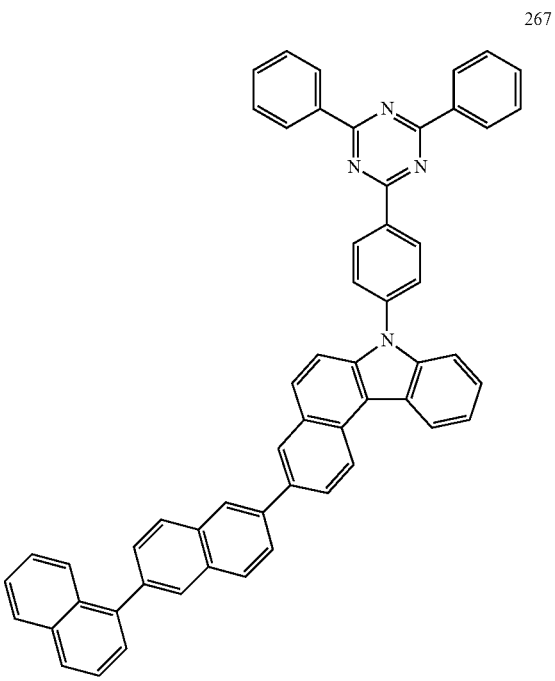

469
-continued
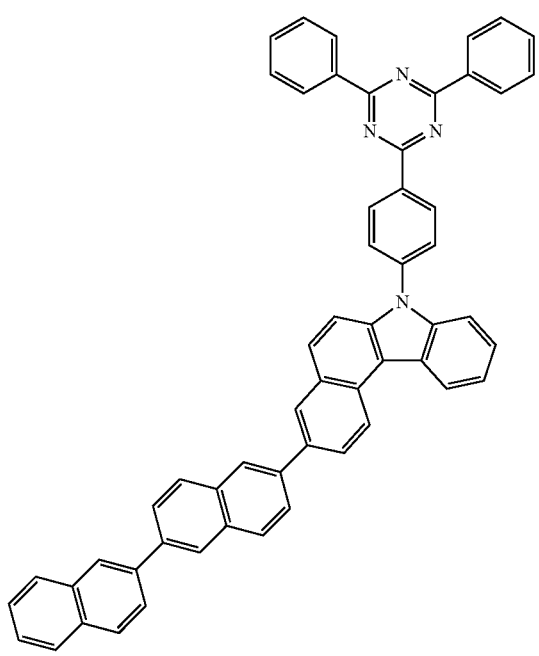
268
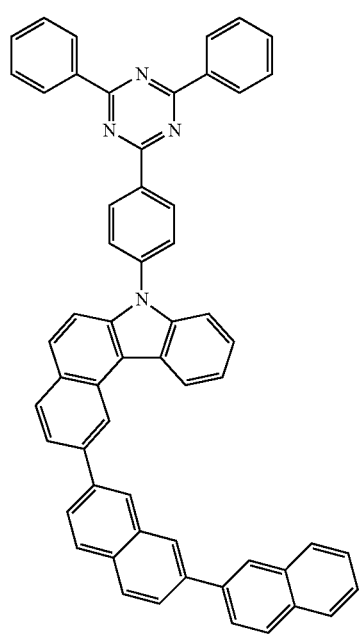
269
470
-continued
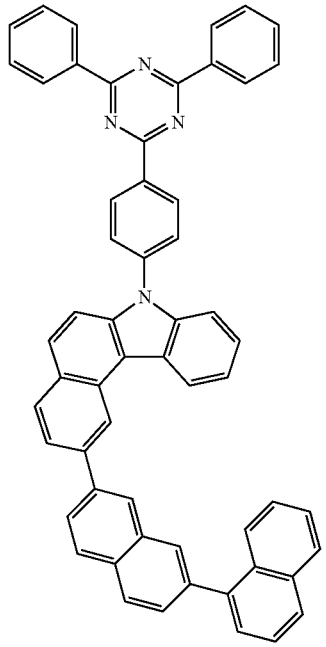
270
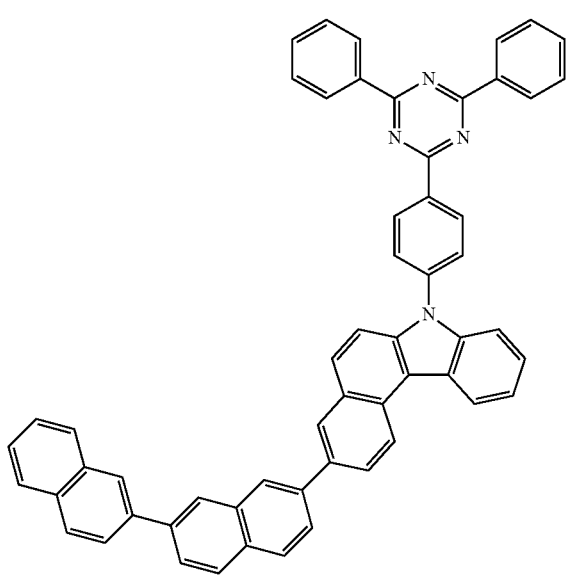
271

-continued
272
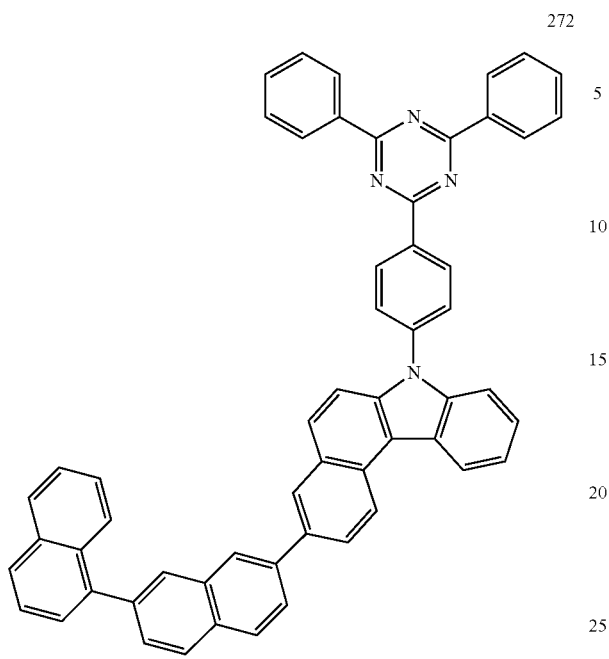
273
274
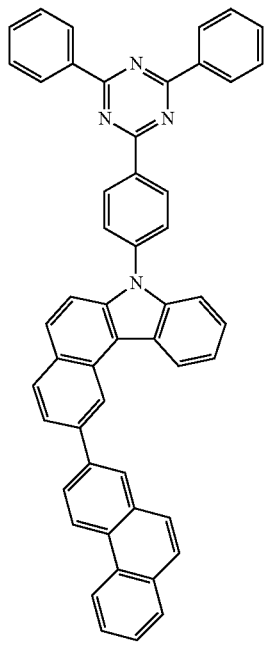
275

473
-continued
276
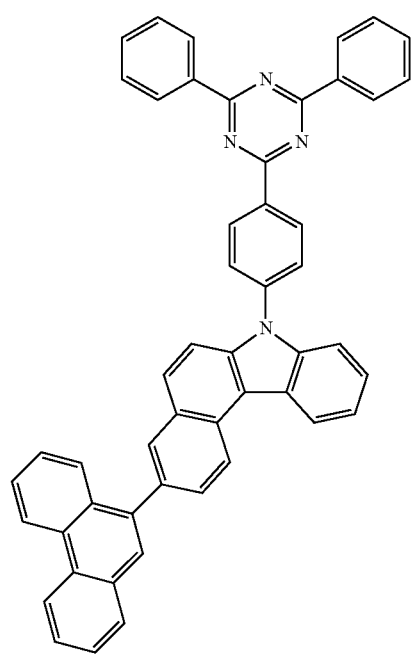
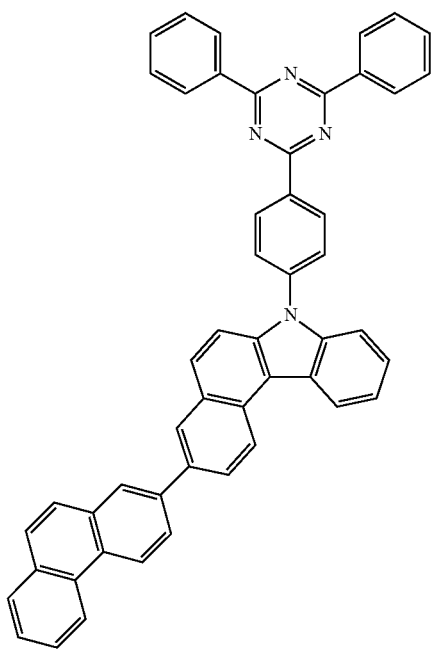
277
474
-continued
278
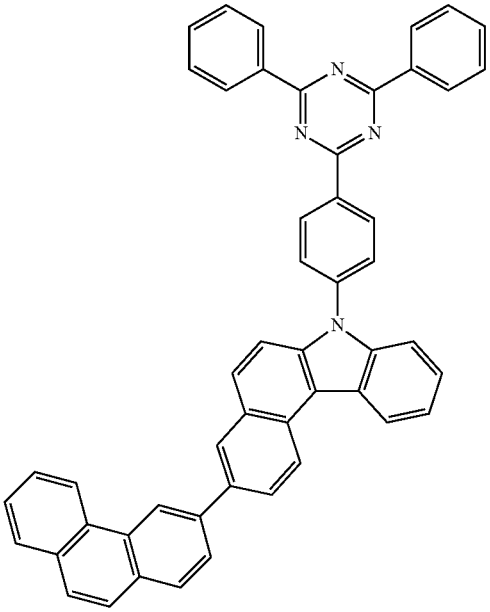
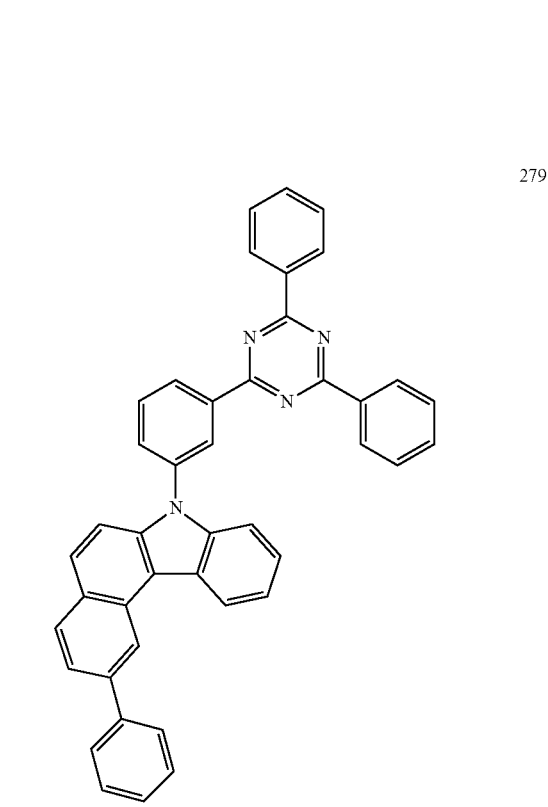
279

475
-continued
280
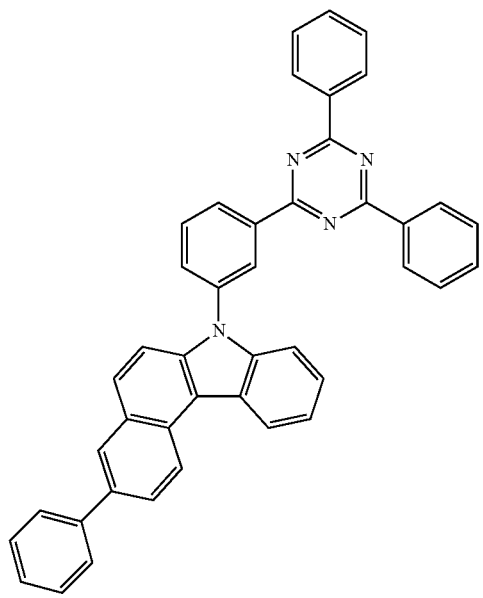
281
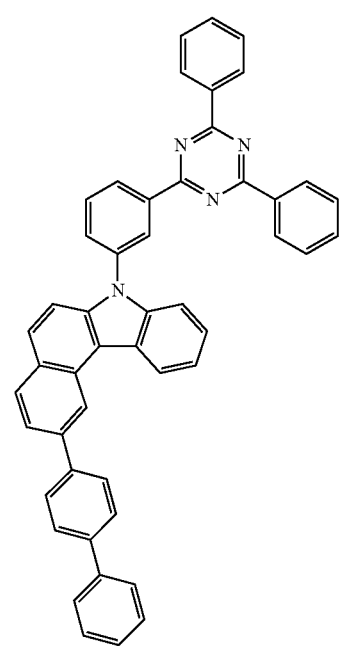
476
-continued
282
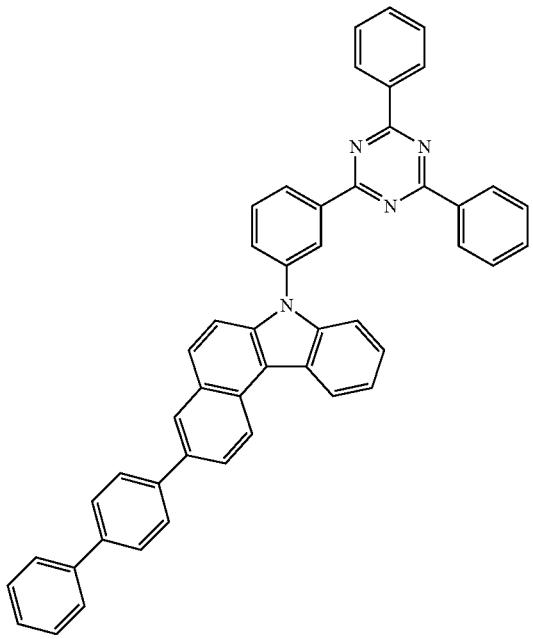
283
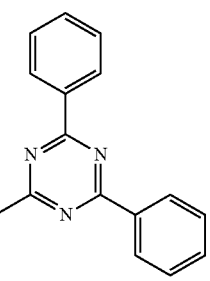

477
-continued
284
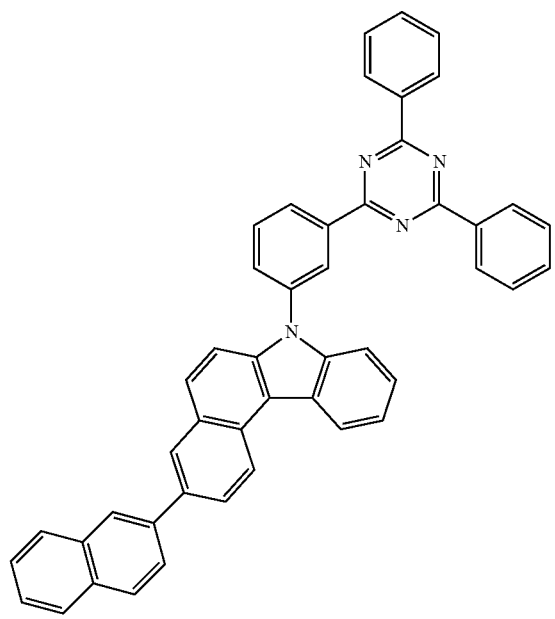
285
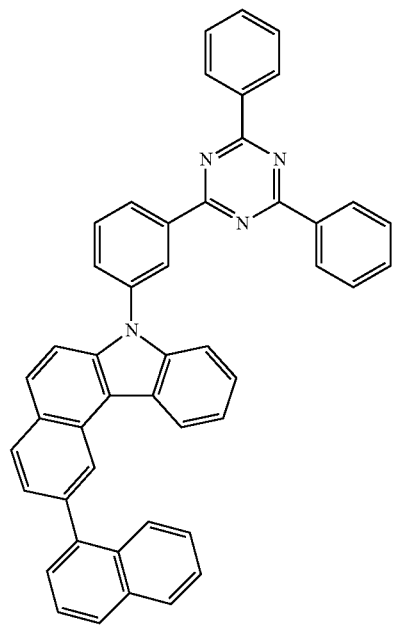
478
-continued
286
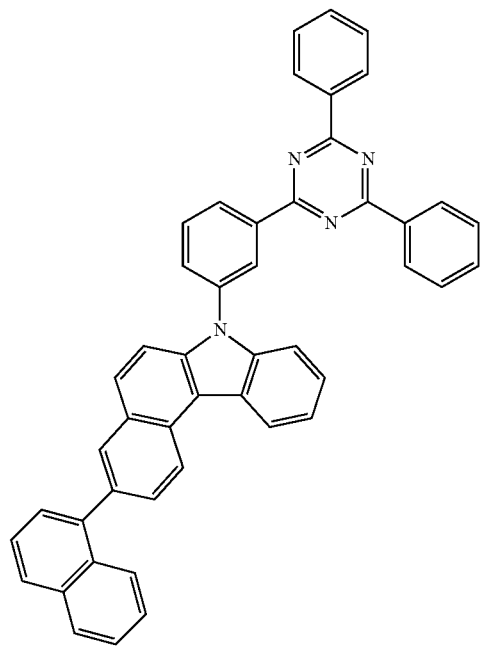
287
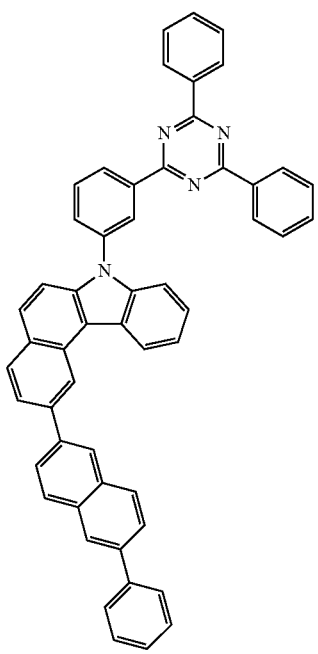

288
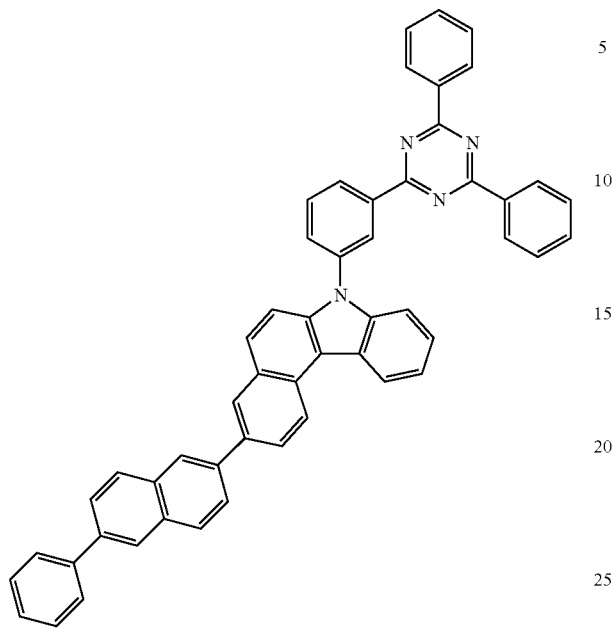
289
290
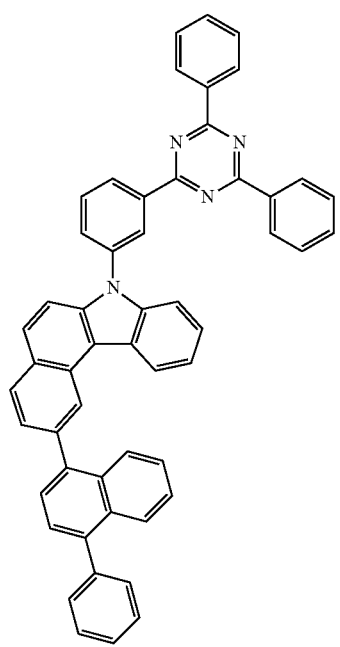
291

-continued
292
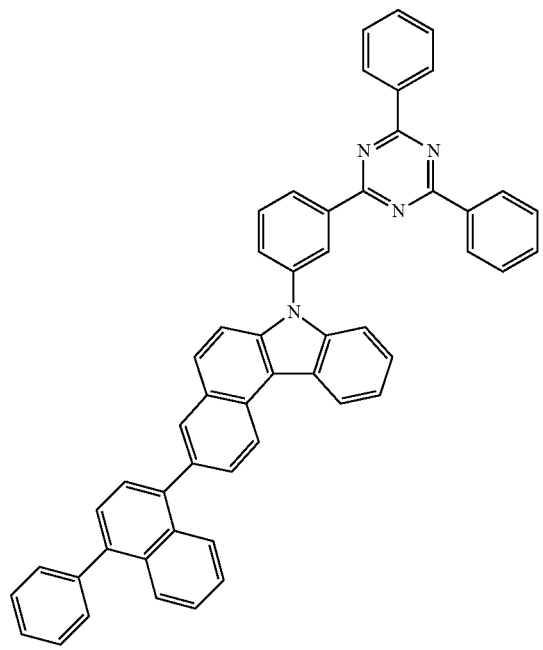
294
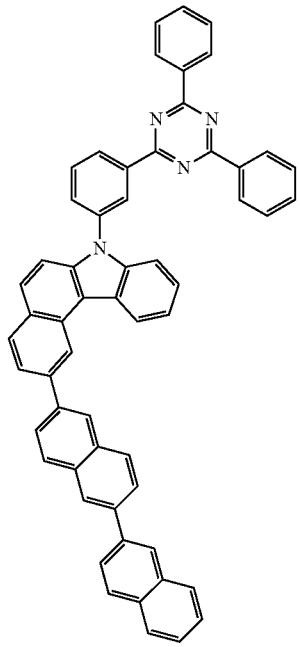
293
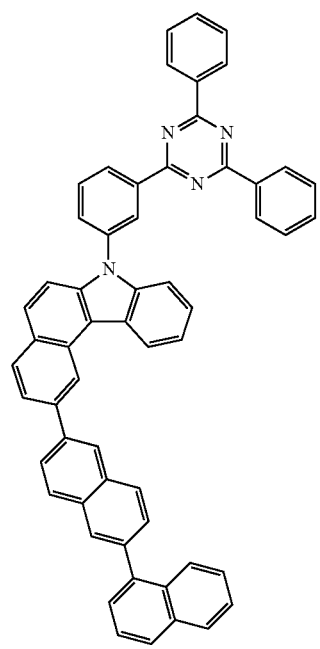
295
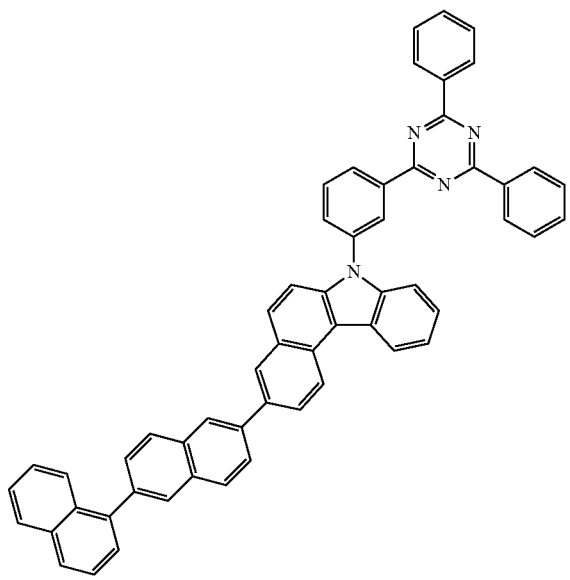

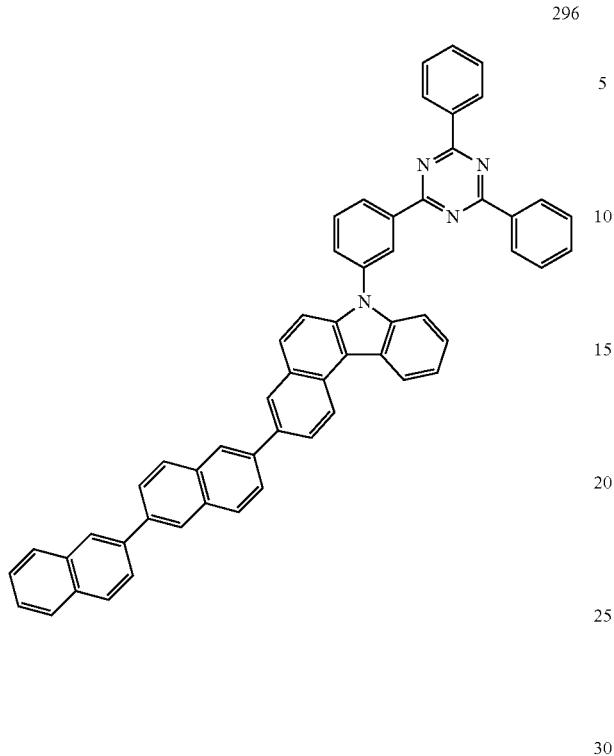
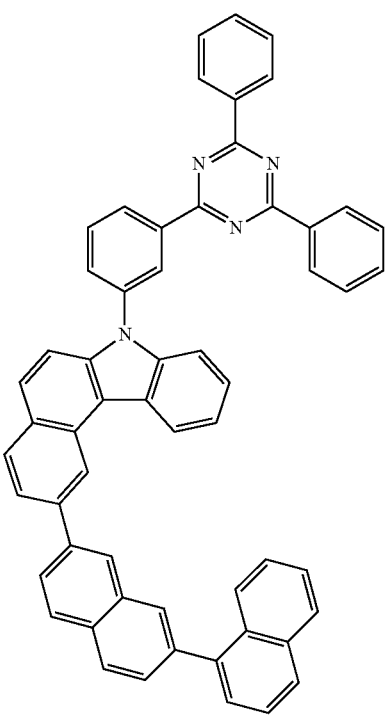
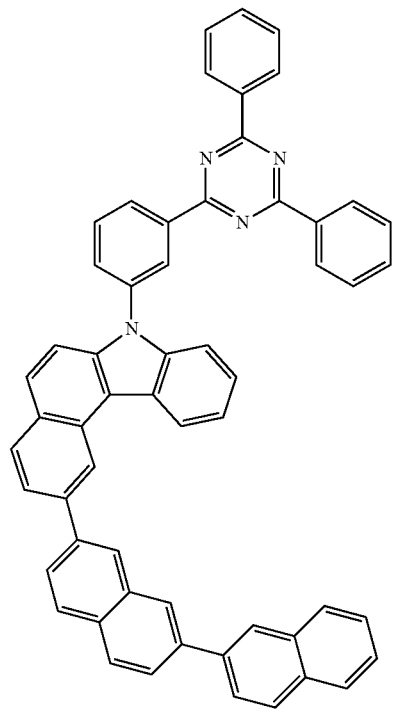

485
-continued
486
-continued
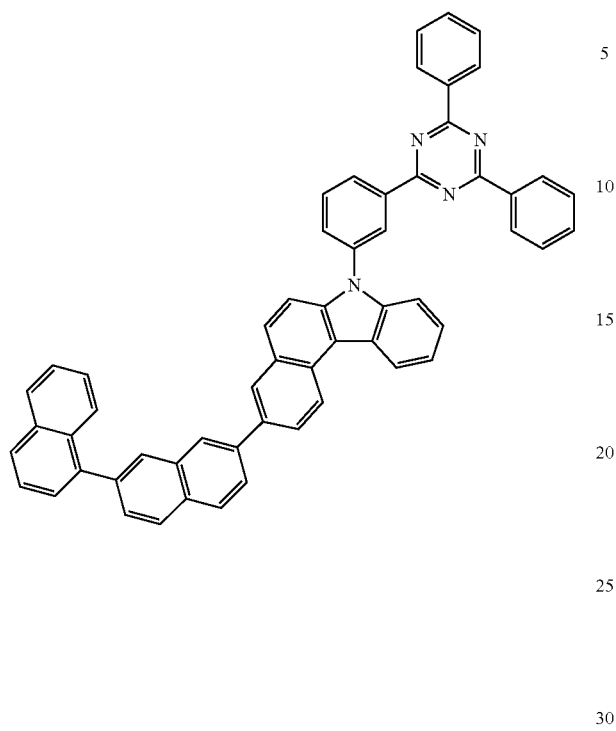
300
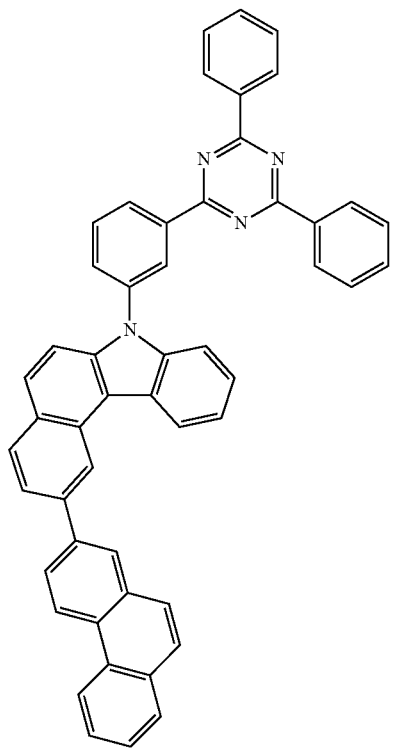
302
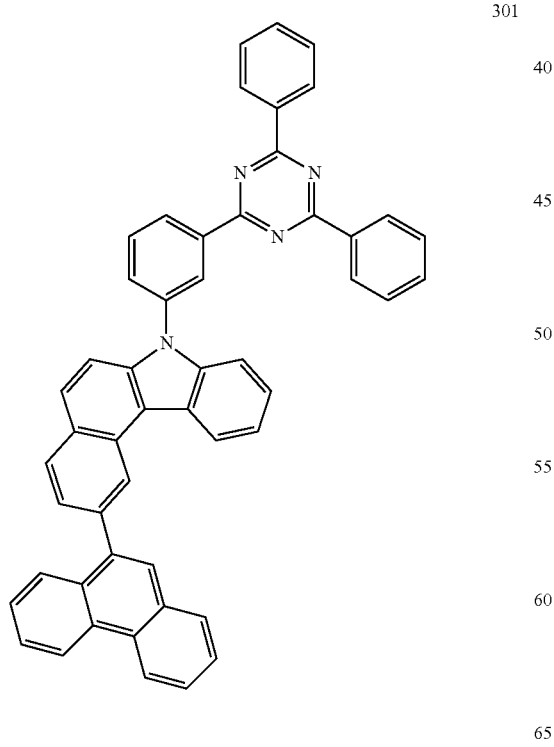
301
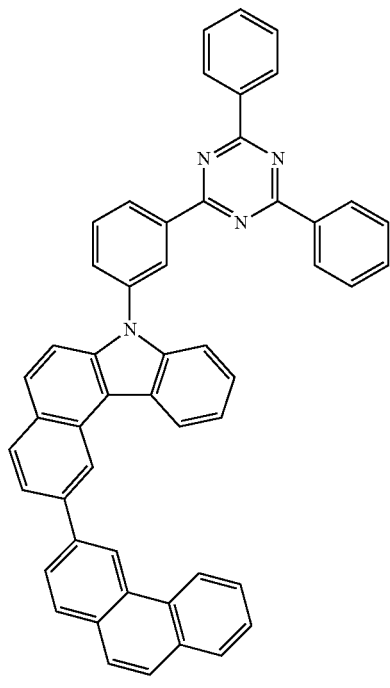
303

487
-continued
304
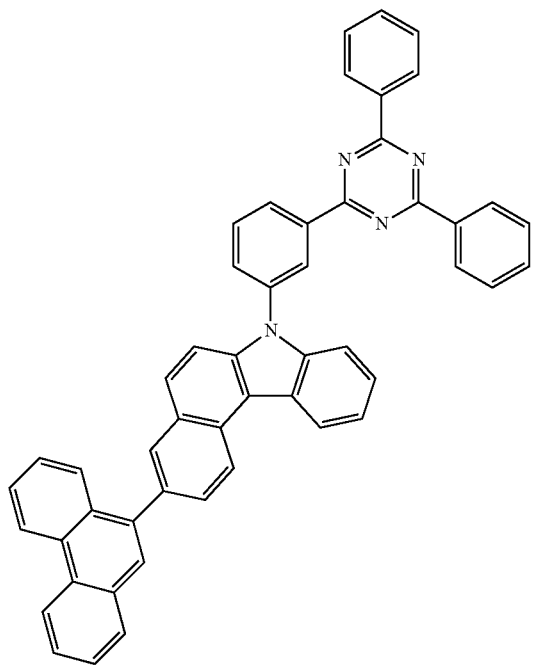
305
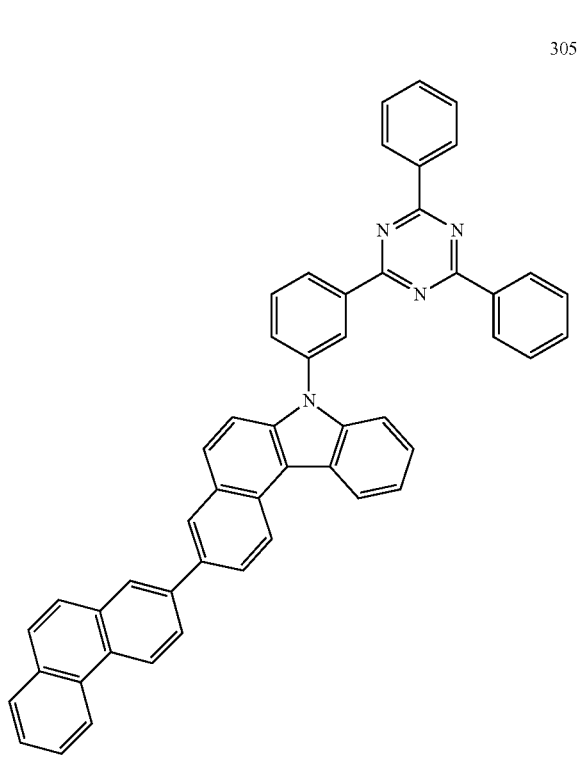
488
-continued
306
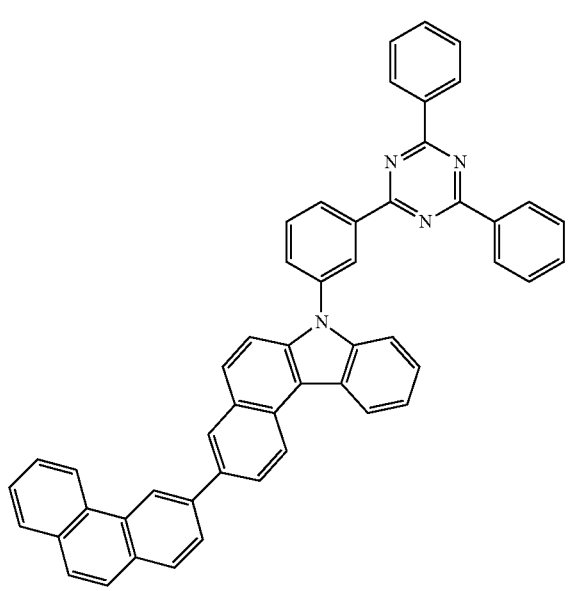
307
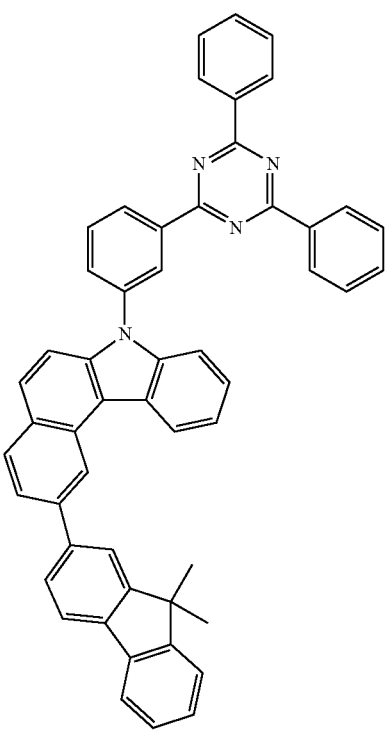

489
-continued
308
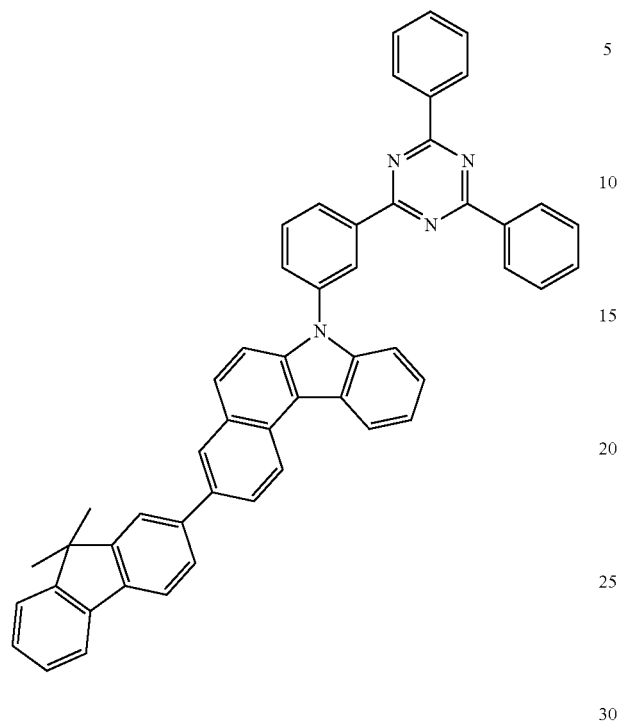
309
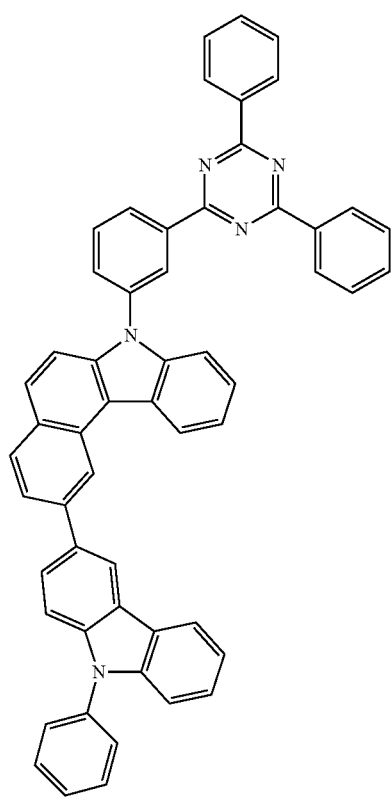
490
-continued
310
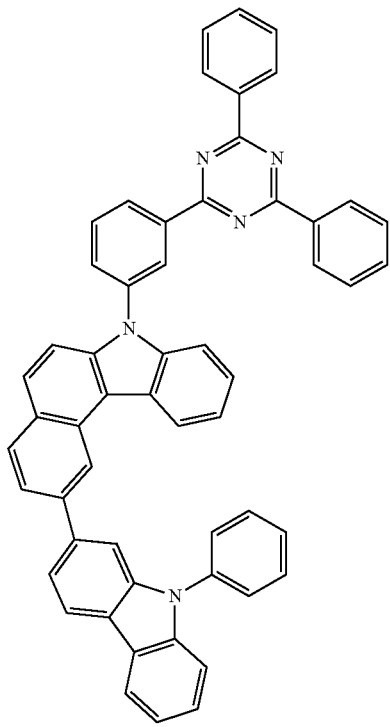
311
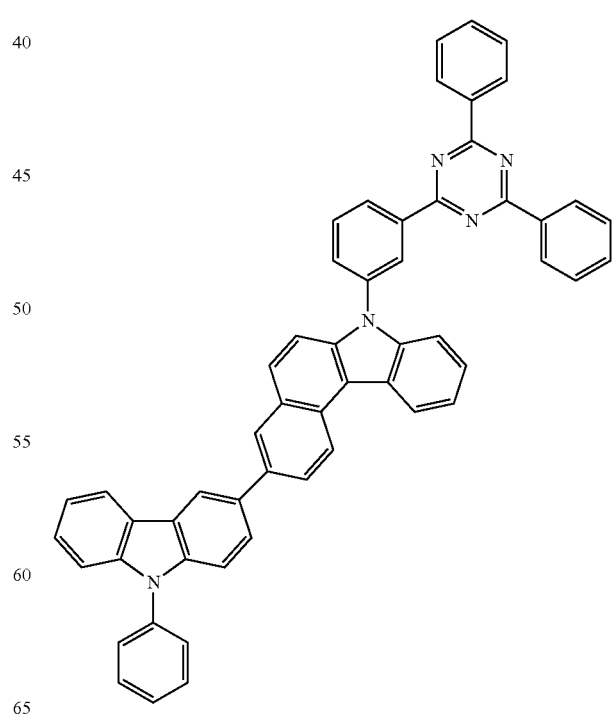

491
-continued
312
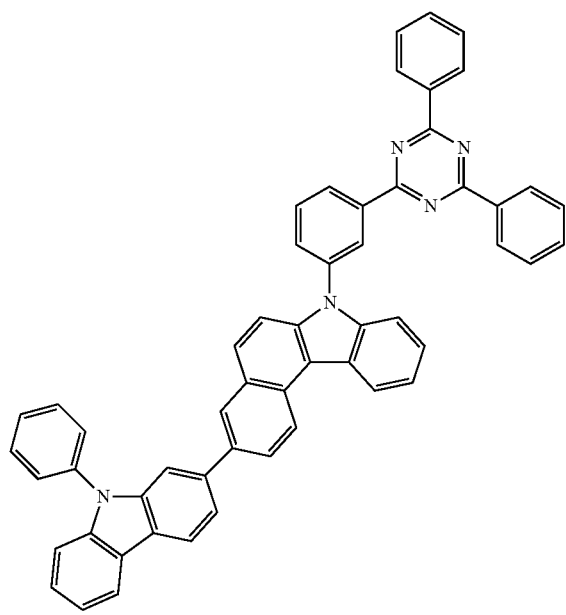
313
492
-continued
315
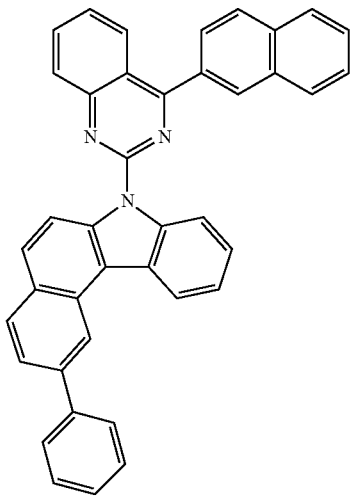
316
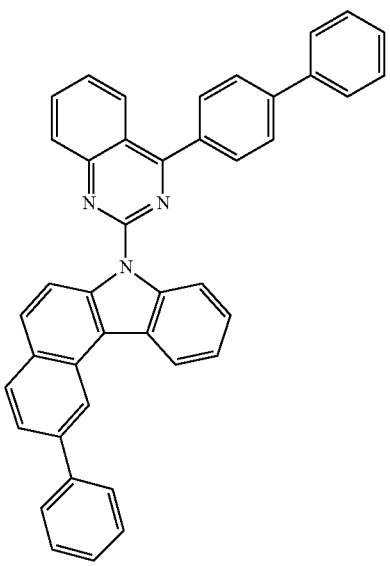
314
317
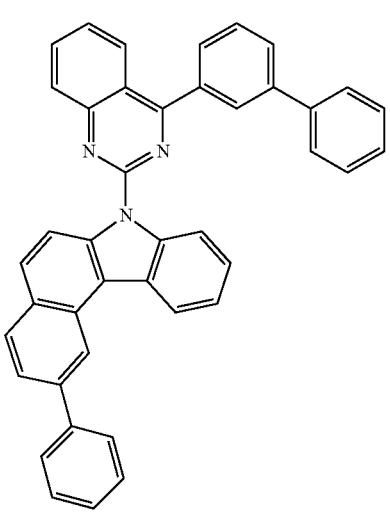

493
-continued
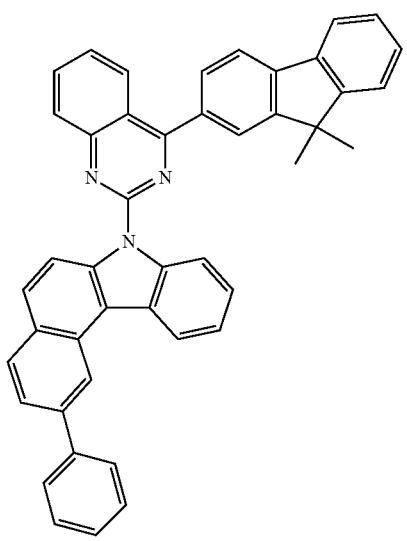
318
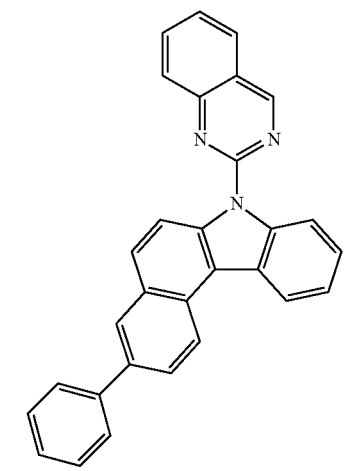
319
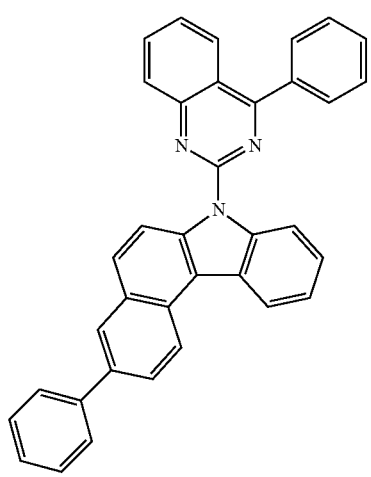
320
494
-continued
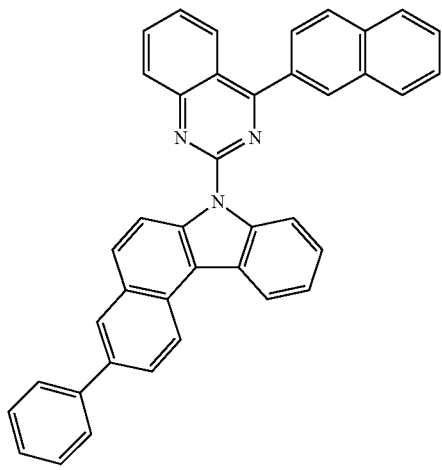
321
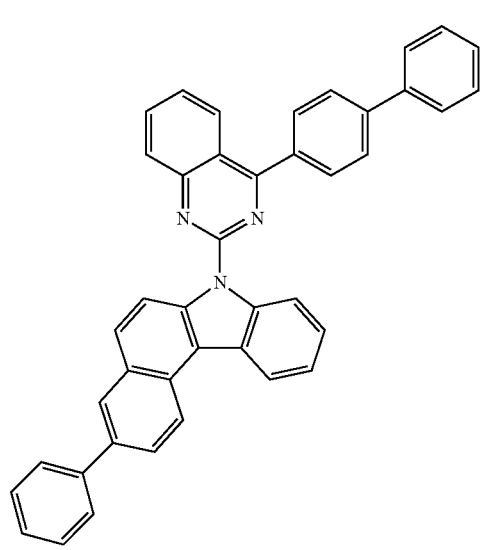
323
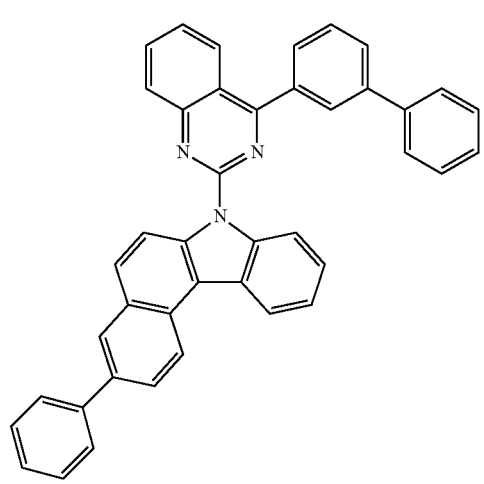
324

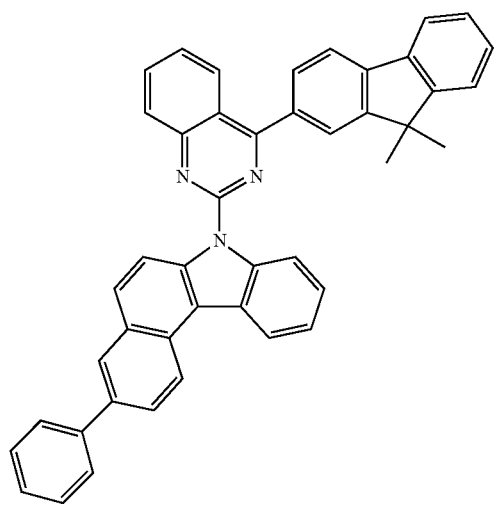
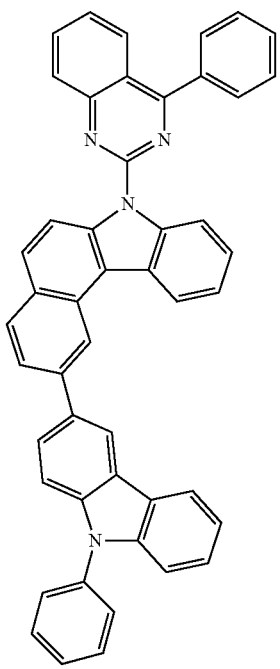

497
-continued
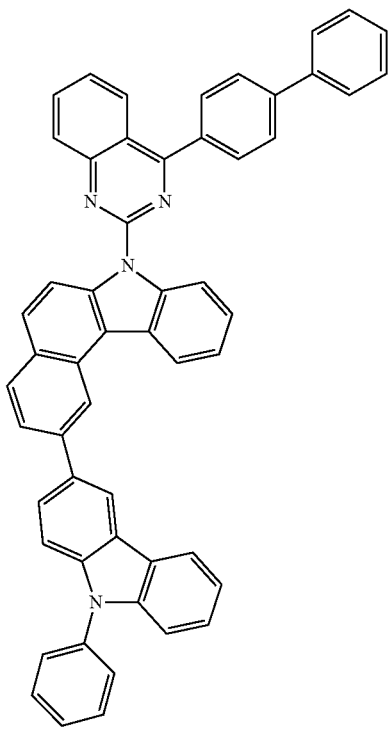
329
498
-continued
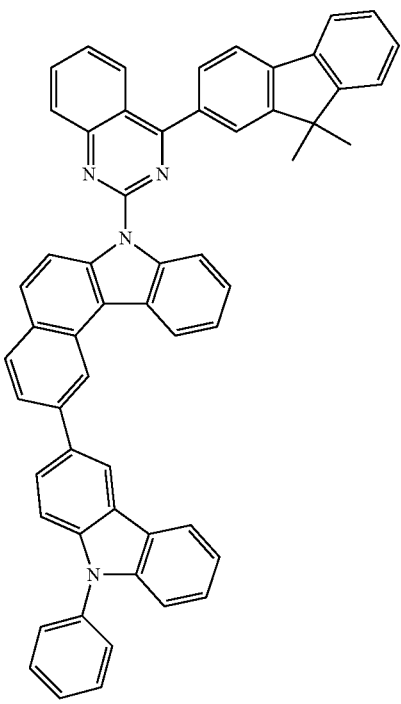
331
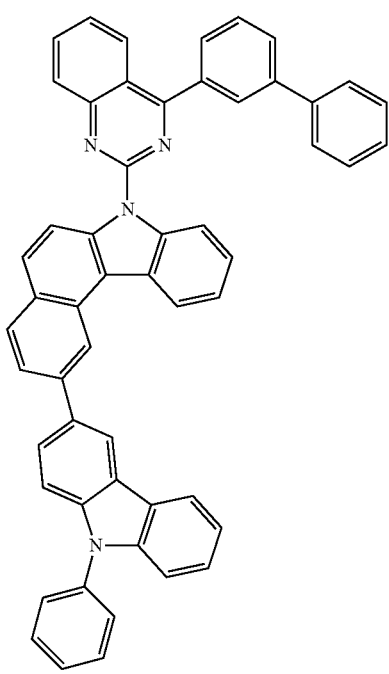
330
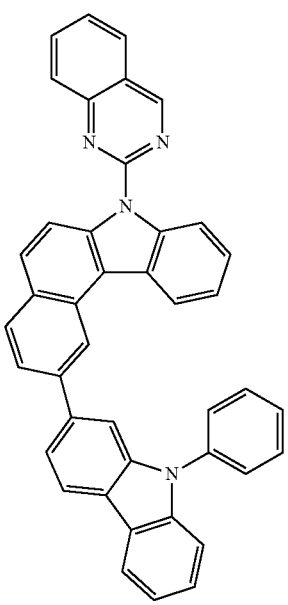
332

499
-continued
333
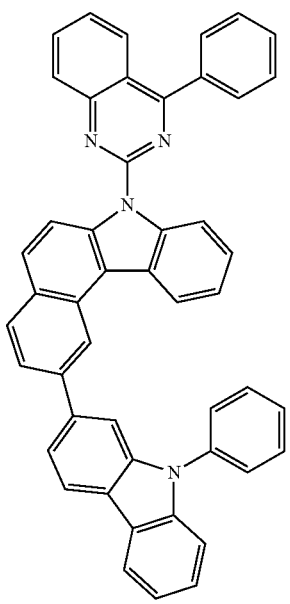
500
-continued
335
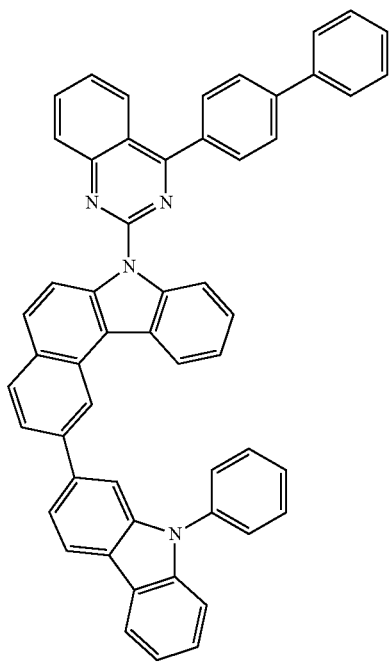
334
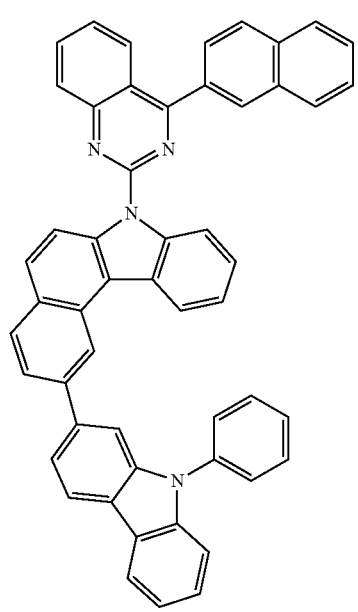
336
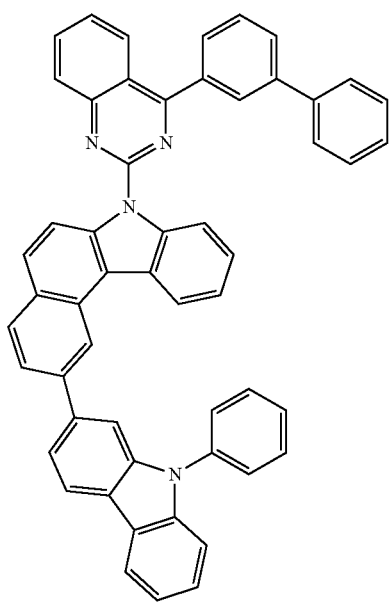

501
-continued
337
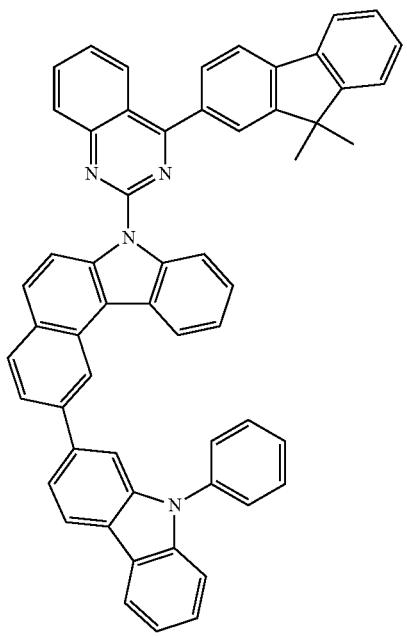
338
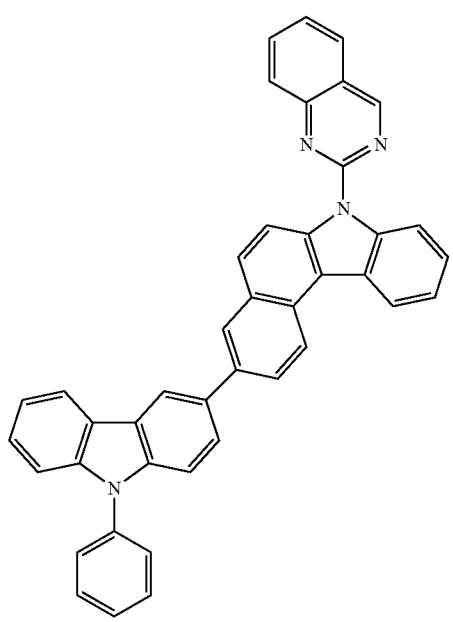
502
-continued
339
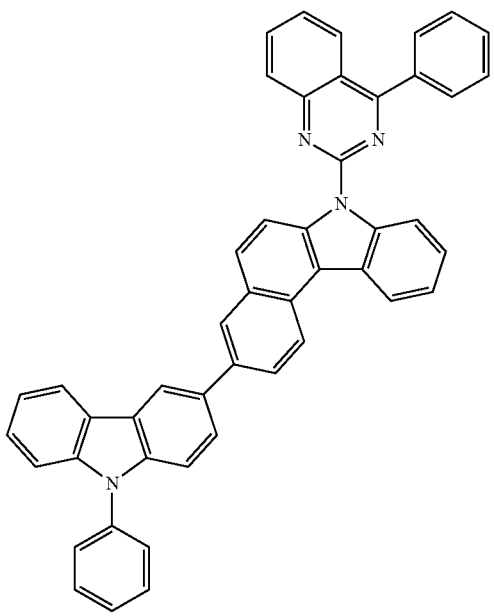
340

503
-continued
504
-continued
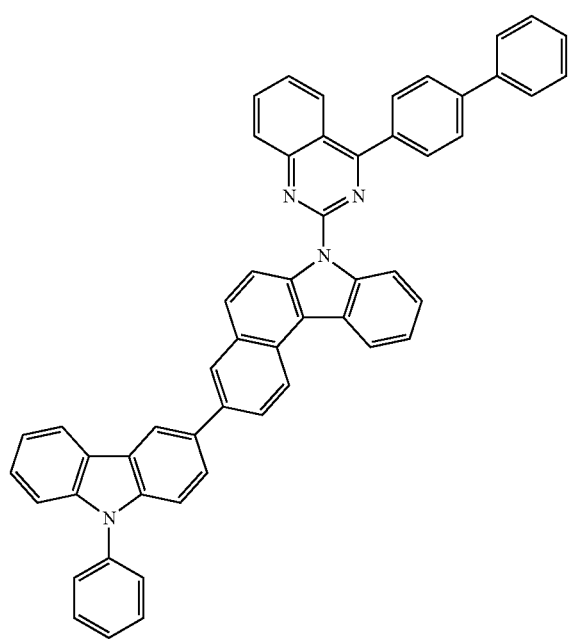
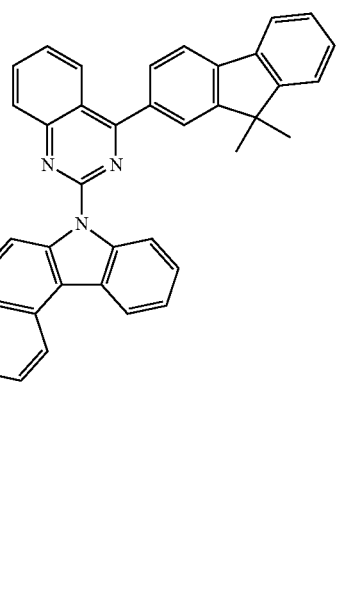
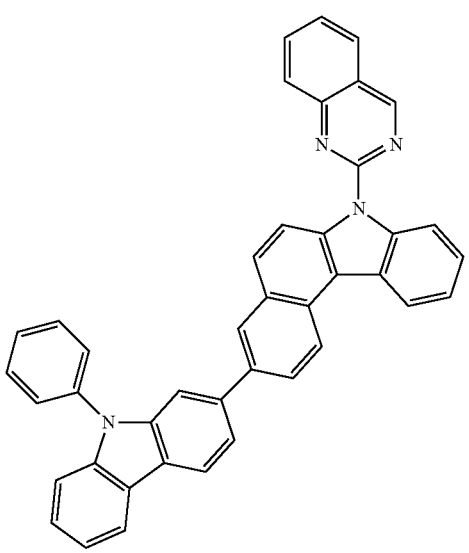

505
-continued
506
-continued
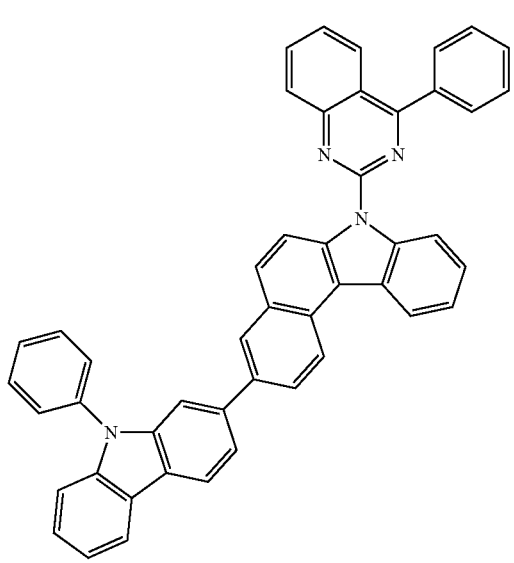
345
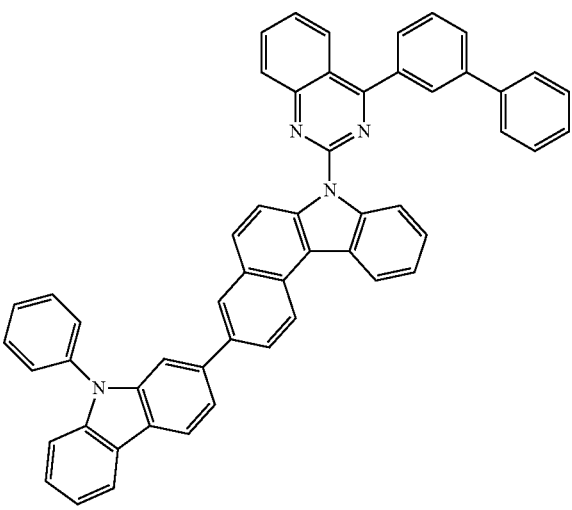
348
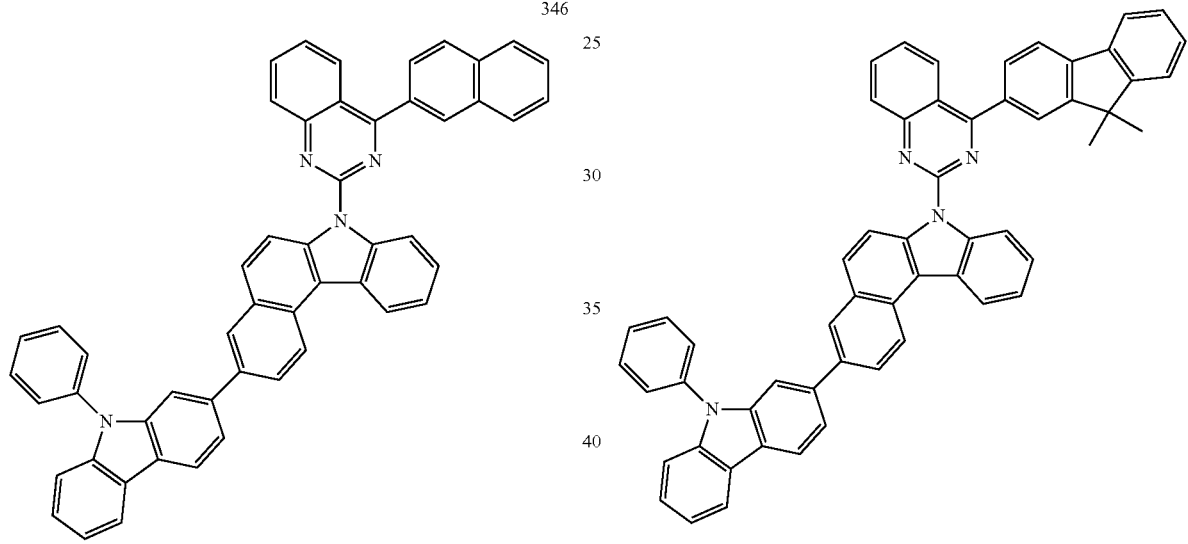
346
349
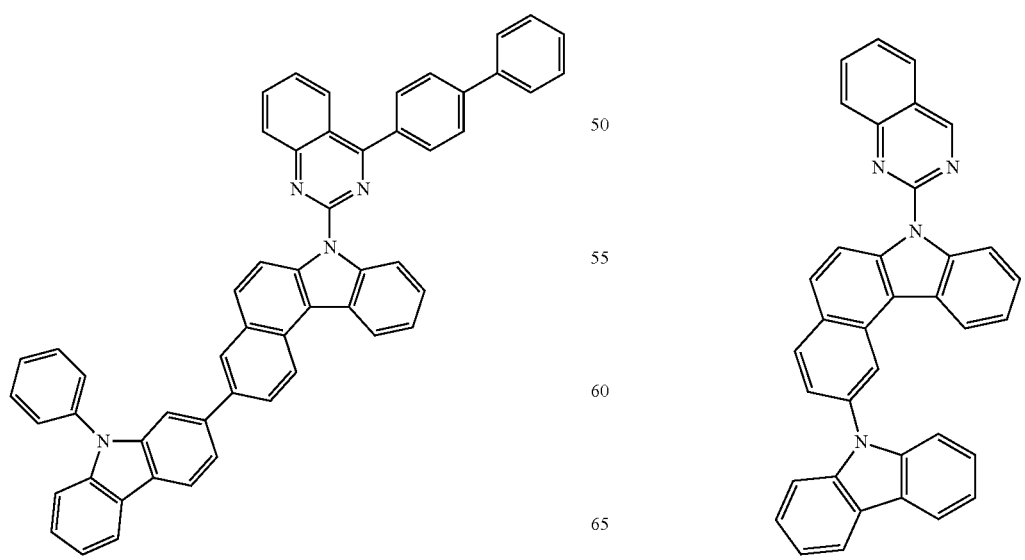
347
350

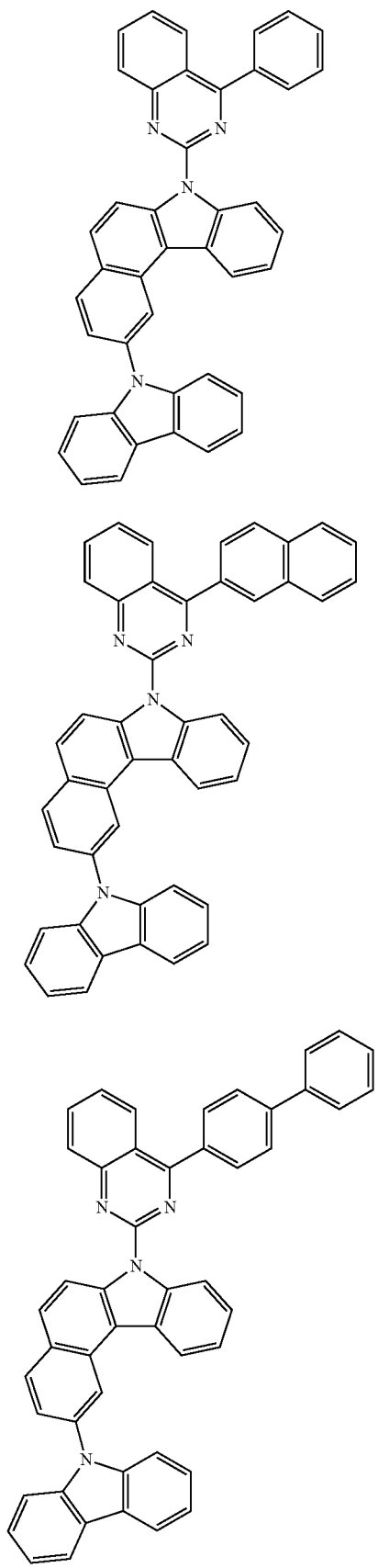

509
-continued
356
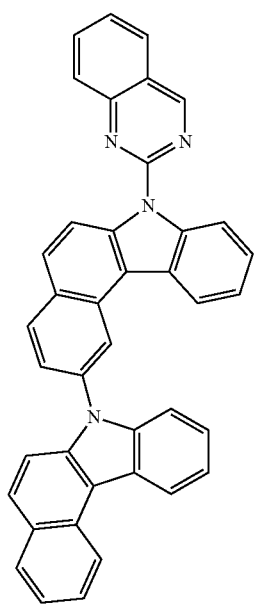
357
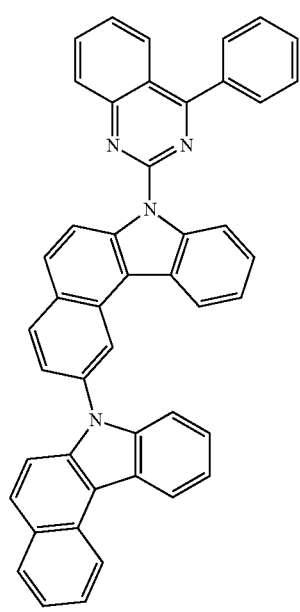
510
-continued
358
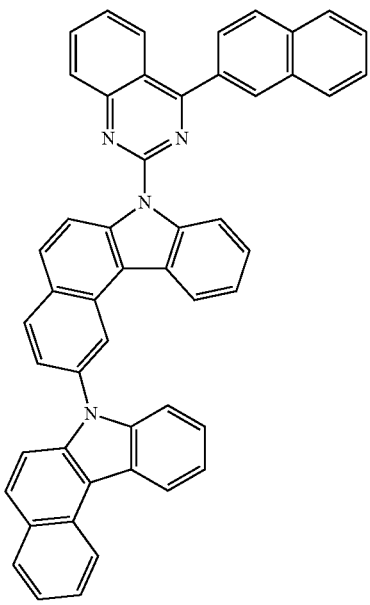
359
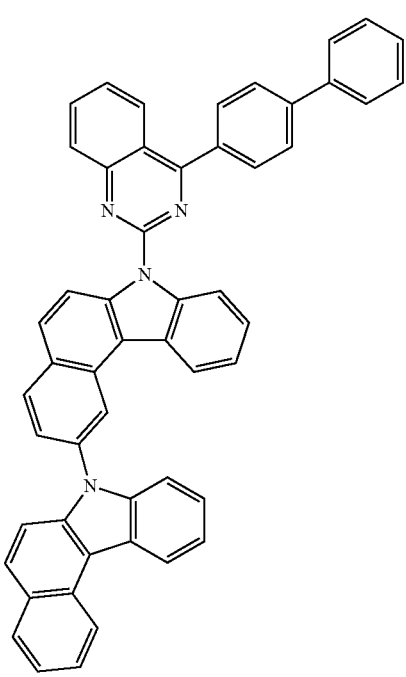

511
-continued
512
-continued
360
361
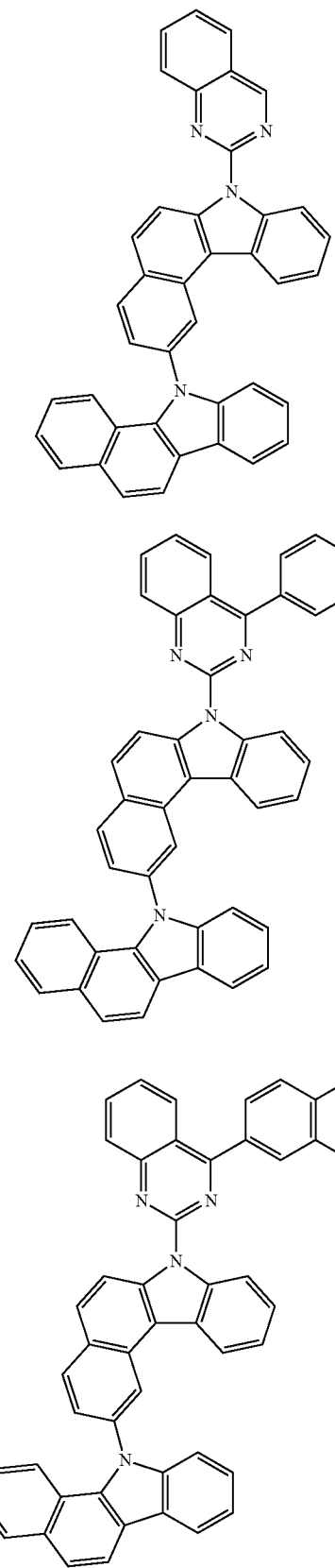
362
363
364

513
-continued
365
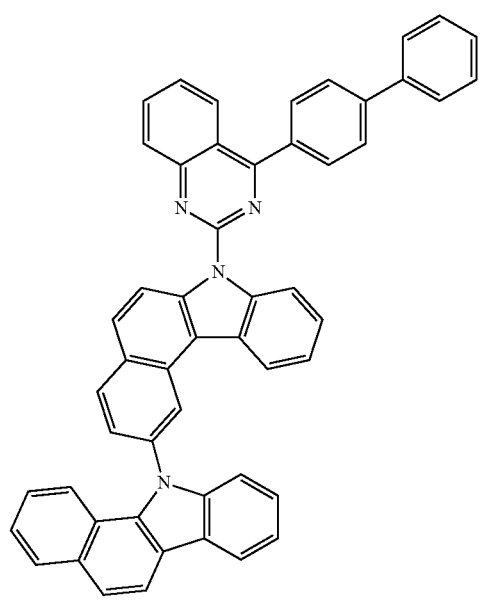
366
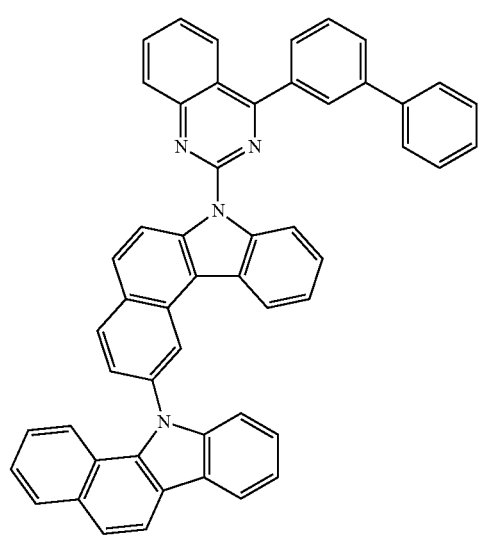
514
-continued
367
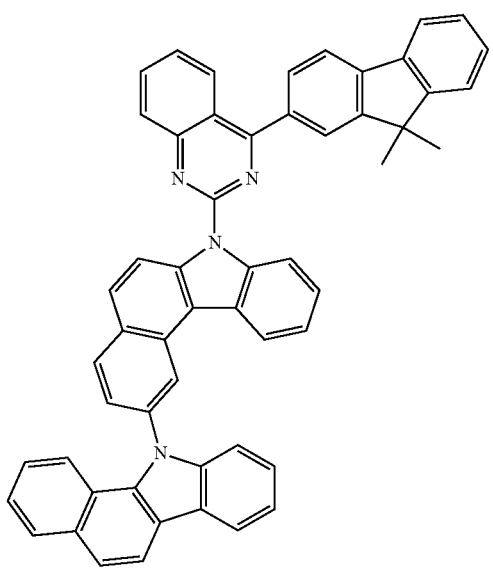
368
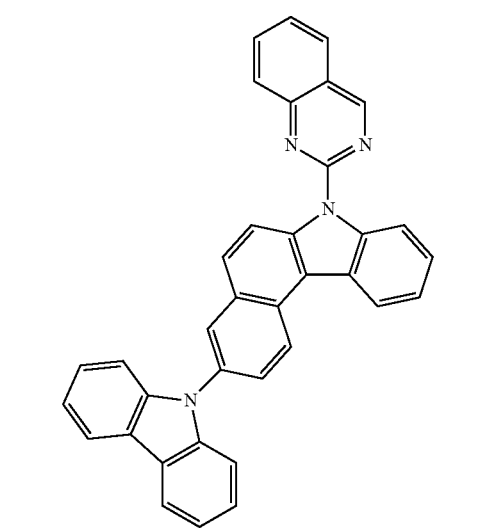
369
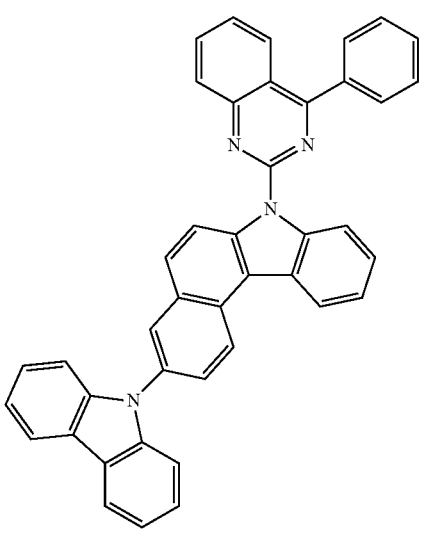

515
-continued
370
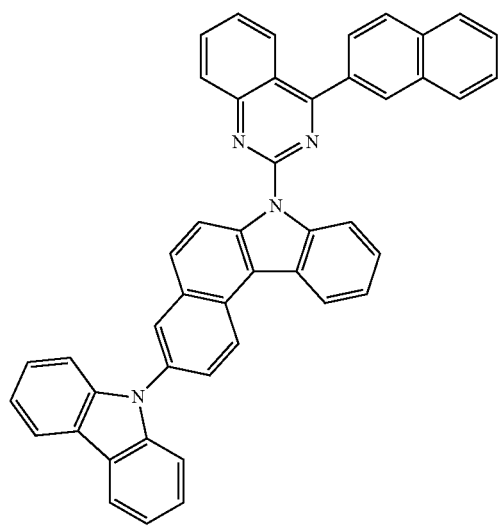
371
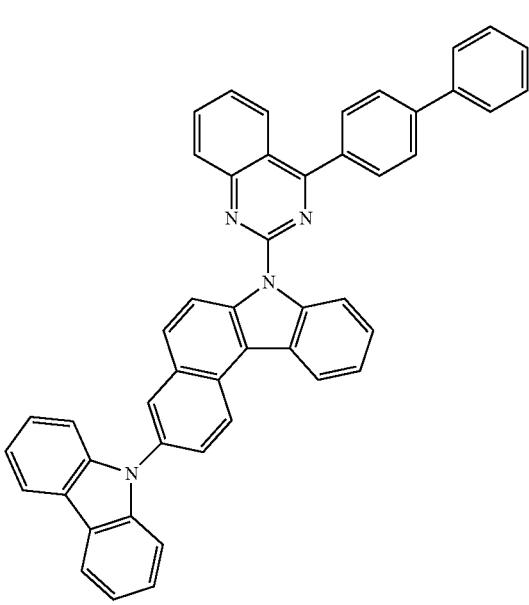
516
-continued
372
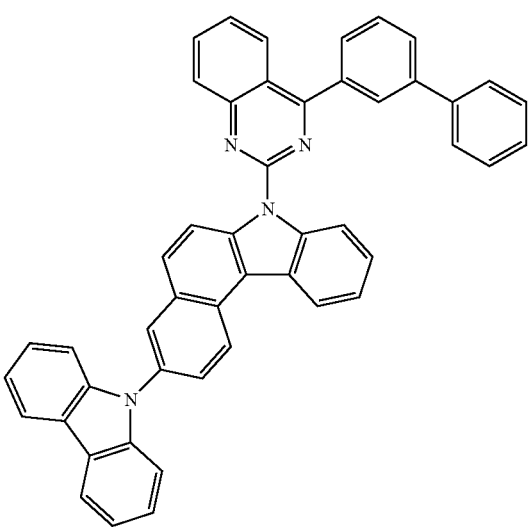
373

517
-continued
374
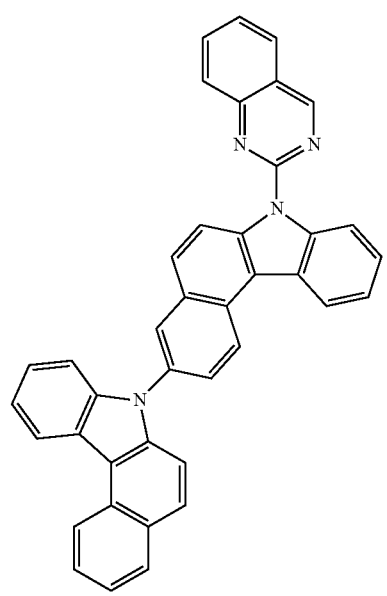
375
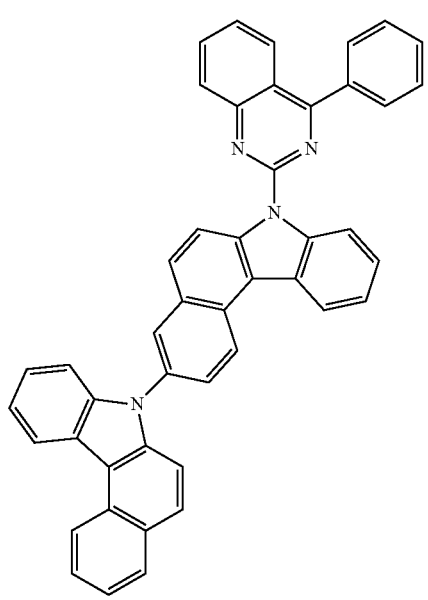
518
-continued
376
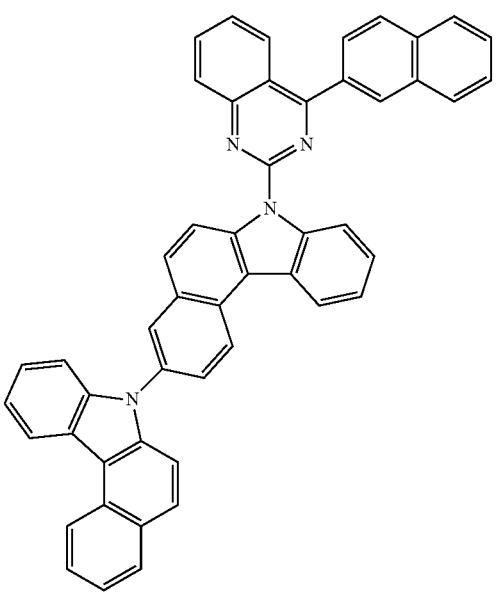
377
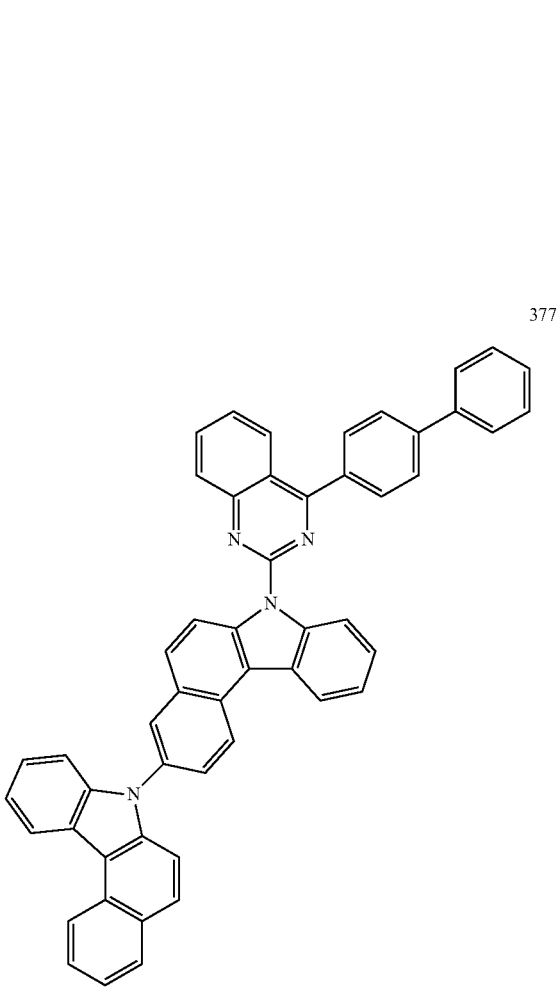

519
-continued
378
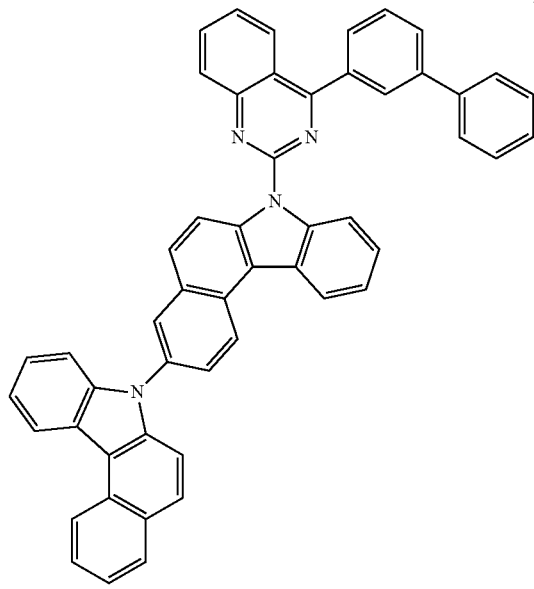
379
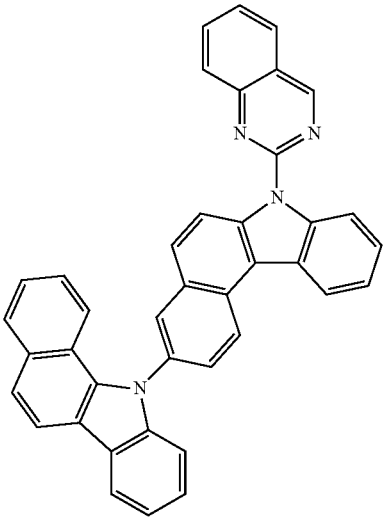
520
-continued
380
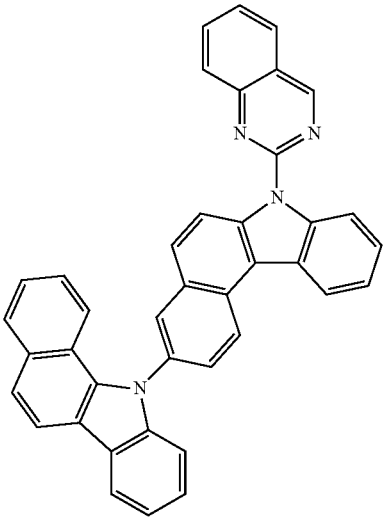
381
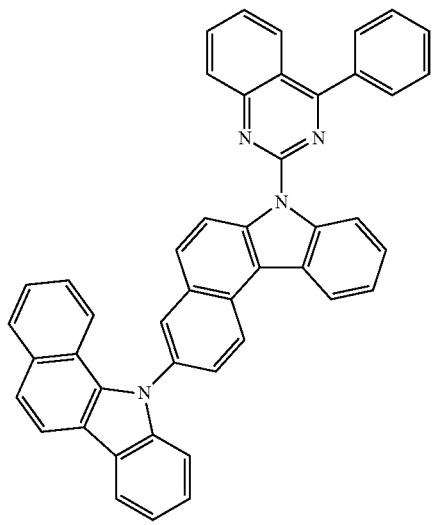
382
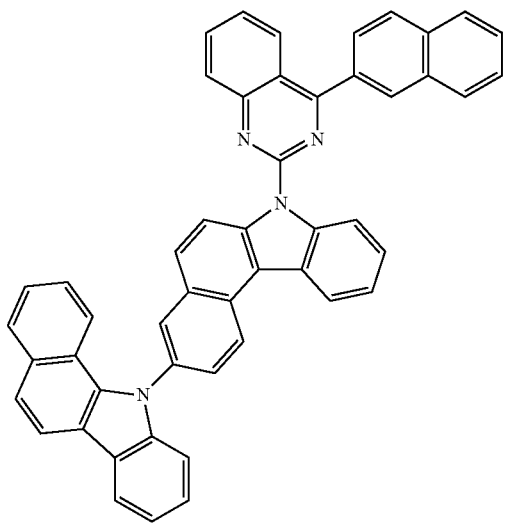

521
-continued
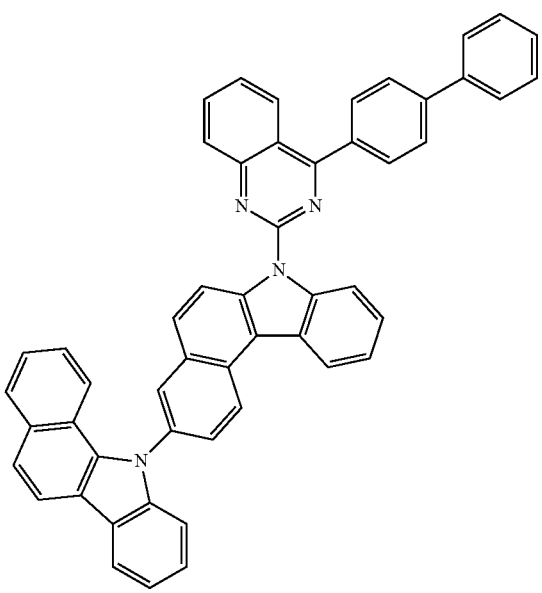
383
522
-continued
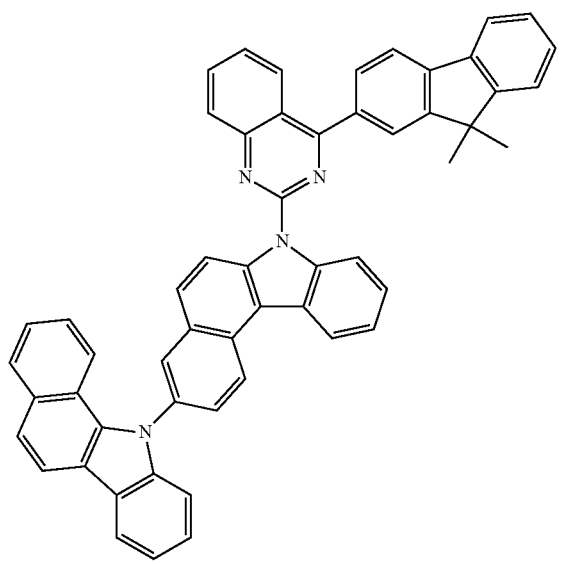
385
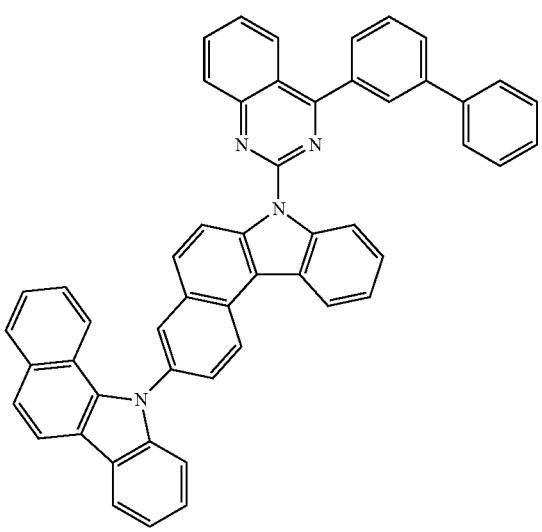
384
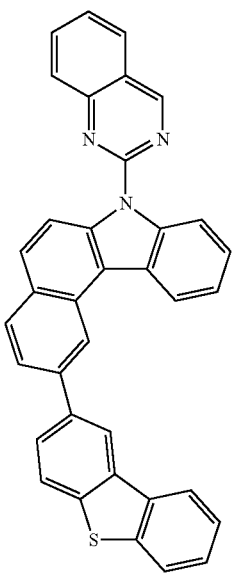
386

523
-continued
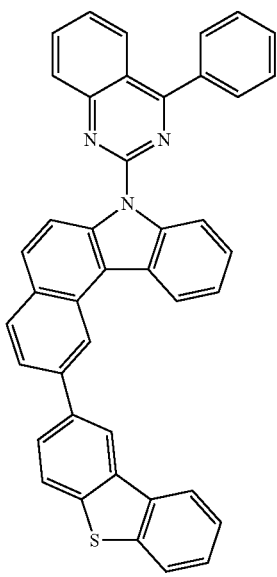
387
524
-continued
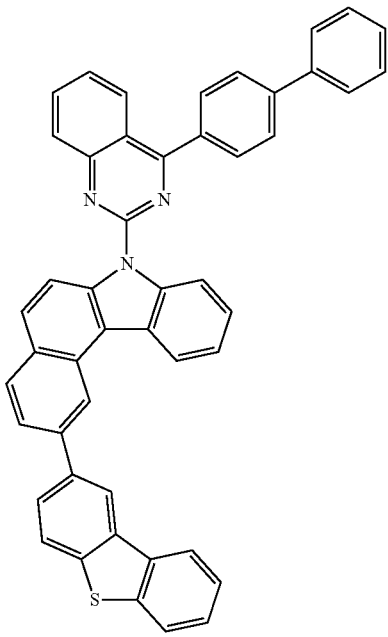
389
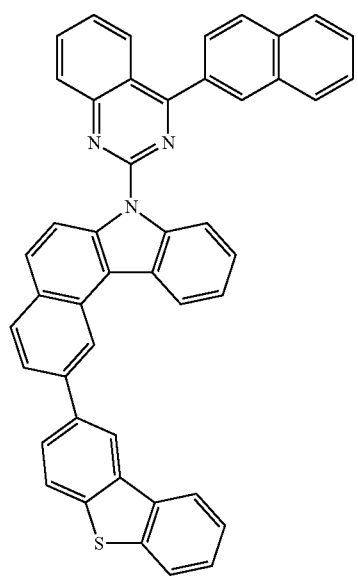
388
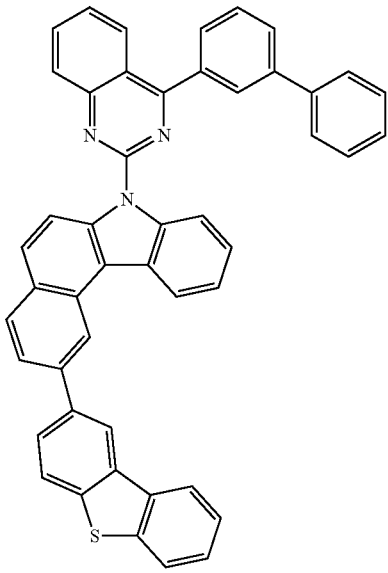
390

391
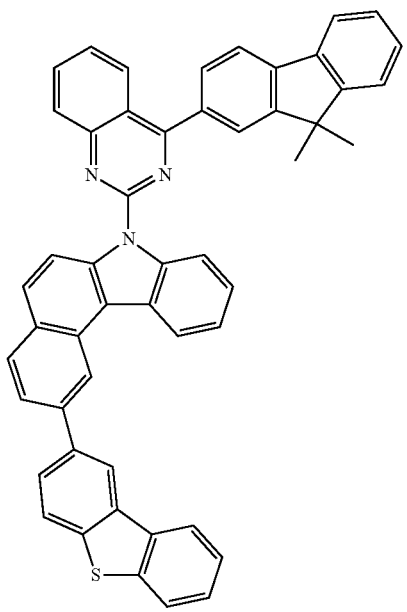
392
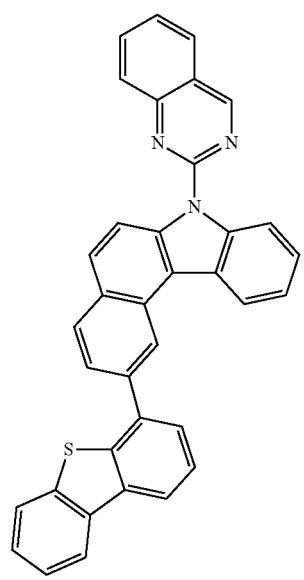
393
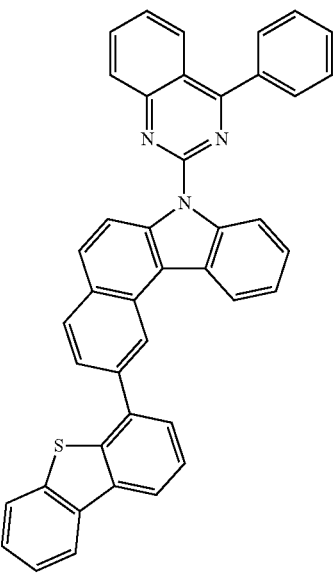
394
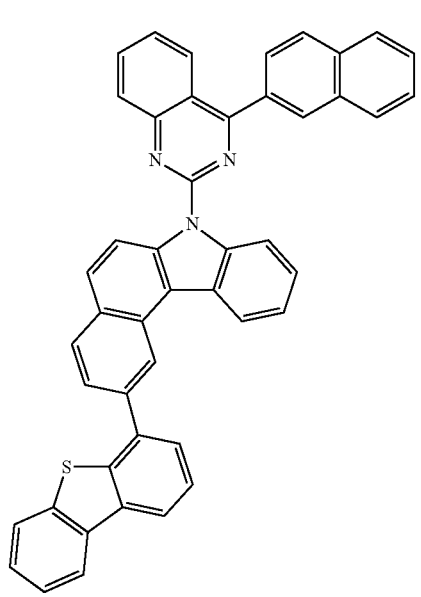

527
-continued
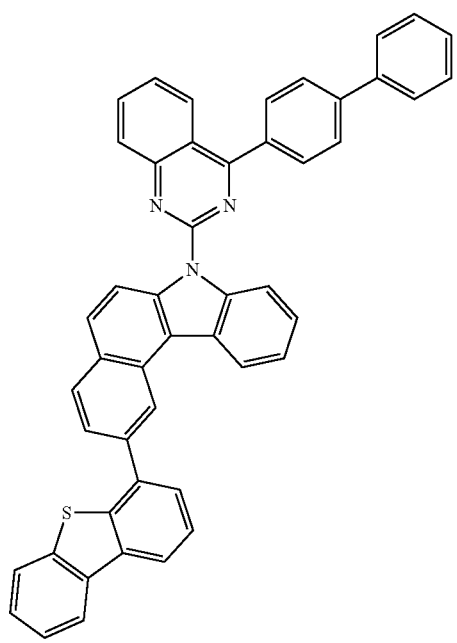
395
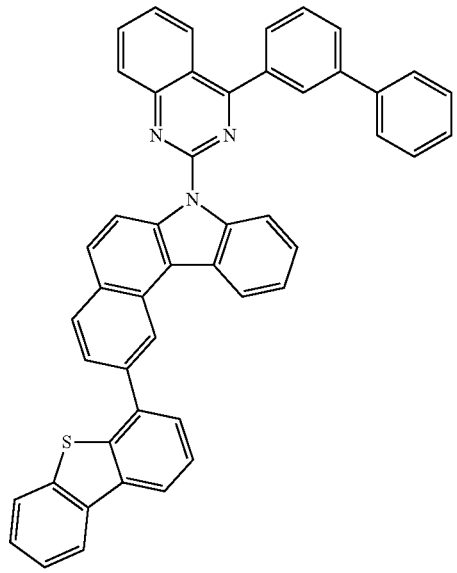
396
528
-continued
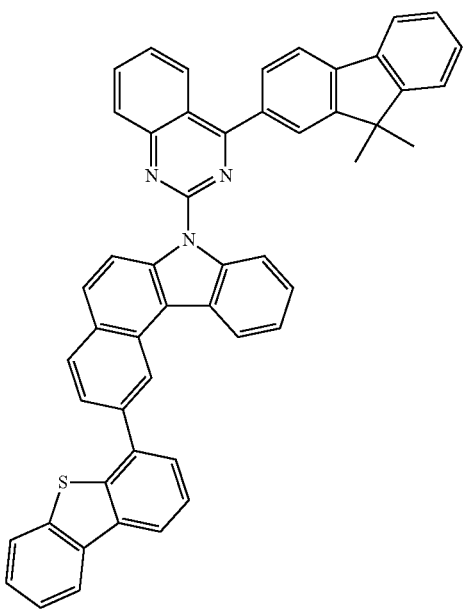
397
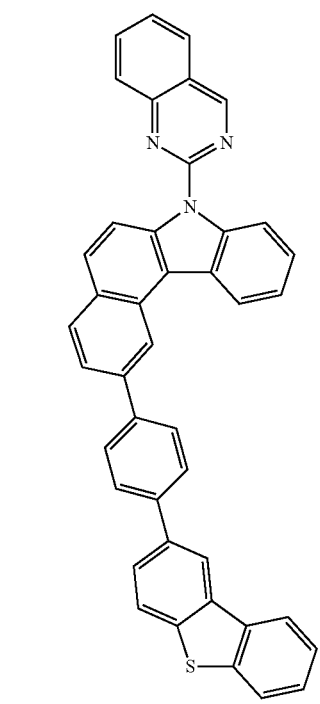
398

529
-continued
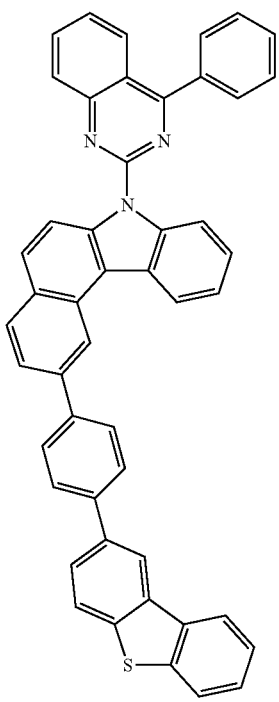
530
-continued
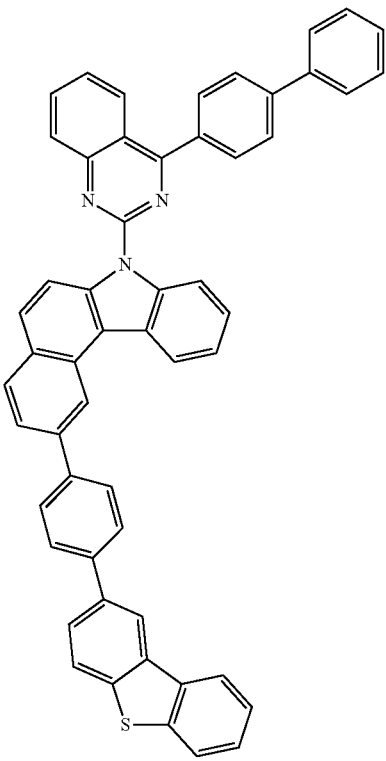
399
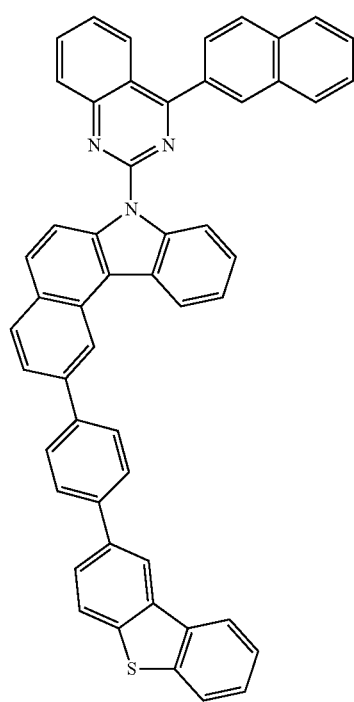
400
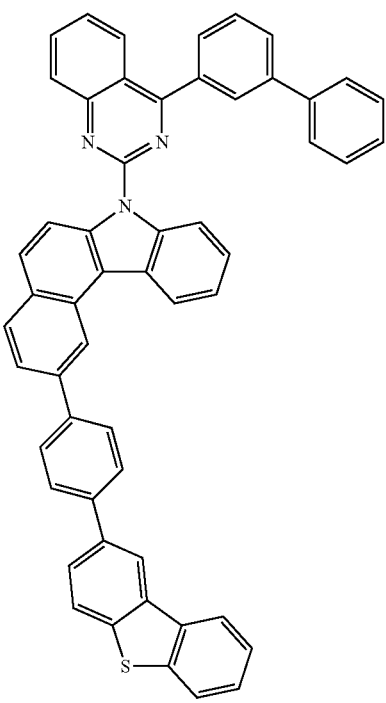
401
402

531
-continued
532
-continued
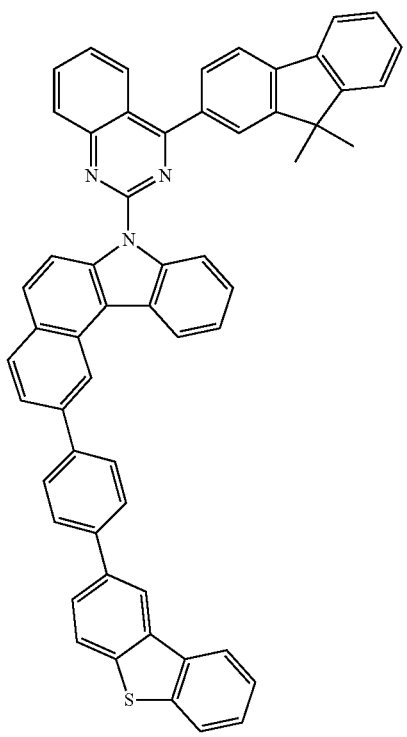
403
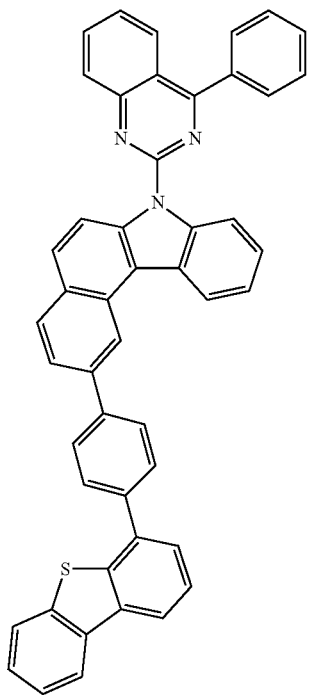
405
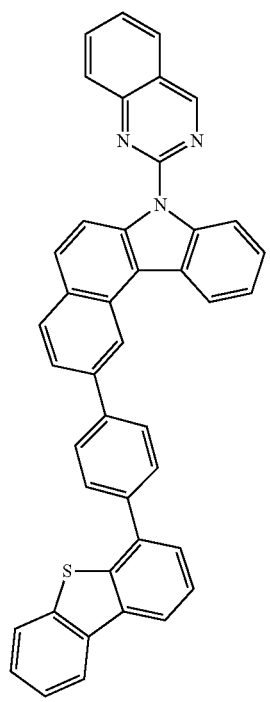
404
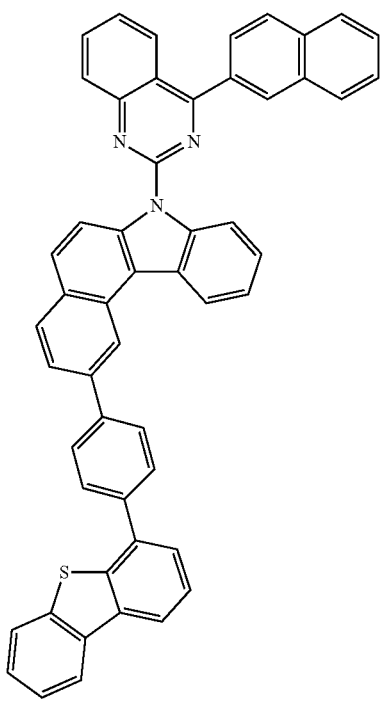
406

533
-continued
407
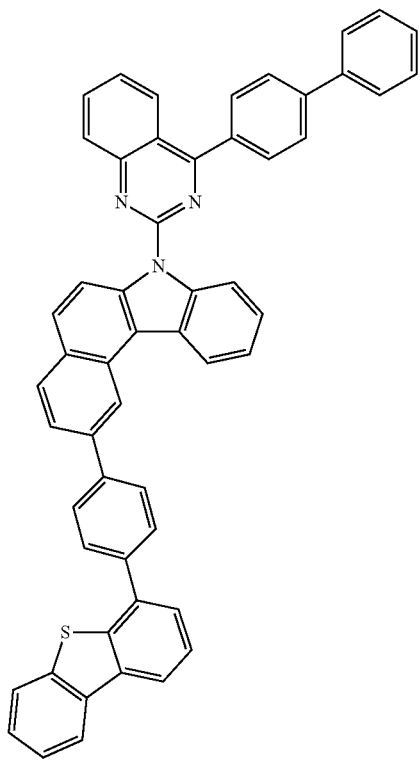
408
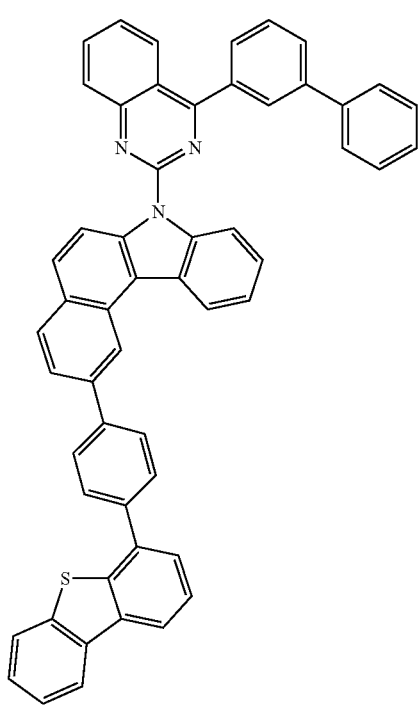
534
-continued
409
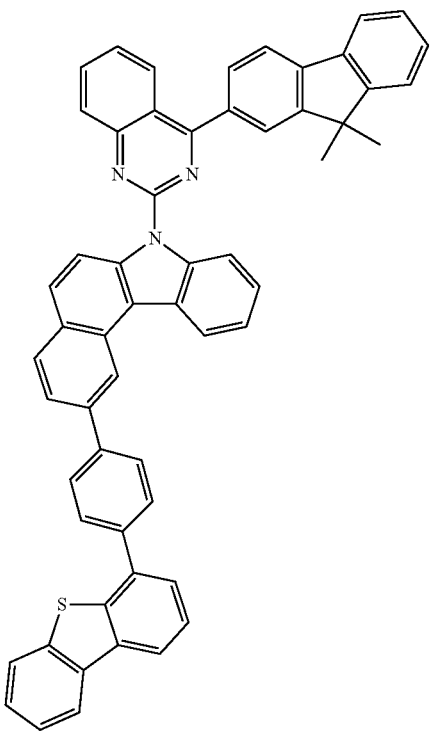
410
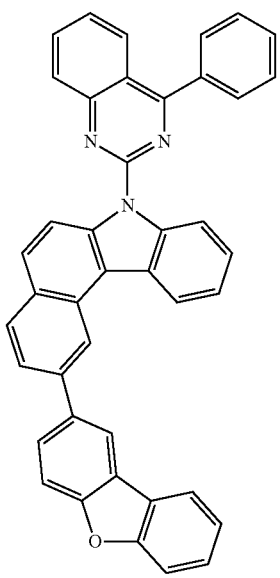

535
-continued
411
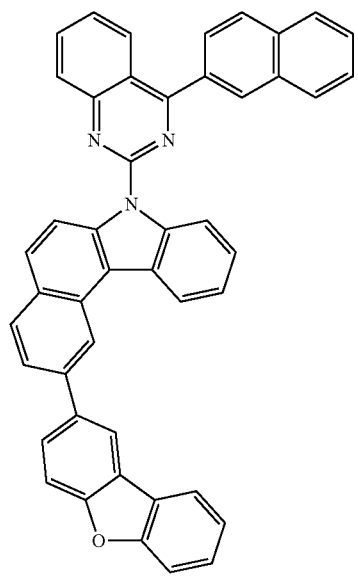
412
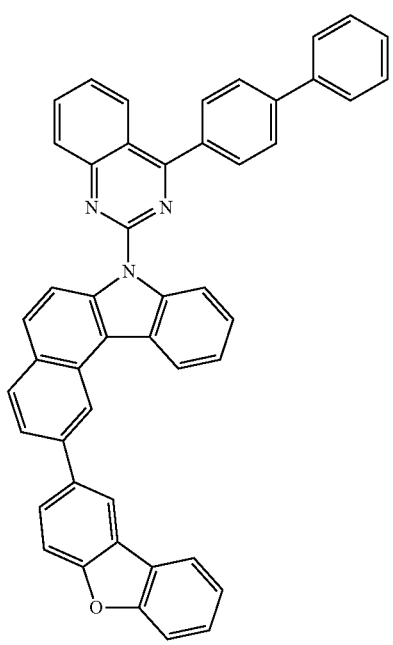
536
-continued
413
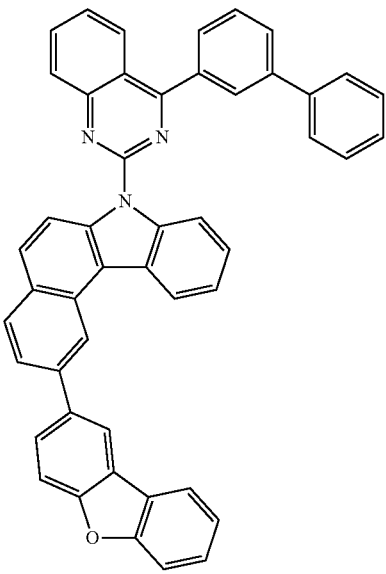
414
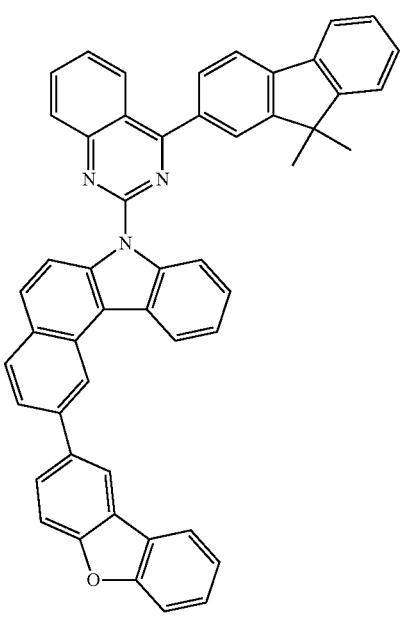

537
-continued
415
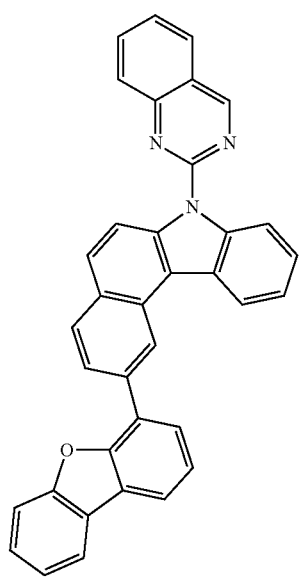
416
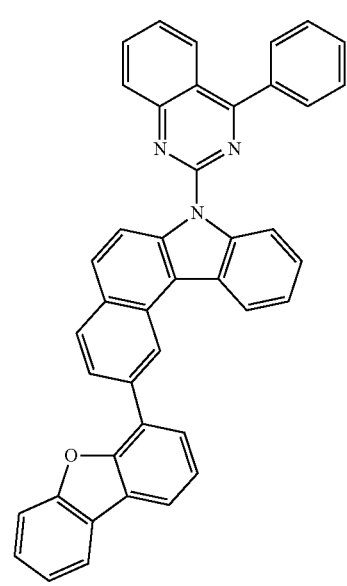
538
-continued
417
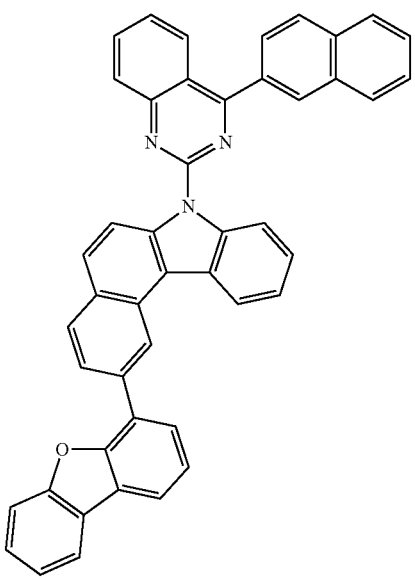
418
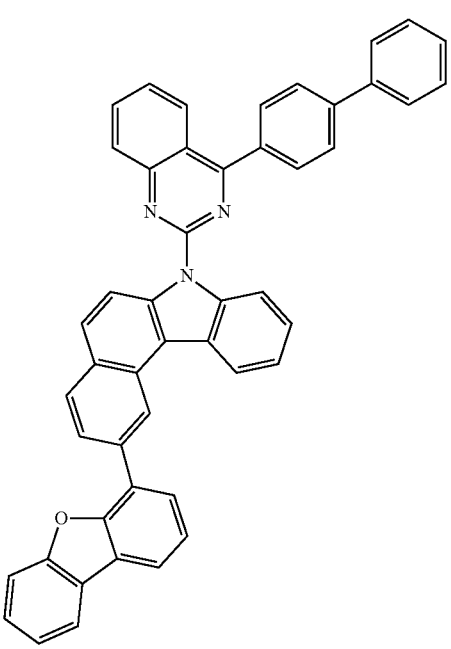

539
-continued
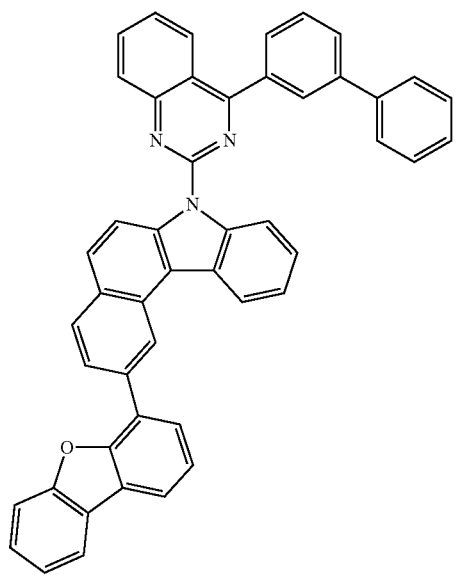
419
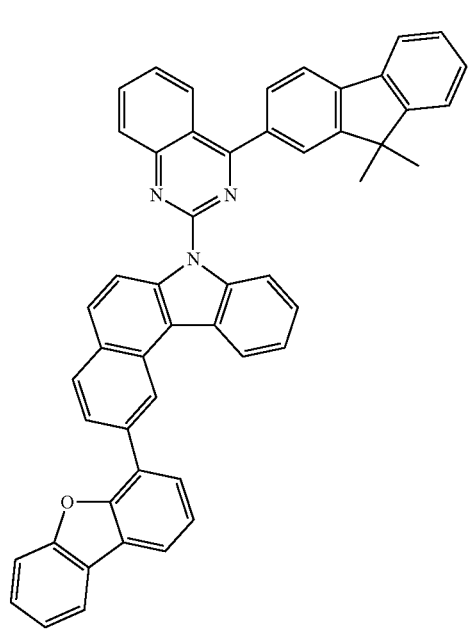
420
540
-continued
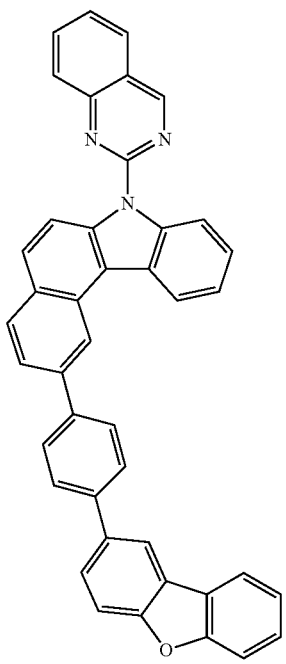
421
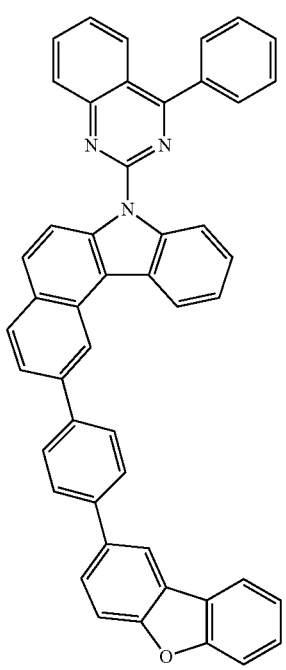
422

541
-continued
423
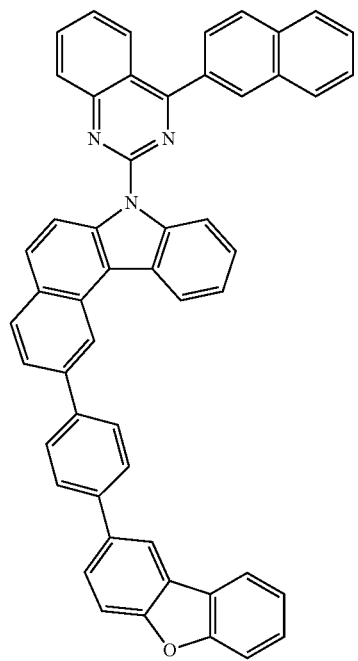
424
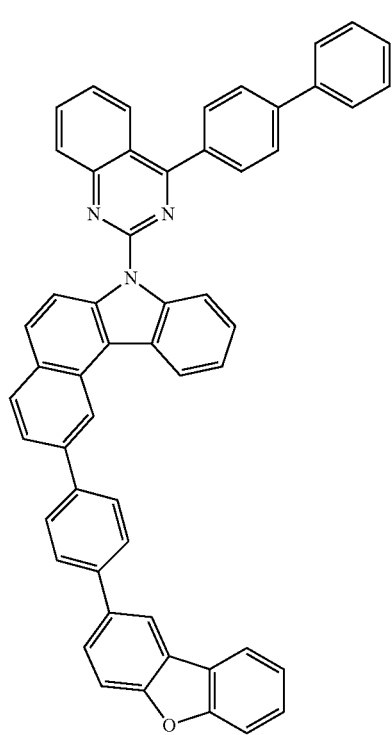
542
-continued
425
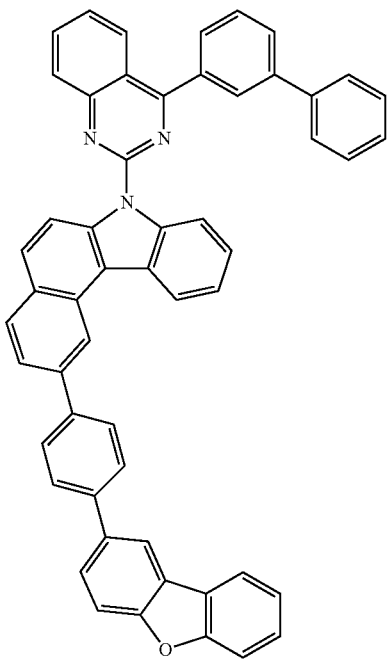
426
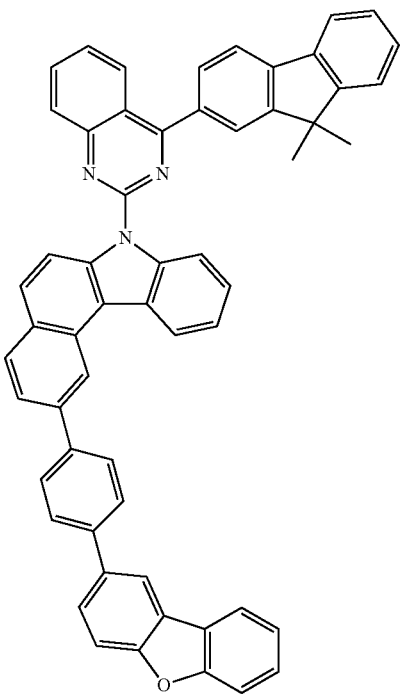

543  544
-continued  -continued
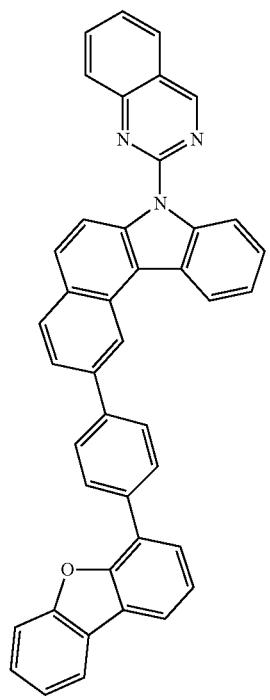
427
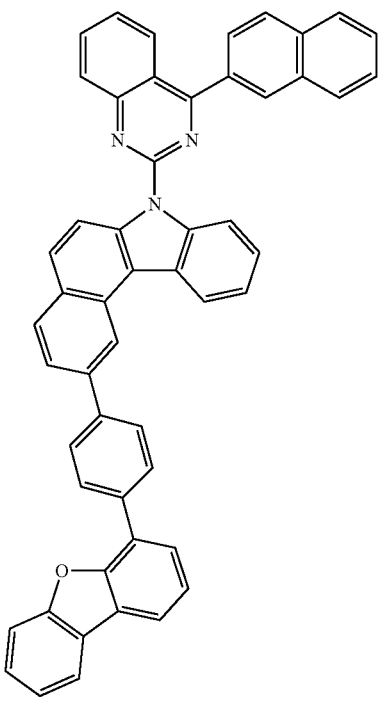
429
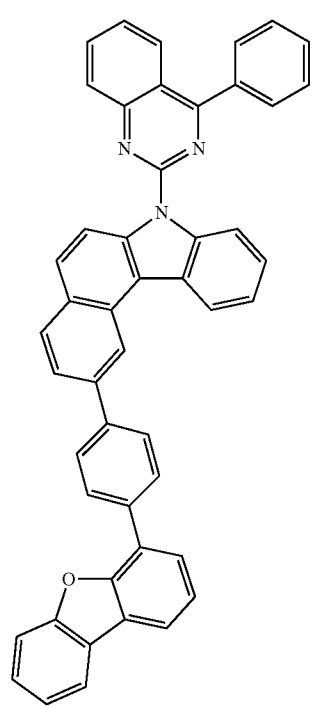
428
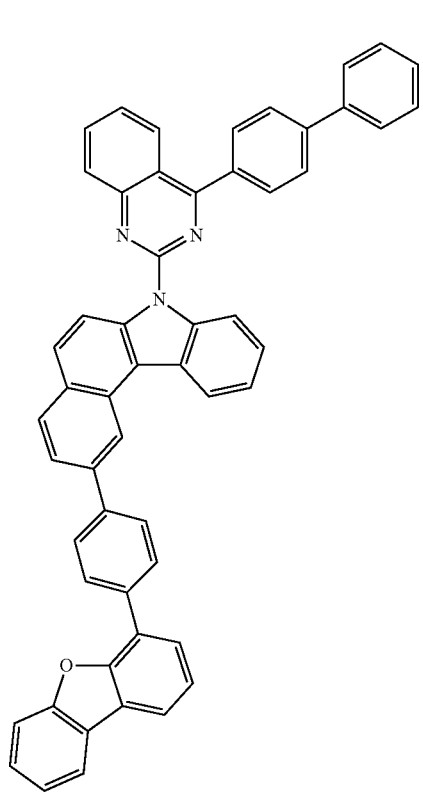
430

545
-continued

431

432

546
-continued

433

434

435

-continued
436
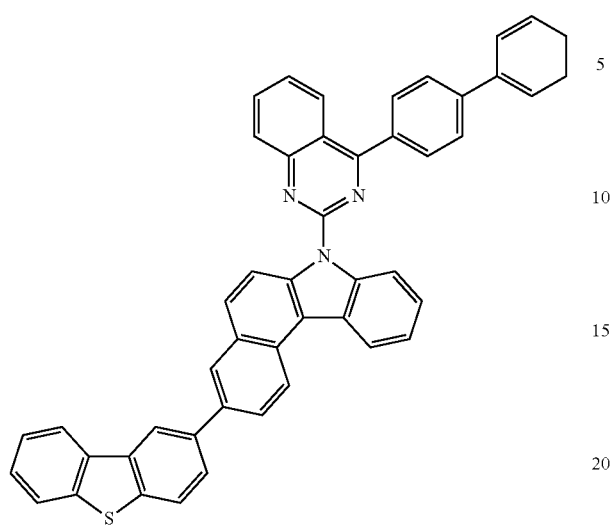
437
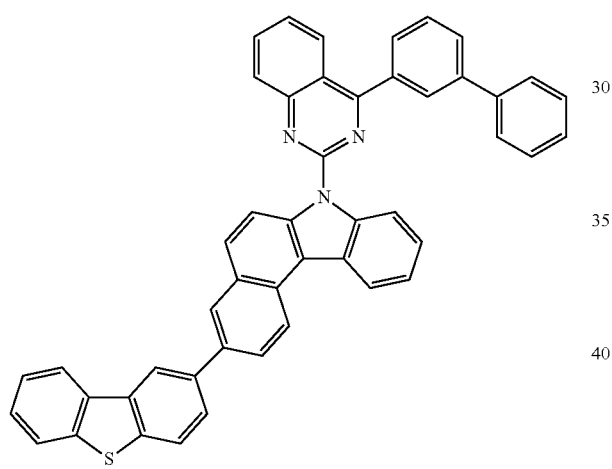
438
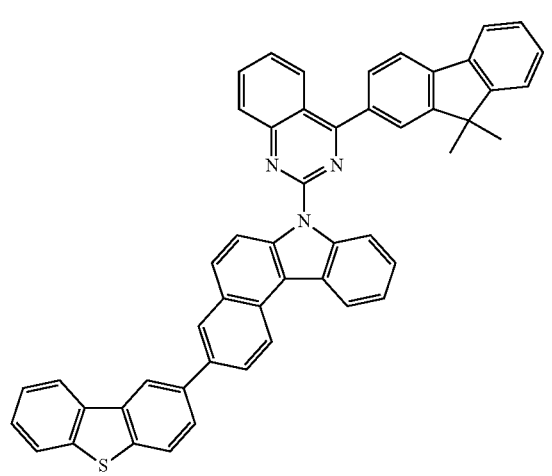
-continued
439
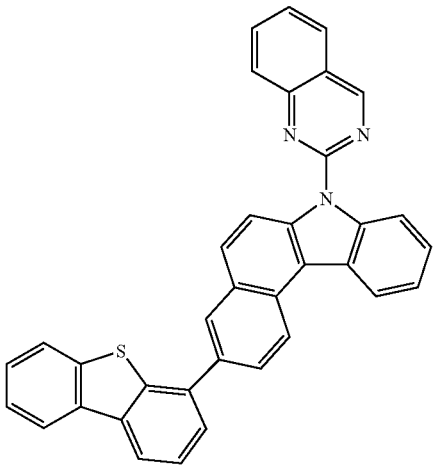
440
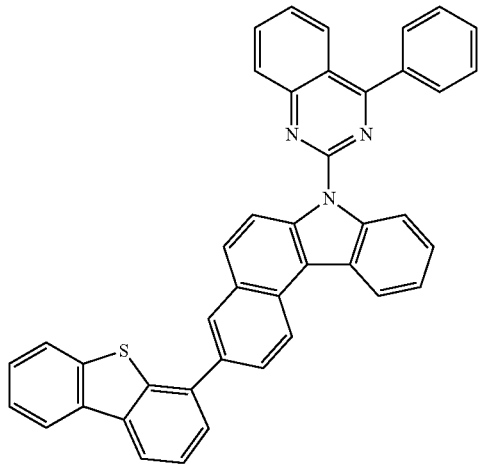
441
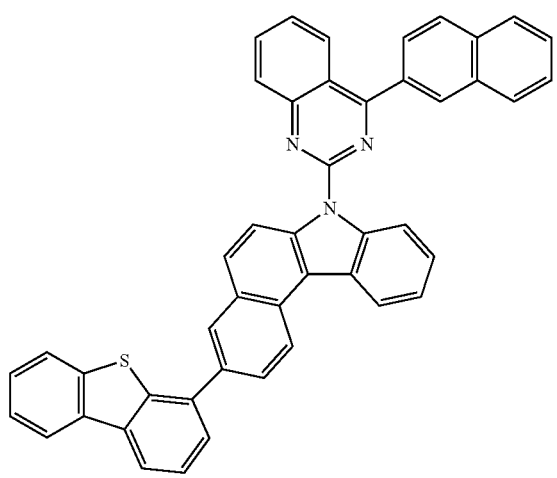

549
-continued
442
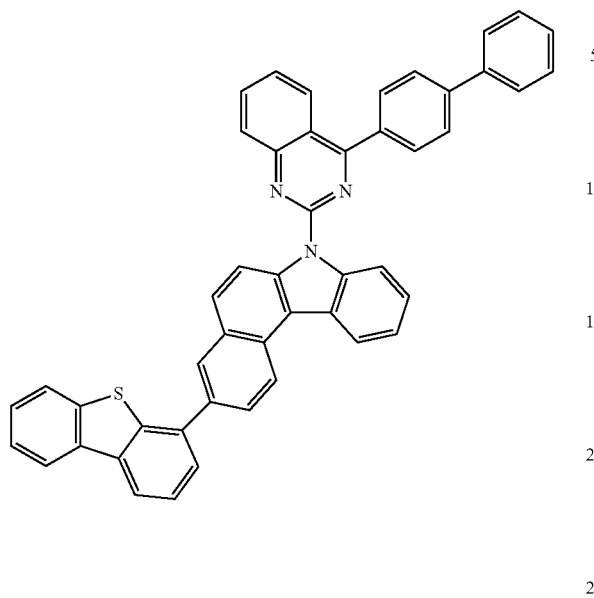
443
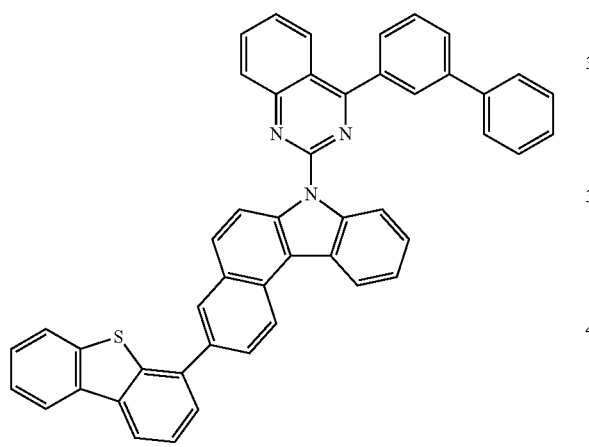
444
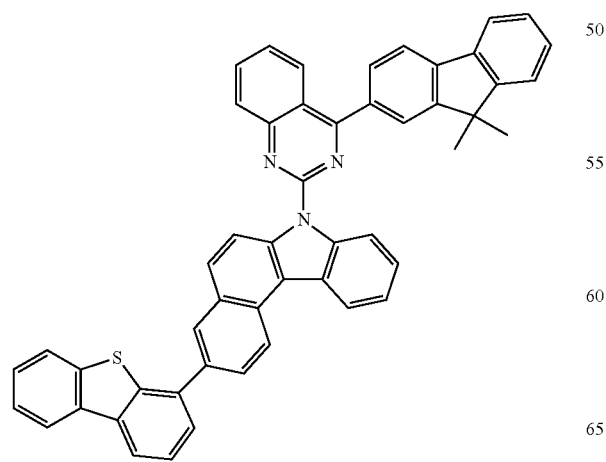
550
-continued
445
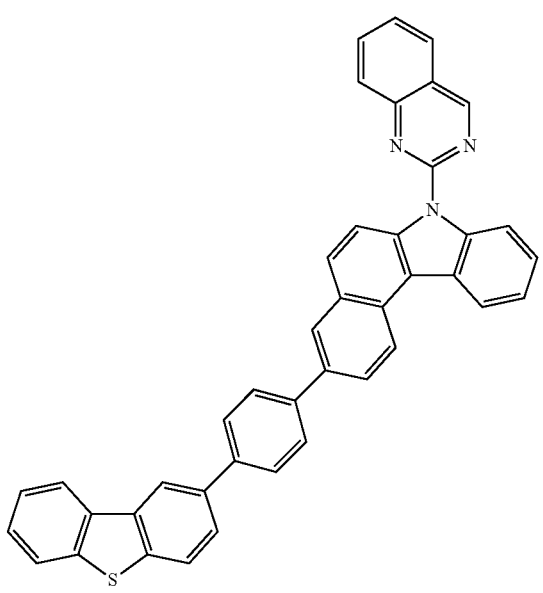
446
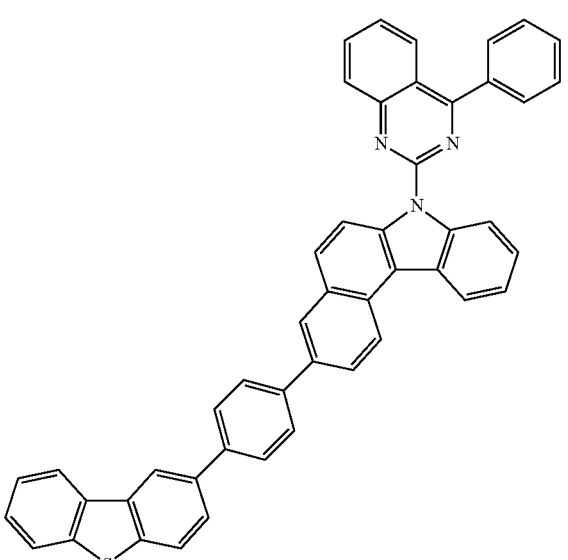

-continued
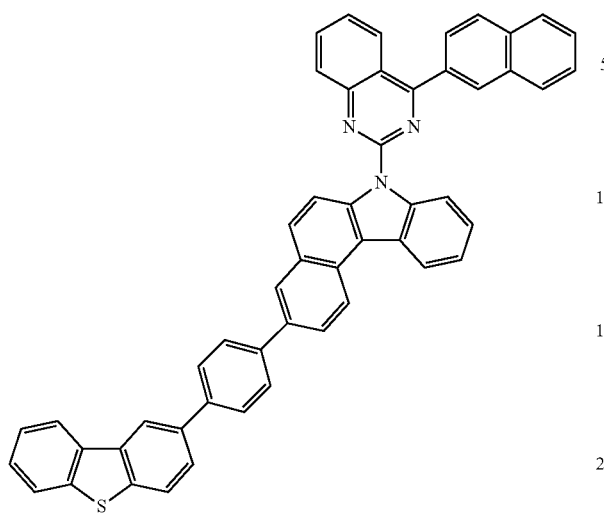
447
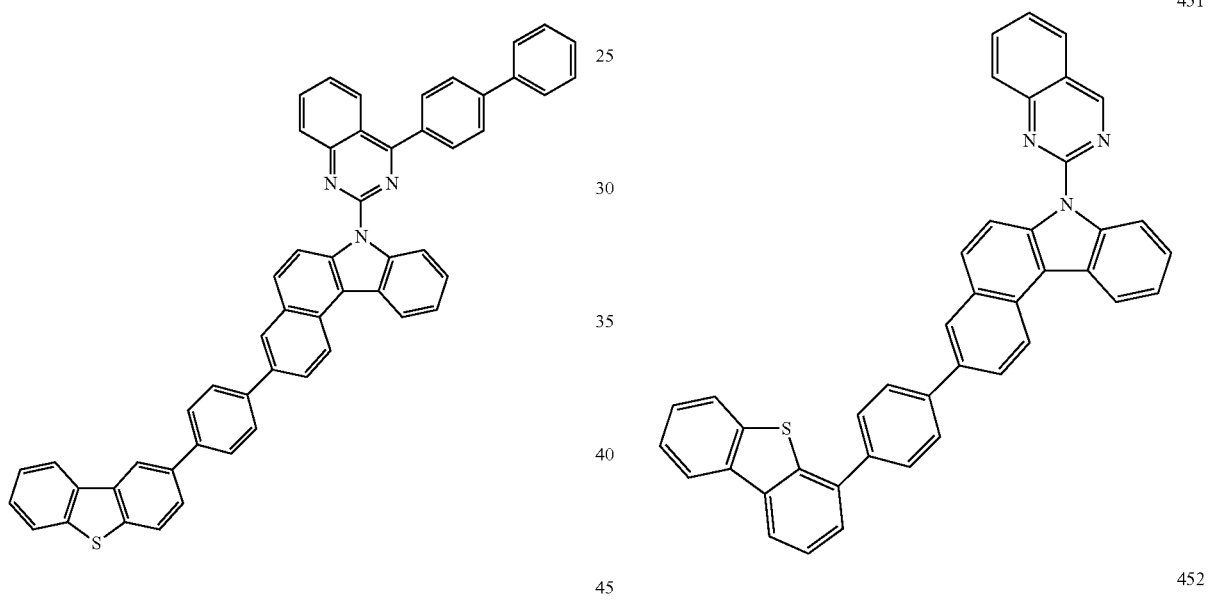
448
449
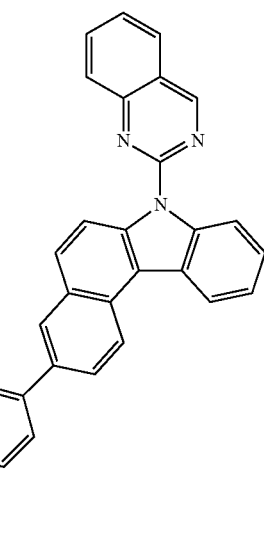
450
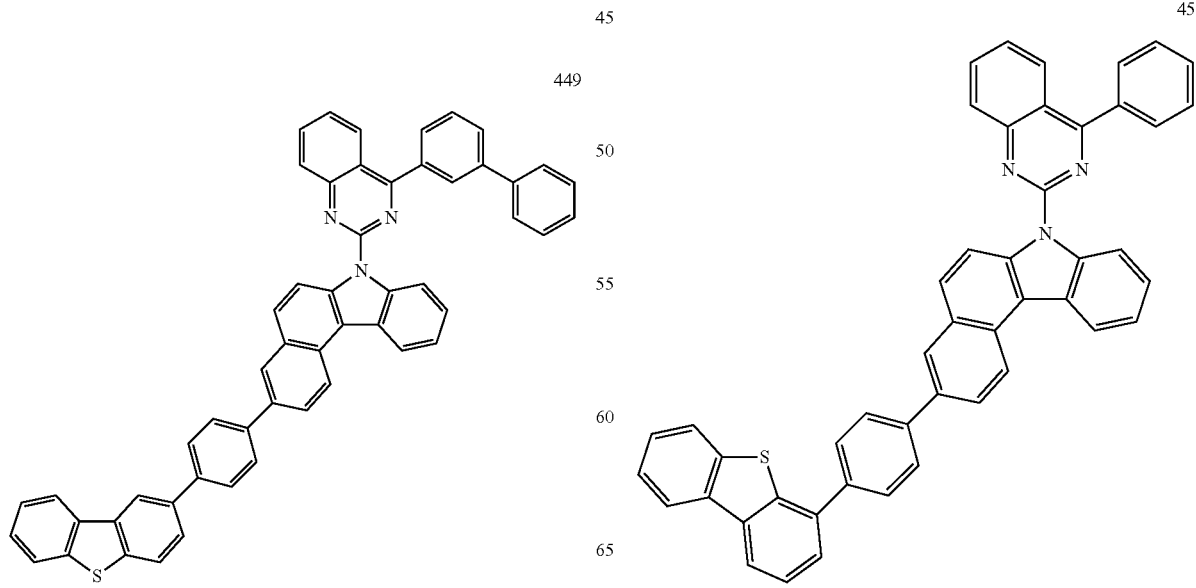
451
452

553
-continued
| 453 | 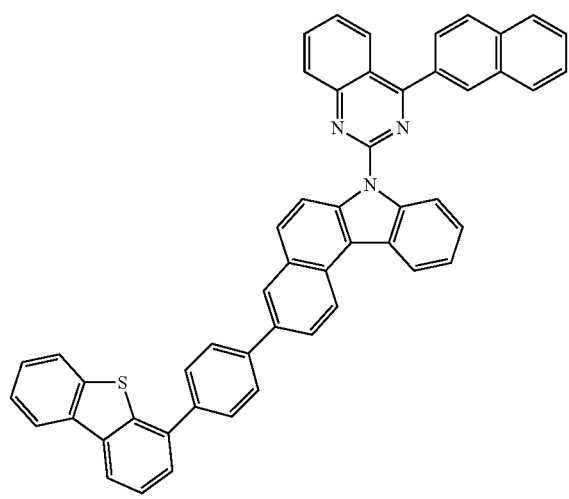 |
| 454 | 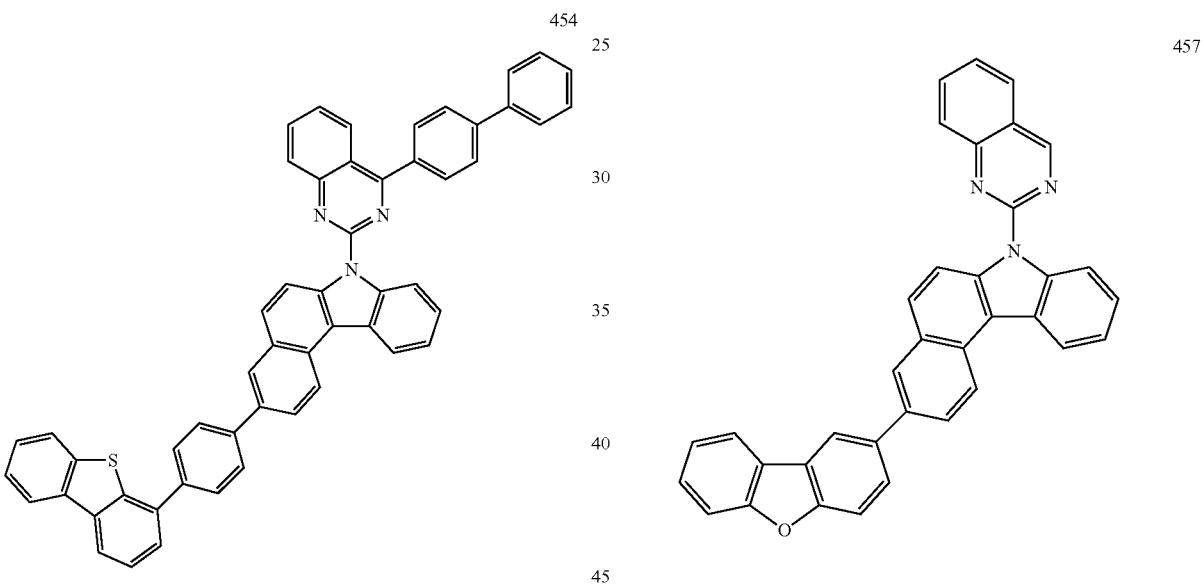 |
| 455 | 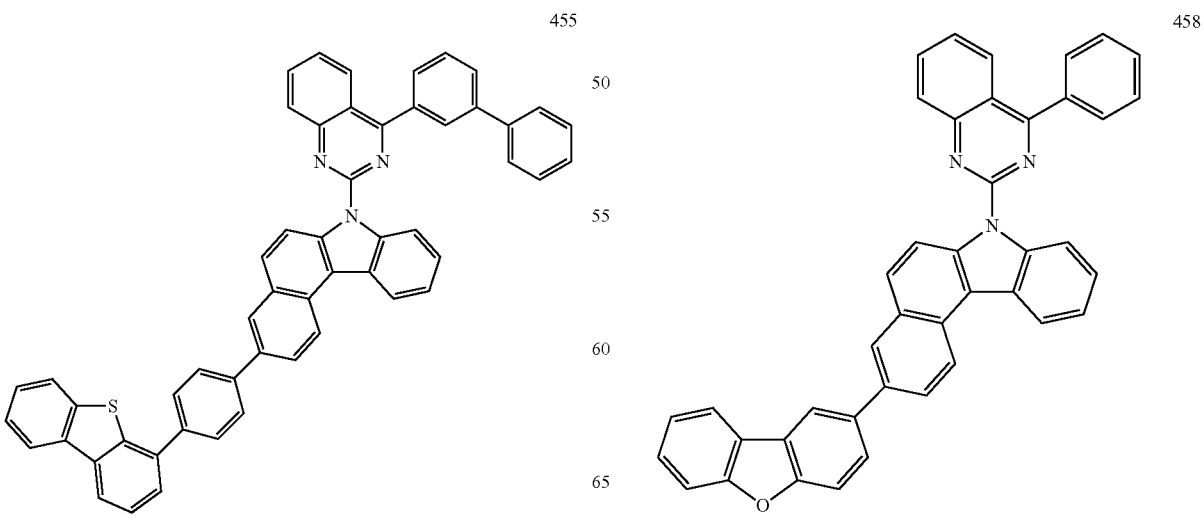 |
554
-continued
| 456 | 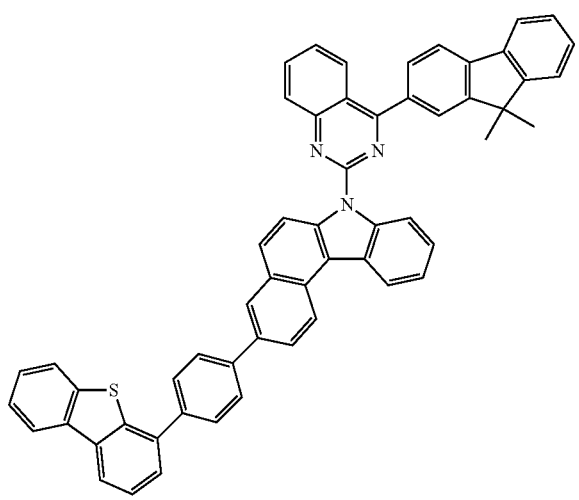 |
| 457 | 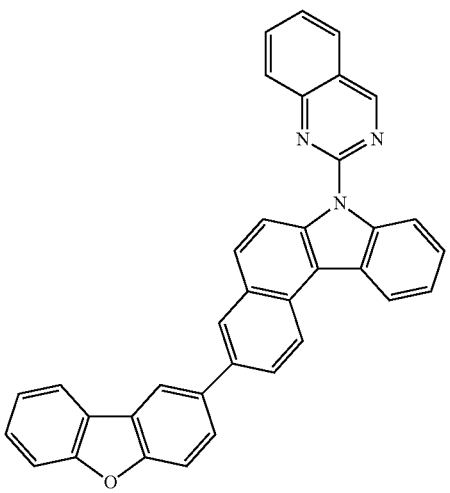 |
| 458 | 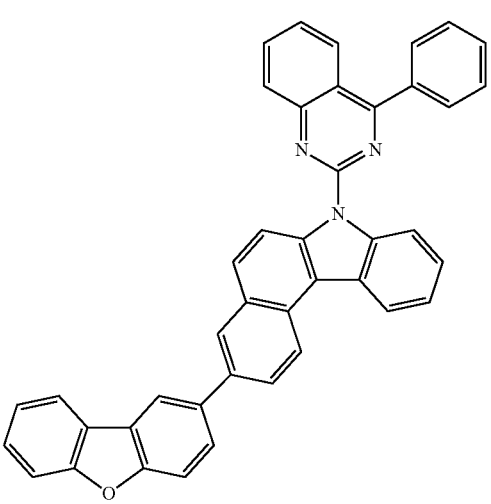 |

-continued
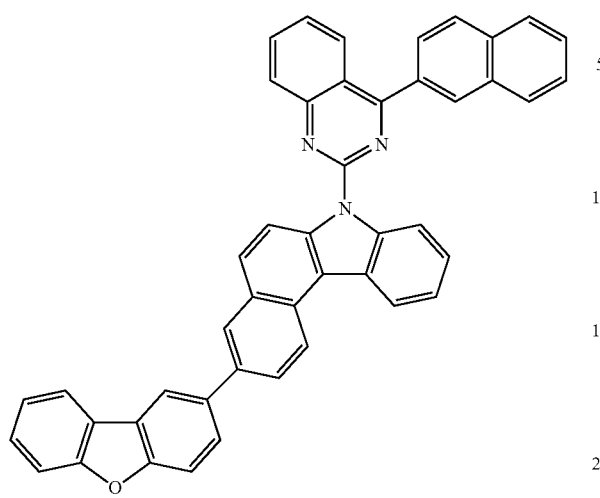
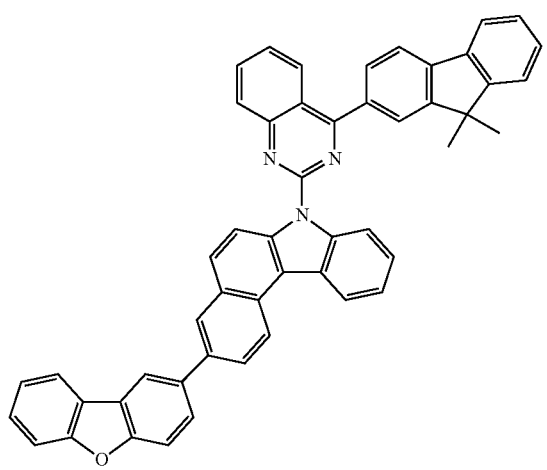
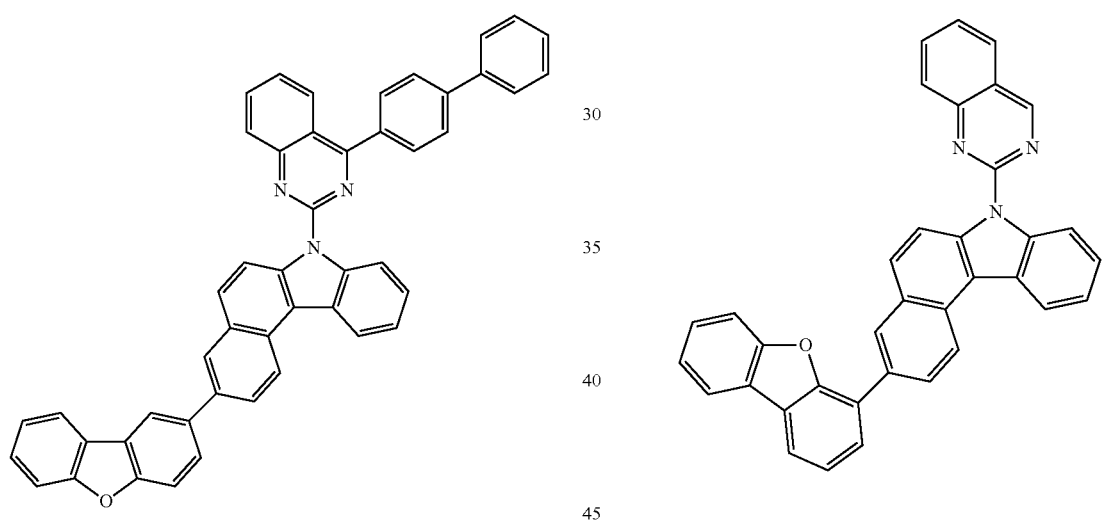
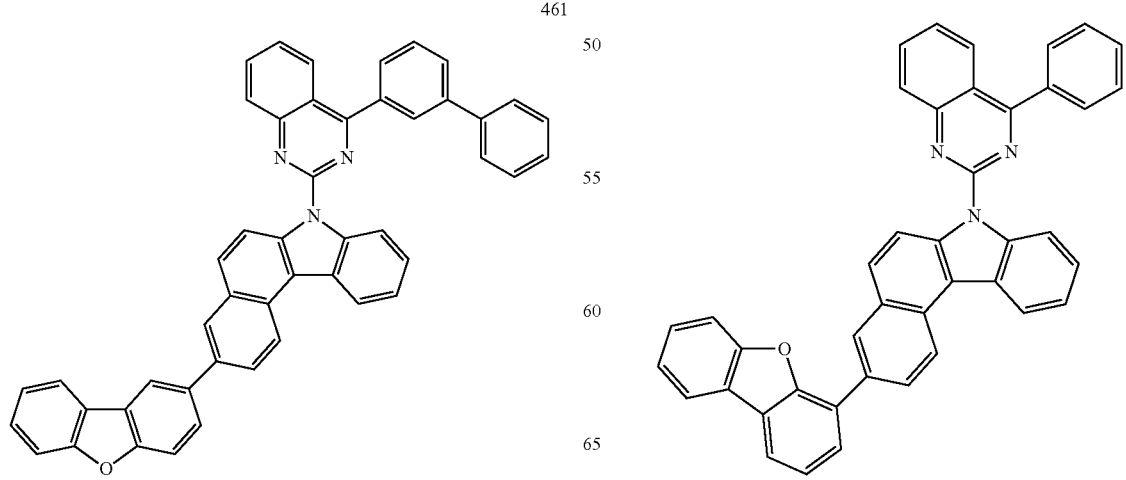

-continued
465
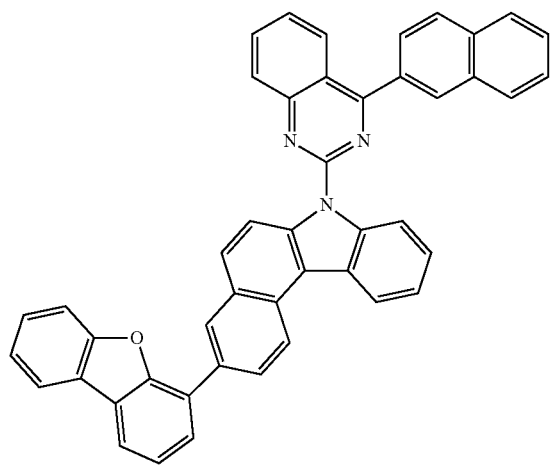
468
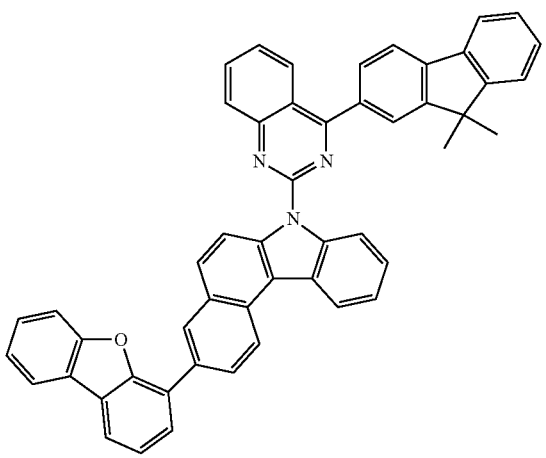
466
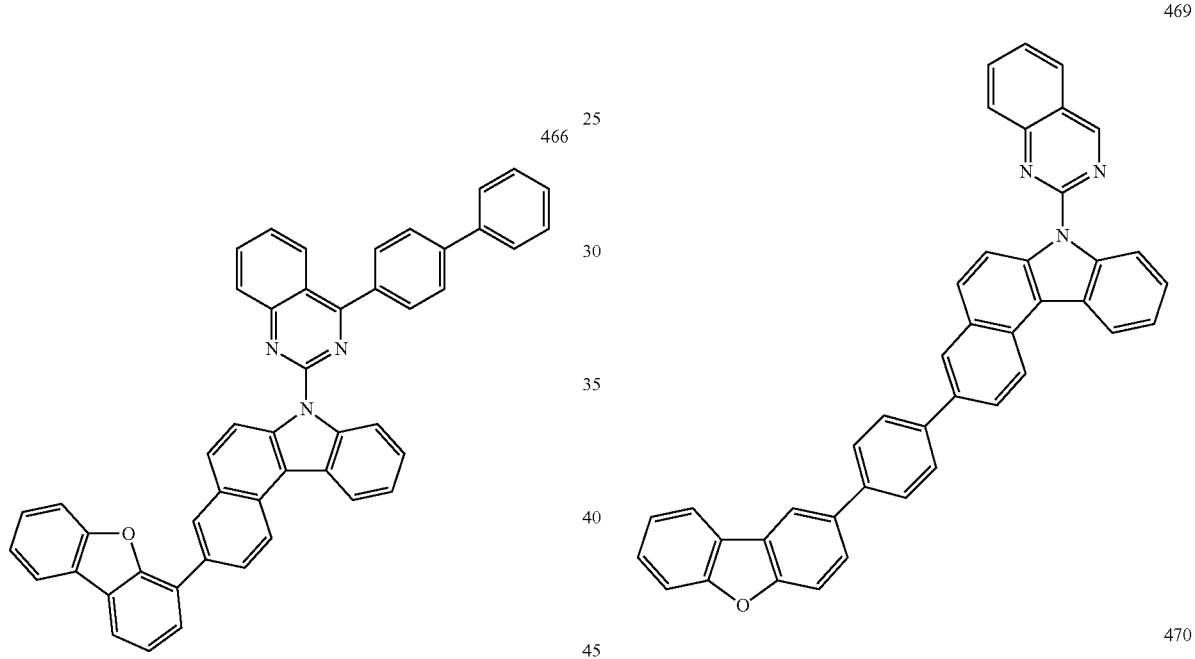
469
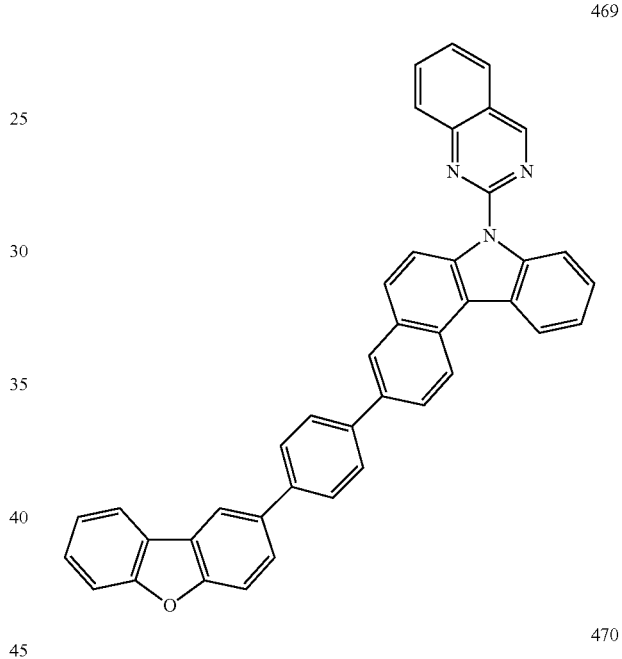
467
470
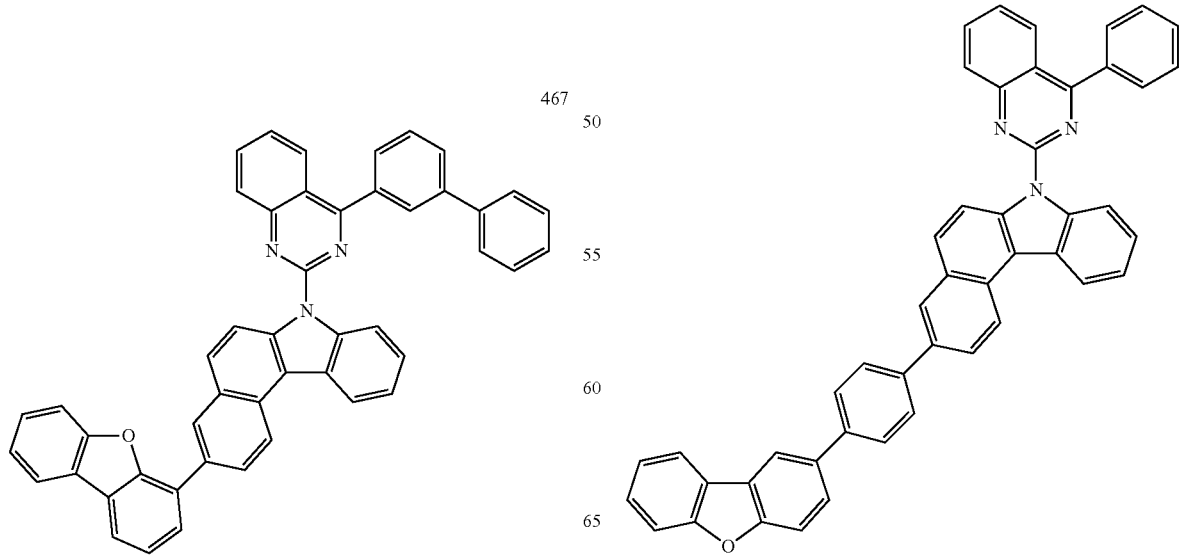

559
-continued
471
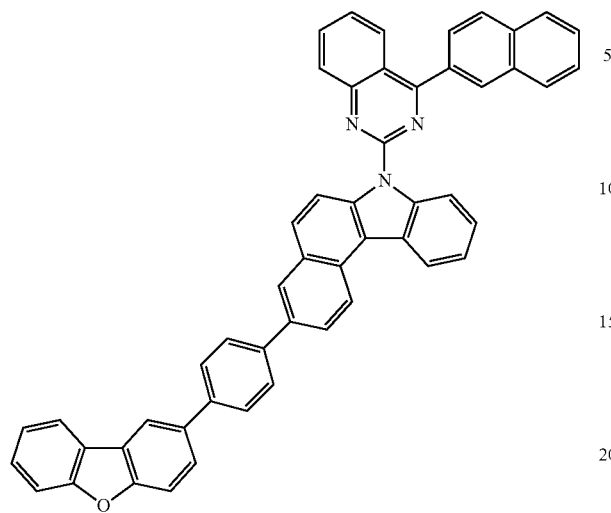
472
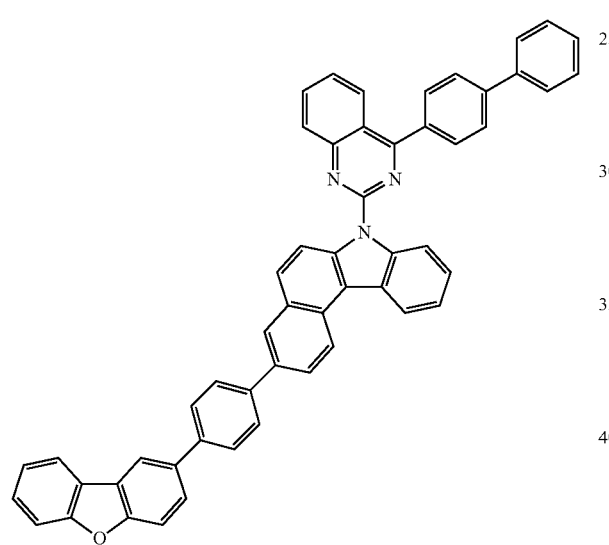
473
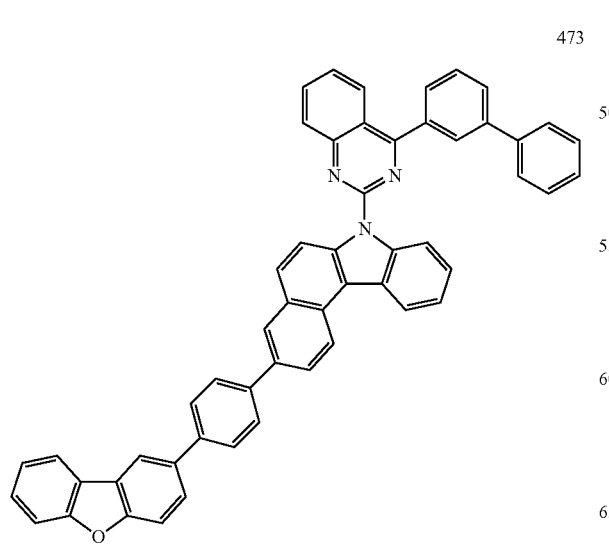
560
-continued
474
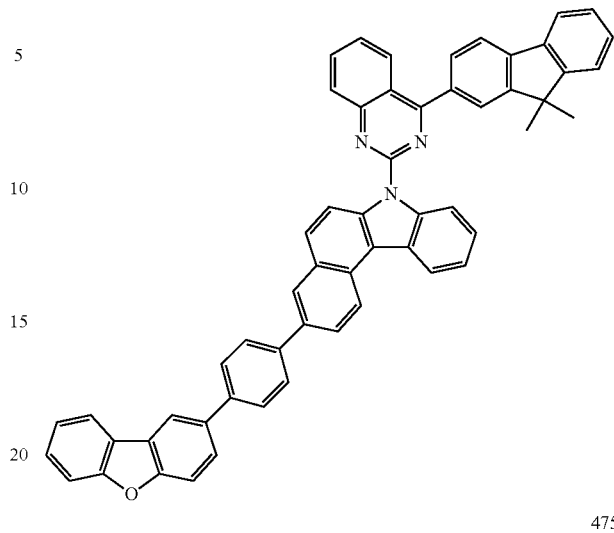
475
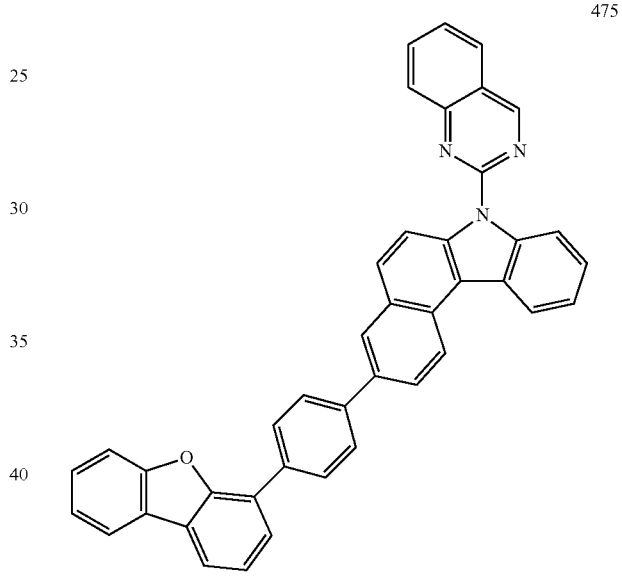
476
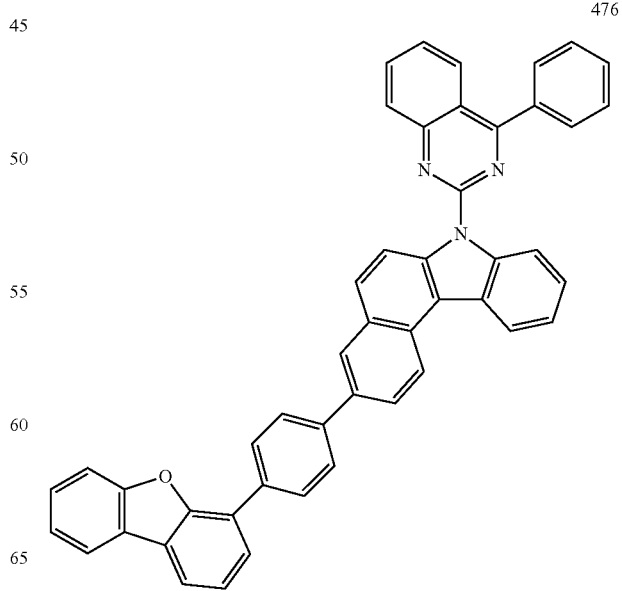

561
-continued
477
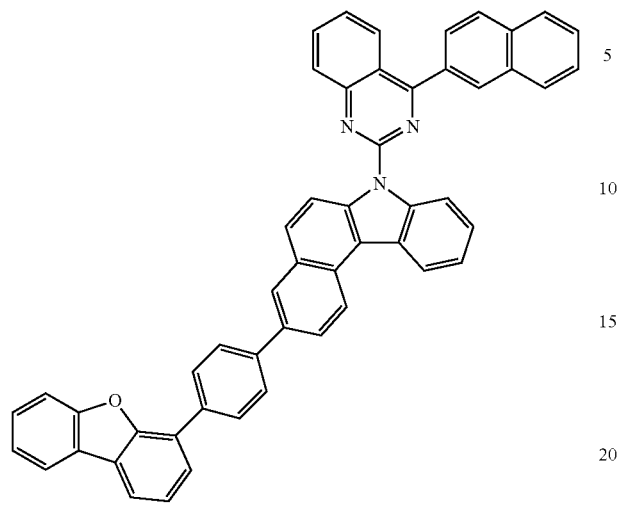
478
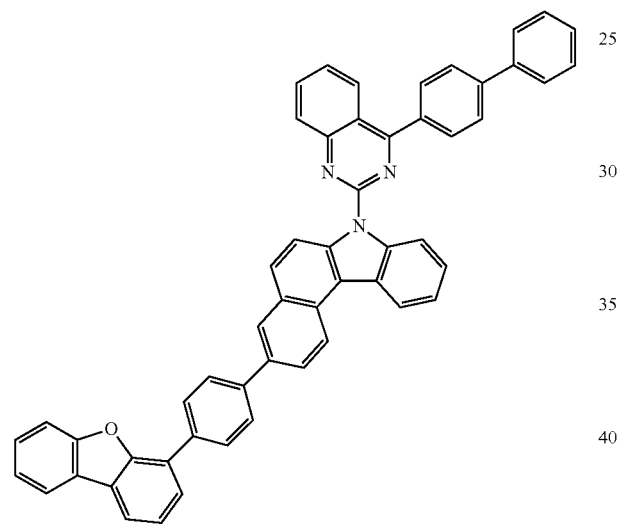
479
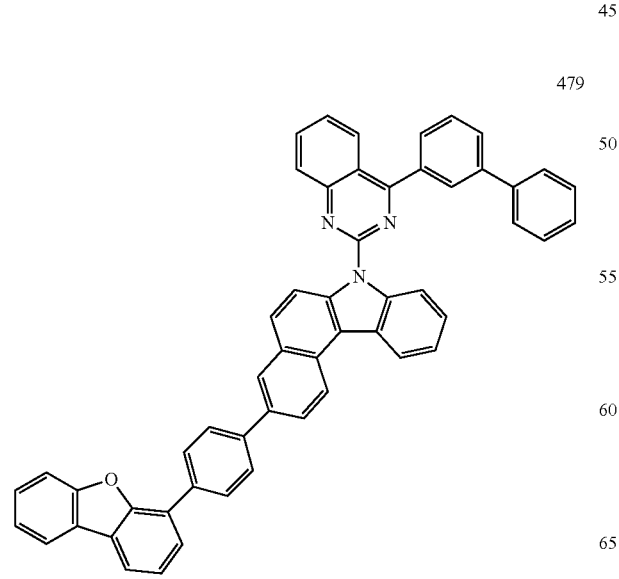
562
-continued
480
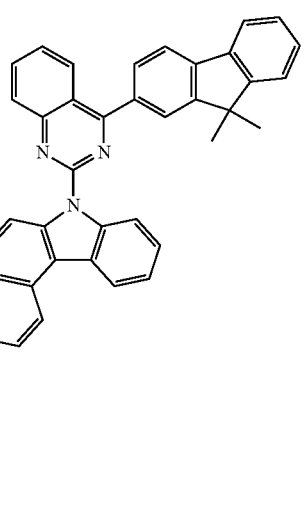
481
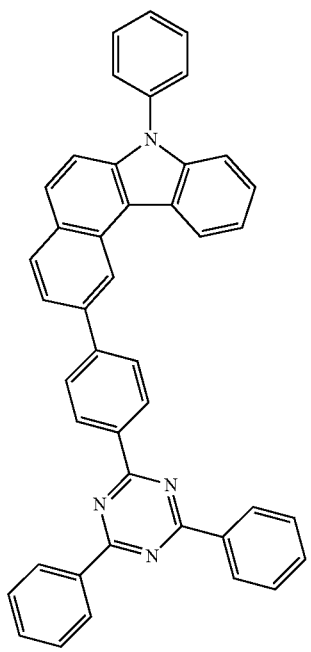

563
-continued
482
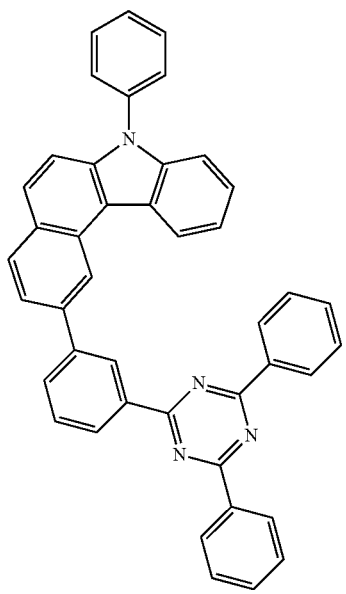
483
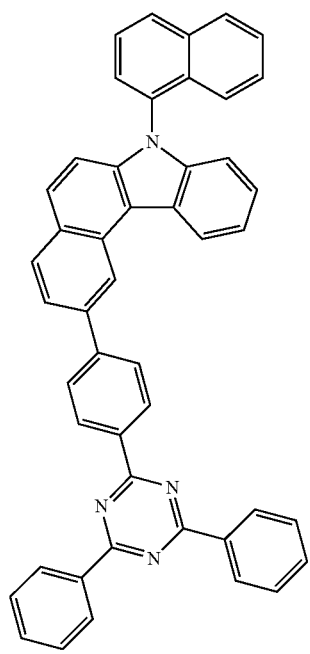
564
-continued
484
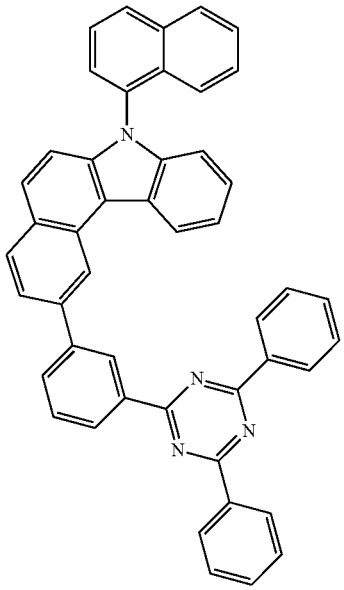
485
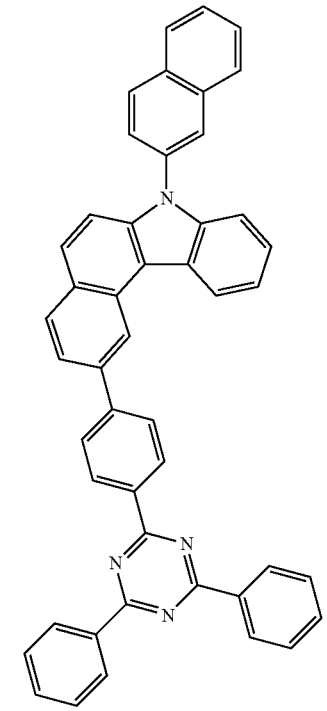

486
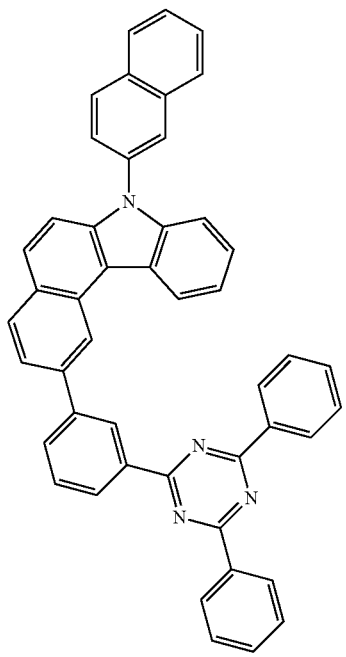
487
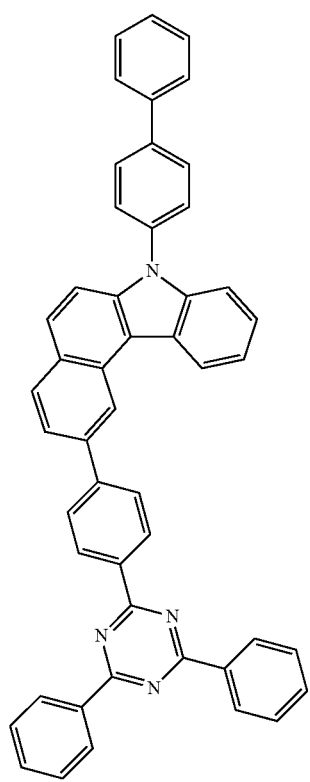
489
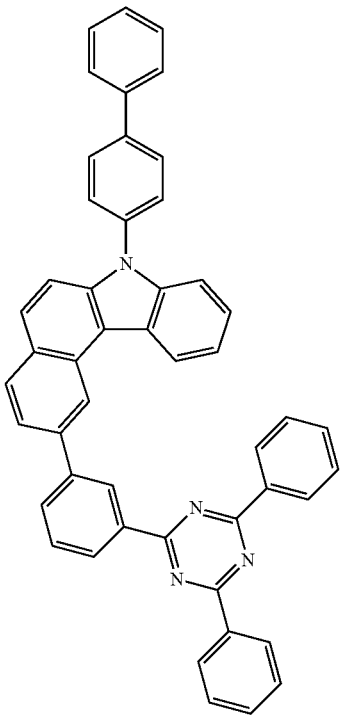
490
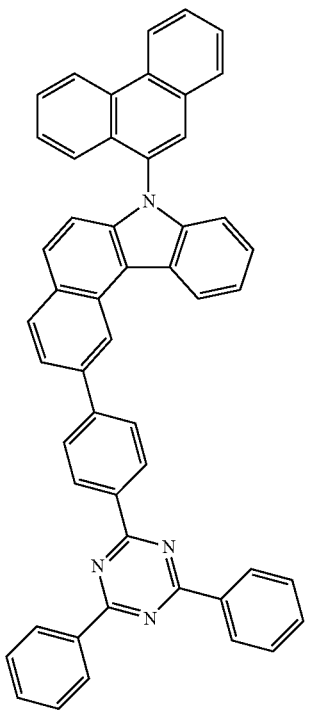

491
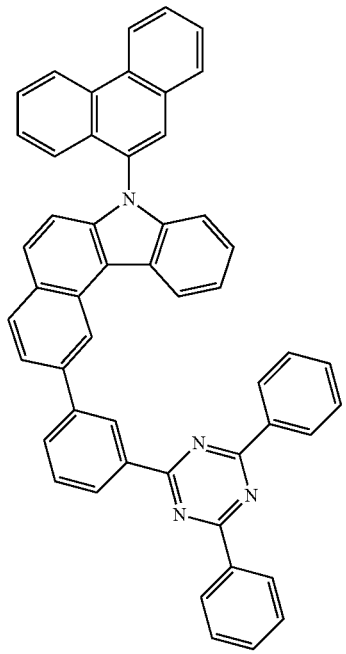
492
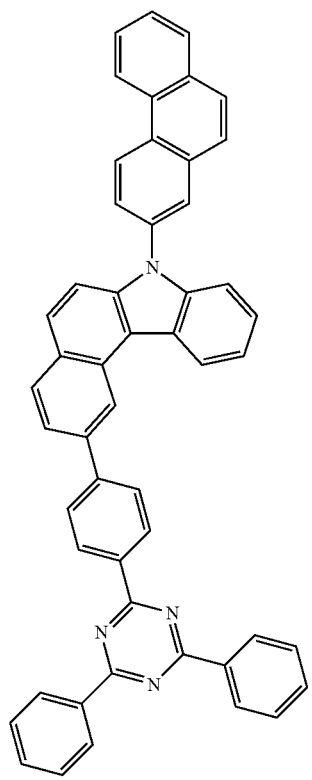
493
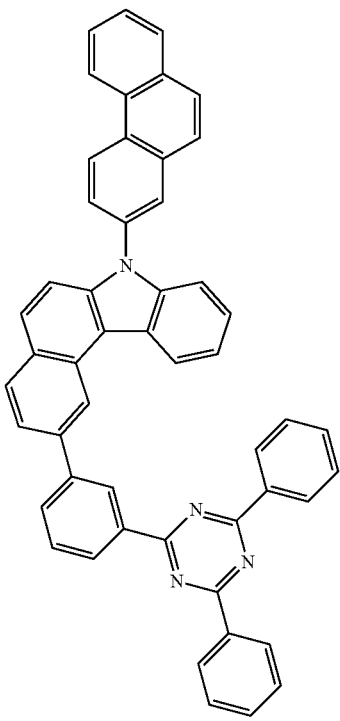
494
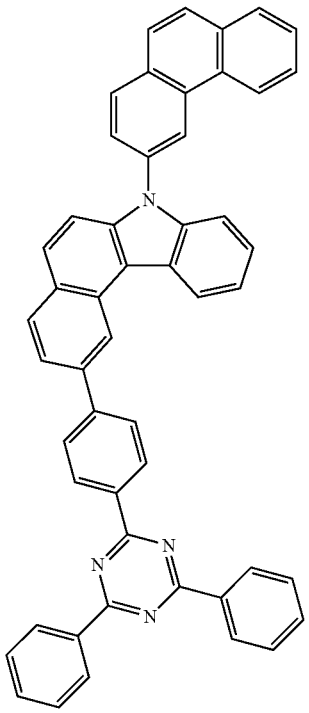

569
-continued
495
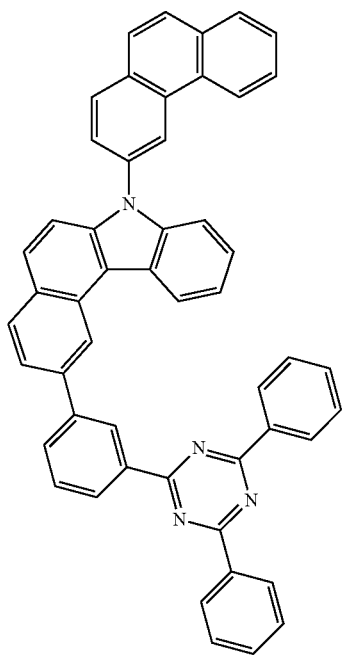
496
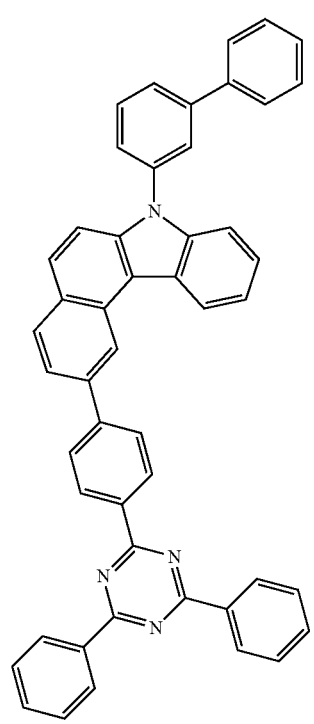
570
-continued
497
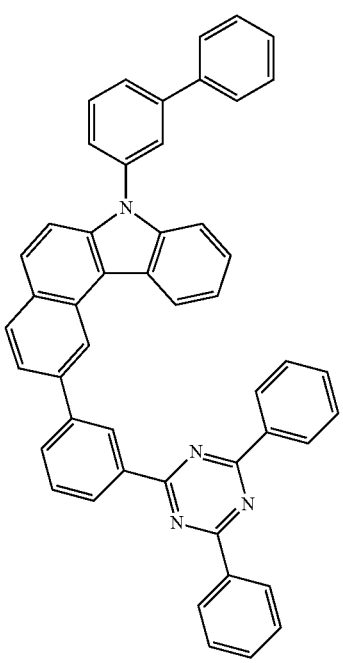
498
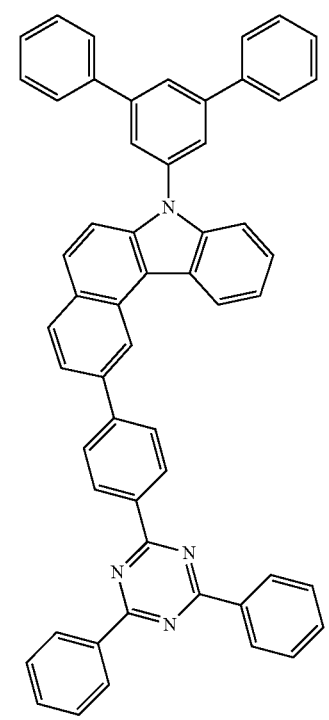

571
-continued
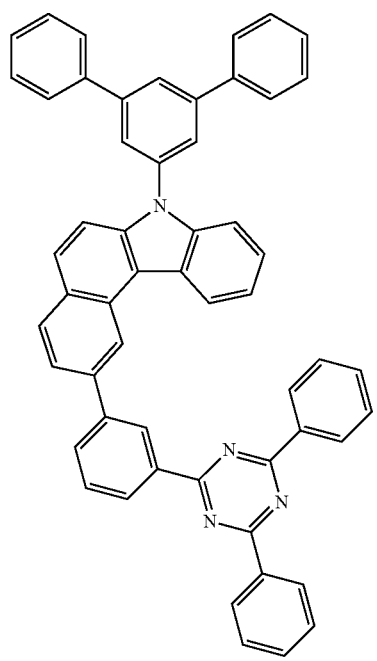
499
572
-continued
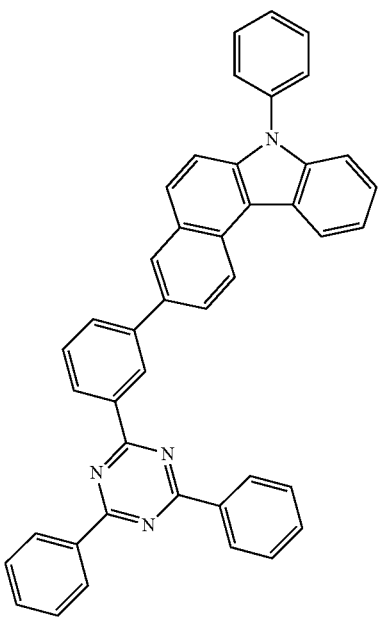
501
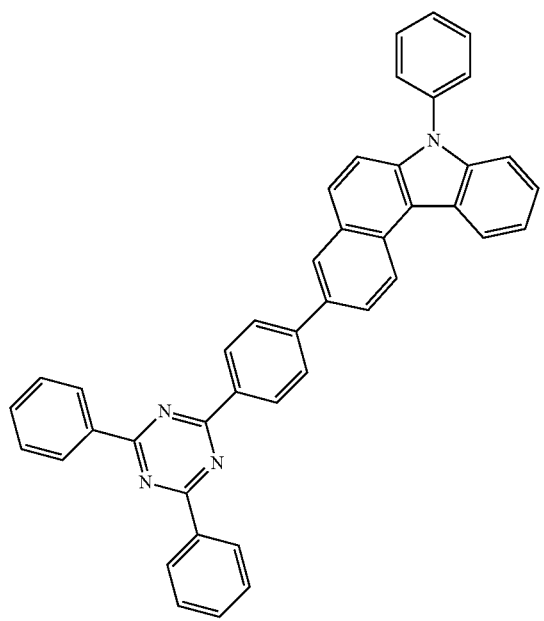
500
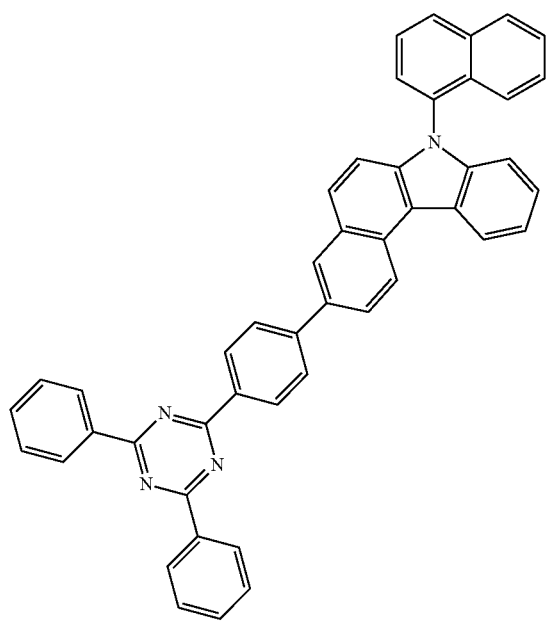
502

573
-continued
574
-continued
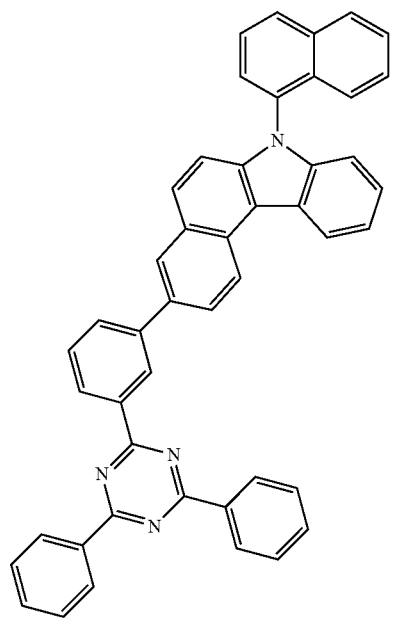
503
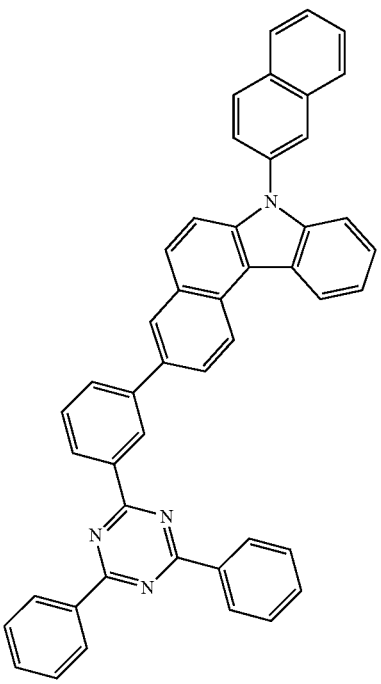
505
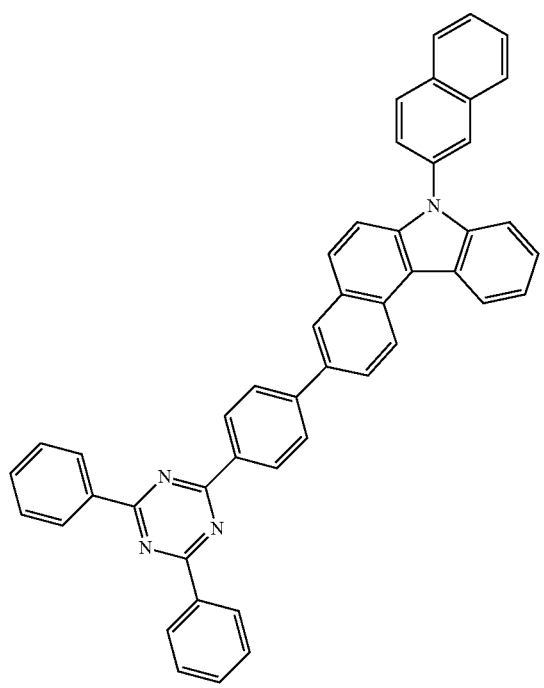
504
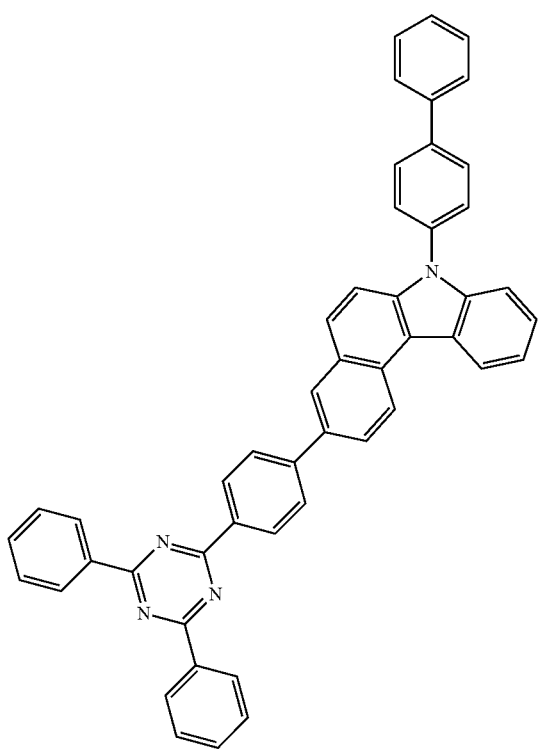
506

575
-continued
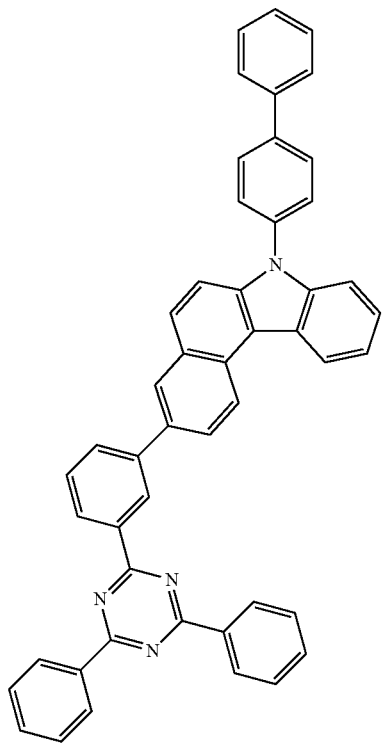
507
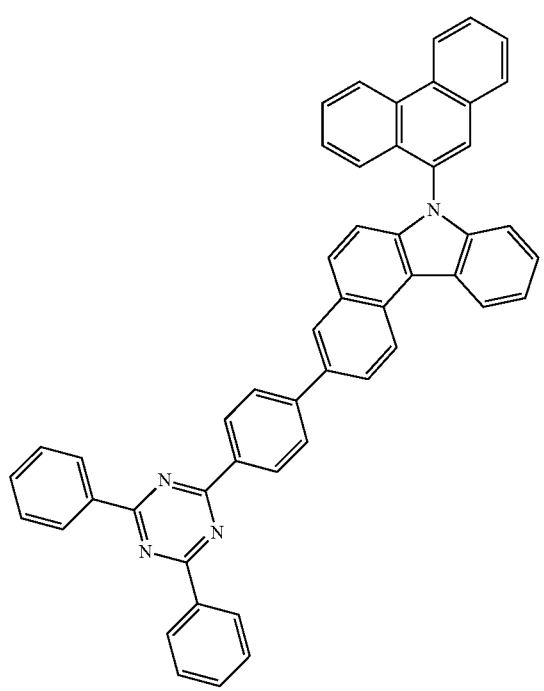
508
576
-continued
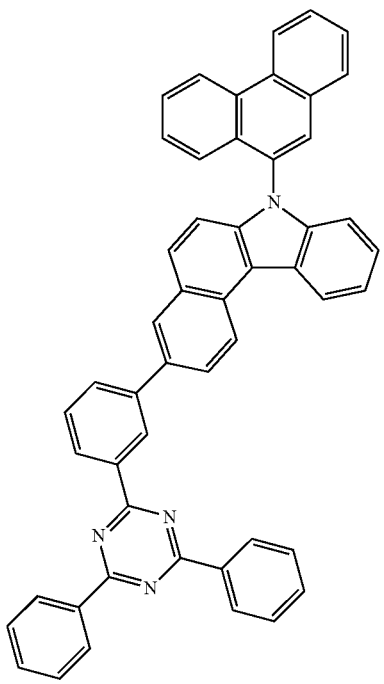
509
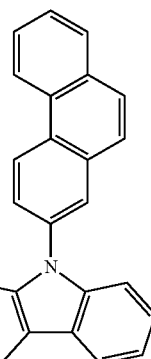
510

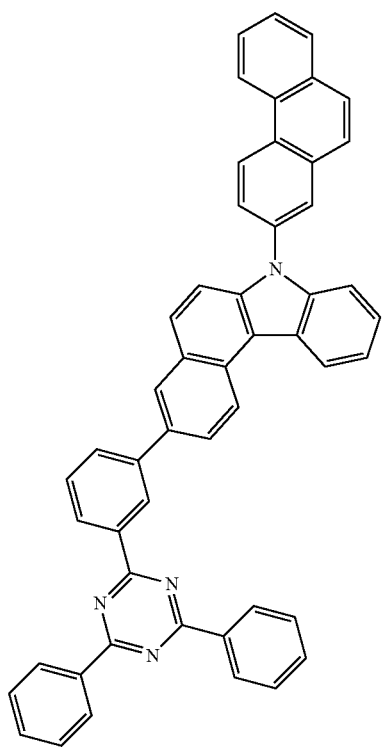
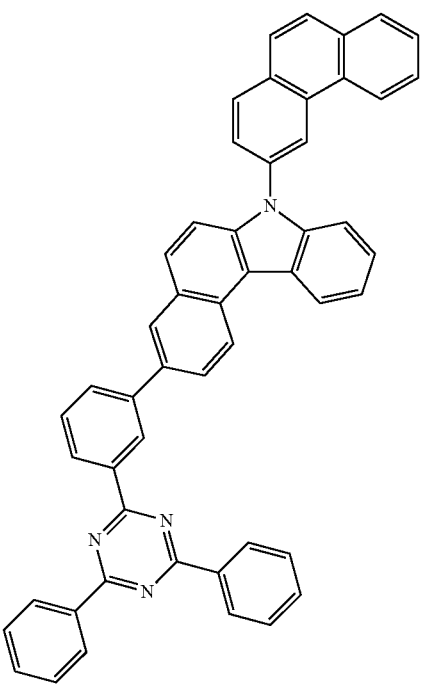
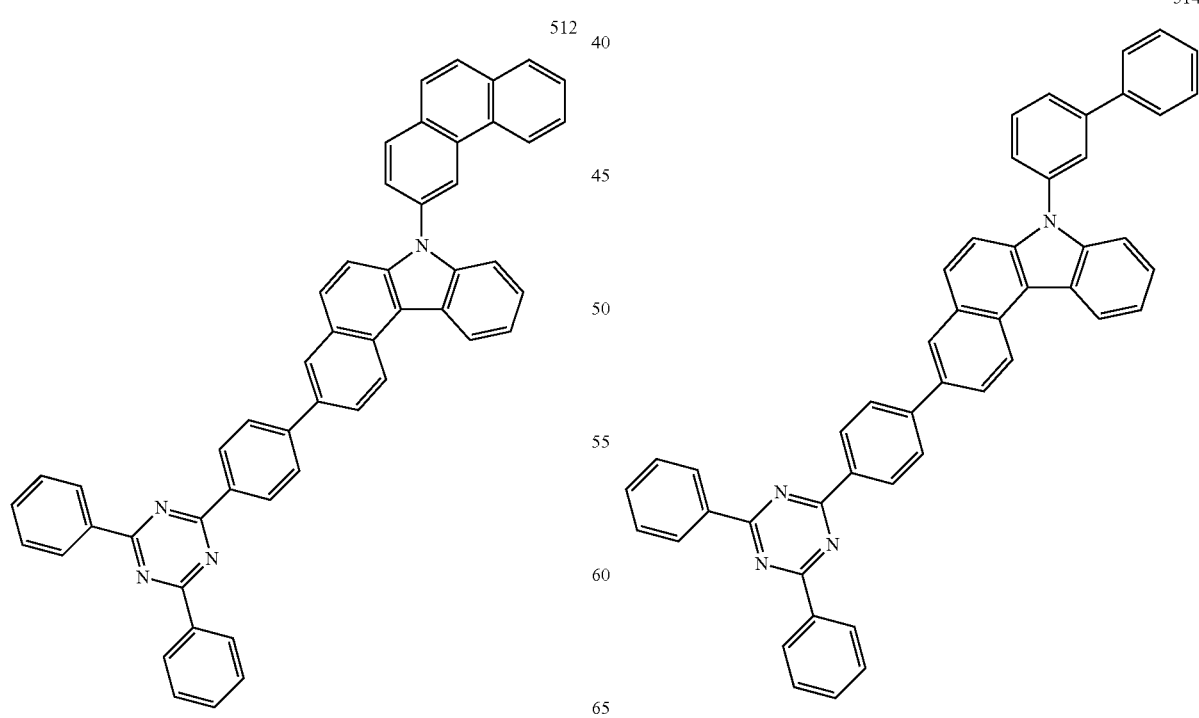

579
-continued
515
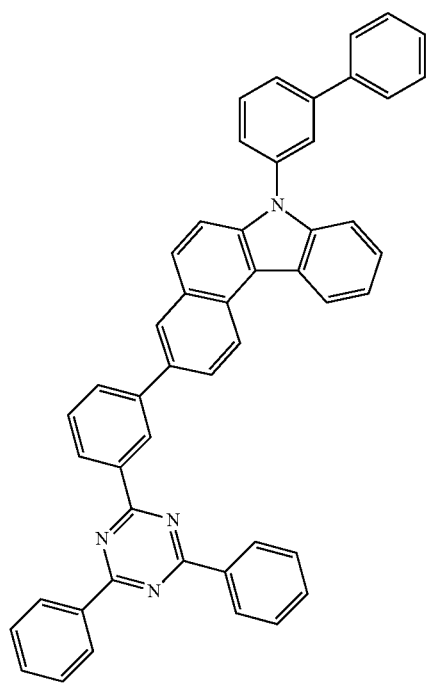
516
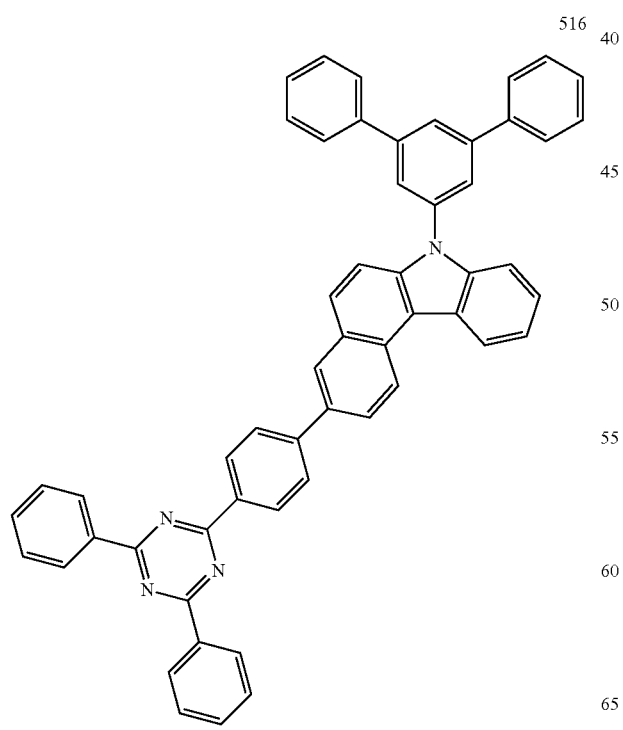
580
-continued
517
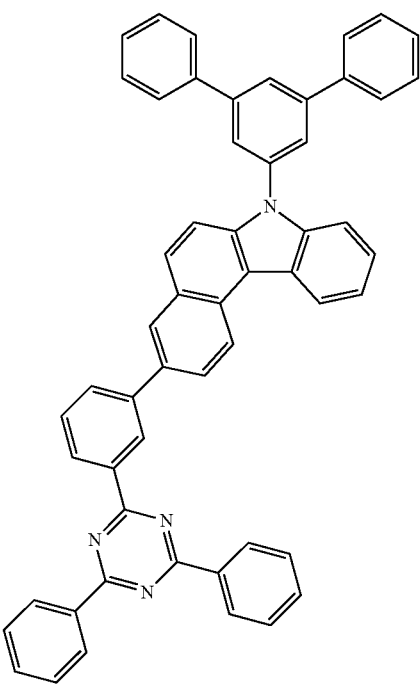
518
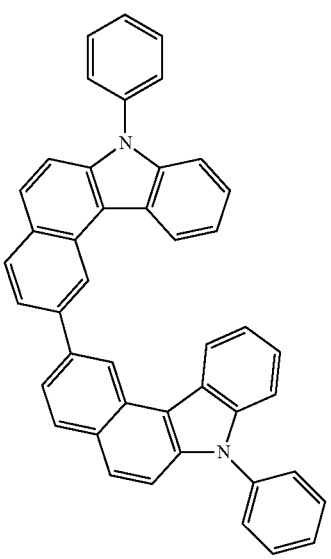

581
-continued
519
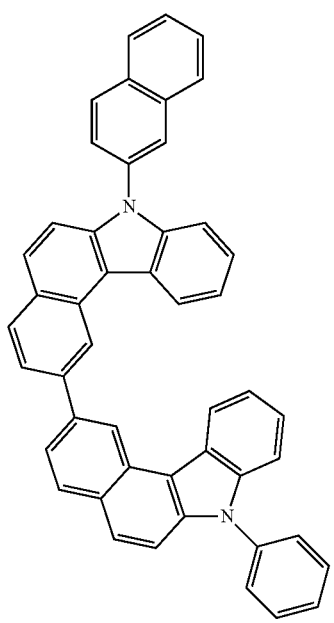
520
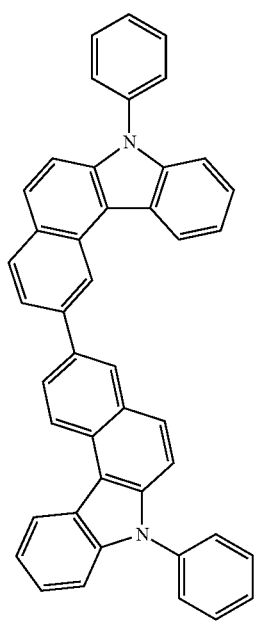
582
-continued
521
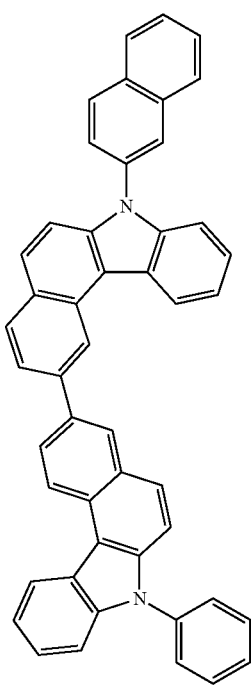
523
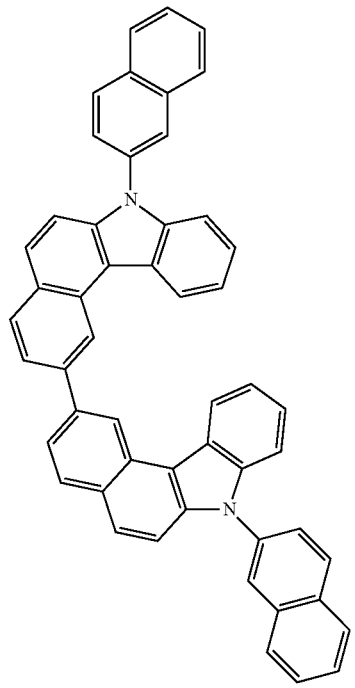

583
-continued
524
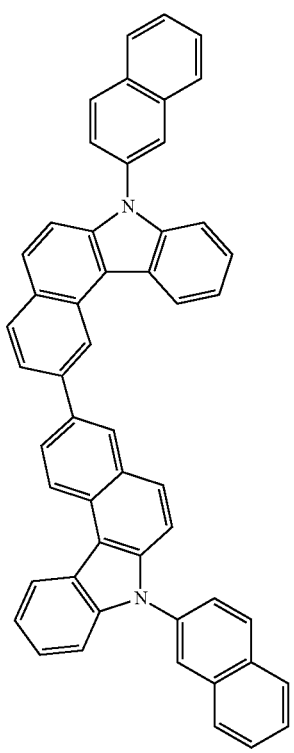
525
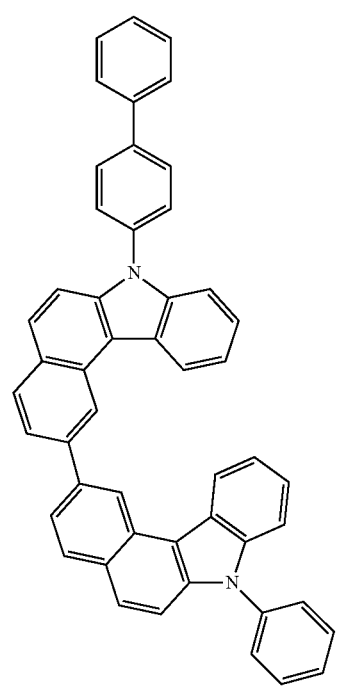
584
-continued
526
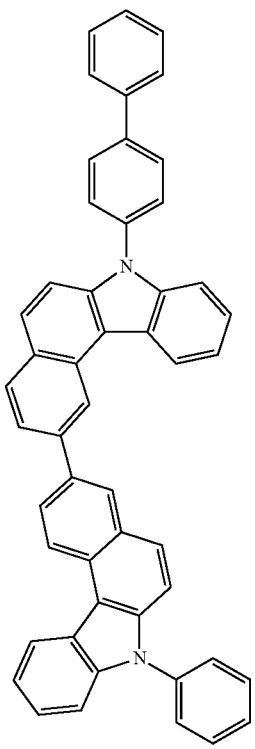
527
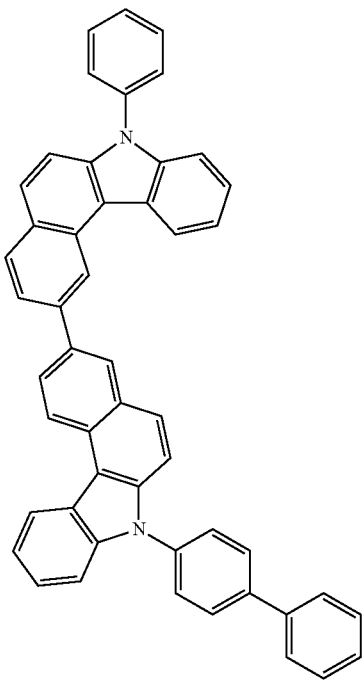

585
-continued
528
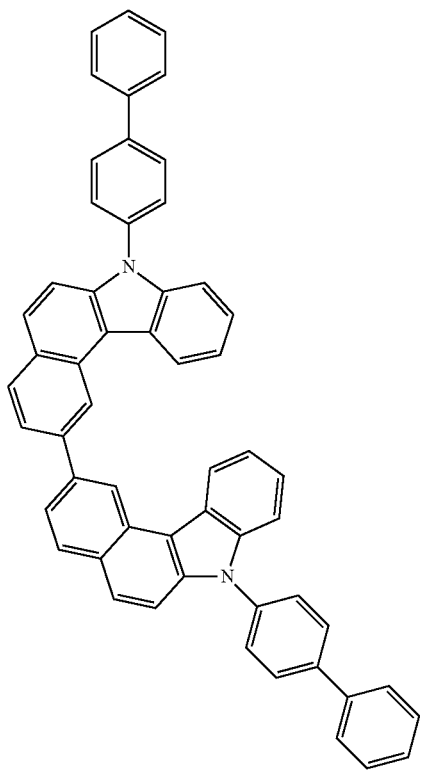
529
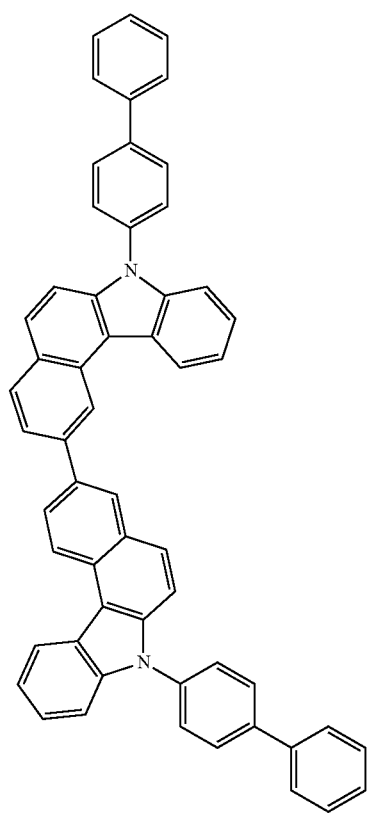
586
-continued
530
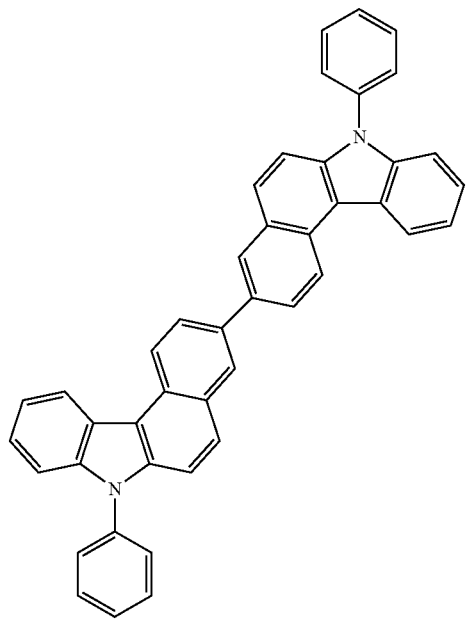
531
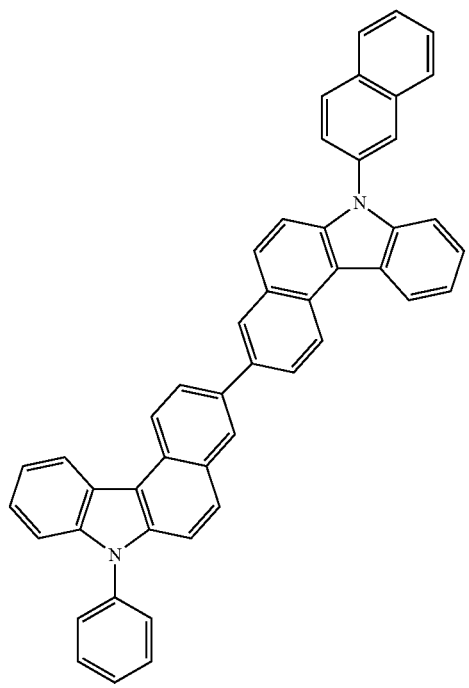

532
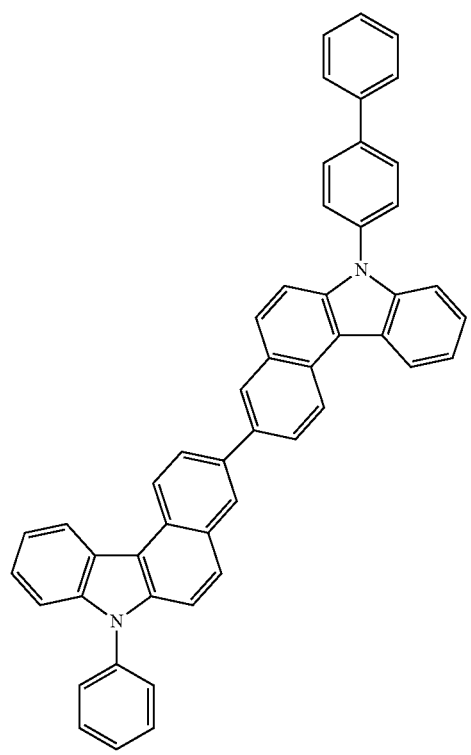
533
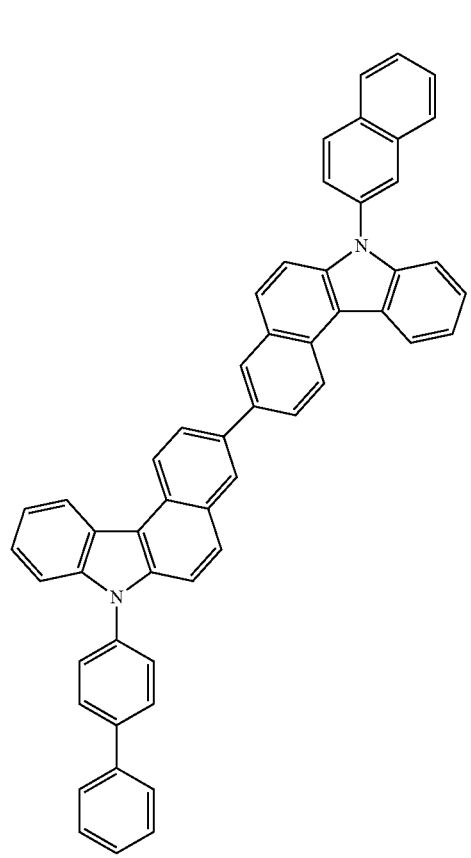
534
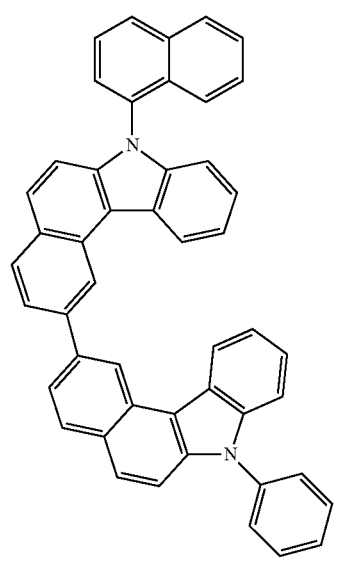
535
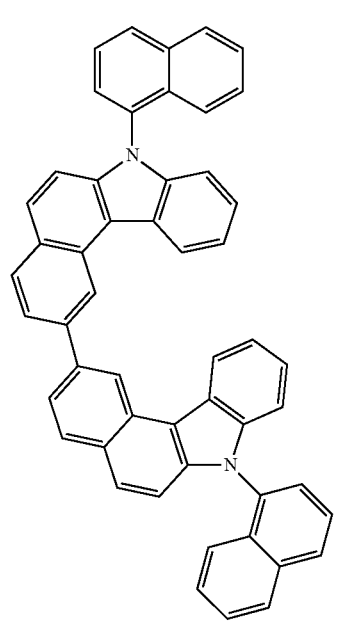

-continued
536
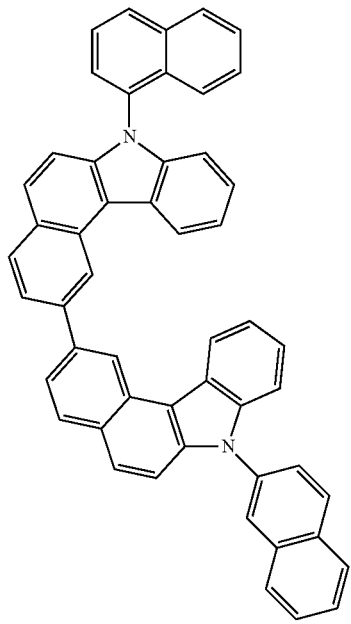
-continued
538
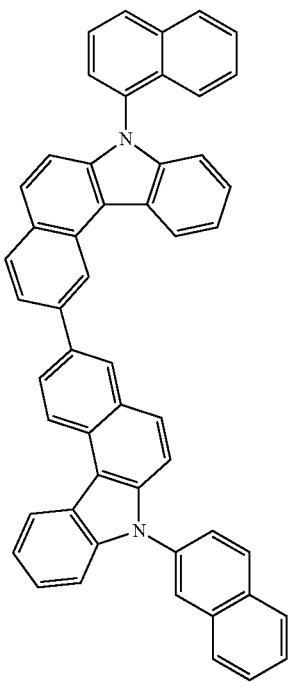
537
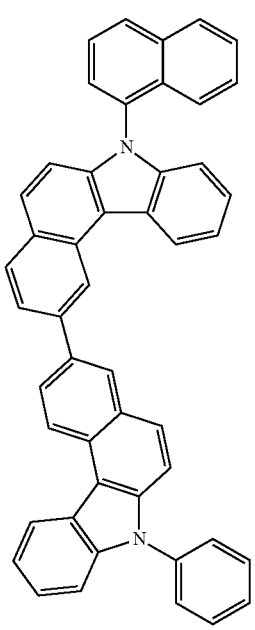
539
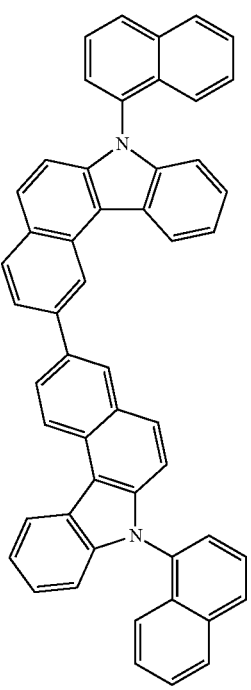

540
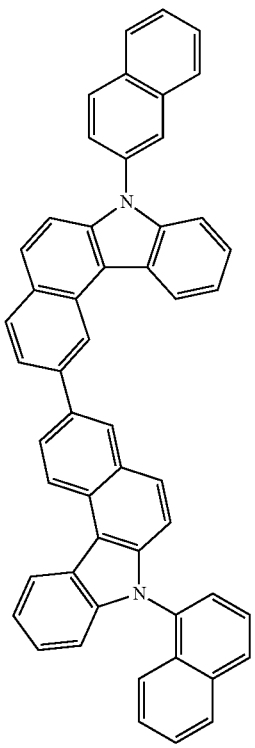
541
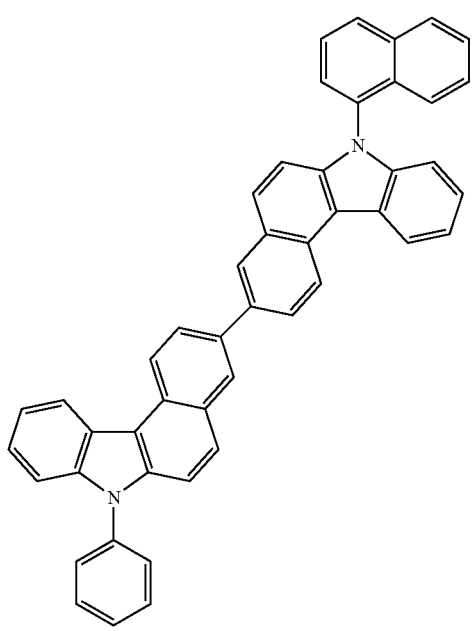
542
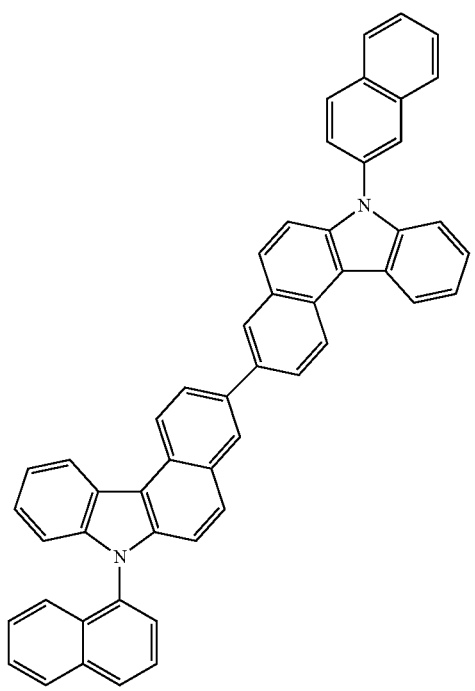
543
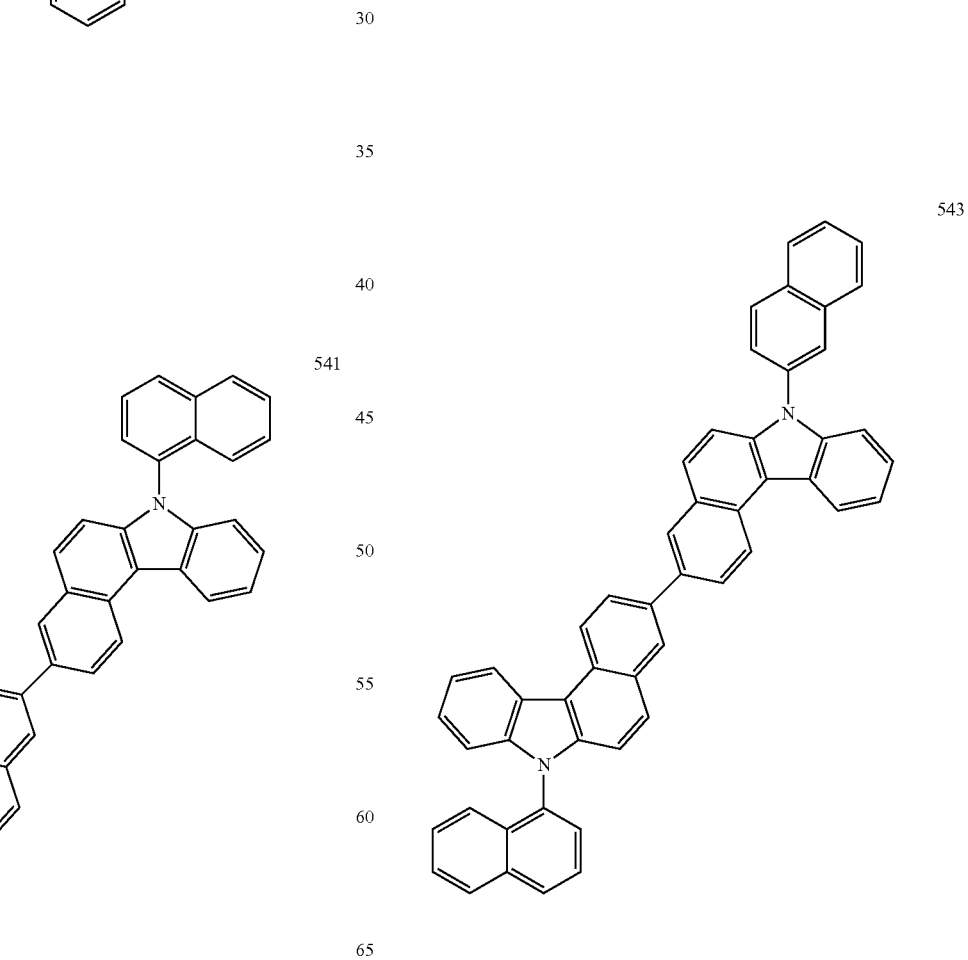

593
-continued
544
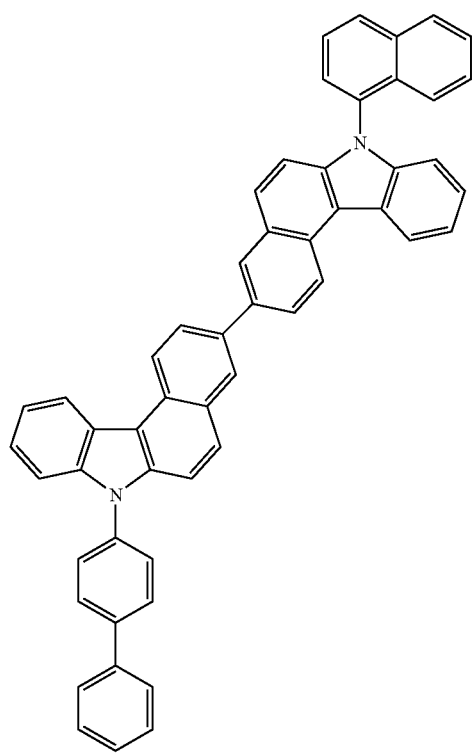
545
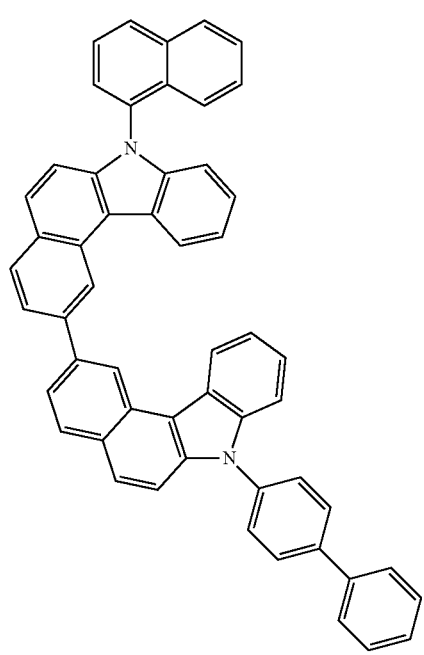
594
-continued
546
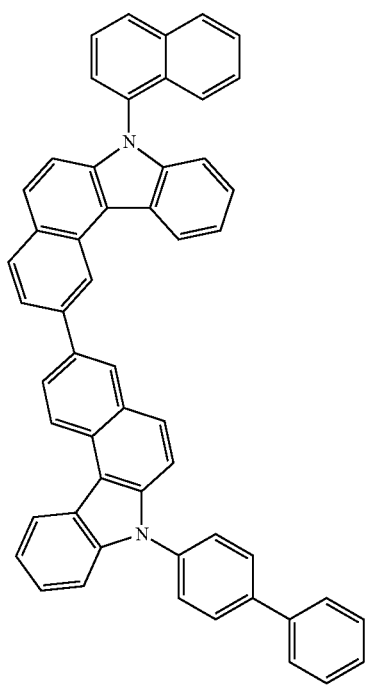
547
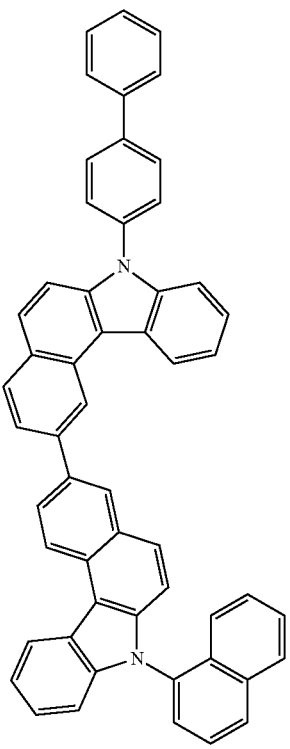

548
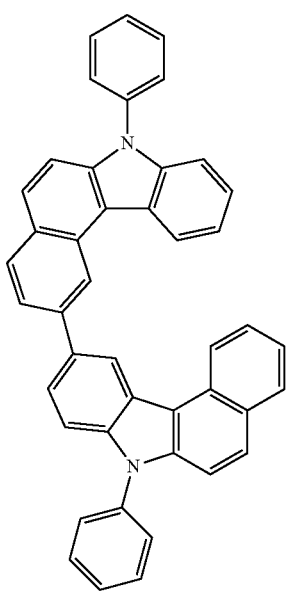
550
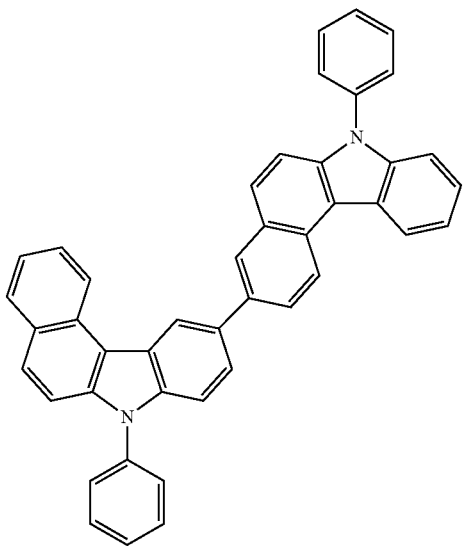
549
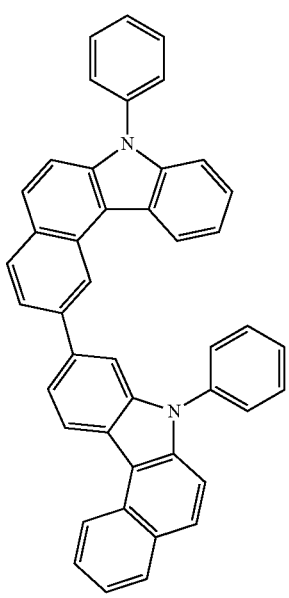
551
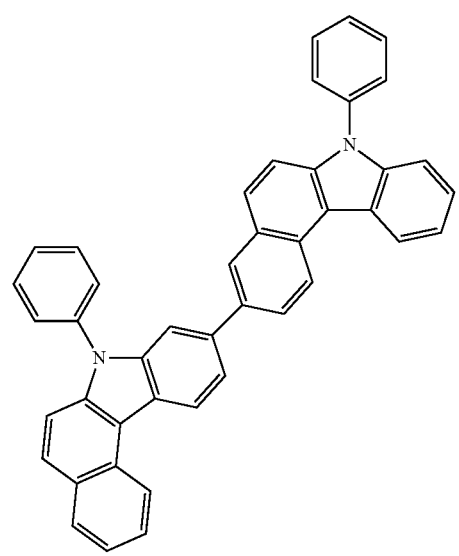

597
-continued
598
-continued
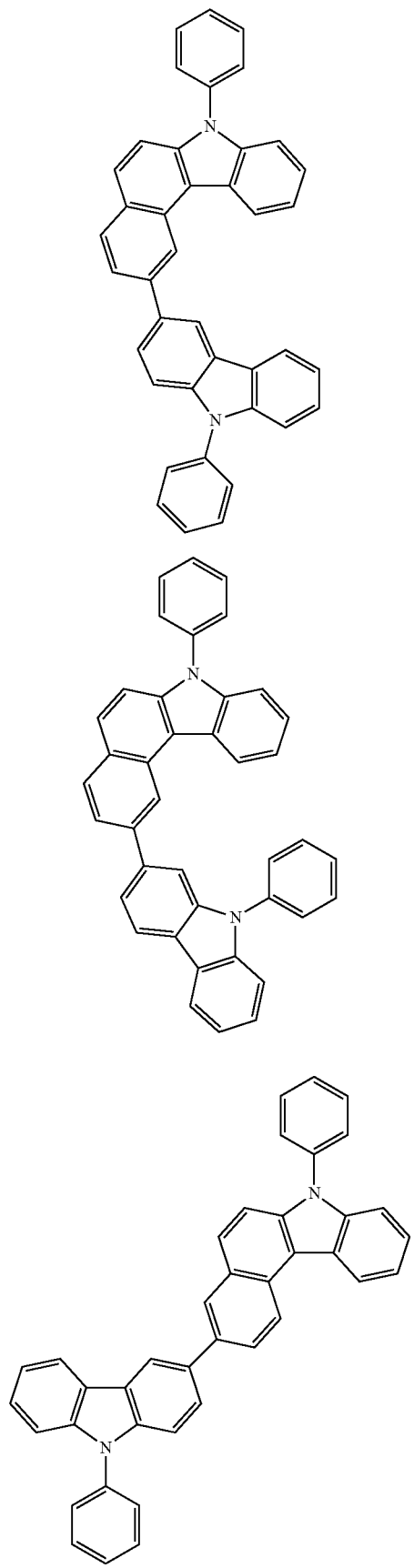
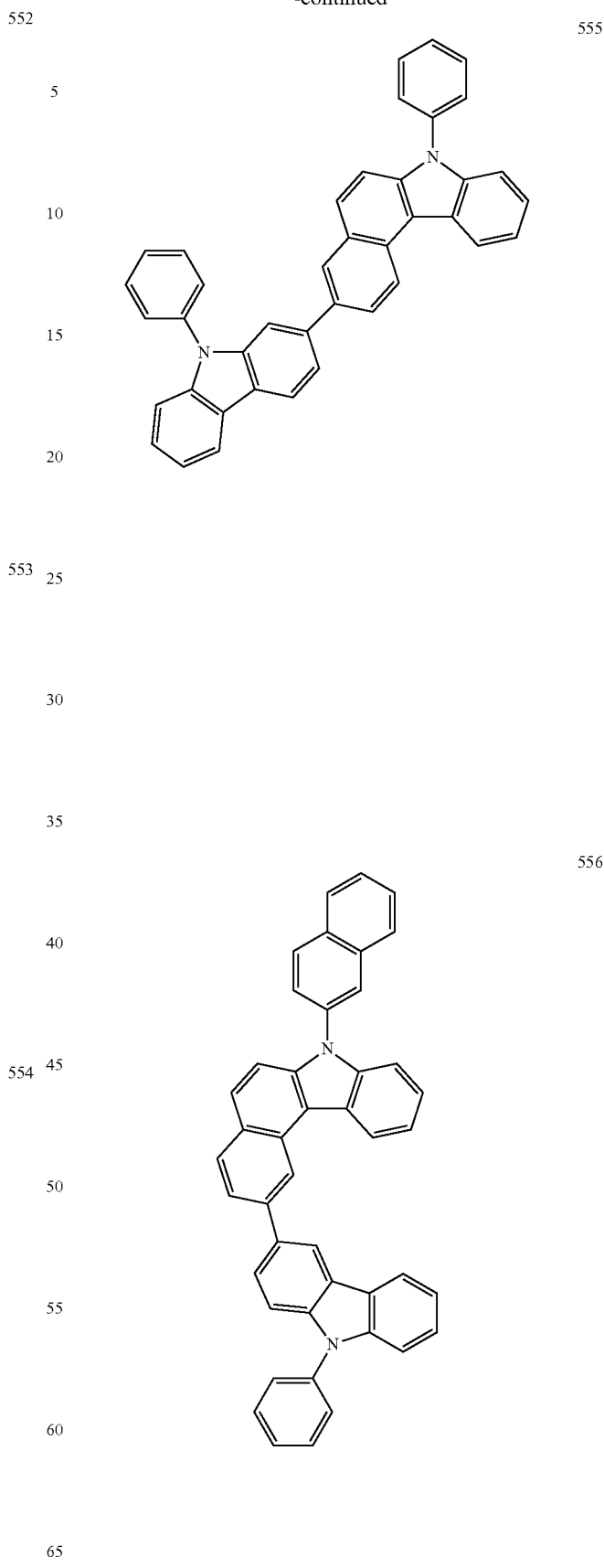

599
-continued
557
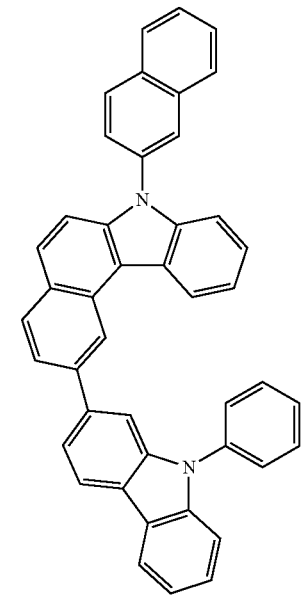
558
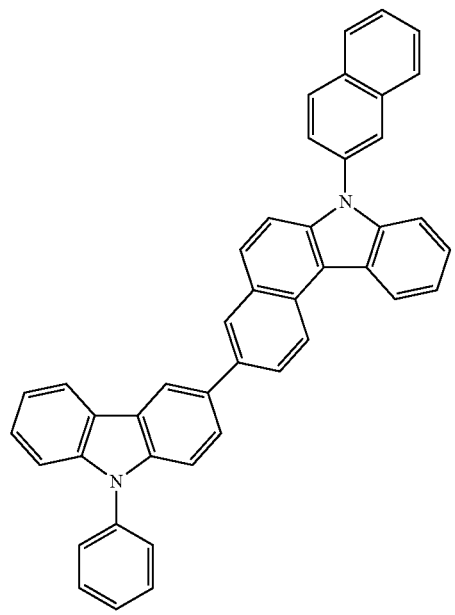
600
-continued
559
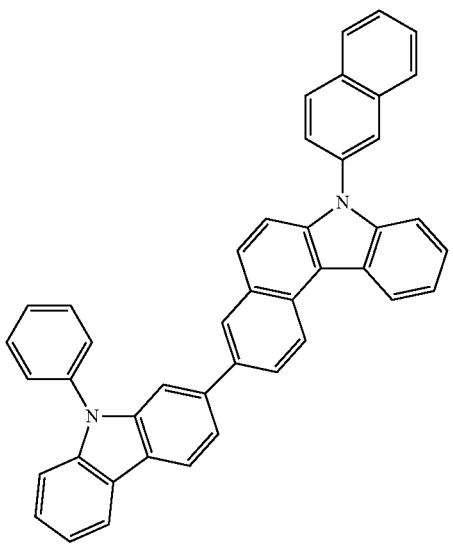
560
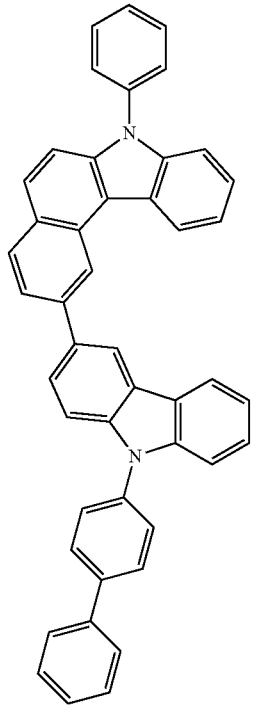

601
-continued
561
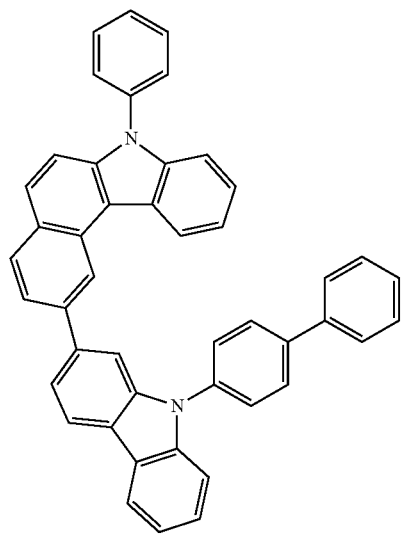
562
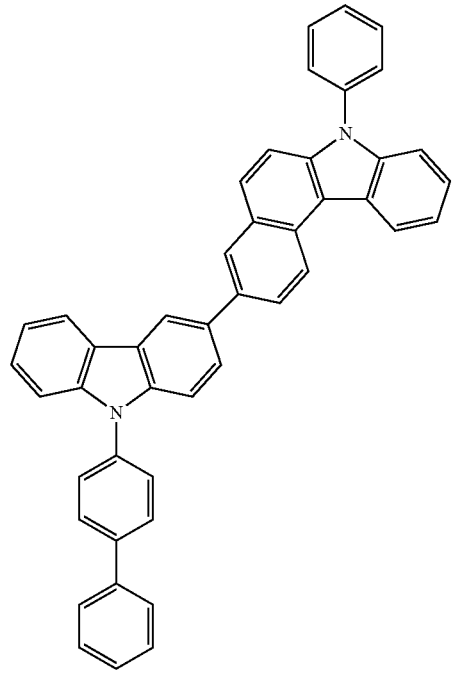
602
-continued
563
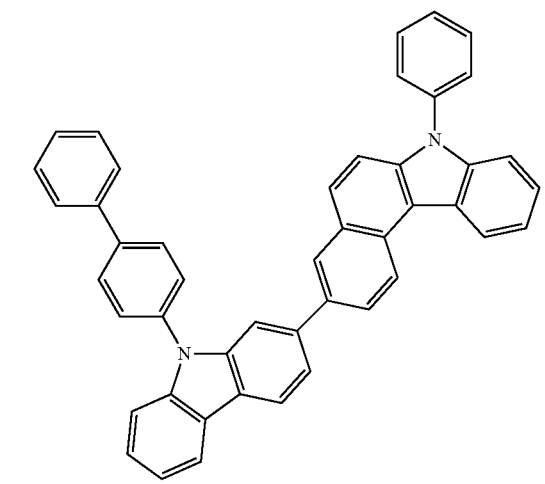
564
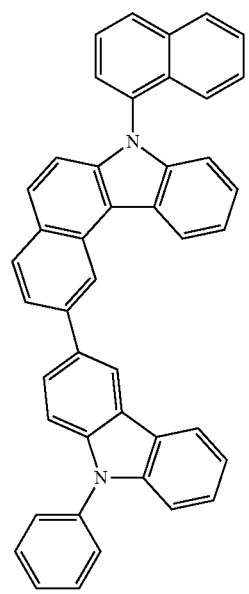

603
-continued
604
-continued
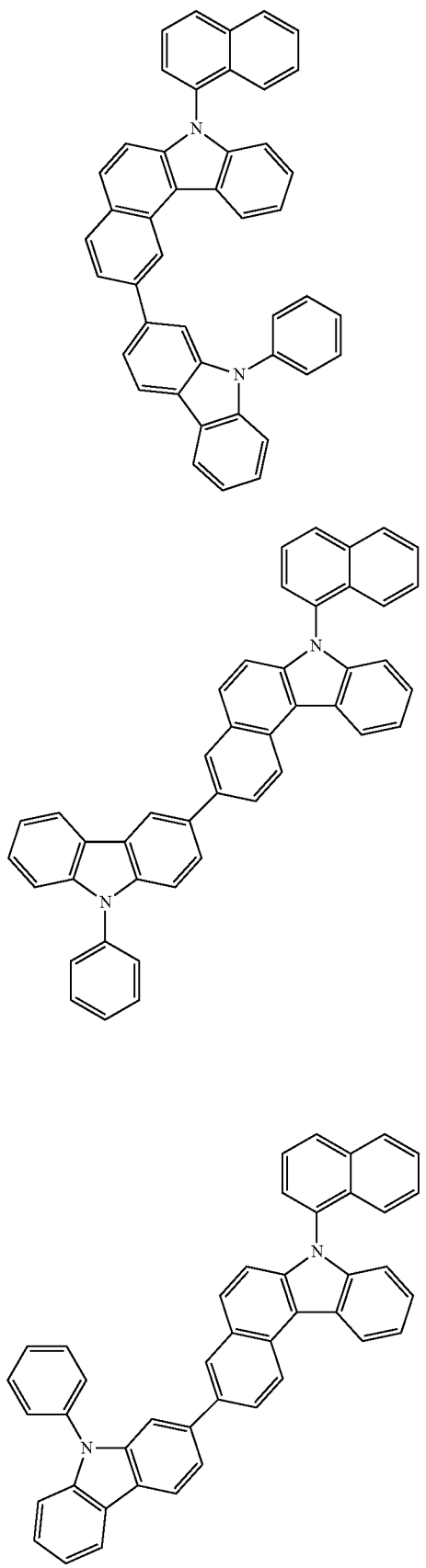
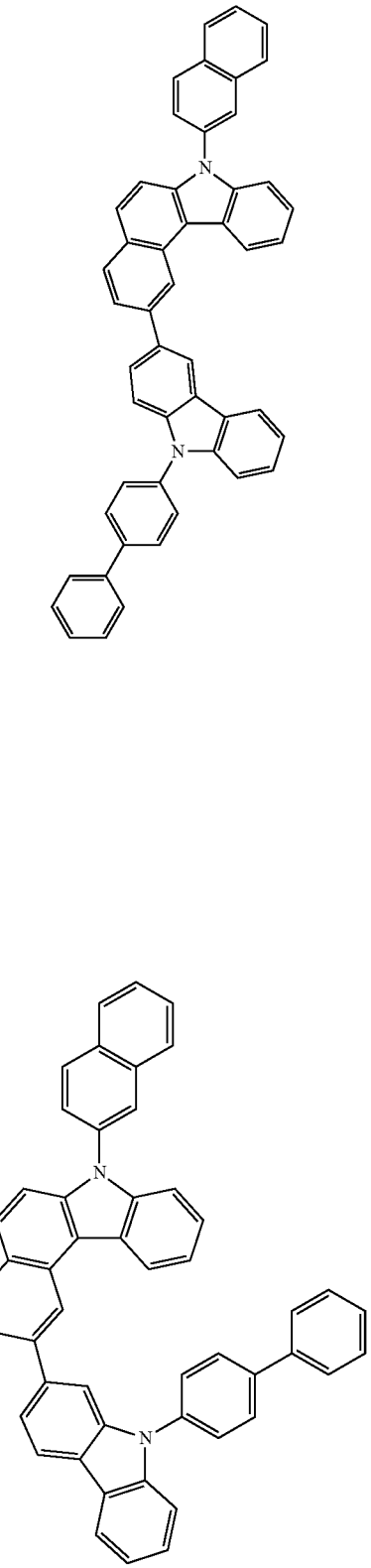

605
-continued
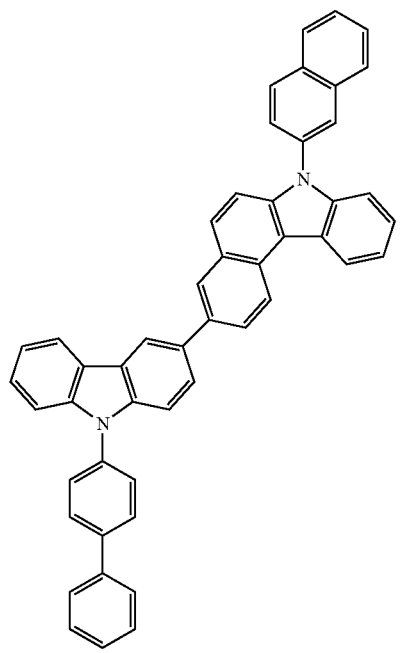
571
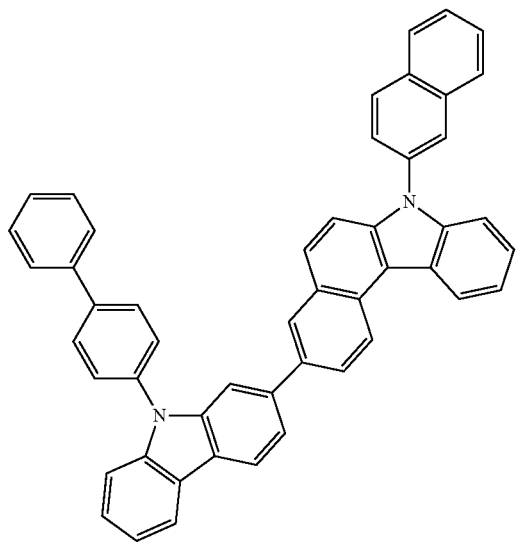
572
606
-continued
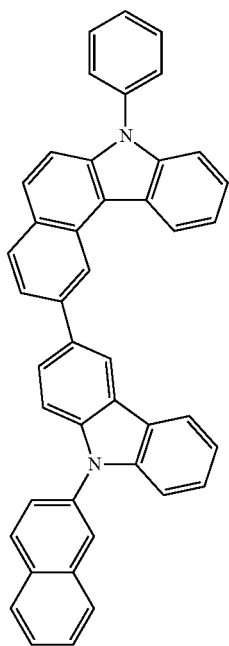
573
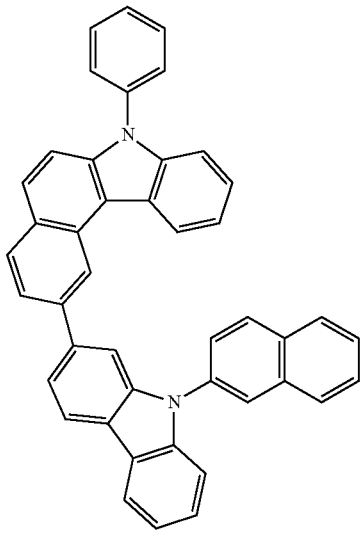
574

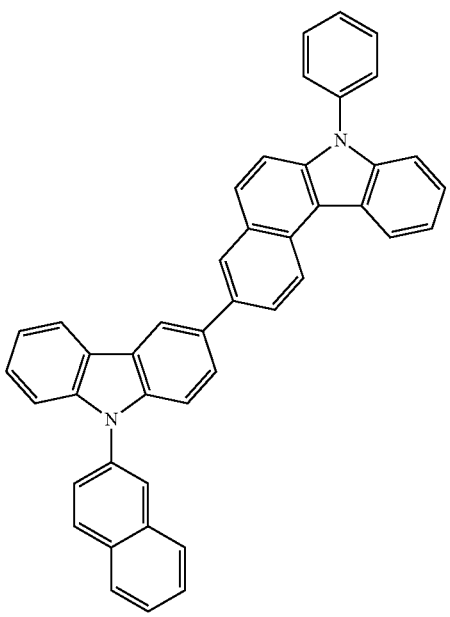
575

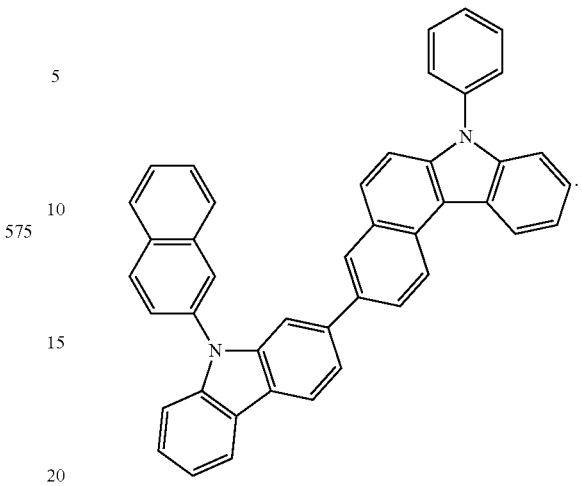
576

16. An organic light emitting device, comprising:
a first electrode;
a second electrode provided to face the first electrode; and
one or more organic material layers provided between the first electrode and the second electrode,
wherein one or more layers of the organic material layers comprise the multicyclic compound including nitrogen of claim 1.

17. The organic light emitting device of claim 16, wherein the organic material layer comprising the multicyclic compound including nitrogen is a hole injection layer; a hole transporting layer; or a layer which simultaneously injects and transports holes.

18. The organic light emitting device of claim 16, wherein the organic material layer comprising the multicyclic compound including nitrogen is an electron injection layer; an electron transporting layer; or a layer which simultaneously injects and transports electrons.

19. The organic light emitting device of claim 16, wherein the organic material layer comprising the multicyclic compound including nitrogen is a light emitting layer.

* * * * *